(12) United States Patent
Tachdjian et al.

(10) Patent No.: US 8,633,186 B2
(45) Date of Patent: Jan. 21, 2014

(54) MODULATION OF CHEMOSENSORY RECEPTORS AND LIGANDS ASSOCIATED THEREWITH

(75) Inventors: Catherine Tachdjian, San Diego, CA (US); Donald S. Karanewsky, Escondido, CA (US); Xiao-Qing Tang, San Diego, CA (US); Xiaodong Li, San Diego, CA (US); Feng Zhang, San Diego, CA (US); Guy Servant, San Diego, CA (US); Qing Chen, San Diego, CA (US); Vincent Darmohusodo, Encinitas, CA (US); Richard Fine, Ridgewood, NJ (US); Joseph R. Fotsing, San Diego, CA (US); Jeffrey Robert Hammaker, San Diego, CA (US); Xinshan Kang, Pine Brook, NJ (US); Rachel D. A. Kimmich, San Diego, CA (US); Boris Klebansky, Demarest, NJ (US); Haitian Liu, San Diego, CA (US); Goran Petrovic, San Diego, CA (US); Marketa Rinnova, Urbana, IL (US); Sara Adamski-Werner, San Diego, CA (US); Jeffrey Yamamoto, San Diego, CA (US); Hong Zhang, San Diego, CA (US); Albert Zlotnik, San Diego, CA (US); Mark Zoller, La Jolla, CA (US); Karen Zoller, legal representative, La Jolla, CA (US)

(73) Assignee: Senomyx Inc., San Diego, CA (US)

( * ) Notice: Subject to any disclaimer, the term of this patent is extended or adjusted under 35 U.S.C. 154(b) by 277 days.

(21) Appl. No.: 12/663,634

(22) PCT Filed: Jun. 3, 2008

(86) PCT No.: PCT/US2008/065650
§ 371 (c)(1),
(2), (4) Date: Apr. 14, 2011

(87) PCT Pub. No.: WO2008/154221
PCT Pub. Date: Dec. 18, 2008

(65) Prior Publication Data
US 2011/0224155 A1 Sep. 15, 2011

Related U.S. Application Data

(63) Continuation-in-part of application No. 11/760,592, filed on Jun. 8, 2007, and a continuation-in-part of application No. 11/836,074, filed on Aug. 8, 2007, now Pat. No. 7,928,111.

(60) Provisional application No. 61/027,410, filed on Feb. 8, 2008.

(51) Int. Cl.
*C07D 239/95* (2006.01)
*C07D 285/16* (2006.01)
*A61K 31/517* (2006.01)
*A61K 31/54* (2006.01)

(52) U.S. Cl.
USPC ............................................ 514/222.8; 544/11

(58) Field of Classification Search
USPC ........................................ 544/11; 514/222.8
See application file for complete search history.

(56) References Cited

U.S. PATENT DOCUMENTS

| | | | |
|---|---|---|---|
| 3,278,532 A * | 10/1966 | Houlihan | .......................... 544/11 |
| 3,843,804 A | 10/1974 | Evers et al. | |
| 3,845,770 A | 11/1974 | Theeuwes et al. | |
| 3,857,972 A | 12/1974 | Evers et al. | |
| 3,916,899 A | 11/1975 | Theeuwes et al. | |
| 3,957,783 A | 5/1976 | Hirohashi et al. | |
| 3,960,860 A | 6/1976 | Katz et al. | |
| 4,146,716 A | 3/1979 | Cox et al. | |
| 4,196,207 A | 4/1980 | Webber et al. | |
| 4,377,580 A | 3/1983 | Ueda et al. | |
| 4,765,539 A | 8/1988 | Noakes et al. | |
| 5,112,598 A | 5/1992 | Biesalski | |
| 5,380,541 A | 1/1995 | Beyts et al. | |

(Continued)

FOREIGN PATENT DOCUMENTS

| | | |
|---|---|---|
| EP | 0530994 A1 | 3/1993 |
| WO | WO 03/001876 A2 | 1/2003 |

(Continued)

OTHER PUBLICATIONS

Wright, John Journal of Organic Chemistry (1965), 30(11), 3960-2.*

(Continued)

*Primary Examiner* — Kahsay Habte
(74) *Attorney, Agent, or Firm* — Cooley LLP

(57) ABSTRACT

The present invention includes methods for identifying modifiers of chemosensory receptors and their ligands, e.g., by determining whether a test entity is suitable to interact with one or more interacting sites within the Venus flytrap domains of the chemosensory receptors, and modifiers capable of modulating chemosensory receptors and their ligands. The present invention also includes modifiers of chemosensory receptors and their ligands having Formula (I), its subgenus, and specific compounds. Furthermore, the present invention includes ingestible compositions comprising the modifiers of chemosensory receptors and their ligands and methods of using the modifiers of chemosensory receptors and their ligands to enhance the sweet taste of an ingestible composition or treat a condition associated with a chemosensory receptor. In addition, the present invention include processes for preparing the modifiers of chemosensory receptors and their ligands.

16 Claims, 13 Drawing Sheets

(56) References Cited

U.S. PATENT DOCUMENTS

| | | | |
|---|---|---|---|
| 5,504,095 | A | 4/1996 | Nakane et al. |
| 5,556,611 | A | 9/1996 | Biesalski |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | van der Linden et al. |
| 7,105,650 | B2 | 9/2006 | Adler |
| 7,928,111 | B2 | 4/2011 | Tachdjian et al. |
| 2003/0008344 | A1 | 1/2003 | Adler et al. |
| 2003/0054448 | A1 | 3/2003 | Adler et al. |
| 2003/0232407 | A1 | 12/2003 | Zoller et al. |
| 2004/0127435 | A1 | 7/2004 | Carson et al. |
| 2005/0032158 | A1 | 2/2005 | Adler et al. |
| 2006/0045953 | A1 | 3/2006 | Tachdjian et al. |
| 2006/0135552 | A1 | 6/2006 | Malherbe et al. |
| 2007/0104709 | A1 | 5/2007 | Li et al. |
| 2008/0306053 | A1 | 12/2008 | Tachdjian et al. |
| 2008/0306093 | A1 | 12/2008 | Servant et al. |
| 2011/0230502 | A1 | 9/2011 | Tachdjian et al. |

FOREIGN PATENT DOCUMENTS

| | | |
|---|---|---|
| WO | WO 03/022214 A2 | 3/2003 |
| WO | WO 2007/004709 A1 | 1/2007 |
| WO | WO 2007/047988 A2 | 4/2007 |

OTHER PUBLICATIONS

Goya et al. Archiv der Pharmazie (Weinheim, Germany) (1984), 317(9), 777-81.*
Office Action for U.S. Appl. No. 13/051,586, mailed Jun. 21, 2012.
Albrecht et al., "Synthesis of 1,2,6-Thiadiazine 1,1-Dioxides via Isoxazolylsulfamides," J. Org. Chem. 44:4191-4194 (1979).
Alderman, "A Review of Cellulose Ethers in Hydrophilic Matrices for Oral Controlled-Release Dosage Forms," Int. J. Pharm. Tech. & Prod. Mfr. 5(3):1-9 (1984).
Bamba et al., "Release mechanisms in Gelforming Sustained Release Preparations," Int. J. Pharm. 2:307-315 (1979).
Bellur et al., "Synthesis of 4-(3-hydroxyalkyl)pyrimidines by ring transformation reactions of 2-alkylidenetetrahydrofurans with amidines," Tetrahedron 62:5426-5434 (2006).
Berge et al., "Pharmaceutical Salts," J. Pharm. Sci. 66(1):1-19 (1977).
Blackburn et al., "Identification and characterization of aminopiperidinequinolones and quinazolinones as MCHr1 antagonists," Bioorg. & Med. Chem. Lett. 16:2621-2627 (2006).
Boarland et al., "Monosubstituted Pyrimidines, and the Action of Thiourea on Chloropyrimidines," J. Chem. Soc. 1218-1221 (1951).
Brown, et al., "Evolution of a Series of Peptidoleukotriene Antagonists: Synthesis and Structure-Activity Relationships of 1,6-Disubstituted Indoles and Indazoles," J. Med. Chem. 33:1771-1781 (1990).
Buck et al., "A Novel Multigene Family May Encode Odorant Receptors: A Molecular Basis for Odor Recognition," Cell 65(1):175-187 (1991).
Chandrashekar et al., "T2Rs Function as Bitter Taste Receptors," Cell 100:703-711 (2000).
Clauβ et al., "Cycloadditionen von Halogensulfonylisocyanaten an Acetylene," Tetrahedron Lett. 2:119-122 (1970).
Da Settimo et al.,"Naphtho[1,2-d]isothiazole Acetic Acid Derivatives as a Novel Class of Selective Aldose Reductase Inhibitors," J. Med. Chem. 48:6897-6907 (2005).
Dorwald, "Side Reactions in Organic Synthesis: A Guide to Successful Synthesis Design," Weinheim: Wiley-VCH Verlag Gmbh & o. KGaA, 2005, ISBN: 3-527-31021-5.
During et al., "Controlled Release of Dopamine from a Polymeric Brain Implant: In Vivo Characterization," Ann. Neurol. 25:351-356 (1989).
Elmegeed et al., "Novel synthesizes aminosteroidal heterocycles intervention for inhibiting iron-induced oxidative stress," Eur. J. Med. Chem. 40:1283-1294 (2005).

El-Sherbeny et al., "Novel Pyridothienopyrimidine and Pyridothienothiazine Derivatives as Potential Antiviral and Antitumor Agents," Med. Chem. Res. 10:122-135 (2000).
Etter et al., "An Enolized Sulfonamide Formed by Strong Hydrogen Bonding to Triphenylphosphine Oxide," J. Org. Chem. 51:5405-5408 (1986).
Francis et al., "Anxiolytic Properties of Certain Annelated [1,2,4]Triazolo[1,5-c]pyrimidin-5(6H)-ones," J. Med. Chem. 34:2899-2906 (1991).
Goya et al., "Fused 1,2,6-Thiadiazines: Tetrahydrobenzo[b]thieno[2,3-c] [1,2,6]thiadiazine 2,2-Dioxides," Arch. Pharm. (Weinheim) 317:777-781 (1984).
Goya et al., "N-Glucosyl-5-Amino-4-Carbamoyl- and 4-Ethoxycarbonylimidazoles as Potential Precursors of 4-Oxoimidazo[4,5-c]-1,2,6-thiadiazine 2,2-Dioxides," Heterocycles 24:3451-3458 (1986).
Hauser et al., "Synthesis of 5-Phenyl-4,6-Dimethyl-2-Pyrimidol and Derivatives from the Cyclization of Urea with 3-Phenyl-2,4-Pentanedione," J. Org. Chem. 18:588-593 (1953).
Hirayama et al., "The Discovery of YM-60828: A Potent, Selective and Orally-Bioavailable Factor Xa Inhibito," Bioorg. & Med. Chem. 10:1509-1523 (2002).
Hirota et al., "Synthesis and Biological Evaluation of 2,8-Disubstituted 9-Benzyladenines: Discovery of 8-Mercaptoadenines as Potent Interferon-Inducers," Bioorg. Med. Chem. 11:2715-2722 (2003).
Hoon et al., Putative Mammalian Taste Receptors: A Class of Taste-Specific GPCRs with Distinct Topographic Selectivity. Cell 96:541-551 (1991).
Howard et al., "Intracerebral drug delivery in rats with lesion-induced memory deficits," J. Neurosurg. 71:105-112 (1989).
Hu et al., "Organic Reactions in Ionic Liquids: Gewald Synthesis of 2-Aminothiophenes Catalyzed by Ethylenediammonium Diacetate," Synthetic Communication 34:3801-3806 (2004).
Jordan, "Tamoxifen: A Most Unlikely Pioneering Medicine," Nature Reviews: Drug Discovery 2003, vol. 2, pp. 205-213.
Jung et al., "Discovery of Novel and Potent thiazoloquinazolines as Selective Aurora A and B Kinase Inhibitors," J. Med. Chem. 49:955-970 (2006).
Kamal et al., "Cyclization of 2-(Carbamoyloxy)- and 2-(Sulfamoyloxy)benzoates Mediated by Liver Microsomes," J. Org. Chem. 53:4112-4114 (1988).
Kamal et al., "Enzymatic Cyclization of 2-(Carbamoyloxy)Benzoates, 2-(Sulfamoyloxy)-Benzoates and 2-(Carbamoyloxy)benzopenones with Yeast and Lipase," Heterocycles 29:1391-1397 (1989).
Kanbe et al., "Discovery of thiochroman derivatives bearing a carboxy-containing side chain as orally active pure antiestrogens," Bioorg. & Med. Chem. Lett. 16:4090-4094 (2006).
Kanuma et al., "Lead optimization of 4-(dimethylamino)quinazolines, potent and selective antagonists for the melanin-concentrating hormone receptor 1," Bioorg. & Med. Chem. Lett. 15:3853-3856 (2005).
Khabnadideh et al., "Design, synthesis and evaluation of 2,4-diaminoquinazolines as inhibitors of trypanosomal and leishmanial dihydrofolate reductase," Bioorg. Med. Chem. 13:2637-2649 (2005).
Klinger et al., "Inhibition of Carbonic Anhydrase-II by Sulfamate and Sulfamide Groups: An Investigation Involving Direct Thermodynamic Binding Measurements," J. Med. Chem. 49:3496-3500 (2006).
Kyte et al., "A Simple Method for Displaying the Hydropathic Character of a Protein," J. Mol. Biol. 157:105-132 (1982).
Langer et al., "Chemical and Physical Structure of Polymers as Carriers for Controlled Release of Bioactive Agents: A Review," J. Macromol. Sci. Rev. Macromol Chem. 23:61-126 (1983).
Langer, "New Methods of Drug Delivery," Science 249:1527-1533 (1990).
Lee et al., "Acetonitrile-Mediated Synthesis of 2,4-Dichloroquinoline from 2-Ethynyl-aniline and 2,4-Dichloroquinazoline from Anthranilonitrile," Synlett, 2006 No. 1:65-68 (2006).

(56) References Cited

OTHER PUBLICATIONS

Leistner et al., "Eine einfache Synthese von 2-Alhylthio-4-amino-thieno[2,3-d]pyrimidinen,"Arch. Pharm. (Weinheim) 322:227-230 (1989).
Levy et al., "Inhibition of Calcification of Bioprosthetic Heart Valves by Local Controlled-Release Diphosphonate," Science 228:190-192 (1985).
Li et al., "Human receptors for sweet and umami taste," Proc. Natl. Acad. Sci. USA 99:4692-4696 (2002).
Linkies et al., "Ein neues Verfahren zur Herstellung von 6-Methyl-1,2,3-oxathiazin-4(3H)-on-2,2-dioxid Kaliumsalz (Acesulfam-K)," Synthesis 405-406 (1990).
Liu et al., "Discovery of a new class of 4-anilinopyrimidines as potent c-Jun N-terminal kinase inhibitors: Synthesis and SAR studies," Bioorg. & Med. Chem. Lett. 17:668-672 (2007).
Naganawa et al., "Further optimization of sulfonamide analogs as EP1 receptor antagonists: Synthesis and evaluation of bioisosteres for the carboxylic acid group," Bioorg. Med. Chem. 14:7121-7137 (2006).
Nie et al., "Distinct Contributions of T1R2 and T1R3 Taste Receptor Subunits to the Detection of Sweet Stimuli," Curr. Biol. 15(21):1948-1952 (2005).
Pal et al., "Synthesis and Cyclooxygenase-2 (COX-2) Inhibiting Properties of 1,5-Diarylpyrazoles Possessing N-Substitution on the Sulfonamide (-$SO_2NH_2$) Moiety," Letters in Drug Design & Discovery 2:329-340 (2005).
Rad-Moghadam et al., "One-pot Three-component Synthesis of 2-Substituted 4-Aminoquinazolines," J. Heterocyclic Chem. 43:913-916 (2006).
Rasmussen et al., "The Electrophilic Addition of Chlorosulfonyl Isocyanate to Ketones. A Convenient Synthesis of Oxazines, Oxathiazines, and Uracils," J. Org. Chem. 38:2114-2115 (1978).
Reddy et al., "An Efficient Synthesis of 3,4-Dihydro-4-Imino-2(1H)-Quinazolinones," Synthetic Commun. 18:525-530 (1988).
Robinson et al., "Sulfonamide Ligands Attained through Opening of Saccharin Derivatives," Eur. J. Org. Chem. 19:4483-4489 (2006).
Rodriguez-Hahn et al., "A Study of the Thorpe-Ziegler Reaction in Very Mild Conditions," Synthetic Commun. 14:967-972 (1984).
Roy et al., "Auto-Redox Reaction: Tin(II) Chloride-Mediated One-Step Reductive Cyclization Leading to the Synthesis of Novel Biheterocyclic 5,6-Dihydro-quinazolino[4,3-b]quinazolin-8-ones with Three-Point Diversity," J. Org. Chem. 71:382-385 (2006).
Saudek et al., "A Preliminary Trial of the Programmable Implantable Medication System for Insulin Delivery," N. Engl. J Med. 321:574-579 (1989).
Seijas et al., "Microwave enhanced synthesis of 4-aminoquinazolines," Tetrahedron Lett. 41:2215-2217 (2000).
Sharma et al., "Synthesis and QSAR studies on 5-[2-(2-methylprop 1-enyl)-1H benzimidazol-lyl]-4,6-diphenyl-pyrimidin-2-(5H)-thione derivatives as antibacterial agents," Eur. J. Med. Chem. 41:833-840(2006).
Silve et al., "Delineating a Ca2+ Binding Pocket within the Venus Flytrap Module of the Human Calcium Sensing Receptor," The Journal of Biological Chemistry, Nov. 2005, vol. 280, pp. 37917-37923.
Tripathi et al., "Reaction of Flavanones with Chlorosulphonyl Isocyanate," Indian J. Chem. Sect. B 26B:1082-1083 (1987).
Uehling et al., "Biarylaniline Phenethanolamines as Potent and Selective $\beta_3$ Adrenergic Receptor Agonists," J. Med. Chem. 49:2758-2771 (2006).
Verma et al., "Osmotically Controlled Oral Drug Delivery," Drug Dev. Ind. Pharm. 26:695-708 (2000).
Verschoyle et al., "Pharmacokinetics of Isotretinoin (ISO) in Rats Following Oral Dosing or Aerosol Inhalation," British J. Cancer 80, Suppl. 2:96 Abstract No. P269 (1999).
Vippagunta et al., "Crystalline solids," Adv. Drug Deliv. Rev. 48:3-26 (2001).
Wilson et al., "Synthesis of 5-deazaflavin derivatives and their activation of p53 in cells," Bioorg. & Med. Chem. 15:77-86 (2007).
Wilson, "Traceless Solid-Phase Synthesis of 2,4-Diaminoquinazolines," Org. Lett. 3:585-588 (2000).

Winkler et al., "Synthesis and microbial transformation of β-amino nitriles," Tetrahedron 61:4249-4260 (2005).
Wright, "The Reaction of Sulfamide with α- and β-Diketones. The Preparation of 1,2,5-thiadiazole 1,1-Dioxides and 1,2,6-Thiadiazine 1,1-Dioxides," J. Org. Chem. 29:1905-1909 (1964).
Xu et al., "Oxidative cyclization of N-alky-o-methyl-arenesulfonamides to biologically important saccharin derivatives," Tetrahedron 62:7902-7910 (2006).
Xu et al., "Purine and Pyrididine Nucleotides Inhibit a Noninactivating K1 Current and Depolarize Adrenal Cortical Cells through a G Protein-coupled Receptor," Molecular Pharmacology, 1999, vol. 55, pp. 364-376.
Yamada et al., "Discovery of Novel and Potent Small-Molecule inhibitors of NO and Cytokine Production as Antisepsis Agents: Synthesis and Biological Activity of Alkyl 6-(N-Substituted sulfamoyl)cyclohex-1-ene-1-carboxylate," J. Med. Chem. 48:7457-7467 (2005).
Yoshizawa et al., "Efficient solvent-free Thrope reaction," Green Chem. 4:68-70 (2002).
Zunszain et al., "Search for the pharmacophore in prazosin for Transport-P," Bioorg. & Med. Chem. 13:3681-3689 (2005).
Young, "International Search Report," 5 pages, based on International Application No. PCT/US2008/065650 (mailed Nov. 20, 2008).
Young, "Written Opinion of the International Searching Authority," 19 pages, based on International Application No. PCT/US2008/065650 (mailed Nov. 20, 2008).
Vakili, Office Action, U.S. Appl. No. 11/760,592, 13 pages (mailed Jan. 7, 2010).
Vakili, Office Action, U.S. Appl. No. 11/760,592, 19 pages (mailed Oct. 7, 2010).
Willis, Office Action, U.S. Appl. No. 11/836,074, 7 pages (mailed Nov. 8, 2010).
Willis, Office Action, U.S. Appl. No. 11/836,074, 18 pages (mailed Jun. 10, 2009).
Willis, Office Action, U.S. Appl. No. 11/836,074, 18 pages (mailed Jun. 23, 2008).
Willis, Office Action, U.S. Appl. No. 11/836,074, 11 pages (mailed Sep. 29, 2009).
Willis, Office Action, U.S. Appl. No. 11/836,074, 13 pages (mailed Oct. 30, 2008).
Campillo et al., "A study of peculiar tautomerism of pyrido[2,3-c][1,2,6]thiadiazine 2,2-dioxide system," J. Mol. Struct. 678:83-89 (2004).
Chien et al., "Nucleosides XI. Synthesis and Antiviral Evaluation of 5'-Alkylthio-5'-deoxy Quinazolinone Nucleoside Derivatives as S-Adenosyl-L-homocysteine Analogs," Chem. Pharm. Bull. 52(12):1422-1426 (2004).
Corbett et al., "Novel 2,2-Dioxide-4,4-disubstituted-1,3-H-2,1,3-benzothiadiazines as Non-Nucleside Reverse Transcriptase Inhibitors," Bioorg. Med. Chem. Lett. 10:193-195 (2000).
Dominguez et al., "Efficient synthesis of 4,4-disubstituted-3,4-dihydro-1H-2,1,3-benzothiadiazine 2,2-dioxides," Tetrahedron Lett. 41:9825-9828 (2000).
European Search Report, EP Appl. No. 12175764.5, 16 pages (Feb. 22, 2013).
Garcia-Munoz et al., "Synthesis of Purine-Like Ring Systems Derived From 1,2,6-Thiadiazine 1,1-Dioxide," J. Heterocyclic Chem. 13:793-796 (1976).
Goya and Martinez, "Synthesis and Cytostatic Screening of an $SO_2$ Analogue of Doridosine," Arch. Pharm. (Weinheim) 321:99-101 (1988).
Goya et al., "Fused 1,2,6-Thiadiazines: Tetrahydrobenzo[b]thieno[2,3-c][1,2,6]thisdiazine 2,2-Dioxides," Arch. Pharm. (Weinheim) 317:777-781 (1984).
Goya et al., CAPLUS Accession No. 1987:18628, 2 pages, abstract of ES 531159 A1 (1985).
Meyer, Jr. and Skibo, "Synthesis of Fused [1,2,6]Thiadiazine 1,1-Dioxides as Potential Transition-State Analogue Inhibitors of Xanthine Oxidase and Guanase," J. Med. Chem. 22(8):944-948 (1979).
Reddy et al., "An Efficient Synthesis of 3,4-Dihydro-4-Imino-2(1H)-Quinazolinones," Synth. Commun. 18(5):525-530 (1988).

(56) References Cited

OTHER PUBLICATIONS

Rosowsky and Modest, "Quinazolines. III. Synthesis of 1,3-Diaminobenzo[f]quinazoline and Related Compounds," *J. Org. Chem.* 31:2607-2613 (1966).

Srivastava et al., "Solid Phase Synthesis of Structurally Diverse Pyrimido[4,5-d] Pyrimidines for the Potential Use in Combinatorial Chemistry," Bioorg. Med. Chem. Lett. 9:965-966 (1999).

Goya et al., "Aminopyrido [2,3-c] [1,2,6] Thiadiazine 2,2-Dioxides: Synthesis and Physico-chemical Properties," *Chemica Scripta*, 26:607-611 (1986).

Goya et al., "Synthesis of 2S-Dioxo Isosteres of Purine and Pyrimidine Nucleosides IV. Selective Glycosylation of 4-Amino-5H-Imidazo [4,5-c] -1,2,6-Thiadiazine 2,2-Dioxide," *Nucleosides & Nucleotides*, 6(3), 631-642 (1987).

Goya and Paez, "Pteridine Analogues; Synthesis and Physico-Chemical Properties of 7-Oxopyrazino [2,3-c][1,2,6] thiadiazine 2,2-Dioxides," *Liebigs Ann. Chem.*, 121-124 (1988).

Keith, "Synthesis and Reduction of some 1*H*-2,1,3-Benzothiadiazin-4(3H)one 2,2-Dioxides," *J. Heterocyclic Chem.*, 15:1521-1523 (1978).

Martinez et al., "Benzothiadiazine Dioxide Dibenzyl Derivatives as Potent Human Cytomegalovirus Inhibitors: Synthesis and Comparative Molecular Field Analysis," *J. Med. Chem.*, 43:3218-3225 (2000).

Wright, "The Synthesis of 2,1,3-Benzothiadiazine 2,2-Dioxides and 1,2,3-Benzoxathiazine 2,2-Dioxides," *Journal of Organic Chemistry* 30(11):3960-3962 (1965).

Cheng et al., "Potential Purine Antagonists XII. Synthesis of I-Alkyl(aryl)-4,6-disubstituted Pyrazolo[3,4-d]pyrimidines" Journal of Organic Chemistry, Jun. 1, 1958 23(I):852-861.

Supplementary European Search Report based on EP Application No. 08770047, mailed on Sep. 14, 2009.

European Search Opinion based on EP Application No. 08770047, mailed on Sep. 14, 2009.

* cited by examiner

| gene model (contig mRNA transcript): | Contig Label | Contig | mrna | protein | mrna orientation | transcript | snp count |
|---|---|---|---|---|---|---|---|
| | reference | NT_021937 | NM_138697 | NP_619642 | forward | plus strand 8, coding | |

| Region | Contig position | mRNA pos | dbSNP rs# cluster id | Hetero-zygosity | Validation | 3D | OMIM | Function | dbSNP allele | Protein residue | Codon pos | Amino acid pos |
|---|---|---|---|---|---|---|---|---|---|---|---|---|
| exon_1 | 1152801 | 1 | | | | | | start codon | | | | 1 |
| exon_1 | 1152811 | 11 | rs35375592 | 0.034 | | | | nonsynonymous | A | Tyr [Y] | 2 | 4 |
| | | | | 0.034 | | | | contig reference | G | Cys [C] | 2 | 4 |
| exon_2 | 1168473 | 329 | rs41278020 | N.D. | | | | nonsynonymous | T | Val [V] | 2 | 110 |
| | | | | N.D. | | | | contig reference | C | Ala [A] | 2 | 110 |
| exon_3 | 1172598 | 1039 | rs10864628 | 0.128 | Yes | Yes | | nonsynonymous | G | Glu [E] | 1 | 347 |
| | | | | 0.128 | Yes | Yes | | contig reference | A | Lys [K] | 1 | 347 |
| | 1172626 | 1067 | rs41307749 | N.D. | N | | | nonsynonymous | G | Cys [C] | 2 | 356 |
| | | | | N.D. | N | | | contig reference | C | Ser [S] | 2 | 356 |
| | 1172673 | 1114 | rs34160967 | 0.137 | N | | | nonsynonymous | A | Thr [T] | 1 | 372 |
| | | | | 0.137 | N | | | contig reference | G | Ala [A] | 1 | 372 |
| exon_5 | 1174423 | 1520 | rs35118458 | 0.059 | N | | | nonsynonymous | A | Gln [Q] | 2 | 507 |
| | | | | 0.059 | N | | | contig reference | G | Arg [R] | 2 | 507 |
| exon_6 | 1176292 | 1807 | rs41278022 | N.D. | N | | | nonsynonymous | T | Cys [C] | 1 | 603 |
| | | | | N.D. | N | | | contig reference | C | Arg [R] | 1 | 603 |
| | 1176759 | 2274 | rs34857011 | 0.126 | | | | synonymous | A | Glu [E] | 3 | 758 |
| | | | | 0.126 | | | | contig reference | G | Glu [E] | 3 | 758 |

FIG. 1

| | | | | | | | | |
|---|---|---|---|---|---|---|---|---|
| exon_4 | 2000188 | 1457 | rs28374389 | N.D. | | nonsynonymous | G | Val [V] | 1 | 486 |
| | | | | N.D. | | contig reference | A | Ile [I] | 1 | 486 |
| | 2000300 | 1345 | rs9439751 | N.D. | | synonymous | A | Leu [L] | 3 | 448 |
| | | | | N.D. | | contig reference | G | Leu [L] | 3 | 448 |
| | 2000315 | 1330 | rs35775756 | N.D. | | synonymous | T | Asp [D] | 3 | 443 |
| | | | | N.D. | | contig reference | C | Asp [D] | 3 | 443 |
| exon_3 | 2005063 | 1244 | rs35605435 | N.D. | | nonsynonymous | A | Ile [I] | 1 | 415 |
| | | | | N.D. | | contig reference | G | Val [V] | 1 | 415 |
| | 2005356 | 951 | rs34545913 | N.D. | | nonsynonymous | C | Pro [P] | 2 | 317 |
| | | | | N.D. | | contig reference | G | Arg [R] | 2 | 317 |
| | 2005357 | 950 | rs34447754 | N.D. | | nonsynonymous | G | Gly [G] | 1 | 317 |
| | | | | N.D. | | contig reference | C | Arg [R] | 1 | 317 |
| | 2005424 | 883 | rs28470550 | N.D. | Yes | synonymous | G | Thr [T] | 3 | 294 |
| | | | | N.D. | Yes | contig reference | T | Thr [T] | 3 | 294 |
| | 2005735 | 572 | rs35874116 | N.D. | | nonsynonymous | G | Val [V] | 1 | 191 |
| | | | | N.D. | | contig reference | A | Ile [I] | 1 | 191 |
| exon_1 | 2010471 | 27 | rs9701796 | N.D. | 0/0 | nonsynonymous | G | Cys [C] | 2 | 9 |
| | | | | N.D. | 0/0 | contig reference | C | Ser [S] | 2 | 9 |
| exon_1 | 2010496 | 2 | | | | start codon | | | | 1 |

FIG. 2B

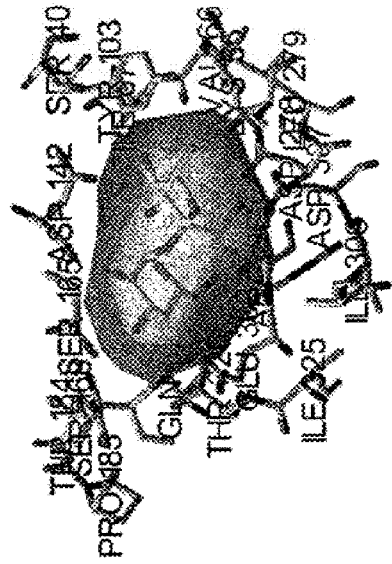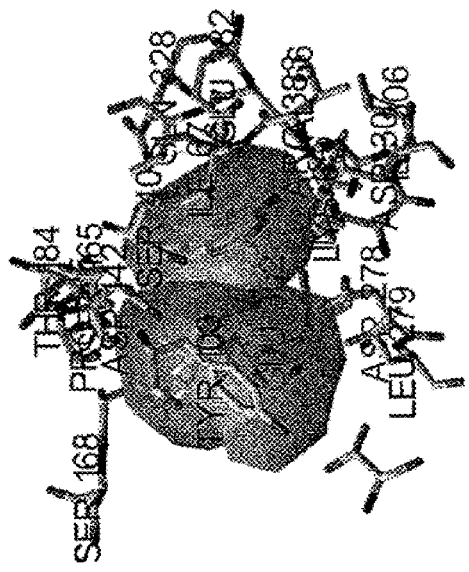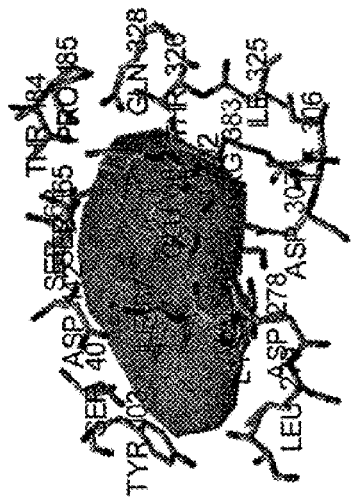
FIG. 10B
FIG. 10C
FIG. 10A

MODULATION OF CHEMOSENSORY RECEPTORS AND LIGANDS ASSOCIATED THEREWITH

CROSS-REFERENCE TO RELATED APPLICATIONS

This application is a U.S. National Stage application of International Application No. PCT/US2008/065650, filed on Jun. 3, 2008 and published as WO 2008/154221, which claims priority to U.S. patent application Ser. No. 11/760,592, entitled "Modulation of Chemosensory Receptors and Ligands Associated Therewith", filed Jun. 8, 2007; U.S. patent application Ser. No. 11/836,074, entitled "Modulation of Chemosensory Receptors and Ligands Associated Therewith", filed Aug. 8, 2007; and U.S. Patent Application Ser. No. 61/027,410, entitled "Modulation of Chemosensory Receptors and Ligands Associated Therewith", filed Feb. 8, 2008. This application is also a continuation-in-part of U.S. patent application Ser. Nos. 11/760,592 and 11/836,074. The content of these applications are herein incorporated by reference in their entirety for all purposes.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Sensations associated with taste are thought to involve distinct signaling pathways mediated by receptors, i.e., metabotropic or ionotropic receptors. Cells which express taste receptors, when exposed to certain chemical stimuli, elicit taste sensation by depolarizing to generate an action potential, which is believed to trigger the sensation. This event is believed to trigger the release of neurotransmitters at gustatory afferent neuron synapses, thereby initiating signaling along neuronal pathways that mediate taste perception.

As such, taste receptors specifically recognize molecules that elicit specific taste sensation. These molecules are also referred to herein as "tastants." Many taste receptors belong to the 7-transmembrane receptor superfamily, which are also known as G protein-coupled receptors (GPCRs). Other tastes are believed to be mediated by channel proteins. G protein-coupled receptors control many physiological functions, such as endocrine function, exocrine function, heart rate, lipolysis, carbohydrate metabolism, and transmembrane signaling.

For example, family C of G-protein coupled receptors (GPCRs) from humans comprises eight metabotropic glutamate (mGlu(1-8)) receptors, two heterodimeric gamma-aminobutyric acid(B) (GABA(B)) receptors, a calcium-sensing receptor (CaR), three taste (T1R) receptors, a promiscuous L-alpha-amino acid receptor (GPRC6A), and five orphan receptors. The family C GPCRs are characterized by a large amino-terminal domain, which binds the endogenous orthosteric agonists. Additionally, allosteric modulators which bind to the seven transmembrane domains of the receptors have also been reported.

In general, upon ligand binding to a GPCR, the receptor presumably undergoes a conformational change leading to activation of a G protein. G proteins are comprised of three subunits: a guanyl nucleotide binding α-subunit, a β-subunit, and a γ-subunit. G proteins cycle between two forms, depending on whether GDP or GTP is bound to the α-subunit. When GDP is bound, the G protein exists as a heterotrimer: the $G_{\alpha\beta\gamma}$ complex. When GTP is bound, the α-subunit dissociates from the heterotrimer, leaving a $G_{\beta\gamma}$ complex. When a $G_{\alpha\beta\gamma}$ complex operatively associates with an activated G protein-coupled receptor in a cell membrane, the rate of exchange of GTP for bound GDP is increased and the rate of dissociation of the bound $G_\alpha$ subunit from the $G_{\alpha\beta\gamma}$ complex increases. The free $G_\alpha$ subunit and $G_{\beta\gamma}$ complex are thus capable of transmitting a signal to downstream elements of a variety of signal transduction pathways. These events form the basis for a multiplicity of different cell signaling phenomena, including for example the signaling phenomena that are identified as neurological sensory perceptions such as taste and/or smell.

Mammals are believed to have five basic taste modalities: sweet, bitter, sour, salty, and umami (the taste of monosodium glutamate). Numerous physiological studies in animals have shown that taste receptor cells may selectively respond to different chemical stimuli. In mammals, taste receptor cells are assembled into taste buds that are distributed into different papillae in the tongue epithelium. Circumvallate papillae, found at the very back of the tongue, contain hundreds to thousands of taste buds. By contrast, foliate papillae, localized to the posterior lateral edge of the tongue, contain dozens to hundreds of taste buds. Further, fungiform papillae, located at the front of the tongue, contain only a single or a few taste buds.

Each taste bud, depending on the species, contains 50-150 cells, including precursor cells, support cells, and taste receptor cells. Receptor cells are innervated at their base by afferent nerve endings that transmit information to the taste centers of the cortex through synapses in the brain stem and thalamus. Elucidating the mechanisms of taste cell signaling and information processing is important to understanding the function, regulation, and perception of the sense of taste.

The gustatory system has been selected during evolution to detect nutritive and beneficial compounds as well as harmful or toxic substances. Outside the tongue, expression of $G\alpha_{gust}$ has also been localized to gastric and pancreatic cells, suggesting that a taste-sensing mechanism may also exist in the gastrointestinal (GI) tract. Expression of taste receptors has also been found in the lining of stomach and intestine, suggesting that taste receptors may play a role in molecular sensing of therapeutic entities and toxins.

Complete or partial sequences of numerous human and other eukaryotic chemosensory receptors are currently known. Within the last several years, a number of groups including the present assignee Senomyx, Inc. have reported the identification and cloning of genes from two GPCR families that are involved in taste modulation and have obtained experimental results related to the understanding of taste biology. These results indicate that bitter, sweet and amino acid taste, also referred as umami taste, are triggered by activation of two types of specific receptors located at the surface of taste receptor cells (TRCs) on the tongue i.e., T2Rs and T1Rs. It is currently believed that at least 26 to 33 genes encode functional receptors (T2Rs) for bitter tasting substances in human and rodent respectively.

By contrast there are only 3 T1Rs, T1R1, T1R2 and T1R3, which are involved in umami and sweet taste. Structurally, the T1R and T2R receptors possess the hallmark of G protein-coupled receptors (GPCRs), i.e., 7 transmembrane domains flanked by small extracellular and intracellular amino- and carboxyl-termini respectively.

T2Rs have been cloned from different mammals including rats, mice and humans. T2Rs comprise a novel family of human and rodent G protein-coupled receptors that are expressed in subsets of taste receptor cells of the tongue and palate epithelia. These taste receptors are organized in clusters in taste cells and are genetically linked to loci that influence bitter taste. The fact that T2Rs modulate bitter taste has been demonstrated in cell-based assays. For example, mT2R-5, hT2R-4 and mT2R-8 have been shown to be activated by bitter molecules in in vitro gustducin assays, providing experimental proof that T2Rs function as bitter taste receptors. See also T2Rs disclosed in U.S. Pat. No. 7,105,650.

T1R family members in general include T1R1, T1R2, and T1R3, e.g., rT1R3, mT1R3, hT1R3, rT1R2, mT1R2, hT1R2, and rT1R1, mT1R1 and hT1R1. It is known that the three T1R gene members T1R1, T1R2 and T1R3 form functional heterodimers that specifically recognize sweeteners and amino acids. It is generally believed that T1R2/T1R3 combination recognizes natural and artificial sweeteners while the T1R1/T1R3 combination recognizes several L-amino acids and monosodium glutamate (MSG), respectively. For example, co-expression of T1R1 and T1R3 in recombinant host cells results in a hetero-oligomeric taste receptor that responds to umami taste stimuli. Umami taste stimuli include by way of example monosodium glutamate and other molecules that elicit a "savory" taste sensation. By contrast, co-expression of T1R2 and T1R3 in recombinant host cells results in a hetero-oligomeric sweet taste receptor that responds to both naturally occurring and artificial sweeteners.

There is a need in the art to develop various ways of identifying compounds or other entities suitable for modifying receptors and their ligands associated with chemosensory or chemosensory related sensation or reaction. In addition, there is a need in the art for compounds or other entities with such characteristics.

BRIEF SUMMARY OF THE INVENTION

The present invention is based, at least in part, on the discovery that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Accordingly, the present invention provides screening methods for identifying modifiers of chemosensory receptors and their ligands as well as modifiers capable of modulating chemosensory receptors and their ligands.

In one embodiment, the present invention provides a method of screening for a candidate of a chemosensory receptor ligand modifier. The method comprises determining whether a test entity is suitable to interact with a chemosensory receptor via an interacting site within the Venus flytrap domain of the chemosensory receptor.

In another embodiment, the present invention provides a method of screening for a candidate of a chemosensory receptor ligand modifier. The method comprises determining whether a test entity is suitable to interact with a chemosensory receptor via a first interacting site within the Venus flytrap domain of the chemosensory receptor, wherein the first interacting site is identified in light of a second interacting site identified based on the interaction between a chemosensory receptor ligand and the chemosensory receptor.

In yet another embodiment, the present invention provides a method of screening for a candidate of a chemosensory receptor modifier. The method comprises determining whether a test entity is suitable to interact with a chemosensory receptor via an interacting site within the Venus flytrap domain of the chemosensory receptor, wherein the interacting site includes an interacting residue selected from the group consisting of N143, S144, I167, S40, S144, S165, Y103, D142, P277, K65, R383, D307, E302, D278, P185, T184, I326, E302, V384, A305, I325, I306, D307, E382, I279, I67, V66, V309, S303, T242, F103, Q328, and S168 of T1R2 and a combination thereof, wherein a test entity suitable to interact with the interacting site of the chemosensory receptor is indicative of a candidate of a chemosensory receptor modifier.

In yet another embodiment, the present invention provides a method of modulating the activity of a chemosensory receptor ligand. The method comprises contacting a chemosensory receptor ligand modifier with a cell containing T1R2 Venus flytrap domain in the presence of a chemosensory receptor ligand, wherein the chemosensory receptor ligand modifier interacts with an interacting site of the chemosensory receptor.

In still another embodiment, the present invention provides a chemosensory receptor ligand modifier, wherein in the presence of a chemosensory receptor ligand it interacts with T1R2 Venus flytrap domain via at least three interacting residues selected from the group consisting of N143, S144, I167, S40, S144, S165, Y103, D142, P277, K65, R383, D307, E302, D278, P185, T184, T326, E302, V384, A305, I325, I306, E382, I279, I67, V66, V309, S303, T242, F103, Q328, and S168 of T1R2.

In still another embodiment, the present invention provides a chemosensory receptor ligand modifier having a structure of Formula (I):

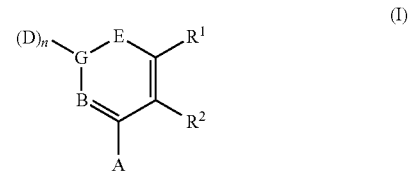

or a tautomer, salt, solvate, and/or ester thereof, wherein:

G forms a single bond with either D or E and a double bond with the other of D or E;

$R^1$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^3$, —S(O)$_a$R$^3$, —NR$^3$R$^4$, —CONR$^3$R$^4$, —CO$_2$R$^3$, —NR$^3$CO$_2$R$^4$, —NR$^3$CONR$^4$R$^5$, —NR$^3$CSNR$^4$R$^5$, —NR$^3$C(=NH)NR$^4$R$^5$, —SO$_2$NR$^3$R$^4$, —NR$^4$SO$_2$R$^3$, —NR$^3$SO$_2$NR$^4$R$^5$, —B(OR$^3$)(OR$^4$), —P(O)(OR$^3$)(OR$^4$) or —P(O)(R$^3$)(OR$^4$);

$R^2$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^6$, S(O)$_b$R$^6$, —NR$^6$R$^7$, —CONR$^6$R$^7$, —CO$_2$R$^6$, —NR$^6$CO$_2$R$^7$, —NR$^6$CONR$^7$R$^8$, —NR$^6$CSNR$^7$R$^8$, —NR$^6$C(=NH)NR$^7$R$^8$, —SO$_2$NR$^5$R$^6$, —NR$^5$SO$_2$R$^6$, —NR$^5$SO$_2$NR$^6$R$^7$, —B(OR$^5$)(OR$^6$), —P(O)(OR$^5$)(OR$^6$), or —P(O)(R$^5$)(OR$^6$); or alternatively, $R^1$ and $R^2$, together with the atoms to which they are bonded, form an aryl, substituted aryl, heteroaryl, substituted heteroaryl, cycloalkyl, substituted cycloalkyl, cycloheteroalkyl or substituted cycloheteroalkyl ring wherein the ring is optionally fused to another aryl, substituted aryl, heteroaryl, substituted heteroaryl, cycloalkyl, substituted cycloalkyl, cycloheteroalkyl or substituted cycloheteroalkyl ring;

with the proviso that $R^1$ and $R^2$ are not both hydrogen;

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —NO$_2$, —OR$^9$, —S(O)$_c$R$^9$, —NR$^9$COR$^{10}$, —NHOR$^9$, —NR$^9$R$^{10}$, —NOR$^9$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$, —NR$^9$C(=NH)NR$^{10}$R$^{11}$, —B(OR$^{10}$)(OR$^{11}$), —P(O)(OR$^{10}$)(OR$^{11}$) or —P(O)(R$^{10}$)(OR$^{11}$);

B is —N— or —C(R$^{12}$)—;

R$^{12}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{13}$R$^{14}$, —CN, —OR$^{13}$, —S(O)$_d$R$^{13}$, —CO$_2$R$^{13}$ or —CONR$^{13}$R$^{14}$;

G is —C— or —S(O)$_2$—;

provided that when G is —S(O)$_2$—, then G forms a single bond with E;

when the bond between D and G is a single bond, then D is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —OR$^{15}$, —NH—OR$^{15}$, —S(O)$_e$R$^{15}$, —NR$^{15}$R$^{16}$, —NH—NHR$^{15}$, —CO$_2$R$^{15}$, or —CONR$^{15}$R$^{16}$;

when G forms a double bond with D, then D is =O, =S, =N—OR$^{15}$, or =N—NHR$^{15}$;

n is 0 when G is —S(O)$_2$—, and n is 1 when G is —C—;

E is —NR$^{17}$—, —N— or —C(R$^{18}$)—;

provided that E is —NR$^{17}$— only when G forms a single bond with E;

R$^{17}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl or —CO$_2$R$^{19}$;

R$^{18}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{20}$R$^{21}$, —CN, —OR$^{20}$, —S(O)$_f$R$^{20}$, —CO$_2$R$^{20}$ or —CONR$^{20}$R$^{21}$;

a, b, c, d, e and f are independently 0, 1 or 2; and

R$^3$, R$^4$, R$^5$, R$^6$, R$^7$, R$^8$, R$^9$, R$^{10}$, R$^{11}$, R$^{13}$, R$^{14}$, R$^{15}$, R$^{16}$, R$^{18}$, R$^{20}$, and R$^{21}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^3$ and R$^4$, R$^4$ and R$^5$, R$^6$ and R$^7$, R$^7$ and R$^8$, R$^9$ and R$^{10}$, R$^{10}$ and R$^{11}$, R$^{13}$ and R$^{14}$, R$^{15}$ and R$^{16}$, or R$^{20}$ and R$^{21}$, together with the atoms to which they are bonded, form a cycloheteroalkyl or substituted cycloheteroalkyl ring.

In one embodiment of Formula (I), the compound of the present invention has structural Formula (II):

(II)

wherein:

Y forms a single bond with either W or Z and a double bond with the other of W or Z;

W is —C(R$^{24}$)—, —S—, —N—, —N(R$^{25}$)—, or —O—;

Y is —C(R$^{26}$)— or —N—;

Z is —C(R$^{27}$)—, —S—, —N—, —N(R$^{28}$)—, or —O—;

R$^{24}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{29}$, —S(O)$_g$R$^{29}$, —NR$^{29}$R$^{30}$, —CONR$^{29}$R$^{30}$, —CO$_2$R$^{29}$, —SO$_2$NR$^{29}$R$^{30}$, —NR$^{29}$SO$_2$R$^{30}$, —B(OR$^{29}$)(OR$^{30}$), —P(O)(OR$^{29}$)(OR$^{30}$) or —P(O)(R$^{29}$)(OR$^{30}$);

R$^{26}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —NO$_2$, —OR$^{31}$, —S(O)$_h$R$^{31}$, —OCOR$^{31}$, —NR$^{31}$R$^{32}$, —CONR$^{31}$R$^{32}$, —CO$_2$R$^{31}$, —SO$_2$NR$^{31}$R$^{32}$, —NR$^{31}$SO$_2$R$^{32}$, —B(OR$^{31}$)(OR$^{32}$), —P(O)(OR$^{31}$)(OR$^{32}$) or —P(O)(R$^{31}$)(OR$^{32}$);

R$^{27}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —NO$_2$, —OR$^{33}$, —S(O)$_i$R$^{33}$, —OCOR$^{33}$, —NR$^{33}$R$^{34}$, —CONR$^{33}$R$^{34}$, —COR$^{33}$, —CO$_2$R$^{33}$, —SO$_2$NR$^{33}$R$^{34}$, —NR$^{33}$SO$_2$R$^{34}$, —B(OR$^{33}$)(OR$^{34}$), —P(O)(OR$^{33}$)(OR$^{34}$) or —P(O)(R$^{33}$)(OR$^{34}$) or alternatively R$^{24}$ and R$^{26}$ or R$^{26}$ and R$^{27}$ together with the atoms to which they are bonded form a cycloalkyl, substituted cycloalkyl, cycloheteroalkyl or substituted cycloheteroalkyl ring;

g, h and i are independently 0 or 1;

R$^{25}$ and R$^{28}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and R$^{29}$, R$^{30}$, R$^{31}$, R$^{32}$, R$^{33}$, and R$^{34}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively R$^{29}$ and R$^{30}$, R$^{31}$ and R$^{32}$ or R$^{33}$ and R$^{34}$ together with the atoms to which they are bonded form a cycloheteroalkyl or substituted cycloheteroalkyl ring; and with the following provisos:

(a) when W is —O— or —S— or —NR$^{25}$, then Z is —C(R$^{27}$) or —N—; and (b) when Z is —O— or —S— or —NR$^{28}$, then W is —C(R$^{24}$) or —N—.

In one embodiment of Formula (I), the compound of the present invention has structural Formula (III):

(III)

wherein:

H is —C(R$^{35}$)— or —N—;

I is —C(R$^{36}$) or —N—;

J is —C(R$^{37}$)— or —N—;

K is —C(R$^{38}$)— or —N—;

$R^{35}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —NO$_2$, —OR$^{39}$, S(O)$_j$R$^{39}$, —OCOR$^{39}$, —NR$^{39}$R$^{40}$, —CONR$^{39}$R$^{40}$, —CO$_2$R$^{39}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$);

$R^{36}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —NO$_2$, —OR$^{41}$, —S(O)$_k$R$^{41}$, —OCOR$^{41}$, —NR$^{41}$R$^{42}$, —CONR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$);

$R^{37}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —NO$_2$, —OR$^{43}$, —S(O)$_l$R$^{43}$, —OCOR$^{43}$, —NR$^{43}$R$^{44}$, —CONR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$);

$R^{38}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —CN, —NO$_2$, —OR$^{45}$, —S(O)$_m$R$^{45}$, —OCOR$^{45}$, —NR$^{45}$R$^{46}$, —CONR$^{45}$R$^{46}$, —COR$^{45}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$); or alternatively $R^{36}$ and $R^{37}$ or $R^{37}$ and $R^{38}$ taken together with the atom to which they are bonded, form a cycloalkyl, substituted cycloalkyl, cycloheteroalkyl, or substituted cycloheteroalkyl ring;

j, k, l and m are independently 0, 1 or 2; and $R^{39}$, $R^{40}$, $R^{41}$, $R^{42}$, $R^{43}$, $R^{44}$, $R^{45}$, and $R^{46}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively $R^{39}$ and $R^{40}$, $R^{41}$ and $R^{42}$, $R^{43}$ and $R^{44}$ or $R^{45}$ and $R^{46}$ together with the atoms to which they are bonded form a cycloheteroalkyl or substituted cycloheteroalkyl ring;

with the proviso that at most, two of H, I, J and K are —N—.

In one embodiment, the present invention provides an ingestible composition comprising a chemosensory receptor ligand modifier, wherein in the presence of a chemosensory receptor ligand it interacts with T1R2 Venus flytrap domain via at least three interacting residues selected from the group consisting of N143, S144, I167, S40, S144, S165, Y103, D142, P277, K65, R383, D307, E302, D278, P185, T184, T326, E302, V384, A305, I325, I306, E382, I279, I67, V66, V309, S303, T242, F103, Q328, and S168 of a human T1R2. In one embodiment, the chemosensory receptor ligand modifier is a compound having structural Formula (I), (II), or (III), or a tautomer, salt, solvate, and/or ester thereof. In another embodiment, the ingestible composition further comprises one or more sweeteners.

In one embodiment, the present invention provides a method of enhancing the sweet taste of an ingestible composition comprising contacting the ingestible composition or precursors thereof with a chemosensory receptor ligand modifier to form a modified ingestible composition. In one embodiment, the chemosensory receptor ligand modifier is a compound having structural Formula (I), (II), or (III), or a tautomer, salt, solvate, and/or ester thereof.

In one embodiment, the present invention provides a method of treating a condition associated with a chemosensory receptor comprising administering to a subject in need of such treatment an effective amount of an entity selected from the group consisting of a chemosensory receptor modifier, chemosensory receptor ligand modifier, and a combination thereof, wherein the entity interacts with an interacting site of the chemosensory receptor. In one embodiment, the chemosensory receptor ligand modifier is a compound having structural Formula (I), (II), or (III), or a tautomer, salt, solvate, and/or ester thereof.

BRIEF DESCRIPTION OF THE FIGURES

FIG. 1 contains exemplary human T1R1 polymorphic variations.

FIG. 10 shows exemplary interacting spaces and residues associated with an interacting site for sucralose and one of the compounds of the present invention.

DETAILED DESCRIPTION OF THE INVENTION

Figure 2A:
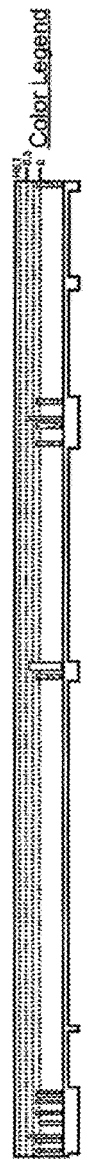
FIG. 2 contains exemplary human T1R2 polymorphic variations.
Figure 3:
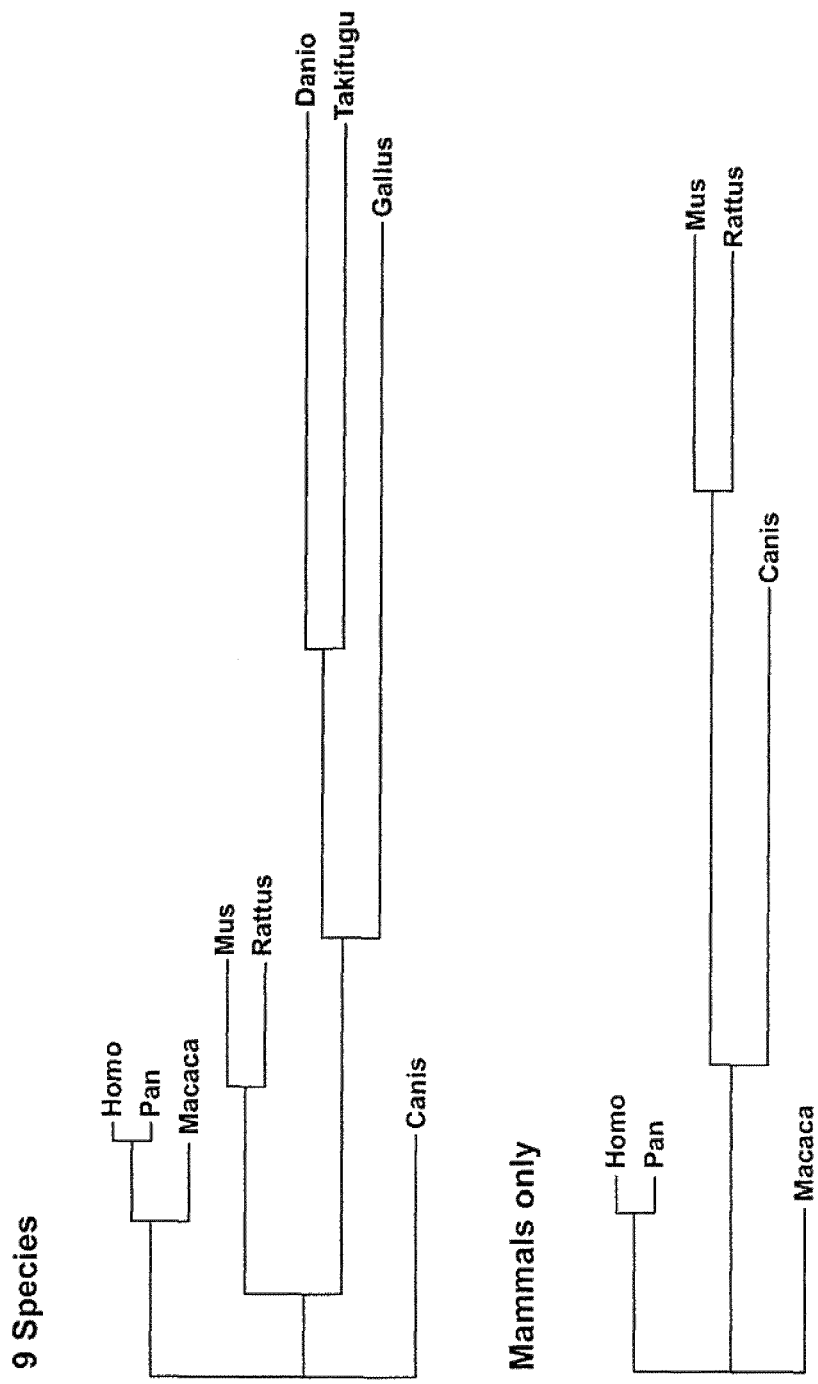
FIG. 3 shows the dendograms for the sequence alignments of T1R1.
Figure 4:
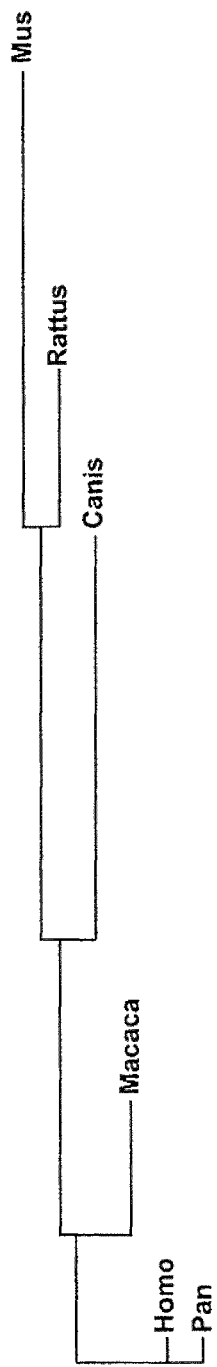
FIG. 4 shows the dendograms for the sequence alignments of T1R2.
Figure 5:
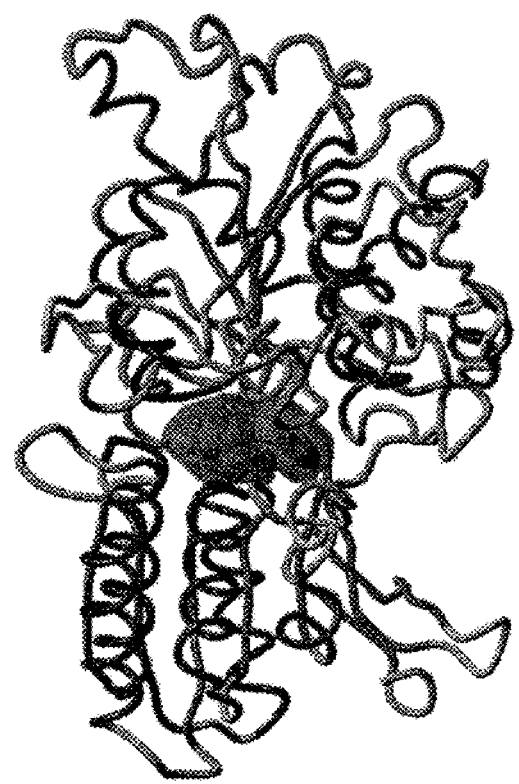
FIG. 5 shows exemplary interacting spaces for sucralose and one of the compound of the present invention. Protein is represented as a ribbon diagram.
Figure 6:
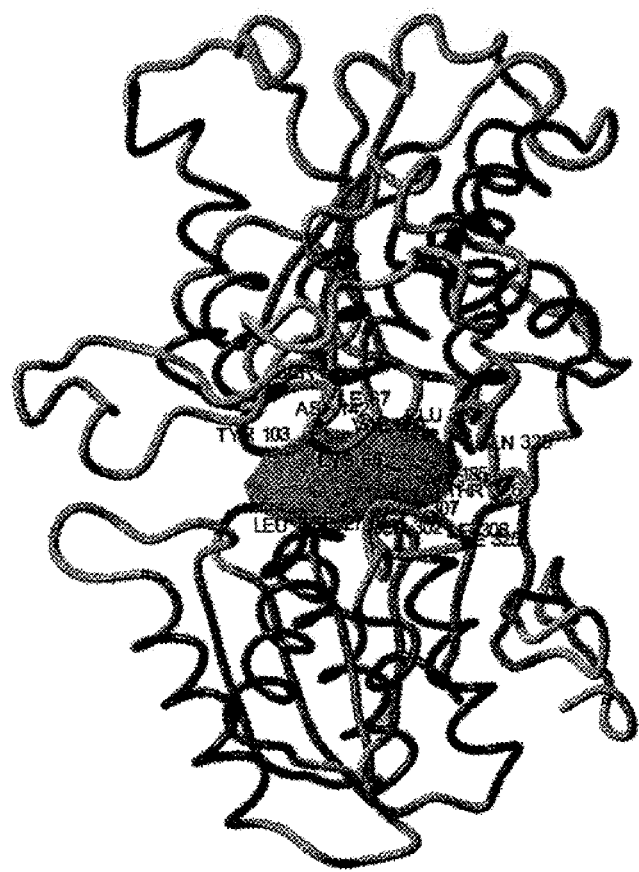
FIG. 6 shows exemplary interacting spaces and residues for sucralose and one of the compounds of the present invention. Protein is represented as a ribbon diagram.
Figure 7A:
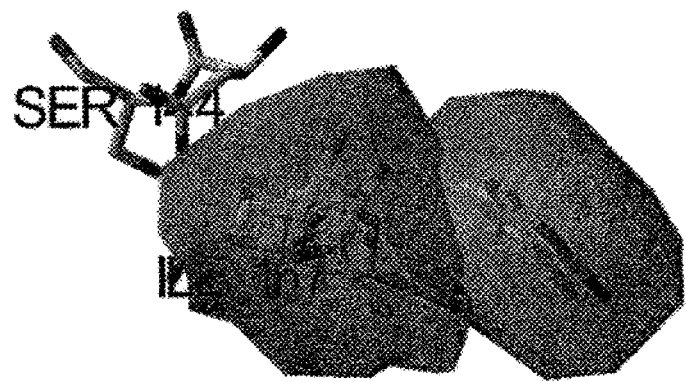
FIG. 7 shows exemplary interacting spaces and residues associated with the hinge region for sucralose and one of the compounds of the present invention.
Figure 7B:
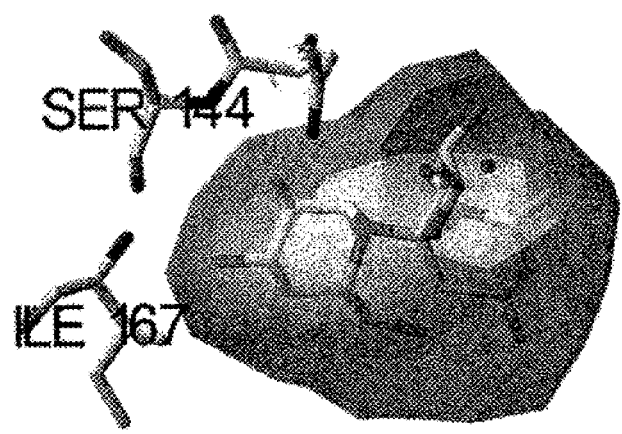
Figure 8A:
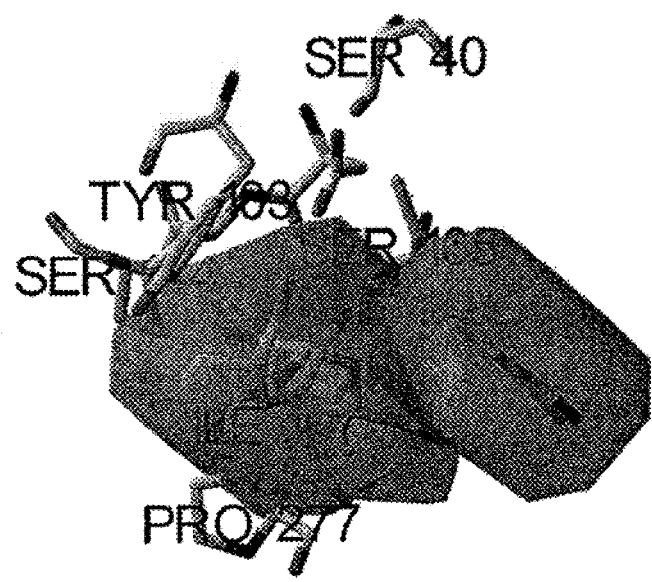
FIG. 8 shows exemplary partial interacting surfaces and interacting residues proximal to the hinge region for sucrose and sucralose.
Figure 8B:
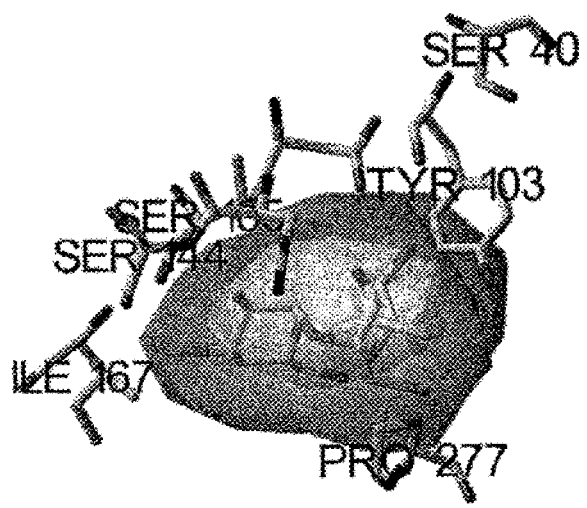
Figure 9A:
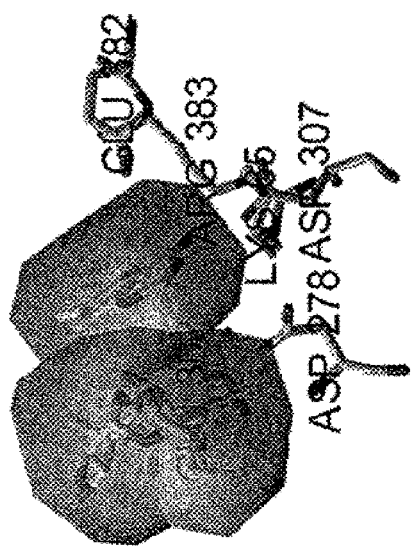
FIG. 9 shows exemplary interacting spaces and residues associated with the lobes for sucralose and one of the compounds of the present invention.
Figure 9B:
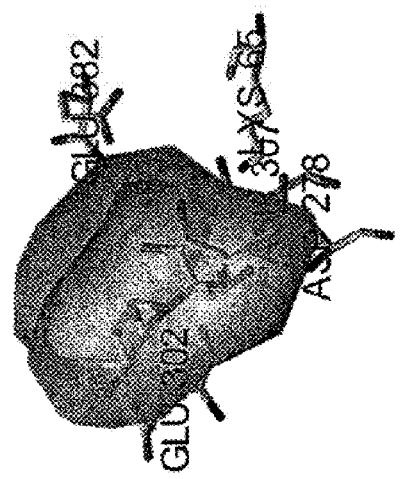
Figure 9C:
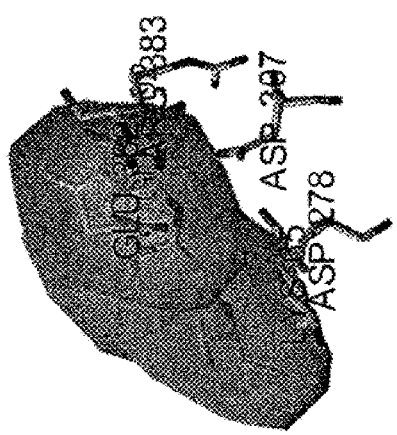

Prior to specifically describing the invention, the following definitions are provided.

The term "T1R" family includes polymorphic variants, alleles, mutants, and homologs that: (1) have about 30-40% amino acid sequence identity, more specifically about 40, 50, 60, 70, 75, 80, 85, 90, 95, 96, 97, 98, or 99% amino acid sequence identity to the T1Rs known or disclosed, e.g., in patent application U.S. Ser. No. 10/179,373 filed on Jun. 26, 2002, Ser. No. 09/799,629 filed on Apr. 5, 2001 and U.S. Ser. No. 10/035,045 filed on Jan. 3, 2002, over a window of about 25 amino acids, optimally 50-100 amino acids; (2) specifically bind to antibodies raised against an immunogen comprising an amino acid sequence selected from the group consisting of the T1R sequences disclosed infra, and conservatively modified variants thereof; (3) specifically hybridize (with a size of at least about 100, optionally at least about 500-1000 nucleotides) under stringent hybridization conditions to a sequence selected from the group consisting of the T1R DNA sequences disclosed infra, and conservatively modified variants thereof; (4) comprise a sequence at least about 40% identical to an amino acid sequence selected from the group consisting of the T1R amino acid sequences disclosed infra or (5) are amplified by primers that specifically hybridize under stringent hybridization conditions to the described T1R sequences.

In particular, these "T1Rs" include taste receptor GPCRs referred to as hT1R1, hT1R2, hT1R3, rT1R1, rT1R2, rT1R3, mT1R1, mT1R2, and mT1R3 having the nucleic acid sequences and amino acid sequences known or disclosed, e.g., in U.S. Ser. No. 10/179,373 filed on Jun. 26, 2002, U.S. Ser. No. 09/799,629 filed on Apr. 5, 2001 and U.S. Ser. No. 10/035,045 filed on Jan. 3, 2002, and variants, alleles, mutants, orthologs and chimeras thereof which specifically bind and/or respond to sweet, umami, or any other chemosensory related ligands including activators, inhibitors and enhancers. Also T1Rs include taste receptor GPCRs expressed in humans or other mammals, e.g., cells associated with taste and/or part of gastrointestinal system including without any limitation, esophagus, stomach, intestine (small and large), colon, liver, biliary tract, pancreas, gallbladder, etc. Also, T1R polypeptides include chimeric sequences derived from portions of a particular T1R polypeptide such as T1R1, T1R2 or T1R3 of different species or by combining portions of different T1Rs wherein such chimeric T1R sequences are combined to produce a functional sweet or umami taste receptor. For example chimeric T1Rs may comprise the extracellular region of one T1R, i.e., T1R1 or T1R2 and the transmembrane region of another T1R, either T1R1 or T1R2.

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al., *Cell* 96:541-51 (1999); Buck et al., *Cell* 65:175-87 (1991)). These regions can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). These regions are useful for making chimeric proteins and for in vitro assays of the invention, e.g., ligand binding assays.

"Extracellular domains" therefore refers to the domains of chemosensory receptors, e.g., T1R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful, for in vitro ligand binding assays.

"Transmembrane domain," which comprises the seven transmembrane "regions," refers to the domains of chemosensory receptors, e.g., T1R polypeptides that lie within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte et al., *J. Mol. Biol.* 157:105-32 (1982)), or in Stryer, supra.

"Cytoplasmic domains" refers to the domains of chemosensory receptors, e.g., T1R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII).

The phrase "functional effects" or "activity" in the context of the disclosed assays for testing compounds that modulate a chemosensory receptor, e.g., enhance T1R family member mediated signal transduction such as sweet or umami receptor functional effects or activity includes the determination of any parameter that is indirectly or directly under the influence of the particular chemosensory receptor, e.g., functional, physical and chemical effects. It includes, without any limitation, ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

The term "determining the functional effect" or receptor "activity" means assays for a compound that increases or decreases a parameter that is indirectly or directly under the influence of a chemosensory receptor, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte chemosensory receptor, e.g., T1R gene expression; tissue culture cell chemosensory receptor, e.g., T1R expression; transcriptional activation of chemosensory receptor, e.g., T1R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modifiers" of chemosensory receptor, e.g., T1R proteins are used interchangeably to refer to inhibitory, activating, or modulating molecules identified using in vitro and in vivo assays for chemosensory signal transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate chemosensory signal transduction, e.g., agonists. Modifiers include compounds that, e.g., alter, directly or indirectly, the activity of a receptor or the interaction of a receptor with its ligands, e.g., receptor ligands and optionally bind to or interact with activators or inhibitors; G Proteins; kinases (e.g., homologs of rhodopsin kinase and beta adrenergic receptor kinases that are involved in deactivation and desensitization of a receptor); and arrestins, which also deactivate and desensitize receptors. Modifiers include genetically modified versions of chemosensory receptors, e.g., T1R family members, e.g., with altered activity, as well as naturally occurring and synthetic ligands, antagonists, agonists, small chemical molecules and the like. The term "chemosensory receptor ligand modifier" as used herein includes chemosensory receptor ligand enhancer. In the present invention this includes, without any limitation, sweet ligands (agonists or antagonists), umami ligands (agonists and antagonists), sweet enhancers and umami enhancers and sweet taste or umami taste inhibitors.

"Enhancer" herein refers to a compound that modulates (increases) the activation of a particular receptor, preferably the chemosensory, e.g., T1R2/T1R3 receptor or T1R1/T1R3 receptor but which by itself does not result in substantial activation of the particular receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto.

"Putative enhancer" herein refers to a compound identified, e.g., in silico or not, as a potential enhancer using assays which are described herein but which enhancer activity has not yet been confirmed in vivo, e.g., in suitable taste tests.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "extra-cellular domain" and chemosensory receptor, e.g., T1R receptor regions or compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or nonpolar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and OCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gin; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W.H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., extra-cellular domain or any region therewith of T1R2 or T1R1. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(O)—O—CH$_2$— for —C(O)—NH—), aminomethylene —CH$_2$(NH)—, ethylene, olefin —CH═CH—, ether —CH$_2$O—, thioether —CH$_2$S—, tetrazole (CN$_4$), thiazole, retroamide, thioamide or ester (see, e.g., Spatola, Chemistry and Biochemistry of Amino Acids, Peptides and Proteins, Vol. 7, 267-357, Marcell Dekker, Peptide Backbone Modifications, NY (1983)). A polypeptide can also be characterized as a mimetic by containing all or some non-natural residues in place of naturally occurring amino acid residues; non-natural residues are well described in the scientific and patent literature.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined hereinbelow. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl; prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms (C$_1$-C$_{20}$ alkyl). In other embodiments, an alkyl group comprises from 1 to 10 carbon atoms (C$_1$-C$_{10}$ alkyl). In still other embodiments, an alkyl group comprises from 1 to 6 carbon atoms (C$_1$-C$_6$ alkyl). It is noted that when an alkyl group is further connected to another atom, it becomes an "alkylene" group. In other words, the term "alkylene" refers to a divalent alkyl. For example, —CH$_2$CH$_3$ is an ethyl, while —CH$_2$CH$_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined hereinbelow. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanylene," "alkenylene," and "alkynylene" are used. In some embodiments, an alkylene group comprises from 1 to 20 carbon atoms (C$_1$-C$_{20}$ alkylene). In other embodiments, an alkylene group comprises from 1 to 10 carbon atoms (C$_1$-C$_{10}$ alkylene). In still other embodiments, an alkylene group comprises from 1 to 6 carbon atoms (C$_1$-C$_6$ alkylene).

"Alkanyl," by itself or as part of another substituent, refers to a saturated branched, straight-chain or cyclic alkyl radical derived by the removal of one hydrogen atom from a single carbon atom of a parent alkane. The term "alkanyl" includes "cycloakanyl" as defined hereinbelow. Typical (alkanyl) groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The term "alkenyl" includes "cycloalkenyl" as defined hereinbelow. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—R$^{199}$, where R$^{199}$ is alkyl or substituted alkyl as defined herein.

"Acyl" by itself or as part of another substituent refers to a radical —C(O)R$^{200}$, where R$^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octacene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms (C$_6$-C$_{20}$ aryl). In other embodiments, an aryl group comprises from 6 to 15 carbon atoms (C$_6$-C$_{15}$ aryl). In still other embodiments, an aryl group comprises from 6 to 15 carbon atoms (C$_6$-C$_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is $(C_6-C_{30})$arylalkyl, e.g., the alkanyl, alkenyl or alkynyl moiety of the arylalkyl group is $(C_1-C_{10})$alkyl and the aryl moiety is $(C_6-C_{20})$aryl. In other embodiments, an arylalkyl group is $(C_6-C_{20})$arylalkyl, e.g., the alkanyl, alkenyl or alkynyl moiety of the arylalkyl group is $(C_1-C_8)$alkyl and the aryl moiety is $(C_6-C_{12})$aryl. In still other embodiments, an arylalkyl group is $(C_6-C_{15})$arylalkyl, e.g., the alkanyl, alkenyl or alkynyl moiety of the arylalkyl group is $(C_1-C_5)$alkyl and the aryl moiety is $(C_6-C_{10})$aryl.

"Cycloalkyl," by itself or as part of another substituent, refers to a saturated or unsaturated cyclic alkyl radical, as defined herein. Similarly, "Cycloalkylene," by itself or as part of another substituent, refers to a saturated or unsaturated cyclic alkylene radical, as defined herein. Where a specific level of saturation is intended, the nomenclature "cycloalkanyl", "cycloalkenyl", or "cycloalkynyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3-C_{10}$ cycloalkyl). In other embodiments, the cycloalkyl group comprises from 3 to 7 ring atoms ($C_3-C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkanylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O) NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Cycloheteroalkyl," or "Heterocyclyl," by itself or as part of another substituent, refers to a saturated or unsaturated cyclic alkyl radical in which one or more carbon atoms (and optionally any associated hydrogen atoms) are independently replaced with the same or different heteroatom. Similarly, "Cycloheteroalkylene," by itself or as part of another substituent, refers to a saturated or unsaturated cyclic alkylene radical in which one or more carbon atoms (and optionally any associated hydrogen atoms) are independently replaced with the same or different heteroatom. The cycloheteroalkyl may be further substituted by one or more heteroatoms including, but not limited to, N, P, O, S, and Si, which attach to the carbon atoms of the cycloheteroalkyl via monovalent or multivalent bond. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1-C_6$)alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated or N-oxides.

Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule. The term "tautomer" as used herein refers to isomers that change into one another with great ease so that they can exist together in equilibrium. For example, the following compounds A and B are tautomers of each other:

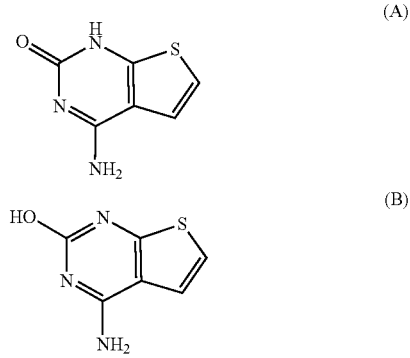

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$)alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$)alkyl and the heteroaryl moiety is a 5-10 membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Patient" includes humans. The terms "human" and "patient" are used interchangeably herein.

"Pharmaceutically acceptable" refers to being suitable for use in contact with the tissues of humans and animals without undue toxicity, irritation, allergic response, and the like, commensurate with a reasonable benefit/risk ratio, and effective for their intended use within the scope of sound medical judgment.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Saccharide ring" is also known as sugar ring and includes monosaccharide, disaccharide, and polysaccharide ring. Preferably, the saccharide ring is a monosacharide ring. Examples of monosaccharides include glucose (dextrose), fructose, galactose, xylose and ribose. By "derivative of saccharide ring", it is meant the non-natural or artificial saccharide ring wherein the stereochemistry centers are partially or completely different from those of the natural saccharide ring.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N=O$ or $R_3N\rightarrow O$).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —Cl, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)$OR^b$, -alkylene-C(O)$NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

The present invention is based, at least in part, on the discovery that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Accordingly, the present invention provides screening methods for identifying chemosensory receptor modifiers as well as chemosensory receptor ligand modifiers. In addition, the present invention provides compounds and compositions capable of modulating chemosensory receptors as well as chemosensory receptor ligands.

According to one aspect of the present invention, it provides methods of screening for chemosensory receptor modifiers by determining whether a test entity is suitable to interact with a chemosensory receptor via one or more interacting sites within the extra-cellular domain of the chemosensory receptor, e.g., the Venus flytrap domain of the chemosensory receptor. According to another aspect of the present invention, it provides methods of screening for chemosensory receptor ligand modifiers by determining whether a test entity is suitable to interact with a chemosensory receptor, and optionally its ligand via one or more interacting sites within the extra-cellular domain, e.g., the Venus flytrap domain of the chemosensory receptor, optionally in the presence of a chemosensory receptor ligand.

In general, the extra-cellular domain of a chemosensory receptor refers to the extra-cellular amino-terminus of a chemosensory receptor and usually includes a ligand-binding domain and a cysteine-rich linker domain, which connects the ligand-binding domain and the rest of the protein. In Class C GPCRs, the ligand binding domain is generally referred to as a Venus flytrap domain, the structure of which has been elucidated, e.g., using X-ray crystallography.

A Venus flytrap domain typically consists of two relatively rigid lobes connected by three strands forming a flexible "hinge" region. In the absence of a ligand, the Venus flytrap domain tends to adopt open conformations with well-separated lobes as well as closed conformations with lobes closer together. In one example, the Venus flytrap domain includes a region from amino acid 36 to amino acid 509 of human T1R1, amino acid 31 to amino acid 507 of human T1R2, and/or amino acid 35 to amino acid 511 of human T1R3.

The Venus flytrap domain of the present invention includes any ligand binding domain or ligand interacting domain within the extra-cellular domain of a chemosensory receptor. In one embodiment, the Venus flytrap domain of the present invention includes any ligand binding domain of a member of the T1R family. In another embodiment, the Venus flytrap domain of the present invention includes any extra-cellular domain of a chemosensory receptor with a structure comprising two lobes connected by a hinge region. In yet another embodiment, the Venus flytrap domain of the present invention includes any domain corresponding to the structure and/or function of a region including amino acid 36 to amino acid 509 of human T1R1, amino acid 31 to amino acid 507 of human T1R2, and/or amino acid 35 to amino acid 511 of human T1R3. In still another embodiment, the Venus flytrap domain of the present invention includes any ligand binding domain of T1R1, T1R2, and/or T1R3 as well as any polymorphic variation, allele, or mutation thereof. Exemplary illustrations of polymorphic variations for T1R1 and T1R2 are shown in FIGS. 1-4.

According to the present invention, a chemosensory receptor can be any receptor associated with chemosensory sensation or chemosensory ligand triggered signal transduction, e.g., via taste receptors or taste related receptors expressed in taste bud, gastrointestinal tract, etc. In one embodiment, a chemosensory receptor is a receptor that belongs to the 7-transmembrane receptor superfamily or G protein-coupled receptors (GPCRs). In another embodiment, a chemosensory receptor is a receptor carrying out signal transduction via one or more G proteins. In yet another embodiment, a chemosensory receptor is a receptor that belongs to family C or class C of GPCRs. In yet another embodiment, a chemosensory receptor is a receptor that belongs to the T1R family. In yet another embodiment, a chemosensory receptor is a receptor of T1R1, T1R2, T1R3, or their equivalences or variances or a combination thereof. In still another embodiment, a chemosensory receptor is a hetero-dimer of T1R2 and T1R3, or their equivalences or variances.

According to the present invention, an interacting site within the Venus flytrap domain of a chemosensory receptor can be one or more interacting residues or a three dimensional interacting space or a combination thereof. In one embodiment, the interacting site of the present invention is within the Venus flytrap domain of T1R2. In another embodiment, the interacting site of the present invention is within the Venus flytrap domain of T1R3. In yet another embodiment, the interacting site of the present invention is within the Venus flytrap domain of both T1R2 and T1R3.

Usually such an interacting site can be determined by any suitable means known or later discovered in the art. For example, such interacting site can be determined based on computer modeling, e.g., using software such as Homology or Modeller (by Accelrys Corporation) to construct three dimensional homology models of a chemosensory receptor Venus flytrap domain, e.g., the T1R2 and/or T1R3 Venus flytrap domains based on crystal structures of homologous Venus flytrap domains.

Such an interacting site can also be determined, e.g., based on X-ray crystallography and the three dimensional structure of a chemosensory receptor determined therefrom, e.g., the T1R2, T1R3, or T1R2/T1R3 heterodimer. Alternatively, for example, such an interacting site can be determined based on molecular mechanical techniques, e.g., normal mode analysis, loop generation techniques, Monte Carlo and/or molecular dynamics simulations to explore motions and alternative conformations of the Venus flytrap domains, docking simulations to dock candidate receptor ligands and candidate receptor ligand modifiers into these models or into experimentally determined structures of chemosensory receptors, e.g., T1R1 and T1R2.

In addition, for example, such an interacting site can be determined based on mutagenesis, e.g., site-directed mutagenesis or a combination of two or more suitable methods known or later discovered, e.g., methods described herein.

In one example, such an interacting site is located in part of a chemosensory receptor, e.g., T1R2 and can be determined in the presence or absence of the other part of the chemosensory receptor, e.g., T1R3. In another example, such an interacting site can be determined in the presence or absence of a chemosensory receptor modifier and/or chemosensory receptor ligand modifier.

In one embodiment, the interacting site within the Venus flytrap domain of a chemosensory receptor includes one or more interacting residues of the Venus flytrap domain of a chemosensory receptor. According to the present invention, the interacting residue of the Venus flytrap domain of a chemosensory receptor is a residue associated with any direct or indirect interaction between a chemosensory receptor and a chemosensory receptor modifier or a chemosensory receptor ligand modifier or both.

In one example, the interacting residue of the present invention includes any residue of a chemosensory receptor associated with an interaction between a chemosensory receptor modifier and a chemosensory receptor. In another example, the interacting residue of the present invention includes any residue of a chemosensory receptor associated with an interaction between a chemosensory receptor ligand modifier and a chemosensory receptor. In yet another example, the interacting residue of the present invention includes any residue of a chemosensory receptor associated with an interaction between a chemosensory receptor, a chemosensory receptor modifier and a chemosensory receptor ligand modifier.

In still another example, the interacting residue of the present invention includes any residue of a chemosensory receptor associated with an interaction between a chemosensory receptor and a sweet flavor entity, e.g. any natural or synthesized sweet flavor compound including, without any limitation, non-caloric sweet flavor compounds, reduced caloric sweet flavor compounds, non-target caloric sweet flavor compounds, etc. Exemplary sweet flavor compounds include, without any limitation, cyclamic acid, mogroside, tagatose, maltose, galactose, mannose, sucrose, fructose, lactose, aspartame, neotame and other aspartame derivatives, saccharin, sucralose, acesulfame K, glucose, erythritol, D-tryptophan, glycine, mannitol, sorbitol, maltitol, lactitol, isomalt, hydrogenated glucose syrup (HGS), hydrogenated starch hydrolyzate (HSH), stevioside, rebaudioside A and other sweet Stevia-based glycosides, alitame, carrelame and other guanidine-based sweeteners, tagatose, xylitol, high fructose corn syrup, etc.

In still another example, the interacting residue of the present invention includes any residue of a chemosensory receptor associated with an interaction between a chemosensory receptor and a sweet flavor entity enhancer. In still another example, the interacting residue of the present invention includes any residue of a chemosensory receptor associated with an interaction between a chemosensory receptor, a sweet flavor entity, and a sweet flavor entity enhancer.

In another instance, the interacting residue of the present invention is a residue within the Venus flytrap domain of a chemosensory receptor, wherein any mutation of which could result in a change of the activity of the chemosensory receptor or the impact of a chemosensory receptor ligand to the chemosensory receptor or both. For example, the interacting residue of the present invention can include any residue within the Venus flytrap domain of a chemosensory receptor, wherein the mutation of which results in a detectable change, e.g., qualitative or quantitative change of the activity of the chemosensory receptor in response to a chemosensory receptor modifier and/or chemosensory receptor ligand modifier.

In yet another instance, the interacting residue of the present invention is a residue within the Venus flytrap domain of a chemosensory receptor that interacts or forms productive interaction(s), e.g., van der Waals, burial of hydrophobic atoms or atomic groups, hydrogen bonds, ring stacking interactions, or salt-bridging electrostatic interactions with a chemosensory receptor modifier or chemosensory receptor ligand modifier, or both.

In still another instance, the interacting residue of the Venus flytrap domain of a chemosensory receptor can be any residue constituting one or more interacting structural components of the Venus flytrap domain, which are associated, directly or indirectly, with the interaction between a chemosensory receptor and a chemosensory receptor modifier or a chemosensory receptor ligand modifier or both. For example, the Venus flytrap domain structure of a chemosensory receptor generally includes two lobes joint by a hinge region. Residues constituting an interacting structural component of the Venus flytrap domain can be, e.g., residues constituting the hinge region, the inner side of each lobe, or residues on each lobe that are brought into close proximity during activation or conformational change of the Venus flytrap domain, including without any limitation, residues on the inner surfaces of the lobes pointing towards each other or on the tips of the lobes where the residues are partially exposed to solvent but still close to residues on the opposite lobe, etc.

Exemplary interacting residues of the Venus flytrap domain of a chemosensory receptor include any one or more residues of 1) N143, S144, and I167 of a human T1R2, 2) S40, S144, S165, Y103, D142, and P277 of a human T1R2, 3) K65, R383, D307, E302, and D278 of a human T1R2, 4) I167, P185, T184, T326, E302, V384, A305, I325, I306, R383, D307, E382, D278, I279, I67, V66, V309, D142, S165, S40, S303, T242, F103, Q328, and S168 of a human T1R2, 5) N143, S144, I167, K65, R383, D307, E302, D278, P185, T184, T326, E302, V384, A305, I325, I306, D307, E382, I279, I67, V66, V309, D142, S165, S40, S303, T242, F103, Q328, and S168 of a human T1R2, and 6) N143, I167, K65, R383, D307, E302, D278, P185, T184, T326, V384, A305, I325, I306, D307, E382, I279, I67, V66, V309, D142, S165, S40, S303, T242, F103, Q328, and S168 of a human T1R2.

Exemplary interacting residues of the Venus flytrap domain of a chemosensory receptor with respect to a chemosensory receptor modifier include one or more residues of 1) N143, S144, and I167 of a human T1R2, 2) S40, S144, S165, Y103, D142, and P277 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) N143 and I167 of a human T1R2, 5) S40, S165, Y103, D142, and P277 of a human T1R2, and 6) I167, P185, T184, T326, V384, A305, I325, I306, R383, D307, E382, D278, I279, I67, V66, V309, D142, S165, S40, S303, T242, F103, Q328, and S168 of a human T1R2.

Exemplary interacting residues of the Venus flytrap domain of a chemosensory receptor with respect to a sweet flavor entity such as sucrose and sucralose include one or more residues of S40, S144, Y103, D142, P277 of a human T1R2. Exemplary interacting residues of the Venus flytrap domain of a chemosensory receptor with respect to a sweet flavor entity such as saccharin or acesulfame K include one or more residues of K65, R383, D307, E302, and D278 of a human T1R2.

Exemplary interacting residues of the Venus flytrap domain of a chemosensory receptor with respect to a chemosensory receptor ligand modifier, e.g., chemosensory receptor ligand enhancer include one or more residues of 1) K65, R383, D307, E302, and D278 of a human T1R2, 2) S40, S144, S165, Y103, D142, and P277 of a human T1R2, and 3) I167, P185, T184, T326, E302, V384, A305, I325, I306, R383, D307, E382, D278, I279, I67, V66, V309, D142, S165, S40, S303, T242, F103, Q328, and S168 of a human T1R2.

In the context of the present invention, any reference to a particular interacting residue, e.g., N143 of a human T1R2 receptor, includes all of its corresponding residues, e.g., 1) any residue of a human or non-human T1R2 that corresponds to the same position in any method of sequence alignment, 2) any residue of a human or non-human T1R2 that corresponds to the same position in any method of computer modeling in the presence or absence of a ligand or ligand modifier, 3) any residue of a human or non-human T1R2 that corresponds to the structural or functional role of the particular interacting residue, 4) any residue of a human or non-human T1R2 that is a polymorphic variation, alleles, mutation, etc. of the particular residue, 5) any residue of a human or non-human T1R2 that is a conservative substitution or conservatively modified variant of the particular residue, and 6) any corresponding residue of a human or non-human T1R2 in its modified form, e.g., artificial chemical mimetic of the particular interacting residue or un-modified form, e.g., naturally occurring form.

In another embodiment, the interacting site within the Venus flytrap domain of a chemosensory receptor is a three dimensional interacting space within the Venus flytrap domain outlined or defined, partially or entirely, by interacting residues or one or more interfaces, e.g., interacting points, lines or surfaces between a chemosensory receptor and one or more chemosensory receptor modifiers or chemosensory receptor ligand modifiers or a combination thereof. According to the present invention, a residue outlining or lining a space includes any residue having one or more backbones and/or side-chain atoms that are positioned so that they can potentially interact with atoms of a chemosensory receptor ligand or chemosensory receptor ligand modifier or both.

For example, the interacting space of the present invention can be any partial or whole space within the Venus flytrap domain that is usually occupied by one or more chemosensory receptor modifiers or chemosensory receptor ligand modifiers when they interact with a chemosensory receptor individually or together. In one example, the interacting space of the present invention is a space within the Venus flytrap domain usually occupied by a chemosensory receptor modifier, e.g., sweet flavor entity. In another example, the interacting space of the present invention is a space within the Venus flytrap domain usually occupied by a chemosensory receptor ligand modifier, e.g., sweet flavor enhancer in the presence of a chemosensory receptor ligand. In yet another example, the interacting space of the present invention is a space within the Venus flytrap domain usually occupied by a chemosensory receptor modifier, e.g., sweet flavor entity and a chemosensory receptor ligand modifier, e.g., sweet flavor entity enhancer. In still another example, the interacting space of the present invention is a space within the Venus flytrap domain that is defined, shaped, or transformed into based on an interaction between a chemosensory receptor and its ligand or its ligand modifier occurred partially or entirely outside of the space.

According to the present invention, the Venus flytrap domain of a chemosensory receptor can be generally viewed as two lobes joined by a hinge region. Exemplary interacting space within the Venus flytrap domain of a chemosensory receptor includes any space associated with the hinge region, the inner side of one or two lobes, the tip of one or two lobes or a combination thereof of a chemosensory receptor.

Exemplary interacting space within the Venus flytrap domain of a chemosensory receptor with respect to a chemosensory receptor modifier includes any space within the Venus flytrap domain outlined or at least partially defined by the hinge region. According to the present invention, the hinge region usually comprises residues that are close to the three strands connecting the two lobes. In one example, the hinge region comprises residues that are homologous to residues observed coordinating agonists and antagonists in crystal structures of one or more Venus flytrap domains such as that of the mGluR receptor. In another example, the hinge region of T1R2 includes residues N143, S144, and I167 of T1R2.

Exemplary interacting sites within the Venus flytrap domain of a chemosensory receptor with respect to a chemosensory receptor ligand modifier include any space outlined or at least partially defined by the inner side of one or two lobes away from the hinge region, as well as residues on the tips of the lobes that are brought into close proximity to residues on the other lobe.

In yet another embodiment, the interacting site within the Venus flytrap domain of a chemosensory receptor is a combination of one or more interacting residues with an interacting space of the chemosensory receptor. For example, the interacting site of a chemosensory receptor can be interacting residues associated with one interacting structural component of a chemosensory receptor in combination with a three dimensional space adjacent, e.g., not less than 1 Angstrom and not more than 30 Angstroms, to that interacting structural component. Another example of the interacting site of a chemosensory receptor includes interacting residues associated with one interacting structural component of a chemosensory receptor in combination with a three dimensional space apart from the interacting structural component.

In general, the screening methods provided by the present invention can be carried out by any suitable means known or later discovered. In one embodiment, the screening methods provided by the present invention are carried out in silica, e.g., via "virtue screening" using any suitable computer modeling system or via specific or rational design of a compound using any suitable computer design system.

In another embodiment, the screening methods provided by the present invention are carried out via biological assays, e.g., high throughput screening of interactions between compounds and a chemosensory receptor or its fragments, e.g., genetically modified chemosensory receptors or fragments thereof such as mutated Venus flytrap domains of chemosensory receptors. In yet another embodiment, the screening methods provided by the present invention are carried out via a combination of biological assay(s) and computer modeling and/or design. For example, the screening methods provided by the present invention can be a combination of high-throughput screening of interactions between computer designed or pre-screened compounds and mutated Venus flytrap domains of chemosensory receptors.

In one example, the screening method provided by the present invention for chemosensory receptor modifiers includes determining an interacting site using a known chemosensory receptor modifier, e.g., structurally similar to a chemosensory receptor modifier of interest and then determining whether a test entity is suitable to interact with the chemosensory receptor via the interacting site so determined.

In another example, the screening method provided by the present invention for chemosensory receptor modifiers includes determining whether a test entity is suitable to interact with a chemosensory receptor via a predetermined interacting site, e.g., an interacting site selected or determined prior to screening, including without any limitation, selected or determined based on known chemosensory receptor modifiers or desired characteristics of a chemosensory receptor modifiers.

In yet another example, the screening method provided by the present invention for chemosensory receptor ligand modifiers includes determining a docking site for a chemosensory receptor ligand and subsequently determining whether a test entity is suitable to interact with the chemosensory receptor ligand via an interacting site selected in light of the docking of the chemosensory receptor ligand. According to the present invention, docking process can include any known or later discovered methods. For instance, docking can be a process in which the center of mass, orientations, and internal degrees of freedom of a molecule are modified to fit them into a predetermined space in a structural model. In one example, docking can be a process which includes translating and rotating a chemosensory receptor ligand relative to the chemosensory receptor structural model, e.g., the Venus flytrap domain of a chemosensory receptor model while simultaneously adjusting internal torsional angles of the chemosensory receptor ligand to fit it into the interacting site of the chemosensory receptor. An example of a widely used docking program is GLIDE from Schroedinger, Inc.

In yet another example, the screening method provided by the present invention for chemosensory receptor ligand modifiers includes determining a docking site for a chemosensory receptor ligand and subsequently determining an interacting site using a known modifier of the chemosensory receptor ligand and then determining whether a test entity is suitable to interact with the chemosensory receptor ligand via the interacting site so determined.

In yet another example, the screening method provided by the present invention for chemosensory receptor ligand modifiers includes determining whether a test entity is suitable to interact with a chemosensory receptor via a predetermined interacting site for chemosensory receptor ligand modifiers.

In still another example, the screening method provided by the present invention for chemosensory receptor ligand modifiers includes determining whether a test entity is suitable to interact with a chemosensory receptor by determining, e.g., concurrently whether a chemosensory receptor ligand and the test entity are suitable to interact with the chemosensory receptor in a predetermined interacting site of the chemosensory receptor or an interacting site determined using known chemosensory receptor ligand and its modifier of interest.

In still another example, the screening method provided by the present invention for chemosensory receptor ligand modifiers includes determining whether a test entity is suitable to interact with a chemosensory receptor via an interacting site, either pre-determined or not, as well as whether a test entity is suitable to interact with a chemosensory receptor ligand.

In still another example, the screening method provided by the present invention for chemosensory receptor ligand modifiers includes determining whether a test entity is suitable to interact with a chemosensory receptor via an interacting site, either pre-determined or not, as well as whether such interaction can stabilize a conformation, e.g., a semi-closed or closed conformation within the Venus flytrap domain formed by the interaction between a chemosensory receptor ligand and a chemosensory receptor, e.g., by forming productive additional interactions within the hinge region, lobes of the Venus flytrap domain, or tips of the flytrap domain via van der Waals, burial of hydrophobic atoms or atomic groups, hydrogen bonds, ring stacking interactions, or salt-bridging electrostatic interactions, etc.

In general, any suitable means known or later discovered can be used to determine whether a test entity is suitable to interact with an interacting site of the present invention. For example, one could determine the suitability of a test entity based on whether part or all of a test entity fits into a particular space entailed by an interacting site, e.g., whether a test entity fits into a particular space entailed by an interacting site substantially the same way a known chemosensory receptor modifier or chemosensory receptor ligand modifier does.

Alternatively one could determine the suitability of a test entity with respect to an interacting site based on whether it forms interactions with a chemosensory receptor similar to the interactions formed by a known chemosensory receptor modifier or chemosensory receptor ligand modifier when they interact with the interacting site.

In addition, one could determine the suitability of a test entity based on whether it forms productive interactions with an interacting site, e.g., van der Waals, burial of hydrophobic atoms or atomic groups, hydrogen bonds, ring stacking interactions, or salt-bridging electrostatic interactions, etc. In one embodiment, one could determine the suitability of a test entity being a chemosensory receptor ligand modifier based on whether it forms productive interactions with an interacting site without forming van der Waals overlapping with one or more atoms of a chemosensory receptor or the chemosensory receptor ligand, e.g., in the context of one or more conformations of the Venus flytrap domain in light of the possible flexibility of the Venus flytrap domain.

According to the present invention, a test entity suitable to interact with one or more interacting sites within the Venus flytrap domain of a chemosensory receptor is indicative of a candidate for a chemosensory receptor modifier or chemosensory receptor ligand modifier. In one embodiment, a test entity suitable to interact with one or more interacting sites within the Venus flytrap domain of T1R2 is indicative of a candidate for a T1R2 receptor modifier or T1R2 receptor ligand modifier. In another embodiment, a test entity suitable to interact with one or more interacting sites within the Venus flytrap domain of T1R2 is indicative of a candidate for a T1R receptor modifier or T1R receptor ligand modifier. In yet another embodiment, a test entity suitable to interact with one or more interacting sites within the Venus flytrap domain of T1R2 is indicative of a candidate for a receptor modifier or receptor ligand modifier for a receptor of GPCR superfamily. In still another embodiment, a test entity suitable to interact with one or more interaction sites within the Venus flytrap domain of a chemosensory receptor is indicative of a candidate for a receptor modifier or receptor ligand modifier of a receptor that corresponds to the chemosensory receptor or belongs to the same family or class as of the chemosensory receptor.

According to the present invention, a test entity suitable to interact with one or more interacting sites within the Venus flytrap domain of a chemosensory receptor is indicative of a candidate for a chemosensory receptor modifier or chemosensory receptor ligand modifier. In one embodiment, a test entity suitable to interact with one or more interacting sites within the Venus flytrap domain of T1R2 is indicative of a candidate for a T1R2 receptor modifier or T1R2 receptor ligand modifier.

In one example, a test entity suitable to interact with one or more interacting sites containing one or more interacting residues of K65, D278, L279, D307, R383, and V384 of human T1R2 is indicative of a candidate for a T1R2 receptor ligand enhancer.

In another example, a test entity suitable to interact with one or more interacting sites containing one or more interacting residues of S40, S144, Y103, D142, and P277 of human T1R2 is indicative of a candidate for a T1R2 receptor ligand enhancer with respect to sucrose or sucralose or any ligand with a structure similar to sucrose or sucralose or any ligand interacting with T1R2 in a way similar to that of sucrose or sucralose, e.g., via one or more interacting spaces and/or residues used by sucrose or sucralose.

In the context of the present application, any reference to a modifier, e.g. enhancer or inhibitor of a T1R2 receptor or T1R2 receptor ligand includes a modifier for any T1R receptor, any receptor of GPCR super-family, or any receptor corresponding to T1R2 receptor, e.g., any receptor with a structure, function, or expression pattern overlapping or similar to that of T1R2. In the present invention, a test entity can be any compound or molecule, e.g., any compound or entity that potentially could be a source for a desired chemosensory receptor modifier or chemosensory receptor ligand modifier. For example, a test entity can be a member of a combinatorial library, a member of a natural compound library, a "specifically designed" compound that is designed based on various desirable features or rationales, etc.

In general, a chemosensory receptor modifier or ligand includes any compound or entity capable of interacting with, e.g., binding to a chemosensory receptor or modulating the structure or function of a chemosensory receptor, e.g., activate, deactivate, increase, or decrease the signal transduction activity of a chemosensory receptor, especially via G-protein signal transduction pathway.

In one embodiment, a chemosensory receptor modifier or ligand is a compound or entity with sweet flavor including without any limitation any natural or synthesized sweet flavor compound, e.g., non-caloric sweet flavor compounds, reduced caloric sweet flavor compounds, non-target caloric sweet flavor compounds, etc. Exemplary sweet flavor compounds include, without any limitation, cyclamic acid, mogroside, tagatose, maltose, galactose, mannose, sucrose, fructose, lactose, aspartame, neotame and other aspartame derivatives, saccharin, sucralose, acesulfame K, glucose, erythritol, D-tryptophan, glycine, mannitol, sorbitol, maltitol, lactitol, isomalt, hydrogenated glucose syrup (HGS), hydrogenated starch hydrolyzate (HSH), stevioside, rebaudioside A and other sweet Stevia-based glycosides, alitame, carrelame and other guanidine-based sweeteners, tagatose, xylitol, high fructose corn syrup, etc.

In another embodiment, a chemosensory receptor modifier or ligand (used interchangeably in the present invention) is a compound or entity capable of activating a chemosensory receptor, e.g., activating the G-protein signal transduction pathway associated with the chemosensory receptor. In yet another embodiment, a chemosensory receptor modifier or ligand is a compound or entity capable of blocking or decreasing the activation of a chemosensory receptor. In still another embodiment, a chemosensory receptor modifier or ligand is a compound or entity capable of modulating the activity of a chemosensory receptor and inducing a therapeutically desirable reaction or signal transduction. In still another embodiment, a chemosensory receptor modifier or ligand is a chemosensory receptor ligand modifier.

According to the present invention, a chemosensory receptor ligand modifier includes any compound or entity capable of interacting or modulating the activity of a chemosensory receptor modifier or the activity of a chemosensory receptor in the presence of a chemosensory receptor modifier. In one embodiment, a chemosensory receptor ligand modifier is an enhancer of a chemosensory receptor modifier. In another embodiment, a chemosensory receptor ligand modifier is an antagonist of a chemosensory receptor modifier. In yet another embodiment, a chemosensory receptor ligand modifier is an enhancer of a chemosensory receptor modifier without having substantial activity of the chemosensory receptor modifier. In still another embodiment, a chemosensory receptor ligand modifier is an enhancer of a sweet flavored compound without having substantial sweet flavor by itself, e.g., as judged by animals or humans such as majority of a panel of at least eight human taste testers, via procedures commonly known in the field. In still yet another embodiment, a chemosensory receptor ligand modifier is an enhancer or inhibitor of a chemosensory receptor modifier and capable of inducing a desirable therapeutic reaction or signal transduction.

According to another aspect of the present invention, it provides chemosensory receptor ligand modifiers. In one embodiment, it provides chemosensory receptor ligand modifiers identified by the screen methods of the present invention. In another embodiment, it provides chemosensory receptor ligand modifiers capable of interacting with a chemosensory receptor via an interacting site of the present invention. In yet another embodiment, it provides chemosensory receptor ligand modifiers capable of interacting with a chemosensory receptor via one or more interacting residues of the chemosensory receptor. In still another embodiment, it provides chemosensory receptor ligand modifiers capable of interacting with a chemosensory receptor via an interacting space within the Venus flytrap domain that is outlined, defined, or shaped, partially or entirely, by interacting residues of the chemosensory receptor. In still yet another embodiment, it provides chemosensory receptor ligand modifiers excluding, e.g., natural or synthesized sweet enhancers known prior to the present invention.

In the context of the present invention, "capable of interacting with" or "interacting with" means that a compound or molecule binds to or forms one or more molecular interactions, e.g., productive interactions with another molecule, e.g., a chemosensory receptor. Exemplary molecular interactions, e.g., productive interactions include van der Waals, burial of hydrophobic atoms or atomic groups, hydrogen bonds, ring stacking interactions, salt-bridging electrostatic interactions, or a combination thereof.

In one embodiment, the present invention provides chemosensory receptor ligand modifiers capable of interacting with a chemosensory receptor via a group of interacting residues or a space within the Venus flytrap domain that is outlined, shaped, or defined, partially or entirely by the group or any subgroup of interacting residues, optionally in the presence of a chemosensory receptor ligand, e.g., 1) S40, S144, S165, Y103, D142, P277 of a human T1R2, 2) K65, R383, D307, E302, and D278 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) S40, S144, S165, Y103, D142, P277, K65, R383, D307, E302, and D278 of a human T1R2, 5) S40, S144, S165, Y103, D142, P277, I167, P185, T184, T326, E302, V384, A305, I325, I306, R383, D307, E382, D278, I279, I67, V66, V309, S303, T242, F103, Q328, and S168 of a human T1R2, 6) K65, R383, D307, E302, D278, I167, P185, T184, T326, E302, V384, A305, I325, I306, E382, I279, I67, V66, V309, D142, S165, S40, S303, T242, F103, Q328, and S168 of a human T1R2, 7) S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2, 8) N143, S144, and I167 of a human T1R2, or 9) N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In another embodiment, the present invention provides chemosensory receptor ligand enhancers capable of interacting with a chemosensory receptor in the presence of a chemosensory receptor ligand via one or more interacting residues of K65, D278, L279, D307, R383, V384 of a human T1R2.

In yet another embodiment, the present invention provides sucrose or sucralose enhancers capable of interacting with a chemosensory receptor in the presence of sucrose or sucralose via one or more interacting residues of S40, S144, Y103, D142, P277 of a human T1R2.

In still another embodiment, the present invention provides chemosensory receptor ligand modifiers capable of interacting with a chemosensory receptor, optionally in the presence of a chemosensory receptor ligand via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In still another embodiment, the present invention provides chemosensory receptor ligand modifiers capable of interacting with a chemosensory receptor to stabilize a conformation, e.g., semi-closed or closed conformation formed by the interaction between a chemosensory receptor and a chemosensory receptor ligand.

In still yet another embodiment, the present invention provides chemosensory receptor ligand modifiers, e.g., saccharin, saccharin analogues, acesulfame K, acesulfame K analogues, or any compound capable of interacting with a chemosensory receptor via an interacting site that is similar to or overlaps with an interacting site used by saccharin or acesulfame K. In one example, the present invention provides chemosensory receptor ligand enhancers, e.g., saccharin, saccharin analogues, acesulfame K, or acesulfame K analogues that interact with a chemosensory receptor via an interacting site including one or more interacting residues of K65, R383, D307, E302 and D278 of a human T1R2.

According to yet another aspect of the present invention, it provides chemosensory receptor modifiers. In one embodiment, it provides chemosensory receptor modifiers identified by the screen methods of the present invention. In another embodiment, it provides chemosensory receptor modifiers capable of interacting with a chemosensory receptor via an interacting site of the present invention. In yet another embodiment, it provides chemosensory receptor modifiers capable of interacting with a chemosensory receptor via one or more interacting residues of the chemosensory receptor. In still another embodiment, it provides chemosensory receptor modifiers capable of interacting with a chemosensory receptor via an interacting space within the Venus flytrap domain that is outlined, defined, or shaped, partially or entirely, by interacting residues of the chemosensory receptor. In still yet another embodiment, it provides chemosensory receptor modifiers excluding, e.g., natural or synthesized sweet flavor entities known prior to the present invention.

In one embodiment, the present invention provides chemosensory receptor modifiers capable of interacting with a chemosensory receptor via a group of interacting residues or a space within the Venus flytrap domain that is outlined, shaped, or defined, partially or entirely by the group or any subgroup of interacting residues, e.g., 1) S40, S144, S165, Y103, D142, P277 of a human T1R2, 2) K65, R383, D307, E302, and D278 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) S40, S144, S165, Y103, D142, P277, K65, R383, D307, E302, and D278 of a human T1R2, 5) S40, S144, S165, Y103, D142, P277, I167, P185, T184, T326, E302, V384, A305, I325, I306, R383, D307, E382, D278, I279, I67, V66, V309, S303, T242, F103, Q328, and S168 of a human T1R2, 6) K65, R383, D307, E302, D278, I167, P185, T184, T326, E302, V384, A305, I325, I306, E382, I279, I67, V66, V309, D142, S165, S40, S303, T242, F103, Q328, and S168 of a human T1R2, 7) S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2, 8) N143, S144, and I167 of a human T1R2, or 9) N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In still another embodiment, the present invention provides chemosensory receptor modifiers capable of interacting with a chemosensory receptor via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, 5303, T242, F103, Q328, and S168 of a human T1R2.

According to still another aspect of the present invention, it provides methods for modulating a chemosensory receptor and/or its ligand by modulating one or more interacting sites of the chemosensory receptor. For example, one can modulate a chemosensory receptor by contacting, in vivo or in vitro, a chemosensory receptor modifier or chemosensory receptor ligand modifier or both, (e.g., optionally excluding natural sweet flavor entity or sweet enhancers known prior to the present invention) with cells containing the chemosensory receptor, wherein the chemosensory receptor modifier or chemosensory receptor ligand is capable of interacting with or targeting one or more interacting sites of the chemosensory receptor.

In one embodiment, the method of modulating a chemosensory receptor and/or its ligand is by modulating one or more interacting residues or interacting spaces or a combination thereof. In another embodiment, the method of modulating a chemosensory receptor and/or its ligand is by interacting with one or more interacting residues in the presence of a chemosensory receptor ligand. In yet another embodiment, the method of modulating a chemosensory receptor or its ligand includes modulating the impact of a chemosensory receptor ligand on the chemosensory receptor by interacting with the chemosensory receptor via one or more interacting residues in the presence of the chemosensory receptor ligand.

In yet another embodiment, the method of modulating a chemosensory receptor and/or its ligand is by interacting with the chemosensory receptor via a group of interacting residues or a space outlined, shaped, or defined, partially or entirely, by the group or subgroup of interacting residues, optionally in the presence of a chemosensory receptor ligand, e.g., 1) S40, S144, S165, Y103, D142, P277 of a human T1R2, 2) K65, R383, D307, E302, and D278 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) S40, S144, S165, Y103, D142, P277, K65, R383, D307, E302, and D278 of a human T1R2, 5) S40, S144, S165, Y103, D142, P277, I167, P185, T184, T326, E302, V384, A305, I325, I306, R383, D307, E382, D278, I279, I67, V66, V309, S303, T242, F103, Q328, and S168 of a human T1R2, 6) K65, R383, D307, E302, D278, I167, P185, T184, T326, E302, V384, A305, I325, I306, E382, I279, I67, V66, V309, D142, S165, S40, S303, T242, F103, Q328, and S168 of a human T1R2, 7) S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2, 8) N143, S144, and I167 of a human T1R2, or 9) N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In yet another embodiment, the method of modulating a chemosensory receptor and/or its ligand is by interacting with the chemosensory receptor via one or more interacting residues of N143, S144, and I167 of a human T1R2.

In yet another embodiment, the method of modulating a chemosensory receptor and/or its ligand is by interacting with the chemosensory receptor, optionally in the presence of a chemosensory receptor ligand via one or more interacting residues of K65, D278, L279, D307, R383, V384 of a human T1R2.

In still another embodiment, the method of modulating a chemosensory receptor and/or its ligand is by interacting with the chemosensory receptor, optionally in the presence of sucrose or sucralose via one or more interacting residues of S40, S144, Y103, D142, P277 of a human T1R2.

In still another embodiment, the method of enhancing a chemosensory receptor and/or its ligand is by interacting with the chemosensory receptor, optionally in the presence of a chemosensory receptor ligand via one or more interacting residues of K65, D278, L279, D307, R383, V384, S40, S144, Y103, D142, P277 of a human T1R2.

In still another embodiment, the method of modulating a chemosensory receptor and/or its ligand is by interacting with the chemosensory receptor, optionally in the presence of a chemosensory receptor ligand via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In still another embodiment, the method of modulating a chemosensory receptor and/or its ligand is by interacting with the chemosensory receptor, optionally in the presence of a chemosensory receptor ligand via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

According to the present invention, a method of modulating a chemosensory receptor and/or its ligand includes modulating the activity, structure, function, expression, and/or modification of a chemosensory receptor as well as modulating, treating, or taking prophylactic measure of a condition, e.g., physiological or pathological condition, associated with a chemosensory receptor.

In general, a physiological or pathological condition associated with a chemosensory receptor includes a condition associated with a taste, e.g., sweet, umami, bitter, sour, salty, or a combination thereof or a condition associated with, e.g., gastrointestinal system, metabolic disorders, functional gastrointestinal disorders, etc.

In one embodiment, the method of the present invention, e.g., modulating a chemosensory receptor and/or its ligand includes modulating, increasing or decreasing a sweet or umami taste or a subject's reaction, physiological or otherwise, to a sweet or umami taste. In another embodiment, the method of the present invention, e.g., modulating a chemosensory receptor and/or its ligand includes enhancing a sweet or umami taste or a subject's reaction, physiological or otherwise, to a sweet or umami taste.

In yet another embodiment, the method of the present invention, e.g., modulating a chemosensory receptor and/or its ligand includes modulation, treatment, and/or prophylactic measure of a condition associated with gastrointestinal system including without any limitation conditions associated with esophageal motility (e.g., cricopharyngeal achalasia, globus hystericus, achalasia, diffuse esophageal spasm and related motor disorders, scleroderma involving the esophagus, etc.), inflammatory disorders (e.g., gastroesophageal reflux and esophagitis, infectious esophagitis, etc.), peptic ulcer, duodenal ulcer, gastric ulcer, gastrinoma, stress ulcers and erosions, drug-associated ulcers and erosions, gastritis, esophageal cancer, tumors of the stomach, disorders of absorption (e.g., absorption of specific nutrients such as carbohydrate, protein, amino acid, fat, cholesterol and fat-soluble vitamins, water and sodium, calcium, iron, water-soluble vitamins, etc.), disorders of malabsorption, defects in mucosal function (e.g., inflammatory or infiltrative disorders, biochemical or genetic abnormalities, endocrine and metabolic disorders, protein-losing enteropathy, etc.), autoimmune diseases of the digestive tract (e.g., celiac disease, Crohn's disease, ulcerative colitis, etc.), irritable bowel syndrome, inflammatory bowel disease, complications of inflammatory bowel disease, extraintestinal manifestations of inflammatory bowel disease, disorders of intestinal motility, vascular disorders of the intestine, anorectial disorders (e.g., hemorrhoids, anal inflammation, etc.), colorectal cancer, tumors of the small intestine, cancers of the anus, derangements of hepatic metabolism, hyperbilirubinemia, hepatitis, alcoholic liver disease and cirrhosis, biliary cirrhosis, neoplasms of the liver, infiltrative and metabolic diseases affecting the liver (e.g., fatty liver, reye's syndrome, diabetic glycogenosis, glycogen storage disease, Wilson's disease, hemochromatosis), diseases of the gallbladder and bile ducts, disorders of the pancreas (e.g., pancreatitis, pancreatic exocrine insufficiency, pancreatic cancer, etc.), endocrine tumors of the gastrointestinal tract and pancreas, etc.

In still another embodiment, the method of the present invention, e.g., modulating a chemosensory receptor and/or its ligand includes modulation, treatment, and/or prophylactic measure of a condition associated with metabolic disorders, e.g., appetite, body weight, food or liquid intake or a subject's reaction to food or liquid intake, or state of satiety or a subject's perception of a state of satiety, nutrition intake and regulation, (e.g., protein-energy malnutrition, physiologic impairments associated with protein-energy malnutrition, etc.), obesity, secondary obesity (e.g., hypothyroidism, Cushing's disease, insulinoma, hypothalamic disorders, etc.), eating disorders (e.g., anorexia nervosa, bulimia, etc.), vitamin deficiency and excess, insulin metabolism, diabetes (type I and type II) and complications thereof (e.g., circulatory abnormalities, retinopathy, diabetic nephropathy, diabetic neuropathy, diabetic foot ulcers, etc.), glucose metabolism, fat metabolism, hypoglycemia, hyperglycermia, hyperlipoproteinemias, etc.

In still yet another embodiment, the method of the present invention, e.g., modulating a chemosensory receptor and/or its ligand includes modulation, treatment, and/or prophylactic measure of a condition associated with functional gastrointestinal disorders, e.g., in the absence of any particular pathological condition such as peptic ulcer and cancer, a subject has abdominal dyspepsia, e.g., feeling of abdominal distention, nausea, vomiting, abdominal pain, anorexia, reflux of gastric acid, or abnormal bowel movement (constipation, diarrhea and the like), optionally based on the retention of contents in gastrointestinal tract, especially in stomach. In one example, functional gastrointestinal disorders include a condition without any organic disease of the gastrointestinal tract, but with one or more reproducible gastrointestinal symptoms that affect the quality of life of a subject, e.g., human.

Exemplary functional gastrointestinal disorders include, without any limitation, functional dyspepsia, gastroesophageal reflux condition, diabetic gastroparesis, reflux esophagitis, postoperative gastrointestinal dysfunction and the like, nausea, vomiting, sickly feeling, heartburn, feeling of abdominal distention, heavy stomach, belching, chest writhing, chest pain, gastric discomfort, anorexia, dysphagia, reflux of gastric acid, abdominal pain, constipation, diarrhea, breathlessness, feeling of smothering, low incentive or energy level, pharyngeal obstruction, feeling of foreign substance, easy fatigability, stiff neck, myotonia, mouth dryness (dry mouth, thirst, etc.) tachypnea, burning sensation in the gastricintestinal tract, cold sensation of extremities, difficulty in concentration, impatience, sleep disorder, headache, general malaise, palpitation, night sweat, anxiety, dizziness, vertigo, hot flash, excess sweating, depression, etc.

In still yet another embodiment, the method of the present invention, e.g., modulating a chemosensory receptor and/or its ligand includes increasing or promoting digestion, absorption, blood nutrient level, and/or motility of gastrointestinal tract in a subject, e.g., promotion of gastric emptying (e.g., clearance of stomach contents), reduction of abdominal distention in the early postprandial period, improvement of anorexia, etc. In general, such promotion can be achieved either directly or via increasing the secretion of a regulatory entity, e.g., hormones, etc.

In still yet another embodiment, the method of the present invention, e.g., modulating a chemosensory receptor and/or its ligand includes increasing one or more gastrointestinal functions of a subject, e.g., to improve the quality of life or healthy state of a subject.

In still yet another embodiment, the method of the present invention, e.g., modulating a chemosensory receptor and/or its ligand includes modulating the activity of T1R (e.g., T1R1, T1R2, or T1R3) expressing cells, e.g., liver cells (e.g., hepatocytes, endothelial cells, Kupffer cells, Stellate cells, epithelial cells of bile duct, etc.), heart cells (e.g., endothelial, cardiac, and smooth muscle cells, etc.), pancreatic cells (e.g., alpha cell, beta cell, delta cell, neurosecretory PP cell, D1 cell, etc.), cells in the nipple (e.g., ductal epithelial cells, etc.), stomach cells (e.g., mucous cells, parietal cells, chief cells, G cells, P/D1 cells), intestinal cells (e.g., enteroendocrine cells, brush cells, etc.), salivary gland cells (e.g., Seromucous cells, mucous cells, myoepithelial cells, intercalated duct cell, striated duct cell, etc.), L cells (e.g., expressing GLP-1, etc.), enterochromaffin cells (e.g., expressing serotonin), enterochromaffin-like cells, G cells (e.g., expressing gastrin), D cells (delta cells, e.g., expressing somatostatin), I cells (e.g., expressing cholecystokinin (CCK), K cells (e.g., expressing gastric inhibitory polypeptide), P/D1 cells (e.g., expressing ghrelin), chief cells (e.g., expressing pepsin), and S cells (e.g., expressing secretin). In one example, the method of the present invention includes increasing the expression level of T1R in T1R expressing cells. In another example, the method of the present invention includes increasing the secretion level of T1R expressing cells.

In still yet another embodiment, the method of the present invention, e.g., modulating a chemosensory receptor and/or its ligand includes modulating the expression, secretion, and/ or functional level of T1R expressing cells associated with hormone, peptide, enzyme producing. In one example, the method of the present invention includes modulating the level of glucose, e.g., inhibitors of a chemosensory receptor such as T1R2 can be used to decrease glucose level (e.g., glucose absorption) in a subject. In another example, the method of the present invention includes modulating the level of incretins, e.g., agonist of a chemosensory receptor such as T1R2 can be used to increase glucagons-like peotide 1 (GLP-1) and thus increase the production of insulin. In yet another example, the method of the present invention includes modulating the expression, secretion, and/or activity level of hormones or peptides produced by T1R expressing cells or gastrointestinal hormone producing cells, e.g., ligands for 5HT receptors (e.g., serotonin), incretins (e.g., GLP-1 and glucose-dependent insulinotropic polypeptide (GIP)), gastrin, secretin, pepsin, cholecystokinin, amylase, ghrelin, leptin, somatostatin, etc. In still another example, the method of the present invention includes modulating the pathways associated with hormones, peptides, and/or enzymes secreted by T1R expressing cells.

Exemplary chemosensory receptor ligand modifiers provided by the present invention and/or suitable to be used for methods of the present invention include compounds of the following formulae.

In one embodiment of the present invention, the chemosensory receptor ligand modifier is a compound having a structural Formula (I):

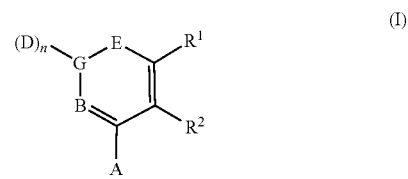

or a tautomer, salt, solvate, and/or ester thereof, wherein:

G forms a single bond with either D or E and a double bond with the other of D or E;

$R^1$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^3$, —S(O)$_a$R$^3$, —NR$^3$R$^4$, —CONR$^3$R$^4$, —CO$_2$R$^3$, —NR$^3$CO$_2$R$^4$, —NR$^3$CONR$^4$R$^5$, —NR$_3$CSNR$^4$R$^5$, —NR$^3$C(=NH)NR$^4$R$^5$, —SO$_2$NR$^3$R$^4$, —NR$^4$SO$_2$R$^3$, —NR$^3$SO$_2$NR$^4$R$^5$, —B(OR$^3$)(OR$^4$), —P(O)(OR$^3$)(OR$^4$) or —P(O)(R$^3$)(OR$^4$);

$R^2$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^6$, —S(O)$_b$R$^6$, —NR$^6$R$^7$, —CONR$^6$R$^7$, —CO$_2$R$^6$, —NR$^6$CO$_2$R$^7$, —NR$^6$CONR$^7$R$^8$, —NR$^6$CSNR$^7$R$^8$, —NR$^6$C(=NH)NR$^7$R$^8$, —SO$_2$NR$^5$R$^6$, —NR$^5$SO$_2$R$^6$, —NR$^5$SO$_2$NR$^6$R$^7$, —B(OR$^5$)(OR$^6$), —P(O)(OR$^5$)(OR$^6$), or —P(O)(R$^5$)(OR$^6$); or alternatively, $R^1$ and $R^2$, together with the atoms to which they are bonded, form an aryl, substituted aryl, heteroaryl, substituted heteroaryl, cycloalkyl, substituted cycloalkyl, cycloheteroalkyl or substituted cycloheteroalkyl ring wherein the ring is optionally fused to another aryl, substituted aryl, heteroaryl, substituted heteroaryl, cycloalkyl, substituted cycloalkyl, cycloheteroalkyl or substituted cycloheteroalkyl ring;

with the proviso that $R^1$ and $R^2$ are not both hydrogen;

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —NO$_2$, —OR$^9$, —S(O)$_c$R$^9$, —NR$^9$COR$^{10}$, —NHOR$^9$, —NR$^9$R$^{10}$, —NOR$^9$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$, —NR$^9$C(=NH)NR$^{10}$R$^{11}$, —B(OR$^{10}$)(OR$^{11}$), —P(O)(OR$^{10}$)(OR$^{11}$) or —P(O)(R$^{10}$)(OR$^{11}$);

B is —N— or —C(R$^{12}$)—;

$R^{12}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{13}$R$^{14}$, —CN, —OR$^{13}$, —S(O)$_d$R$^{13}$, —CO$_2$R$^{13}$ or —CONR$^{13}$R$^{14}$;

G is —C— or —S(O)$_2$—;

provided that when G is —S(O)$_2$—, then G forms a single bond with E;

when the bond between D and G is a single bond, then D is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl, substituted heteroarylalkyl, —OR$^{15}$, —NH—OR$^{15}$, —S(O)$_e$R$^{15}$, —NR$^{15}$R$^{16}$, —NH—NHR$^{15}$, —CO$_2$R$^{15}$, or —CONR$^{15}$R$^{16}$;

when G forms a double bond with D, then D is =O, =S, =N—OR$^{15}$, or =N—NHR$^{15}$;

n is 0 when G is —S(O)$_2$—, and n is 1 when G is —C—;

E is —NR$^{17}$—, —N— or —C(R$^{18}$)—;

provided that E is —NR$^{17}$— only when G forms a single bond with E;

R$^{17}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl or —CO$_2$R$^{19}$;

R$^{18}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{20}$R$^{21}$, —CN, —OR$^{20}$, —S(O)$_f$R$^{20}$, —CO$_2$R$^{20}$ or —CONR$^{20}$R$^{21}$;

a, b, c, d, e and f are independently 0, 1 or 2; and

R$^3$, R$^4$, R$^5$, R$^6$, R$^7$, R$^8$, R$^9$, R$^{10}$, R$^{11}$, R$^{13}$, R$^{14}$, R$^{15}$, R$^{16}$, R$^{18}$, R$^{20}$, and R$^{21}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively, R$^3$ and R$^4$, R$^4$ and R$^5$, R$^6$ and R$^7$, R$^7$ and R$^8$, R$^9$ and R$^{10}$, R$^{10}$ and R$^{11}$, R$^{13}$ and R$^{14}$, R$^{15}$ and R$^{16}$, or R$^{20}$ and R$^{21}$, together with the atoms to which they are bonded, form a cycloheteroalkyl or substituted cycloheteroalkyl ring.

In one embodiment of Formula (I), R$^1$ and R$^2$, together with the atoms to which they are bonded, form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring.

In one embodiment of Formula (I), the chemosensory receptor ligand modifier is a compound having a structural Formula (II),

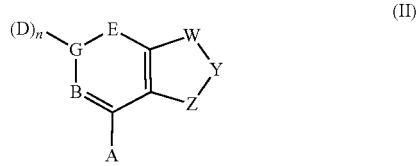

(II)

wherein:

Y forms a single bond with either W or Z and a double bond with the other of W or Z;

W is —C(R$^{24}$)—, —S—, —N—, —N(R$^{25}$)—, or —O—;

Y is —C(R$^{26}$)— or —N—;

Z is —C(R$^{27}$)—, —S—, —N—, —N(R$^{28}$)—, or —O—;

R$^{24}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{29}$, —S(O)$_g$R$^{29}$, —NR$^{29}$R$^{30}$, —CONR$^{29}$R$^{30}$, —CO$_2$R$^{29}$, —SO$_2$NR$^{29}$R$^{30}$, —NR$^{29}$SO$_2$R$^{30}$, —B(OR$^{29}$)(OR$^{30}$), —P(O)(OR$^{29}$)(OR$^{30}$) or —P(O)(R$^{29}$)(OR$^{30}$);

R$^{26}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{31}$, —S(O)$_h$R$^{31}$, —NR$^{31}$R$^{32}$, —CONR$^{31}$R$^{32}$, —CO$_2$R$^{31}$, —OCOR$^{31}$, —SO$_2$NR$^{31}$R$^{32}$, —NR$^{31}$SO$_2$R$^{32}$, —B(OR$^{31}$)(OR$^{32}$), —P(O)(OR$^{31}$)(OR$^{32}$) or —P(O)(R$^{31}$)(OR$^{32}$);

R$^{27}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{33}$, —S(O)$_i$R$^{33}$, —NR$^{33}$R$^{34}$, —CONR$^{33}$R$^{34}$, —COR$^{33}$, —CO$_2$R$^{33}$, —OCOR$^{33}$, —SO$_2$NR$^{33}$R$^{34}$, —NR$^{33}$SO$_2$R$^{34}$, —B(OR$^{33}$)(OR$^{34}$), —P(O)(OR$^{33}$)(OR$^{34}$) or —P(O)(R$^{33}$)(OR$^{34}$); or alternatively R$^{24}$ and R$^{26}$ or R$^{26}$ and R$^{27}$ together with the atoms to which they are bonded form a cycloalkyl, substituted cycloalkyl, cycloheteroalkyl or substituted cycloheteroalkyl ring;

g, h and i are independently 0 or I;

R$^{25}$ and R$^{28}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and R$^{29}$, R$^{30}$, R$^{31}$, R$^{32}$, R$^{33}$, and R$^{34}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively R$^{29}$ and R$^{30}$, R$^{31}$ and R$^{32}$, or R$^{33}$ and R$^{34}$ together with the atoms to which they are bonded form a cycloheteroalkyl or substituted cycloheteroalkyl ring; and with the following provisos:

(a) when W is —O— or —S— or —NR$^{25}$, then Z is —C(R$^{27}$) or —N—; and (b) when Z is —O— or —S— or —NR$^{28}$, then W is —C(R$^{24}$) or —N—.

In one embodiment of Formula (II), (D)$_n$-G is

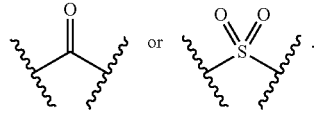

In one embodiment of Formula (II), the compound of the present invention has structural Formula (IIa):

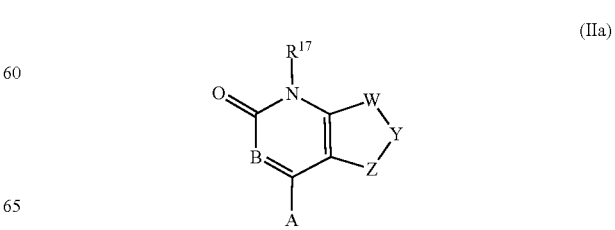

(IIa)

with the following provisos:

(a) when W is —O— or —S— or —NR$^{25}$, then Z is —C(R$^{27}$)— or —N—;

(b) when Z is —O— or —S— or —NR$^{28}$, then W is —C(R$^{24}$)— or —N—; and (c) when B is —N—, then A is not halo.

In one embodiment of Formula (IIa), the compound of the present invention has structural Formula (IIb):

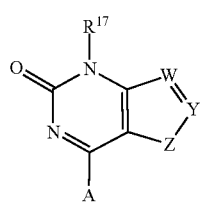

(IIb)

wherein, W is —C(R$^{24}$)— or —N—; Y is —C(R$^{26}$)— or —N—; and Z is —S—, —N(R$^{28}$)— or —O—.

In one embodiment of Formula (IIb), W is —C(R24)-, and Y is —C(R26)-.

In one embodiment of Formula (IIb), W is —C(R$^{24}$)—; Y is —C(R$^{26}$)—; R$^{24}$ is hydrogen, alkyl, substituted alkyl, acyl, substituted acyl, heteroalkyl, substituted heteroalkyl, —CN, —NO$_2$, —OR$^{29}$, —S(O)$_g$R$^{29}$, —OCOR$^{29}$, —NR$^{29}$R$^{30}$, —CONR$^{29}$R$^{30}$ or —CO$_2$R$^{29}$; and R$^{26}$ is hydrogen, alkyl, substituted alkyl, acyl, substituted acyl, heteroalkyl, substituted heteroalkyl, —CN, —NO$_2$, —OR$^{31}$, —OCOR$^{31}$, —S(O)$_h$R$^{31}$, —NR$^{31}$R$^{32}$, —CONR$^{31}$R$^{32}$ or —CO$_2$R$^{31}$. In a preferred embodiment, R$^{24}$ is hydrogen, —CF$_3$, alkyl or substituted alkyl; and R$^{26}$ is hydrogen, —CF$_3$, alkyl or substituted alkyl.

In one embodiment of Formula (IIb), W is —C(R$^{24}$)—; and Y is —C(R$^{26}$)—; A is hydrogen, alkyl, substituted alkyl, aryl, substituted aryl, —CN, —NO$_2$, —S(O)$_c$R$^9$, —NR$^9$R$^{10}$, —CONR$^9$R$^{10}$, —CO$_2$R$^9$ or —NR$^9$CO$_2$R$^{10}$; R$_{17}$ is hydrogen, alkyl, substituted alkyl, arylalkyl, or substituted arylalkyl; R$^{24}$ is hydrogen, alkyl, substituted alkyl, acyl, substituted acyl, heteroalkyl, substituted heteroalkyl, —CN, —NO$_2$, —OR$^{29}$, —S(O)$_g$R$^{29}$, —OCOR$^{29}$, —NR$^{29}$R$^{30}$, —CONR$^{29}$R$^{30}$ or —CO$_2$R$^{29}$; and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$.

In one embodiment of Formula (IIb), W is —C(R$^{24}$)—; and Y is —C(R$^{26}$)—; A is —NR$^9$COR$^{10}$, —NHOR$^9$, —NR$^9$R$^{10}$, —NOR$^9$, —CONR$^9$R$^{10}$, —CO$_2$R$^9$, —NR$^9$CO$_2$R$^{10}$, —OR$^9$, —NR$^9$CONR$^{10}$R$^{11}$, —NR$^9$CSNR$^{10}$R$^{11}$ or —NR$^9$C(=NH)NR$^{10}$R$^{11}$; R$^{17}$ is hydrogen, alkyl, substituted alkyl, arylalkyl, or substituted arylalkyl; R$^{24}$ is hydrogen, alkyl, substituted alkyl, acyl, substituted acyl, heteroalkyl, substituted heteroalkyl, —CN, —NO$_2$, —OR$^{29}$, —S(O)$_g$R$^{29}$, —OCOR$^{29}$, —NR$^{29}$R$^{30}$, —CONR$^{29}$R$^{30}$ or —CO$_2$R$^{29}$; and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$. In a preferred embodiment, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$; R$^{17}$ is hydrogen, methyl, ethyl, propyl, iso-propyl, n-butyl, iso-butyl, sec-butyl, t-butyl, phenyl or benzyl; and R$^{24}$ is hydrogen, —CF$_3$, methyl, ethyl, propyl, iso-propyl, n-butyl, iso-butyl, sec-butyl or t-butyl; and R$^{26}$ is hydrogen, —CF$_3$, methyl, ethyl, propyl, iso-propyl, n-butyl, iso-butyl, sec-butyl or t-butyl. In a more preferred embodiment, A is —NH$_2$, R$^{17}$ is hydrogen or methyl, R$^{24}$ is hydrogen, —CF$_3$, methyl or ethyl, and R$^{26}$ is hydrogen, —CF$_3$, methyl or ethyl.

In some embodiments of Formula (IIb), R$^{28}$ is hydrogen, alkyl or arylalkyl.

In some embodiments of Formula (IIb), R$^{28}$ is hydrogen, methyl or benzyl.

In some specific embodiments of Formula (IIb), the compounds have structural formula selected from the group consisting of:

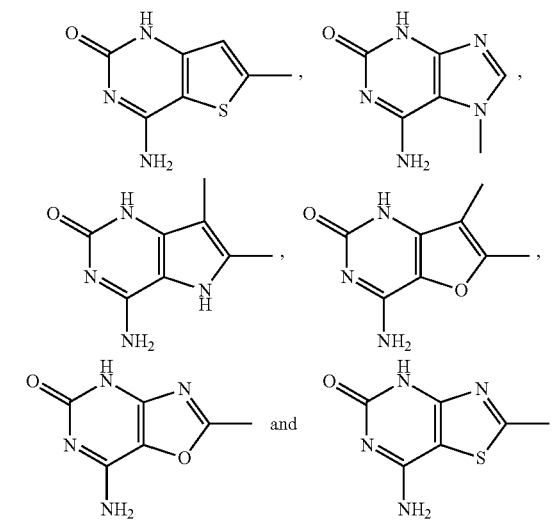

or a tautomer, salt, solvate, and/or ester thereof. In some preferred embodiments, the salt of these compounds is hydrochloride or trifluoroacetate salt.

In one embodiment of Formula (IIa), the compound of the present invention has structural Formula (IIc):

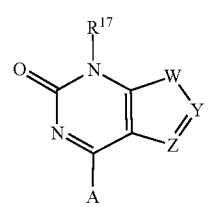

(IIc)

wherein, W is —S—, —N(R$^{25}$)—, or —O—; Y is —C(R$^{26}$)— or —N—; and Z is —C(R$^{27}$)— or —N—. In a preferred embodiment, Y is —C(R$^{26}$)—, and Z is —C(R$^{27}$)—.

In one embodiment of Formula (IIa), W is —S—, —N(R$^{25}$)—, or —O—; Y is —C(R$^{26}$)— or —N—; Z is —C(R$^{27}$)— or —N—; R$^{27}$ is hydrogen, alkyl, substituted alkyl, acyl, substituted acyl, heteroalkyl, substituted heteroalkyl, —CN, —NO$_2$, —OR$^{33}$, —S(O)$_i$R$^{33}$, —OCOR$^{33}$, —NR$^{33}$R$^{34}$, —CONR$^{33}$R$^{34}$ or —CO$_2$R$^{33}$; and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$.

In one embodiment of Formula (IIa), W is —S—, —N(R$^{25}$)—, or —O—; Y is —C(R$^{26}$)— or —N—; Z is —C(R$^{27}$)— or —N—; R$^{26}$ and R$^{27}$ together with the atom to which they are bonded form a cycloalkyl, substituted cycloalkyl, cycloheteroalkyl or substituted cycloheteroalkyl ring.

In one embodiment of Formula (IIa), W is —S—, —N(R$^{25}$)—, or —O—; Y is —C(R$^{26}$)— or —N—; Z is —C(R$^{27}$)— or —N—; A is hydrogen, alkyl, substituted alkyl, aryl, substituted aryl, —NR$^9$COR$^{10}$, —NHOR$^9$, —NOR$^9$, —OR$^9$, —NR$^9$CONR$^{10}$R$^{11}$, —NR$^9$CSNR$^{10}$R$^{11}$ or —NR$^9$C(=NH)NR$^{10}$R$^{11}$, —CN, —NO$_2$, —S(O)$_c$R$^9$, —NR$^9$R$^{10}$, —C(O)NR$^9$R$^{10}$, —CO$_2$R$^9$ or —NR$^9$CO$_2$R$^{10}$; and R$^{17}$ is hydrogen, alkyl, substituted alkyl, arylalkyl, or substituted arylalkyl.

In one embodiment of Formula (IIa), W is —S—, —N(R$^{25}$)—, or —O—; Y is —C(R$^{26}$)— or —N—; Z is —C(R$^{27}$)— or —N—; A is hydrogen, alkyl, substituted alkyl, aryl, substituted aryl, —NR$^9$COR$^{10}$, —NHOR$^9$, —NOR$^9$, —OR$^9$, —NR$^9$CONR$^{10}$R$^{11}$, —NR$^9$CSNR$^{10}$R$^{11}$ or —NR$^9$C(=NH)NR$^{10}$R$^{11}$, —CN, —NO$_2$, —S(O)$_c$R$^9$, —NR$^9$R$^{10}$, —NR$^9$C(O)R$^{10}$, —C(O)NR$^9$R$^{10}$, —CO$_2$R$^9$ or —NR$^9$CO$_2$R$^{16}$; R$^{17}$ is hydrogen, alkyl, substituted alkyl, arylalkyl, or substituted arylalkyl; R$^{27}$ is hydrogen, alkyl, substituted alkyl, acyl, substituted acyl, heteroalkyl, substituted heteroalkyl, —CN, —NO$_2$, —OR$^{33}$, —S(O)$_i$R$^{33}$, —OCOR$^{33}$, —NR$^{33}$R$^{34}$, —C(O)NR$^{33}$R$^{34}$ or —CO$_2$R$^{33}$; and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OC(O)R$^{31}$, —NR$^{31}$R$^{32}$, —C(O)NR$^{31}$R$^{32}$ or —CO$_2$R$^{31}$, or alternatively R$^{26}$ and R$^{27}$ together with the atom(s) to which they are bonded form a cycloalkyl, substituted cycloalkyl, cycloheteroalkyl or substituted cycloheteroalkyl ring. In a more preferred embodiment, A is —NH$_2$; R$^{17}$ is hydrogen, methyl, ethyl, propyl, iso-propyl, n-butyl, iso-butyl, sec-butyl, t-butyl, phenyl or benzyl; R$^{26}$ and R$^{27}$ are independently hydrogen, alkanyl, substituted alkanyl, alkoxy, carboxylic acid, carboxylic acid amide, or carboxylic acid ester; or alternatively, R$^{26}$ and R$^{27}$ together with the atom(s) to which they are bonded form a cycloalkyl, substituted cycloalkyl, cycloheteroalkyl or substituted cycloheteroalkyl ring.

In some specific embodiments of Formula (IIa), the compounds have structural formula selected from the group consisting of:

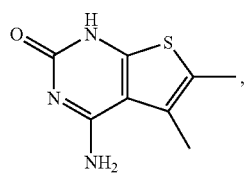
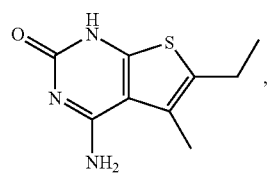

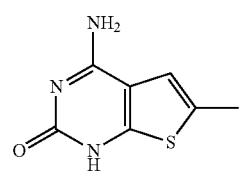
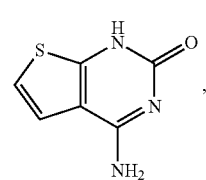

-continued

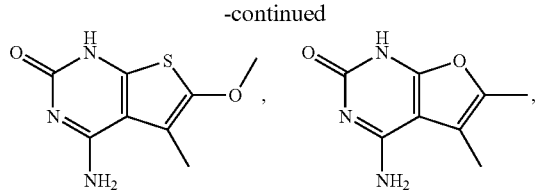

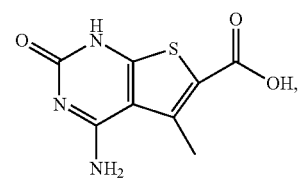

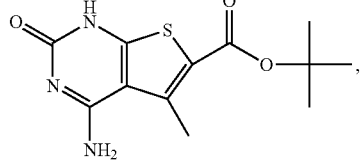

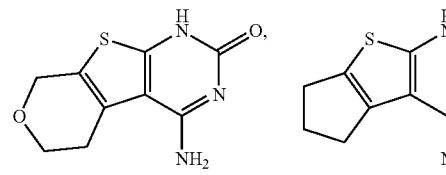

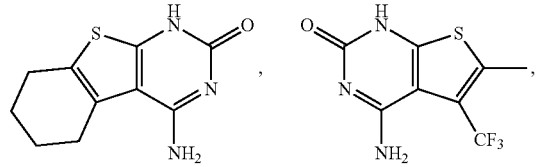

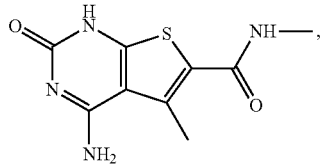

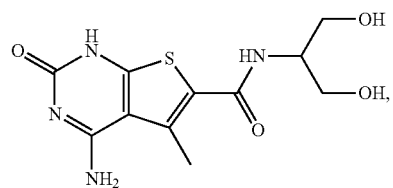

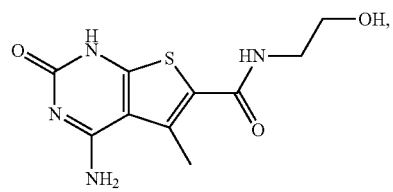

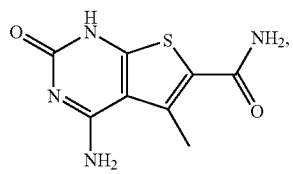

-continued

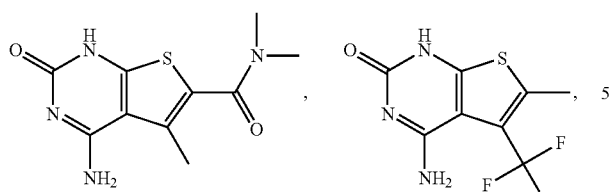

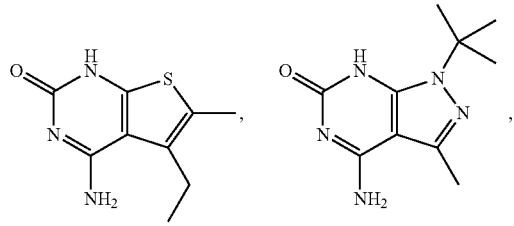

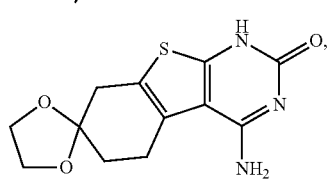

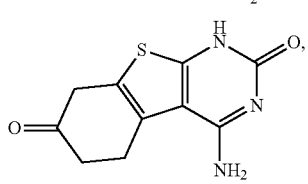

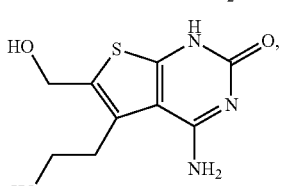

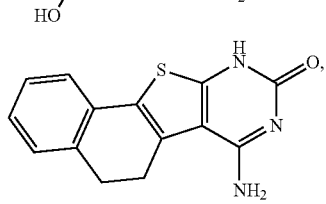

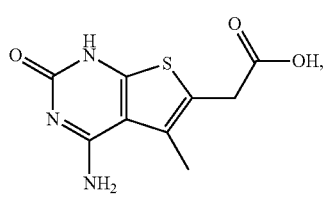

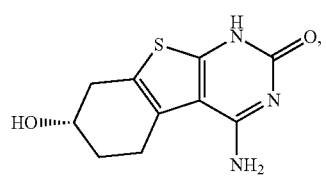

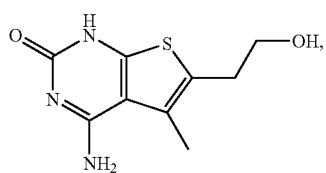

-continued

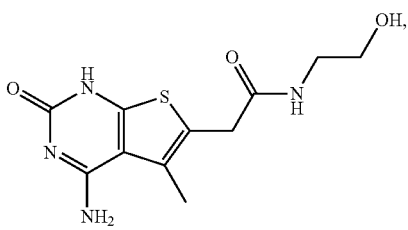

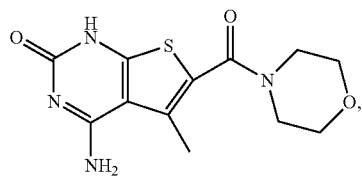

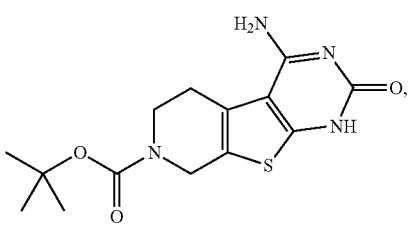

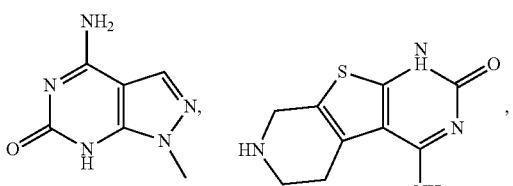

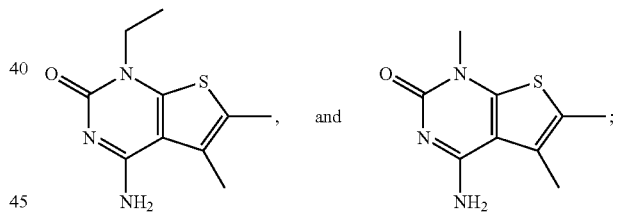

or a tautomer, salt, solvate, and/or ester thereof. In some preferred embodiments, the salt of these compounds is hydrochloride or trifluoroacetate salt.

In one embodiment of Formula (II), the compound of the present invention has structural Formula (IIe):

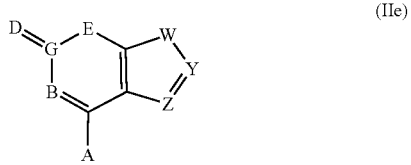

(IIe)

wherein, G forms a single bond with E and a double bond with D; B is —N—; E is —NR$^{17}$—; D is =S, =N—OR$^{15}$, or =N—NHR$^{15}$; W is —S—, —N(R$^{25}$)— or —O—; Y is —C(R$^{26}$)—; and Z is —C(R$^{27}$)—.

In one embodiment of Formula (II), the compound of the present invention has structural Formula (IIf):

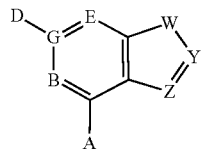
(IIf)

wherein,

G forms a double bond with E and a single bond with D;

B is —N—;

E is —N—;

D is —OR$^{15}$, —NH—OR$^{15}$, —NH—NHR$^{15}$, —S(O)$_e$R$^{15}$, or —NR$^{15}$R$^{16}$;

W is —S—, —N(R$^{25}$)— or —O—;

Y is —C(R$^{26}$)—; and

Z is —C(R$^{27}$)—.

In one embodiment of Formula (IIe) or (IIf), A is hydrogen, alkyl, substituted alkyl, aryl, substituted aryl, —OR$^9$, —SR$^9$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$. More preferably, R$^{17}$ is hydrogen, alkyl, substituted alkyl, arylalkyl, or substituted arylalkyl; R$^{26}$ and R$^{27}$ are independently hydrogen, alkanyl, substituted alkanyl, alkoxy; or alternatively, R$^{26}$ and R$^{27}$ together with the atom(s) to which they are bonded form a cycloalkyl, substituted cycloalkyl, cycloheteroalkyl or substituted cycloheteroalkyl ring.

In some specific embodiments of Formula (IIe) or (IIf), the compound of the present invention has structural formula selected from the group consisting of

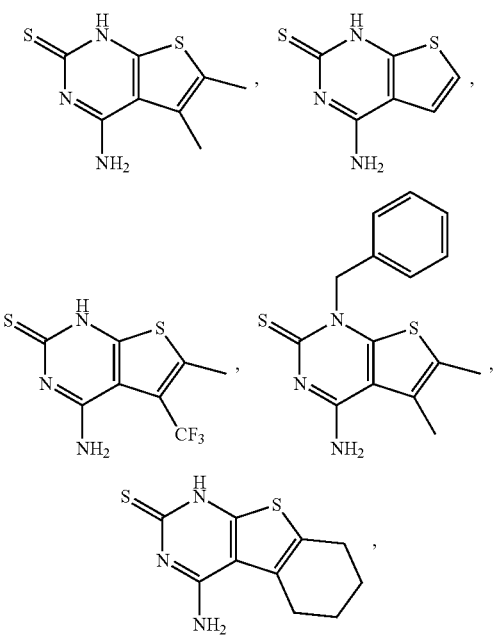

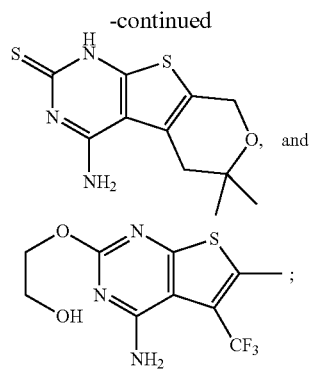

or a tautomer, salt, solvate, and/or ester thereof. In some preferred embodiments, the salt of these compounds is hydrochloride or trifluoroacetate salt.

In a embodiment of Formula (II), the compound of the present invention has structural Formula (IId):

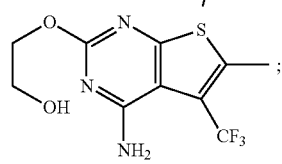
(IId)

with the following provisos:

(a) when W is —O— or —S— or —NR$^{25}$, then Z is —C(R$^{27}$)— or —N—; and (b) when Z is —O— or —S— or —NR$^{28}$, then W is —C(R$^{24}$)— or —N—.

In a embodiment of Formula (IId), W is —S—, NR$^{25}$, —O—; Y is —CR$^{26}$—; Z is —C(R$^{27}$)—; and W and Y forms a single bond and Y and Z forms a double bond.

In a embodiment of Formula (IId), W is —C(R$^{24}$)—; Y is —CR$^{26}$—; Z is —S—, —NR$^{28}$—, —O—; and W and Y forms a double bond and Y and Z forms a single bond.

In a embodiment of Formula (IId), W is —S—, NR$^{25}$, —O—; Y is —N—; Z is —C(R$^{27}$)—; and W and Y forms a single bond and Y and Z forms a double bond.

In a embodiment of Formula (IId), W is —NR$^{25}$; Y is —N—; and Z is —C(R$^{27}$)—; and Y forms a single bond with each of W and a double bond with Z.

In some embodiments of Formula (IId), A is hydrogen, alkyl, substituted alkyl, aryl, substituted aryl, —OR$^9$, —SR$^9$, —CN; —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$. Preferably, R$^{17}$ is hydrogen. More preferably, R$^{26}$ and R$^{27}$ are independently hydrogen, alkanyl, substituted alkanyl, alkoxy, carboxylic acid, carboxylic acid ester; or alternatively, R$^{26}$ and R$^{27}$ together with the atom(s) to which they are bonded form a cycloalkyl or substituted cycloalkyl ring.

In some specific embodiments of Formula (IId), the compound of the present invention has structural formula selected from the group consisting of:

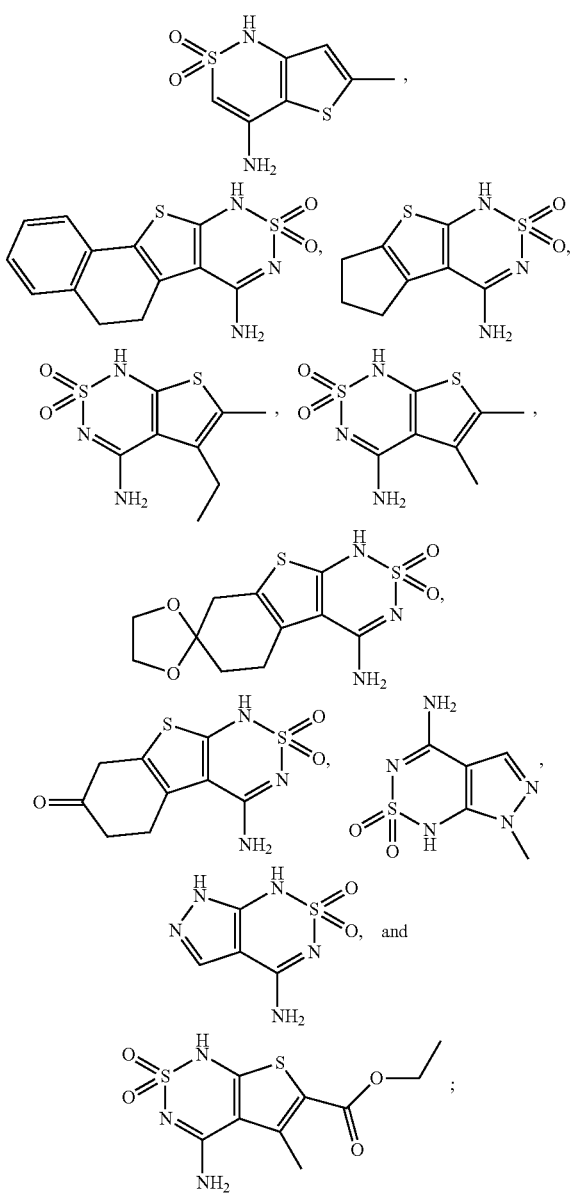

or a tautomer, salt, solvate, and/or ester thereof. In some preferred embodiments, the salt of these compounds is hydrochloride salt or trifluoroacetate salt.

In one embodiment of Formula (I), the chemosensory receptor ligand modifier is a compound having a structural Formula (III):

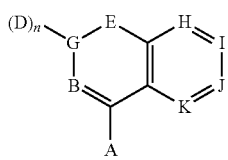

(III)

wherein:
H is —C($R^{35}$)— or —N—;
I is —C($R^{36}$) or —N—;
J is —C($R^{37}$)— or —N—;
K is —C($R^{38}$)— or —N—;

$R^{35}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —$NO_2$, —$OR^{39}$, —S(O)$_j R^{39}$, —$NR^{39}R^{40}$, —$CONR^{39}R^{40}$, —$CO_2R^{39}$, —$SO_2NR^{39}R^{40}$, —$NR^{39}SO_2R^{40}$, —B($OR^{39}$)($OR^{40}$), —P(O)($OR^{39}$)($OR^{40}$) or —P(O)($R^{39}$)($OR^{40}$);

$R^{36}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —$NO_2$, —$OR^{41}$, —S(O)$_k R^{41}$, —$NR^{41}R^{42}$, —$CONR^{41}R^{42}$, —$CO_2R^{41}$, —$OCOR^{41}$, —$SO_2NR^{41}R^{42}$, —$NR^{41}SO_2R^{42}$, —B($OR^{41}$)($OR^{42}$), —P(O)($OR^{41}$)($OR^{42}$) or —P(O)($R^{41}$)($OR^{42}$);

$R^{37}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —$NO_2$, —$OR^{43}$, —S(O)$_l R^{43}$, —$NR^{43}R^{44}$, —$CONR^{43}R^{44}$, —$CO_2R^{43}$, —$OCOR^{43}$, —$SO_2NR^{43}R^{44}$, —$NR^{43}SO_2R^{44}$, —B($OR^{43}$)($OR^{44}$), —P(O)($OR^{43}$)($OR^{44}$) or —P(O)($R^{43}$)($OR^{44}$); or alternatively $R^{36}$ and $R^{37}$, taken together with the atom to which they are bonded, form a cycloalkyl, substituted cycloalkyl, cycloheteroalkyl, or substituted cycloheteroalkyl ring;

$R^{38}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —$NO_2$, —$OR^{45}$, —S(O)$_m R^{45}$, —$NR^{45}R^{46}$, —$CONR^{45}R^{46}$, —$COR^{45}$, —$CO_2R^{45}$, —$OCOR^{45}$, —$SO_2NR^{45}R^{46}$, —$NR^{45}SO_2R^{46}$, —B($OR^{45}$)($OR^{46}$), —P(O)($OR^{45}$)($OR^{46}$) or —P(O)($R^{45}$)($OR^{46}$);

j, k, l and m are independently 0, 1 or 2; and $R^{39}$, $R^{40}$, $R^{41}$, $R^{42}$, $R^{43}$, $R^{44}$, $R^{45}$, and $R^{46}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively $R^{39}$ and $R^{40}$, $R^{41}$ and $R^{42}$, $R^{43}$ and $R^{44}$, or $R^{45}$ and $R^{46}$ together with the atoms to which they are bonded form a cycloheteroalkyl or substituted cycloheteroalkyl ring;

with the proviso that at most, two of H, I, J and K are —N—. By "at most two of H, I, J and K are —N—", it is meant that there are zero nitrogen atom, one nitrogen atom, or two nitrogen atoms among H, I, I and K.

In one embodiment of Formula (III), (D)$_n$-G is

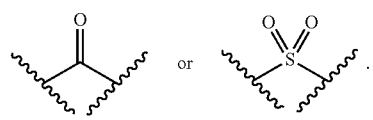

In one embodiment of Formula (III), the compound of the present invention has structural Formula (IIIa):

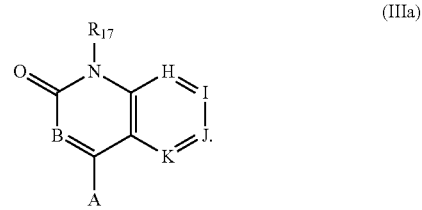

(IIIa)

In one embodiment of Formula (IIIa), A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^9$, —NO$_2$, —S(O)$_c$R$^9$, —NHOR$^9$, —NR$^9$COR$^{10}$, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$, or —NR$^9$C(=NH)NR$^{10}$R$^{11}$. Preferably, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$.

In one embodiment of Formula (IIIa), R$^{17}$ is hydrogen, alkyl, substituted alkyl, arylalkyl, or substituted arylalkyl. Preferably, R$^{17}$ is hydrogen, methyl, ethyl, propyl, iso-propyl, n-butyl, iso-butyl, sec-butyl, t-butyl, phenyl or benzyl.

In one embodiment of Formula (IIIa), H is —C(R$^{35}$)—; I is —C(R$^{36}$); J is —C(R$^{37}$)—; and K is —C(R$^{38}$)—.

In one embodiment of Formula (IIIa), A is hydrogen, alkyl, substituted alkyl, aryl, substituted aryl, —CN, —OR$^9$, —NO$_2$, —S(O)$_c$R$^9$, —NHOR$^9$, —NR$^9$COR$^{10}$, —NR$^9$R$^{10}$, —CONR$^9$R$^{10}$, —CO$_2$R$^9$ or —NR$^9$CO$_2$R$^{10}$; and R$^{17}$ is hydrogen, alkyl, substituted alkyl, arylalkyl, or substituted arylalkyl.

In one embodiment of Formula (IIIa), A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$; and R$^{17}$ is hydrogen, methyl, ethyl, propyl, iso-propyl, n-butyl, iso-butyl, sec-butyl, t-butyl, phenyl or benzyl.

In one embodiment of Formula (IIIa), R$^{35}$ is hydrogen, alkyl, substituted alkyl, halo, heteroalkyl, substituted heteroalkyl, —CN, —NO$_2$, —OR$^{39}$, —S(O)R$^{39}$, —OCOR$^{39}$, —NR$^{39}$COR$^{40}$, —CONR$^{39}$R$^{40}$, —CO$_2$R$^{39}$, NR$^{39}$R$^{40}$, —SO$_2$NR$^{39}$R$^{40}$, or —NR$^{39}$SO$_2$R$^{40}$; R$^{36}$ is hydrogen, alkyl, substituted alkyl, halo, heteroalkyl, substituted heteroalkyl, —CN, —NO$_2$, —OR$^{41}$, —S(O)$_j$R$^{41}$, —OCOR$^{41}$, NR$^{41}$R$^{42}$, —NR$^{41}$COR$^{42}$, —CONR$^{41}$R$^{42}$, —CO$_2$R$^{41}$, —SO$_2$NR$^{41}$R$^{42}$, or —NR$^{41}$SO$_2$R$^{42}$; R$^{37}$ is hydrogen, alkyl, substituted alkyl, halo, heteroalkyl, substituted heteroalkyl, —CN, —NO$_2$, —OR$^{43}$, —S(O)$_j$R$^{43}$, —OCOR$^{43}$, NR$^{43}$R$^{44}$, —NR$^{43}$COR$^{44}$, —CONR$^{43}$R$^{44}$, —CO$_2$R$^{43}$, —SO$_2$NR$^{43}$R$^{44}$, or —NR$^{43}$SO$_2$R$^{44}$; or alternatively R$^{36}$ and R$^{37}$, together with the atoms to which they are bonded, form a cycloheteroalkyl or substituted cycloheteroalkyl ring; and R$^{38}$ is hydrogen, alkyl, substituted alkyl, halo, heteroalkyl, substituted heteroalkyl, —CN, —NO$_2$, —OR$^{45}$, —S(O)$_j$R$^{45}$, —OCOR$^{45}$, NR$^{45}$R$^{46}$, —NR$^{45}$COR$^{46}$, —CONR$^{45}$R$^{46}$, —CO$_2$R$^{45}$, —SO$_2$NR$^{45}$R$^{46}$, —NR$^{45}$SO$_2$R$^{46}$. It is preferable that R$^{38}$ is hydrogen, alkanyl, substituted alkanyl, alkenyl, substituted alkenyl, cycloalkanyl, substituted cycloalkanyl, cycloalkenyl, substituted cycloalkenyl, halo, heteroalkyl, substituted heteroalkyl, —CN, —NO$_2$, —OR$^{45}$, —S(O)$_j$R$^{45}$, —OCOR$^{45}$, NR$^{45}$R$^{46}$, —NR$^{45}$COR$^{46}$, —CONR$^{45}$R$^{46}$, —CO$_2$R$^{45}$, —SO$_2$NR$^{45}$R$^{46}$, —NR$^{45}$SO$_2$R$^{46}$. It is also preferable that A is —NH$_2$, R$^{17}$ is hydrogen, methyl, ethyl or benzyl; and R$^{35}$, R$^{36}$, R$^{37}$ and R$^{38}$ are independently hydrogen, fluoro, chloro, bromo, methyl, trifluoromethyl, ethyl, isopropyl, cyclopropyl, propenyl, methylpropenyl, butenyl, methylbutenyl, substituted propenyl, substituted methylpropenyl, substituted butenyl, substituted methylbutenyl, —NH-alkanyl, —NH-(substituted alkanyl), —OH, —OCH$_3$, —O-cycloalkanyl, —O-benzyl, —CO$_2$H.

In some specific embodiments of Formula (IIIa), the compound has structural formula selected from the group consisting of

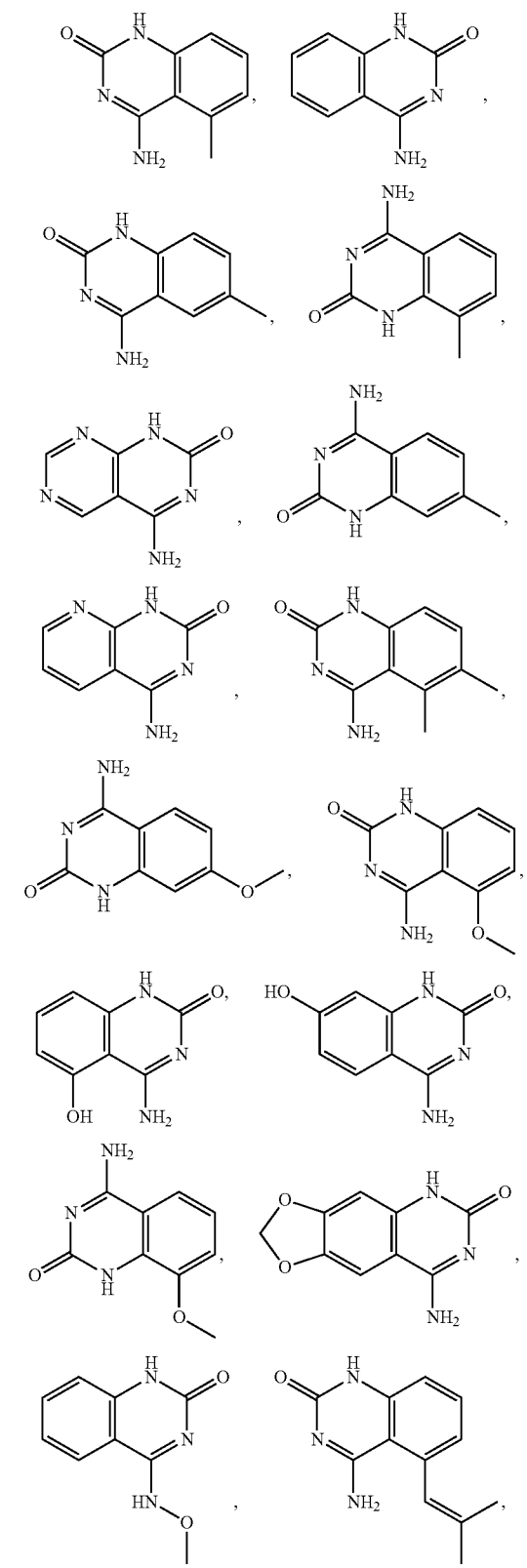

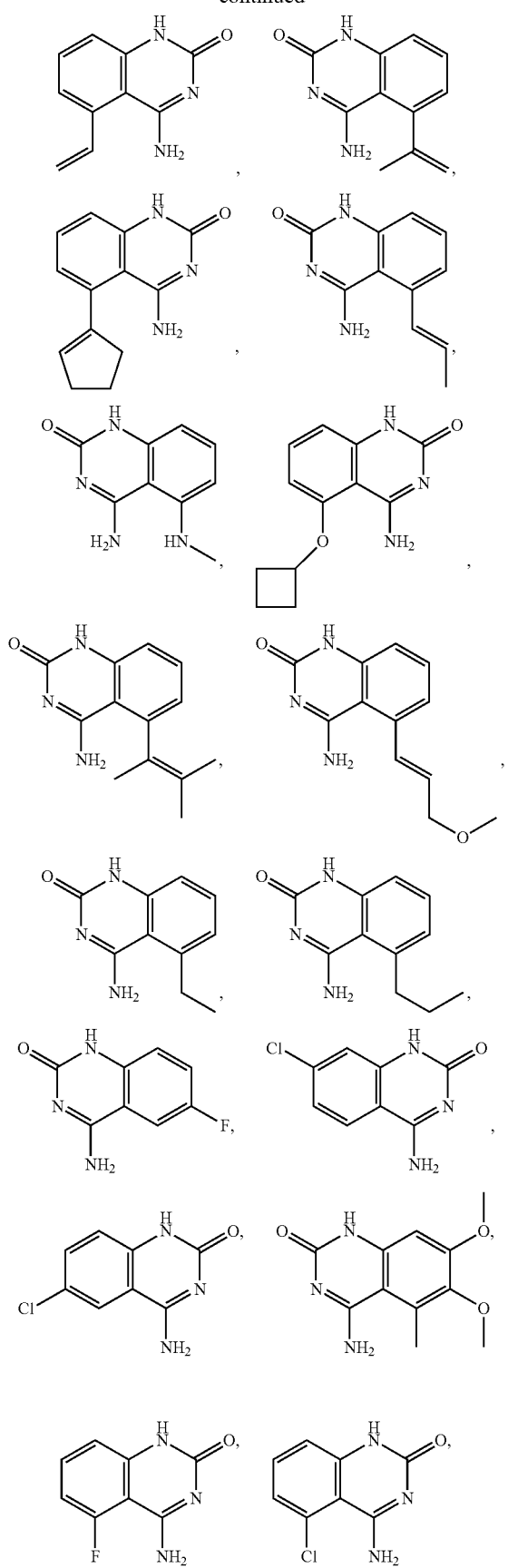
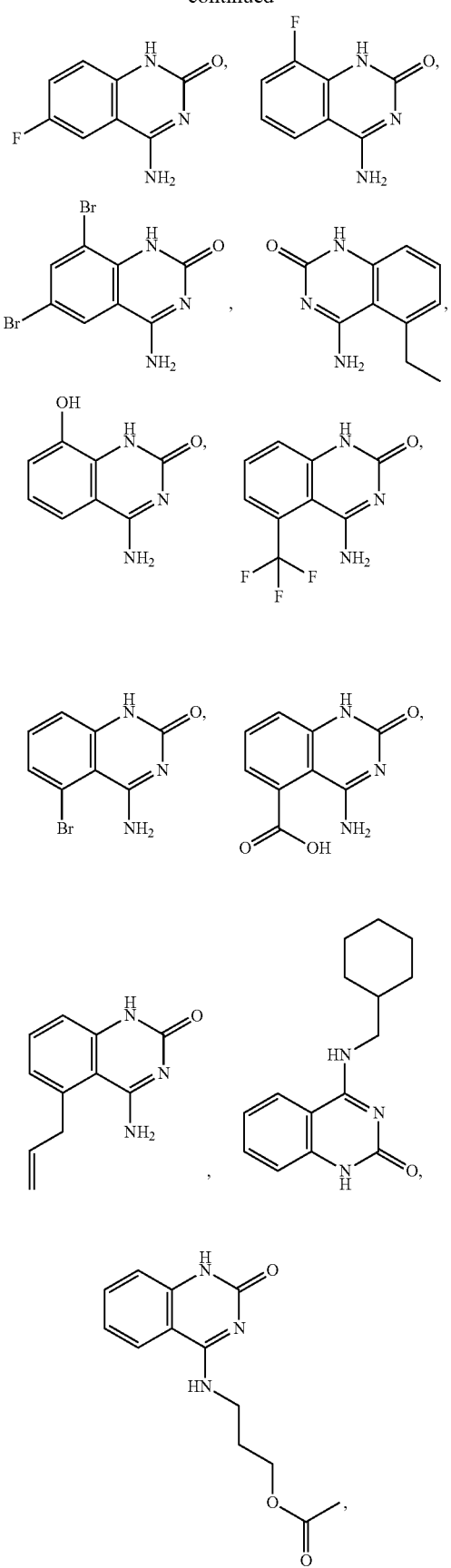

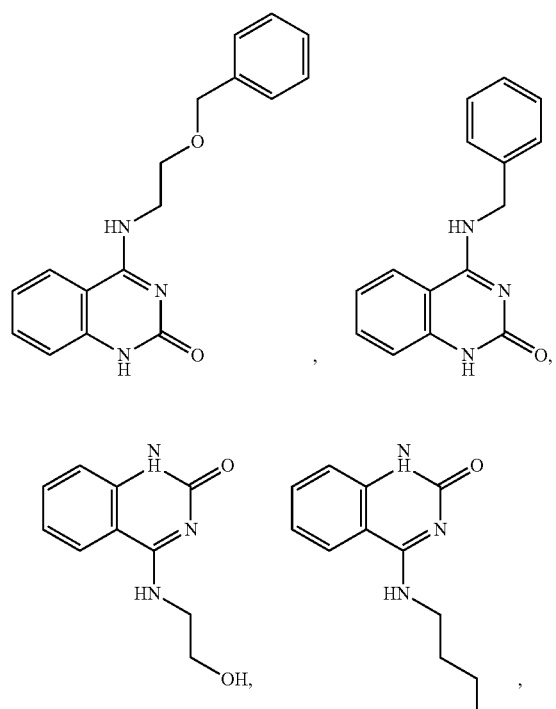
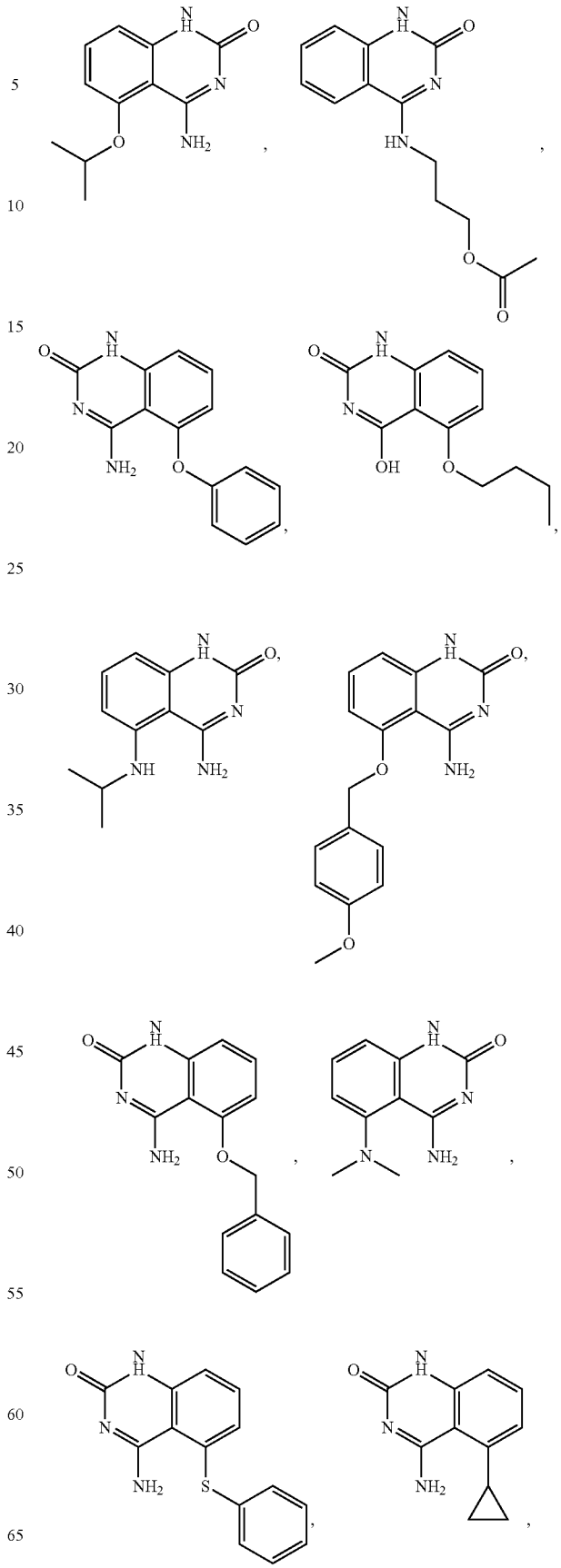

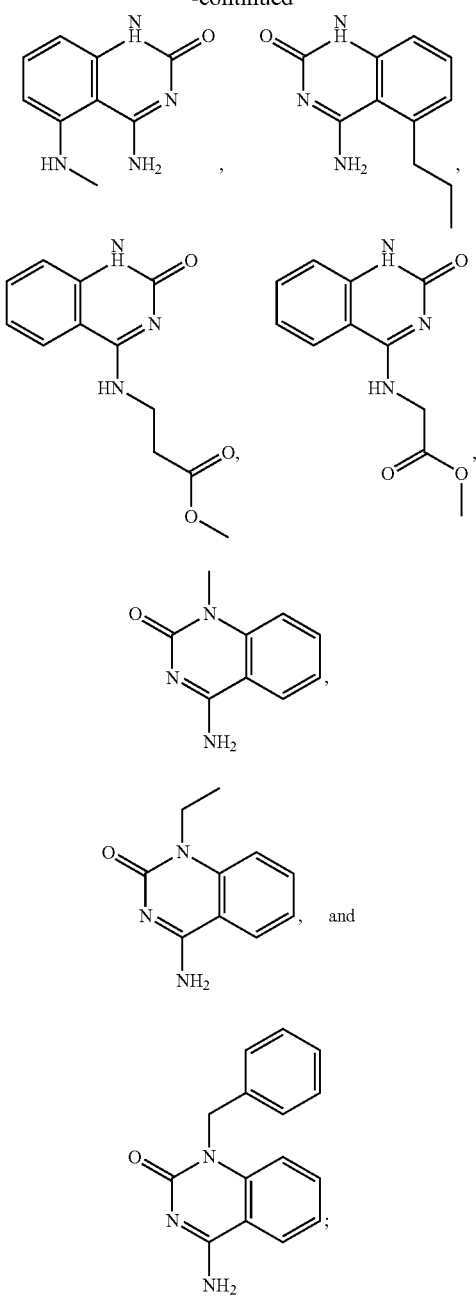

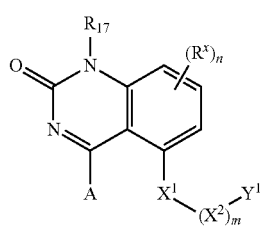

or a tautomer, salt, solvate, and/or ester thereof. In some preferred embodiments, the salt of these compounds is hydrochloride or trifluoroacetate salt.

In one embodiment of Formula (IIIa), the compound of the present invention has structural Formula (IIIa1):

(IIIa1)

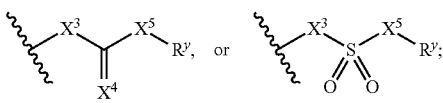

wherein,

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^9$, —NO$_2$, —S(O)$_c$R$^9$, —NOR$^9$, —NHOR$^9$, —NR$^9$COR$^{10}$, —NR$^9$R$^{10}$, —CONR$^9$R$^{10}$, —CO$_2$R$^9$ or —NR$^9$CO$_2$R$^{10}$;

R$^{17}$ is hydrogen, alkyl, substituted alkyl, arylalkyl, or substituted arylalkyl;

X$^1$ is —CH$_2$—, —O—, —NR$^9$—, —S—, —S(O)—, or —S(O)$_2$—;

X$^2$ is alkylene, substituted alkylene, heteroalkylene, or substituted heteroalkylene;

m is 0 or 1;

Y$^1$ is cycloheteroalkyl, substituted cycloheteroalkyl, or

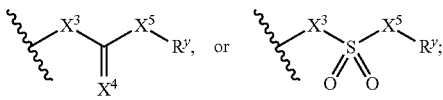

X$^3$ and X$^5$ are independently a covalent bond, —O— or —NR$^9$—;

X$^4$ is O, NR$^9$, N—OR$^9$, or S;

R$^x$ is halo, —NO$_2$, —CN, —OH, —NH$_2$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

n is 0, 1, 2, or 3;

R$^y$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl, —NR$^9$R$^{10}$; and each R$^9$ and R$^{10}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

with the proviso that when X$^1$ is —O— or —S—, and m is zero; then X$^3$ is not —O—.

In one embodiment of Formula (IIIa1), X$^1$ is —CH$_2$—; and Y$^1$ is

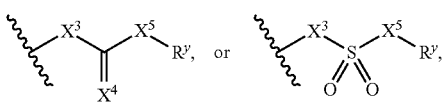

In one embodiment of Formula (IIIa1), X$^1$ is —O—, —NR$^9$—, or —S—; m is 0 or 1, and Y$^1$ is cycloheteroalkyl or substituted cycloheteroalkyl.

In one embodiment of Formula (IIIa1), X$^1$ is —O—, —NR$^9$—, or —S—; m is 1, and Y$^1$ is

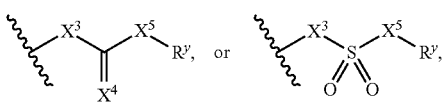

In some embodiments of Formula (IIIa1), X$^2$ is methylene, ethylene, propylene, dimethylethylene, methylcyclopropylene, or cyclopropylmethylene.

In some embodiments of Formula (IIIa1), A is hydrogen, alkyl, substituted alkyl, —CN, —OR$^9$, —NO$_2$, —S(O)$_c$R$^9$, —NOR$^9$, —NHOR$^9$, —NR$^9$COR$^{10}$, —NR$^9$R$^{10}$, —CONR$^9$R$^{10}$, —CO$_2$R$^9$ or —NR$^9$CO$_2$R$^{10}$.

In some embodiments of Formula (IIIa1), R$^{17}$ is hydrogen, alkyl, substituted alkyl.

In some embodiments of Formula (IIIa1), $Y^1$ is cycloheteroalkyl or substituted cycloheteroalkyl. It is preferable that $Y^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, or substituted oxetanyl. It is also preferable that the substituted cycloheteroalkyl comprises one or more substituents selected from the group consisting of alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^9$, —NO$_2$, —S(O)$_c$R$^9$, —NOR$^9$, —NHOR$^9$, —NR$^9$COR$^{10}$, —NR$^9$R$^{10}$, —CONR$^9$R$^{10}$, —CO$_2$R$^9$, and —NR$^9$CO$_2$R$^{10}$.

In some embodiments of Formula (IIIa1), $X^4$ is O.

In some embodiments of Formula (IIIa1), —X$^3$—C(X$^4$)—X$^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —O—C(NH)—O—, —NH—C(NH)—O—, —O—C(NH)—NH—, —C(N—OH)—, or —C(S)—.

In some embodiments of Formula (IIIa1), A is hydrogen, alkyl, substituted alkyl, or —NR$^9$R$^{10}$; R$^{17}$ is hydrogen; and $Y^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, or substituted oxetanyl.

In some embodiments of Formula (IIIa1), A is hydrogen, alkyl, substituted alkyl, or —NR$^9$R$^{10}$; R$^{17}$ is hydrogen; $Y^1$ is —X$^3$—C(X$^4$)—X$^5$—; and —X$^3$—C(X$^4$)—X$^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —O—C(NH)—O—, —NH—C(NH)—O—, —O—C(NH)—NH—, —C(N—OH)—, or —C(S)—.

In some specific embodiments of Formula (IIIa1), the compound has structural formula selected from the group consisting of

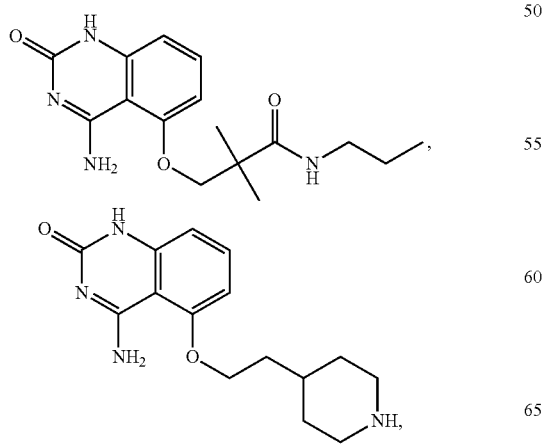
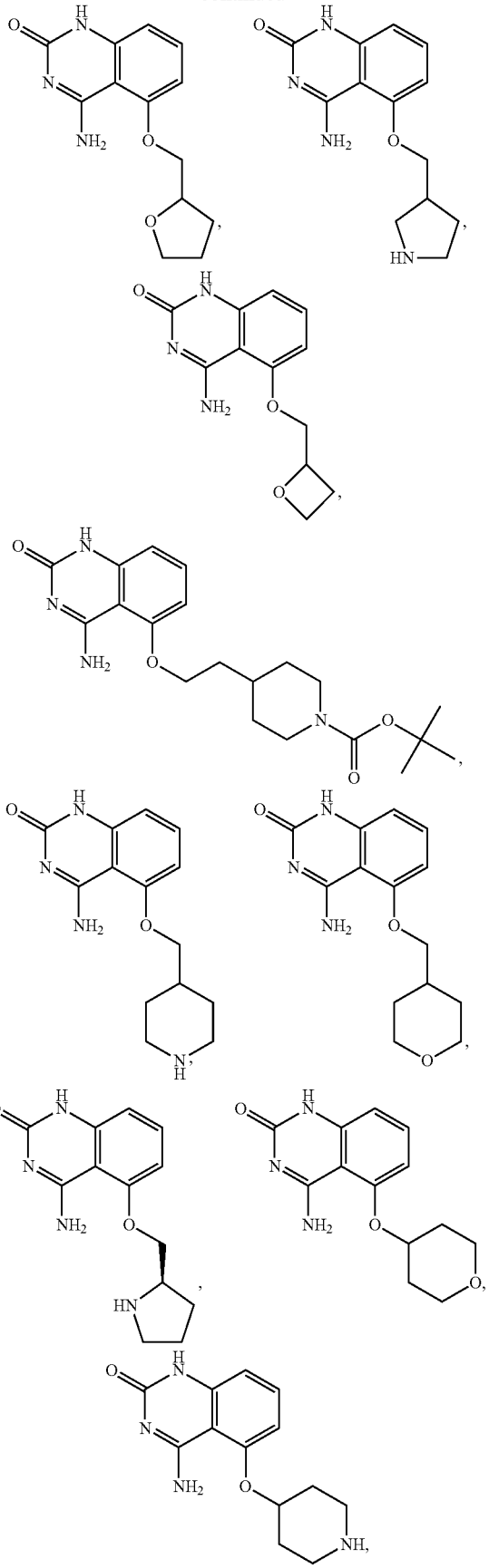

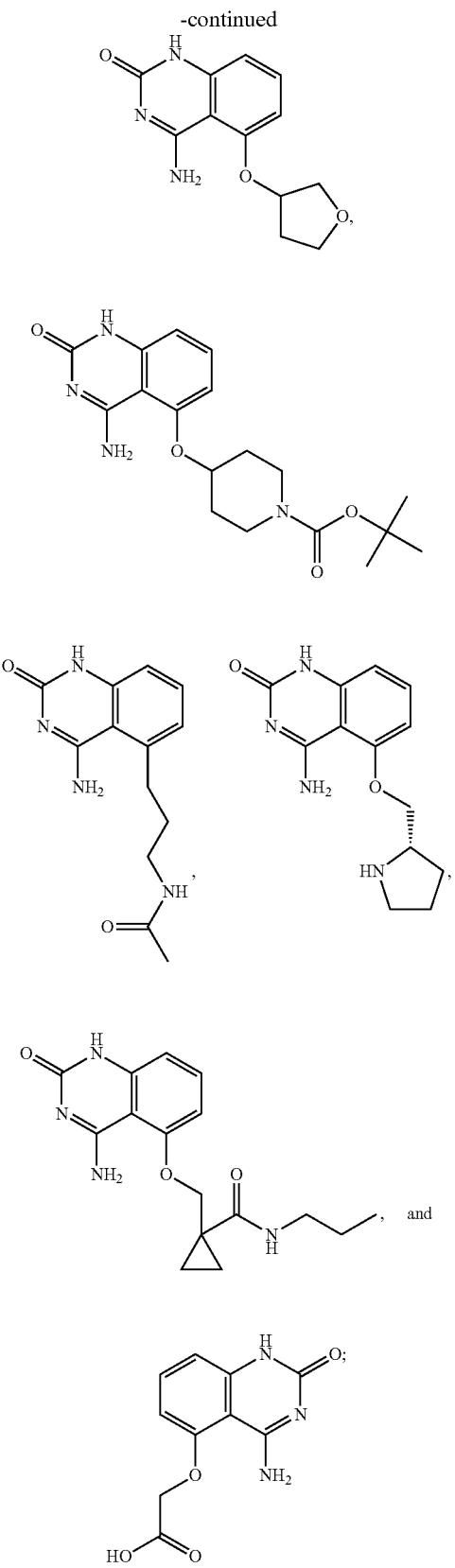

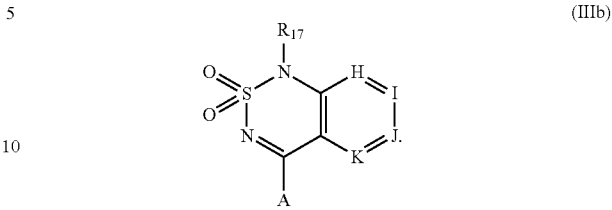

or a tautomer, salt, solvate, and/or ester thereof. In some preferable embodiments, the salt of these compounds is hydrochloride or trifluoroacetate salt.

In one embodiment of Formula (III), the compound of the present invention has structural Formula (IIIb):

In one embodiment of Formula (IIIb), A is hydrogen, alkyl, substituted alkyl, aryl, substituted aryl, —CN, —NO$_2$, —OR$^9$, —S(O)$_c$R$^9$, —NR$^9$COR$^{10}$, —NHOR$^9$, —NR$^9$R$^{10}$, —NOR$^9$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$, or —NR$^9$C(=NH)NR$^{10}$R$^{11}$.

In one embodiment of Formula (IIIb), R$^{17}$ is hydrogen, alkyl, or substituted alkyl.

In one embodiment of Formula (IIIb), A is hydrogen, alkyl, substituted alkyl, aryl, substituted aryl, —OR$^1$, —SR$^1$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$; and R$^{17}$ is hydrogen, alkyl, or substituted alkyl.

In one embodiment of Formula (IIIb), H is —C(R$^{35}$)— or —N—; I is —C(R$^{36}$)—; J is —C(R$^{37}$)—; and K is —C(R$^{38}$)— or —N—.

In one embodiment of Formula (IIIb), H is —C(R$^{35}$)—; I is —C(R$^{36}$)—; J is —C(R$^{37}$)—; and K is —C(R$^{38}$)—.

In one embodiment of Formula (IIIb), R$^{35}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —NO$_2$, —OR$^{39}$, —S(O)$_j$R$^{39}$, —OCOR$^{39}$, —NR$^{39}$R$^{40}$, —CONR$^{39}$R$^{40}$, —CO$_2$R$^{39}$, —SO$_2$NR$^{39}$R$^{40}$, —NR$^{39}$SO$_2$R$^{40}$; R$^{36}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —NO$_2$, —OR$^{41}$, —S(O)$_k$R$^{41}$, —OCOR$^{41}$, —NR$^{41}$R$^{42}$, —CONR$^{41}$R$^{42}$, —CO$_2$R$^{41}$, —SO$_2$NR$^{41}$R$^{42}$, —NR$^{41}$SO$_2$R$^{42}$; R$^{37}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —NO$_2$, —OR$^{43}$, —S(O)$_l$R$^{43}$, —OCOR$^{43}$, —NR$^{43}$R$^{44}$, —CONR$^{43}$R$^{44}$, —CO$_2$R$^{43}$, —SO$_2$NR$^{43}$R$^{44}$, —NR$^{43}$SO$_2$R$^{44}$; R$^{38}$ is hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —NO$_2$, —OR$^{45}$, —S(O)$_m$R$^{45}$, —OCOR$^{45}$, —NR$^{45}$R$^{46}$, —CONR$^{45}$R$^{46}$, —COR$^{45}$, —CO$_2$R$^{45}$, —SO$_2$NR$^{45}$R$^{46}$, —NR$^{45}$SO$_2$R$^{46}$.

In one embodiment of Formula (IIIb), A is —NH$_2$, R$^{17}$ is hydrogen, methyl, ethyl or benzyl; and R$^{35}$, R$^{36}$, R$^{37}$ and R$^{38}$ are independently hydrogen, fluoro, chloro, bromo, —CN, alkanyl, substituted alkanyl, alkenyl, substituted alkenyl, alkynyl, substituted alkynyl, cycloalkanyl, substituted cycloalkanyl, cycloalkenyl, substituted cycloalkenyl, heteroalkanyl, substituted heteroalkanyl, cycloheteroalkyl, substituted cycloheteroalkyl, —O-alkanyl, —O-(substituted alkanyl), —O-alkenyl, —O-(substituted alkenyl), —NH-alkanyl, —NH-(substituted alkanyl), —NH-alkenyl, —NH- (substituted alkenyl), —S-alkanyl, —S-(substituted alkanyl), —S-alkenyl, or —S-(substituted alkenyl).
In some specific embodiments of Formula (Mb), the compound has structural formula selected from the group consisting of:
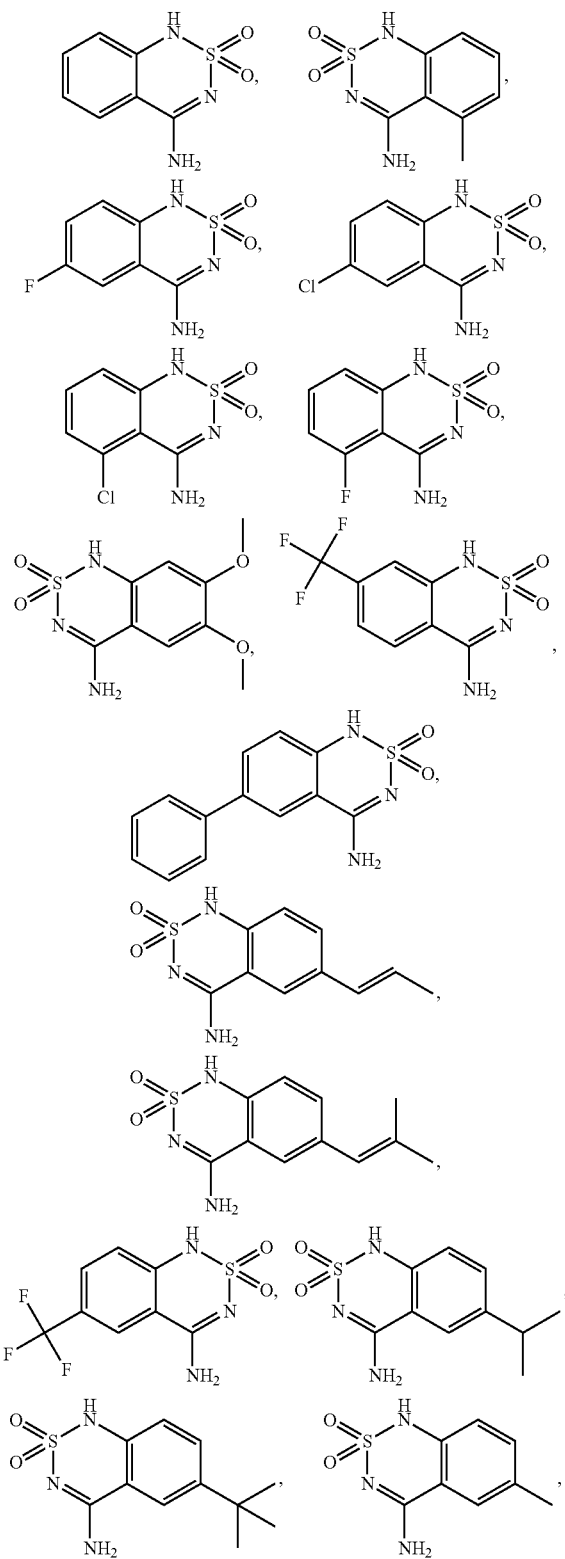
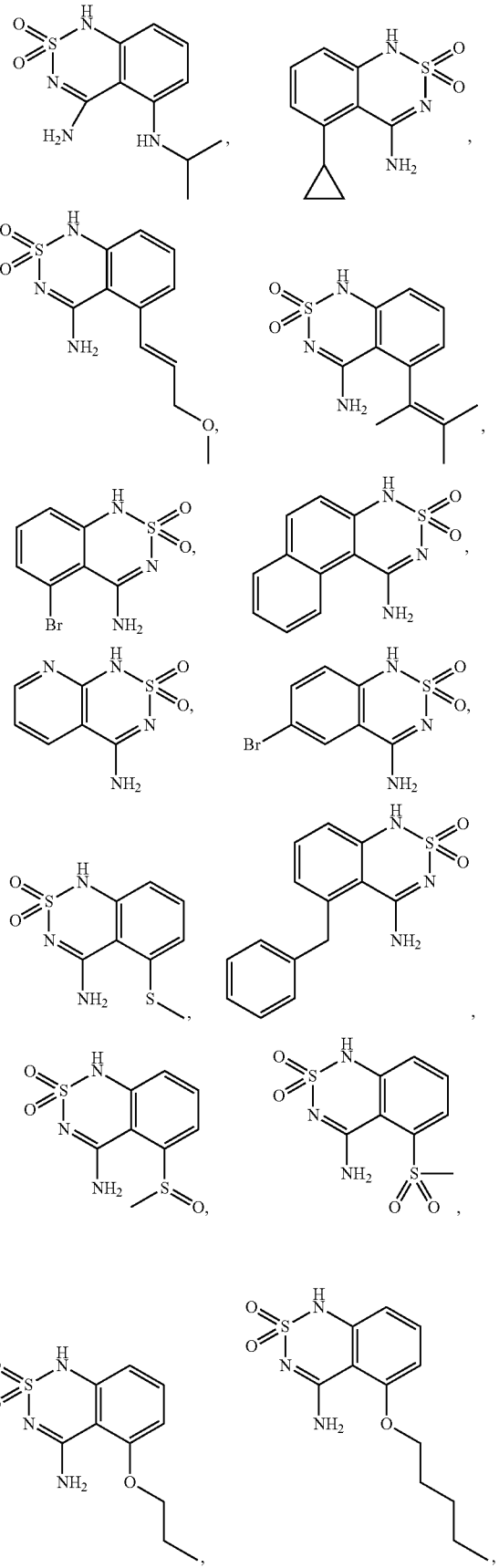

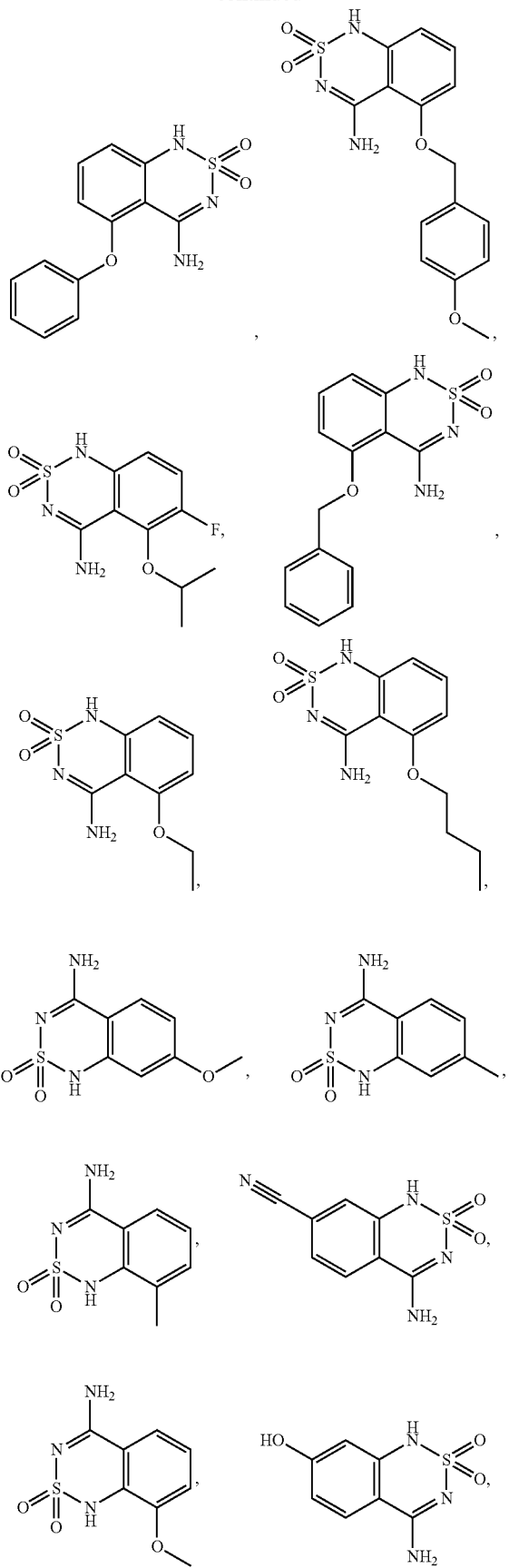
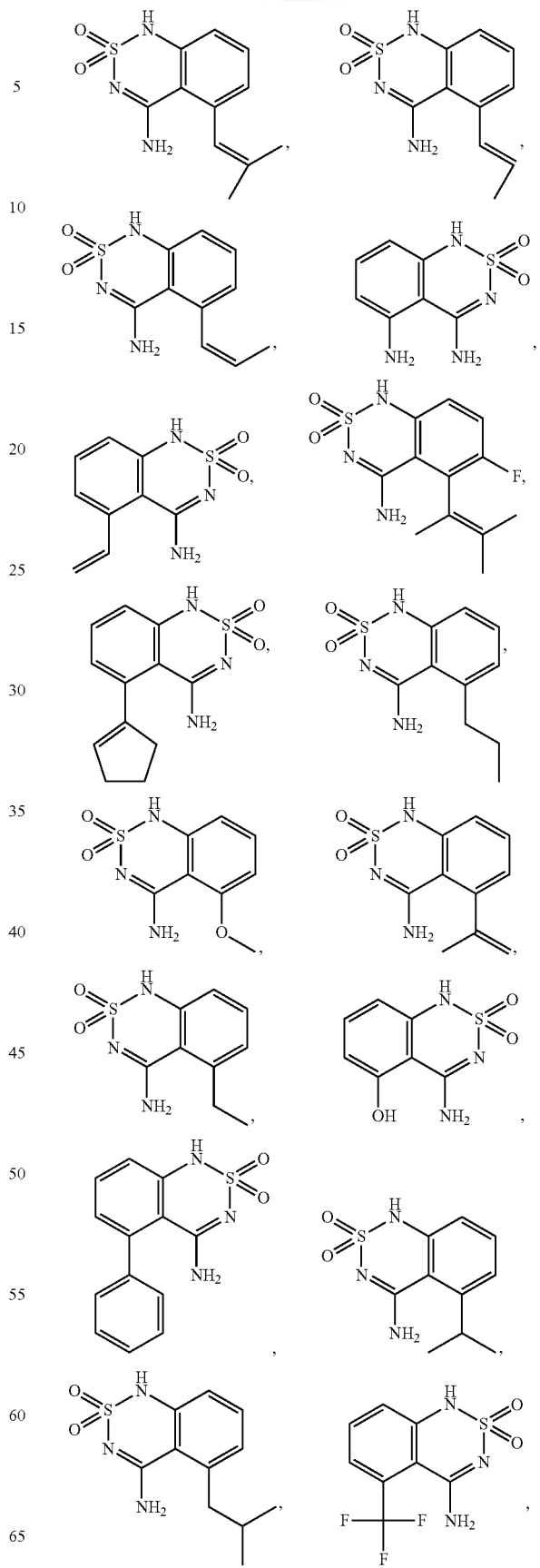

-continued
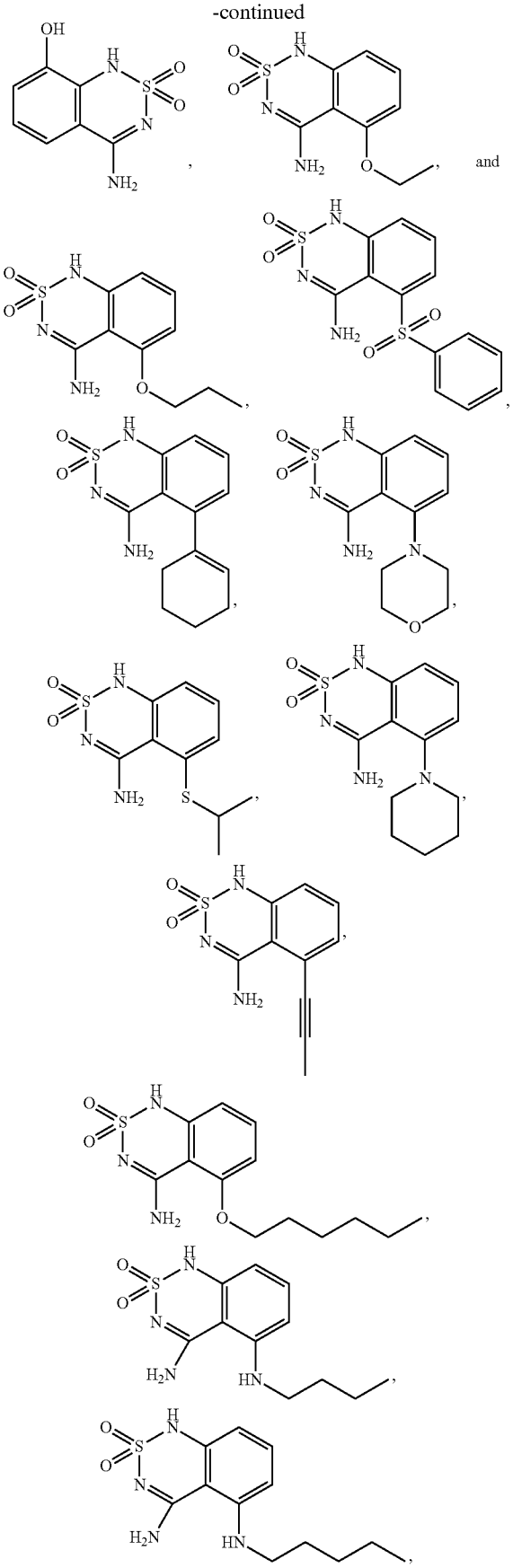
-continued
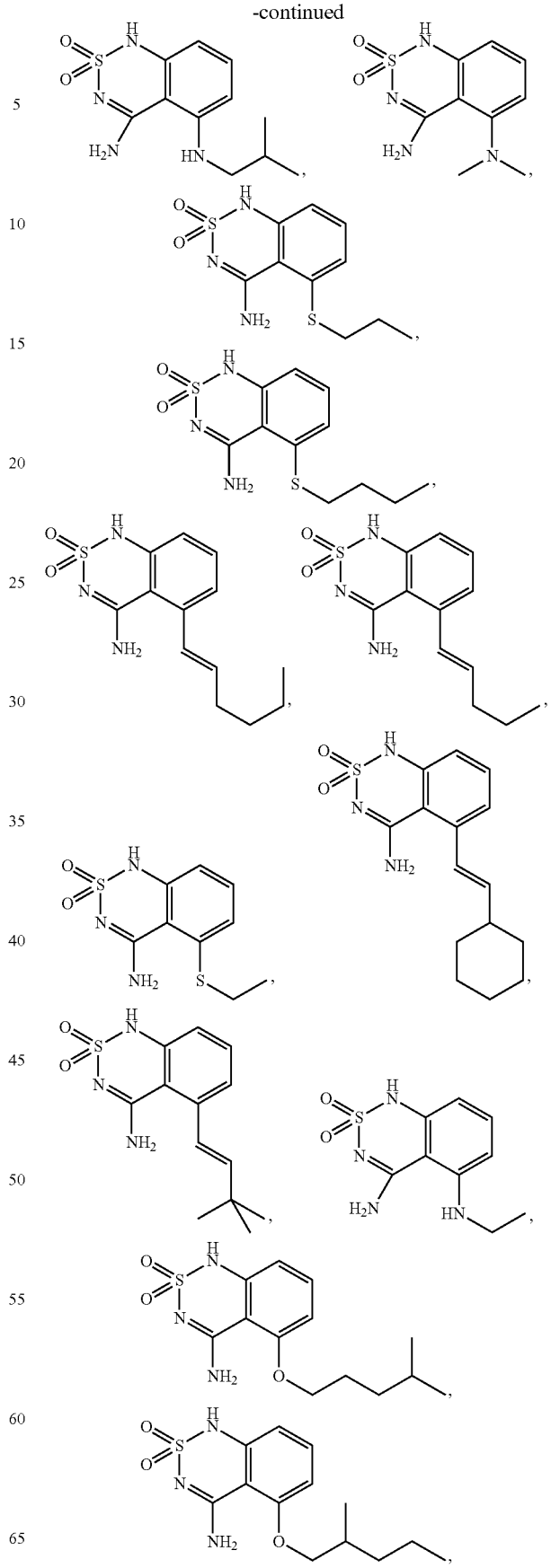

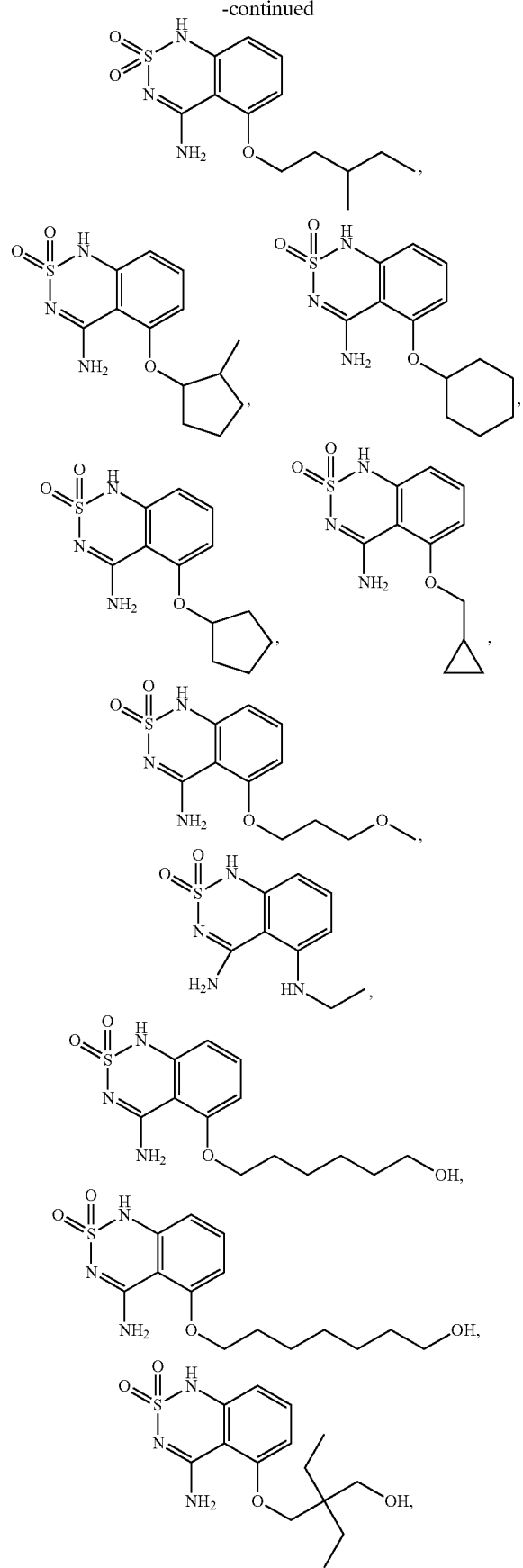
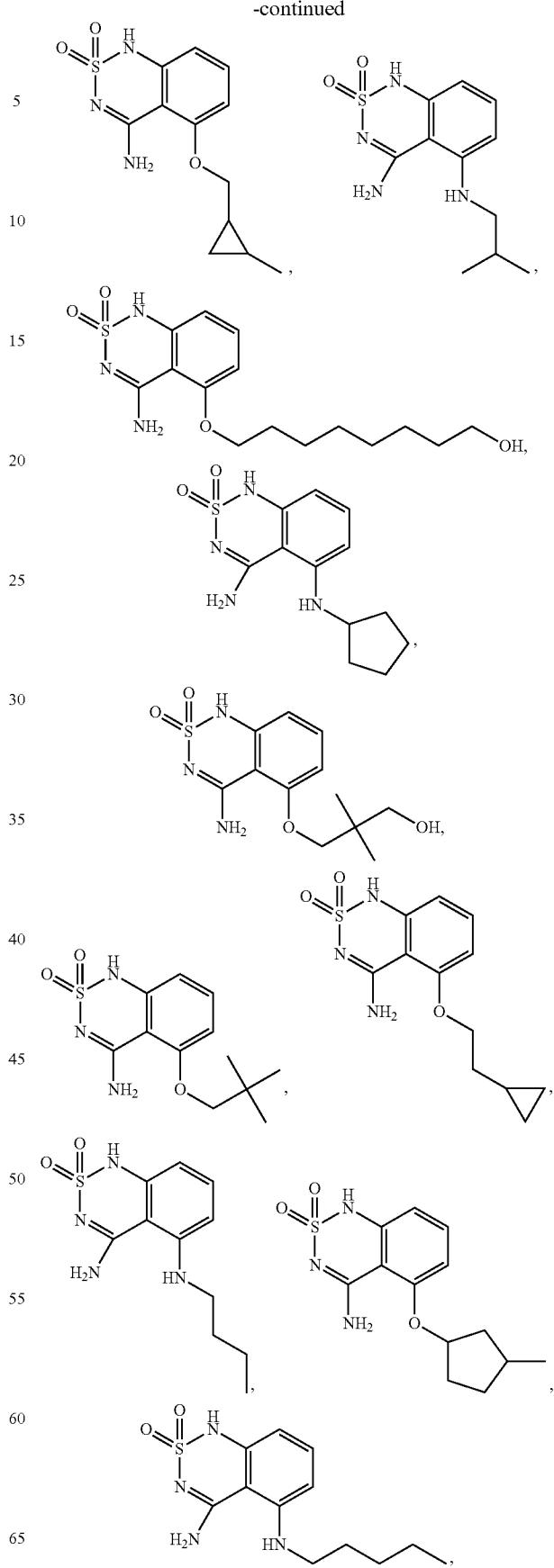

-continued
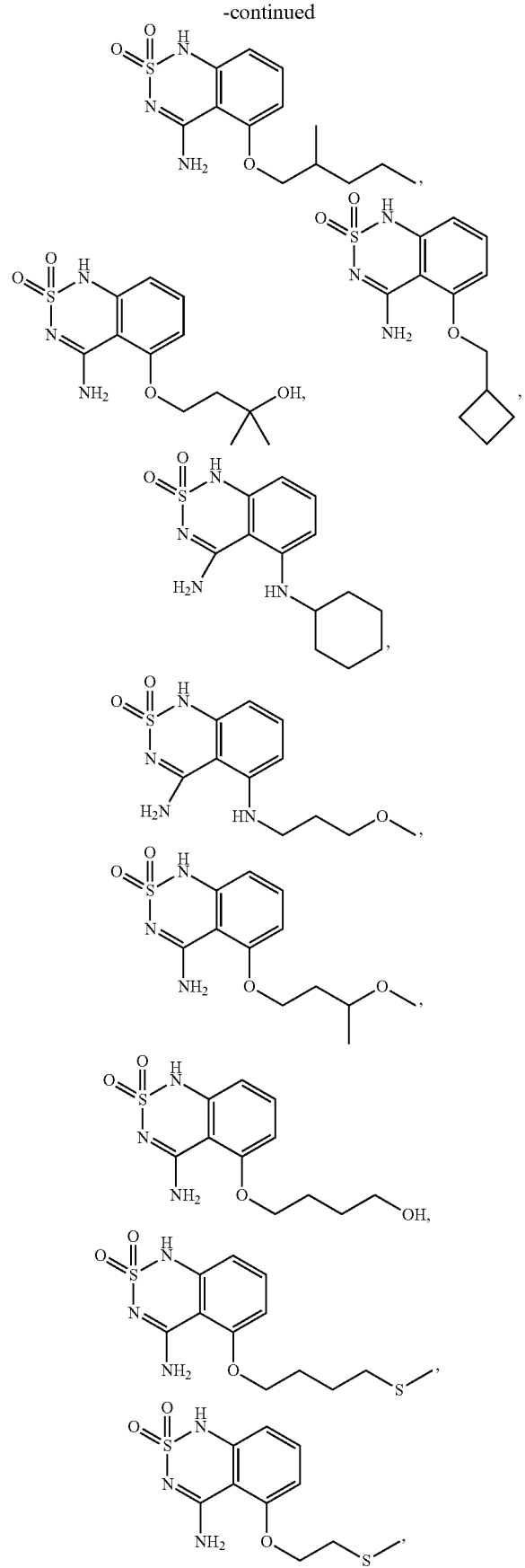
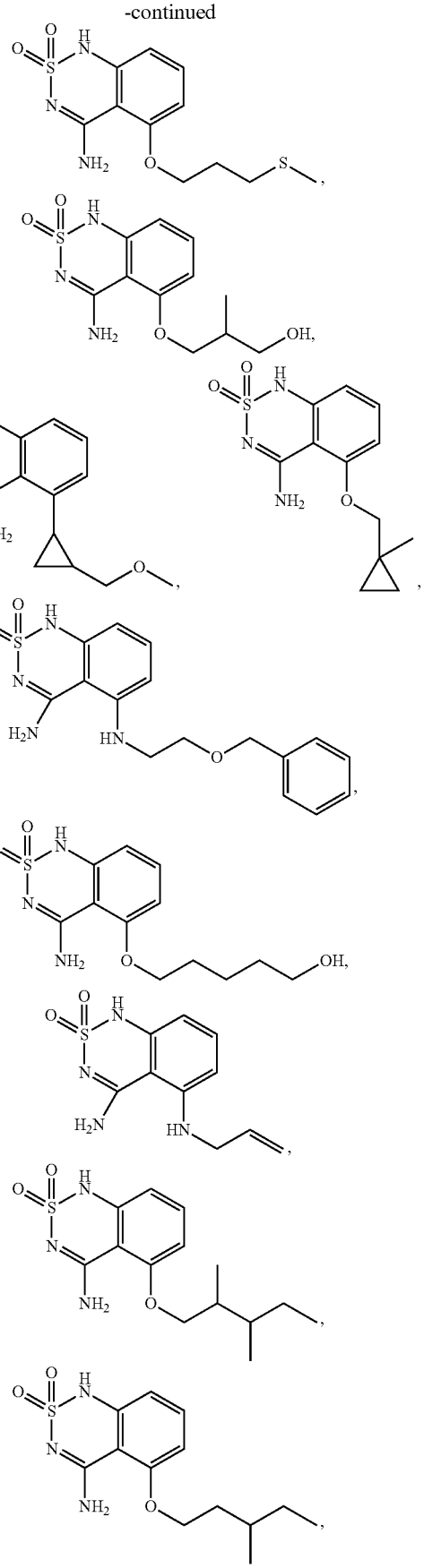

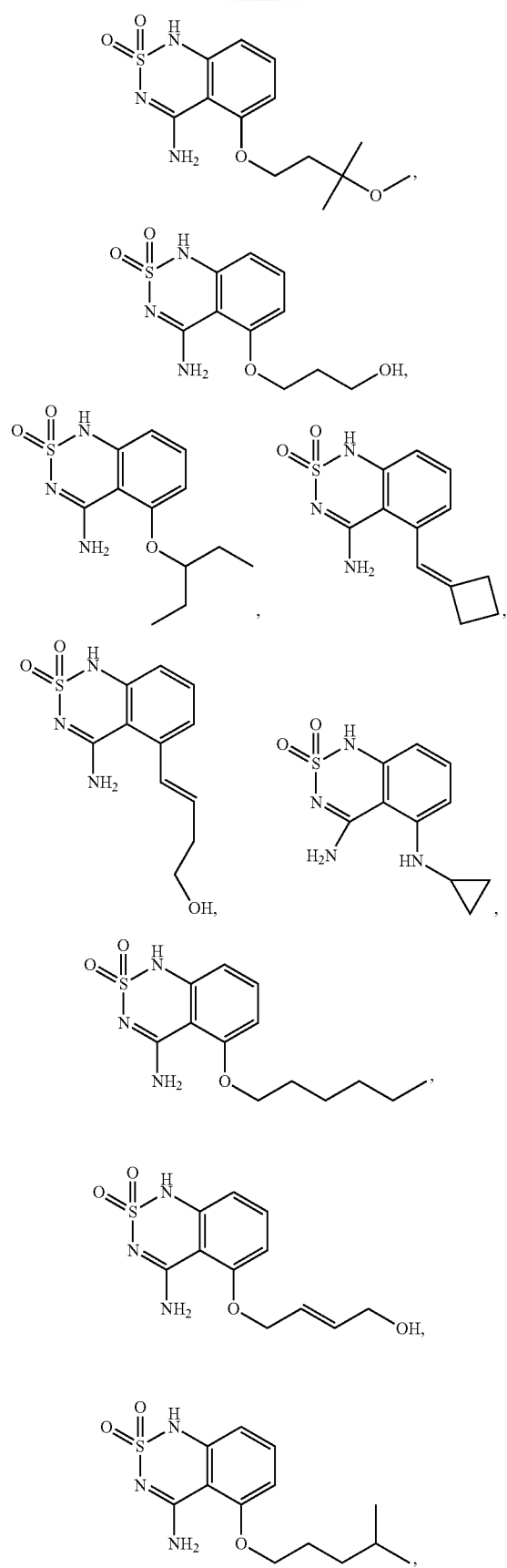
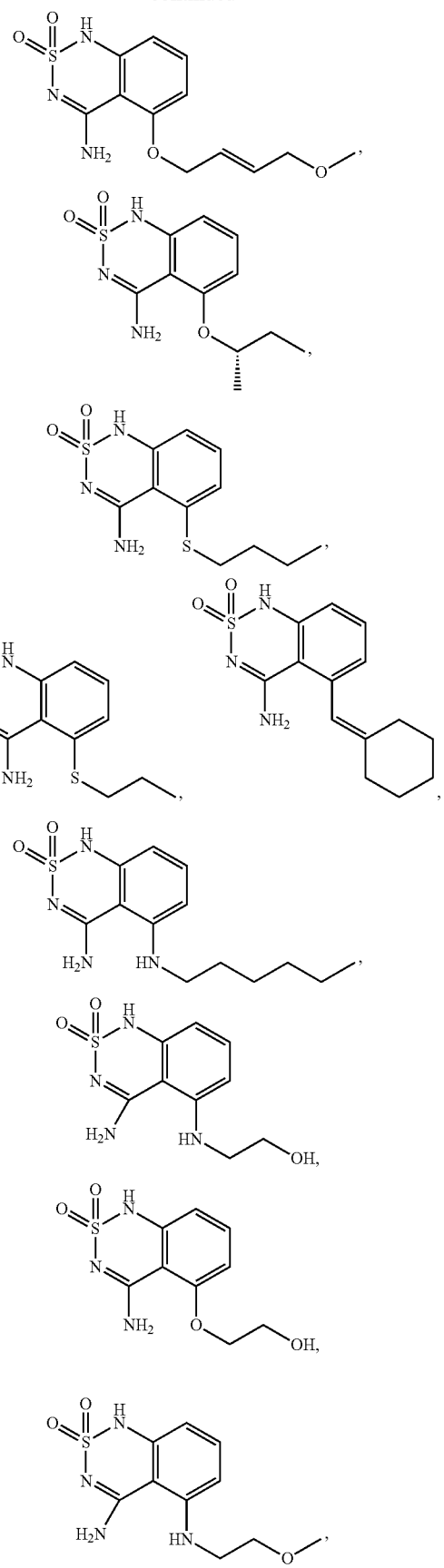

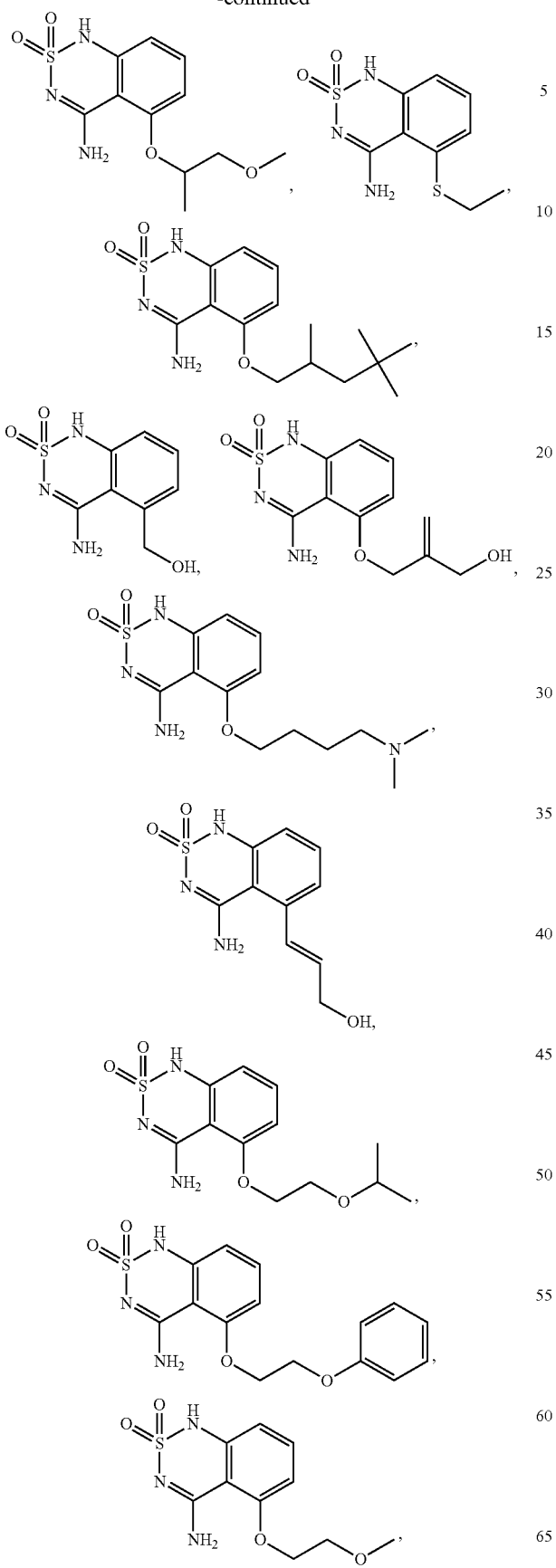
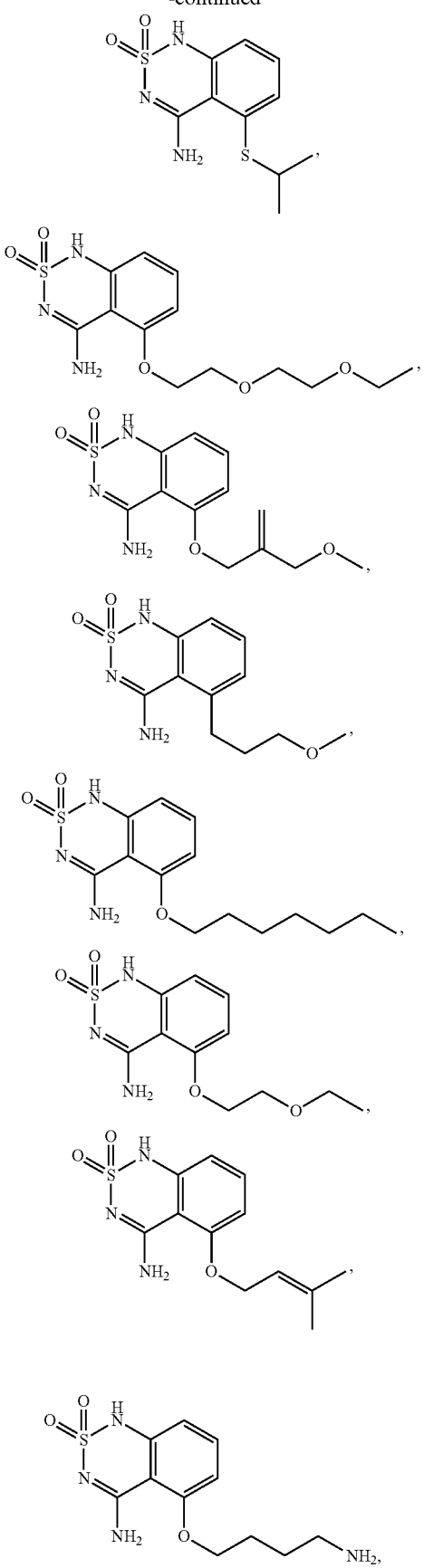

-continued

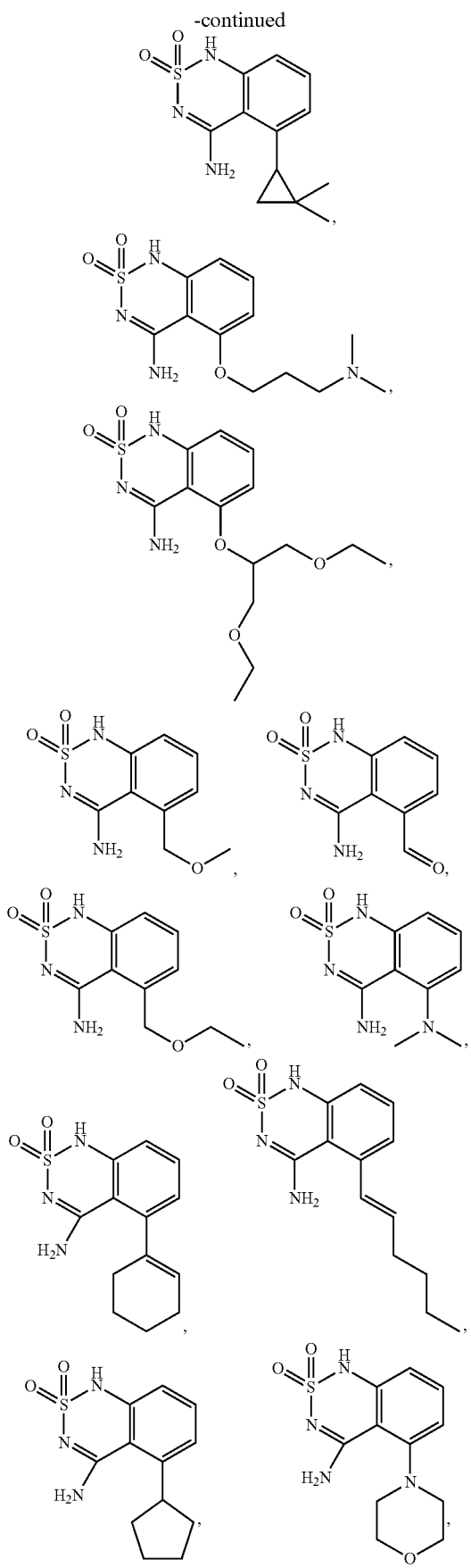

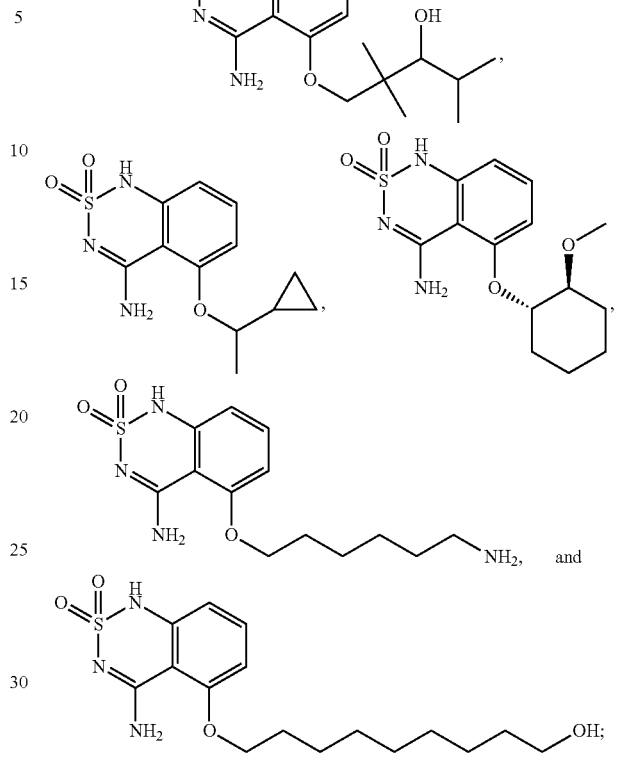

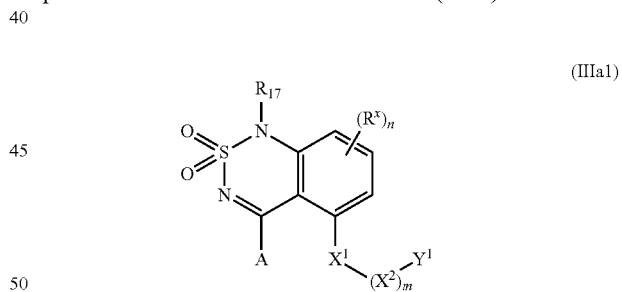

or a tautomer, salt, solvate, and/or ester thereof. In some preferred embodiments, the salt of these compounds is hydrochloride or trifluoroacetate salt.

In one embodiment of Formula (IIIb), the compound of the present invention has structural Formula (IIIb1):

(IIIa1)

wherein,

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^9$, —NO$_2$, —S(O)$_c$R$^9$, —NOR$^9$, —NHOR$^9$, —NR$^9$COR$^{10}$, —NR$^9$R$^{10}$, —CONR$^9$R$^{10}$, —CO$_2$R$^9$ or —NR$^9$CO$_2$R$^{10}$;

R$^{17}$ is hydrogen, alkyl, substituted alkyl, arylalkyl, or substituted arylalkyl;

X$^1$ is —CH$_2$—, —O—, —NR$^9$—, —S—, —S(O)—, or —S(O)$_2$—;

X$^2$ is alkylene, substituted alkylene, heteroalkylene, or substituted heteroalkylene;

m is 0 or 1;

$Y^1$ is heteroaryl, substituted heteroaryl, cycloheteroalkyl, substituted cycloheteroalkyl, or

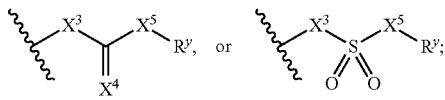

$X^3$ and $X^5$ are independently a covalent bond, —O— or —$NR^9$—;

$X^4$ is O, $NR^9$, N—$OR^9$, or S;

$R^x$ is halo, —$NO_2$, —CN, —OH, —$NH_2$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

n is 0, 1, 2, or 3;

$R^y$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl, —$NR^9R^{10}$; and each $R^9$ and $R^{10}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

with the proviso that when $X^1$ is —O— or —S—, and m is zero; then $X^3$ is not —O—.

In one embodiment of Formula (IIIb1), $X^1$ is —$CH_2$—; and $Y^1$ is

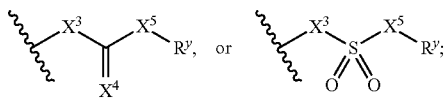

In one embodiment of Formula (IIIb1), $X^1$ is —O—, —$NR^9$—, or —S—; m is 0 or 1, and $Y^1$ is cycloheteroalkyl or substituted cycloheteroalkyl.

In one embodiment of Formula (IIIb1), $X^1$ is —O—, —$NR^9$—, or —S—; m is 1, and $Y^1$ is

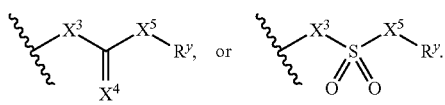

In some embodiments of Formula (IIIb1), $X^2$ is alkanylene, substituted alkanylene, heteroalkanylene, substituted heteroalkanylene, alkenylene, substituted alkenylene, heteroalkenylene, or substituted heteroalkenylene.

In some embodiments of Formula (IIIb1), $X^2$ is methylene, ethylene, propylene, iso-propylene, butylene, iso-butylene, sec-butylene, pentylene, hexylene, heptylene, dimethylethylene, methylcyclopropylene, cyclopropylmethylene, ethenylene, propenylene, or butenylene.

In one embodiment of Formula (IIIb1), A is hydrogen, alkyl, substituted alkyl, —CN, —$NO_2$, —$OR^9$, —$S(O)_cR^9$, —$NR^9COR^{10}$, —$NHOR^9$, —$NR^9R^{10}$, —$NOR^9$, —$CONR^9R^{10}$, —$CO_2R^9$, —$NR^9CO_2R^{10}$, —$NR^9CONR^{10}R^{11}$, —$NR^9CSNR^{10}R^{11}$, —$NR^9C(=NH)NR^{10}R^{11}$.

In one embodiment of Formula (IIIb1), $R^{17}$ is hydrogen, alkyl, or substituted alkyl.

In one embodiment of Formula (IIIb1), $Y^1$ is cycloheteroalkanyl, substituted cycloheteroalkanyl, cycloheteroalkenyl, or substituted cycloheteroalkenyl. It is preferable that $Y^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, substituted oxetanyl, saccharide ring or its derivative, substituted saccharide ring or its derivative.

In one embodiment of Formula (IIIb1), $Y^1$ is heteroaryl or substituted heteroaryl. It is preferable that $Y^1$ is pyridinyl, substituted pyridinyl, pyrrolyl, substituted pyrrolyl, furanyl, substituted furanyl, pyrazolyl, substituted pyrazolyl, isoxazolyl, substituted isoxazolyl, oxazolyl, and substituted oxazolyl. It is also preferable that the substituted cycloheteroalkanyl or the substituted cycloheteroalkenyl comprises one or more substituents selected from the group consisting of alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$OR^9$, —$NO_2$, —$S(O)_cR^9$, —$NOR^9$, —$NHOR^9$, —$NR^9COR^{10}$, —$NR^9R^{10}$, —$CONR^9R^{10}$, —$CO_2R^9$, and —$NR^9CO_2R^{10}$.

In one embodiment of Formula (IIIb1), Y is

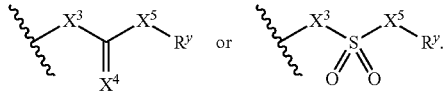

It is preferable that $X^4$ is O.

In one embodiment of Formula (IIIb1), —$X^3$—$C(X^4)$—$X^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —O—C(NH)—O—, —NH—C(NH)—O—, —O—C(NH)—NH—, —C(N—OH)—, or —C(S)—.

In one embodiment of Formula (IIIb1), A is hydrogen, alkyl, substituted alkyl, or —$NR^9R^{10}$; $R^{17}$ is hydrogen; and $Y^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, substituted oxetanyl, monosaccharide ring, substituted monosaccharide ring, pyridinyl, substituted pyridinyl, pyrrolyl, substituted pyrrolyl, furanyl, substituted furanyl, pyrazolyl, substituted pyrazolyl, isoxazolyl, substituted isoxazolyl, oxazolyl, or substituted oxazolyl.

In one embodiment of Formula (IIIb1), A is hydrogen, alkyl, substituted alkyl, or —$NR^9R^{10}$; $R^{17}$ is hydrogen; $Y^1$ is —$X^3$—$C(X^4)$—$X^5$—; and —$X^3$—$C(X^4)$—$X^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —NH—C(NH)—O—, —O—C(NH)—NH—, —$S(O)_2$—, —NH—$S(O)_2$—, —$S(O)_2$—NH—, —O—$S(O)_2$—, —$S(O)_2$—O—, —C(N—OH)—, or —C(S)—.

In some specific embodiments of Formula (IIIb1), the compound has structural formula selected from the group consisting of

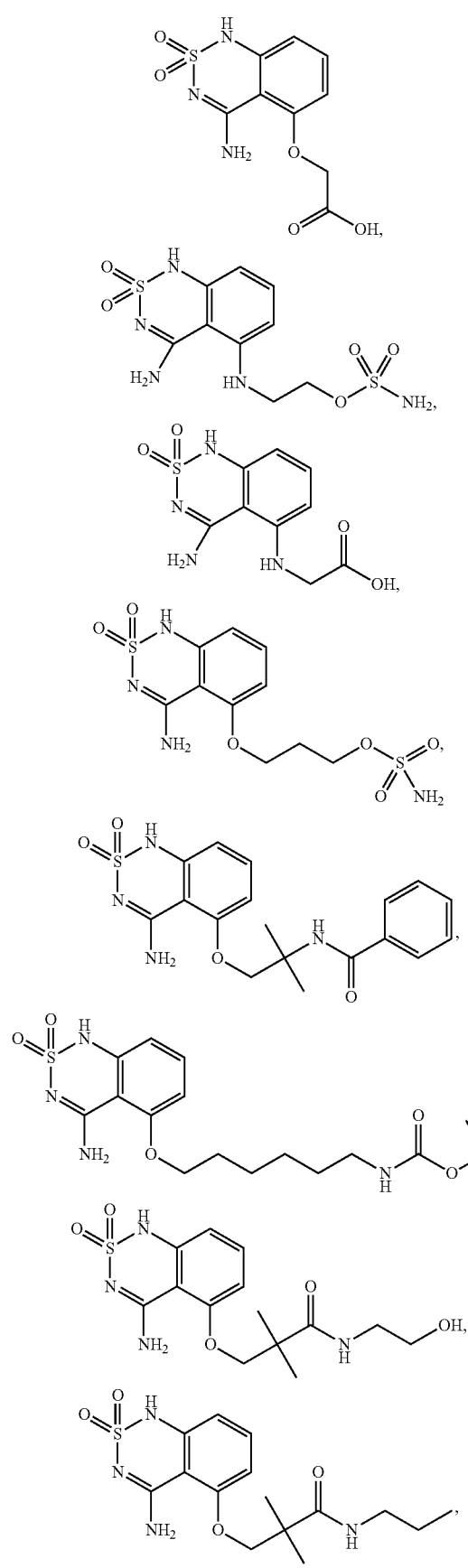
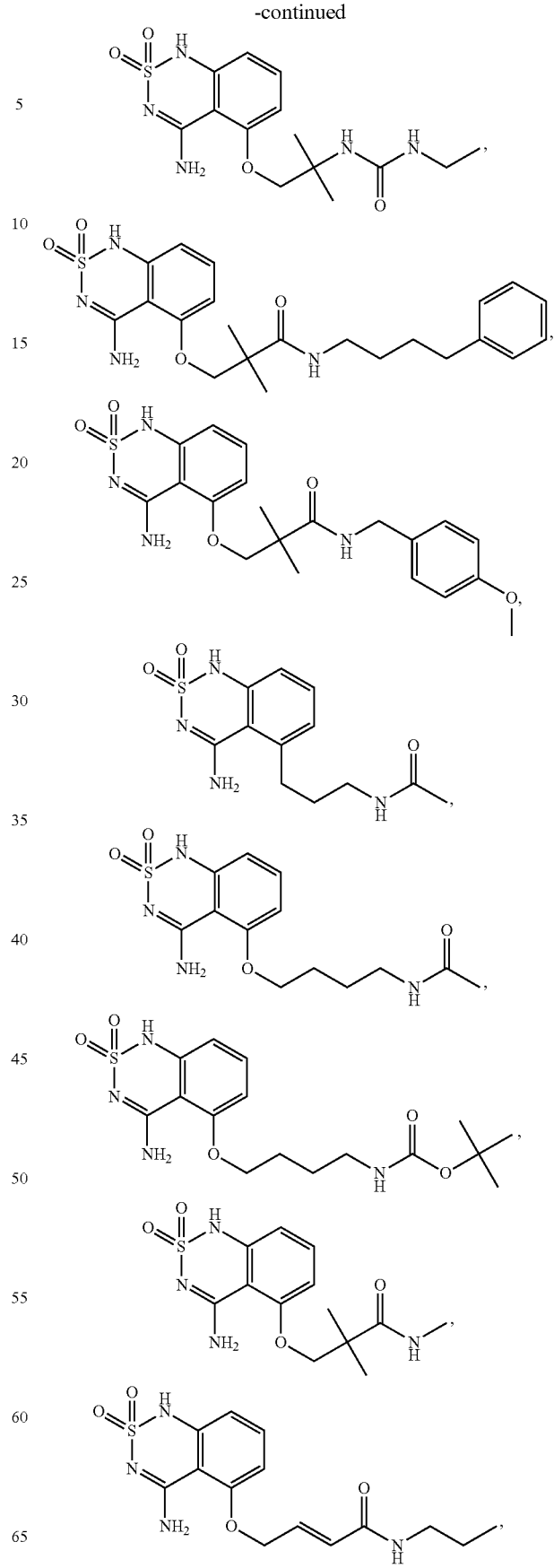
-continued

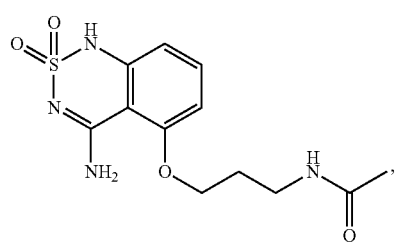
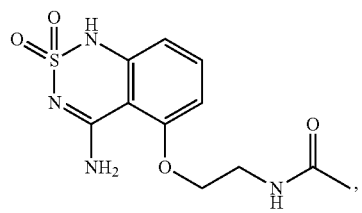
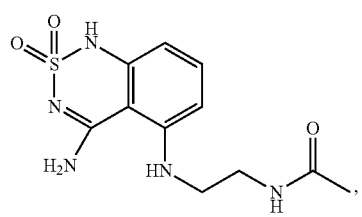
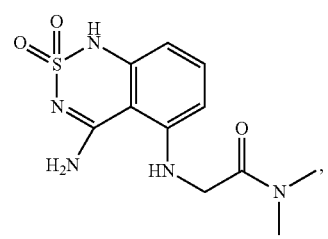
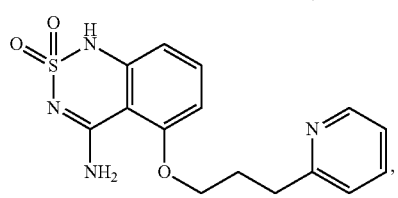
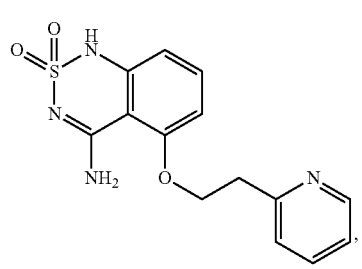
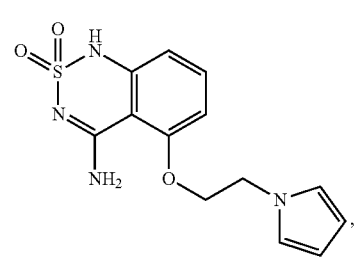
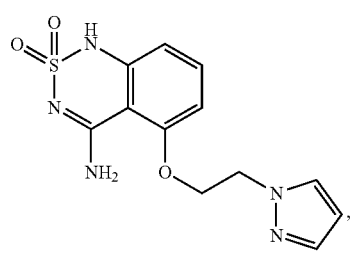
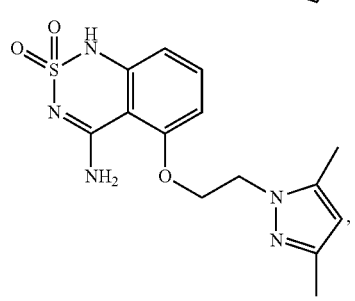
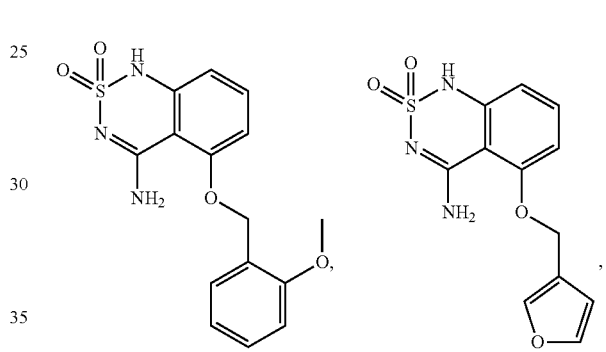
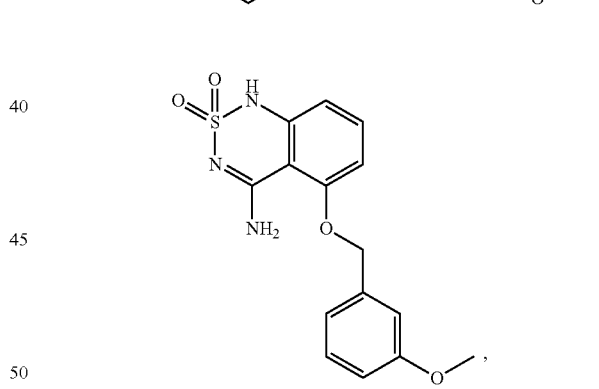
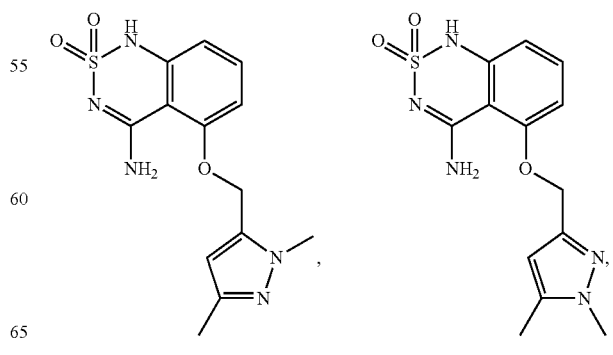

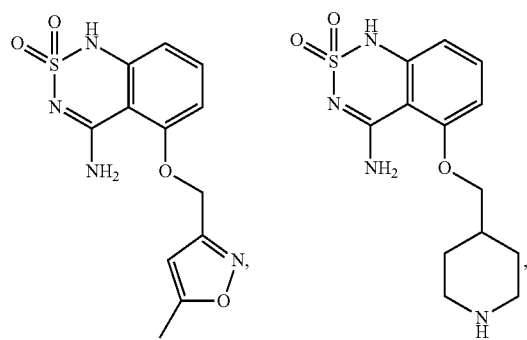
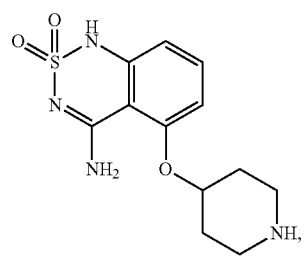
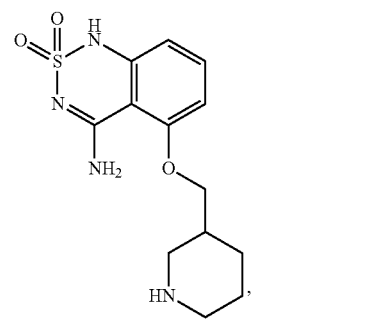
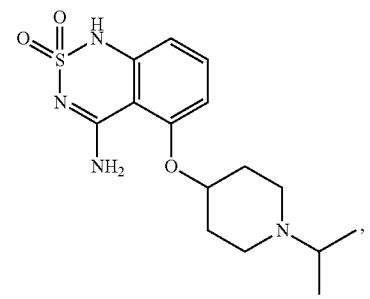
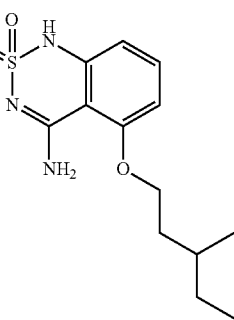
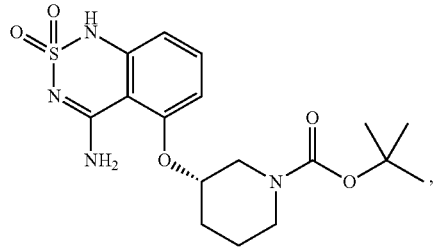
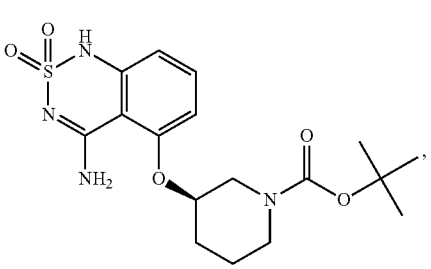
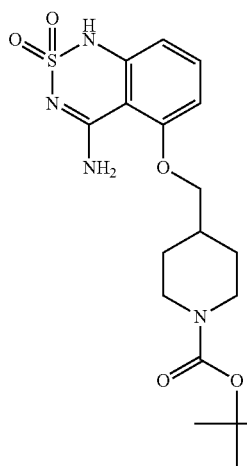
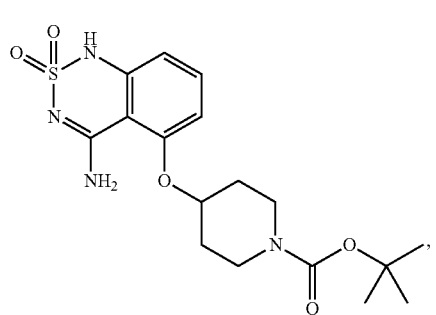
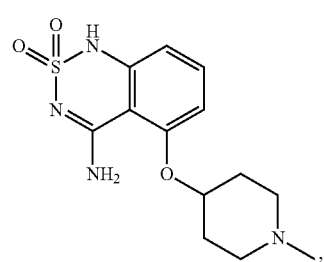

85
-continued
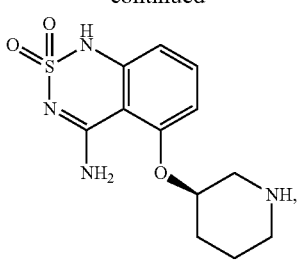
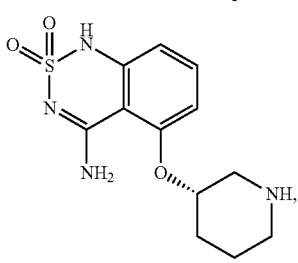
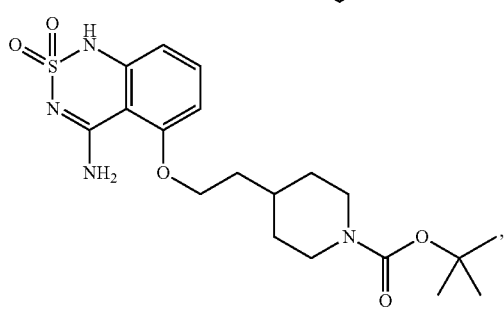
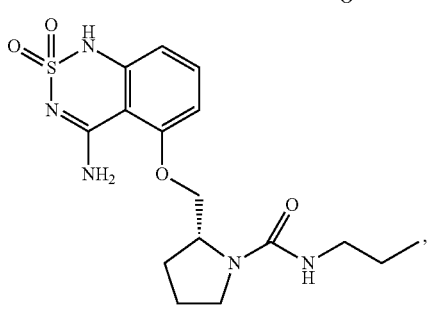
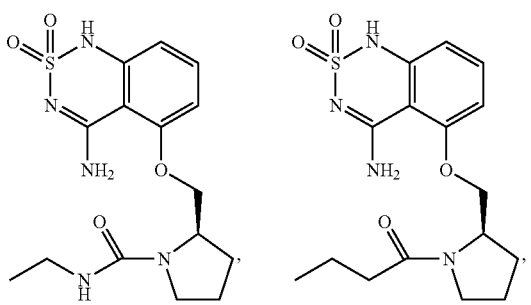
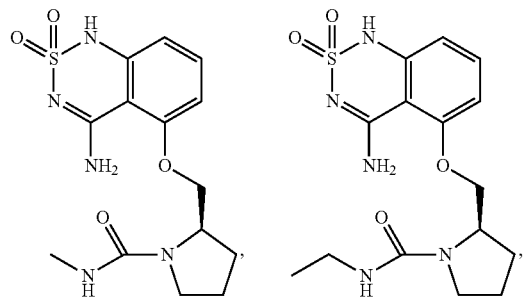
86
-continued
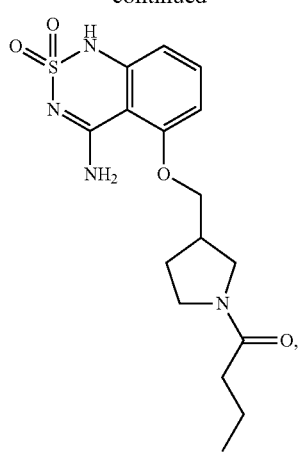
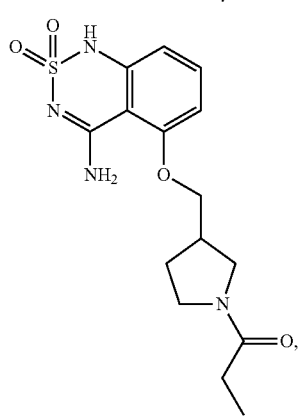
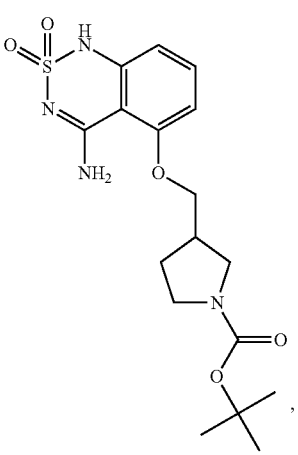
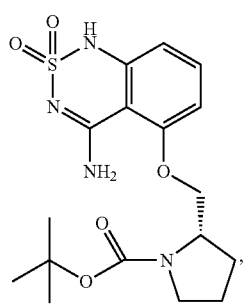
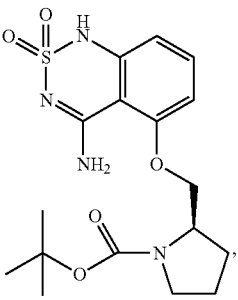
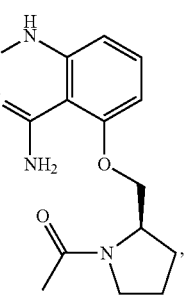

87
-continued
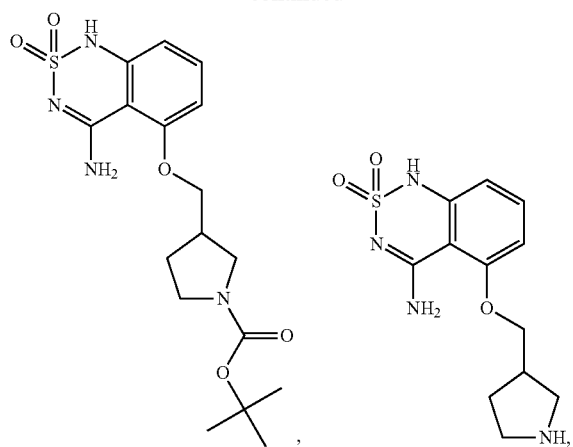
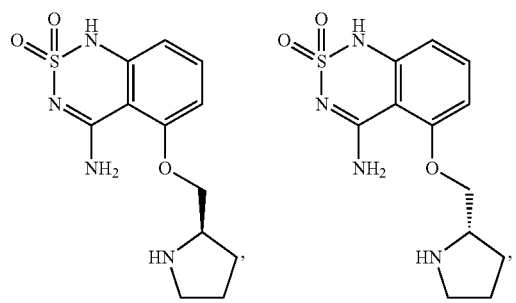
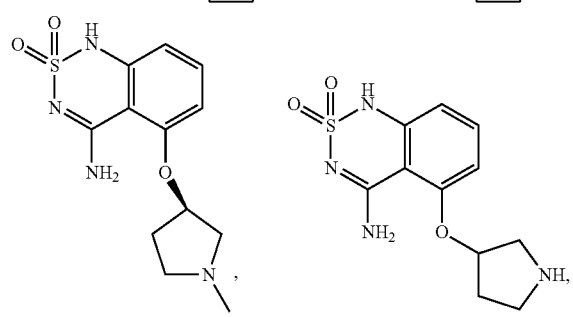
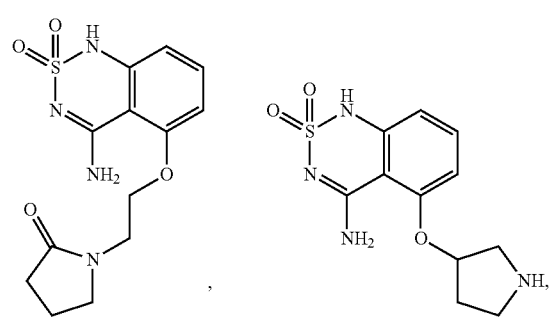
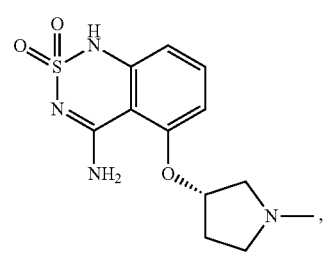
88
-continued
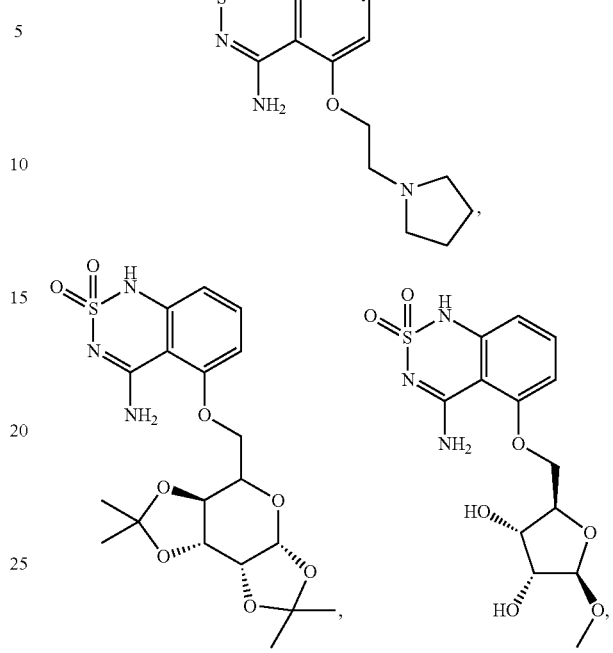
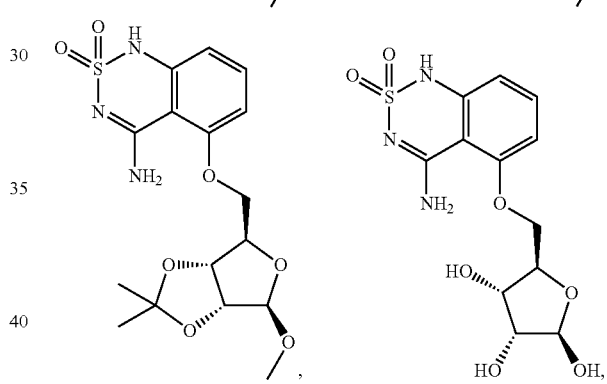
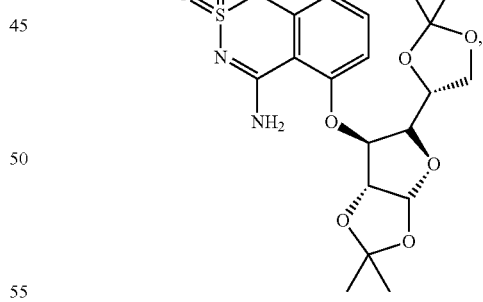
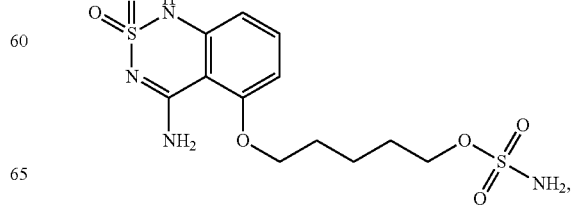

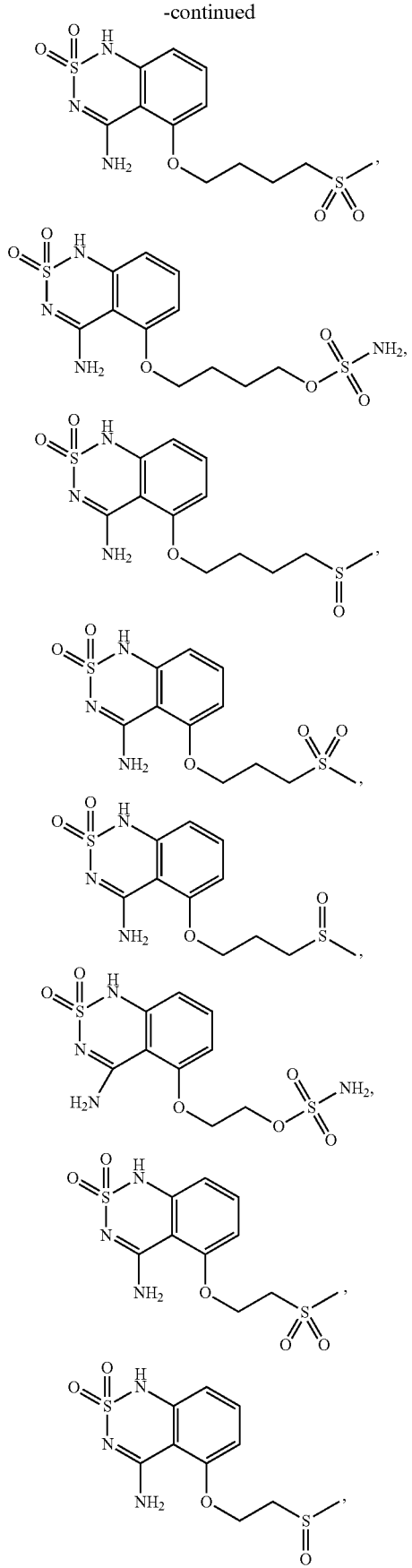
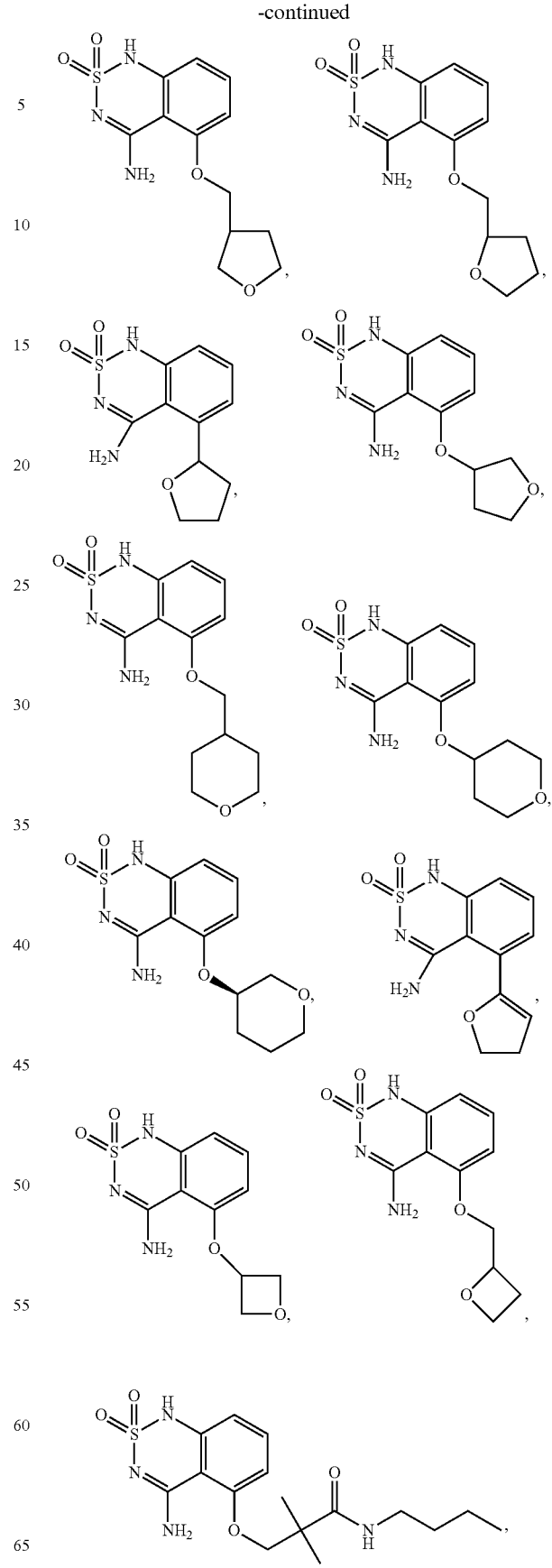

91
-continued
92
-continued
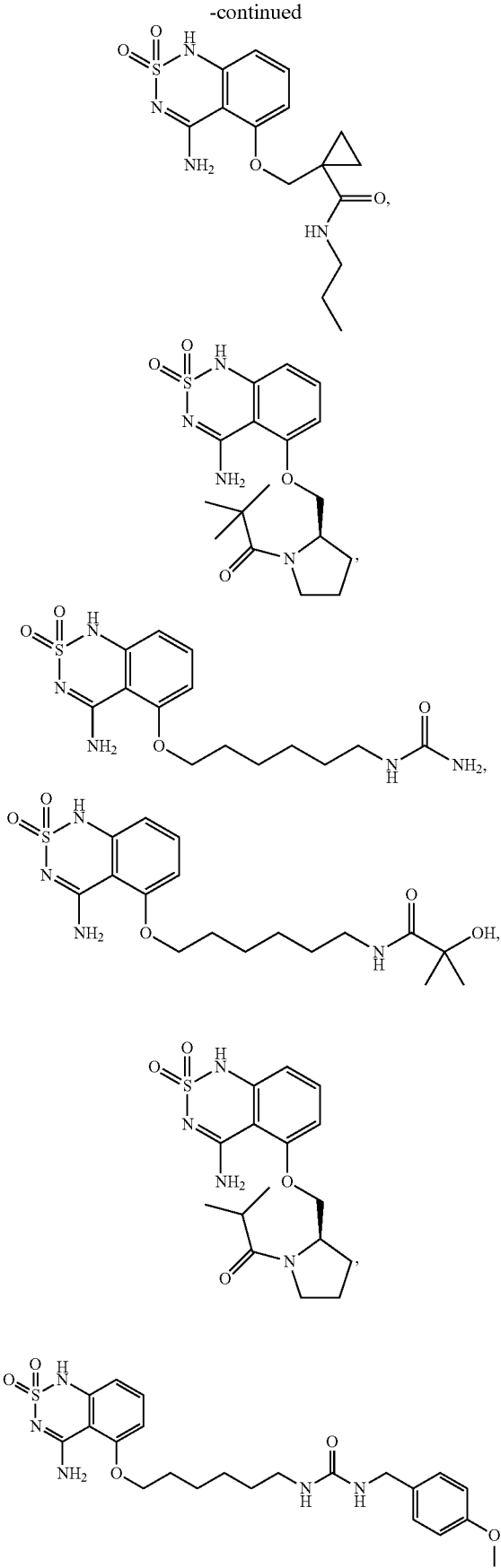
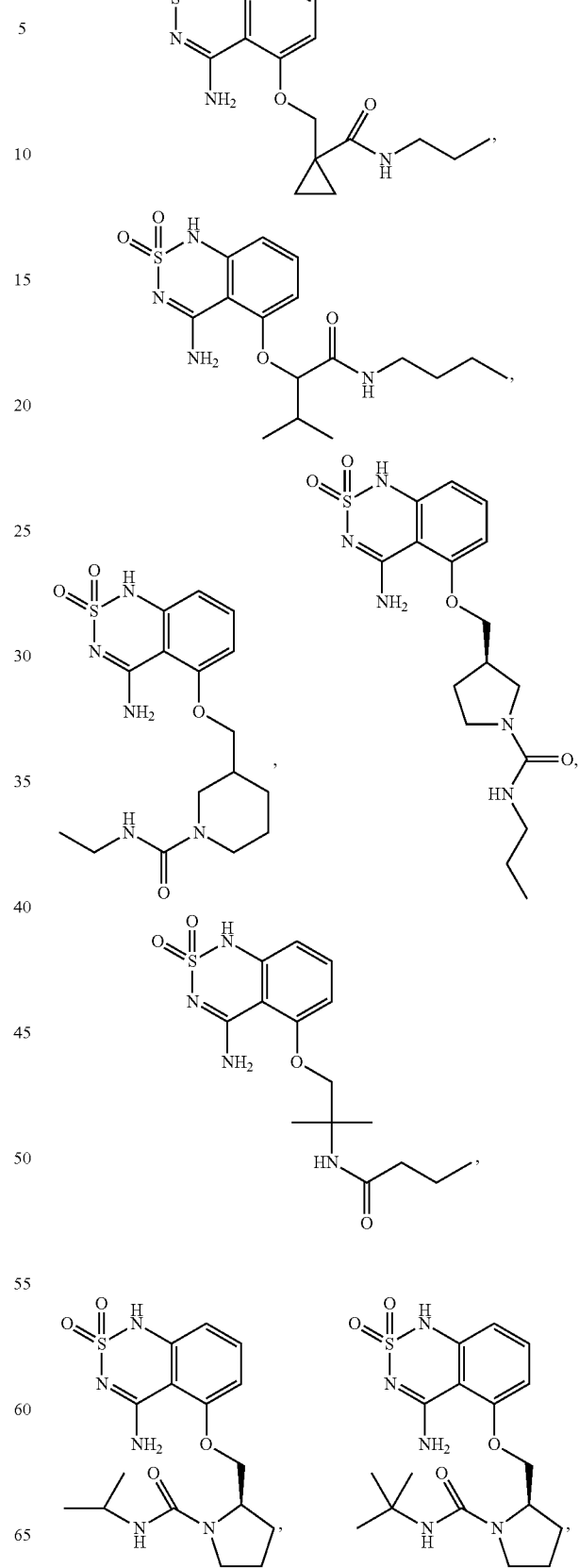

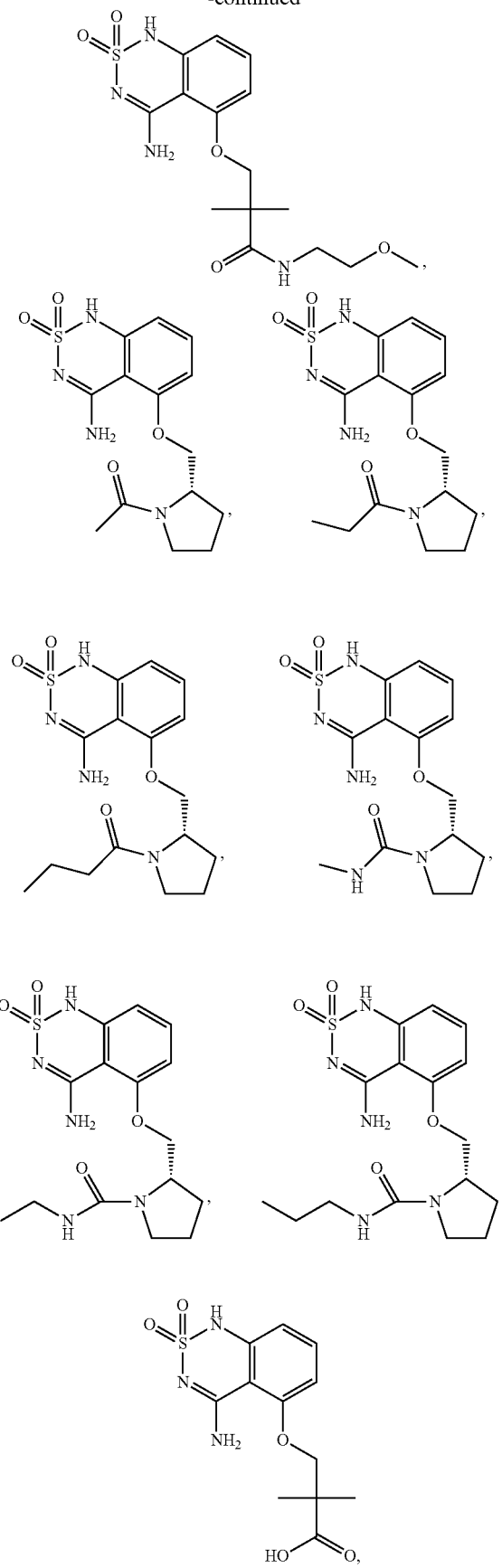

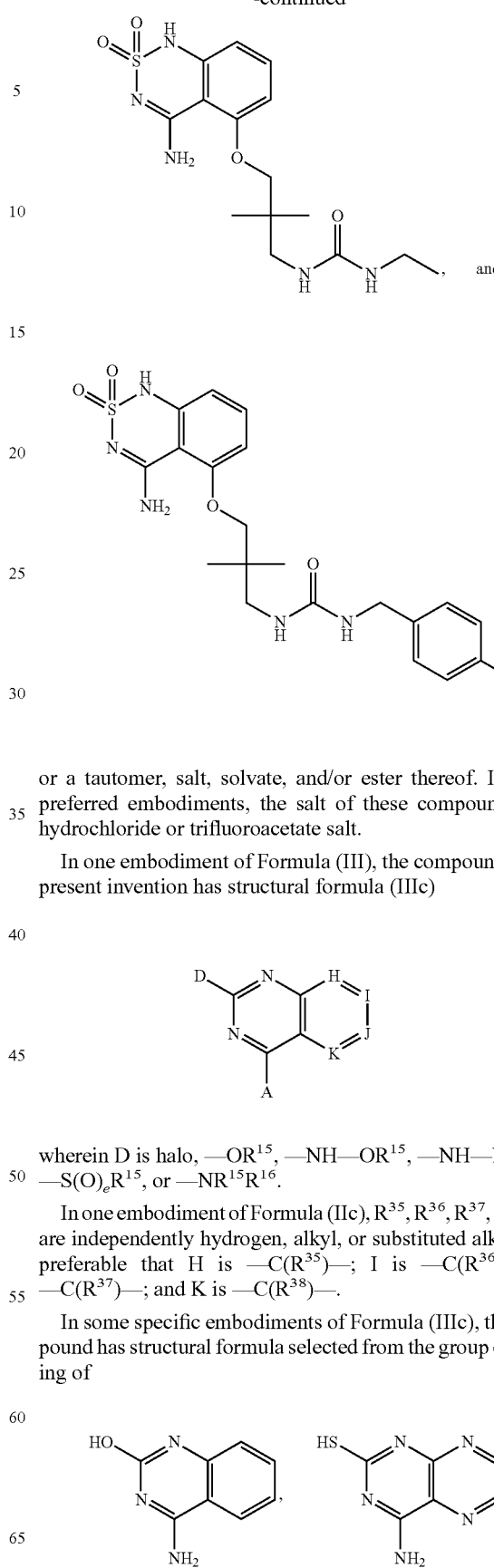

or a tautomer, salt, solvate, and/or ester thereof. In some preferred embodiments, the salt of these compounds is a hydrochloride or trifluoroacetate salt.

In one embodiment of Formula (III), the compound of the present invention has structural formula (IIIc)

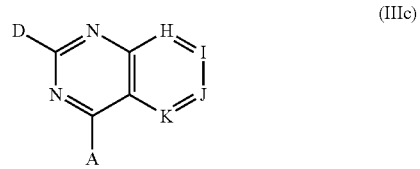

wherein D is halo, —$OR^{15}$, —NH—$OR^{15}$, —NH—$NHR^{15}$, —$S(O)_eR^{15}$, or —$NR^{15}R^{16}$.

In one embodiment of Formula (IIc), $R^{35}$, $R^{36}$, $R^{37}$, and $R^{38}$ are independently hydrogen, alkyl, or substituted alkyl. It is preferable that H is —$C(R^{35})$—; I is —$C(R^{36})$; J is —$C(R^{37})$—; and K is —$C(R^{38})$—.

In some specific embodiments of Formula (IIIc), the compound has structural formula selected from the group consisting of

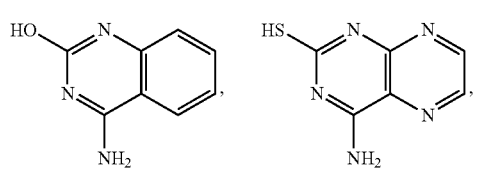

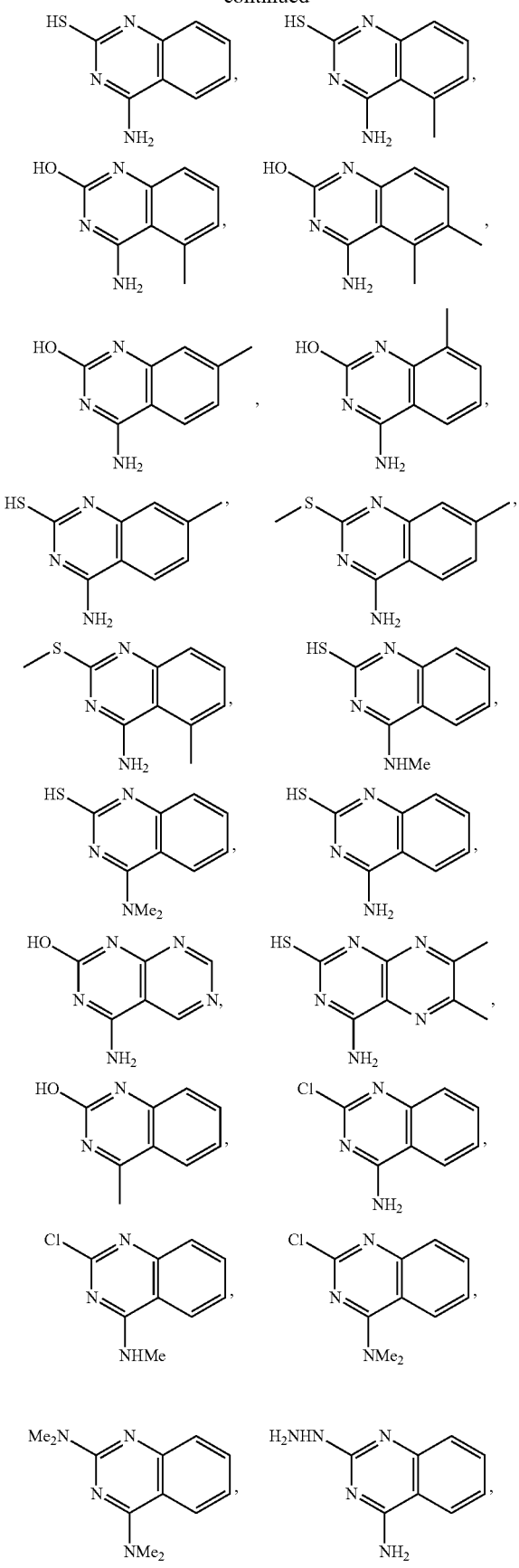

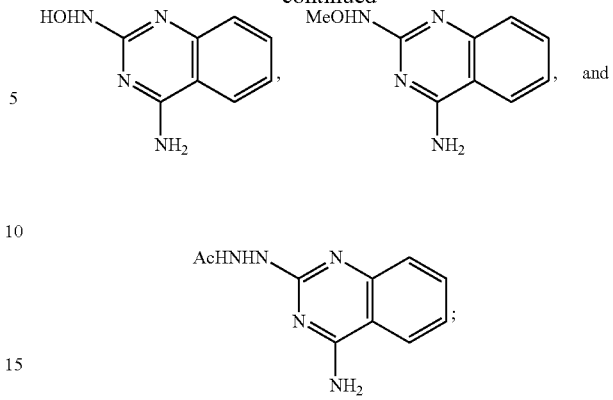

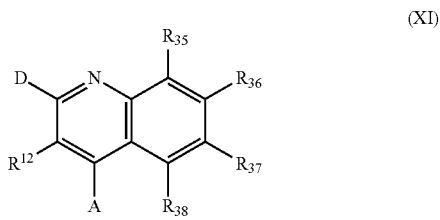

or a tautomer, salt, solvate, and/or ester thereof. In some preferred embodiments, the salt of these compounds is hydrochloride or trifluoroacetate salt.

In one embodiment of Formula (III), the compound of the present invention has structural Formula (XI):

$$(XI)$$

wherein, $R^{12}$ is hydrogen, —OH, —SH, —CN, —CH$_2$OH or —CO$_2$H;

D is —OH or —SH; and

A is —OH, —NH$_2$, —NHCH$_3$, —N(CH$_3$)$_2$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;

provided that when $R^{12}$ is hydrogen, then $R^{35}$, $R^{36}$, $R^{37}$, and $R^{38}$ are not hydrogen.

In one embodiment of Formula (XI), $R^{12}$ is —OH, —SH, —CN, —CH$_2$OH or —CO$_2$H; and A is —NH$_2$, —NHCH$_3$, —N(CH$_3$)$_2$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$.

In some embodiments of Formula (XI), when $R^{36}$, $R^{37}$, $R^{38}$ and $R^{35}$ are hydrogen, D is —OH, and A is —CO$_2$H; then $R^{12}$ is not —CO$_2$H or —OH;

when $R^{36}$, $R^{37}$, $R^{38}$ and $R^{35}$ are hydrogen, D is —OH, and A is —NH$_2$; then $R^{12}$ is not —CO$_2$H or CN;

when $R^{36}$, $R^{38}$ and $R^{35}$ are hydrogen, $R^{37}$ is —OMe, D is —OH, and A is —CH$_2$OH; then $R^{12}$ is not —CH$_2$OH; and when $R^{36}$, $R^{38}$ and $R^{35}$ are hydrogen, $R^{37}$ is hydrogen or methyl, D is —OH, and A is —CO$_2$H; then $R^{12}$ is not —SH.

In one embodiment of Formula (III), the compound of the present invention has structural Formula (XII):

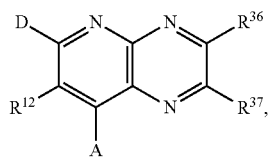

(XII)

wherein $R^{12}$ is hydrogen, —OH, —SH, —CN, —CH$_2$OH or —CO$_2$H;

D is —SH or —OH;

A is —OH, —NH$_2$, —NHCH$_3$, —N(CH$_3$)$_2$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;

$R^{36}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{41}$R$^{42}$, —CO$_2$R$^{41}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$); and $R^{37}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$).

In one embodiment of Formula (XII), $R^{12}$ is —OH, —SH, —CN, —CH$_2$OH or —CO$_2$H.

In one embodiment of Formula (III), the compound of the present invention has structural Formula (XIII):

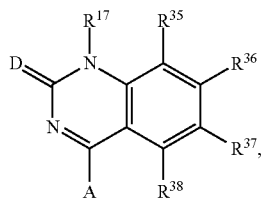

(XIII)

wherein:

D is =O or =S;

A is —OH, NH$_2$, —NHCH$_3$, —N(CH$_3$)$_2$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;

$R^{17}$ is hydrogen, alkyl, aryl, arylalkyl.

In one embodiment of Formula (XIII), when A is —NH$_2$, and $R^{35}$, $R^{36}$, $R^{37}$ and $R^{38}$ are hydrogen; then $R^{17}$ is not methyl, ethyl or phenyl.

In some specific embodiments of Formula (XIII), the compound has structural formula selected from the group consisting of

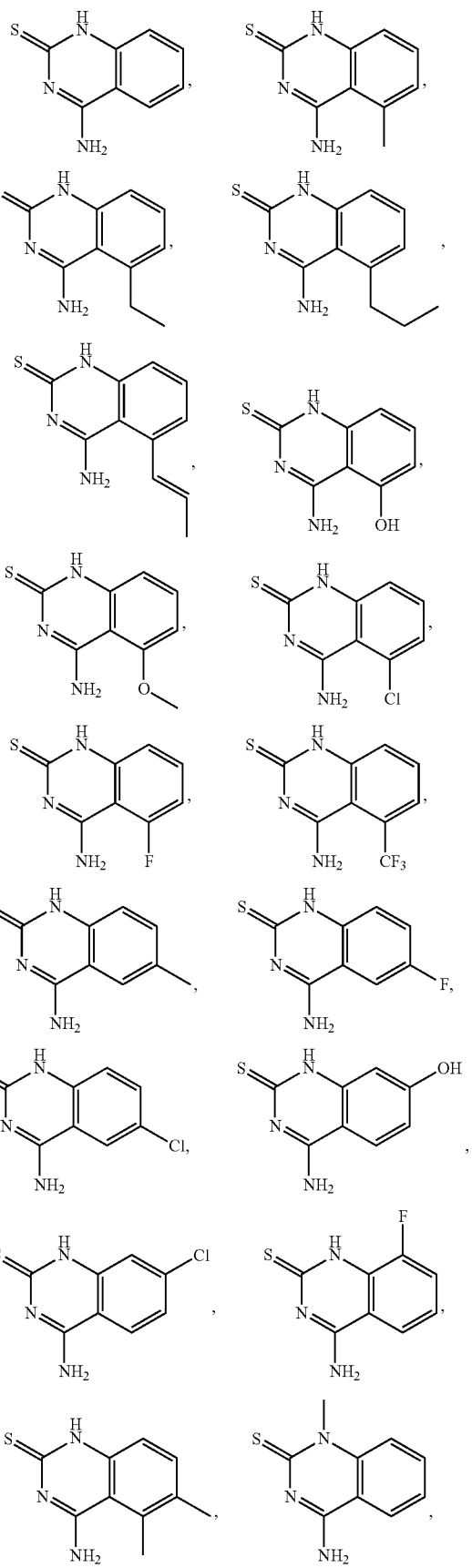

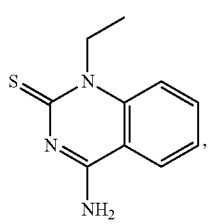 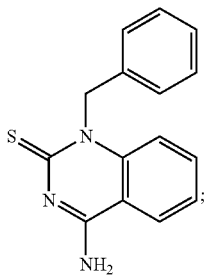

or a tautomer, salt, solvate, and/or ester thereof. In some preferred embodiments, the salt of these compounds is hydrochloride or trifluoroacetate salt.

In one embodiment of Formula (III), the compound of the present invention has structural Formula (XIV):

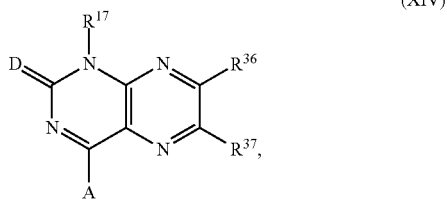

wherein A is —OH, —$NH_2$, —$NHCH_3$, —$N(CH_3)_2$, —NHC(O)$CH_3$, —NHC(O)O$CH_3$, —NHC(O)$NH_2$, —NHC(S)$NH_2$, —NHC(NH)$NH_2$, —CN, —$CH_2$OH, —$CH_2NH_2$, —$CH_2NHCH_3$, —$CH_2N(CH_3)_2$, —$CO_2$H, —$CONH_2$, —$CONHCH_3$, or —$CH_2$NHC(O)$CH_3$; and $R^{17}$ is alkyl, aryl, or arylalkyl.

In one embodiment of Formula (I), the chemosensory receptor ligand modifier is a compound having a structural Formula (IV):

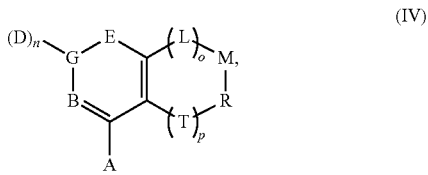

wherein:
L is —$CHR^{60}$—, —$NR^{47}$—, —O— or —S—;
M is —$CHR^{61}$—, —$NR^{48}$—, —O— or —S—;
R is —$CHR^{62}$—, —$NR^{49}$—, —O— or —S—;
T is —$CHR^{63}$—, —$NR^{50}$—, —O— or —S—;
o and p are independently 0, 1, or 2;

$R^{60}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —$NO_2$, —$OR^{64}$, —$S(O)_tR^{64}$, —$OCOR^{64}$, —$NR^{64}COR^{65}$, —$NR^{64}R^{65}$, —$CONR^{64}R^{65}$, —$CO_2R^{64}$, —$SO_2NR^{64}R^{65}$, —$NR^{64}SO_2R^{65}$, —$B(OR^{64})(OR^{65})$, —$P(O)(OR^{64})(OR^{65})$ or —$P(O)(R^{64})(OR^{65})$;

$R^{61}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —$NO_2$, —$OR^{66}$, —$S(O)_uR^{66}$, —$OCOR^{66}$, —$NR^{66}COR^{67}$, —$NR^{66}R^{67}$, —$CONR^{66}R^{67}$, —$CO_2R^{66}$, —$SO_2NR^{66}R^{67}$, —$NR^{66}SO_2R^{67}$, —$B(OR^{66})(OR^{67})$, —$P(O)(OR^{66})(OR^{67})$ or —$P(O)(R^{66})(OR^{67})$;

$R^{62}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —$NO_2$, —$OR^{68}$, —$S(O)_vR^{68}$, —$OCOR^{68}$, —$NR^{68}COR^{69}$, —$NR^{68}R^{69}$, —$CONR^{68}R^{69}$, —$CO_2R^{68}$, —$SO_2NR^{68}R^{69}$, —$NR^{68}SO_2R^{69}$, —$B(OR^{68})(OR^{69})$, —$P(O)(OR^{68})(OR^{69})$ or —$P(O)(R^{68})(OR^{69})$;

$R^{63}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —$NO_2$, —$OR^{70}$, —$S(O)_xR^{70}$, —$OCOR^{70}$, —$NR^{70}COR^{71}$, —$NR^{70}R^{71}$, —$CONR^{70}R^{71}$, —$CO_2R^{70}$, —$SO_2NR^{70}R^{71}$, —$NR^{70}SO_2R^{71}$, —$B(OR^{70})(OR^{71})$, —$P(O)(OR^{70})(OR^{71})$ or —$P(O)(R^{70})(OR^{71})$; or alternatively $R^{60}$ and $R^{61}$, $R^{61}$ and $R^{62}$, or $R^{62}$ and $R^{63}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring;

t, u, v and x are independently 0, 1 or 2;

$R^{64}$ to $R^{71}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively $R^{64}$ and $R^{65}$, $R^{66}$ and $R^{67}$, $R^{68}$ and $R^{69}$, or $R^{70}$ and $R^{71}$ together with the atoms to which they are bonded form a cycloheteroalkyl or substituted cycloheteroalkyl ring; and $R^{47}$ to $R^{50}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl;

with the proviso that at most only one of L, M, R and T is a heteroatom.

In one embodiment of Formula (IV), B is —N—, and E is —$NR^{17}$— or —N—. It is preferable that G is —C—.

In one embodiment of Formula (IV), the compound of the present invention has structural Formula (XV):

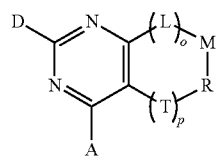

wherein D is —SH or —OH; and A is —OH, —$NH_2$, —$NHCH_3$, —$N(CH_3)_2$, —NHC(O)$CH_3$, —NHC(O)O$CH_3$, —NHC(O)$NH_2$, —NHC(S)$NH_2$, —NHC(NH)$NH_2$, —CN, —$CH_2$OH, —$CH_2NH_2$, —$CH_2NHCH_3$, —$CH_2N(CH_3)_2$, —$CO_2$H, —$CONH_2$, —$CONHCH_3$, or —$CH_2$NHC(O)$CH_3$.

In some specific embodiments of Formula (XV), the compound has structural formula selected from the group consisting of

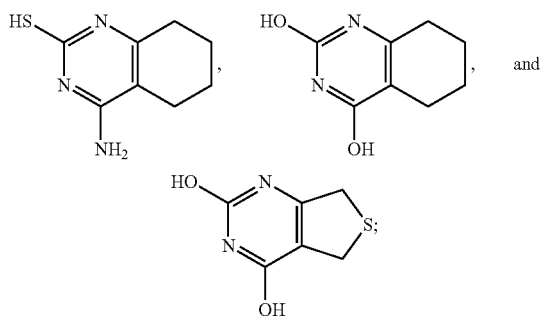

or a tautomer, salt, solvate, and/or ester thereof. In some preferred embodiments, the salt of these compounds is hydrochloride or trifluoroacetate salt.

In one embodiment of Formula (IV), B is —N—; E is —NR$^{17}$— or —N—; A is hydrogen, alkyl, substituted alkyl, aryl, substituted aryl, —OR$^9$, —SR$^9$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$; and D is =O, =S, =N—OR$^{15}$.

In one embodiment of Formula (IV), the compound of the present invention has structural Formula (IVb):

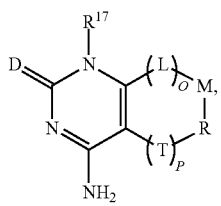

(IVb)

wherein L is —CHR$^{60}$—; M is —CHR$^{61}$—; R is —CHR$^{62}$—; T is —CHR$^{63}$—.

In some specific embodiments of Formula (IV), the compound has structural formula selected from the group consisting of:

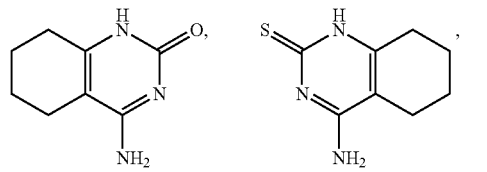

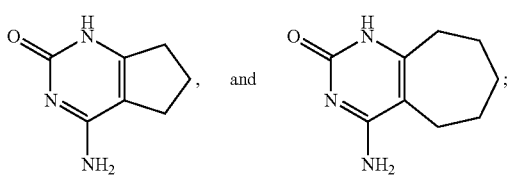

or a tautomer, salt, solvate, and/or ester thereof. In some preferred embodiments, the salt of these compounds is hydrochloride or trifluoroacetate salt.

In one embodiment of Formula (IV), the compound of the present invention has structural Formula (IVa):

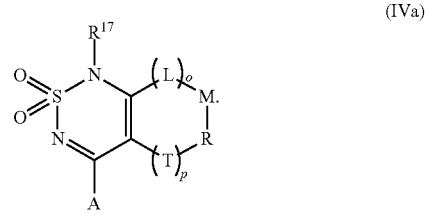

(IVa)

In one embodiment of Formula (IVa), L is —CHR$^{60}$—; M is —CHR$^{61}$—; R is —CHR$^{62}$—; and T is —CHR$^{63}$—. It is preferable that A is hydrogen, alkyl, substituted alkyl, aryl, substituted aryl, —OR$^9$, —SR$^9$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$.

In some specific embodiments of Formula (IVa), the compound has structural formula selected from the group consisting of:

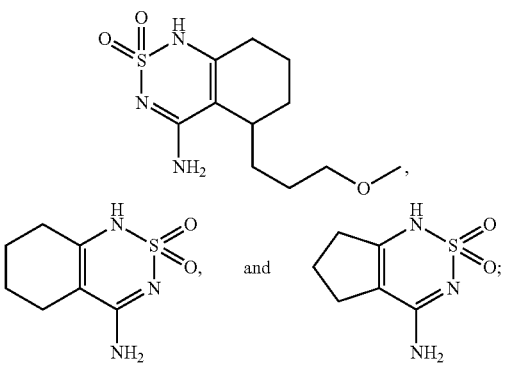

or a tautomer, salt, solvate, and/or ester thereof. In some preferred embodiments, the salt of these compounds is hydrochloride or trifluoroacetate salt.

In one embodiment of Formula (II), the compound of the present invention has structural Formula (Va):

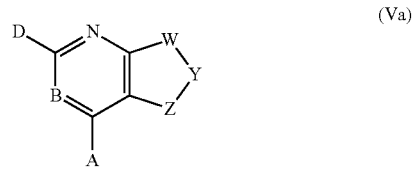

(Va)

wherein D is hydrogen, alkyl, aryl, halo, —OH, —NH$_2$, —SR$^{15}$, —CO$_2$H or —CONH$_2$; A is —NH$_2$, —NHCH$_3$, —N(CH$_3$)$_2$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$; and R$^{15}$ is hydrogen, alkyl, substituted alkyl, arylalkyl.

In one embodiment of Formula (Va), Y forms a single bond with W and a double bond with Z; W is —C(R$^{24}$)— or —N—; Y is —C(R$^{26}$)— or —N—; and Z is —S—, —N(R$^{28}$), or —O—

In one embodiment of Formula (Va), Y forms a double bond with W and a single bond with Z; W is —S—, —N($R^{25}$), or —O—; Y is —C($R^{26}$)— or —N—; and Z is —C($R^{27}$)— or —N—.

In some embodiments of Formula (Va), wherein B is —C($R^{12}$)—.

In one embodiment of Formula (Va), the compound of the present invention has structural Formula (V):

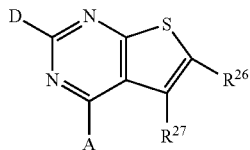

(V)

wherein:

$R^{26}$ is hydrogen, alkyl, halo, —$CO_2R^{54}$, —$CONR^{54}R^{55}$, —$SO_2NR^{54}R^{55}$, —$NR^{54}SO_2R^{55}$, —$B(OR^{54})(OR^{55})$, —$P(O)(OR^{54})(OR^{55})$ or —$P(O)(R^{54})(OR^{55})$;

$R^{27}$ is hydrogen, alkoxy, alkyl, substituted alkyl, halo, —CN, —$C(O)NR^{56}R^{57}$, —$CO_2R^{56}$, —$SO_2NR^{56}R^{57}$, —$NR^{56}SO_2R^{57}$, —$B(OR^{56})(OR^{57})$, —$P(O)(OR^{56})(OR^{57})$ or —$P(O)(R^{56})(OR^{57})$; or alternatively $R^{52}$ and $R^{53}$ together with the atoms to which they are bonded form a cycloheteroalkyl or substituted cycloheteroalkyl ring and $R^{54}$, $R^{55}$, $R^{56}$, and $R^{57}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively $R^{54}$ and $R^{55}$ or $R^{56}$ and $R^{57}$ together with the atoms to which they are bonded form a cycloheteroalkyl or substituted cycloheteroalkyl ring;

provided that when $R^{26}$ and $R^{27}$ are hydrogen, and D is —SH; then A is —$NH_2$.

In one embodiment of Formula (V), when D is methyl, A is dimethylamino, and $R^{53}$ is hydrogen; then $R^{52}$ is not methyl, ethyl or carboxyl;

when D is methyl, A is dimethylamino, and $R^{53}$ is methyl; then $R^{52}$ is not methyl;

when D is —$SCH_3$, A is dimethylamino, and $R^{53}$ is hydrogen; then $R^{52}$ is not carboethoxy;

when D is hydrogen, A is dimethylamino, and $R^{53}$ is hydrogen; then $R^{52}$ is not carboxyl or carboethoxy;

when D is hydrogen, A is dimethylamino and $R^{53}$ is methyl; then $R^{52}$ is not methyl;

when D is hydrogen, A is methylamino and $R^{53}$ is hydrogen; then $R^{52}$ is not methyl, ethyl or carboethoxy;

when D is hydrogen, A is methylamino and $R^{53}$ is methyl; then $R^{52}$ is not methyl or carboethoxy;

when D is hydrogen, A is methylamino and $R^{53}$ is —$CH_2NMe$; then $R^{52}$ is not methyl or carboethoxy;

when D is phenyl, A is methylamino and $R^{53}$ is hydrogen then $R^{52}$ is not methyl; and when D is phenyl, A is —$NH(CO)CH_3$ and $R^{53}$ is methyl then $R^{52}$ is not carbomethoxy.

In one embodiment of Formula (V), the compound of the present invention has structural formula (VI):

(VI)

wherein D is hydrogen, —$CH_3$, —$C_2H_5$, phenyl or benzyl.

In one embodiment of Formula (V), the compound of the present invention has structural formula (VII):

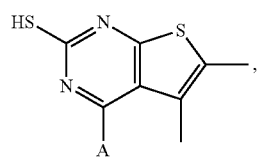

(VII)

wherein A is hydrogen, —$CH_3$, —$C_2H_5$, phenyl or benzyl.

In one embodiment of Formula (V), the compound of the present invention has structural formula (VIII):

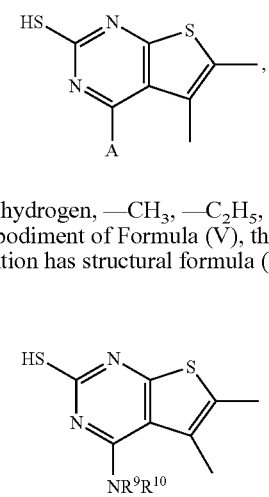

(VIII)

wherein
$R^9$ and $R^{10}$ are independently hydrogen, —$CH_3$, —$C_2H_5$, phenyl or benzyl; and
provided that both $R^9$ and $R^{10}$ are not hydrogen.

In one embodiment of Formula (V), the compound of the present invention has structural formula (IX):

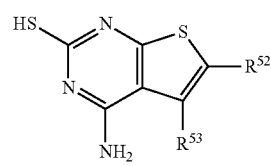

(IX)

wherein
$R^{52}$ is alkyl, substituted alkyl, —CN, —$C(O)NR^{54}R^{55}$, —$CO_2R^{54}$, —$SO_2NR^{54}R^{55}$, —$NR^{54}SO_2R^{55}$, —$B(OR^{54})(OR^{55})$, —$P(O)(OR^{54})(OR^{55})$, or —$P(O)(R^{54})(OR^{55})$;

$R^{53}$ is alkyl, $CO_2R^{56}$ or —$CONR^{56}R^{52}$, —$SO_2NR^{56}R^{52}$, —$NR^{56}SO_2R^{57}$, —$B(OR^{56})(OR^{57})$, —$P(O)(OR^{56})(OR^{52})$ or —$P(O)(R^{56})(OR^{52})$; and $R^{54}$ to $R^{57}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively $R^{52}$ and $R^{53}$ together with the atoms to which they are bonded form a cycloheteroalkyl or substituted cycloheteroalkyl ring.

In one embodiment of Formula (V), the compound of the present invention has structural formula (X):

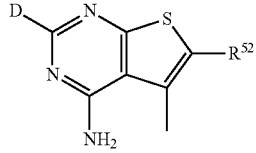

wherein,

D is —OH, —SH or —NH$_2$,

R$^{52}$ is alkyl, substituted alkyl, alkoxy, —CN, —C(O)NR$^{54}$R$^{55}$, —CO$_2$R$^{54}$, —SO$_2$NR$^{54}$R$^{55}$, —NR$^{54}$SO$_2$R$^{55}$, —B(OR$^{54}$)(OR$^{55}$), —P(O)(OR$^{54}$)(OR$^{55}$), —P(O)(R$^{54}$)(OR$^{55}$), R$^{54}$ and R$^{55}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively R$^{54}$ and R$^{55}$ together with the atoms to which they are bonded form a cycloheteroalkyl or substituted cycloheteroalkyl ring.

In some specific embodiments of Formula (Va), the compound has structural formula selected from the group consisting of

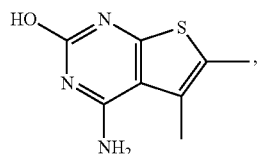 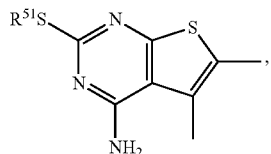

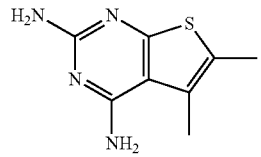 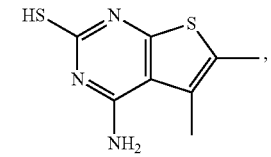

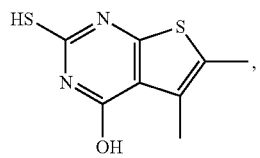 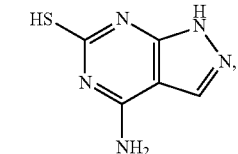

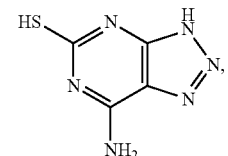 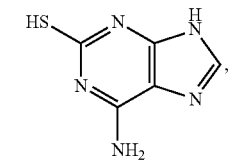

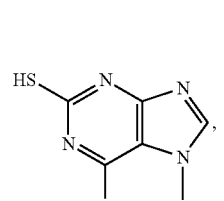 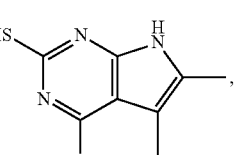

-continued

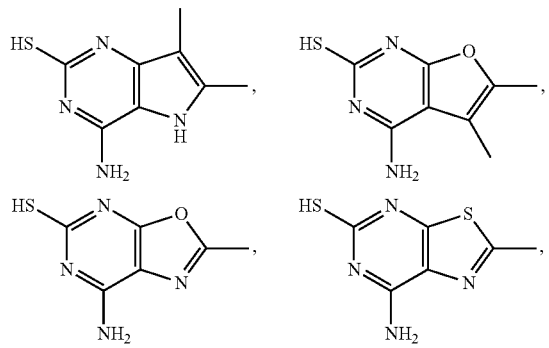

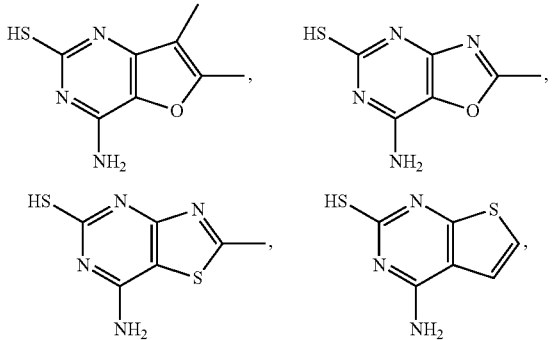

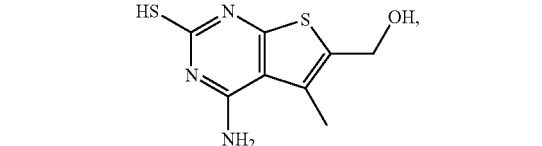

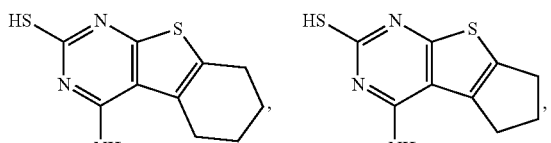

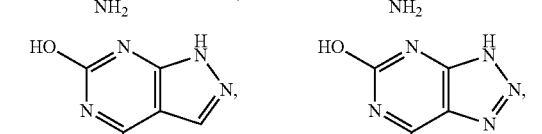


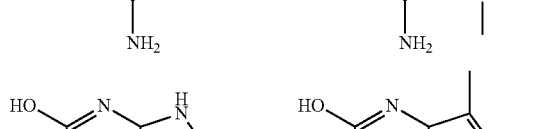

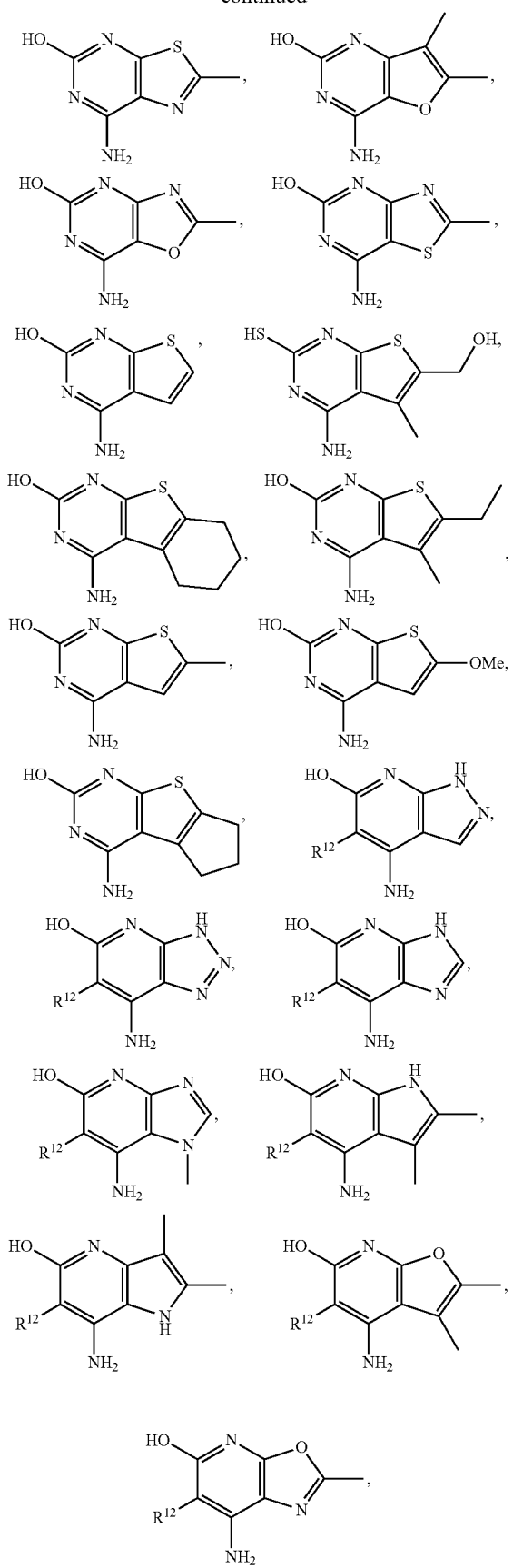
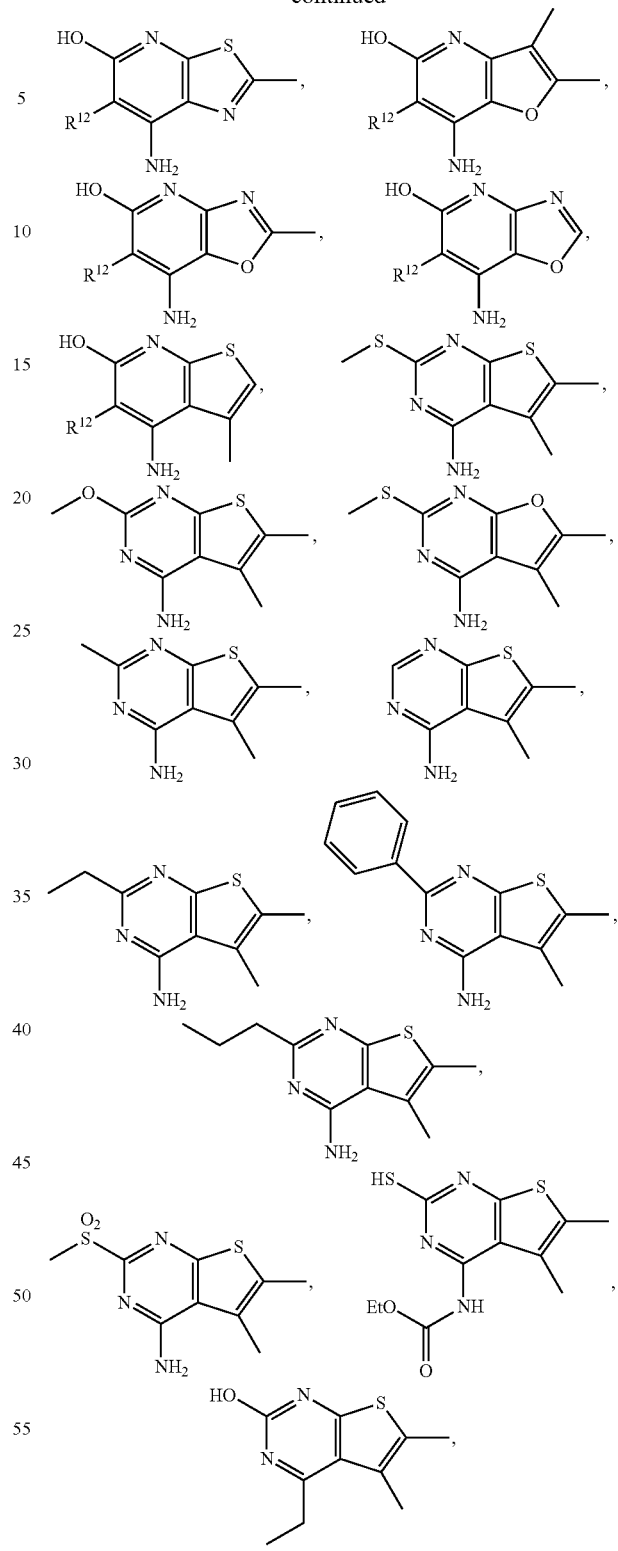
wherein,
$R^{12}$ is —OH, —SH, —CN, —CH$_2$OH, or —CO$_2$H; and
$R^{51}$ is —CH$_3$, —CH$_2$CH$_3$, benzyl, or —CH$_2$CO$_2$CH$_2$CH$_3$;
or a tautomer, salt, solvate, and/or ester thereof. In some preferred embodiments, the salt of these compounds is hydrochloride or trifluoroacetate salt.

In another embodiment of the present invention, the chemosensory receptor ligand modifier is a compound having a structure Formula (XVI):

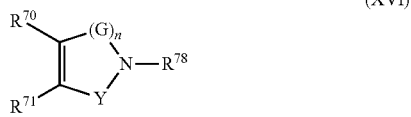

or a tautomer, salt, solvate, and/or ester thereof wherein:

n is 1, 2 or 3;

each G is independently —C($R^{77}$)($R^{79}$)—, —C(O)—, —$NR^{77}$— or —S(O)$_2$—;

provided that when n is greater than one then only one G is —C(O)—, —C(S), —S(O)$_2$— or —$NR^{77}$—;

Y is —C(O)—, —C(S) or —S(O)$_2$—;

$R^{70}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{72}$, —S(O)$_a$R$^{72}$, —NR$^{72}$R$^{73}$, —CONR$^{72}$R$^{73}$, —CO$_2$R$^{72}$, —NR$^{72}$CO$_2$R$^{73}$, —NR$^{72}$CONR$^{73}$R$^{74}$, —NR$^{72}$CSNR$^{73}$R$^{74}$ or —NR$^{72}$C(=NH)NR$^{73}$R$^{74}$, —SO$_2$NR$^{72}$R$^{73}$, —NR$^{72}$SO$_2$R$^{73}$, —NR$^{72}$SO$_2$NR$^{73}$R$^{74}$, —B(OR$^{72}$)(OR$^{73}$), —P(O)(OR$^{72}$)(OR$^{73}$) or —P(O)(R$^{72}$)(OR$^{73}$);

a and b are independently 0, 1 or 2;

$R^{71}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{74}$, —S(O)$_b$R$^{74}$, —NR$^{74}$R$^{75}$, —CONR$^{74}$R$^{75}$, —CO$_2$R$^{74}$, —NR$^{74}$CO$_2$R$^{75}$, —NR$^{74}$CONR$^{75}$R$^{76}$, —NR$^{74}$CSNR$^{75}$R$^{76}$ or —NR$^{74}$C(=NH)NR$^{75}$R$^{76}$, —SO$_2$NR$^{74}$R$^{75}$, —NR$^{74}$SO$_2$R$^{75}$, —NR$^{74}$SO$_2$NR$^{75}$R$^{76}$, —B(OR$^{74}$)(OR$^{75}$), —P(O)(OR$^{74}$)(OR$^{75}$), —P(O)(R$^{74}$)(OR$^{75}$) or alternatively, $R^{71}$ and $R^{72}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

$R^{72}$ to $R^{76}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{72}$ and $R^{73}$, $R^{73}$ and $R^{74}$, $R^{74}$ and $R^{75}$ and $R^{75}$ and $R^{76}$ together with the atoms to which they are bonded form a cycloheteroalkyl or substituted cycloheteroalkyl ring; and $R^{77}$ to $R^{79}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{77}$ and $R^{79}$, together with the atoms to which they are bonded form a cycloalkyl, substituted cycloalkyl, cycloheteroalkyl or substituted cycloheteroalkyl ring.

In some embodiments of Formula (XVI), when G is —C(O)— and $R^{78}$ is hydrogen, $R^{71}$ and $R^{72}$ do not form a phenyl ring. In other embodiments, $R^{70}$ and $R^{71}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring.

In still other embodiments of Formula (XVI), a compound of structural formula (XVII), (XVIII), (XIX) or (XX) is provided:

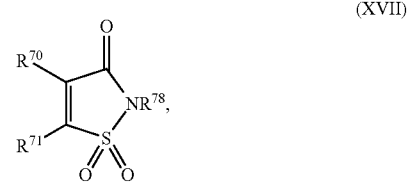

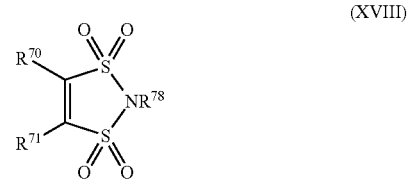

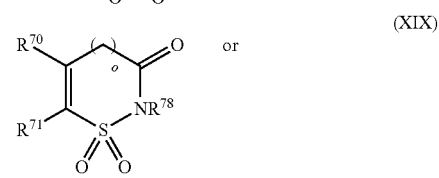

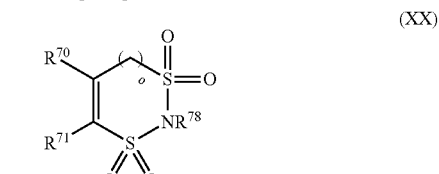

where o is 1 or 2.

In some embodiments, $R^{70}$ and $R^{71}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring.

In another embodiment of Formula (XVI), the chemosensory receptor ligand modifier is a compound having a structure Formula (XXI):

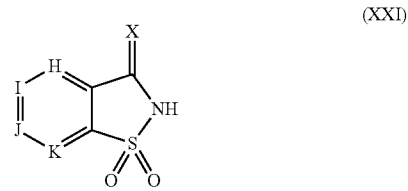

wherein:

X is O or S;

H is —N— or —CR$^{81}$—;

I is —N— or —CR$^{82}$—;

J is —N— or —CR$^{83}$—;

K is —N— or —CR$^{84}$—;

with the proviso that no more than 2 of H, I, J or K are —N—;

R$^{81}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{85}$R$^{86}$, —CO$_2$R$^{85}$, —SO$_2$NR$^{85}$R$^{86}$, —NR$^{85}$SO$_2$R$^{86}$, —B(OR$^{85}$)(OR$^{86}$), —P(O)(OR$^{85}$)(OR$^{86}$) or —P(O)(R$^{85}$)(OR$^{86}$);

R$^{82}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{88}$R$^{87}$, —CO$_2$R$^{88}$, —SO$_2$NR$^{88}$R$^{87}$, —NR$^{88}$SO$_2$R$^{87}$, —B(OR$^{88}$)(OR$^{87}$), —P(O)(OR$^{88}$)(OR$^{87}$) or —P(O)(R$^{88}$)(OR$^{87}$);

R$^{83}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{90}$R$^{89}$, —CO$_2$R$^{90}$, —SO$_2$NR$^{90}$R$^{89}$, —NR$^{90}$SO$_2$R$^{89}$, —B(OR$^{90}$)(OR$^{89}$), —P(O)(OR$^{90}$)(OR$^{89}$) or —P(O)(R$^{90}$)(OR$^{89}$);

R$^{84}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{92}$R$^{91}$, —CO$_2$R$^{90}$, —SO$_2$NR$^{92}$R$^{91}$, —NR$^{92}$SO$_2$R$^{91}$, —B(OR$^{92}$)(OR$^{91}$), —P(O)(OR$^{92}$)(OR$^{91}$) or —P(O)(R$^{92}$)(OR$^{91}$); and R$^{85}$ to R$^{91}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively R$^{85}$ and R$^{86}$, R$^{87}$ and R$^{88}$, R$^{89}$ and R$^{90}$, or R$^{91}$ and R$^{92}$ together with the atoms to which they are bonded form a cycloalkyl, substituted cycloalkyl, cycloheteroalkyl or substituted cycloheteroalkyl ring;

provided that R$^{81}$, R$^{82}$, R$^{83}$ and R$^{84}$ are not all hydrogen.

In some embodiments of Formula (XXII), R$^{81}$, R$^{82}$, R$^{83}$ and R$^{84}$ are independently hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NHMe, —CO$_2$H, —CO$_2$CH$_3$, —SO$_2$N(CH$_3$)$_2$, —NHSO$_2$CH$_3$, —B(OH)$_2$ or —P(O)(OH)$_2$.

In still other embodiments of Formula (XXII), compounds having the structures below are provided:

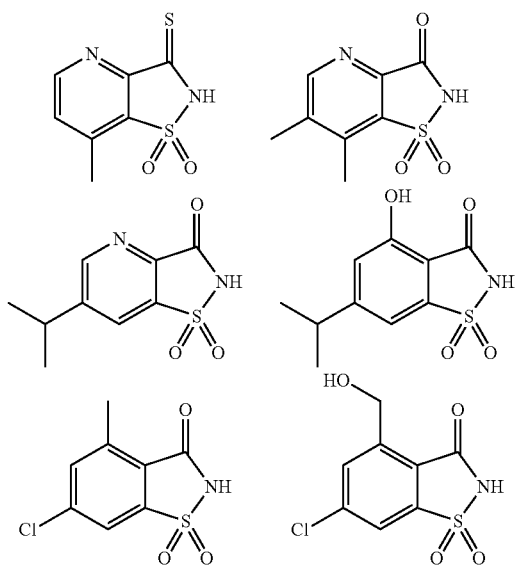

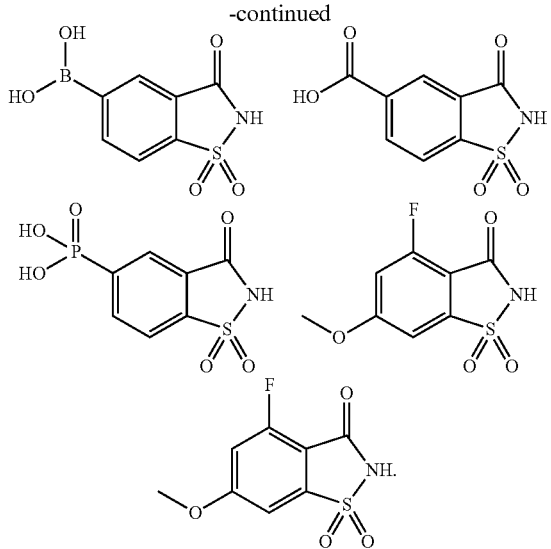

-continued

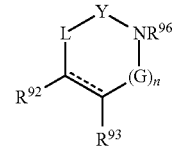

In another embodiment of the present invention, the chemosensory receptor ligand modifier is a compound having a structure Formula (XXII):

(XXII)

or a tautomer, salt, solvate, and/or ester thereof, wherein:

each G is independently —C(R$^{94}$)(R$^{95}$)—, —C(O)—, —NR$^{94}$— or —S(O)$_2$—;

n is 1, 2 or 3;

provided that when n is greater than one then only one G is —C(O)—, —S(O)$_2$— or —NR$^{94}$—;

Y is —C(O)—, —C(S)— or —S(O)$_2$—;

L is —C(R$^{104}$)(R$^{105}$)—, —O—, or —NR$^{104}$—;

R$^{92}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{98}$, —S(O)$_y$R$^{98}$, —NR$^{98}$R$^{99}$, —CONR$^{98}$R$^{99}$, —CO$_2$R$^{98}$, —NR$^{98}$CO$_2$R$^{99}$, —NR$^{98}$CONR$^{99}$R$^{100}$, —NR$^{98}$CSNR$^{99}$R$^{100}$ or —NR$^{98}$C(=NH)NR$^{99}$R$^{100}$, —SO$_2$NR$^{98}$R$^{99}$, —NR$^{98}$SO$_2$R$^{99}$, —NR$^{98}$SO$_2$NR$^{99}$R$^{100}$, —B(OR$^{98}$)(OR$^{99}$), —P(O)(OR$^{98}$)(OR$^{99}$) or —P(O)(R$^{98}$)(OR$^{99}$);

R$^{93}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —S(O)$_z$R$^{101}$, —NR$^{101}$R$^{102}$, —CONR$^{101}$R$^{102}$, —CO$_2$R$^{101}$, —NR$^{101}$CO$_2$R$^{102}$, —NR$^{101}$CONR$^{102}$R$^{103}$, —NR$^{101}$CSNR$^{102}$R$^{103}$ or —NR$^{101}$C(=NH)NR$^{102}$R$^{103}$, —SO$_2$NR$^{101}$R$^{102}$, —NR$^{101}$SO$_2$R$^{102}$, —NR$^{101}$SO$_2$NR$^{102}$, R$^{103}$, —B(OR$^{101}$)(OR$^{102}$), —P(O)(OR$^{101}$)(OR$^{102}$), —P(O)(R$^{101}$)(OR$^{102}$) or alternatively, R$^{92}$ and R$^{93}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

y and z are independently 0, 1 or 2;

$R^{98}$ to $R^{103}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{98}$ and $R^{99}$, $R^{99}$ and $R^{100}$, $R^{101}$ and $R^{102}$, or $R^{102}$ and $R^{103}$ together with the atoms to which they are bonded form a cycloalkyl, substituted cycloalkyl, cycloheteroalkyl or substituted cycloheteroalkyl ring;

$R^{94}$ to $R^{95}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{94}$ and $R^{95}$, together with the atoms to which they are bonded form a cycloalkyl, substituted cycloalkyl, cycloheteroalkyl or substituted cycloheteroalkyl ring;

$R^{96}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and $R^{104}$ to $R^{105}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{104}$ and $R^{105}$, together with the atoms to which they are bonded form a cycloalkyl, substituted cycloalkyl, cycloheteroalkyl or substituted cycloheteroalkyl ring.

In some embodiments, when L is O, $R^{95}$ is hydrogen, $R^{92}$ is methyl and the bond connecting the carbon atoms bonded to $R^{92}$ and $R^{93}$ is a double bond then $R^{93}$ is not hydrogen.

In some embodiments of Formula (XXII), a compound of structural formula (XXIII) is provided:

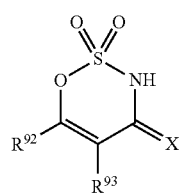

(XXIII)

where when $R^{92}$ is —CH$_3$ then $R^{93}$ is not hydrogen and that both $R^{92}$ and $R^{93}$ are not hydrogen.

In some embodiments of Formula (XXII), $R^{92}$ and $R^{93}$ are independently are independently hydrogen, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —SCH$_3$, —C(O)NHMe, —CO$_2$H, —CO$_2$CH$_3$, —SO$_2$N(CH$_3$)$_2$, —NHSO$_2$CH$_3$, —B(OH)$_2$ or —P(O)(OH)$_2$. In other embodiments, $R^{92}$ and $R^{93}$ together with the atoms to which they are attached form a cycloalkyl, cycloheteroalkyl, aryl or heteroaryl ring.

In other embodiments of Formula (XXII), compounds having the structures below are provided:

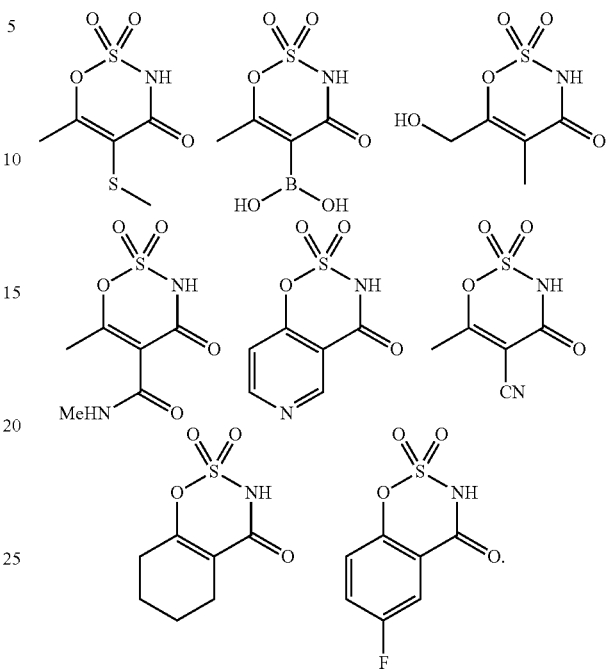

The definitions and substituents for various genus and sub-genus of the present compounds have been described above in detail. It should be understood by one skilled in the art that any combination of the definitions and substituents described above should not result in a inoperable species or compound. By "inoperable species or compound", it is meant a compound structure that violates the relevant scientific principle (such as, for example, a carbon atom connecting to more than four covalent bonds) or is so unstable that separation of the compound from a reaction is impossible (such as, for example, more than three carbonyl groups connecting to each other continuously).

In one embodiment, the present invention provides a process of preparing a compound having structural Formula (a):

(a)

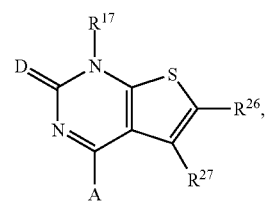

comprising reacting a compound having structural Formula (b)

(b)

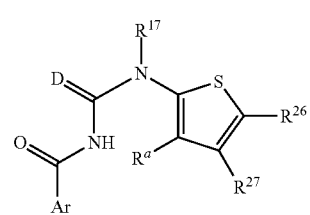

with a base, wherein D is oxygen or sulfur; A is —NH$_2$ or —OR$^b$; R$^{17}$ is hydrogen, alkyl, substituted alkyl, aryl, substituted aryl, arylalkyl, or substituted arylalkyl; R$^{26}$ and R$^{27}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{31}$, —S(O)$_h$R$^{31}$, —NR$^{31}$R$^{32}$, —CONR$^{31}$R$^{32}$, —CO$_2$R$^{31}$, —SO$_2$NR$^{31}$R$^{32}$, or —NR$^{31}$SO$_2$R$^{32}$; or alternatively R$^{26}$ and R$^{27}$, together with the atoms to which they are bonded, form a cycloalkyl, substituted cycloalkyl, heterocycloalkyl, or substituted heterocycloalkyl ring; Ar is aryl or substituted aryl; and R$^a$ is —CN, —C(O)R$^b$, —C(O)OR$^b$, —C(O)N(R$^b$)$_2$; each R$^b$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; h is 0, 1 or 2; and R$^{31}$ and R$^{32}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively R$^{31}$ and R$^{32}$, together with the atoms to which they are bonded, form a cycloheteroalkyl or substituted cycloheteroalkyl ring. It is preferable that the base is an inorganic base, such as NaOH.

In one embodiment, the compound having structural Formula (b) is prepared by reacting a compound having structural Formula (c):

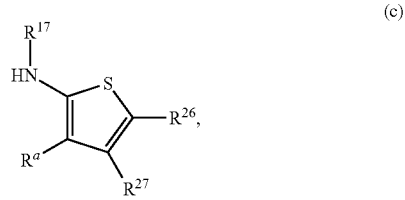

with a compound having structural Formula (d):

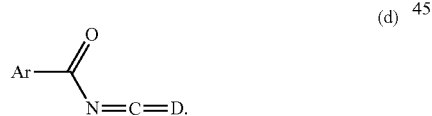

Preferably, the above Ar group is phenyl or substituted phenyl.

In another embodiment, the present invention provides a process of preparing a compound having structural Formula (e):

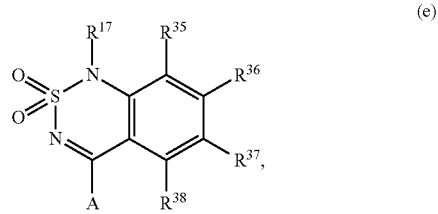

comprising reacting a compound having structural Formula (f)

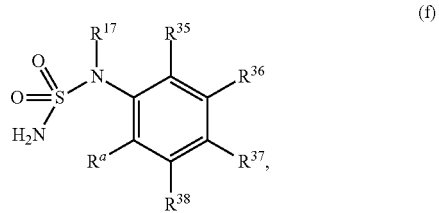

with a base, wherein A is —NH$_2$ or —OR$^b$; R$^{17}$ is hydrogen, alkyl, substituted alkyl, aryl, substituted aryl, arylalkyl, or substituted arylalkyl; R$^{35}$, R$^{36}$, R$^{37}$, and R$^{38}$ are each independently hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —NO$_2$, —OR$^{41}$, —S(O)$_k$R$^{41}$, —NR$^{41}$R$^{42}$, —CONR$^{41}$R$^{42}$, —CO$_2$R$^{41}$, SO$_2$NR$^{41}$R$^{42}$, and —NR$^{41}$SO$_2$R$^{42}$; or alternatively, R$^{35}$ and R$^{36}$, R$^{36}$ and R$^{37}$, or R$^{37}$ and R$^{38}$, together with the atoms to which they are bonded, form a cycloalkyl, substituted cycloalkyl, heterocycloalkyl, or substituted heterocycloalkyl ring; R$^a$ is —CN, —C(O)R$^b$, —C(O)OR$^b$, —C(O)N(R$^b$)$_2$; each R$^b$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; and R$^{41}$ and R$^{42}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively R$^{41}$ and R$^{42}$, together with the atoms to which they are bonded, form a cycloheteroalkyl or substituted cycloheteroalkyl ring. It is preferable that the base is an inorganic base, such as NaOH.

In another embodiment, the present invention provides a process of preparing a compound having structural Formula (e):

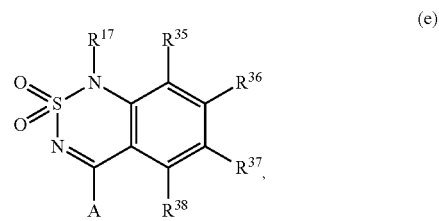

comprising reacting a compound having structural Formula (g)

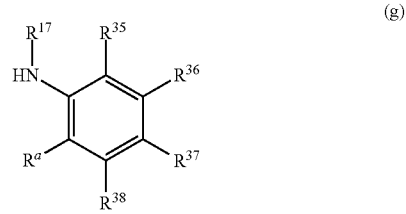

with $NH_2S(O)_2NH_2$ or $Cl-S(O)_2-NH_2$ in the presence of a base to provide directly a compound having structural Formula (e); or alternatively to provide the compound having structural formula (f) as described above which is further reacted with a base to provide a compound having structural Formula (e). It is preferable that the base is an organic base, such as DBU.

In general, the compounds of the present invention, e.g., compounds with the formulae described herein can be synthesized according to the processes described above and the following exemplary procedures and/or schemes.

As discussed hereinabove, a salt of the compound of the present invention generally can be formed by reacting the compound with an acid or base. In one embodiment, the present invention further provides a synthetic method for preparing a salt of the compound having any of the above-mentioned structural formula at a large scale. The synthetic method enables preparation of a large quantity of a salt of the present compound quickly and economically. The synthetic method can be applied in either a laboratory setting or an industrial setting. One example of the synthetic method is described in details as Example 165 hereinbelow.

Roy et al., *J. Org. Chem.* 2006, 71, 382; Jung et al., *J. Med. Chem.* 2006, 49, 955; Khabnadideh et al., *Bioorg. Med. Chem.* 2005, 13, 2637). The amino group in the starting material A can be further functionalized by alkylation (Brown et al., *J. Med. Chem.* 1990, 33, 1771) or reductive amination (Uehling et al., *J. Med. Chem.* 2006, 49, 2758, etc.) to provide the corresponding N-monosubstituted 2-amino nitriles, 2-amino ketones or 2-amino carboxyl derivatives C. The coupling reaction of A or C with iso(thio)cyanates such as, for example, benzoyliso(thio)cyanates and subsequent cyclization by treatment with NaOH provides the pyrimidin-2(1H)-(thi)one derivatives E including, but not limited to, fused pyrimidin-2(1H)-(thi)ones such as quinazolin-2(1H)-(thi)one and pyrido[2,3-d]pyrimidin-2(1H)-(thi)one derivatives (El-Sherbeny et al., *Med. Chem. Rev.* 2000, 10, 122 and references cited therein; Reddy et al., *Synthetic Commun.* 1988, 18, 525; Wilson, *Org. Lett.* 2001, 3, 585, and references cited therein). Direct cyclization of A or C with (thio)ureas in the presence of NaOH also results in the formation of pyrimidin-2(1H)-(thi)one derivatives E (Scheme 1) (Naganawa et al., *Bioorg. Med. Chem.* 2006, 14, 7121 and references cited therein).

Scheme 1

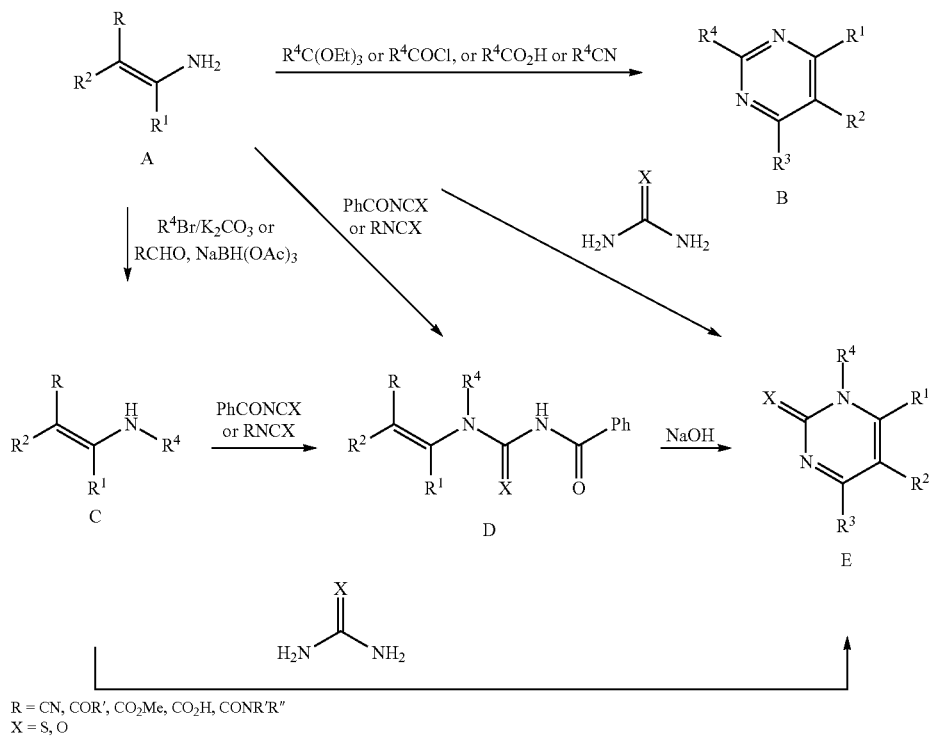

R = CN, COR', CO$_2$Me, CO$_2$H, CONR'R''
X = S, O

In general, the compounds of the present invention, e.g., compounds with the formulae described herein can be synthesized according to the following exemplary procedures and/or schemes.

Pyrimidines B including fused pyrimidine derivatives such as quinazolines and pyrido[2,3-d]pyrimidines are synthesized from 2-amino nitriles, 2-amino ketones, or 2-amino carboxyl derivatives A by reaction with the corresponding carboxyl derivatives as illustrated in Scheme 1 (Rad-Moghadam et al., *J. of Heterocyclic Chem.* 2006, 43, 913;

Pyrimidines B and pyrimidin-2(1H)-(thi)ones E can also be prepared from corresponding 1,3-dicarbonyl derivatives and α,β-unsaturated carbonyl derivatives by condensation with guanidines, amidines, or (thio)urea derivatives as shown in Scheme 2 (Sharma et al., *Eur. J. Med. Chem.* 2006, 41, 83, and references cited therein; Bellur et al., *Tetrahedron* 2006, 62, 5426 and references cited therein; Hauser et al., *J. Org. Chem.* 1953, 18, 588).

Scheme 2

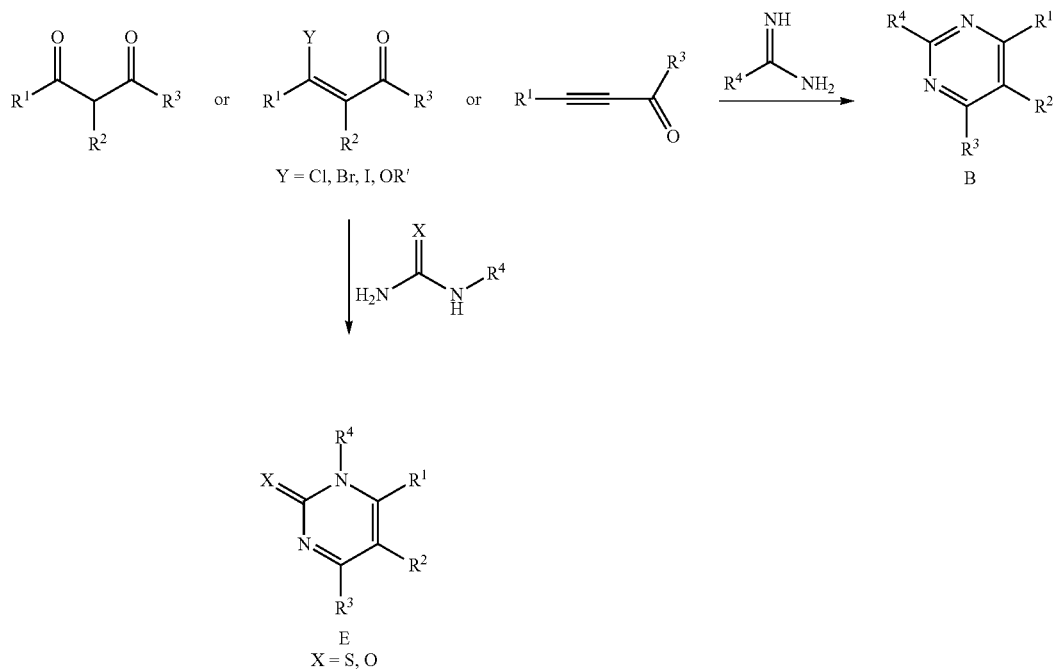

Various pyrimidines and pyrimidin-2(1H)-(thi)ones as well as their fused pyrimidine and pyrimidin-2(1H)-(thi)one derivatives such as quinazolines and quinazolin-2(1H)-ones can be synthesized from pyrimidine-2,4(1H,3H)-dione derivatives as well as the fused pyrimidine-2,4(1H,3H)-diones such as quinazoline-2,4(1H,3H)-dione and pyrido[2,3-d]pyrimidine-2,4(1H,3H)-dione derivatives (Scheme 3). Reaction of pyrimidine-2,4(1H,3H)-dione derivatives with phosgene or POCl$_3$ provides the corresponding 2,4-dichloropyrimidines (Lee et al., *Synlett*. 2006, 65 and references cited therein). Subsequent displacements of the two chlorides with various nucleophiles resulted in the formation of pyrimidines and pyrimidin-2(1H)-(thi)ones as well as fused pyrimidine and pyrimidin-2(1H)-(thi)one derivatives (Kanuma et al., *Bioorg. & Med. Chem. Lett.* 2005, 15, 3853 and references cited therein; Liu et al., *Bioorg. & Med. Chem. Lett.* 2007, 17, 668; Wilson et al., *Bioorg. & Med. Chem.* 2007, 15, 77; Boarland et al., *J. Chem. Soc.* 1951, 1218).

Scheme 3

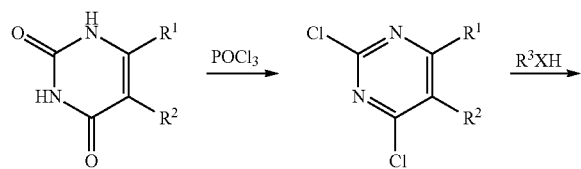

-continued

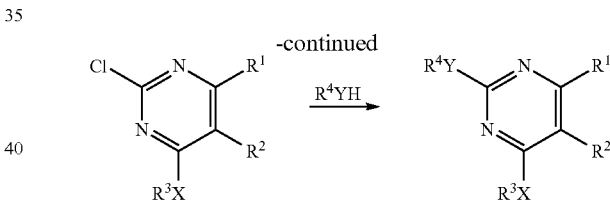

Similarly, [1,2,6]thiadiazine-2,2-dioxides and fused [1,2,6]thiadiazine-2,2-dioxide derivatives such as, for example, 1H-benzo[c][1,2,6]thiadiazine-2,2-dioxides are also synthesized from 2-amino nitriles, 2-amino ketones, or 2-amino carboxyl derivatives A or C (Scheme 4), by reaction with NH$_2$SO$_2$Cl (Hirayama et al., *Bioorg. & Med. Chem.* 2002, 10, 1509; Kanbe et al., *Bioorg. & Med. Chem. Lett.* 2006, 16, 4090 and references cited therein) or NH$_2$SO$_2$NH$_2$ (Maryanoff et al., *J. Med. Chem.* 2006, 49, 3496, and references cited therein) and followed by cyclization in the presence of NaOH (Goya et al., *Heterocycles*, 1986, 24, 3451; Albrecht et al., *J. Org. Chem.* 1979, 44, 4191; Goya et al., *Arch. Pharm. (Weinheim)* 1984, 317, 777). The condensation of the corresponding 1,3-dicarbonyl derivatives, α,β-unsaturated carbonyl derivatives with sulfamide derivatives (Scheme 4) also results in the formation of [1,2,6]thiadiazine-2,2-dioxide derivatives (Wright, *J. Org. Chem.* 1964, 29, 1905).

Scheme 4

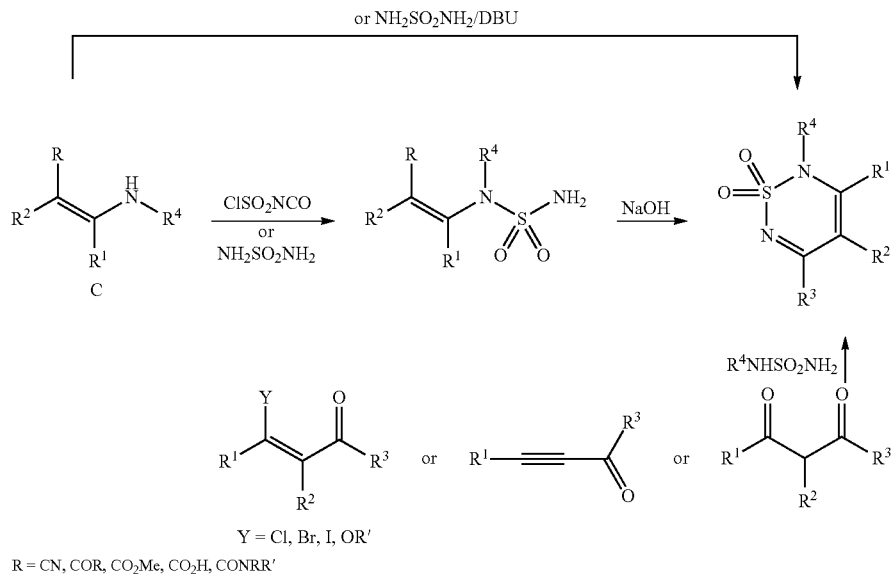

Methods for the synthesis of thieno[2,3-d]pyrimidine derivatives are described in Scheme 5. 2-Amino thiophene derivatives 303 are synthesized via the Gewald reaction (Chen et al., *Synthetic Communication* 2004, 34, 3801 and references cited therein; Elmegeed et al., *Eur. J. Med. Chem.* 2005, 40, 1283 and references cited therein). Compound 303 can be cyclized with the corresponding carboxyl derivatives to give the thieno[2,3-d]pyrimidine derivatives 304 (Rad-Moghadam, *J. Heterocyclic Chem.* 2006, 43, 913; Seijas et al., *Tetrahedron Lett.* 2000, 41, 2215, and references cited therein; Jung et al., *J. Med. Chem.* 2006, 49, 955.).

Scheme 5

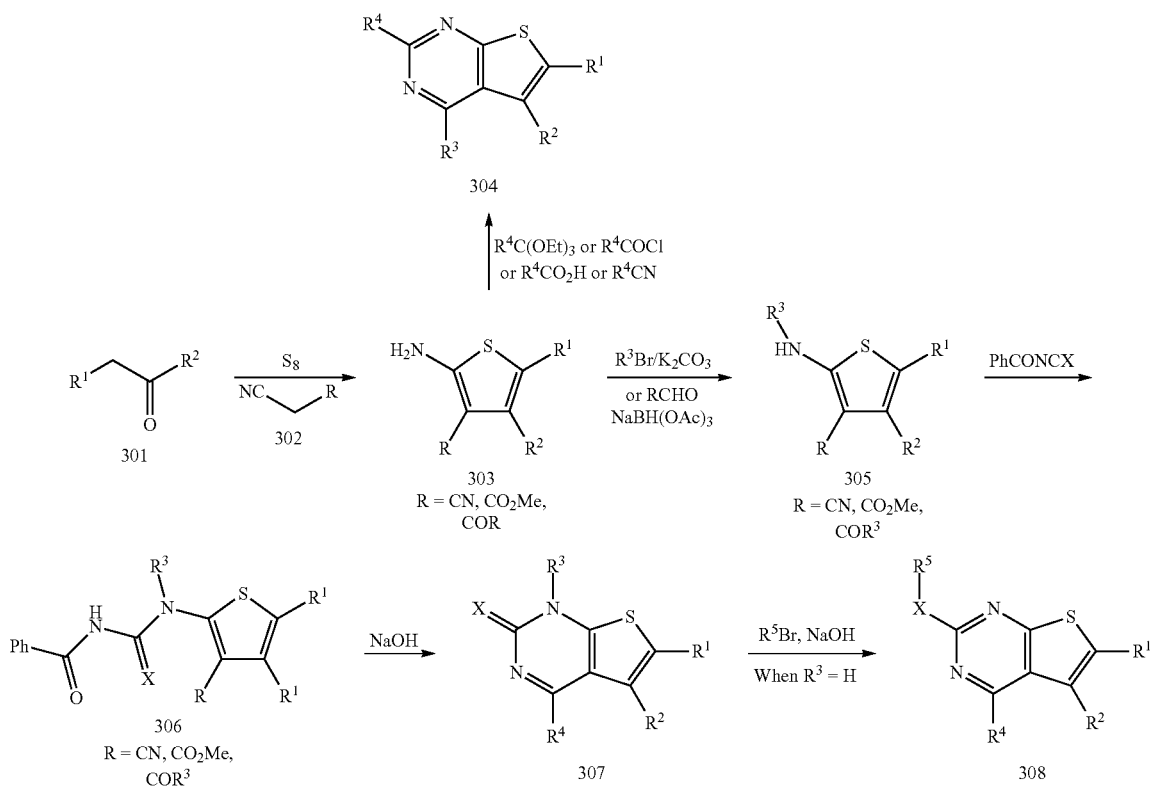

-continued

When R³ = NH₂ | RCO₂H or RCOCl or RSO₂Cl or RCHO or RNCO or RNCS

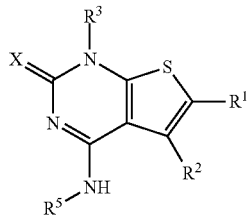

309

X = S, O

2-Amino thiophene derivatives 303 can be further alkylated by either treatment with R₃Br/K₂CO₃ or with RCHO/ NaBH(OAc)₃ to give the N-alkylated 2-amino thiophene derivatives 305 (Brown et al., *J. Med. Chem.* 1990, 33, 1771; Uehling et al., *J. Med. Chem.* 2006, 49, 2758 and references cited therein), which are then reacted, for example, with benzoyliso(thio)cyanate to give the corresponding benzoyl (thio) urea derivatives 306. Compounds 306 may be cyclized by treatment with NaOH to provide thieno[2,3-d]pyrimidine derivatives 7 (El-Sherbeny et al., *Med. Chem. Rev.* 2000, 10, 122, and references cited therein; Reddy et al., *Synthetic Commun.* 1988, 18, 525; Wilson, *Org. Lett.* 2001, 3, 585 and references cited therein). When R³=H, compounds 307 may be reacted with R₅Br/NaOH to give the alkylated products 8 (Hirota et al., *Bioorg. Med. Chem.* 2003, 11, 2715.). When R⁴=NH₂, the amino group can be further functionalized to give the products 309.

Similarly, quinazolin-2(1H)-one and quinazolin-2(1H)-thione derivatives 402 were synthesized from various 2-aminobenzoic acid derivatives, 2-aminobenzonitrile derivatives, 2-aminoacetophenone derivatives and 2-aminobenzamide derivatives 400 as shown in Scheme 6. Coupling reaction of compounds 400 with benzoyl iso(thio)cyanates lead to the formation of corresponding benzoyl (thio)urea derivatives 401. Their cyclization in the presence of NaOH provides the quinazolin-2(1H)-(thi)one derivatives 402 (El-Sherbeny, *Med. Chem. Rev.* 2000, 10, 122 and references cited therein; Reddy et al., *Synthetic Commun.* 1988, 18, 525; Wilson, *Org. Lett.* 2001, 3, 585 and references cited therein).

Scheme 6

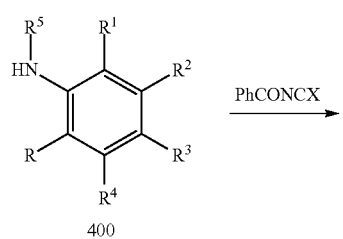

400

-continued

401

R = CN, COR', CO₂Me, CO₂H, CONR'R''
X = S, O

402

1H-benzo[c][1,2,6]thiadiazine-2,2-dioxide derivatives 404 are synthesized from the same starting materials 400 (Scheme 7) via their reactions with sulfamide or sulfamoyl chloride, followed by cyclization with NaOH. Direct reaction of compounds 400 with sulfamide in the presence of DBU at the elevated temperature also resulted in the formation of 1H-benzo[c][1,2,6]thiadiazine-2,2-dioxide derivatives 404 (Maryanoff et al., *J. Med. Chem.* 2006, 49, 3496, and references cited therein).

Scheme 7

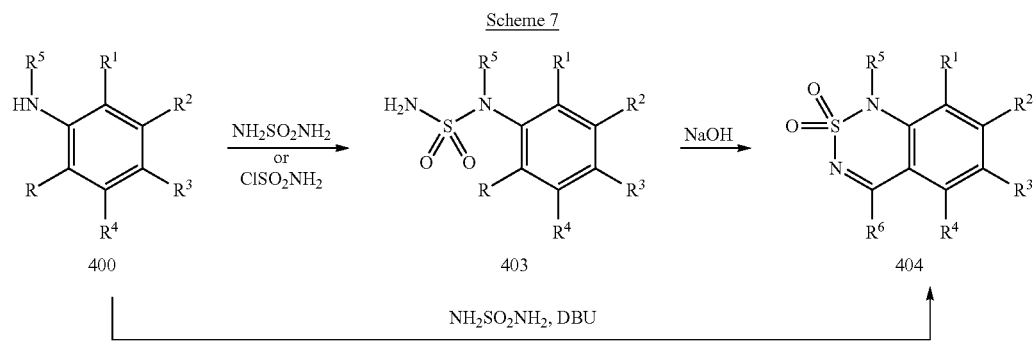

R = CN, COR', CO₂Me, CO₂H, CONR'R"

Quinazoline derivatives are also synthesized from quinazoline-2,4(1H,3H)-diones (Scheme 8). Reaction of quinazoline-2,4(1H,3H)-diones with POCl₃ provided the corresponding dichloroquinazolines (Zunszain et al., *Bioorg. & Med. Chem.* 2005, 13, 3681 and references cited therein). Subsequent displacements of the two chlorides with various nucleophiles resulted in formation of quinazoline derivatives (Scheme 8) (Kanuma et al., *Bioorg. & Med. Chem. Lett.* 2005, 15, 3853 and references cited therein; Blackburn, *Bioorg. & Med. Chem. Lett.* 2006, 16, 2621).

Scheme 8

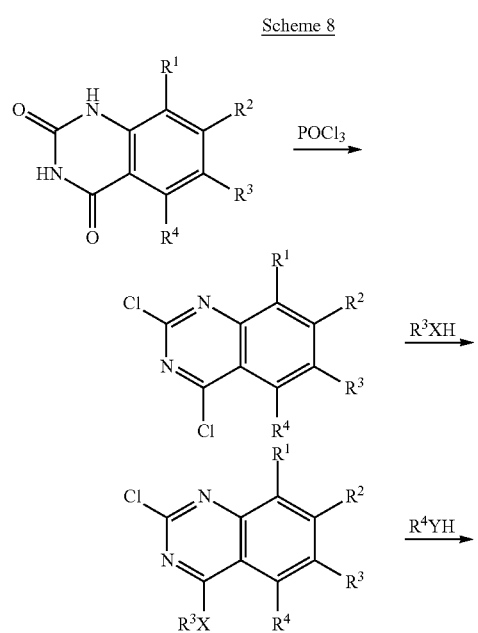

-continued

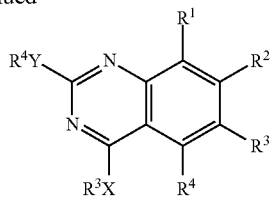

4-Amino-5,6,7,8-tetrahydroquinazolin-2(1H)-(thi)one derivatives and 4-amino-5,6,7,8-tetrahydro-1H-benzo[c][1,2,6]thiadiazine-2,2-dioxide derivatives, as well as structural analogs with different ring sizes, as shown in Scheme 9, are generally synthesized according to the methods described therein. Thorpe-Ziegler cyclization of dinitriles in the presence of base provides β-amino-α,β-unsaturated nitrile derivatives (Winkler et al., *Tetrahedron* 2005, 61, 4249; Yoshizawa et al., *Green Chem.* 2002, 4, 68, and references cited therein; Rodriguez-Hahn et al., *Synthetic Commun.* 1984, 14, 967, and references cited therein; Francis et al., *J. Med. Chem.* 1991, 34, 2899). The β-amino-α,β-unsaturated nitrites may be reacted, for example, with benzoyliso(thio)cyanate and subsequently cyclized by treatment with NaOH to provide 4-amino-5,6,7,8-tetrahydroquinazolin-2(1H)-(thi)one derivatives (El-Sherbeny et al., *Med. Chem. Rev.* 2000, 10, 122, and references cited therein; Reddy et al., *Synthetic Commun.* 1988, 18, 525) as well as their structural analogs with different ring sizes (Scheme 9). Similarly reaction of β-amino-α,β-unsaturated nitrile derivatives with sulfamoyl chloride, followed by treatment with NaOH provides 4-amino-5,6,7,8-tetrahydro-1H-benzo[c][1,2,6]thiadiazine-2,2-dioxide derivatives, as well as structural analogs with different ring size (Scheme 9) (Hirayama et al., *Bioorg.& Med. Chem.* 2002, 10, 1509; Kanbe et al., *Bioorg. & Med. Chem. Lett.* 2006, 16, 4090 and references cited therein).

Scheme 9

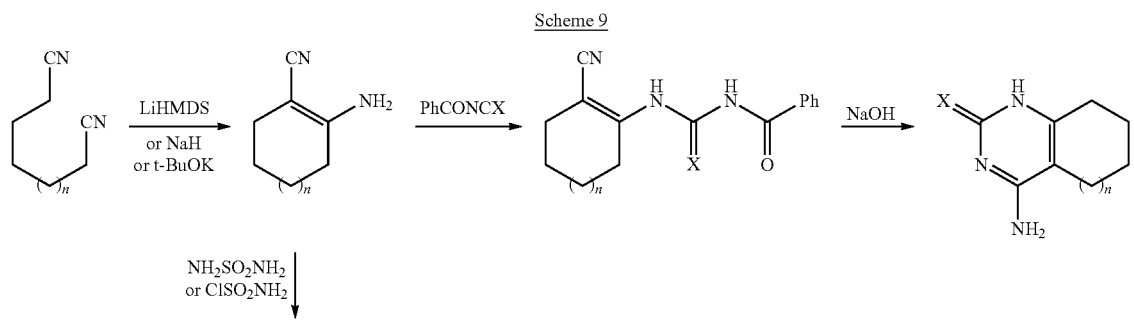

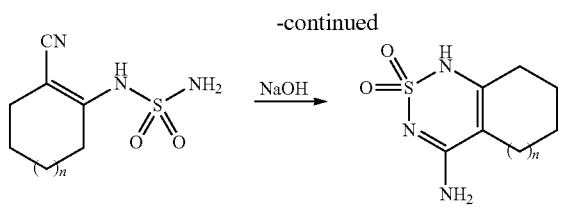

n = 0-5
X = S, O

Acesulfame and fused acesulfame derivatives C such as benzo[e][1,2,3]oxathiazin-4(3H)-one-2,2-dioxides can be synthesized via the reaction of 1,3-dicarbonyl derivatives A or 2-hydroxy carboxyl derivatives B and D with $SO_3$ or $ClSO_2NH_2$, as described in Scheme 10 (Linkies et al, *Synthesis* 1990, 405 and references cited therein; Ahmed et al., *J. Org. Chem.* 1988, 53, 4112; Ahmed et al., *Heterocycles* 1989, 29, 1391).

Scheme 10

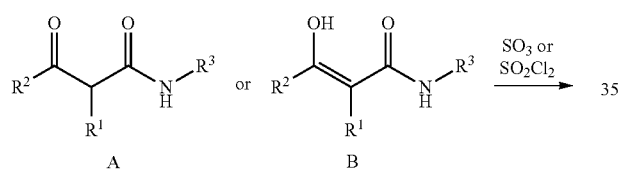

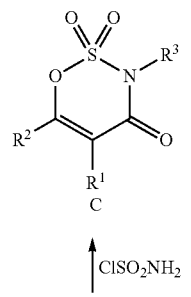

Acesulfame derivatives C can also be synthesized via cyclization of alkynes or enols with $FSO_2NCO$ (Clauss et al., *Tetrahedron Lett.* 1970, 2, 119) or $ClSO_2NCO$ (Rasmussen et al., *J. Org. Chem.* 1973, 38, 2114; Etter et al., *J. Org. Chem.* 1986, 51, 5405; Tripathi et al., *Indian J. Chem. Sect. B* 1987, 26B, 1082.) as shown in Scheme 11.

Scheme 11

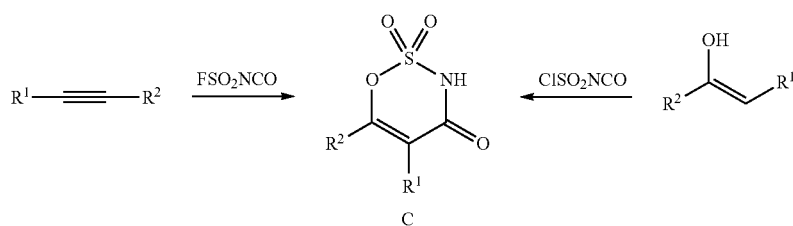

Saccharin derivatives may be synthesized by direct oxidative cyclization of N-alkyl-o-methyl-arenesulfonamides as shown in Scheme 12 (Xu et al., *Tetrahedron* 2006, 62, 7902 and references cited therein; Pal et al., *Letters in Drug Design & Discovery* 2005, 2, 329). Cyclization of o-carboxyl-arenesulfonyl chloride derivatives with primary amines can also provide saccharin derivatives (Robinson et al., *Eur. J. Org. Chem.* 2006, 19, 4483 and references cited therein; Yamada et al., *J. Med. Chem.* 2005, 48, 7457 and references cited therein; Da Settimo et al., *J. Med. Chem.* 2005, 48, 6897). Other heteroaromatic fused isothiazol-3(2H)-one-1,1-dioxide derivatives may be synthesized similarly.

Scheme 12

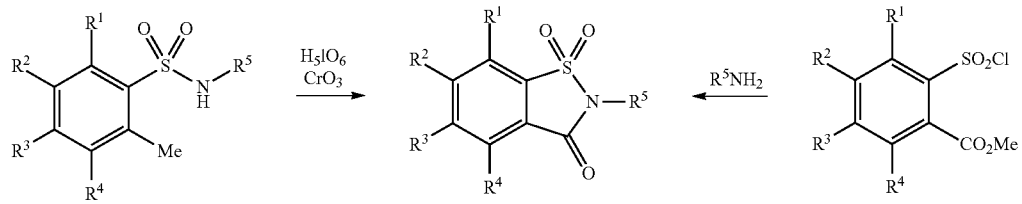

According to the present invention, chemosensory receptor modifiers or chemosensory receptor ligand modifiers of the present invention can be used for one or more methods of the present invention, e.g., modulating a chemosensory receptor and/or its ligands. In general, chemosensory receptor modifiers and chemosensory receptor ligand modifiers of the present invention are provided in a composition, such as, e.g., an ingestible composition. As used herein, an "ingestible composition" includes any substance intended for oral consumption either alone or together with another substance. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that use sucralose and or other sweeteners.

The ingestible composition also includes pharmaceutical, medicinal or comestible composition, or alternatively in a formulation, e.g., a pharmaceutical or medicinal formulation or a food or beverage product or formulation.

In one embodiment, the chemosensory receptor modifiers or chemosensory receptor ligand modifiers provided by the present invention can be used at very low concentrations on the order of a few parts per million, in combination with one or more known sweeteners, natural or artificial, so as to reduce the concentration of the known sweetener required to prepare an ingestible composition having the desired degree of sweetness.

Commonly used known or artificial sweeteners for use in such combinations of sweeteners include but are not limited to the common saccharide sweeteners, e.g., sucrose, fructose, glucose, and sweetener compositions comprising natural sugars, such as corn syrup (including high fructose corm syrup) or other syrups or sweetener concentrates derived from natural fruit and vegetable sources, semi-synthetic "sugar alcohol" sweeteners such as erythritol, isomalt, lactitol, mannitol, sorbitol, xylitol, maltodextrin, and the like, and artificial sweeteners such as aspartame, saccharin, acesulfame-K, cyclamate, sucralose, and alitame. Sweeteners also include cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners, etc. The term "sweeteners" also includes combinations of sweeteners as disclosed herein.

Chemosensory receptor modifiers and chemosensory receptor ligand modifiers of the present invention can also be provided, individually or in combination, with any ingestible composition known or later discovered. For example, the ingestible composition can be a comestible compostion or noncomestible composition. By "comestible composition", it is meant any composition that can be consumed as food by humans or animals, including solids, gel, paste, foamy material, semi-solids, liquids, or mixtures thereof. By "noncomestible composition", it is meant any composition that is intended to be consumed or used by humans or animals not as food, including solids, gel, paste, foamy material, semi-solids, liquids, or mixtures thereof. The noncomestible composition includes, but is not limited to medical composition, which refers to a noncomestible composition intended to be used by humans or animals for therapeutic purposes. By "animal", it includes any non-human animal, such as, for example, farm animals and pets.

In one embodiment, the chemosensory receptor modifiers and chemosensory receptor ligand modifiers are added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that use sucralose and or other sweeteners.

In general, over the counter (OTC) product and oral hygiene product generally refer to product for household and/or personal use which may be sold without a prescription and/or without a visit to a medical professional. Examples of the OTC products include, but are not limited to Vitamins and dietary supplements; Topical analgesics and/or anaesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anaesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral hygiene product include, but are not limited to mouth cleaning strips, toothpaste, toothbrushes, mouthwashes/dental rinses, denture care, mouth fresheners at-home teeth whiteners and dental floss.

In another embodiment, the chemosensory receptor modifiers and chemosensory receptor ligand modifiers are added to food or beverage products or formulations. Examples of food and beverage products or formulations include, but are not limited to sweet coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also include the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavoured drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh, instant, and combined coffee; tea, such as black, green, white, oolong, and flavored tea; and other hot drinks including flavour-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The read meal include products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages, ideally so as to enable the reduction in concentration of previously known saccharide sweeteners, or artificial sweeteners.

Typically at least a chemosensory receptor modulating amount, a chemosensory receptor ligand modulating amount, a sweet flavor modulating amount, a sweet flavoring agent amount, or a sweet flavor enhancing amount of one or more of the chemosensory receptor modifiers or chemosensory receptor ligand modifiers of the present invention will be added to the comestible or medicinal product, optionally in the presence of known sweeteners, e.g., so that the sweet flavor modified comestible or medicinal product has an increased sweet taste as compared to the comestible or medicinal product prepared without the modifiers of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the comestible or medicinal product or composition will of course depend on many variables, including the specific type of comestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the chemosensory receptor modifiers and/or chemosensory receptor ligand modifiers is for modulating (inducing, enhancing or inhibiting) the sweet taste or other taste properties of other natural or synthetic sweet tastants, and comestible compositions made therefrom. A broad but also low range of concentrations of the compounds or entities of the present invention would typically be required, from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

In yet another embodiment, the chemosensory receptor modifier and chemosensory receptor ligand modifier of the present invention can be provided in pharmaceutical compositions containing a therapeutically effective amount of one or more compounds of the present invention, preferably in purified form, together with a suitable amount of a pharmaceutically acceptable vehicle, so as to provide the form for proper administration to a patient.

When administered to a patient, the compounds of the present invention and pharmaceutically acceptable vehicles are preferably sterile. Water is a preferred vehicle when a compound of the present invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of the present invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, $20^{th}$ Edition, 2000).

For topical administration a compound of the present invention may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, the compounds of the present invention are formulated in accordance with routine procedures as a pharmaceutical composition adapted for intravenous administration to human beings. Typically, compounds of the present invention for intravenous administration are solutions in sterile isotonic aqueous buffer. For injection, a compound of the present invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the present invention is administered by infusion, it can be dispensed, for example, with an infusion bottle containing sterile pharmaceutical grade water or saline. When the compound of the present invention is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound of the present invention may also be formulated in rectal or vaginal pharmaceutical compositions such as suppositories or retention enemas, e.g., containing conventional suppository bases such as cocoa butter or other glycerides.

In addition to the formulations described previously, a compound of the present invention may also be formulated as a depot preparation. Such long acting formulations may be administered by implantation (for example, subcutaneously or intramuscularly) or by intramuscular injection. Thus, for example, a compound of the present invention may be formulated with suitable polymeric or hydrophobic materials (for example, as an emulsion in an acceptable oil) or ion exchange resins, or as sparingly soluble derivatives, for example, as a sparingly soluble salt.

When a compound of the present invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

A compound of the present invention, and/or pharmaceutical composition thereof, will generally be used in an amount effective to achieve the intended purpose. For use to treat or prevent diseases or disorders the compounds of the present invention and/or pharmaceutical compositions thereof, are administered or applied in a therapeutically effective amount.

The amount of a compound of the present invention that will be effective in the treatment of a particular disorder or condition disclosed herein will depend on the nature of the disorder or condition and can be determined by standard clinical techniques known in the art. In addition, in vitro or in vivo assays may optionally be employed to help identify optimal dosage ranges. The amount of a compound of the present invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the compounds of the present invention are delivered by oral sustained release administration. Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound of the present invention per kilogram body weight. Dosage ranges may be readily determined by methods known to the artisan of ordinary skill the art.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the present invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

Preferably, a therapeutically effective dose of a compound of the present invention described herein will provide therapeutic benefit without causing substantial toxicity. Toxicity of compounds of the present invention may be determined using standard pharmaceutical procedures and may be readily ascertained by the skilled artisan. The dose ratio between toxic and therapeutic effect is the therapeutic index. A compound of the present invention will preferably exhibit particularly high therapeutic indices in treating disease and disorders. The dosage of a compound of the present invention described herein will preferably be within a range of circulating concentrations that include an effective dose with little or no toxicity.

In certain embodiments of the present invention, the compounds of the present invention and/or pharmaceutical compositions thereof can be used in combination therapy with at least one other agent. The compound of the present invention and/or pharmaceutical composition thereof and the other agent can act additively or, more preferably, synergistically. In some embodiments, a compound of the present invention and/or pharmaceutical composition thereof is administered concurrently with the administration of another agent, which may be part of the same pharmaceutical composition as the compound of the present invention or a different pharmaceutical composition. In other embodiments, a pharmaceutical composition of the present invention is administered prior or subsequent to administration of another agent.

In still another embodiment, the chemosensory receptor modifiers and chemosensory receptor ligand modifiers of the present invention and/or pharmaceutical compositions thereof may be advantageously used in human medicine.

When used to treat and/or prevent diseases or disorders, the compounds described herein and/or pharmaceutical compositions may be administered or applied singly, or in combination with other agents. The compounds and/or pharmaceutical compositions thereof may also be administered or applied singly, in combination with other active agents.

Methods of treatment and prophylaxis by administration to a patient of a therapeutically effective amount of a compound described herein and/or pharmaceutical composition thereof are provided herein. The patient may be an animal, more preferably, a mammal and most preferably, a human.

In one example, the compounds described herein and/or pharmaceutical compositions thereof, are administered orally. The compounds of the present invention and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound described herein and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the compounds and/or pharmaceutical compositions thereof into the bloodstream.

In another example, it may be desirable to administer one or more compounds of the present invention and/or pharmaceutical composition thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the condition.

In yet another example, it may be desirable to introduce one or more compounds of the present invention and/or pharmaceutical compositions thereof into the central nervous system by any suitable route, including intraventricular, intrathecal and epidural injection. Intraventricular injection may be facilitated by an intraventricular catheter, for example, attached to a reservoir, such as an Ommaya reservoir.

A compound of the present invention and/or pharmaceutical composition thereof may also be administered directly to the lung by inhalation. For administration by inhalation, a compound of the present invention and/or pharmaceutical composition thereof may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the present invention and/or pharmaceutical compositions thereof directly to the lung.

Alternatively, a Dry Powder Inhaler ("DPI") device may be used to administer a compound of the invention and/or pharmaceutical composition thereof to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the present invention and a suitable powder base such as lactose or starch for these systems.

Another type of device that may be used to deliver a compound of the present invention and/or pharmaceutical composition thereof to the lung is a liquid spray device supplied, for example, by Aradigm Corporation, Hayward, Calif. Liquid spray systems use extremely small nozzle holes to aerosolize liquid drug formulations that may then be directly inhaled into the lung.

In yet another example, a nebulizer is used to deliver a compound of the present invention and/or pharmaceutical composition thereof to the lung. Nebulizers create aerosols from liquid drug formulations by using, for example, ultrasonic energy to form fine particles that may be readily inhaled (see e.g., Verschoyle et al., *British J. Cancer*, 1999, 80, Suppl. 2, 96). Examples of nebulizers include devices supplied by Sheffield Pharmaceuticals, Inc (See, Armer et al., U.S. Pat. No. 5,954,047; van der Linden et al., U.S. Pat. No. 5,950,619; van der Linden et al., U.S. Pat. No. 5,970,974), and Batelle Pulmonary Therapeutics, Columbus, Ohio.

In yet another example, an electrohydrodynamic ("EHD") aerosol device is used to deliver a compound of the present invention and/or pharmaceutical composition thereof to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering a compound of the present invention and/or pharmaceutical composition thereof to the lung with an EHD aerosol device and such optimization is routinely performed by one of skill in the art. EHD aerosol devices may more efficiently deliver compounds to the lung than other pulmonary delivery technologies.

In yet another example, the compounds of the present invention and/or pharmaceutical compositions thereof can be delivered in a vesicle, in particular a liposome (Langer, 1990, *Science* 249:1527-1533; Treat et al., in "Liposomes in the Therapy of Infectious Disease and Cancer," Lopez-Berestein and Fidler (eds.), Liss, New York, pp. 353-365 (1989); see generally "Liposomes in the Therapy of Infectious Disease and Cancer," Lopez-Berestein and Fidler (eds.), Liss, New York, pp. 353-365 (1989)).

In yet another example, the compounds of the present invention and/or pharmaceutical compositions thereof can be delivered via sustained release systems, preferably oral sustained release systems. In one embodiment, a pump may be used (See, Langer, supra, Sefton, 1987, *CRC Crit. Ref Biomed Eng.* 14:201; Saudek et al., 1989, *N. Engl. J. Med.* 321:574).

In yet another example, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105).

In still other embodiments, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, *Int. J. Pharm. Tech. & Prod. Mfr.*, 1984, 5(3) 1-9). Factors affecting drug release are well known to the skilled artisan and have been described in the art (Bamba et al., *Int. J. Pharm.*, 1979, 2, 307).

In yet another example, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another example, osmotic delivery systems are used for oral sustained release administration (Verma et al., *Drug Dev. Ind. Pharm.,* 2000, 26:695-708). In yet other embodiments, OROS™ osmotic devices are used for oral sustained release delivery devices (Theeuwes et al., U.S. Pat. No. 3,845,770; Theeuwes et al., U.S. Pat. No. 3,916,899).

In still another example, a controlled-release system can be placed in proximity of the target of the compounds and/or pharmaceutical composition of the invention, thus requiring only a fraction of the systemic dose (See, e.g., Goodson, in "Medical Applications of Controlled Release," supra, vol. 2, pp. 115-138 (1984). Other controlled-release systems discussed in Langer, 1990, *Science* 249:1527-1533 may also be used.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Experiment 1

Modeling and Identification of Potential Chemosensory Receptor Ligand Enhancer General Procedure The general procedures for identifying a potential chemosensory receptor ligand enhancer is summarized as the following.

1. Constructing a model of the structure of the Venus flytrap T1R2 domain

2. Docking a chemosensory receptor ligand, e.g., a sweetener into the active site of the structure of the Venus flytrap domain of T1R2, with or without T1R3 present 3. Docking a chemosensory receptor ligand enhancer, e.g., a sweet enhancer into the active site in the presence of the chemosensory receptor ligand, e.g., the sweetener 4. Selecting a chemosensory receptor ligand enhancer, e.g., sweet enhancer candidate based on two criteria: a) it fits the active site in the model, and b) it forms productive interactions with the Venus flytrap domain of T1R2 and with the chemosensory receptor ligand, e.g., the sweetener. Interactions can be van der Waals, burial of hydrophobic atoms or atomic groups, hydrogen bonds, ring stacking interactions, or salt-bridging electrostatic interactions. Key residues for such interactions include the hinge residues, the near active site, the pincer residues, e.g., interacting residues described in the present invention. Candidates are not restricted to fitting completely within the active site, as it is open and chemosensory receptor ligand enhancer candidates may extend beyond the active site as long as they partially extend into it.

Model of the Structure

A model of the structure of the Venus Flytrap T1R2 domain may come from crystal structures of T1R2 or of T1R2 complexed with T1R3. The domains may be in open or in closed form, and may or may not be APO or contain a ligand. Alternatively a model of the structure of the Venus Flytrap T1R2 domain may be built using standard homology modeling methods using crystal structures of available Venus flytrap domains such as the mGluR receptor Venus flytrap domains as templates to construct the model.

An example of a procedure for building such a model is to use the commercial software Homology or Modeller from the Accelrys Corporation that is well documented in the literature and available commercially. Alternative conformations of the model may further be explored using additional molecular mechanical techniques that may include but are not limited to normal mode analysis to explore relative movement of the lobes of the model, loop generation techniques to generate alternative conformations of loops in the model, or Monte Carlo and/or molecular dynamics simulations.

Docking

A chemosensory receptor ligand, e.g., sweetener was first docked into the active site of T1R2. Its modeled pose in the active site was selected by its ability to form productive van der Waals, ring stacking, hydrogen bonding, and/or salt bridging interactions with interacting residues within the active site of the Venus flytrap domain of T1R2.

A candidate for a chemosensory receptor ligand modifier, e.g., sweet enhancer was then docked into the active site in the presence of the ligand, e.g., the sweetener described in the previous paragraph. Its active pose and its candidacy as a potential chemosensory receptor ligand modifier, e.g., sweet enhancer was based on its ability to form productive interactions in the form of van der Waals, ring stacking, hydrogen bonding, and/or salt bridging interactions with interacting residues described in the present invention, with additional residues of the T1R2 domain, and optionally with the chemosensory receptor ligand, e.g., the sweetener placed in the active site as described above.

Candidate for Chemosensory Receptor Ligand Modifiers

A molecule was considered a candidate if it can be docked into the active site in the presence of a chemosensory receptor ligand, e.g., sweetener, forming productive interactions with interacting residues described in the present invention. We defined two spaces within the active site: a first space occupied by a chemosensory receptor ligand, e.g., sweetener, and a second space occupied by a chemosensory receptor ligand modifier, e.g., enhancer. Modeling and mutagenesis results established key residues that were considered to be likely to line these spaces for the chemosensory receptor ligand, e.g., sweeteners and chemosensory receptor ligand modifier, e.g., sweet enhancers. In the context of our study, "residue lining the space" meant that the residue had backbone and/or side-chain atoms that were positioned so that they can potentially interact with atoms of the chemosensory receptor ligand, e.g., sweetener (space #1) and/or chemosensory receptor ligand modifier, e.g., sweet enhancer (space #2). While the chemosensory receptor ligand, e.g., sweetener and chemosensory receptor ligand modifier, e.g., sweet enhancer themselves cannot occupy the same space, their corresponding spaces may overlap due to the ability of residues to contact both the chemosensory receptor ligand, e.g., sweetener and the chemosensory receptor ligand modifier, e.g., sweet enhancer, due to protein flexibility, due to ligand flexibility, and due to the potential for multiple binding modes for a chemosensory receptor ligand, e.g., sweetener or chemosensory receptor ligand modifier, e.g., sweet enhancer. Information on important residues lining space #1 and space #2 came from modeling and docking and from site directed mutagenesis.

The hinge residues are considered to be associated with the first space (space #1).

We have discovered that one of the spaces occupied by a chemosensory receptor ligand, e.g., sweetener is partially lined by residues herein called hinge residues. Many Venus flytrap domains have been crystallized with agonists including mGluR1, mGluR2, and mGluR3 that show agonists forming interactions with homologous residues to those identified herein for T1R2. Many chemosensory receptor ligands, e.g., sweeteners docked to the model of T1R2 can be docked to this region. Our site directed mutagenesis also provides strong evidence to support the finding that hinge residues or residues spatially adjacent to it are key residues to the activation of a chemosensory receptor, e.g., T1R2 related receptor. Since chemosensory receptor ligands, e.g., sweeteners vary in size, there are additional residues lining this first space for larger residues where the list of these additional residues is dependent, partially on the size of the chemosensory receptor ligand, e.g., sweetener.

Pincer residues are considered to be associated with the second space (space #2).

Venus flytrap domains are known to transition from an "open" state to a "closed" state on agonist binding. The flytrap domain is comprised of two lobes commonly referred to in the literature as the upper lobe and lower lobe. In the "open" state the lobes are further apart, while in the closed state the lobes undergo a relative motion that brings the upper and lower lobe closer together. In addition to direct stabilization of the closed state of T1R2 by the agonist, our modeling study has demonstrated that there is additional stabilization of the closed state through interactions of residues on the upper lobe with corresponding residues on the lower lobe that are herein called the "pincer residues". We have discovered that an interacting site, e.g., interacting space for a chemosensory receptor ligand modifier, e.g., sweet enhancer is the space that is partially lined by these pincer residues, since additional interactions in this region can further stabilize the closed, agonized form of the Venus flytrap domain. Our site directed mutagenesis study also provides evidence to support the finding that pincer residues and residues spatially adjacent to them are key residues associated with modulation of chemosensory receptor ligand, e.g., enhancement activity of the ligand.

The first space and second space can be swapped.

In the above discussion the chemosensory receptor modifier, e.g., sweetener binds to the hinge while the chemosensory receptor ligand modifier, e.g., sweet enhancer binds to the pincer region. This is just one example and should not be construed restrictively. For example, our modeling and docking study has also demonstrated that a likely binding mode for saccharine as an agonist (sweetener) involves binding to the pincer region. Such result was further supported by our site-directed mutagenesis. With a chemosensory receptor modifier, e.g., sweetener bound to the pincer region there is opportunity for further stabilization of the closed form of the Venus flytrap domain through binding of a chemosensory receptor ligand modifier, e.g., sweet enhancer to the hinge region.

Procedural Definitions.

1. Docking.

Docking is generally considered as the process of translating and rotating the candidate molecule relative to a chemosensory receptor, e.g., T1R2 structural model while simultaneously adjusting internal torsional angles of the candidate molecule to fit the candidate molecule into the active site of the chemosensory receptor, e.g., T1R2 structural model. Poses of the candidate molecule (positions, relative orientations, and internal torsions) are selected based on whether the molecule fits the active site, and whether the molecule can form productive van der Waals interactions, hydrogen bonds, ring stacking interactions, and salt bridge interactions with residues of the active site and with the chemosensory receptor ligand, e.g., sweetener. Key residues can be identified. A candidate is considered more likely if it interacts with sets of residues in the active site as the hinge region, the near active site, the pincer residues, and the totality of the active site. It is also considered more likely if it forms direct interactions with a chemosensory receptor ligand, e.g., a sweetener.

2. Homology Modeling

Homology modeling is generally considered as the process of constructing a model of the Venus flytrap domain of a chemosensory receptor, e.g., T1R2 from its amino acid sequence and from the three dimensional coordinates of one or more homologous Venus flytrap domain proteins. Homology modeling may be performed using standard methods well-described in the literature and available in commercial software such as the Homology program or Modeler from the Accelrys Corporation. Models based on experimentally determined structures of open and closed forms, as well as animation of models using normal mode analysis, were used to define the pincer residues discussed above.

Exemplary Illustrations of Modeling Studies

FIGS. 5 to 10 illustrate interacting spaces and residues associated with one of our molecular modeling studies.

Experiment 2

Mutagenesis Study for Identification of Chemosensory Receptor Ligand Modifier: Enhancer In our previous patent applications (International Publication No. WO07047988 and International Publication No. WO070104709), we described a method using human-rat chimeric sweet-umami chimeric receptors to map the binding sites of sweet and umami tastants. Our data demonstrated that a number of sweeteners, including sucrose, fructose, aspartame, neotame, D-tryptophan (D-Trp), Acesulfame K, saccharin and dulcin, all interact with the T1R2 Venus flytrap domain (VFT), while the umami tastants, including L-glutamate, inosine-5'-monophosphate (IMP), and guanosine-5'-monophosphate (GMP), all interact with the T1R1 Venus flytrap domain.

Under the guidance of molecular modeling, we performed site-directed mutagenesis on human T1R2 VFT. The mutagenesis was done using the routine PCR-based method. Human T1R2 mutants were transiently transfected into HEK293 cell together with the human T1R3 wild type cDNA, and the transfected cells were characterized using an automated FLIPR machine or a calcium imaging system as described in our previous patent applications. In order to control for plasma membrane expression, protein folding and other factors that might contribute to changes in receptor activity, we used 2 sweeteners which interact with other domains of the human sweet receptor as positive controls. The 2 control sweeteners were cyclamate and compound X (Senomyx). It is known from our previous data that cyclamate interacts with the human T1R3 transmembrane domain, while compound X interacts with the human T1R2 transmembrane domain.

The mutagenesis data for a number of sweeteners are summarized in the following tables. Based on the data, we concluded that 6 residues (S40, S144, S165, Y103, D142, P277) are critical for interaction with those sweeteners.

| Mutagenesis data on FLIPR | | | | | | | |
|---|---|---|---|---|---|---|---|
| | Aspartame (15 Mm) | D-Trp (20 mM) | Fructose (200 mM) | Sucrose (200 mM) | Sucralose (3.2 mM) | Cyclamate (80 mM) | S3819 (25 μM) |
| WT | +++ | +++ | +++ | +++ | +++ | +++ | +++ |
| V384F | ++ | ++ | ++ | ++ | ++ | +++ | +++ |
| V384A | ++ | ++ | ++ | ++ | ++ | +++ | +++ |
| E382A | + | ++ | + | + | ++ | ++ | ++ |
| S165I | — | — | + | + | ++ | ++ | ++ |
| D278A | ++ | ++ | ++ | + | — | +++ | +++ |
| K65A | ++ | ++ | + | + | + | ++ | ++ |
| S165A | +++ | ++ | ++ | ++ | ++ | ++ | +++ |
| I67A | +++ | +++ | +++ | +++ | ++ | +++ | +++ |
| N143A | +++ | ++ | ++ | ++ | +++ | +++ | +++ |
| S303A | +++ | +++ | ++ | ++ | ++ | +++ | +++ |
| Q328A | +++ | +++ | ++ | +++ | ++ | +++ | +++ |
| T184A | +++ | ++ | ++ | +++ | +++ | +++ | +++ |
| T242A | +++ | ++ | ++ | ++ | ++ | +++ | +++ |
| L279A | +++ | +++ | ++ | ++ | ++ | ++ | +++ |
| T326A | ++ | ++ | ++ | ++ | ++ | ++ | ++ |

| Mutagenesis data on calcium imaging | | | | | | | |
|---|---|---|---|---|---|---|---|
| | Aspartame (15 mM) | D-Trp (20 mM) | Fructose (200 mM) | Sucrose (200 mM) | Sucralose (3.2 mM) | Cyclamate (80 mM) | S3819 (25 μM) |
| WT | ++ | ++ | ++ | ++ | ++ | ++ | ++ |
| I167A | + | + | + | + | + | + | + |
| Y103A | — | + | + | + | — | + | + |
| D278A | + | + | + | + | — | ++ | ++ |
| D307A | + | + | — | — | + | + | + |
| E302A | — | + | + | + | + | + | + |
| S165I | — | — | + | + | + | + | + |
| S40A | — | — | — | — | — | + | + |
| D142A | — | — | — | — | — | + | + |
| R383A | — | — | — | — | — | — | + |
| A305F | — | — | — | — | — | — | + |
| Y215A | — | — | — | — | — | — | — |
| D142I | — | — | — | — | — | — | — |

| Additional mutations on R383 | | | | | | | |
|---|---|---|---|---|---|---|---|
| | Aspartame (15 mM) | Neotame (80 μM) | Sucrose (200 mM) | Sucralose (3.2 mM) | D-Trp (20 mM) | Cyclamate (80 mM) | S3819 (25 μM) |
| WT | ++ | +++ | ++ | +++ | +++ | +++ | +++ |
| R383H | + | ++ | + | ++ | ++ | ++ | ++ |
| R383Q | — | + | — | + | + | + | + |
| R383I | — | — | — | — | — | — | — |
| R383F | — | ++ | — | — | + | + | + |
| R383K | — | + | — | + | + | + | + |
| R383N | — | + | — | + | + | + | + |
| R383S | — | + | — | + | + | + | + |
| R383A | — | — | — | — | — | — | + |

Figure 11:
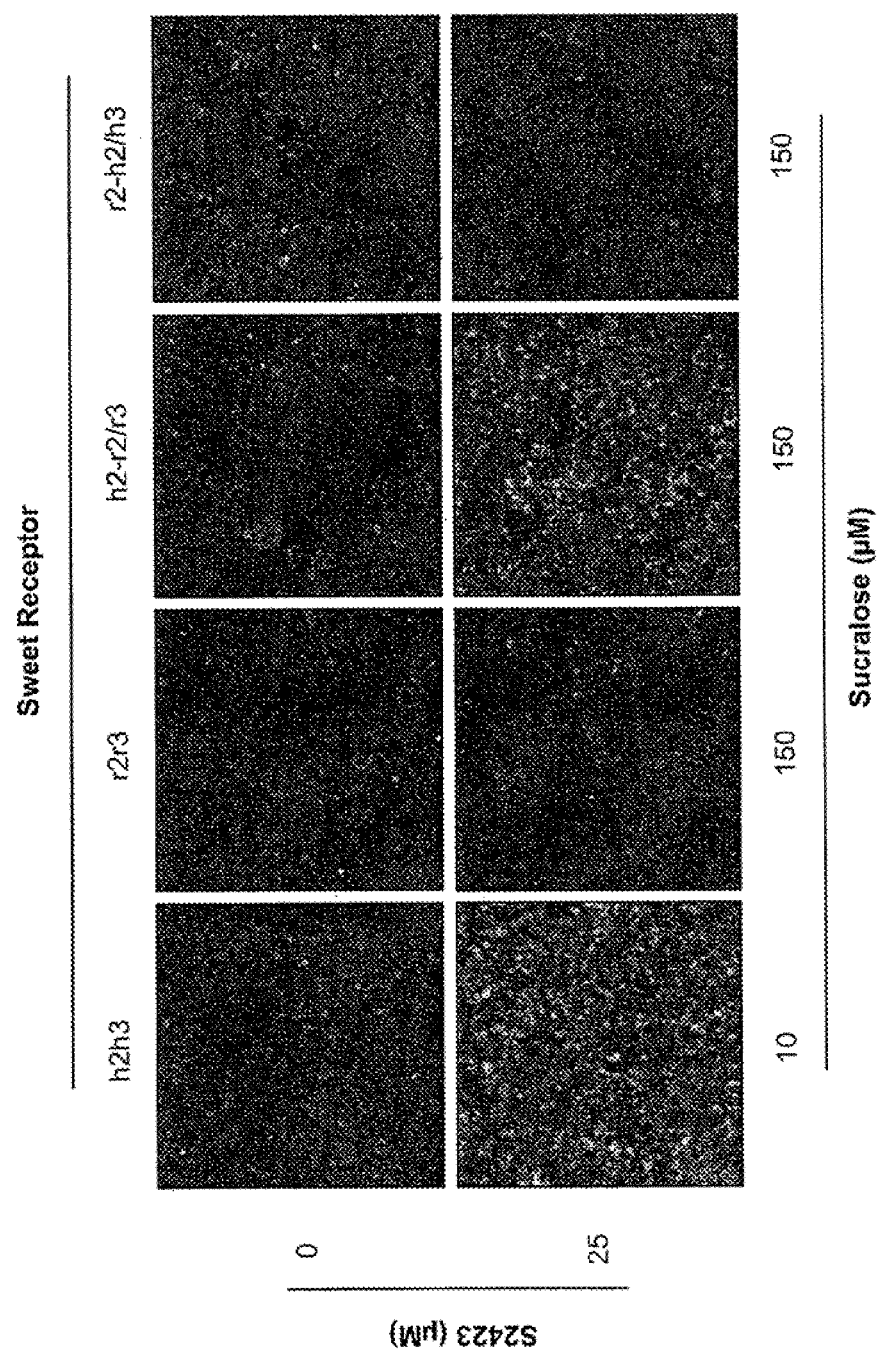
FIG. 11 shows exemplary results for mapping studies using human-rat chimeric receptors.

The sweet enhancer, compound A, is selective for the human sweet receptor, and inactive on the rat sweet receptor. Using the previously described human-rat chimeric receptors, we mapped the binding site of compound A to hT1R2 VFT. As shown in FIG. 11, compound A enhanced the sucralose activity on human sweet receptor (h2/h3) but not rat sweet receptor (r2/r3). When we replaced the rat receptor T1R2 VFT with its human counterpart (h2-r2/r3), the receptor can be enhanced by compound A. On the other hand, when we replaced the human receptor T1R2 VFT with its rat counterpart (r2-h2/h3), the receptor can no longer be enhanced by compound A. We conclude that compound A interacts with human T1R2 VFT. Due to the different sensitivity of human and rat receptors to sucralose, different sucralose concentrations were used to achieve ~EC20 of the different receptors.

Following compound A, 8 more analogues have been identified to enhance the sucralose activity of human sweet receptor. The same mapping experiments were carried out on these 8 analogues, and we observed the same activity pattern as compound A as summarized in the following table. We conclude that all 8 compound A analogues interact with human T1R2 VFT.

Figure 12:
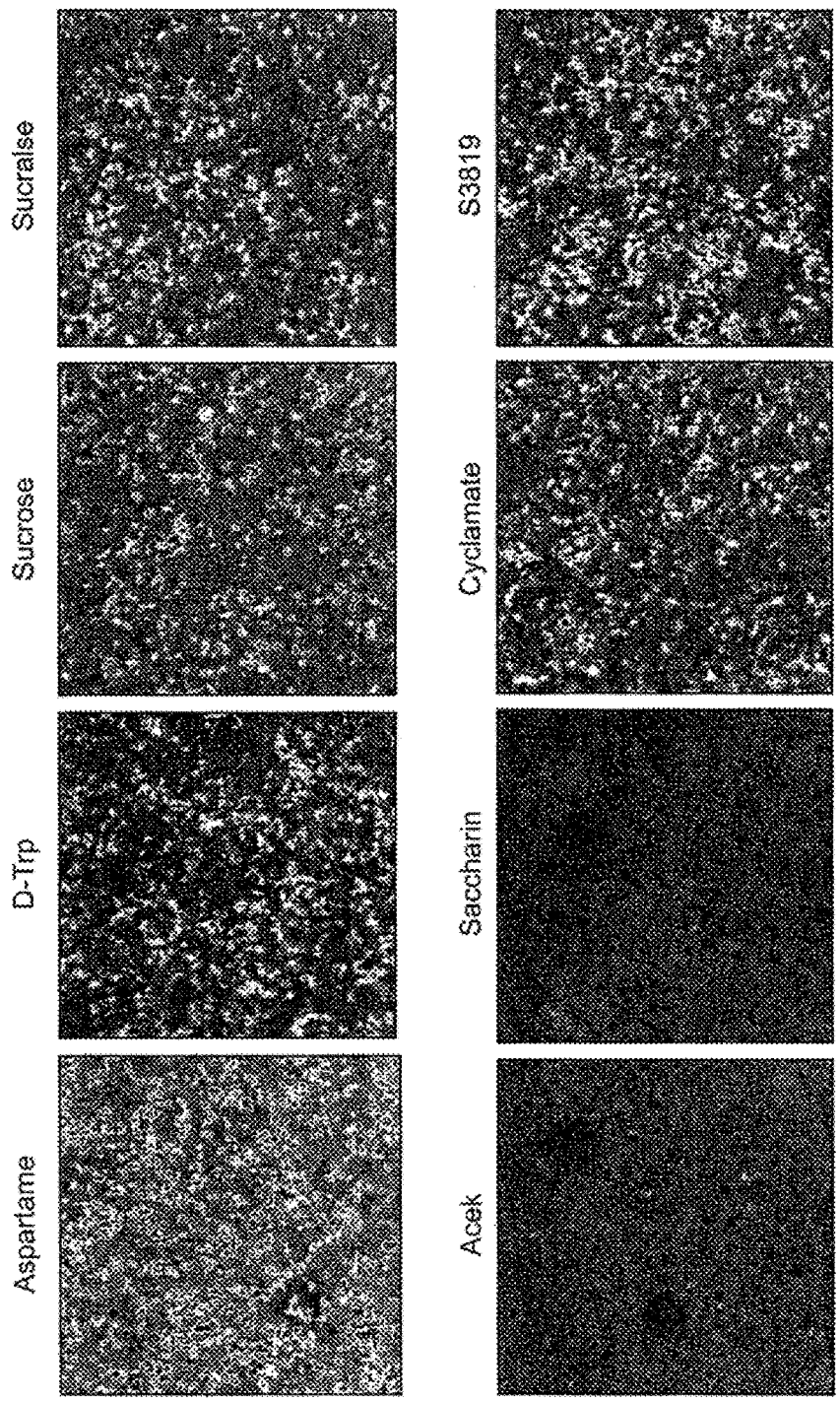
FIG. 12 shows results for exemplary mutagenesis results.

After mapping the enhancers to human T1R2 VFT, we performed mutagenesis analysis to further define the interaction site. As summarized in the following table, six residues (K65, D278, L279, D307, R383, V384) were identified as critical for the activities of compound A and analogous. These compounds, namely, compounds A and A1 to A8, are representative compounds of the present invention including Compounds of structural Formula (I) and its subgeneric formulas. Interestingly, V384 is also important for the activities of 2 structurally related sweeteners (as shown in FIG. 12), saccharin and acesulfame K (AceK), indicating that these sweeteners might occupy similar space in the human T1R2 VFT. The concentrations for the sweeteners are Aspartame (15 mM), D-Trp (20 mM), Sucrose (200 mM), Sucralose (3.2 mM), AceK (8 mM), Saccharin (3.2 mM), Cyclamate (80 mM), S3819 (25 μM).

| | h2/h3 | r2/r3 | h2-r2/r3 | r2-h2/h3 |
|---|---|---|---|---|
| Compound A (25 μM) | + | − | + | − |
| Compound A1 (25 μM) | + | − | + | − |
| Compound A2 (25 μM) | + | − | + | − |
| Compound A3 (25 μM) | + | − | + | − |
| Compound A4 (25 μM) | + | − | + | − |
| Compound A5 (25 μM) | + | − | + | − |
| Compound A6 (25 μM) | + | − | + | − |
| Compound A7 (25 μM) | + | − | + | − |
| Compound A8 (100 μM) | + | − | + | − |

| hT1R2 | Sucralose | Enhancement Activity (at 25 μM) for Compound A and its analogs | | | | | | | | |
|---|---|---|---|---|---|---|---|---|---|---|
| | | A | A4 | A1 | A5 | A2 | A6 | A3 | A8 | A7 |
| WT | ++ | ++ | ++ | +++ | ++ | +++ | ++ | + | ++ | +++ |
| V384A | ++ | ++ | ++ | +++ | ++ | +++ | ++ | + | ++ | +++ |
| E382A | ++ | ++ | ++ | +++ | ++ | +++ | ++ | + | ++ | +++ |
| Y103A | — | + | + | ++ | + | ++ | + | + | ++ | ++ |
| P277A | + | ++ | + | +++ | + | +++ | + | + | ++ | +++ |
| D278A* | — | ++ | + | +++ | + | +++ | + | + | + | ++ |
| K65A | + | — | — | — | — | — | — | — | — | — |
| L279A | ++ | — | — | — | — | — | — | — | — | — |
| V384F | ++ | + | + | + | + | + | + | — | — | + |
| S165I | ++ | ++ | ++ | +++ | ++ | +++ | ++ | + | ++ | +++ |
| I67A | ++ | ++ | ++ | +++ | ++ | +++ | ++ | + | ++ | +++ |
| S165A | ++ | + | ++ | +++ | ++ | +++ | ++ | + | ++ | +++ |
| N143A | ++ | ++ | ++ | +++ | ++ | +++ | ++ | + | ++ | +++ |
| T326A | ++ | ++ | ++ | +++ | ++ | +++ | ++ | + | ++ | +++ |
| T242A | ++ | ++ | ++ | +++ | ++ | +++ | ++ | + | ++ | +++ |
| S303A | ++ | ++ | ++ | +++ | ++ | +++ | ++ | + | ++ | +++ |
| Q328A | ++ | ++ | ++ | +++ | ++ | +++ | ++ | + | ++ | +++ |
| T184V | ++ | ++ | ++ | +++ | ++ | +++ | ++ | + | ++ | +++ |
| T184A | ++ | ++ | ++ | +++ | ++ | +++ | ++ | + | ++ | +++ |
| V64M | ++ | ++ | ++ | +++ | ++ | +++ | ++ | + | ++ | +++ |

-continued

| hT1R2 | Sucralose | A | A4 | A1 | A5 | A2 | A6 | A3 | A8 | A7 |
|---|---|---|---|---|---|---|---|---|---|---|
| S168T | ++ | ++ | ++ | +++ | ++ | +++ | ++ | + | ++ | +++ |
| R383H | ++ | ++ | ++ | +++ | ++ | +++ | ++ | + | ++ | +++ |
| S40T | + | ++ | ++ | +++ | ++ | +++ | ++ | + | ++ | +++ |
| I167A | + | + | + | ++ | + | ++ | + | + | + | ++ |
| E302A | + | + | + | ++ | + | ++ | + | + | + | ++ |
| R383F | + | — | — | — | — | — | — | — | — | — |
| D307A | + | — | — | — | — | — | — | — | — | — |
| D142A | — | + | + | ++ | + | ++ | + | + | + | ++ |
| S40A | — | + | + | ++ | + | ++ | + | + | + | ++ |
| R383A | — | + | + | ++ | + | ++ | + | + | + | ++ |
| A305F | — | — | — | — | — | — | — | — | — | — |

*D278 is a critical residue for the enhancers, because all enhancers in the above table show agonist activity on D278A mutant, i.e., they activate the mutant receptor in the absence of sucralose.

Experiment 3

Chemical Synthesis of the Compounds of the Present Invention

Example 1

4-Amino-5,6-dimethylthieno[2,3-d]pyrimidine-2(1H)-thione

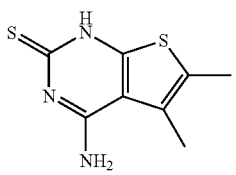

7

A solution of N-(3-cyano-4,5-dimethylthiophen-2-ylcarbamothioyl)benzamide (example 1a) (1.90 g, 6.03 mmol) and NaOH (2 N, 8.3 mL) in EtOH (25 mL) was stirred at 100° C. under nitrogen for half an hour. After cooling to room temperature, the clear reaction solution was filtered and the filtrate was carefully neutralized with 10% AcOH with vigorous stirring at 0° C. The resultant precipitate was collected by filtration, washed with warm water and then 20% EtOH in water to give the final product 4-amino-5,6-dimethylthieno[2,3-d]pyrimidine-2(1H)-thione (1.11 g, 87%) as an off-white solid. M.p.: >260° C. $^1$H NMR (400 MHz, DMSO-$d_6$) δ 2.25 (s, 3H), 2.26 (s, 3H). MS 212 (MH$^+$).

Example 1a

N-(3-Cyano-4,5-dimethylthiophen-2-ylcarbamothioyl)benzamide

To a solution of 2-amino-4,5-dimethylthiophene-3-carbonitrile (1.52 g, 10.0 mmol) in 1,4-dioxane (20 mL) was added benzoylisothiocyanate (1.63 g, 10.0 mmol). The reaction mixture was then stirred at room temperature under nitrogen overnight. The precipitation was collected by filtration, washed with EtOAc/Hexanes (1:4), and dried under vacuum overnight to give N-(3-Cyano-4,5-dimethylthiophen-2-ylcarbamothioyl)benzamide as a white solid. $^1$H NMR (400 MHz, CDCl$_3$) δ 2.23 (s, 3H), 2.31 (s, 3H), 7.58-7.54 (m, 2H), 7.68-7.66 (m, 1H), 7.94 (d, J=7.2 Hz, 2H), 9.13 (bs, 1H). MS 316 (MH$^+$).

Example 2

4-Aminoquinazoline-2(1H)-thione

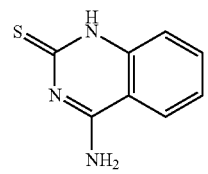

153

Prepared as in example 1 from N-(2-cyanophenylcarbamothioyl)benzamide (Example 2a). $^1$H NMR (400 MHz, DMSO-$d_6$) δ 7.25 (dt, J=1.0, 8.2 Hz, 1H), 7.35 (d, J=8.2 Hz, 1H), 7.65 (dt, J=1.0, 8.2 Hz, 1H), 8.05 (dd, J=1.0, 8.1 Hz, 1H), 8.30 (s, 1H), 8.35 (s, 1H), 12.34 (s, 1H). MS 178 (MH$^+$).

Example 2a

N-(2-Cyanophenylcarbamothioyl)benzamide

Prepared as in Example 1a from 2-aminobenzonitrile and benzoyl isothiocyanate as a pale-yellow solid. $^1$H NMR (400 MHz, DMSO-$d_6$) δ 7.35-7.56 (m, 3H), 7.67 (t, 1H), 7.75-7.76 (d, J=5.2 Hz, 2H), 7.89-7.91 (d, J=7.2 Hz, 2H), 7.98-8.01 (dd, J=1.6 Hz, J=8.2 Hz, 2H), 11.90 (s, 1H), 12.54 (s, 1H). MS 282 (MH$^+$).

Example 3

4-Amino-5-methylquinazoline-2(1H)-thione

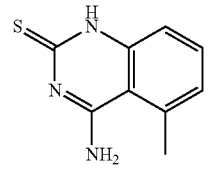

155

Prepared as in example 1 from N-(2-cyano-3-methylphenylcarbamothioyl)benzamide (Example 3a) as an off-white solid. M.p.: >250° C. $^1$H NMR (400 MHz, DMSO-$d_6$) δ 2.68 (s, 3H), 7.03 (d, J=6.8 Hz, 1H), 7.13 (b, 1H), 7.22 (d, J=6.8 Hz, 1H), 7.48 (t, J=6.8 Hz, 1H), 8.50 (b, 1H), 12.26 (s, 1H). $^{13}$C NMR (DMSO-$d_6$) δ 23.26, 109.86, 114.37, 127.16, 134.31, 136.97, 143.57, 160.58, 179.67. MS 192 (MH$^+$).

Example 3a

N-(2-Cyanophenylcarbamothioyl)benzamide

Prepared as in example 1a from 2-amino-6-methylbenzonitrile and benzoyl isothiocyanate as a pale-yellow solid.

¹H NMR (400 MHz, DMSO-d₆) δ 7.40 (m, 1H), 7.52-7.69 (m, 5H), 7.98-8.01 (m, 2H), 11.99 (s, 1H), 12.54 (s, 1H). MS 296 (MH⁺).

Example 4

4-amino-5,6-dimethylthieno[2,3-d]pyrimidin-2(1H)-one

A solution of N-(3-cyano-4,5-dimethylthiophen-2-ylcarbamoyl)benzamide (example 4a) (44.35 g, 148.1 mmol) and NaOH (2 N, 204 mL) in EtOH (400 mL) was stirred at 100° C. under nitrogen for four hours. The clear reaction solution was filtered and the filtrate was cooling to room temperature, and then was carefully neutralized with 10% AcOH (~120 mL) with vigorous stirring at 0° C. After stirring overnight from 0° C. to room temperature, the resultant precipitate was collected by filtration, washed with warm water (60-70° C., 150 mL×4) and 20% EtOH in water (200 mL×2), and then dried at 50° C. under vacuum overnight to give the final product 4-amino-5,6-dimethylthieno[2,3-d]pyrimidin-2(1H)-one (27.7 g, 96%) as a white solid. ¹H NMR (400 MHz, DMSO-d₆) δ 7.98 (brs, 1H), 2.24 (s, 3H), 2.19 (s, 3H). MS 196 (MH⁺).

Example 4a

N-(3-cyano-4,5-dimethylthiophen-2-ylcarbamoyl)benzamide

To a solution of 2-amino-4,5-dimethylthiophene-3-carbonitrile (example 4b) (25 g, 164.5 mmol) in 1,4-dioxane (600 mL) was added benzoyl isocyanate (24.2 g, 164.5 mmol). The reaction mixture was then stirred at room temperature under nitrogen overnight. The precipitate was collected by filtration, washed with 1,4-dioxane (20 mL×3), and dried under vacuum at 40° C. for 3 hours to give N-(3-cyano-4,5-dimethylthiophen-2-ylcarbamoyl)benzamide (44.35 g, 90%) as a white solid. ¹H NMR (400 MHz, DMSO-d₆) δ 2.10 (s, 3H), 2.24 (s, 3H), 7.52-7.56 (m, 2H), 7.64-7.69 (m, 1H), 8.01-8.03 (m, 2H), 11.57 (brs, 1H), 12.05 (brs, 1H). MS 300 (MH⁺).

Example 4b 2-amino-4,5-dimethylthiophene-3-carbonitrile

To a solution of butanone (162.0 mL, 1.8 mol), sulfur (57.99 g, 1.8 mol), and malononitrile (119.49 g, 1.8 mol) in anhydrous Ethanol (1.2 L) was added at 0° C. triethylamine (251.4 mL, 1.8 mol). The reaction was stirred at 0° C. for 15 minutes then heated at 80° C. for 70 minutes. After cooling to room temperature, ethanol (920 mL) was removed reduced pressure and aqueous NaCl (30%, 750 mL) was added. The resulting mixture was stirred for 10 minutes and extracted with diethyl ether (1 L). The aqueous layer was further extracted with diethyl ether (500 mL) and the insoluble solids were removed by filtration after which the organic layer was separated and combined with the first diethyl ether extract. The combined organic extract was dried over MgSO₄, filtered and concentrated under reduced pressure. The residue was stirred for 2 hours in dichloromethane (300 mL) and a solid was collected. More solid was isolated from the dichloromethane solution cooled to −78° C. The combined solid product was refluxed in dichloromethane (600 mL) for 10 minutes then stirred at room temperature for 30 minutes and cooled to −78° C. The resultant precipitate was collected by filtration to give the crude product (115 g). The filtrate was concentrated and the residue was chromatographed on silica gel (eluent: dichloromethane) to provide a solid that was combined with the previous crude product. The resulting residue was purified by flash chromatography on silica gel (dichloromethane) to yield 2-amino-4,5-dimethylthiophene-3-carbonitrile (105 g, 38%) as an off white solid. ¹H NMR (400 MHz, DMSO-d₆) δ 1.93 (d, J=1.2 Hz, 3H), 2.07 (d, J=1.2 Hz, 3H), 3.33 (s, 2H). MS 153 (MH⁺).

Example 5

4-Amino-5,6-butylenethieno[2,3-d]pyrimidine-2(1H)-thione

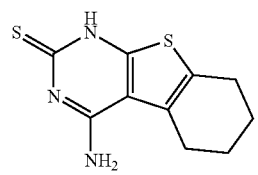

Prepared as in Example 1 from N-(3-cyano-4,5,6,7-tetrahydrobenzo[b]thiophen-2-ylcarbamothioyl)benzamide (Example 5a). ¹H NMR (400 MHz, DMSO-d₆) δ 1.75 (m, 4H), 2.62 (m, 2H), 2.74 (m, 2H). MS 238 (MH⁺).

Example 5a

N-(3-Cyano-4,5,6,7-tetrahydrobenzo[b]thiophen-2-ylcarbamothioyl)-benzamide

Prepared as in example 1a from 2-amino-4,5,6,7-tetrahydrobenzo[b]thiophene-3-carbonitrile (example 5b) and benzoylisothiocyanate as a pale-yellow solid. MS 342 (MH⁺).

Example 5b

2-Amino-4,5,6,7-tetrahydrobenzo[b]thiophene-3-carbonitrile

A solution of cyclohexanone (1.96 g, 20.0 mmol), malononitrile (1.32 g, 20.0 mmol), sulfur (640 mg, 20.0 mmol), and triethylamine (2.03 g, 20 mmol) in EtOH (50 mL) was refluxed for 6 h under nitrogen. The solvent was removed under reduced pressure and the residue partitioned between EtOAc and water. The organic layer was separated, washed with brine, and dried over Na₂SO₄. After evaporation of the solvent, the residue was purified by chromatography on silica gel eluting with EtOAc/Hexanes (2:3) to give the title product as a yellow solid. ¹H NMR (400 MHz, CDCl₃) δ 1.79 (m, 4H), 2.50 (m, 4H), 4.59 (s, 2H). MS 179 (MH⁺).

Example 6

4-Amino-5-methylquinazolin-2(1H)-one

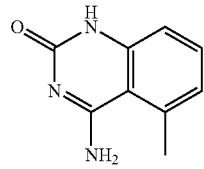

Prepared as in example 1 from N-(2-cyano-3-methylphenylcarbamoyl)benzamide (example 6a). $^1$H NMR (400 MHz, DMSO-d$_6$) δ 3.04 (s, 3H), 7.43 (d, J=7.2 Hz, 1H), 7.51 (d, J=7.2 Hz, 1H), 7.97 (t, J=7.2 Hz, 1H). MS 176 (MH$^+$).

Example 6a

N-(2-Cyano-3-methylphenylcarbamoyl)benzamide

Prepared as in example 1a from 2-amino-6-methylbenzonitrile and benzoyl isocyanate as an off-white solid. $^1$H NMR (400 MHz, DMSO-d$_6$) δ 7.19 (d, J=7.6 Hz, 1H), 7.52-7.68 (m, 5H), 8.02-8.08 (m, 2H), 11.32 (s, 1H), 11.46 (s, 1H). MS 280 (MH$^+$).

Example 7

4-Amino-6-ethyl-5-methylthieno[2,3-d]pyrimidin-2(1H)-one

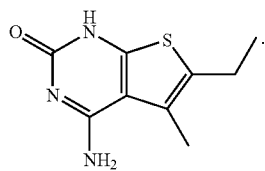

Prepared as in Example 1 from N-(3-cyano-5-ethyl-4-methylthiophen-2-ylcarbamoyl)benzamide (Example 7a). $^1$H NMR (400 MHz, DMSO-d$_6$) δ 1.11 (t, J=7.6 Hz, 3H), 2.26 (s, 3H), 2.60-2.67 (q, J=7.6 Hz, 2H). MS 210 (MH$^+$).

Example 7a

N-(3-Cyano-5-ethyl-4-methylthiophen-2-ylcarbamoyl)benzamide

Prepared as in example 1a from 2-amino-5-ethyl-4-methylthiophene-3-carbonitrile (example 7b) and benzoyl isocyanate as a pale-yellow solid. MS 314 (MH$^+$).

Example 7b

2-Amino-5-ethyl-4-methylthiophene-3-carbonitrile

Prepared as in example 5b from 2-pentanone, malononitrile, and sulfur as a yellow solid. MS 167 (MH$^+$).

Example 8

4-Amino-6-methylthieno[2,3-d]pyrimidin-2(1H)-one

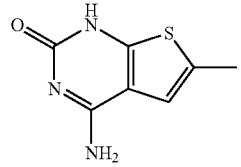

Prepared as in Example 1 from N-(3-cyano-5-methylthiophen-2-ylcarbamoyl)benzamide (Example 8a). $^1$H NMR (400 MHz, DMSO-d$_6$) δ 2.34 (s, 3H), 6.97 (s, 1H), 7.50 (s, 1H). MS 182 (MH$^+$).

Example 8a

N-(3-Cyano-5-methylthiophen-2-ylcarbamoyl)benzamide

Prepared as in Example 1a from 2-amino-5-methylthiophene-3-carbonitrile and benzoyl isocyanate as a white solid. $^1$H NMR (400 MHz, DMSO-d$_6$) δ 2.36 (d, J=1.2 Hz, 3H), 6.89 (d, J=1.2 Hz, 1H), 7.55 (t, J=8.0 Hz, 2H), 7.66 (d, J=7.2 Hz, 1H), 8.03-8.01 (m, 2H), 11.60 (brs, 1H), 12.08 (bs, 1H). MS 286 (MH$^+$).

Example 9

4-Amino-6-(hydroxymethyl)-5-methylthieno[2,3-d]pyrimidine-2(1H)-thione

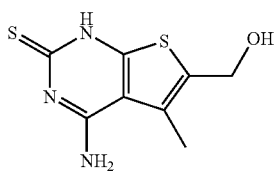

Prepared as in Example 1 from N-(3-cyano-5-(hydroxymethyl)-4-methylthiophen-2-ylcarbamothioyl)benzamide (Example 9a). $^1$H NMR (400 MHz, DMSO-d$_6$) δ 2.30 (s, 3H), 4.54-4.55 (d, J=5.2 Hz, 2H), 5.54 (t, 1H). MS 228 (MH$^+$).

Example 9a

N-(3-Cyano-5-(hydroxymethyl)-4-methylthiophen-2-ylcarbamothioyl)-benzamide

Prepared as in example 1a from 2-amino-5-(hydroxymethyl)-4-methylthiophene-3-carbonitrile (Example 9b) and benzoyl isothiocyanate as a yellow solid. MS 332 (MH$^+$).

Example 9b

2-Amino-5-(hydroxymethyl)-4-methylthiophene-3-carbonitrile

Prepared as in example 5b from 4-hydroxybutan-2-one, malononitrile, and sulfur as a yellow solid. $^1$H NMR (400 MHz, DMSO-d$_6$) δ 1.97 (s, 3H), 4.30-4.31 (d, J=5.6 Hz, 2H), 5.10 (t, 1H), 7.00 (s, 2H).

Example 10

4-Amino-5,6,7,8-tetrahydroquinazoline-2(1H)-thione

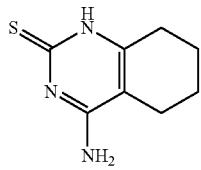

201

Prepared as in Example 1 from N-(2-cyanocyclohex-1-enylcarbamothioyl)benzamide (Example 10a) as a white solid. $^1$H NMR (400 MHz, DMSO-d$_6$) δ 1.60-1.65 (m, 4H), 2.13 (m, 2H), 2.38 (m, 2H), 6.93 (s, 1H), 7.56 (s, 1H), 11.84 (s, 1H). MS 182 (MH$^+$).

Example 10a

N-(2-Cyanocyclohex-1-enylcarbamothioyl)benzamide

Prepared as in Example 1a from 2-aminocyclohex-1-enecarbonitrile (Example 10b) and benzoyl isothiocyanate as a white solid. MS 286 (MH$^+$).

Example 10b

2-Aminocyclohex-1-enecarbonitrile

A stirred mixture of 1,7-heptanedinitrile (24.44 g, 0.2 mol) and t-BuOK (22.44 g, 0.2 mol) was heated at 80° C. for 3 h under nitrogen. The mixture was then cooled down to room temperature and stored at that temperature overnight. The residue was treated with water, and extracted with ether (2×). The combined organic layers were washed with brine, dried over Na$_2$SO$_4$, filtered and concentrated. The residue was purified by recrystallization from MeOH to give the title compound as a white solid (18.2 g, 75%). $^1$H NMR (400 MHz, CDCl$_3$) δ 1.58-1.71 (m, 4H), 2.12-2.20 (m, 4H), 4.23 (bs, 2H). MS 123 (MH$^+$).

Example 11

4-Amino-6-methylthieno[2,3-d]pyrimidin-2(1H)-one

69

Prepared as in Example 1 from N-(3-cyanothiophen-2-ylcarbamoyl)benzamide (Example 11a). $^1$H NMR (400 MHz, DMSO-d$_6$) δ 6.97 (s, J=5.2 Hz, 1H), 7.31 (d, J=6.0 Hz, 1H), 7.60 (s, 2H), 11.38 (bs, 1H). MS 168 (MH$^+$).

Example 11a

N-(3-Cyanothiophen-2-ylcarbamoyl)benzamide

Prepared as in Example 1a from 2-aminothiophene-3-carbonitrile and benzoyl isocyanate as a white solid. $^1$H NMR (400 MHz, DMSO-d$_6$) δ 7.23-7.19 (m, 2H), 7.55 (t, J=8.0 Hz, 2H), 7.70-7.66 (m, 1H), 8.04-8.02 (m, 2H), 11.62 (bs, 1H), 12.18 (bs, 1H). MS 272 (MH$^+$).

Example 12

4-Aminoquinazolin-2(1H)-one

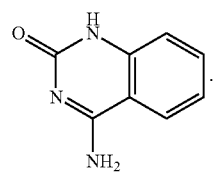

149

Prepared as in Example 1 from N-(2-cyanophenylcarbamoyl)benzamide (Example 12a) as a white solid (156 mg, 41%). $^1$H NMR (400 MHz, DMSO-d$_6$) δ 7.12-7.20 (m, 2H), 7.59-7.63 (m, 1H), 8.08-8.10 (d, 1H), 8.60 (b, 2H), 11.2 (b, 1H). $^{13}$C NMR (DMSO-d$_6$) δ 108.72, 115.98, 122.32, 125.51, 135.38, 142.96, 154.96, 163.51. MS 162 (MH$^+$).

Example 12a

N-(2-Cyanophenylcarbamoyl)benzamide

Prepared as in Example 1a from 2-aminobenzonitrile and benzoyl isocyanate as a white powder (661 mg, 59%). $^1$H NMR (400 MHz, DMSO-d$_6$) δ 7.27-7.29 (t, 1H), 7.52-7.56 (t, 1H), 7.64-7.74 (m, 2H), 7.82-7.85 (dd, 1H), 8.02-8.04 (m, 2H), 8.22-8.24 (d, 1H). MS 266 (MH$^+$).

Example 13

4-Amino-6-methoxy-5-methylthieno[2,3-d]pyrimidin-2(1H)-one

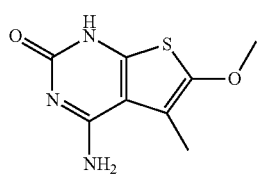

79

Prepared as in Example 1 from N-(3-cyano-5-methoxy-4-methylthiophen-2-ylcarbamoyl)benzamide (Example 13a). $^1$H NMR (400 MHz, DMSO-d$_6$) δ 2.19 (s, 3H), 3.78 (s, 3H), 2.74 (s, 2H). MS 212 (MH$^+$).

Example 13a

N-(3-Cyano-5-methoxy-4-methylthiophen-2-ylcarbamoyl)benzamide

Prepared as in Example 1a from 2-amino-5-methoxy-4-methylthiophene-3-carbonitrile (example 13b) and benzoyl isocyanate as an off-white solid. $^1$H NMR (400 MHz, DMSO-$d_6$) δ 2.03 (s, 3H), 3.86 (s, 3H), 7.54 (t, J=7.2 Hz, 2H), 7.67 (t, J=7.6 Hz, 1H), 8.01-8.03 (d, J=8.4 Hz, 2H), 11.60 (s, 1H), 12.03 (s, 1H). MS 316 (MH$^+$).

Example 13b

2-Amino-5-methoxy-4-methylthiophene-3-carbonitrile

Prepared as in Example 5b from 1-methoxypropan-2-one, malononitrile, and sulfur as a brown solid. MS 169 (MH$^+$).

Example 14

4-Amino-6-methylquinazolin-2(1H)-one

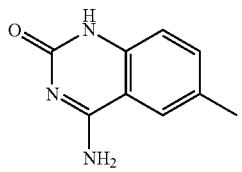

161

Prepared as in Example 1 from N-(2-cyano-4-methylphenylcarbamoyl)benzamide (Example 14a) as a white solid (259 mg, 57%). $^1$H NMR (400 MHz, DMSO-$d_6$) δ 2.29 (s, 3H), 6.99-7.05 (m, 1H), 7.35-7.37 (d, 1H), 7.72 (b, 2H), 7.79 (s, 1H) 10.55 (bs, 1H). MS 176 (MH$^+$).

Example 14a

N-(2-Cyano-4-methylphenylcarbamoyl)benzamide

Prepared as in Example 1a from 2-amino-5-methylbenzonitrile (Example 14b) as a white powder (724 mg, 46%). MS 280 (MH$^+$).

Example 14b

2-Amino-5-methylbenzonitrile

5-Methyl-2-nitrobenzonitrile (1.92 g, 11.84 mmol) was added in portions to a stirred solution of SnCl$_2$ (11.22 g, 59.2 mmol) in conc. HCl (12 mL) and EtOH (12 mL). The reaction temperature was maintained at 20-30° C. using an ice bath. The reaction mixture was then stirred at room temperature for 1 h and poured into an ice cold aqueous solution of NaOH (6N, app. 30 mL) to neutralize to pH7. The product was extracted into EtOAc, washed with brine, dried over MgSO$_4$ and concentrated to provide the title product (1.56 g, 99%) as a yellow-brown solid. $^1$H NMR (400 MHz, DMSO-$d_6$) δ 2.21 (s, 3H), 5.79 (bs, 2H), 6.68-6.71 (d, 1H), 7.10-7.13 (dd, 1H), 7.15 (s, 1H). $^{13}$C NMR (DMSO-$d_6$) δ 20.13, 93.99, 116.12, 118.94, 125.38, 132.32, 135.76, 150.21. MS 133 (MH$^+$).

Example 15

4-Amino-8-methylquinazolin-2(1H)-one

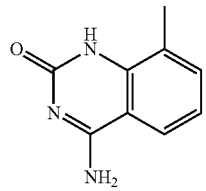

165

Prepared as in Example 1 from N-(2-cyano-6-methylphenylcarbamoyl)benzamide (Example 15a) as a white solid (60 mg, 56%). $^1$H NMR (400 MHz, DMSO-$d_6$) δ 2.29 (s, 3H), 6.96-7.00 (t, 1H), 7.37-7.38 (d, 1H), 7.70-7.72 (b, 2H), 7.80-7.82 (d, 1H), 9.87 (bs, 1H). MS 176 (MH$^+$).

Example 15a

N-(2-Cyano-6-methylphenylcarbamoyl)benzamide

Prepared as in Example 1a from 2-amino-3-methylbenzonitrile (Example 15b) and benzoyl isocyanate as a white powder (186 mg, 67%). MS 280 (MH$^+$).

Example 15b

2-Amino-3-methylbenzonitrile

To a solution of 2-bromo-6-methylaniline (126 μL, 1 mmol) in dry NMP (3 mL) was added CuCN (197 mg, 2.2 mmol). The mixture was irradiated in a microwave at 220° C. for 40 minutes, cooled to room temperature and poured into a mixture of ammonia (50% w/v, 10 mL) and ice. The mixture was stirred for 30 min and the product was extracted with dichloromethane (3×20 mL). The organic layers were combined, washed with water and brine, dried over MgSO$_4$ and concentrated. The crude material was purified on silica gel (50% EtOAc/hexanes) to yield a brown oil that crystallized on standing (128 mg, 96%). $^1$H NMR (400 MHz, DMSO-$d_6$) δ 2.08 (s, 3H), 5.68 (bs, 2H), 6.51-6.55 (t, 1H), 7.17-7.19 (d, 1H), 7.22-7.24 (dd, 1H). MS 133 (MH$^+$).

Example 16

4-Aminopyrimido[4,5-d]pyrimidin-2(1H)-one

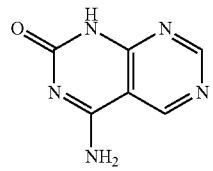

181

Prepared as in Example 1 from N-(2-cyano-4,5-dimethylfuran-3-ylcarbamoyl)benzamide (Example 16a). $^1$H NMR (400 MHz, DMSO-$d_6$) δ 8.91 (s, 1H), 8.92 (s, 1H), 9.24 (s, 2H), 11.50 (b, 1H). MS 164 (MH$^+$).

Example 16a

N-(2-Cyano-4,5-dimethylfuran-3-ylcarbamoyl)benzamide

Prepared as in Example 1a from 4-aminopyrimidine-5-carbonitrile and benzoyl isocyanate as an off-white powder. MS 268 (MH$^+$).

Example 17

4-Amino-7-methylquinazoline-2(1H)-thione

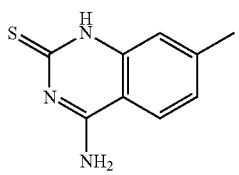

167

Prepared as in Example 1 from N-(2-cyano-5-methylphenylcarbamothioyl)benzamide (Example 17a). $^1$H NMR (400 MHz, DMSO-$d_6$) δ 2.35 (s, 3H), 7.08 (d, J=8.0 Hz, 1H), 7.13 (s, 1H), 7.93 (d, J=8.0 Hz, 1H), 8.21 (s, 1H), 8.24 (s, 1H), 12.26 (s, 1H). MS 192 (MH$^+$).

Example 17a

N-(2-Cyano-5-methylphenylcarbamothioyl)benzamide

Prepared as in Example 1a from 2-amino-4-methylbenzonitrile and benzoyl isothiocyanate as a pale-yellow powder. $^1$H NMR (400 MHz, DMSO-$d_6$) δ 7.32 (d, J=8.0 Hz, 1H), 7.51-7.58 (m, 3H), 7.67 (t, J=7.8 Hz, 1H), 7.78 (d, J=8.0 Hz, 1H), 7.98-8.01 (m, 2H), 11.88 (s, 1H), 12.49 (s, 1H). MS 296 (MH$^+$).

Example 18

4-Amino-5,6-dimethylfuro[2,3-d]pyrimidin-2(1H)-one

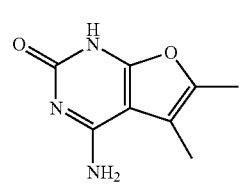

23

Prepared as in Example 1 from N-(2-cyano-4,5-dimethylfuran-3-ylcarbamoyl)benzamide (Example 18a). $^1$H NMR (400 MHz, DMSO-$d_6$) δ 2.11 (s, 3H), 2.20 (s, 3H). MS 180 (MH$^+$).

Example 18a

N-(2-Cyano-4,5-dimethylfuran-3-ylcarbamoyl)benzamide

Prepared in a similar manner to Example 1a from 2-amino-4,5-dimethylfuran-3-carbonitrile and benzoyl isocyanate as an off-white solid. MS 284 (MH$^+$).

Example 19

4-Amino-7-methylquinazolin-2(1H)-one

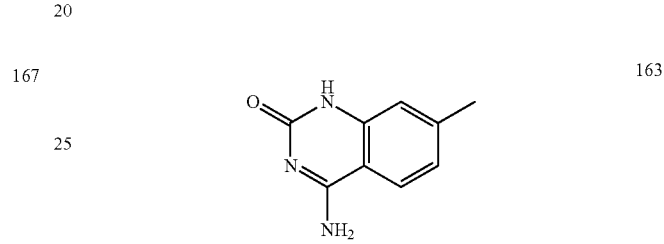

163

Prepared as in Example 1 from N-(2-cyano-5-methylphenylcarbamoyl)benzamide (Example 19a). $^1$H NMR (400 MHz, DMSO-$d_6$) δ 2.59 (s, 3H), 7.37 (s, 1H), 7.49 (d, J=7.2 Hz, 1H), 8.21 (d, J=7.2 Hz, 1H). MS 176 (MH$^+$).

Example 19a

N-(2-Cyano-5-methylphenylcarbamoyl)benzamide

Prepared as in Example 1a from 2-amino-4-methylbenzonitrile and benzoyl isocyanate as a white solid. $^1$H NMR (400 MHz, DMSO-$d_6$) δ 7.10-7.13 (m, 1H), 7.54 (t, J=7.8 Hz, 2H), 7.66 (t, J=7.8 Hz, 1H), 7.71 (d, J=8.0 Hz, 1H), 8.02-8.04 (m, 2H), 8.07 (s, 1H), 11.32 (s, 1H), 11.44 (s, 1H). MS 280 (MH$^+$).

Example 20

4-Amino-1-benzyl-5,6-dimethylthieno[2,3-d]pyrimidine-2(1H)-thione

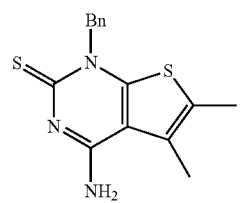

127

Prepared as in Example 1 from N-(benzyl(3-cyano-4,5-dimethylthiophen-2-yl)carbamothioyl)benzamide (Example 20a). MS 302 (MH$^+$).

Example 20a

N-(Benzyl(3-cyano-4,5-dimethylthiophen-2-yl)carbamothioyl)-benzamide

Prepared as in Example 1a from 2-(benzylamino)-4,5-dimethylthiophene-3-carbonitrile (Example 20b) and benzoyl isothiocyanate. MS 406 (MH$^+$).

Example 20b 2-(Benzylamino)-4,5-dimethylthiophene-3-carbonitrile

To a solution of 2-amino-4,5-dimethylthiophene-3-carbonitrile (151 mg, 1.0 mmol) and benzaldehyde (106 mg, 1 mmol) in 15 mL of 4% acetic acid in dichloroethane was added silica supported cyanoborohydride (2.0 g. 2.0 mmol). The reaction was placed in a microwave reactor for 5 minutes at 135° C. Silica supported cyanoborohydride was removed by filtration, and the product was purified by prep HPLC using acetonitrile/water as solvent. MS 243 (MH$^+$).

Example 21

4-Amino-1-ethyl-5,6-dimethylthieno[2,3-d]pyrimidin-2(1H)-one

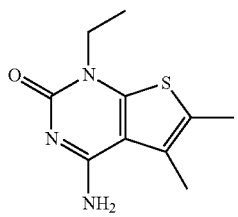

129

Prepared as in Example 1 from N-((3-cyano-4,5-dimethylthiophen-2-yl)(ethyl)carbamoyl)benzamide (Example 21a). MS 224 (MH$^+$).

Example 21a

N-((3-Cyano-4,5-dimethylthiophen-2-yl)(ethyl)carbamoyl)benzamide

Prepared in a similar manner to Example 1a from 2-(ethylamino)-4,5-dimethylthiophene-3-carbonitrile (Example 21b) and benzoyl isocyanate. MS 328 (MH$^+$).

Example 21b 2-(Ethylamino)-4,5-dimethylthiophene-3-carbonitrile

To a mixture of 2-(benzylamino)-4,5-dimethylthiophene-3-carbonitrile (302 mg, 10 mmol), potassium carbonate (276 mg, 2.0 mmol), and a catalytic amount of potassium iodide in acetonitrile (1 mL) in a 20 mL microwave vial was added ethyl iodide (310 mg, 2.0 mmol). The reaction vial was placed in a microwave reactor for 15 minutes at 165° C. The reaction mixture was dissolved in ethyl acetate and washed with water and brine. The ethyl acetate portion was dried over sodium sulfate and solvent was evaporated under reduced pressure, and the product was purified by prep HPLC using acetonitrile/water as solvent. MS 181 (MH$^+$).

Example 22

4-Amino-1,5,6-trimethylthieno[2,3-d]pyrimidin-2(1H)-one

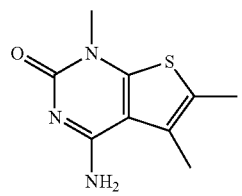

131

Prepared as in Example 1 from N-((3-cyano-4,5-dimethylthiophen-2-yl)(methyl)carbamoyl)benzamide (Example 22a). MS 210 (MH$^+$).

Example 22a

N-((3-Cyano-4,5-dimethylthiophen-2-yl)(methyl)carbamoyl)-benzamide

Prepared as in Example 1a from 4,5-dimethyl-2-(methylamino)thiophene-3-carbonitrile (Example 22b) and benzoyl isocyanate. MS 314 (MH$^+$).

Example 22b 4,5-Dimethyl-2-(methylamino)thiophene-3-carbonitrile

Prepared as in Example 21b from 2-amino-4,5-dimethylthiophene-3-carbonitrile and methyl iodide.

Example 23

1H-Benzo[c][1,6]thiadiazin-4-amine-2,2-dioxide

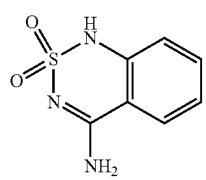

159

A stirred mixture of 2-cyanoaniline (236 mg, 2.0 mmol), sulfamide (192 mg, 2.0 mmol) and DBU (304 mg, 2.0 mmol) was heated at 160° C. under nitrogen for 3 days. After cooling to room temperature, the reaction mixture was diluted with water and extracted three times with EtOAc. The aqueous layer was removed under vacuum and the residue was purified by chromatography on silica gel eluting with 10% MeOH in dichloromethane to give the title compound as a pale yellow solid. $^1$H NMR (400 MHz, DMSO-d$_6$) δ 7.03 (dd, J=0.8, 8.0

Hz, 1H), 7.12 (dt, J=0.8, 8.0 Hz, 1H), 7.56 (dt, J=0.8, 8.0 Hz, 1H), 7.85 (dd, J=0.8, 8.0 Hz, 1H). MS 198 (MH⁺).

Example 24

5-Methyl-1H-benzo[c][1,2,6]thiadiazin-4-amine-2,2-dioxide

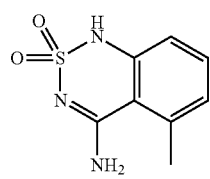

A solution of N-(2-cyano-3-methylphenyl)sulfamide (Example 24a) (211 mg, 1.0 mmol) in EtOH was treated with NaOH (2.0 N, 1.0 mL, 2.0 mmol) and the resultant solution was heated to 100° C. and stirred at that temperature for 0.5 h. After cooling to room temperature, the clear reaction solution was filtered and the filtration was carefully neutralized with 10% AcOH while with vigorous stirring at 0° C. The resultant precipitate was collected by filtration, washed with warm water and 20% EtOH in water to give the title product 5-Methyl-1H-benzo[c][1,2,6]thiadiazin-4-amine-2,2-dioxide as an off-white solid. $^1$H NMR (400 MHz, DMSO-$d_6$) δ 2.59 (s, 3H), 6.85-6.87 (d, J=8.4 Hz, 1H), 6.92-6.94 (d, J=7.2 Hz, 1H), 7.24 (s, 1H), 7.37 (t, J=7.6 Hz, 1H), 8.24 (s, 1H), 10.76 (s, 1H). MS 212 (MH⁺).

Example 24a

N-(2-Cyano-3-methylphenyl)sulfamide

A solution of 2-amino-6-methylbenzonitrile (1.32 g, 10 mmol) and sulfamide (4.81 g, 50 mmol) in dry 1,4-dioxane (50 mL) was refluxed under nitrogen for 3 days. After the reaction mixture was cooled down to room temperature, the precipitate was filtered and washed with dioxane. The filtrate was concentrated under reduced pressure, and the residue was purified by chromatography on silica gel eluting with EtOAc/hexanes (3:7) to give the title compound as a pale-white solid. $^1$H NMR (400 MHz, DMSO-$d_6$) δ 2.44 (s, 3H), 7.19-7.21 (m, 3H), 7.39-7.41 (d, J=8.4 Hz, 1H), 7.53 (t, J=8.0 Hz, 1H), 9.41 (s, 1H).

Example 25

5,6-Dimethyl-2-(methylthio)thieno[2,3-d]pyrimidin-4-amine

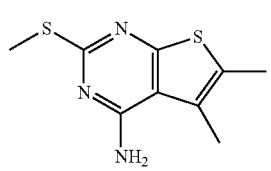

To a suspension of N-(3-cyano-4,5-dimethylthiophen-2-ylcarbamothioyl)-benzamide (Example 1a) (1.33 g, 4.22 mmol) in ethanol (25 mL) was added NaOH (2.0 N, 5.8 mL) at room temperature under nitrogen. After stirring at 100° C. under nitrogen for 0.5 h, the reaction mixture was cooled in an ice bath and MeI (0.8 mL) was added dropwise. After stirring for another 0.5 h, the resulting precipitate was collected by filtration, rinsed with water, 20% EtOH/H₂O, and dried under vacuum to give the title compound (840 mg, 89%). $^1$H NMR (400 MHz, DMSO-$d_6$) δ 2.32 (s, 3H), 2.34 (s, 3H), 2.42 (s, 3H), 6.93 (bs, 2H). MS 226 (MH⁺).

Example 26

2-Methoxy-5,6-dimethylthieno[2,3-d]pyrimidin-4-amine

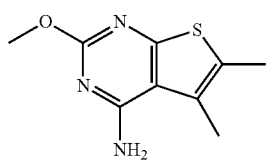

Prepared in a similar manner to Example 25 from N-(3-cyano-4,5-dimethylthiophen-2-ylcarbamoyl)benzamide (Example 4a) and methyl iodide in 86% yield. $^1$H NMR (400 MHz, CDCl₃) δ 2.35 (s, 3H), 2.36 (s, 3H), 3.53 (s, 3H), 6.0 (bs, 2H). MS 210 (MH⁺).

Example 27

5,6-Dimethyl-2-(methylthio)furo[2,3-d]pyrimidin-4-amine

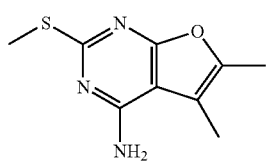

Prepared as in Example 25 from N-(2-cyano-4,5-dimethylfuran-3-ylcarbamothioyl)benzamide (Example 27a). $^1$H NMR (400 MHz, DMSO-$d_6$) δ 2.16 (s, 3H), 2.23 (s, 3H), 2.41 (s, 3H), 6.92 (s, 2H). MS 210 (MH⁺).

Example 27a

N-(2-Cyano-4,5-dimethylfuran-3-ylcarbamothioyl)benzamide

Prepared as in Example 1a from 2-amino-4,5-dimethylfuran-3-carbonitrile and benzoyl isothiocyanate. MS 300 (MH⁺).

Example 28

7-Methyl-2-(methylthio)quinazolin-4-amine

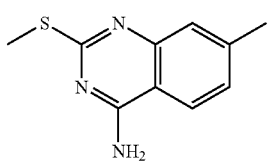

Prepared as in Example 25 from N-(2-cyano-5-methylphenylcarbamothioyl)benzamide (Example 17a). $^1$H NMR (400 MHz, DMSO-$d_6$) δ 2.40 (s, 3H), 2.45 (s, 3H), 7.17 (dd, J=2.0, 8.8 Hz, 1H), 7.32 (s, 1H), 7.71 (b, 2H), 8.01 (d, J=8.4 Hz, 1H). MS 206 (MH$^+$).

Example 29

5-Methyl-2-(methylthio)quinazolin-4-amine

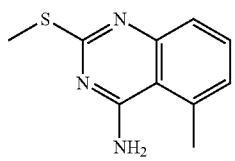

Prepared as in Example 25 from N-(2-cyano-3-methylphenylcarbamothioyl)benzamide (Example 3a). $^1$H NMR (400 MHz, DMSO-$d_6$) δ 2.46 (s, 2.75 (s, 3H), 7.11 (d, J=7.2 Hz, 1H), 7.33 (d, J=7.2 Hz, 1H), 7.51 (dd, J=0.8, 7.2 Hz, 1H). MS 206 (MH$^+$).

Example 30

5,6-Dimethylthieno[2,3-d]pyrimidine-2,4-diamine

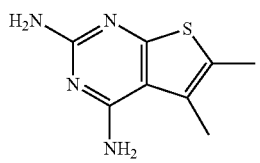

A mixture of 2-amino-4,5-dimethylthiophene-3-carbonitrile (500 mg, 3.29 mmol), cyanoguanidine (276.6 mg, 3.29 mmol) and HCl (2 N, 1.5 mL) in water (10 mL) was refluxed under nitrogen for 2 h. The reaction mixture was cooled to room temperature, and basified with diluted NaOH aqueous solution to PH 7~8. After evaporation of water, the residue was purified by preparative HPLC eluting with acetonitrile and water to give the title compound (33 mg, 5%). $^1$H NMR (400 MHz, DMSO-$d_6$) δ 2.22 (s, 3H), 2.27 (s, 3H), 5.85 (bs, 2H), 6.29 (bs, 2H). MS 195 (MH$^+$).

Example 31

2,5,6-Trimethylthieno[2,3-d]pyrimidin-4-amine

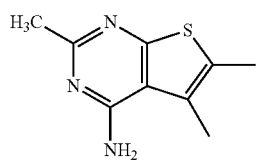

A mixture of 2-amino-4,5-dimethylthiophene-3-carbonitrile (200 mg, 1.32 mmol), ammonia acetate (204 mg, 2.64 mmol), and triethyl orthoacetate (2.0 mL) was stirred in a sealed tube at 120° C. overnight. After the reaction mixture was cooling down to room temperature, the precipitate was collected by filtration, rinsed with EtOAc and dried in the air to give title compound (52 mg, 60%) as a yellow solid. $^1$H NMR (400 MHz, CDCl$_3$) δ 2.41 (s, 3H), 2.45 (s, 3H), 2.56 (s, 3H), 5.28 (bs, 2H). MS 194 (MH$^+$).

Example 32

5,6-Dimethylthieno[2,3-d]pyrimidin-4-amine

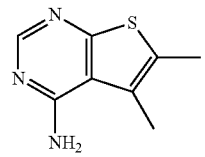

Prepared as in Example 31 from 2-amino-4,5-dimethylthiophene-3-carbonitrile and triethyl orthoformate. $^1$H NMR (400 MHz, DMSO-$d_6$) δ 2.36 (s, 3H), 2.39 (s, 3H), 6.85 (bs, 2H), 8.14 (s, 1H). MS 180 (MH$^+$).

Example 33

2-Ethyl-5,6-dimethylthieno[2,3-d]pyrimidin-4-amine

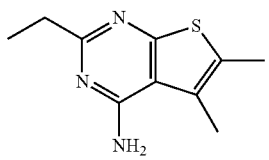

Prepared as in Example 31 from 2-amino-4,5-dimethylthiophene-3-carbonitrile and triethyl orthopropanate. $^1$H NMR (400 MHz, DMSO-$d_6$) δ 1.19 (t, J=7.6 Hz, 3H), 2.33 (s, 3H), 2.36 (s, 3H), 2.61 (q, J=7.6 Hz, 2H), 6.74 (bs, 2H). MS 208 (MH$^+$).

Example 34

5,6-Dimethyl-2-phenylthieno[2,3-d]pyrimidin-4-amine

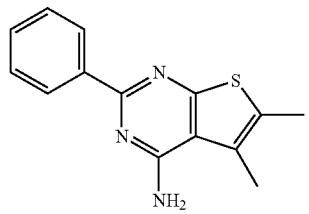

A mixture of 2-amino-4,5-dimethylthiophene-3-carbonitrile (152 mg, 1.0 mmol), ammonia acetate (308.3 mg, 4.0 mmol) and triethyl orthobenzoate (2.0 mL) in a sealed tube was put in a microwave at 200° C. for 20 min. After the reaction mixture was cooled to room temperature, it was diluted with EtOAc, washed with saturated NaHCO$_3$ and H$_2$O. The solvent was removed by vacuum and the residue was purified by preparative HPLC eluting with acetonitrile and water to give the title compound (80 mg, 31%). $^1$H NMR (400 MHz, CDCl$_3$) δ 2.45 (s, 3H), 2.48 (s, 3H), 5.34 (bs, 2H), 7.46-7.43 (m, 3H), 8.4-8.38 (m, 2H). MS 256 (MH$^+$).

Example 35

5,6-Dimethyl-2-propylthieno[2,3-d]pyrimidin-4-amine

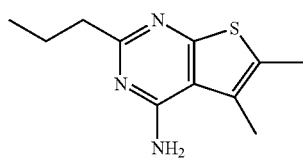

123

Prepared as in Example 34 from 2-amino-4,5-dimethylthiophene-3-carbonitrile and triethyl orthobutanate. $^1$H NMR (400 MHz, DMSO-d$_6$) δ 0.87 (t, J=7.6 Hz, 3H), 1.72-1.67 (m, 2H), 2.33 (s, 3H), 2.36 (s, 3H), 2.57 (t, J=7.2 Hz, 2H), 6.73 (bs, 2H). MS 222 (MH$^+$).

Example 36

5,6-Dimethyl-2-(methylsulfonyl)thieno[2,3-d]pyrimidin-4-amine

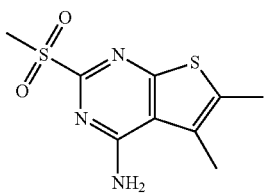

125

To a suspension of 5,6-dimethyl-2-(methylthio)thieno[2,3-d]pyrimidin-4-amine (Example 1) (200 mg, 0.89 mmol) in DCM (25 mL) was added m-chloroperoxybenzoic acid (767 mg, 4.44 mmol). After stirring at room temperature overnight, the reaction mixture was diluted with EtOAc, washed with water and brine, dried over Na$_2$SO$_4$, filtered and evaporated. The residue was purified by preparative HPLC eluting with acetonitrile and water to give the title compound (45 mg, 20%). $^1$H NMR (400 MHz, DMSO-d$_6$) δ 2.42 (s, 6H), 3.27 (s, 3H). MS 258 (MH$^+$).

Example 37

Ethyl 5,6-dimethyl-2-thioxo-1,2-dihydrothieno[2,3-d]pyrimidin-4-ylcarbamate

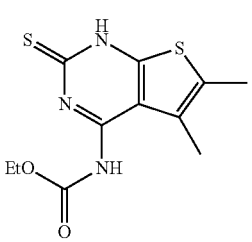

133

To a suspension of 4-amino-5,6-dimethylthieno[2,3-d]pyrimidine-2(1H)-thione (211 mg, 1 mmol) in DMF (5 mL) was added Et$_3$N (0.21 mL, 1.5 mmol) and ethyl chloroformate (0.143 mL, 1.5 mmol). The reaction mixture was stirred at room temperature overnight, then diluted with EtOAc, washed with water and brine, dried over Na$_2$SO$_4$, filtered and evaporated. The residue was purified on Biotage SP-1 eluting with EtOAc/hexane to give the title compound (154 mg, 54%). $^1$H NMR (400 MHz, DMSO-d$_6$) δ 1.22 (t, J=7.2 Hz, 3H), 2.38 (s, 3H), 2.39 (s, 3H), 4.25 (q, J=7.2 Hz, 2H), 7.25-7.21 (m, 2H). MS 284 (MH$^+$)

Example 38

2-Chloroquinazolin-4-amine

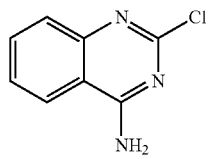

185

To a solution of 2,4-dichloroquinazoline (2.0 g, 10 mmol) in THF (10 mL), was added ammonia (28-30% in water, 18 mL). The reaction mixture was stirred at room temperature overnight. The reaction mixture was diluted with EtOAc, washed with saturated NaHCO$_3$, water and brine, dried over Na$_2$SO$_4$, filtered and evaporated. The resulting solid was washed with EtOAc to give the title compound (1.3 g, 72%). $^1$H NMR (400 MHz, DMSO-d$_6$) δ 7.52-7.48 (m, 1H), 7.6-7.58 (m, 1H), 7.8-7.76 (m, 1H), 8.22-8.20 (m, 1H), 8.32 (bs, 2H).

Example 39

2-Chloro-N-methylquinazolin-4-amine

187

Prepared as in Example 38 from 2,4-dichloroquinazoline and methylamine. $^1$H NMR (400 MHz, DMSO-d$_6$) δ 2.98 (d, J=4.4 Hz, 3H), 7.53-7.49 (m, 1H), 7.61-7.58 (m, 1H), 7.79-7.75 (m, 1H), 88.19-8.17 (m, 1H), 78 (bs, 1H).

Example 40

2-Chloro-N,N-dimethylquinazolin-4-amine

189

Prepared as in Example 38 from 2,4-dichloroquinazoline and dimethylamine. ¹H NMR (400 MHz, CDCl₃) δ 3.42 (s, 6H), 7.42-7.39 (m, 1H), 7.72-7.70 (m, 1H), 7.79-7.77 (m, 1H), 8.03-8.01 (m, 1H). MS 208 (MH⁺).

Example 41

N2,N2,N4,N4-Tetramethylquinazoline-2,4-diamine

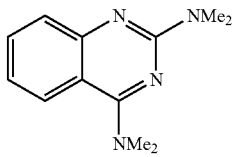
191

Prepared as in Example 38 from 2,4-dichloroquinazoline and dimethylamine. ¹H NMR (400 MHz, CDCl₃) δ 3.27-3.23 (m, 12H), 7.01-6.97 (m, 1H), 7.51-7.47 (m, 2H), 7.80-7.78 (m, 1H). MS 217 (MH⁺).

Example 42

2-Hydrazinylquinazolin-4-amine

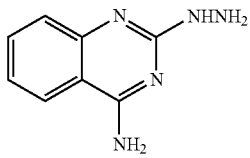
193

A mixture of 2-chloroquinazolin-4-amine (Example 38) (100 mg, 0.56 mmol) and hydrazine (0.09 mL, 2.79 mmol) in ethanol (5 mL) was heated in a sealed tube at 80° C. overnight. After the reaction mixture was cooled down, the resulting precipitate was collected by filtration, rinsed with ethanol and dried in the air to give the title compound (84 mg, 86%). ¹H NMR (400 MHz, DMSO-d₆) δ 4.2 (bs, 2H), 4.6 (bs, 2H), 7.0 (t, J=7.2 Hz, 1H), 7.27 (d, J=8.0 Hz, 1H), 7.43 (s, 1H), 7.61 (s, 1H), 7.87 (d, J=7.6 Hz, 1H).

Example 43

2-(Hydroxyamino)quinazolin-4-amine

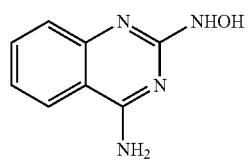
195

Prepared as in Example 42 from 2-chloroquinazolin-4-amine (Example 38) and hydroxylamine. ¹H NMR (400 MHz, DMSO-d₆) δ 7.44-7.35 (m, 2H), 7.78-7.74 (m, 2H), 8.24-8.22 (m, 1H), 8.95-8.76 (m, 2H). MS 177 (MH⁺).

Example 44

2-(Methoxyamino)quinazolin-4-amine

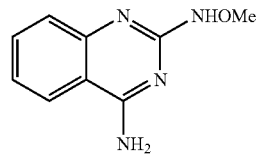
197

Prepared as in Example 42 from 2-chloroquinazolin-4-amine (Example 38) and methoxylamine. ¹H NMR (400 MHz, DMSO-d₆) δ 3.79 (s, 3H), 7.48-7.44 (m, 1H), 7.86-7.80 (m, 2H), 8.27 (d, J=8.0 Hz, 1H), 8.99 (s, 1H), 9.16 (s, 1H), 12.39-12.08 (m, 1H). MS 191 (MH⁺).

Example 45

N'-(4-Aminoquinazolin-2-yl)acetohydrazide

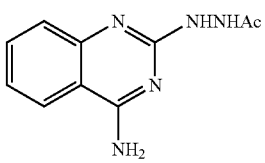
199

Prepared as in Example 42 from 2-chloroquinazolin-4-amine (Example 38) and methoxylamine. ¹H NMR (400 MHz, DMSO-d₆) δ 1.86 (s, 3H), 7.09 (t, J=7.2 Hz, 1H), 7.27 (d, J=8.4 Hz, 1H), 7.54-7.44 (m, 3H), 8.04-7.99 (m, 2H), 9.63 (s, 1H). MS 218 (MH⁺).

Example 46

4-(Methylamino)quinazoline-2(1H)-thione

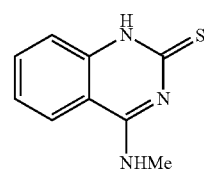
175

A mixture of 2-chloro-N-methylquinazolin-4-amine (Example 39) (100 mg, 0.52 mmol), thiourea (47.5 mg, 0.62 mmol) and formic acid (0.02 mL, 0.52 mmol) in ethanol (5 mL) was refluxed for 1.5 h. After cooling to room temperature, the reaction mixture was neutralized with diluted NaOH aqueous solution. The solvent was removed under vacuum and the residue was purified by preparative HPLC eluting with acetonitrile and water to give the title compound (18 mg, 18%). ¹H NMR (400 MHz, DMSO-d₆) δ 2.99 (d, J=4.8 Hz, 3H), 7.25 (t, J=7.6 Hz, 1H), 7.35 (d, J=8.0 Hz, 1H), 7.65-7.61 (m, 1H), 8.0 (d, J=8.0 Hz, 1H), 8.70 (d, J=4.4 Hz, 1H), 12.32 (s, 1H). MS 192 (MH⁺).

Example 47

4-(Dimethylamino)quinazoline-2(1H)-thione

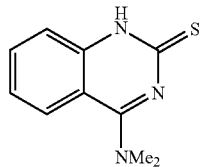

Prepared as in Example 46 from 2-chloro-N,N-dimethylquinazolin-4-amine (Example 40) and thiourea. ¹H NMR (400 MHz, DMSO-d₆) δ 3.31 (s, 6H), 7.24-7.19 (m, 1H), 7.40-7.38 (m, 1H), 7.65-7.61 (m, 1H), 8.00 (d, J=8.0 Hz, 1H), 12.35 (s, 1H). MS 206 (MH⁺).

Example 48

5,6,7,8-Tetrahydroquinazoline-2,4(1H,3H)-dione

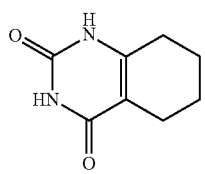

A solution of 2-oxocyclohexanecarbonitrile (615 mg, 5.0 mmol) and urea (600 mg, 10.0 mmol) in 1.25 N HCl in EtOH (20 mL) was refluxed over night. After it was cooled down to 0° C., the precipitation was collected by filtration, washed with EtOH/H₂O, and dried under vacuum overnight to give the product as a white solid. ¹H NMR (400 MHz, CD₃OD) δ 1.67-1.80 (m, 4H), 2.25-2.29 (m, 2H), 2.38-2.42 (m, 2H). MS 167 (MH⁺).

Example 49

5,7-Dihydrothieno[3,4-d]pyrimidine-2,4(1H,3H)-dione

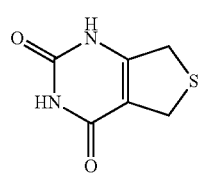

Prepared as in Example 48 from 4-oxotetrahydrothiophene-3-carbonitrile as a white solid. ¹H NMR (400 MHz, DMSO-d₆) δ 3.74 (t, J=3.6 Hz, 2H), 3.96 (t, J=3.6 Hz, 2H), 11.06 (s, 1H), 11.21 (s, 1H). MS 171 (MH⁺).

Example 50

5,6-Dimethyl-2-thioxo-2,3-dihydrothieno[2,3-d]pyrimidin-4(1H)-one

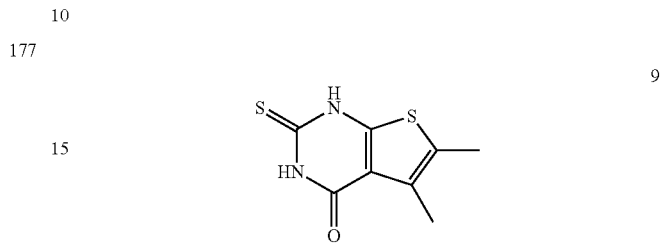

To a suspension of ethyl 4,5-dimethyl-2-thioureidothiophene-3-carboxylate (Example 50a) (37 mg, 0.17 mmol) in dry EtOH (10 mL) was added sodium hydroxide (21 mg, 0.52 mmol). The reaction mixture was then stirred at room temperature for 5 minutes and refluxed for 10 minutes. The reaction mixture was cooled to room temperature, neutralized with 10% AcOH and then concentrated to dryness. The residue was purified by chromatography on silica gel (Gradient 0-50% EtOAc in Hexanes) to give the title compound (8 mg) in 24% yield. ¹H NMR (400 MHz, DMSO-d₆) δ 2.25 (s, 6H), 12.24 (s, 1H), 13.27 (s, 1H). MS 202 (MH⁺).

Example 50a

Ethyl 4,5-dimethyl-2-thioureidothiophene-3-carboxylate

To a solution of ethyl 2-isothiocyanato-4,5-dimethylthiophene-3-carboxylate (Example 50b) (1.21 g, 5.27 mmol) in dichloromethane (10 mL) was added ammonia (7 M in MeOH, 1.12 mL, 7.91 mmol) at 0° C. The reaction mixture was then stirred at room temperature for 3 h, quenched with water and extracted with dichloromethane (3×). The combined organic layers were washed with brine, dried over MgSO₄, filtered and concentrated. The dark orange residue was purified by chromatography on silica gel (Gradient 0-50% EtOAc in Hexanes) to give the title compound (37.1 mg, 3%). ¹H NMR (400 MHz, DMSO-d₆) δ 1.32 (t, 3H, J=7.1 Hz), 2.18 (s, 3H), 2.19 (s, 3H), 4.30 (q, 2H, J=7.1 Hz), 8.43 (s, 2H), 11.38 (s, 1H). MS 259 (MH⁺).

Example 50b

Ethyl 2-isothiocyanato-4,5-dimethylthiophene-3-carboxylate

To a mixture of thiophosgene (5.10 mL, 7.64 mmol) and calcium carbonate (1.05 g, 10.54 mmol) in CHCl₃/H₂O (½ by volume, 6 mL) was added dropwise a solution of ethyl 2-amino-4,5-dimethylthiophene-3-carboxylate (1.05 g, 5.27 mmol) in CHCl₃ (7 mL) at 0° C. over a period of 1 h. The reaction mixture was the stirred for 2.5 h at 0° C., washed with water (3×). The organic layer was dried over MgSO₄, filtered and concentrated to give the title compound (1.21 g, 100%).

$^1$H NMR (400 MHz, DMSO-d$_6$) δ 1.32 (t, 3H, J=7.1 Hz), 2.19 (s, 3H), 2.30 (s, 3H), 4.28 (q, 2H, J=7.1 Hz).

Example 51

4-Ethyl-5,6-dimethylthieno[2,3-d]pyrimidin-2(1H)-one

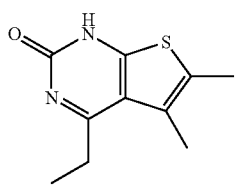

135

To a solution of 1-(4,5-dimethyl-3-propionylthiophen-2-yl)urea (Example 51a) (15.4 mg, 0.068 mmol) in dry EtOH (10 mL) was added sodium hydroxide (8.4 mg, 0.20 mmol). The reaction mixture was then stirred at RT for 30 minutes under nitrogen. The reaction mixture was neutralized with 10% AcOH and then concentrated to dryness. The residue was purified by chromatography on silica gel (Gradient 0-10% MeOH in dichloromethane) to give the title compound (2.7 mg, 19%). $^1$H NMR (400 MHz, CDCl$_3$) δ 1.42 (t, J=7.6 Hz, 3H), 2.31 (s, 3H), 2.33 (s, 3H), 3.06 (q, J=7.6 Hz, 2H). MS 209 (MH$^+$).

Example 51a 1-(4,5-Dimethyl-3-propionylthiophen-2-yl)urea

To a solution of triphosgene (68 mg, 0.224 mmol) in dry dichloromethane (2 mL) was added dropwise a mixture of 1-(2-amino-4,5-dimethylthiophen-3-yl)propan-1-one (Example 51b) (111 mg, 0.605 mmol) and DIEA (0.24 mL, 1.344 mmol) in dry dichloromethane (3.5 mL) over a period of 20 minutes. After the reaction mixture was stirred for 5 minutes, a mixture of ammonia (7 M in MeOH, 0.086 mL, 0.605 mmol) and DIEA (0.24 mL, 1.344 mmol) in dry dichloromethane (2 mL) was added in one portion. The reaction mixture was then stirred at room temperature for 1 h under nitrogen. The reaction mixture was concentrated to dryness. The residue was dissolved in EtOAc (50 mL) and then washed with 10% NaHSO$_4$, 5% NaHCO$_3$, and brine. The organic layer was dried over MgSO$_4$, filtered and concentrated. The yellow residue was purified by chromatography on silica gel (Gradient 0-50% EtOAc in Hexanes) to give the title compound (15.4 mg, 30%). $^1$H NMR (400 MHz, CDCl$_3$) δ 1.18 (t, 3H, J=7.2 Hz), 2.25 (s, 3H), 2.30 (s, 3H), 2.87 (q, 2H, J=7.2 Hz), 4.77 (s, 2H), 11.99 (s, 1H). MS 227 (MH$^+$).

Example 51b 1-(2-Amino-4,5-dimethylthiophen-3-yl)propan-1-one

To a solution of 3-oxopentanenitrile (971 mg, 10 mmol) in dry EtOH (100 mL) was added sulfur (2.57 g, 10 mmol), butanone (0.91 mL, 10 mmol) and morpholine (0.88 mL, 10 mmol) at room temperature under nitrogen. The reaction mixture was then refluxed at 90° C. for 6 h, and then stirred overnight at room temperature under nitrogen. The orange brown reaction mixture was concentrated. The residue was diluted with water, and extracted with EtOAc (2×). The combined organic layers were washed with brine, dried over MgSO$_4$, filtered and concentrated. The residue was purified twice: first by chromatography on silica gel (Gradient 0-25% EtOAc in hexanes), and then by Prep HPLC (0-90% acetonitrile in water) to give the title compound (123 mg, 7%). $^1$H NMR (400 MHz, CDCl$_3$) δ 1.17 (t, 3H, J=7.2 Hz), 2.17 (s, 3H), 2.24 (s, 3H), 2.78 (q, 2H, J=7.2 Hz), 6.81 (s, 2H). MS 184 (MH$^+$).

Example 52

4-Ethyl-5,6-dimethylthieno[2,3-d]pyrimidin-2(1H)-one

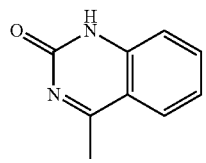

183

To a solution of methylmagnesium bromide (3.0 M in ether, 4.0 mL, 12.0 mmol) in dry ether (5 mL) was added dropwise a solution of 2-aminobenzonitrile (723 mg, 6.0 mmol) in dry ether (5 mL) at RT under nitrogen. After it was refluxed for 2 h under nitrogen, the reaction mixture was cooled down to 0° C. and methyl chloroformate (0.7 mL, 9.0 mmol) was added dropwise. Dry THF (5 mL) was added to dissolve the resultant precipitate. The reaction mixture was then refluxed overnight under nitrogen. The reaction mixture was acidified with 1N HCl and then neutralized with 5% NaHCO$_3$ aqueous solution. The water mixture was washed with EtOAc and the water layer was concentrated. The residue was purified by Prep HPLC ((0-90% acetonitrile in water) to give the title compound (15.2 mg). $^1$H NMR (400 MHz, CD$_3$OD) δ 2.79 (s, 3H), 7.33 (d, J=7.1 Hz, 1H), 7.34 (t, J=7.1 Hz, 1H), 7.75 (td, J=1.2, 7.8 Hz, 1H), 8.03 (dd, J=1.2 8.4 Hz, 1H). MS 161 (MH$^+$).

Example 53

4-aminopyrido[2,3-d]pyrimidin-2(1H)one

174

A solution of N-(3-cyanopyridin-2-ylcarbamoyl)benzamide (example 53a) (360 mg, 1.35 mmol) and NaOH (2 N, 1.85 mL) in EtOH (5 mL) was stirred at 100° C. under nitrogen for half an hour. After cooling to room temperature, the clear reaction solution was filtered and the filtrate was carefully neutralized with 10% AcOH with vigorous stirring at 0° C. The resultant precipitate was collected by filtration, and washed with warm 20% EtOH in water to give the final product 4-aminopyrido[2,3-d]pyrimidin-2(1H)-one (120 mg, 55%) as a white solid. $^1$H NMR (400 MHz, DMSO-d$_6$) δ 7.22

(dd, J=4.4 Hz, 4.8 Hz, 1H), 7.29 (dd, J=4.8 Hz, 1H), 8.24 (dd, J=2 Hz, 1.6 Hz, 1H), 8.59 (dd, J=2 Hz, 1.6 Hz, 1H), 8.66-8.71 (m, 2H), 8.70 (d, J=1.2 Hz, 1H). MS 162 (MH$^+$).

Example 53a

N-(3-cyanopyridin-2-ylcarbamoyl)benzamide

To a solution of 2-amino-3-cyanopyridine (300 mg, 2.5 mmol) in 1,4-dioxane (5 mL) was added benzoyl isocyanate (370 mg, 2.5 mmol). The reaction mixture was then stirred at room temperature under nitrogen overnight. The precipitation was collected by filtration, washed with EtOAc/Hexanes (1:4), and dried under vacuum to give N-(3-cyanopyridin-2-ylcarbamoyl)benzamide as a white solid (360 mg, 54%). MS 266 (MH$^+$).

Example 54

5,6-dimethylquinazoline-2,4(1H,3H)-dione

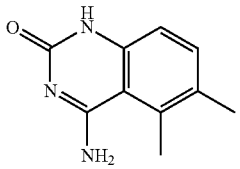

172

Prepared as in Example 53 from N-(2-cyano-3,4-dimethylphenylcarbamoyl)benzamide (Example 54a) as a white solid (90 mg, 66%). $^1$H NMR (400 MHz, DMSO-d$_6$) δ 2.24 (s, 3H), 2.54 (s, 3H), 6.87 (d, J=8.4 Hz, 1H), 7.32 (d, J=8.4 Hz, 1H), 10.51 (s, 1H). MS 189 (MH$^+$).

Example 54a

N-(2-cyano-3,4-dimethylphenylcarbamoyl)benzamide

Prepared as in Example 53a from 6-amino-2,3-dimethylbenzonitrile and benzoyl isocyanate as a off-white solid (210 mg, 72%). $^1$H NMR (400 MHz, DMSO-d$_6$) δ 2.27 (s, 3H), 2.43 (s, 3H), 7.48 (d, J=6.4 Hz, 2H), 7.53 (t, J=8 Hz, 7.6 Hz, 2H), 7.65 (t, J=7.2 Hz, 1H), 7.94 (d, J=8 Hz, 1H), 8.03 (d, J=7.6 Hz, 2H), 11.29 (s, 1H), 11.37 (s, 1H). MS 293 (MH$^+$).

Example 55

4-amino-7-methoxyquinazolin-2(1H)-one

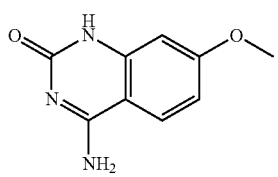

204

Prepared as in example 53 from N-(2-cyano-5-methoxyphenylcarbamoyl)benzamide (Example 55a) as a white solid (24 mg, 37%). $^1$H NMR (400 MHz, DMSO-d$_6$) δ 3.79 (s, 3H), 6.63 (d, J=4 Hz, 1H), 6.67 (dd, J=2.4 Hz, 2.8 Hz, 1H), 7.67 (br, 2H), 7.89 (d, J=8.8 Hz, 1H), 10.61 (s, 1H). MS 191 (MH$^+$).

Example 55a

N-(2-cyano-5-methoxyphenylcarbamoyl)benzamide

Prepared as in Example 53a from 2-amino-4-methoxybenzonitrile and benzoyl isocyanate as white solid (99 mg, 45%). $^1$H NMR (400 MHz, DMSO-d$_6$) δ 3.86 (s, 3H), 6.87 (dd, J=2.5 Hz, 2.4 Hz, 1H), 7.54 (t, J=8 Hz, 2H), 7.66 (t, J=1.2 Hz, 1H), 7.77 (d, J=7.2 Hz, 1H), 7.89 (d, J=8.4 Hz, 1H), 8.03 (d, J=2.8 Hz, 2H), 11.35 (s, 1H), 11.52 (s, 1H). MS 295 (MH$^+$).

Example 56

4-amino-5-methoxyquinazolin-2(1H)-one

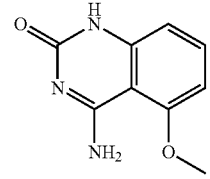

170

Prepared as in example 53 from N-(2-cyano-3-methoxyphenylcarbamoyl)benzamide (Example 56a) as a light yellow solid (35 mg, 51%). $^1$H NMR (400 MHz, DMSO-d$_6$) δ 3.93 (s, 3H), 6.67 (dd, J=7.6 Hz, 8.4 Hz, 2H), 7.45 (t, J=8 Hz, 1H), 7.75 (s, 1H), 7.93-7.97 (br, 1H), 10.69 (s, 1H). MS 191 (MH$^+$).

Example 56a

N-(2-cyano-3-methoxyphenylcarbamoyl)benzamide

Prepared as in Example 53a from 2-amino-6-methoxybenzonitrile and benzoyl isocyanate as light orange solid (118 mg, 41%). $^1$H NMR (400 MHz, DMSO-d$_6$) δ 3.94 (s, 3H), 6.98 (d, J=8 Hz, 1H), 7.54 (t, J=8 hz, 2H), 7.64 (t, J=8.4 Hz, 2H), 7.88 (d, J=8.4 Hz, 1H), 8.04 (d, J=5.6 Hz, 2H), 11.35 (s, 1H), 11.51 (s, 1H). MS 295 (MH$^+$).

Example 57

4-amino-5-hydroxyquinazolin-2(1H)-one

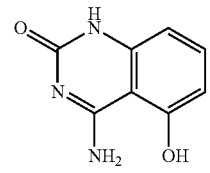

178

Prepared as in example 53 from N-(2-cyano-3-hydroxyphenylcarbamoyl)benzamide (Example 57a) as a green solid (50 mg, 53%). $^1$H NMR (400 MHz, DMSO-d$_6$) δ 6.66 (d, J=8.4 Hz, 1H), 6.73 (d, J=7.6 Hz, 1H), 7.57 (t, J=8.8 Hz, 1H), 9.47 (s, 1H), 9.68 (s, 1H), 11.84 (s, 1H). MS 177 (MH$^+$).

Example 57a

N-(2-cyano-3-hydroxyphenylcarbamoyl)benzamide

Prepared as in Example 53a from 2-amino-6-hydroxybenzonitrile and benzoyl isocyanate as an off-white solid (166 mg, 46%). $^1$H NMR (400 MHz, DMSO-d$_6$) δ 6.76 (d, J=8.4 Hz, 1H), 7.46 (t, J=8 Hz, 1H), 7.54 (t, J=8 Hz, 2H), 7.66-7.73 (m, 2H), 8.04-8.06 (d, J=8 Hz, 2H), 11.24 (s, 1H), 11.30 (s, 1H), 11.42 (s, 1H). MS 281 (MH$^+$).

Example 58

4-amino-7-hydroxyquinazolin-2(1H)-one

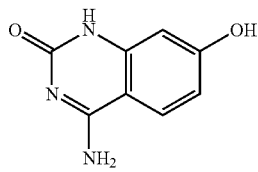

180

Prepared as in example 53 from N-(2-cyano-5-hydroxyphenylcarbamoyl)benzamide (Example 58a) as a light grey solid (104 mg, 41%). $^1$H NMR (400 MHz, DMSO-d$_6$) δ 6.51 (s, 2H), 6.52 (d, J=2.4 Hz, 1H), 7.69-7.72 (br, 1H), 7.82 (d, J=9.2 Hz, 2H), 10.57 (br, 1H). MS 177 (MH$^+$).

Example 58a

N-(2-cyano-5-hydroxyphenylcarbamoyl)benzamide

Prepared as in Example 53a, but refluxed in acetone instead of 1,4-dioxane, from 2-amino-4-hydroxybenzonitrile and benzoyl isocyanate as a yellow solid (399 mg, 94%). MS 281 (MH$^1$).

Example 59

4-amino-8-methoxyquinazolin-2(1H)-one

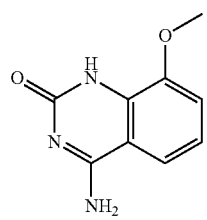

182

Prepared as in example 53 from N-(2-cyano-6-methoxyphenylcarbamoyl)benzamide (Example 59a) as a dark white solid (75 mg, 39%). $^1$H NMR (400 MHz, DMSO-d$_6$) δ 3.86 (s, 3H), 7.02 (t, J=8.4 Hz, 1H), 7.17 (d, J=7.2 Hz, 1H), 7.56 (d, J=7.6 Hz, 1H), 7.85 (br, 2H), 9.73 (s, 1H). MS 191 (MH$^+$).

Example 59a

N-(2-cyano-6-methoxyphenylcarbamoyl)benzamide

Prepared as in Example 53a from 2-amino-3-methoxybenzonitrile and benzoyl isocyanate as a light orange solid (280 mg, 95%). $^1$H NMR (400 MHz, DMSO-d$_6$) δ 3.89 (s, 3H), 7.42 (t, J=3.2 Hz, 2H), 7.46 (d, J=3.6 Hz, 1H), 7.54 (t, J=8 Hz, 2H), 7.66 (t, J=7.6 Hz, 1H), 8.05 (d, J=8.6 Hz, 2H), 10.55 (s, 1H), 11.32 (s, 1H). MS 295 (MH$^+$).

Example 60

8-amino-[1,3]dioxolo[4,5-g]quinazolin-6(5H)-one

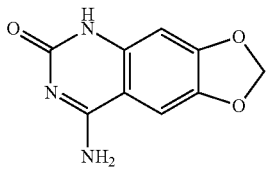

184

Prepared as in example 53 from N-(6-cyanobenzo[d][1,3]dioxol-5-ylcarbamoyl)benzamide (Example 60a) as a light yellow solid (80 mg, 77%). $^1$H NMR (400 MHz, DMSO-d$_6$) δ 6.24 (s, 2H), 6.74 (s, 1H), 7.75 (s, 1H), 9.36 (d, J=10.4 Hz, 1H), 9.80 (d, J=7.2 Hz, 1H), 12.01 (s, 1H). MS 205 (MH$^+$).

Example 60a

N-(6-cyanobenzo[d][1,3]dioxol-5-ylcarbamoyl)benzamide

Prepared as in Example 53a from 6-aminobenzo[d][1,3]dioxole-5-carbonitrile and benzoyl isocyanate as a yellow solid (157 mg, 82%). $^1$H NMR (400 MHz, DMSO-d$_6$) δ 6.19 (s, 2H), 7.42 (s, 1H), 7.54 (t, J=8 Hz, 2H), 7.66 (t, J=7.6 Hz, 1H), 7.74 (s, 1H), 8.03 (d, J=9.2 Hz, 2H), 11.32 (d, J=12.8 Hz, 2H). MS 309 (MH$^+$).

Example 61

4-(Methoxyamino)quinazolin-2(1H)-one

166

To a suspension of 2,4-dichloroquinazoline (995 mg, 5.0 mmol) in dry EtOH (100 mL), were added methoxyamine hydrochloride (569 mg, 5.5 mmol) and NaOH (227 mg, 5.5 mmol) in one portion at 0° C. The reaction mixture was stirred at 0° C. for 1 hour, then placed in a refrigerator at 4° C. for 72 h. Upon completion, the reaction was concentrated, and the residue was dissolved in EtOAc and washed with saturated NaHCO$_3$ (1×) and brine (1×). The organic phase was dried over MgSO$_4$, filtered and concentrated. The crude product was purified by preparative HPLC (10-90% CH$_3$CN in H$_2$O) to provide 4-(methoxyamino)quinazolin-2(1H)-one (556 mg, 36%) as an off-white solid. $^1$H NMR (400 MHz, DMSO-d$_6$) δ 3.68 (s, 3H), 7.02 (t, J=7.4 Hz, 1H), 7.35 (d, J=7.9 Hz, 1H), 7.52 (ddd, J=8.1, 7.0, 1.5 Hz, 1H), 7.77 (dd, J=7.8, 1.4 Hz, 1H), 10.13 (br s, 1H), 10.89 (br s, 1H). MS 192.2 (MH$^+$).

Example 62

4-Ethoxyquinazolin-2(1H)-one

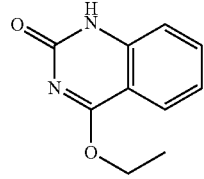

Purification by preparative HPLC (10-90% CH$_3$CN in H$_2$O) of the crude reaction of example 61 also provided 4-ethoxyquinazolin-2(1H)one (90 mg, 9%) as an off-white solid. $^1$H NMR (400 MHz, DMSO-d$_6$) δ 1.35 (t, J=7.0 Hz, 3H), 4.44 (q, J=7.0 Hz, 2H), 7.34 (ddd, J=8.1, 7.0, 1.2 Hz, 1H), 7.46 (dd, J=8.2, 1.0 Hz, 1H), 7.71 (ddd, J=8.5, 7.0, 1.2 Hz, 1H), 8.01 (dd, J=8.2, 1.5 Hz, 1H), 12.25 (br s, 1H). MS 191.1 (MH$^+$).

Example 63

4-Amino-5-methyl-2-oxo-1,2-dihydrothieno[2,3-d]pyrimidine-6-carboxylic acid

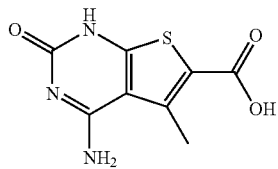

To a solution of tert-butyl 4-amino-5-methyl-2-oxo-1,2-dihydrothieno[2,3-d]pyrimidine-6-carboxylate (example 64a) (10.7 g, 38.03 mmol) in CH$_2$Cl$_2$ (25 mL), was added trifluoroacetic acid (25 mL, 324.5 mmol). The reaction mixture was stirred at rt overnight. The precipitated solid was collected by filtration, and washed with CH$_2$Cl$_2$ to yield 4-Amino-5-methyl-2-oxo-1,2-dihydrothieno[2,3-d]pyrimidine-6-carboxylic acid (6.98 g, 82%) as a light brown solid. $^1$H NMR (400 MHz, DMSO-d$_6$) δ 2.78 (s, 3H). MS 226.0 (MH$^+$).

Example 64 tert-Butyl 4-amino-5-methyl-2-oxo-1,2-dihydrothieno[2,3-d]pyrimidine-6-carboxylate

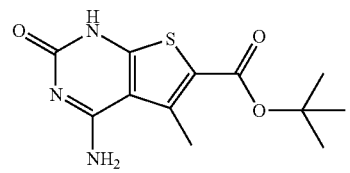

To a suspension of tert-butyl 5-(3-benzoylureido)-4-cyano-3-methylthiophene-2-carboxylate (example 64a) (18 g, 60.52 mmol) in EtOH (200 mL) was added NaOH (75 mL, 2N). The suspension became clear, and the mixture was heated to reflux for 30 min. After cooling to rt, the reaction was filtered, and the filtrate was cooled to 0° C. in an ice/water bath. The solution was neutralized with 10% acetic acid. The precipitated solid was collected by filtration, and heated in EtOH at 80° C. under N$_2$ for 20 min. After cooling to rt, the product was collected by filtration and washed with 10% EtOH in H$_2$O to yield tert-Butyl 4-amino-5-methyl-2-oxo-1,2-dihydrothieno[2,3-d]pyrimidine-6-carboxylate (10.73 g, 63%) as a brown solid. $^1$H NMR (400 MHz, DMSO-d$_6$) δ 1.51 (s, 9H), 2.73 (s, 3H), 3.18 (s, 2H). MS 282.2 (MH$^+$).

Example 64a tert-butyl 5-(3-benzoylureido)-4-cyano-3-methylthiophene-2-carboxylate

To a solution of tert-butyl 5-amino-4-cyano-3-methylthiophene-2-carboxylate (example 64b) (16 g, 67.14 mmol) in dioxane (200 mL), was added benzoyl isocyanate (10 g, 67.14 mmol). The reaction mixture was stirred at rt overnight, and upon completion was diluted with EtOAc, washed with NaHCO$_3$, water, brine, dried over MgSO$_4$, filtered and concentrated to yield tert-butyl 5-(3-benzoylureido)-4-cyano-3-methylthiophene-2-carboxylate (21.78 g, 84%) as a brown solid. $^1$H NMR (400 MHz, DMSO-d$_6$) δ 1.54 (s, 9H), 3.58 (s, 3H), 7.58 (t, J=7.5 Hz, 2H), 7.71 (t, J=7.5 Hz, 1H), 7.88 (d, J=7.5 Hz, 1H), 8.05 (d, J=7.5 Hz, 2H), 12.25 (br s, 1H).

Example 64b tert-butyl 5-amino-4-cyano-3-methylthiophene-2-carboxylate

To a solution of tert-butyl 3-oxobutanoate (30 mL, 183.94 mmol) in dry EtOH (360 mL), were added elemental sulfur (5.90 g, 183.94 mmol), malononitrile (12.16 g, 183.94 mmol) and triethylamine (25.6 mL, 183.94 mmol). The reaction mixture was heated to 80° C., and stirred for 2 h. After cooling to rt, the mixture was concentrated under reduced pressure. The resulting residue was dissolved in EtOAc, washed with NaHCO$_3$, water, brine, dried over MgSO$_4$, filtered and concentrated. The crude residue was purified by flash chromatography on silica gel (20% EtOAc in hexane) to yield tert-butyl 5-amino-4-cyano-3-methylthiophene-2-carboxylate (31.2 g, 73%) as a brown solid.

Example 65

4-Aminoquinolin-2(1H)-one

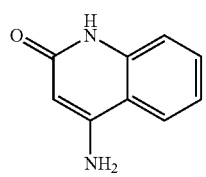

4-Amino-2-oxo-1,2-dihydroquinoline-3-carboxylic acid (Example 64) (0.030 g, 0.15 mmol) was heated neat at 295° C.

for 10 minutes, then cooled to room temperature to give 4-aminoquinolin-2(1H)-one (0.023 g, 99%) as a light yellow solid. M.p.: >250° C. ¹H NMR (400 MHz, DMSO-d₆) δ 5.42 (s, 1H), 6.55 (s, 2H), 7.07 (t, J=7.6 Hz, 1H), 7.19 (d, J=8.0 Hz, 1H), 7.42 (t, J=7.2 Hz, 1H), 7.86 (d, J=7.6 Hz, 1H), 10.71 (s, 1H). MS 161 (MH⁺).

Example 66

4-Amino-2-oxo-1,2-dihydroquinoline-3-carboxylic acid

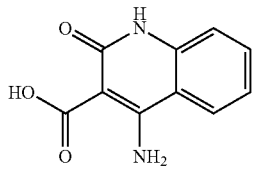

196

Benzyl 4-amino-2-oxo-1,2-dihydroquinoline-3-carboxylate (Example 66a) (0.6 g, 2.04 mmol) was dissolved in DMF (8 mL) and heated at 70° C. under a hydrogen balloon in the presence of 10% Pd/C (0.15 g) for 1 hour. The Pd/C was filtered out and washed with dichloromethane and the solvents were removed under vacuum. The residue was dissolved/suspended in NaOH (2M, 40 mL), stirred at room temperature for 30 minutes and the solution washed with dichloromethane. The aqueous layer was cooled to 0° C. and acidified to pH 1 with 2M HCl. The resultant precipitate was collected and washed with dichloromethane to give 4-amino-2-oxo-1,2-dihydroquinoline-3-carboxylic acid (0.050 g, 12%) as a light yellow solid. M.p.: >250° C. ¹H NMR (400 MHz, DMSO-d₆) δ 7.32 (m, 1H), 7.39 (d, J=7.6 Hz, 1H), 7.69 (m, 1H), 8.27 (d, J=8.4 Hz, 1H), 8.86 (s, 1H), 9.87 (s, 1H), 11.95 (s, 1H). MS 205 (MH⁺).

Example 66a

Benzyl 4-amino-2-oxo-1,2-dihydroquinoline-3-carboxylate

Benzyl 4-chloro-2-oxo-1,2-dihydroquinoline-3-carboxylate (Example 66b) (0.55 g, 1.75 mmol) was dissolved in DMF (8 mL) and 4-methoxybenzylamine (0.56 mL, 4.31 mmol) was added. The reaction was heated at 115° C. for 30 minutes, then cooled to room temperature and poured into ice water. The resultant precipitate was dissolved in 10 mL TFA and stirred at room temperature for 15 minutes, then the mixture was poured into ice water. The resultant precipitate was collected, dissolved in dichloromethane, dried over MgSO₄, filtered and evaporated to give the crude benzyl 4-amino-2-oxo-1,2-dihydroquinoline-3-carboxylate (600 mg) which was used as this without further purification. MS 295 (MH⁺).

Example 66b

Benzyl 4-chloro-2-oxo-1,2-dihydroquinoline-3-carboxylate

Dibenzylmalonate (7.75 mL, 31.6 mmol) was added slowly to a suspension of 60% sodium hydride in mineral oil (1.41 g, 35.3 mmol) in anhydrous DMF (100 mL) at −20° C. under nitrogen. After stirring at room temperature for 30 minutes, isatoic anhydride (5.0 g, 30.7 mmol) was added, and the reaction was heated at 120° C. for 1 hour. The reaction was then cooled to −50° C. and oxalyl chloride (10.7 mL, 123 mmol) was slowly added. The reaction mixture was stirred at room temperature for 2 hours then poured into aqueous NaCl (10%, 750 mL) at 0° C., and the resultant precipitate was filtered out. The precipitate was dissolved in dichloromethane, dried over MgSO₄, filtered and evaporated under reduced pressure. Diethyl ether was added to the residue, and the resultant solid was collected to give benzyl 4-chloro-2-oxo-1,2-dihydroquinoline-3-carboxylate (3.56 g, 37% yield) which was used without further purification. MS 314 (MH⁺).

Example 67

Ethyl 4-hydroxy-2-oxo-1,2-dihydroquinoline-3-carboxylate

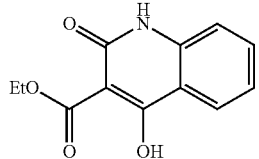

188

Diethylmalonate (11.4 mL, 75.1 mmol) was added slowly to a suspension of 60% sodium hydride in mineral oil (3.09 g, 77.3 mmol) in anhydrous DMF (100 mL) at −10° C. under nitrogen. After stirring at room temperature for 30 minutes, isatoic anhydride (12.0 g, 73.6 mmol) was added, and the reaction was heated at 115° C. for 2.5 hours. The reaction was cooled to room temperature, then poured into ice water (1.4 L) and acidified to pH 4 with 2M HCl. The resultant precipitate was collected, then dissolved/suspended in dichloromethane (450 mL). The dichloromethane solution was filtered out then evaporated to provide a residue that was vigorously triturated with diethyl ether (150 mL) for 1 hour. The solid was collected to give ethyl 4-hydroxy-2-oxo-1,2-dihydroquinoline-3-carboxylate (3.63 g, 21%) as a white solid. M.p.: 190° C. ¹H NMR (400 MHz, DMSO-d₆) δ 1.31 (t, J=7.2 Hz, 3H), 4.35 (q, J=7.2 Hz, 2H), 7.21 (m, 1H), 7.27 (d, J=8.0 Hz, 1H), 7.63 (m, 1H), 7.93 (dd, J=0.8, 8.4 Hz, 1H), 11.51 (s, 1H), 13.40 (s, 1H). MS 234 (MH⁺).

Example 68

Methyl 4-amino-2-oxo-1,2-dihydroquinoline-3-carboxylate

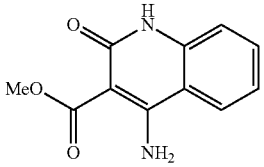

210

Methyl 4-(4-methoxybenzylamino)-2-oxo-1,2-dihydroquinoline-3-carboxylate (Example 68a) (0.841 g, 2.49 mmol) was dissolved in TFA (5 mL) and stirred at room temperature for 30 minutes. The TFA was removed under reduced pressure, and the residue was dissolved in dichloromethane, then precipitated out by adding excess diethyl ether. The resultant solid was collected by filtration, suspended in dichloromethane, and washed with concentrated sodium bicarbonate. The solid was collected to give methyl 4-amino-2-oxo-1,2-dihydroquinoline-3-carboxylate (0.230 g, 42%) as a white solid. M.p.: 236° C. $^1$H NMR (400 MHz, DMSO-d$_6$) δ 3.73 (s, 3H), 7.12 (t, J=8.0 Hz, 1H), 7.17 (d, J=8.0 Hz, 1H), 7.52 (t, J=8.0 Hz, 1H), 8.08 (d, J=8.0 Hz, 1H), 8.38 (bs, 2H), 10.88 (bs, 1H). MS 219 (MH$^+$).

Example 68a methyl 4-(4-methoxybenzylamino)-2-oxo-1,2-dihydroquinoline-3-carboxylate Methyl 4-chloro-2-oxo-1,2-dihydroquinoline-3-carboxylate (Example 69) (0.928 g, 3.91 mmol) was dissolved in DMF (6 mL), and 4-methoxybenzylamine (1.14 mL, 8.78 mmol) was added. The reaction was heated at 90° C. for 30 minutes, then cooled to room temperature and poured into a stirred mixture of 50 mL hexanes and 100 mL ice water. The resultant precipitate was collected by filtration and further chromatographed on silica gel (0% to 20% MeOH in dichloromethane) to give methyl 4-(4-methoxybenzylamino)-2-oxo-1,2-dihydroquinoline-3-carboxylate as an off white solid (0.841 g, 64%). MS 339 (MH$^+$).

Example 69

Methyl 4-chloro-2-oxo-1,2-dihydroquinoline-3-carboxylate

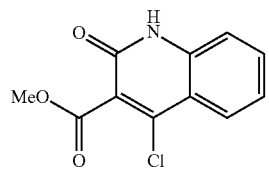

190

Dimethylmalonate (2.2 mL, 19.2 mmol) was added slowly to a suspension of 60% sodium hydride in mineral oil (0.81 g, 20.3 mmol) in anhydrous DMF (100 mL) at −10° C. under nitrogen. After stirring at room temperature for 30 minutes, isatoic anhydride (3.0 g, 18.4 mmol) was added, and the reaction mixture was heated at 115° C. for 2.5 hours. The reaction was then cooled to −40° C. and oxalyl chloride (6 mL, 68.8 mmol) was slowly added. The reaction was stirred at room temperature for 20 minutes, and was then poured into 1200 mL of 10% NaCl at 0° C. The resultant precipitate was collected by filtration to give crude methyl 4-chloro-2-oxo-1,2-dihydroquinoline-3-carboxylate (1.40 g, 32%), which was used without further purification. $^1$H NMR (400 MHz, DMSO-d$_6$) δ 3.87 (s, 3H), 7.39 (m, 2H), 7.70 (m, 1H), 7.92 (d, J=8.4 Hz, 1H), 12.49 (s, 1H). MS 238 (MH$^+$).

Example 70

Methyl 4-hydroxy-2-oxo-1,2-dihydroquinoline-3-carboxylate

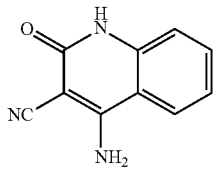

192

Dimethylmalonate (2.2 mL, 19.2 mmol) was added slowly to a suspension of 60% sodium hydride in mineral oil (0.81 g, 20.3 mmol) in anhydrous DMF (50 mL) at −10° C. under nitrogen. After stirring at room temperature for 30 minutes, isatoic anhydride (3.0 g, 18.4 mmol) was added, and the reaction was heated at 115° C. for 2.5 hours. The reaction was cooled to room temperature, then poured into ice water (500 mL) and acidified to pH 2 with 2M HCl. The resultant precipitate was collected by filtration to give crude methyl 4-hydroxy-2-oxo-1,2-dihydroquinoline-3-carboxylate (2.89 g, 72%), which was used without further purification. $^1$H NMR (400 MHz, DMSO-d$_6$) δ 3.86 (s, 3H), 7.23 (m, 2H), 7.63 (m, 1H), 7.94 (dd, J=0.8, 8.0 Hz, 1H), 11.55 (s, 1H), 13.33 (s, 1H). MS 220 (MH$^+$).

Example 71

4-Amino-2-oxo-1,2-dihydroquinoline-3-carbonitrile

200

4-chloro-2-oxo-1,2-dihydroquinoline-3-carbonitrile (example 72) (0.66 g, 3.23 mmol) was suspended in DMF (7 mL), and 4-methoxybenzylamine (0.94 mL, 7.26 mmol) was added. The reaction was heated at 100° C. for 1 hour and the DMF was removed under vacuum. The residue was dissolved in TFA (6 mL) and stirred at room temperature for 30 minutes and dichloromethane (10 mL) was added. The solid product that formed was collected, suspended in water and the solution stirred overnight. The solid was collected by filtration to give 4-amino-2-oxo-1,2-dihydroquinoline-3-carbonitrile (0.150 g, 25%) as a white solid. M.p.: >250° C. $^1$H NMR (400

MHz, DMSO-$d_6$) δ 7.19 (m, 2H), 7.57 (m, 1H), 7.88 (bs, 2H), 8.12 (d, J=7.6 Hz, 1H), 11.23 (s, 1H). MS 186 (MH$^+$).

Example 72

4-chloro-2-oxo-1,2-dihydroquinoline-3-carbonitrile

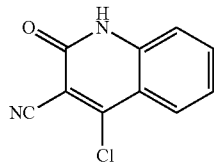

2,4-dichloroquinoline-3-carbonitrile (Example 72a) (0.95 g, 4.26 mmol) and ammonium acetate (0.36 g, 4.67 mmol) were heated in acetic acid (20 mL) at 140° C. for 4 hours, then cooled to room temperature. The reaction was poured into ice water (400 mL), and the resultant precipitate was collected by filtration to give 4-chloro-2-oxo-1,2-dihydroquinoline-3-carbonitrile (0.668 g, 77%) as a light yellow solid. M.p.: >250° C. $^1$H NMR (400 MHz, DMSO-$d_6$) δ 7.42 (m, 2H), 7.79 (m, 1H), 7.96 (d, J=8.4 Hz, 1H), 12.72 (s, 1H). MS 205 (MH$^+$).

Example 72a 2,4-dichloroquinoline-3-carbonitrile

N-cyclohexyl-4-hydroxy-2-oxo-1,2-dihydroquinoline-3-carboxamide (Example 73) (1.18 g, 4.12 mmol) was dissolved in phosphorus oxychloride (15 mL) and triethylamine (1.72 mL, 12.4 mmol) was slowly added. The reaction was heated at 120° C. for 7 hours, then cooled to room temperature and poured carefully into ice water (300 mL). The resultant precipitate was collected by filtration to give 2,4-dichloroquinoline-3-carbonitrile (0.848 g, 92%), which was used without further purification. MS 223 (MH$^+$).

Example 73

N-cyclohexyl-4-hydroxy-2-oxo-1,2-dihydroquinoline-3-carboxamide

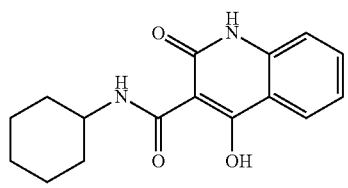

Methyl 4-hydroxy-2-oxo-1,2-dihydroquinoline-3-carboxylate (Example 70) (2.70 g, 12.3 mmol) was suspended in toluene (27 mL), and cyclohexylamine (1.40 g, 14.1 mmol) was added. The reaction was heated at 115° C. for 5 hours, then cooled to room temperature. Diethyl ether (50 mL) was added, and the resultant precipitate was collected by filtration to give N-cyclohexyl-4-hydroxy-2-oxo-1,2-dihydroquinoline-3-carboxamide (1.22 g, 35%) as an off white solid. M.p.: 221° C. $^1$H NMR (400 MHz, DMSO-$d_6$) δ 1.37 (m, 4H), 1.55 (m, 1H), 1.68 (m, 2H), 1.88 (m, 2H), 3.86 (m, 1H), 7.28 (t, J=8.0 Hz, 1H), 7.36 (d, J=8.0 Hz, 1H), 7.68 (t, J=7.6 Hz, 1H), 7.95 (d, J=8.0 Hz, 1H), 10.35 (d, J=7.6 Hz, 1H), 11.83 (bs, 1H). MS 287 (MH$^+$).

Example 74

4-amino-2-oxo-1,2-dihydroquinoline-3-carboxamide

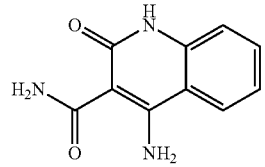

N,N-bis(4-methoxybenzyl)-4-(4-methoxybenzylamino)-2-oxo-2-dihydroquinoline-3-carboxamide (Example 74a) (2.0 g, 3.55 mmol) was dissolved in TFA (15 mL) and the solution was stirred at room temperature for 6 hours. The TFA was removed under vacuum, and the resultant solid was stirred in water overnight, then collected by filtration to give 1.8 grams of crude final product. $^1$H NMR (400 MHz, DMSO-$d_6$) δ 7.18 (m, 2H), 7.25 (d, J=7.2 Hz, 1H), 7.56 (t, J=8.0 Hz, 1H), 8.09 (d, J=7.6 Hz, 2H), 9.83 (d, J=4.8 Hz, 1H), 10.85 (bs, 1H), 11.12 (s, 1H). MS 204 (MH$^+$).

Example 74a

N,N-bis(4-methoxybenzyl)-4-(4-methoxybenzylamino)-2-oxo-1,2-dihydroquinoline-3-carboxamide 4-chloro-N,N-bis(4-methoxybenzyl)-2-oxo-1,2-dihydroquinoline-3-carboxamide (Example 74b) (4.25 g, 9.18 mmol) was dissolved in DMF (20 mL), and 4-methoxybenzylamine (2.68 mL, 20.6 mmol) was added. The reaction was heated at 100° C. for 1.5 hours, then cooled to room temperature and poured into ice water (300 mL). The resultant precipitate was collected by filtration and further chromatographed on silica gel (0% to 20% MeOH in dichloromethane) to give crude N,N-bis(4-methoxybenzyl)-4-(4-methoxybenzylamino)-2-oxo-1,2-dihydroquinoline-3-carboxamide (3.65 g, 71%), which was used without further purification. MS 564 (MH$^+$).

Example 74b 4-chloro-N,N-bis(4-methoxybenzyl)-2-oxo-1,2-dihydroquinoline-3-carboxamide Triethylamine (5.73 mL, 41.2 mmol) was added to phosphorus oxychloride (60 mL), followed by 4-hydroxy-N,N-bis(4-methoxybenzyl)-2-oxo-1,2-dihydroquinoline-3-carboxamide (Example 74c) (6.11 g, 13.7 mmol). The reaction was heated at 65° C. for 4 hours, then cooled to room temperature and carefully poured into ice water (1200 mL). The solution was extracted dichloromethane (2×200 mL. The organic layers were combined and washed with water, dried over MgSO$_4$, filtered and evaporated. The residue was dissolved in dichloromethane (18 mL) and poured into 200 mL of 30% hexanes in diethyl ether. The resultant precipitate was collected by filtration to give crude 4-chloro-N,N-bis(4-methoxybenzyl)-2-oxo-1,2-dihydroquinoline-3-carboxamide (4.25 g, 67%) which was used without further purification. MS 463 (MH$^+$).

Example 74c

4-Hydroxy-N,N-bis(4-methoxybenzyl)-2-oxo-1,2-dihydroquinoline-3-carboxamide

Ethyl 4-hydroxy-2-oxo-1,2-dihydroquinoline-3-carboxylate (Example 67) (3.58 g, 15.4 mmol) and bis(4-methoxybenzyl)amine (4.54 g, 17.6 mmol) were suspended in toluene (36 mL) and heated at 115° C. for 5 hours, then cooled to room temperature. Diethyl ether was added (50 mL), and the resultant precipitate was collected by filtration to give crude 4-hydroxy-N,N-bis(4-methoxybenzyl)-2-oxo-1,2-dihydroquinoline-3-carboxamide (6.45 g, 95%) which was used without further purification.

Example 75

4-Amino-6,7-dihydro-1H-cyclopenta[d]pyrimidin-2(5H)-one

206

A solution of N-(2-cyanocyclopent-1-enylcarbamoyl)benzamide (example 75a) (500 mg, 1.96 mmol) and NaOH (2 N, 2.7 mL) in EtOH (20 mL) was stirred at 100° C. under nitrogen for 2 hours. After cooling to room temperature, the clear reaction solution was filtered and the filtrate was carefully neutralized with 10% AcOH with vigorous stirring at 0° C. The resultant precipitate was collected by filtration, washed with warm water and then 20% EtOH in water to give the final product 4-amino-6,7-dihydro-1H-cyclopenta[d]pyrimidin-2(5H)-one (200 mg, 68%) as a white solid. $^1$H NMR (400 MHz, DMSO-$d_6$) δ 10.57 (brs, 1H), 6.93 (brs, 1H), 6.65 (brs, 1H), 2.56 (t, J=7.2 Hz, 2H), 2.43 (t, J=7.6 Hz, 2H) 1.96-1.89 (m, 2H). MS 152 (MH$^+$).

Example 75a

N-(2-cyanocyclopent-1-enylcarbamoyl)benzamide

To a solution of 2-aminocyclopent-1-enecarbonitrile (400 mg, 3.7 mmol) in 1,4-dioxane (20 mL) was added benzoyl isocyanate (545 g, 3.7 mmol). The reaction mixture was then stirred at room temperature under nitrogen overnight. The precipitate was collected by filtration, washed with 1,4-dioxane, and dried to give N-(2-cyanocyclopent-1-enylcarbamoyl)benzamide (720 mg, 76%) as a white solid. $^1$H NMR (400 MHz, CDCl$_3$) δ 11.33 (s, 1H), 11.22 (brs, 1H), 7.99-7.97 (m, 2H), 7.67-7.63 (m, 1H), 7.54-7.51 (m, 2H), 3.04-3.0 (m, 2H), 2.51-2.47 (m, 2H) 1.95-1.90 (m, 2H). MS 256 (MH$^+$).

Example 76

4-amino-6,7,8,9-tetrahydro-1H-cyclohepta[d]pyrimidin-2(5H)-one

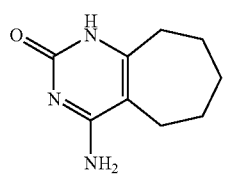

208

Prepared as in example 75 from (Z)—N-(2-cyanocyclohept-1-enylcarbamoyl)benzamide (Example 76a). $^1$H NMR (400 MHz, DMSO-$d_6$) δ 10.29 (brs, 1H), 6.72 (brs, 2H), 2.49-2.46 (m, 2H), 2.38-2.36 (m, 2H) 1.72-1.66 (m, 2H), 1.52-1.48 (m, 2H) 1.41-1.36 (m, 2H). MS 180 (MH$^+$).

Example 76a

(Z)—N-(2-cyanocyclohept-1-enylcarbamoyl)benzamide

Prepared as in Example 75a from (Z)-2-aminocyclohept-1-enecarbonitrile and benzoyl isocyanate as a white solid. MS 284 (MH$^+$).

Example 77

6-Fluoro-1H-benzo[c][1,2,6]thiadiazin-4-amine-2,2-dioxide

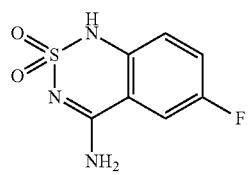

500

A solution of N-(2-cyano-4-fluorophenyl)sulfamide (Example 77a) (211 mg, 1.0 mmol) in EtOH (1 mL) was treated with NaOH (2.0 N, 1.0 mL, 2.0 mmol), and the resultant solution was heated to 100° C. for 0.5 h. After it was cooled down to room temperature the solution was neutralized with 10% AcOH. The resultant precipitate was collected by filtration, washed with water to give 6-fluoro-1H-benzo[c][1,2,6]thiadiazin-4-amine4-2,2-dioxide as an off-white solid. $^1$H NMR (400 MHz, DMSO-$d_6$) δ 7.01-7.05 (dd, J=8.8 Hz, 5.2 Hz, 1H), 7.45-7.5 (m, 1H), 7.80-7.83 (dd, J=9.6 Hz, 2.4 Hz, 1H), 8.24 (s, 1H), 11.03 (s, 1H).

Example 77a

N-(2-Cyano-4-fluorophenyl)sulfamide

A solution of 2-amino-5-fluorobenzonitrile (136 mg, 1 mmol) and sulfamoyl chloride (114 mg, 1 mmol) in DMA (2 mL) was stirred at room temperature for 2 hours. The reaction was purified by Varian HPLC (10% Acetonitrile/Water) to give N-(2-Cyano-4-fluorophenyl)sulfamide as a pale-white solid. $^1$H NMR (400 MHz, DMSO-d$_6$) 7.18 (m, 2H), 7.56-7.60 (dd J=8.8 Hz, 2.8 Hz 2H), 9.44 (s, 1H).

Example 78

6-Chloro-1H-benzo[c][1,2,6]thiadiazin-4-amine-2,2-dioxide

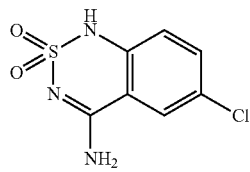

501

Prepared as in Example 77 from N-(2-cyano-4-chlorophenyl)sulfamide (Example 78a). $^1$H NMR (400 MHz, DMSO-d$_6$) δ 7.00-7.03 (d, J=8.8 Hz, 1H), 7.59-7.62 (dd, J=8.8 Hz, 4 Hz, 1H), 8.05-8.06 (d, J=2.4 Hz, 1H), 8.27-8.33 (d, J=25 Hz, 1H), 11.19 (s, 1H).

Example 78a

N-(2-cyano-4-chlorophenyl)sulfamide

Prepared as in Example 77a from 2-amino-5-chlorobenzonitrile and sulfamoyl chloride. $^1$H NMR (400 MHz, DMSO-d$_6$) 7.3 (S, 2H), 7.54-7.56 (d J=9.2 Hz, 1H). 7.74-7.77 (dd J=8.4 Hz, 2 Hz, 1H), 9.67 (s, 1H).

Example 79

5-Chloro-1H-benzo[c][1,2,6]thiadiazin-4-amine-2,2-dioxide

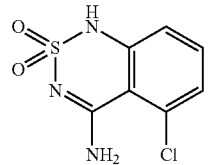

502

Prepared as in Example 77 from 5-chloro-(2-Cyano-3-chlorophenyl)sulfamide (Example 79a). $^1$H NMR (400 MHz, DMSO-d$_6$) δ 7.00-7.03 (m, 1H), 7.20-7.23 (dd, J=8.4 Hz, 1.2 Hz, 1H), 7.48-7.52 (m, 1H), 7.75 (s, 1H), 8.61 (s, 1H), 11.22 (s, 1H).

Example 79a

N-(2-Cyano-3-chlorophenyl)sulfamide

Prepared as in Example 77a from 2-amino-6-chlorobenzonitrile and sulfamoyl chloride.

Example 80

5-Fluoro-1H-benzo[c][1,2,6]thiadiazin-4-amine-2,2-dioxide

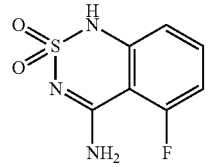

503

Prepared as in Example 77 from N-(2-Cyano-3-fluorophenyl)sulfamide (Example 80a). $^1$H NMR (400 MHz, DMSO-d$_6$) δ 6.84-6.97 (m, 2H), 7.53-7.57 (m, 1H), 7.59 (s, 1H), 8.42 (s, 1H), 11.29 (s, 1H).

Example 80a

N-(2-Cyano-3-fluorophenyl)sulfamide

Prepared as in Example 77a from 2-amino-6-fluorobenzonitrile and sulfamoyl chloride Example 81

6,7-Dimethoxy-1H-benzo[c][1,2,6]thiadiazin-4-amine-2,2-dioxide

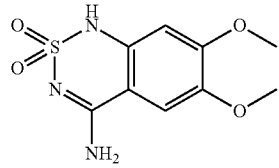

504

Prepared as in Example 77 from N-(2-Cyano-4,5-dimethoxyphenyl)sulfamide (Example 81a). $^1$H NMR (400 MHz, DMSO-d$_6$) δ 3.75-3.79 (d, J=14.4, 6H), 6.48 (s, 1H), 7.38 (s, 1H), 7.89 (b, 1H), 8.04 (b, 1H), 0.64 (s, 1H).

Example 81a

N-(2-Cyano-4,5-dimethoxyphenyl)sulfamide

Prepared as in Example 77a from 2-amino-4,5-dimethoxybenzonitrile and sulfamoyl chloride. $^1$H NMR (400 MHz, DMSO-d$_6$) δ 3.77-3.80 (d, J=14.8, 6H), 7.05 (s, 1H), 7.06 (s, 1H), 7.29 (s, 1H), 9.15 (s, 1H).

Example 82

7-Trifluoromethyl-1H-benzo[c][,6]thiadiazin-4-amine-2,2-dioxide

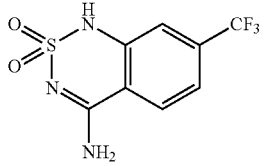

505

Prepared as in Example 77 from N-(2-Cyano-5-trifluoromethylphenyl)sulfamide (Example 82a). ¹H NMR (400 MHz, DMSO-d₆) δ 7.28 (s, 1H), 7.43-7.45 (dd, J=8.8 Hz, 1.6 Hz, 1H), 8.14-8.16 (d, J=7.6 Hz, 1H), 8.41-8.52 (b, 2H), 11.40 (s, 1H).

Example 82a

N-(2-Cyano-5-trifluoromethylphenyl)sulfamide

Prepared as in Example 77a from 2-amino-4-trifluoromethylbenzonitrile and sulfamoyl chloride. ¹H NMR (400 MHz, DMSO-d₆) δ 7.53 (s, 1H), 7.74-7.76 (d, J=8.4 Hz, 1H), 8.01-8.03 (dd, J=8.4 Hz, 1.6 Hz, 1H), 8.23 (s, 1H), 10.16 (b, 1H).

Example 83

6-Phenyl-1H-benzo[c][1,2,6]thiadiazin-4-amine-2,2-dioxide

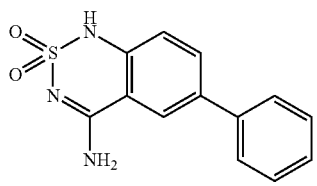

506

Prepared as in Example 77 from N-(2-Cyano-4-phenylphenyl)sulfamide (Example 83a). ¹H NMR (400 MHz, DMSO-d₆) δ 6.72-6.70 (d, J=8 Hz 1H), 6.97-7.0 (m, 1H), 7.08-7.12 (m, 2H), 7.34-7.36 (m, 2H), 7.50-7.53 (dd, J=8.4 Hz, 1.6 Hz, 1H), 7.83 (b, 1H), 7.87 (s, 1H), 8.07 (b, 1H) 10.75 (s, 1H).

Example 83a

N-(2-Cyano-4-phenylphenyl)sulfamide

In a 2 mL microwave vial, phenyl boronic acid (75 mg, 0.6 mmol), N-(2-cyano-4-bromophenyl)sulfamide (Example 83b) (137 mg, 0.5 mmol), and potassium carbonate (400 mg, 1.5 mmol) were dissolved in DME/Water mixture (1.5 mL, DME/Water 4:1). The solution was degassed by bubbling N₂ gas into the reaction solution for 5 minutes and Palladium tetrakis triphenylphospine (25 mg, 0.025 mmol) was added. The reaction was placed in a microwave reactor for 5 minutes at 150° C. The crude reaction was dissolved in water and washed with ethyl acetate. The aqueous solution was evaporated under vacuum to give N-(2-Cyano-4-phenylphenyl)sulfamide.

Example 83b

N-(2-cyano-4-bromolphenyl)sulfamide

Prepared as in Example 77a from 2-amino-5-bromobenzonitrile and sulfamoyl chloride. ¹H NMR (400 MHz, DMSO-d₆) δ 7.31 (s, 2H), 7.48-7.50 (d, J=8 Hz, 1H), 7.85-7.88 (dd, J=9.3 Hz, 1.2 Hz, 1H), 8.05-8.06 (d, J=2.4 Hz, 1H), 9.67 (s, 1H).

Example 84

6-(E)-prop-1-enyl-1H-benzo[c][,6]thiadiazin-4-amine-2,2-dioxide

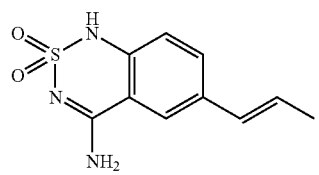

507

Prepared as in Example 77 from N-(2-cyano-4-(E)-prop-1-enylphenyl)sulfamide (Example 84a). ¹H NMR (400 MHz, DMSO-d₆) δ 1.83-1.82 (d, J=5.6 Hz 3H), 6.29-6.25 (m, 2H), 6.85-6.87 (d, J=8.4 Hz, 1H), 7.5-7.53 (dd, J=8.4 Hz, 1.6 Hz, 1H), 7.86 (s, 1H), 7.96 (b, 2H), 10.95 (b, 1H).

Example 84a

N-(2-Cyano-4-(E)-prop-1-enylphenyl)sulfamide

Prepared as in Example 77a from N-(2-cyano-4-bromophenyl)sulfamide (Example 83b) and (E)-prop-1-enylboronic acid.

Example 85

6-(2-methylprop-1-enyl)-1H-benzo[c][1,2,6]thiadiazin-4-amine-2,2-dioxide

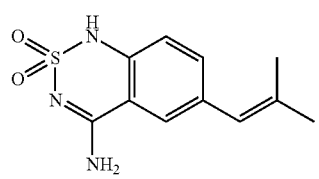

508

Prepared as in Example 77 from N-(2-Cyano-4-(2-methylprop-1-enyl)phenyl)sulfamide (Example 85a). ¹H NMR (400 MHz, DMSO-d₆) δ 1.8-1.85 (dd, J=22.4 Hz, 1.2 Hz, 6H), 6.18 (s, 1H), 6.84-6.86 (d, J=8.4 Hz, 1H), 7.31-7.33 (d, J=8.4 Hz, 1H), 7.66 (s, 1H), 7.78 (b, 2H), 10.91 (b, 1H).

Example 85a

N-(2-Cyano-4-(2-methylprop-1-enyl)phenyl)sulfamide

Prepared as in Example 77a from N-(2-cyano-4-bromophenyl)sulfamide (Example 83b) and 2-methylprop-1-enylboronic acid.

Example 86

6-Trifluoromethyl-1H-benzo[c][,6]thiadiazin-4-amine-2,2-dioxide

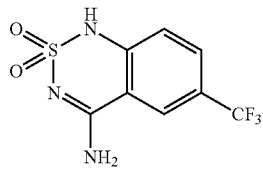

509

Prepared as in Example 77 from N-(2-cyano-4-trifluorophenyl)sulfamide (Example 86a). $^1$H NMR (400 MHz, DMSO-$d_6$) δ 7.14-7.16 (d, J=8.8 Hz, 1H), 7.85-7.88 (dd, J=8.8 Hz, 1.6 Hz, 1H), 8.37-8.39 (d, J=9.6 Hz, 1H), 8.52 (b, 2H), 11.56 (s, 1H).

Example 86a

N-(2-Cyano-4-trifluoromethylphenyl)sulfamide

Prepared as in Example 77a from 2-amino-5-(trifluoromethyl)benzonitrile (Example 86b) and sulfamoyl chloride. $^1$H NMR (400 MHz, DMSO-$d_6$) δ 7.53 (s, 2H), 7.74-7.76 (d, J=8.4 Hz, 1H), 8.01-8.03 (dd, J=8.4 Hz, 1.6 Hz, 1H), 8.23-8.233 (d, J=1.2 Hz, 1H), 10.16 (b, 1H).

Example 86b

2-Amino-5-(trifluoromethyl)benzonitrile

In a 20 mL microwave vial, 2-bromo-4-(trifluoromethyl)aniline (238 mg, 1 mmol) and copper cyanide (90 mg, 1 mmol) were dissolved in N-methylpyrrolidone (NMP) (10 mL). The reaction was placed in a microwave reactor for 5 minutes at 200° C. The crude was dissolved in ethyl acetate and the precipitate was removed by filtration. The clear solution was washed with water. The organic layer was collected, dried over sodium sulfate, and evaporated under vacuum. The residue was purified by Varia HPLC (10% acetonitrile/water) to give the title compound.

Example 87

6-Isopropyl-1H-benzo[c][,6]thiadiazin-4-amine-2,2-dioxide

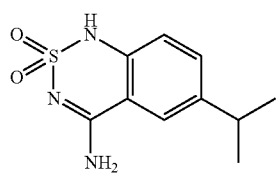

510

Prepared as in Example 77 from N-(2-cyano-4-isopropylphenyl)sulfamide (Example 87a). $^1$H NMR (400 MHz, DMSO-$d_6$) δ 1.18-1.2 (d, J=6.4 Hz, 6H), 2.85 (m, 1H), 6.91-6.93 (d, J=8.8 Hz, 1H), 7.42-7.45 (dd, J=8.8 Hz, 2 Hz 1H), 7.768-7.773 (d, J=2 Hz, 1H), 813 (b, 2H), 10.8 (s, 1H).

Example 87a

N-(2-Cyano-4-isopropylphenyl)sulfamide

Prepared as in Example 77a from 2-Amino-5-isopropylbenzonitrile (Example 87b) and sulfamoyl chloride.

Example 87b

2-Amino-5-isopropylbenzonitrile

Prepared as in Example 86b from 2-bromo-4-isopropylaniline.

Example 88

6-Isobutyl-1H-benzo[c][1,2,6]thiadiazin-4-amine-2,2-dioxide

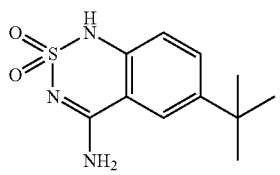

511

Prepared as in Example 77 from N-(2-cyano-4-isobutylphenyl)sulfamide (Example 88a). $^1$H NMR (400 MHz, DMSO-$d_6$) δ 1.27 (s, 9H), 6.92-6.94 (d, J=8.4 Hz, 1H), 7.58-7.61 (dd, J=8.8 Hz, 2.4 Hz 1H), 7.84-7.85 (d, J=2.4 Hz, 1H), 8.06 (b, 1H), 8.33 (b, 1H), 10.8 (s, 1H).

Example 88a

N-(2-Cyano-4-isobutylphenyl)sulfamide

Prepared as in Example 77a from 2-Amino-5-isobutylbenzonitrile (Example 88b) and sulfamoyl chloride.

Example 88b

2-Amino-5-isobutylbenzonitrile

Prepared as in Example 86b from 2-bromo-4-isobutylaniline.

Example 89

6-Methyl-1H-benzo[c][,6]thiadiazin-4-amine-2,2-dioxide

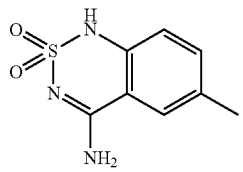

512

Prepared as in Example 77 from N-(2-cyano-4-methylphenyl)sulfamide (Example 89a). MS 212 (MH$^+$).

Example 89a

N-(2-cyano-4-methylphenyl)sulfamide

Prepared as in Example 77a from 2-amino-5-methylbenzonitrile (Example 14b) and sulfamoyl chloride.

Example 90

N⁵-isopropyl-1H-benzo[c][1,2,6]thiadiazine-4,5-diamine-2,2-dioxide

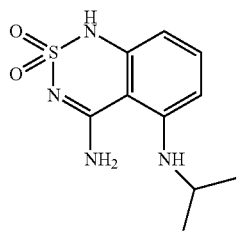

A solution of 2-amino-6-(isopropylamino)benzonitrile sulfamide (Example 90a) (0.14 g, 0.54 mmol) and NaOH (2 N, 0.54 mL) in EtOH (3 mL) was stirred at 90° C. under nitrogen for 0.5 hour. The reaction mixture was cooled to room temperature, and concentrated under vacuum. H₂O (1 mL) was added and the reaction mixture was neutralized to pH~3 with 10% AcOH. The resultant precipitate was extracted with EtOAc, and after evaporation of solvents the residue was purified by preparative thin layer chromatography using a DCM/EtOAc (4:1) solution as eluant, to give N⁵-isopropyl-1H-benzo[c][1,2,6]thiadiazine-4,5-diamine-2,2-dioxide (0.02 g). ¹H NMR (400 MHz, DMSO-d₆) δ 1.11 (d, J=6.4 Hz, 6H), 1.84 (bs, 1H), 5.24 (bs, NH), 6.22-6.19 (m, 2H, NH), 7.09 (t, J=8.0 Hz, 1H), 7.48 (bs, 2H). MS 255 (MH⁺).

Example 90a

2-amino-6-(isopropylamino)benzonitrile sulfamide

To a solution of 2-amino-6-(isopropylamino)benzonitrile (Example 90b) (0.09 g, 0.54 mmol) in DMA (3 mL) was added sulfamoyl chloride (0.19 g, 1.62 mmol). The reaction mixture was stirred at room temperature under nitrogen for 2 hours, diluted with H₂O (5 mL) and extracted with EtOAc. Solvents of the combined organic phases were evaporated and the residue was purified by preparative thin layer chromatography using a Hexane/EtOAc (3:2) solution as eluant, to give 2-amino-6-(isopropylamino)benzonitrile sulfamide (0.14 g). MS 255 (MH⁺).

Example 90b

2-amino-6-(isopropylamino)benzonitrile

To a solution of 2-(isopropylamino)-6-nitrobenzonitrile (Example 90c) (0.21 g, 1.02 mmol) in MeOH (9 mL) was added concentrated HCl (2 mL). Then Fe (0.17 g, 3.07 mmol) was added portionwise, and the reaction mixture was refluxed at 90° C. for 15 minutes. After cooling to room temperature, dilution with H₂O (50 mL) and extraction with DCM (3×50 mL), the combined organic phases were washed with brine, dried over MgSO₄ and the solvents were evaporated to give 2-amino-6-(isopropylamino)benzonitrile (0.19 g, 100%) as a brown oil which was used in the next step without any further purification. MS 176 (MH⁺).

Example 90c

2-(isopropylamino)-6-nitrobenzonitrile

To a solution of 2,6-dinitrobenzonitrile (0.58 g, 3.00 mmol) in DMF (6 mL) was added isopropylamine (0.71 g, 12.00 mmol) and the reaction mixture was stirred at 50° C. under nitrogen for ten minutes. After cooling to room temperature, dilution with H₂O and extraction with EtOAc, solvents of the combined organic phases were evaporated and the residue was purified by flash chromatography (Biotage system, 80 g silicagel column) using a Hexane/EtOAc (3:2) solution as eluant, to give 2-(isopropylamino)-6-nitrobenzonitrile (0.22 g, 35%). ¹H NMR (400 MHz, DMSO-d₆) δ 1.20 (d, J=6.4 Hz, 6H), 3.85-3.80 (m, 1H), 5.94 (d, J=8.0 Hz, NH), 7.26 (d, J=9.0 Hz, 1H), 7.42 (d, J=9.0 Hz, 1H), 7.60 (t, J=8.8 Hz, 1H).

Example 91

6-methyl-1H-thieno[3,2-c][,6]thiadiazin-4-amine-2,2-dioxide

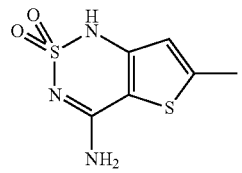

A solution of 3-amino-5-methylthiophene-2-carbonitrile (250 mg, 1.0 eq., 1.81 mmol) and sulfamoyl chloride (2.71 mmol, 1.5 eq., 314 mg) in DMA (5 mL) was stirred at room temperature overnight. Water (30 mL) and NaOH (1.5 eq., 10 N, 2.71 mmol, 271 μL) were added and the mixture was frozen in a dry ice/acetone bath and the volatiles were removed on the lyophilizer. The resulting solid was washed with water and then suspended in EtOH (25 mL, 200 proof). To this suspension was added NaOH (1 N, 2.5 eq., 4.52 mmol, 4.52 mL) and the mixture heated to reflux for 45 minutes. The reaction mixture was cooled to room temperature and quenched with HCl (1 N, 2.5 eq., 4.52 mmol, 4.52 mL). The pH was adjusted to ~1-2 with 1 N HCl and the volatiles removed on a rotary evaporator. The resulting solid was suspended in water (10 mL), stirred, filtered off, and washed with water. The crude product was dried in a vacuum oven to give 6-methyl-1H-thieno[3,2-c][1,2,6]thiadiazin-4-amine-2,2-dioxide (257 mg) as an off-white powder ¹H NMR (400 MHz, DMSO-d₆) δ 2.46 (d, J=0.8 Hz, 3H), 6.53 (q, J=0.8 Hz, 1H), 7.75 (br. s, 2H), 11.34 (s, 1H). ¹H NMR (400 MHz, CD₃OD) δ 2.52 (d, J=0.8 Hz, 3H), 6.55 (q, J=0.8 Hz, 1H). MS 218 (MH⁺).

Example 92

5-cyclopropyl-1H-benzo[c][1,2,6]thiadiazin-4-amine-2,2-dioxide

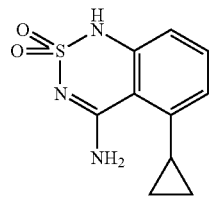

515

A solution of 2-amino-6-cyclopropylbenzonitrile (Example 92a) (1.0 eq., 626 µmol, 99 mg) and sulfamoyl chloride (1.5 eq., 939 µmol, 109 mg) in DMA (1 mL) was stirred in a scintillation vial at room temperature. After 2 hours, NaOH (1.5 eq., 939 µmol, 1N, 939 µL) and water (18 mL) were added and the resulting precipitated product stirred overnight at room temperature. The precipitate was filtered off and washed with water (3×5 mL). The wet precipitate was dissolved in EtOH (5 mL, 200 proof) and NaOH (2.5 eq., 1565 µmol, 1N, 1565 µL) was added. The reaction was heated to 80° C. with stirring overnight. The reaction mixture was cooled to room temperature and HCl (2.5 eq., 1565 µmol, 1N, 1565 µL) was added to the reaction vial. The ethanol and most of the water was removed on the rotary evaporator. The resulting precipitate was suspended in water (5 mL), stirred, filtered off, and washed with water (20 mL). The product was dried in a vacuum oven to give 5-cyclopropyl-1H-benzo[c][1,2,6] thiadiazin-4-amine-2,2-dioxide (41 mg, 28%) as an off-white solid. $^1$H NMR (400 MHz, DMSO-$d_6$) δ 0.71 (m, 2H), 1.04 (m, 2H), 2.401 (m, 1H), 6.85 (d, J=8 Hz, 2H), 7.37 (t+br. s, J=8 Hz, 2H), 8.40 (br. s, 1H), 10.80 (s, 1H). $^1$H NMR (400 MHz, CD$_3$OD) δ 0.89 (m, 2H), 1.15 (m, 2H), 2.36 (m, 1H), 6.90 (d, J=8 Hz, 1H), 6.97 (d, J=8 Hz, 1H), 7.41 (t, J=8 Hz, 1H). MS 238 (MH$^+$).

Example 92a

2-amino-6-cyclopropylbenzonitrile

A 2-5 mL microwave vial containing 2-amino-6-bromobenzonitrile (1.0 eq., 1.0 mmol, 197 mg), cyclopropylboronic acid (1.3 eq., 1.3 mmol, 112 mg), and K$_3$PO$_4$ (3.5 eq., 3.5 mmol, 743 mg) was flushed with nitrogen. To this vial was added toluene (4 mL, Sure-Seal), water (200 µL), tricyclohexylphosphine (0.018 eq., 18.1 µmol, 88% pure, 20% in hexanes, 32 µL), and palladium (II) acetate (0.05 eq. "Pd," trimer, 0.0167 mmol, 12 mg), all under nitrogen. The reaction vial was flushed with nitrogen, capped with a crimp-top septum, and microwaved for 30 minutes at 130° C. The reaction mixture was cooled to room temperature, partitioned between EtOAc (3 mL) and water (1 mL). The layers were separated, the water layer extracted EtOAc (2×3 mL), the combined organic layers dried over sodium sulfate. The EtOAc was filtered through a 0.45 µm PTFE fit to remove finely divided solids and concentrated on a rotary evaporator. The crude product was purified on silica gel (SiliaPrep 80 g cartridge, gradient elution from 10% EtOAc/hexanes to 40% EtOAc/hexanes, loaded in solution in 1:1 hexanes:DCM). The fractions containing product were concentrated on a rotary evaporator to give 2-amino-6-cyclopropylbenzonitrile (99 mg, 62.7%) as a waxy yellow solid. $^1$H NMR (400 MHz, DMSO-$d_6$) δ 0.668 (m, 2H), 0.979 (m, 2H), 1.978 (m, 1H), 5.882 (br. s, 2H), 6.128 (d, J=8 Hz, 1H), 6.546 (d, J=8 Hz, 1H), 7.129 (t, J=8 Hz, 1H).

Example 93

5,6-[4',5'-dihydronaphtho[1',2'-b]]-1H-thieno[2,3-c] [1,2,6]thiadiazin-4-amine-2,2-dioxide

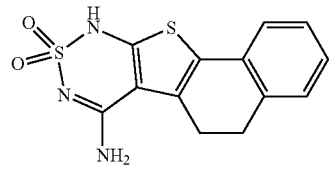

516

A solution of 2-sulfamoylamino-4,5-dihydronaphtho[1,2-b]thiophene-3-carbonitrile (Example 93a) (336 mg, 1.11 mmol) in EtOH (5 mL) was treated with NaOH (2.0 N, 1.1 mL, 2.22 mmol), and the resultant solution was heated to 100° C. and stirred at that temperature for 1.5 h. After it was cooled down to room temperature, the clear solution was filtered, and the filtrate was carefully neutralized with 10% AcOH while it was vigorously stirred at 0° C. The resultant precipitate was collected by filtration, washed with warm water, and 20% EtOH in water to give 105 mg of the title product as an off-white solid in 31% yield. $^1$H NMR (400 MHz, DMSO-$d_6$) δ 2.48 (m, 4H), 5.70 (s, 2H), 6.87-6.89 (d, J=7.6 Hz, 1H), 6.96 (t, 1H), 7.06-7.10 (m, 2H). MS 306 (MH$^+$).

Example 93a

2-sulfamoylamino-4,5-dihydronaphtho[1,2-b] thiophene-3-carbonitrile

To a solution of 2-amino-4,5-dihydronaphtho[1,2-b] thiophene-3-carbonitrile (Example 93b) (250 mg, 1.11 mmol) in dimethylacetamide (5 mL) was added sulfamoyl chloride (385 mg, 3.33 mmol). The reaction mixture was stirred at room temperature under nitrogen for about 1 hr, then it was diluted with water and extracted with EtOAc, the organic layer was washed with brine, dried over Na$_2$SO$_4$, filtered and evaporated to give the crude product which was carried on for next step.

Example 93b

2-amino-4,5-dihydronaphtho[1,2-b]thiophene-3-carbonitrile

A solution of 3,4-dihydronaphthalen-2(1H)-one (2.2 g, 15.05 mmol), malononitrile (994 mg, 15.05 mmol), sulfur (482 mg, 15.05 mmol), and triethylamine (1.52 g, 15.05 mmol) in EtOH (100 mL) was refluxed for 2 hr under nitrogen. The solvent was then removed under reduced pressure and the residue was crystallized from EtOAc/Hexanes to give 2.91 g of the title product as a brown solid in 86% yield. $^1$H NMR (400 MHz, DMSO-d$_6$) δ 2.59 (t, 2H), 2.86 (t, 2H), 6.94 (d, 1H), 7.03 (t, 1H), 7.11-7.16 (m, 2H), 7.48 (s, 2H).

Example 94

5,6-(dihydro-4'H-cyclopenta-1'H)thieno[2,3-c][1,2,6]thiadiazin-4-amine-2,2-dioxide

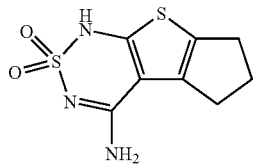

517

Prepared as in Example 93 from 2-sulfamoylamino-5,6-dihydro-4H-cyclopenta[b]thiophene-3-carbonitrile (Example 94a). $^1$H NMR (400 MHz, DMSO-d$_6$) δ 2.15 (m, 2H), 2.53 (m, 2H), 2.68 (m, 2H), 5.39 (s, 2H). MS 244 (MH$^+$).

Example 94a 2-sulfamoylamino-5,6-dihydro-4H-cyclopenta[b]thiophene-3-carbonitrile Prepared as in Example 93a from 2-amino-5,6-dihydro-4H-cyclopenta[b]thiophene-3-carbonitrile (Example 94b). $^1$H NMR (400 MHz, CDCl$_3$) δ 2.41 (m, 2H), 2.82 (m, 2H), 2.89 (m, 2H), 5.46 (s, 1H).

Example 94b 2-amino-5,6-dihydro-4H-cyclopenta[b]thiophene-3-carbonitrile

Prepared as in Example 93b from cyclopentanone. $^1$H NMR (400 MHz, DMSO-d$_6$) δ 2.23 (m, 2H), 2.53 (m, 2H), 2.63 (m, 2H), 7.00 (s, 2H).

Example 95

5-ethyl-6-methyl-1H-thieno[2,3-c][1,2,6]thiadiazin-4-amine-2,2-dioxide

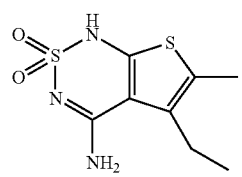

518

Prepared as in Example 93 from 2-sulfamoylamino-4-ethyl-5-methylthiophene-3-carbonitrile (Example 95a). $^1$H NMR (400 MHz, DMSO-d$_6$) δ 1.01 (t, 3H), 2.06 (s, 3H), 2.53 (q, 2H), 5.50 (s, 2H). MS 246 (MH$^+$).

Example 95a 2-sulfamoylamino-4-ethyl-5-methylthiophene-3-carbonitrile

Prepared as in Example 93a from 2-amino-4-ethyl-5-methylthiophene-3-carbonitrile (Example 95b). $^1$H NMR (400 MHz, CDCl$_3$) δ 1.17 (t, 3H), 2.31 (s, 3H), 2.59 (q, 2H), 5.45 (s, 2H).

Example 95b 2-amino-4-ethyl-5-methylthiophene-3-carbonitrile

Prepared as in Example 93b from pentan-3-one. $^1$H NMR (400 MHz, DMSO-d$_6$) δ 1.01 (t, 3H), 2.06 (s, 3H), 2.33 (q, 2H), 6.84 (s, 2H). MS 167 (MH$^+$).

Example 96

5,6-dimethyl-1H-thieno[2,3-c][1,2,6]thiadiazin-4-amine-2,2-dioxide

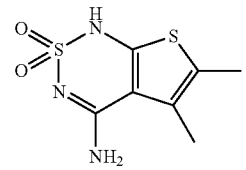

577

Prepared as in Example 93 from 2-sulfamoylamino-4,5-dimethylthiophene-3-carbonitrile (Example 96a). $^1$H NMR (400 MHz, DMSO-d$_6$) δ 2.04 (s, 3H), 2.10 (s, 3H), 5.48 (s, 2H). MS 232 (MH$^+$).

Example 96a 2-sulfamoylamino-4,5-dimethylthiophene-3-carbonitrile

To a solution of 2-amino-4,5-dimethylthiophene-3-carbonitrile (Example 4b) (1.0 g, 6.57 mmol) in 1,4-dioxane (50 mL) was added sulfamide (3.87 g, 40.30 mmol). The reaction mixture was heated to reflux for 24 hr, after cooled to room temperature, the solvent was removed under reduced pressure and the residue was purified by chromatography on silica gel eluting with EtOAc/Hexanes (2:3) to give 300 mg of product as a dark red oil. $^1$H NMR (400 MHz, DMSO-d$_6$) δ 2.09 (3, 3H), 2.26 (s, 3H), 7.32 (s, 2H), 10.17 (s, 1H).

Example 97

(E)-5-(3-Methoxyprop-1-enyl)-1H-benzo[c][1,2,6]thiadiazin-4-amine-2,2-dioxide

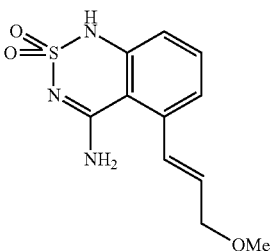

519

A solution of (E)-2-sulfamoylamino-6-(3-methoxyprop-1-enyl)benzonitrile (Example 97a) (139 mg, 0.5 mmol) in EtOH was treated with NaOH (2.0 N, 0.5 mL, 1.0 mmol), and the resultant solution was heated to 100° C., and stirred at that temperature for 4 h. After it was cooled down to room temperature, the clear reaction solution was filtered, and the filtrate was carefully neutralized with 10% AcOH while it was vigorously stirred at 0° C. The resultant precipitate was collected by filtration, washed with warm water, and 20% EtOH in water to give the title product (E)-5-(3-Methoxyprop-1-enyl)-1H-benzo[c][1,2,6]thiadiazin-4-amine-2,2-dioxide (108 mg, 78%) as a white solid. $^1$H NMR (400 MHz, DMSO-$d_6$) δ 3.29 (s, 3H), 4.06 (dd, J=4.8, 1.2 Hz, 2H), 6.26 (dt, J=16.2, 5.0 Hz, 1H), 6.91-6.95 (m, 2H), 6.97 (bs, 1H), 7.16 (d, J=7.2 Hz, 1H), 7.46 (t, J=8.0 Hz, 1H), 8.31 (s, 1H), 10.93 (s, 1H). $^{13}$C NMR (DMSO-$d_6$) δ 58.4, 72.5, 111.6, 117.0, 122.4, 129.0, 132.5, 134.0, 138.1, 143.7, 162.9. MS 268 (MH$^+$).

Example 97a (E)-2-sulfamoylamino-6-(3-methoxyprop-1-enyl)benzonitrile

To a solution of (E)-2-amino-6-(3-methoxyprop-1-enyl)benzonitrile (Example 97b) (188 mg, 1.0 mmol) in DMA was added NH$_2$SO$_2$Cl (347 mg, 3.0 mmol) at 0° C. under nitrogen. The reaction mixture was then stirred at room temperature for 6 hrs, diluted with EtOAc, washed with brine (5×), and dried over Na$_2$SO$_4$. The solvent was evaporated under reduced pressure to give (E)-2-sulfamoylamino-6-(3-methoxyprop-1-enyl)benzonitrile as a pale-yellow solid, which was used in the next step without further purification.

Example 97b (E)-2-amino-6-(3-methoxyprop-1-enyl)benzonitrile

To a solution of 2-amino-6-bromobenzonitrile (1.0 g, 5.0 mmol), (E)-2-(3-methoxypropenyl)-4,4,5,5-tetramethyl-(1,3,2)-dioxaboroane (1.2 g, 6.0 mmol), and K$_2$CO$_3$ (1.38 g, 10.0 mmol) in DME/H$_2$O (4:1, 20 mL) was added Pd(PPh$_3$)$_4$ (289 mg) at room temperature under nitrogen. The reaction mixture was warmed to 85° C. and stirred at that temperature under nitrogen overnight. After it was cooled down to room temperature, the reaction solution was diluted with EtOAc, washed with brine (2×), and dried over Na$_2$SO$_4$. After removal of the solvent, the residue was purified by chromatography on silica gel eluting with 30% EtOAc in hexanes to give the title compound as a pale-yellow solid. $^1$H NMR (400 MHz, CDCl$_3$) δ 3.40 (s, 3H), 4.12 (dd, J=6.0, 1.8 Hz, 2H), 4.42 (s, 2H), 6.42 (dt, J=16.0, 5.8 Hz, 1H), 6.63 (d, J=8.0 Hz, 1H), 6.85 (d, J=16.0 Hz, 1H), 6.93 (d, J=8.0 Hz, 1H), 7.26 (t, J=8.0 Hz, 1H). $^{13}$C NMR (CDCl$_3$) δ 58.2, 72.7, 95.4, 113.6, 115.0, 116.6, 128.5, 130.9, 133.4, 140.3, 150.1. MS 189 (MH$^+$).

Example 98

5-(3-Methylbut-2-en-2-yl)-1H-benzo[c][1,2,6]thiadiazin-4-amine-2,2-dioxide

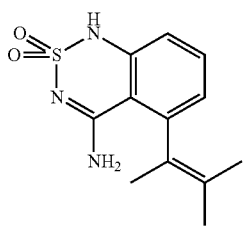

520

Prepared as in Example 97 from 2-amino-6-(3-methylbut-2-en-2-yl)benzonitrile (Example 98a) as a white solid. $^1$H NMR (400 MHz, CDCl$_3$) δ 1.53 (s, 3H), 1.80 (s, 3H), 1.86 (s, 3H), 6.70 (dd, J=7.2, 1.0 Hz, 1H), 6.82 (s, 1H), 6.93 (dd, J=7.2, 1.0 Hz, 1H), 7.46 (t, J=7.2 Hz, 1H), 8.28 (s, 1H), 10.98 (s, 1H). $^{13}$C NMR (DMSO-$d_6$) δ 20.8, 21.4, 22.6, 109.4, 116.8, 124.4, 129.7, 132.0, 134.3, 144.1, 144.6, 162.1. MS 266 (MH$^+$).

Example 98a

2-Amino-6-(3-methylbut-2-en-2-yl)benzonitrile

Prepared as in Example 1a from 2-amino-6-bromobenzonitrile and 3-Methyl-2-buten-2-ylboronic acid as an orange oil. MS 187 (MH$^+$).

Example 99

5-Bromo-1H-benzo[c][1,2,6]thiadiazin-4-amine-2,2-dioxide

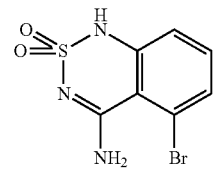

521

Prepared as in Example 97 from 2-amino-6-bromobenzonitrile as a white solid. $^1$H NMR (400 MHz, DMSO-$d_6$) δ 7.03-7.07 (m, 1H), 7.37-7.42 (m, 2H), 7.65 (s, 1H), 8.60 (s, 1H), 11.19 (s, 1H). $^{13}$C NMR (DMSO-$d_6$) δ 113.3, 118.0, 121.0, 129.0, 135.0, 145.5, 161.3. MS 275, 277 (MH$^+$).

Example 100

4H-Naphtho[2,1-c][1,2,6]thiadiazin-1-amine-2,2-dioxide

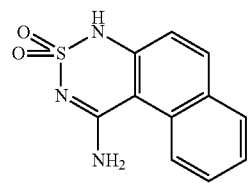

522

Prepared as in Example 97 from 2-amino-1-naphthonitrile as a white solid. $^1$H NMR (400 MHz, DMSO-$d_6$) δ 7.17 (d, J=8.0 Hz, 1H), 7.48 (dt, J=1.2, 8.0 Hz, 1H), 7.63 (dt, f=1.2, 8.0 Hz, 1H), 7.90 (s, 1H), 7.93 (dd, J=1.2, 8.0 Hz, 1H), 8.24 (s, 1H), 8.39 (d, J=8.0 Hz, 1H), 11.42 (s, 1H). $^{13}$C NMR (DMSO-$d_6$) δ 106.3, 118.2, 124.9, 125.4, 129.2, 129.8, 130.0, 130.2, 135.9, 143.7, 163.2. MS 248 (MH$^+$).

Example 101

5,6,7,8-Tetrahydro-1H-benzo[c][1,2,6]thiadiazin-4-amine-2,2-dioxide

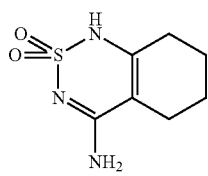

523

Prepared as in Example 97 from 2-aminocyclohex-1-enecarbonitrile (Example 10b) as a pale yellow solid. $^1$H NMR (400 MHz, DMSO-d$_6$) δ 1.54-1.62 (m, 4H), 2.08 (t, J=5.4 Hz, 2H), 2.20 (t, J=5.4 Hz, 2H), 6.94 (s, 1H), 7.41 (s, 1H), 10.53 (s, 1H). $^{13}$C NMR (DMSO-d$_6$) δ 21.6, 22.5, 28.3, 97.6, 150.3, 163.4. MS 202 (MH$^+$).

Example 102

1H-pyrido[2,3-c][1,2,6]thiadiazin-4-amine-2,2-dioxide

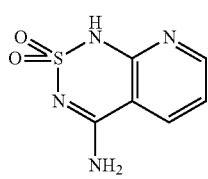

524

A stirred mixture of 2-aminonicotinonitrile (238 mg, 2.0 mmol), sulfamide (192 mg, 2.0 mmol), and 1 mL of DBU was heated at 160° C. under nitrogen overnight. After it was cooled down to room temperature, the reaction mixture was diluted with water, and extracted three times with EtOAc. The aqueous layer was dried down under vacuum, and the residue was purified by chromatography on silica gel eluting with 15% MeOH in dichloromethane to give the title compound as a yellow solid. $^1$H NMR (400 MHz, DMSO-d$_6$) δ 6.87 (t, J=5.6 Hz, 1H), 7.95 (brs, 2H), 8.22 (d, J=5.2 Hz, 1H), 8.39-8.37 (m, 1H), 12.58 (brs, 1H). MS 199 (MH$^+$).

Example 103

6-Bromo-1H-benzo[c][1,2,6]thiadiazin-4-amine

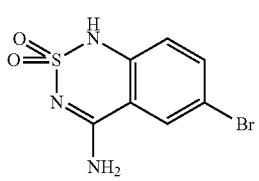

525

Prepared as in Example 97 from 2-amino-5-bromobenzonitrile. $^1$H NMR (400 MHz, DMSO-d$_6$) δ 6.95 (d, J=8.8 Hz, 1H). 7.73-7.70 (m, 1H), 8.17 (d, J=1.6 Hz, 1H), 8.28 (brs, 2H), 11.9 (s, 1H). MS 275, 277 (MH$^+$).

Example 104

5-(Methylthio)-1H-benzo[c][1,2,6]thiadiazin-4-amine-2,2-dioxide

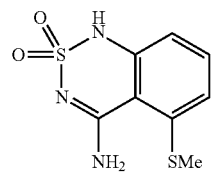

526

Prepared as in Example 97 from 2-sulfamoylamino-6-(methylthio)benzonitrile (Example 104a). $^1$H NMR (400 MHz, DMSO-d$_6$) δ 239 (s, 3H), 6.38-6.36 (m, 1H), 6.47-6.45 (m, 1H), 6.59 (brs, 2H), 6.97-6.93 (m, 1H). MS 244 (MH$^+$).

Example 104a 2-sulfamoylamino-6-(methylthio)benzonitrile

Prepared as in Example 1 from 2-amino-6-(methylthio)benzonitrile (Example 8b) and sulfamoyl chloride. $^1$H NMR (400 MHz, DMSO-d$_6$) δ 2.56 (s, 3H), 7.18 (d, J=8.4 Hz, 1H), 7.26 (s, 2H), 7.33 (d, J=8.0 Hz, 1H), 7.59 (t, J=8.40 Hz, 1H), 9.51 (s, 1H).

Example 104b 2-amino-6-(methylthio)benzonitrile

To a solution of 2-(methylthio)-6-nitrobenzonitrile (Example 104c) (1.5 g, 7.73 mmol) in EtOH (150 ml)/THF (50 ml)/EtOAc (50 ml) was added 200 mg of 10% Pd/C. The reaction mixture was hydrogenated on part shaker overnight. After the filtration, the filtered solution was dried down under vacuum, and the residue was purified by chromatography on silica gel eluting with EtOAc/Hexane to give the title compound (79%). $^1$H NMR (400 MHz, CDCl$_3$) δ 2.51 (s, 3H), 4.47 (s, 2H), 6.53-6.51 (m, 1H), 6.58 (d, J=8.0 Hz, 1H), 7.27-7.21 (m, 1H).

Example 104c 2-(methyl thio)-6-nitrobenzonitrile

To a suspension of 2,6-dinitrobenzonitrile (5.0 g, 25.89 mmol) in 100 mL of anhydrous MeOH was added NaSMe (2.0 g in 100 mL of MeOH) dropwise through addition funnel under nitrogen at 0° C. After the completion of addition, the reaction mixture was stirred at 0° C. for 1 hr. Then 250 mL of water was added to the reaction mixture, the resultant precipitate was collected by filtration and dried in the air to give

Example 105

5,6-(1',2',3',4'-tetrahydro-2',2'-ethylenedioxide-benzo)-1H-thieno[2,3-c][1,2,6]thiadiazin-4-amine-2,2-dioxide

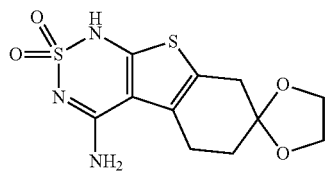

527

Prepared as in Example 97 from 2-amino-5,7-dihydro-4H-spiro[benzo[b]thiophene-6,2'-[1,3]dioxolane]-3-carbonitrile (Example 105a). $^1$H NMR (400 MHz, DMSO-d$_6$) δ 1.80 (t, J=6.0 Hz, 2H), 2.65 (s, 2H), 2.79 (t, J=6.0 Hz, 2H), 3.94-3.91 (m, 4H), 5.99 (brs, 2H). MS 316 (MH$^+$).

Example 105a 2-amino-5,7-dihydro-4H-spiro[benzo[b]thiophene-6,2'-[1,3]dioxolane]-3-carbonitrile A solution of 1,4-dioxaspiro[4.5]decan-8-one (5.0 g, 32.0 mmol), malononitrile (2.11 g, 32.01 mmol), sulfur (1.03 g, 32.0 mmol), and triethylamine (4.5 mL, 32.0 mmol) in EtOH (100 mL) was stirred at room temperature for 1 h under nitrogen. The solvent was then removed under reduced pressure and the residue was treated with EtOAc. The resultant precipitate was collected by filtration and dried in the air to give the title product as a light green solid (44%). $^1$H NMR (400 MHz, DMSO-d$_6$) δ 1.77 (t, J=6.8 Hz, 2H), 2.43 ((t, J=6.4 Hz, 2H), 2.57 (s, 2H), 3.88 (s, 4H), 6.99 (s, 2H). MS 237 (MH$^+$).

Example 106

5,6-(1',2',3',4'-tetrahydro-2'-oxide-benzo)-1H-thieno[2,3-c][1,2,6]thiadiazin-4-amine-2,2-dioxide

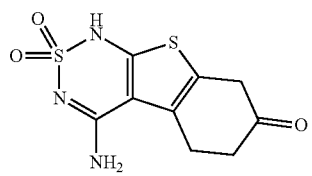

528

A stirred mixture of 5,6-(1',2',3',4'-tetrahydro-2',2'-ethylenedioxide-benzo)-1H-thieno[2,3-c][,6]thiadiazin-4-amine-2,2-dioxide (Example 105) (130 mg, 0.41 mmol), 5 mL of THF and 1 mL of 2 N HCl was refluxed under nitrogen for 2 hrs. After it was cooled down to room temperature, the resultant precipitate was collected by filtration and dried in the air to give the title product as a pink solid. $^1$H NMR (400 MHz, DMSO-d$_6$) δ 2.57 (t, J=6.8 Hz, 2H), 3.10 (t, J=6.4 Hz, 2H), 3.50 (s, 2H), 6.91 (brs, 1H), 7.88 (brs, 1H), 11.81 (brs, 1H). MS 272 (MH$^+$).

Example 107

1,5,6,7-tetrahydrocyclopenta[c][1,2,6]thiadiazin-4-amine-2,2-dioxide

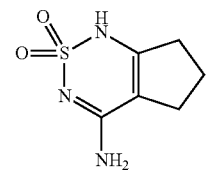

529

A solution of 2-sulfamoylaminocyclopent-1-enecarbonitrile (Example 107a) (108 mg, 0.57 mmol) in EtOH was treated with NaOH (2.0 N, 0.5 mL), and the resultant solution was heated to 100° C. and stirred at that temperature for 4 h. After it was cooled down to room temperature, the reaction solution was carefully neutralized with 2N HCl while it was vigorously stirred at 0° C. The reaction solution was dried down under vacuum, and the residue was purified by chromatography on silica gel eluting with 10% MeOH in dichloromethane to give the title compound. $^1$H NMR (400 MHz, DMSO-d$_6$) 1.69-1.63 (m, 2H), 2.2 (t, J=7.6 Hz, 2H), 2.3 (t, J=6.8 Hz, 2H), 5.12 (s, 2H). MS 188 (MH$^+$).

Example 107a 2-sulfamoylaminocyclopent-1-enecarbonitrile

To a solution of 2-aminocyclopent-1-enecarbonitrile (440 mg, 4.07 mmol) in 10 mL of DMA was added sulfamoyl chloride (941.3 mg, 8.15 mmol), and the resultant mixture was stirred at room temperature under nitrogen for 2 h. Then it was diluted with EtOAc, the organic layer was washed with brine and dried down under vacuum, and the residue was purified by chromatography on silica gel eluting with EtOAc/Hexane to give the title compound. $^1$H NMR (400 MHz, CDCl$_3$) δ 2.04-1.97 (m, 2H), 2.61-2.57 (m, 2H), 2.9-2.86 (m, 2H), 5.66 (s, 2H), 8.04 (s, 1H).

Example 108

5-(Phenylthio)-1H-benzo[c][1,2,6]thiadiazin-4-amine-2,2-dioxide

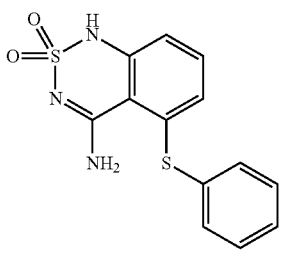

530

Prepared as in Example 97 from 2-sulfamoylamino-6-(Phenylthio)benzonitrile (Example 108a) $^1$H NMR (400 MHz, DMSO-d$_6$) δ 6.43-6.40 (m, 1H), 6.64-6.62 (m, 1H), 6.75 (brs, 2H), 7.01-6.97 (m, 1H), 7.22-7.15 (m, 3H), 7.3-7.26 (m, 2H). MS 306 (MH$^+$)

Example 108a 2-sulfamoylamino-6-(phenylthio)benzonitrile

Prepared as in Example 104a from 2-amino-6-(phenylthio)benzonitrile (Example 108b). $^1$H NMR (400 MHz, DMSO-d$_6$) δ 6.85-6.82 (m, 1H), 7.32 (s, 2H), 7.47-7.42 (m, 6H), 7.53 (t, J=8.0 Hz, 1H), 9.63 (s, 1H).

Example 108b 2-amino-6-(phenylthio)benzonitrile

Prepared as in Example 104b from 2-nitro-6-(phenylthio)benzonitrile (Example 108c). $^1$H NMR (400 MHz, DMSO-d$_6$) δ 6.20 (brs, 2H), 6.32-6.30 (m, 1H), 6.69-6.67 (m, 1H), 7.19 (t, J=8.0 Hz, 1H), 7.4-7.34 (m, 5H).

Example 108c 2-nitro-6-(phenylthio)benzonitrile

To a mixture of 2,6-dinitrobenzonitrile (2.0 g, 10.36 mmol) and K$_2$CO$_3$ (1.43 g, 10.36 mmol) in 5 mL of anhydrous DMF was added PhSH (1.14 ml in 5 mL of DMF) dropwise under nitrogen at 0° C. After the completion of addition, the reaction mixture was stirred at 0° C. for 0.5 hr. Then the reaction mixture was poured into 50 mL of water, the resultant precipitation was collected by filtration, washed with water and dried in the air to give the title product.

Example 109

5-(Methylsulfinyl)-1H-benzo[c][1,2,6]thiadiazin-4-amine-2,2-dioxide

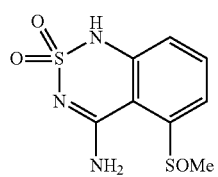

531

Prepared as in Example 107 from 2-sulfamoylamino-6-(methylsulfinyl)benzonitrile (Example 109a) $^1$H NMR (400 MHz, DMSO-d$_6$) δ 2.58 (s, 3H), 6.51 (brs, 2H), 6.78-6.76 (m, 1H), 6.94-6.92 (m, 1H), 7.23-7.19 (m, 1H). MS 260 (MH$^+$)

Example 109a 2-sulfamoylamino-6-(methylsulfinyl)benzonitrile

The mixture of 2-sulfamoylamino-6-(methylthio)benzonitrile (Example 104a) (48 mg, 0.2 mmol) and MCPBA (69 mg, 0.4 mmol) in dichloromethane (16 mL) was heated refluxed overnight. After cooling down, the precipitation was collected by filtration, rinsed with dichloromethane, dried in the air to give the title compound. $^1$H NMR (400 MHz, DMSO-d$_6$) δ 2.83 (s, 3H), 7.35 (brs, 2H), 7.72-6.69 (m, 2H), 7.92 (t, J=8.0 Hz, 1H), 9.87 (brs, 1H).

Example 110

5-(Methylsulfonyl)-1H-benzo[c][1,2,6]thiadiazin-4-amine-2,2-dioxide

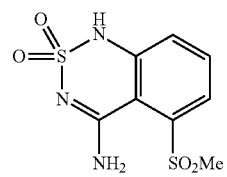

532

Prepared as in Example 107 from 2-sulfamoylamino-6-(methylsulfonyl)benzonitrile (Example 110a). $^1$H NMR (400 MHz, DMSO-d$_6$) δ 3.30 (s, 3H), 6.95-6.93 (m, 1H), 7.01 (bs, 2H), 7.17-7.17 (m, 1H), 7.24-7.21 (m, 1H) MS 276 (MH$^+$)

Example 110a 2-sulfamoylamino-6-(methylsulfonyl)benzonitrile

Prepared as in Example 107a from 2-amino-6-(methylsulfonyl)benzonitrile (Example 109b) $^1$H NMR (400 MHz, DMSO-d$_6$) δ 3.37 (s, 3H), 7.46 (s, 2H), 7.85-7.83 (m, 1H), 7.93-7.91 (m, 2H), 9.92 (s, 1H).

Example 110b 2-amino-6-(methylsulfonyl)benzonitrile

Prepared as in Example 107b from 2-(methylsulfonyl)-6-nitrobenzonitrile (Example 110c). $^1$H NMR (400 MHz, DMSO-d$_6$) δ 3.26 (s, 3H), 6.63 (brs, 2H), 7.15-7.09 (m, 2H), 7.51-7.47 (m, 1H).

Example 110c 2-(methylsulfonyl)-6-nitrobenzonitrile

Prepared as in Example 109a from 2-(methylthio)-6-nitrobenzonitrile (Example 104c) $^1$H NMR (400 MHz, DMSO-d$_6$) δ 3.48 (s, 3H), 8.21 (d, J=7.6 Hz, 1H), 8.49-8.47 (m, 1H), 8.66-8.64 (m, 1H).

Example 111

4-Amino-5-(propyloxy)-1H-benzo[c][1,2,6]thiadiazine-2,2-dioxide

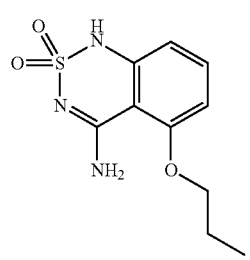

533

To a suspension of 2-sulfamoylamino-6-propoxybenzonitrile (Example 111a) (4.73 g, 18.53 mmol) in ethanol (65 mL), was added aqueous NaOH (2N, 18.6 ml, 37.06 mmol). The resulting clear solution was refluxed for 3 hours under nitrogen. After cooling to room temperature, the resulting solution was filtered, the filtrate was cooled to 0° C. and neutralized with 10% acetic acid. The resulting precipitate was collected by filtration, suspended in 50 ml of ethanol/water (1:1) and warmed to 40° C. for 20 min. The solid was collected by filtration to provide 4-Amino-5-(propyloxy)-1H-benzo[c][1,2,6]thiadiazine-2,2-dioxide (4 g, 85%) as a pale yellow powder. M.p.: 229-230° C. $^1$H NMR (400 MHz, DMSO-d$_6$) δ 0.96 (t, J=7.3 Hz, 3H), 1.81 (sext, J=7.3 Hz, 2H), 4.10 (t, J=6.7 Hz, 2H), 6.60 (d, J=8.6 Hz, 1H), 6.73 (d, J=8.6 Hz, 1H), 7.44 (t, J=8.6 Hz, 1H), 7.81 (br s, 1H), 8.35 (br s, 1H), 10.93 (br s, 1H). $^{13}$C NMR (400 MHz, DMSO-d$_6$) δ 11.07, 22.18, 71.41, 100.93, 105.64, 110.21, 135.53, 145.16, 158.47, 161.10. MS 256 (MH$^+$).

Example 111a

2-Sulfamoylamino-6-propoxybenzonitrile

To a solution of 2-amino-6-propoxybenzonitrile (Example 111b) (4.23 g, 24.01 mmol) in dimethylacetamide (20 mL) under N$_2$ was added sulfamoyl chloride (5.56 g, 48.02 mmol). The reaction mixture was then stirred at room temperature under nitrogen for 4 hours. Upon completion, the reaction was quenched by addition of ice/water (250 mL). The resulting precipitate was collected by filtration, rinsed with water and dried to yield 2-sulfamoylamino-6-propoxybenzonitrile (4.73 g, 77%) as a pale yellow solid. $^1$H NMR (400 MHz, DMSO-d$_6$) δ 1.01 (d, J=7.2 Hz, 3H), 1.76 (sext, J=7.2 Hz, 2H), 4.08 (t, J=6.8 Hz, 2H), 6.96 (d, J=8.5 Hz, 1H), 7.15 (t, J=8.5 Hz, 1H), 7.28 (br s, 2H), 7.57 (d, J=8.5 Hz, 1H), 9.46 (s, 1H). MS 256 (MH$^+$).

Example 111b

2-Amino-6-propoxybenzonitrile

2-Nitro-6-propoxybenzonitrile (Example 111c) (4.95 g, 24.01 mmol) was dissolved in EtOH (50 mL) and THF (15 mL). 10% Pd/C (255 mg, 2.4 mmol) was added, and the reaction was hydrogenated using a Parr apparatus for 12 hours at 40 psi. Upon completion, the reaction was filtered through celite and the filtrate concentrated to provide 2-nitro-6-propoxybenzonitrile (4.3 g, 100%) as a light brown gel. $^1$H NMR (400 MHz, CDCl$_3$) δ 1.05 (d, J=7.4 Hz, 3H), 1.83 (next, J=7.0 Hz, 2H), 3.96 (t, J=7.0 Hz, 2H), 4.38 (br s, 2H), 6.20 (d, J=8.5 Hz, 1H), 6.28 (t, J=8.5 Hz, 1H), 7.19 (d, J=8.5 Hz, 1H).

Example 111c

2-Nitro-6-propoxybenzonitrile

To a solution of 2,6-dinitrobenzonitrile (6 g, 31.07 mmol) in dry DMF (45 mL) at 0° C., was added a solution of sodium (815 mg, 35.42 mmol) in n-propanol (23.5 mL) dropwise over 30 minutes. After compete addition, the reaction mixture was warmed to room temperature and stirred for 2.5 hours. The reaction was poured into an ice/water mixture (250 mL), and the precipitate was collected by filtration and dried to yield 2-nitro-6-propoxybenzonitrile (4.95 g, 77%) as a light brown solid. $^1$H NMR (400 MHz, CDCl$_3$) δ 1.11 (d, J=7.5 Hz, 3H), 1.93 (sext, J=7.5 Hz, 2H), 4.14 (t, J=7.0 Hz, 2H), 7.31 (d, J=8.6 Hz, 1H), 7.69 (t, J=8.6 Hz, 1H), 7.82 (d, J=8.6 Hz, 1H).

Example 112

4-Amino-5-(pentoxy)-1H-benzo[c][1,2,6]thiadiazine-2,2-dioxide

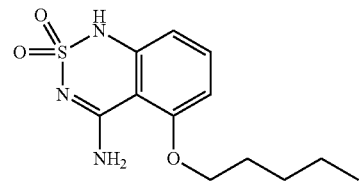

534

Prepared as in Example 111 from 2-sulfamoylamino-6-pentoxybenzonitrile (Example 112a) to provide 4-amino-5-(pentoxy)-1H-benzo[c][,6]thiadiazine-2,2-dioxide (59 mg, 43%). $^1$H NMR (400 MHz, DMSO-d$_6$) δ 0.88 (t, J=7.3 Hz, 3H), 1.35 (m, 4H), 1.80 (quint, J=6.8 Hz, 2H), 4.14 (t, J=6.4 Hz, 2H), 6.59 (d, J=8.2 Hz, 1H), 6.73 (d, J=8.56 Hz, 1H), 7.44 (t, J=8.5 Hz, 1H), 7.81 (br s, 1H), 8.34 (br s, 1H), 10.92 (br s, 1H). MS 284 (MH$^+$).

Example 112a

2-Sulfamoylamino-6-pentoxybenzonitrile

Prepared as in Example 1a from 2-amino-6-pentoxybenzonitrile to provide 2-sulfamoylamino-6-pentoxybenzonitrile.

Example 112b

2-Amino-6-(pentyloxy)benzonitrile

Prepared as in Example 111b from 2-nitro-6-(pentyloxy)benzonitrile to provide 2-Amino-6-(pentyloxy)benzonitrile. MS 205 (MH$^+$).

Example 112c

2-Nitro-6-(pentyloxy)benzonitrile

Prepared as in Example 111c from 2,6-dinitrobenzonitrile and pentanol to provide 2-nitro-6-(pentyloxy)benzonitrile.

Example 113

4-Amino-5-(phenoxy)-1H-benzo[c][1,2,6]thiadiazine-2,2-dioxide

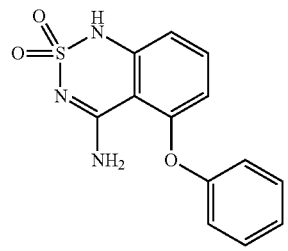

535

Prepared as in Example 111 from 2-sulfamoylamino-6-phenoxybenzonitrile (Example 113a) to provide 4-Amino-5-(phenoxy)-1H-benzo[c][1,2,6]thiadiazine-2,2-dioxide (29 mg, 50%). $^1$H NMR (400 MHz, MeOD) δ 6.39 (dd, J=8.3, 0.8 Hz, 1H), 6.75 (dd, J=8.2, 1.1 Hz, 1H), 7.18 (m, 2H), 7.30 (m, 1H), 7.40 (t, J=8.5 Hz, 1H), 7.48 (m, 2H). MS 290 (MH$^+$).

Example 113a

2-Sulfamoylamino-6-phenoxybenzonitrile

Prepared as in Example 111a from 2-amino-6-phenoxybenzonitrile (Example 113b) to provide 2-sulfamoylamino-6-phenoxybenzonitrile (250 mg, 100%). $^1$H NMR (400 MHz, MeOD) δ 6.60 (d, J=8.6 Hz, 1H), 7.11 (d, J=8.0 Hz, 1H), 7.26 (t, J=7.5 Hz, 1H), 7.39 (d, J=8.3 Hz, 1H), 7.45 (m, 2H), 7.50 (t, J=8.6 Hz, 1H). MS 290 (MH$^+$).

Example 113b

2-Amino-6-phenoxybenzonitrile

To a solution of 2-nitro-6-(phenoxy)benzonitrile (Example 113c) (1.94 g, 8.08 mmol) in MeOH (164 mL) was slowly added concentrated HCl (7.23 mL) followed by iron powder (1.58 g, 28.3 mmol). The reaction was refluxed for 30 min and concentrated in vacuo. The residue was dissolved in EtOAc and washed with 1N NaOH, water and brine. The organic layer was dried over MgSO$_4$, filtered, concentrated and purified by flash chromatography 1:1 Hexane:EtOAc to yield 2-amino-6-phenoxybenzonitrile (384 mg, 22.6%). $^1$H NMR (400 MHz, MeOD) δ 5.97 (d, J=8.3 Hz, 1H), 6.50 (d, J=8.6 Hz, 1H), 7.06 (m, 2H), 7.18 (m, 2H), 7.40 (m, 2H). MS 210 (MH$^+$).

Example 113c

2-Nitro-6-phenoxybenzonitrile

A solution of 2,6-dinitrobenzonitrile (2.0 g, 10.5 mmol), phenol (1.42 g, 15.1 mmol) and K$_2$CO$_3$ (1.45 g, 10.5 mmol) in DMF (20 mL) was stirred at rt under N$_2$ for 4.5 hours. Upon completion, the reaction was diluted with EtOAc (100 mL), washed with H$_2$O, dried over MgSO$_4$, filtered and concentrated. The residue was recrystallized from Hexane/EtOAc to provide 2-nitro-6-phenoxybenzonitrile (1.94 g, 77%). $^1$H NMR (400 MHz, MeOD) δ 7.20 (m, 2H), 7.28 (dd, J=8.6, 1.1 Hz, 1H), 7.34 (m, 1H), 7.51 (m, 2H), 7.78 (t, J=8.7 Hz, 1H), 8.05 (dd, J=8.2, 0.8 Hz, 1H).

Example 114

4-Amino-5-(4-methoxybenzyloxy)-1H-benzo[c][1,2,6]thiadiazine-2,2-dioxide

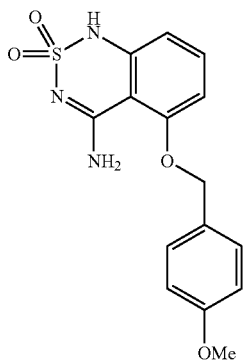

536

Prepared as in Example 111 from 2-sulfamoylamino-6-(4-methoxybenzyloxy)benzonitrile (Example 114a) to provide 4-amino-5-(4-methoxy benzyloxy)-1H-benzo[c][1,2,6]thiadiazine-2,2-dioxide (12 mg, 10%). $^1$H NMR (400 MHz, DMSO-d$_6$) δ 3.76 (s, 3H), 6.72 (d, J=8.4, 1H), 6.80 (d, J=8.1, 1H), 6.95 (m, 2H), 7.48 (m, 3H), 10.89 (br s, 1H), 11.0 (br s, 1H). MS 334 (MH$^+$).

Example 114a

2-Sulfamoylamino-6-(4-methoxybenzyloxy)benzonitrile

To a solution of chlorosulfonyl isocyanate (212 mg, 1.50 mmol) in CH$_2$Cl$_2$ (0.55 mL) at 0° C., was added formic acid (0.575 mL) under N$_2$. The reaction was stirred for 30 min, and a solution of 2-amino-6-(4-methoxybenzyloxy)benzonitrile (Example 114b) (191 mg, 0.75 mmol) in CH$_2$Cl$_2$ (4 mL) was added at 0° C., followed by Et$_3$N (0.627 mL, 4.50 mmol). After 30 min, the reaction was concentrated in vacuo and diluted with water. The pH was adjusted to 7 with concentrated HCl, and purified by reverse phase HPLC (10-90% acetonitrile in water) to provide 2-sulfamoylamino-6-(4-methoxybenzyloxy)benzonitrile (130 mg, 52%). $^1$H NMR (400 MHz, MeOD) δ 3.80 (s, 3H), 5.15 (s, 2H), 6.88 (d, J=8.1 Hz 1H), 6.94 (m, 2H), 7.40 (m, 2H), 7.48 (t, J=8.7 Hz, 1H), 7.75 (dd, J=8.6, 0.8 Hz, 1H).

Example 114b

2-Amino-6-(4-methoxybenzyloxy)benzonitrile

Prepared as in Example 113b from 2-nitro-6-(4-methoxybenzyloxy)benzonitrile (Example 114c) to provide 2-amino-6-(4-methoxybenzyloxy)benzonitrile (451 mg, 22%). $^1$H NMR (400 MHz, MeOD) δ 3.80 (s, 3H), 5.06 (s, 2H), 6.33 (dd, J=8.3, 0.8 Hz, 1H), 6.38 (m, 1H), 6.93 (m, 2H), 7.19 (t, J=8.2 Hz, 1H), 7.38 (m, 2H).

Example 114c

2-Nitro-6-(4-methoxybenzyloxy)benzonitrile

Prepared as in Example 112c from 2,6-dinitrobenzonitrile and 4-methoxybenzyl alcohol to provide 2-nitro-6-(4-methoxybenzyloxy)benzonitrile (2.40 g, 81%). $^1$H NMR (400 MHz, CDCl$_3$) δ 3.82 (s, 3H), 5.26 (s, 2H), 6.93 (m, 2H), 7.35 (dd, J=8.6, 0.7 Hz, 1H), 7.38 (m, 2H), 7.65 (t, J=8.6 Hz, 1H), 7.83 (dd, J=8.2, 0.8 Hz, 1H).

Example 115

4-Amino-5-oxyacetic acid-1H-benzo[c][1,2,3]thiadiazine-2,2-dioxide

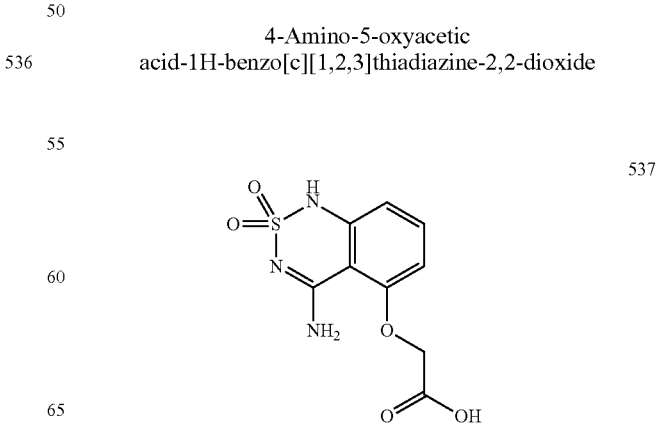

537

Prepared in a similar manner as Example 111 from ethyl 2-(2-cyano-3-(sulfamoylamino)phenoxy)acetate (Example 115a) to provide 4-Amino-5-oxyacetic acid-1H-benzo[c][1,2,3]thiadiazine-2,2-dioxide (74.9 mg, 15%) as a white solid. $^1$H NMR (400 MHz, DMSO-d$_6$) δ 4.88 (s, 2H), 6.65 (dd, J=8.3, 0.8 Hz, 1H), 6.69 (dd, J=8.5, 0.7 Hz, 1H), 7.46 (t, J=8.3 Hz, 1H), 8.42 (br s, 1H), 8.53 (br s, 1H) 11.02 (br s, 1H), 13.49 (br s, 1H). MS 272 (MH$^+$).

Example 115a

Ethyl 2-(2-cyano-3-(sulfamoylamino)phenoxy)acetate

Prepared in a similar manner as Example 111a from ethyl 2-(3-amino-2-cyanophenoxy)acetate (Example 5b) to provide ethyl 2-(2-cyano-3-(sulfamoylamino)phenoxy)acetate (567 mg, 79%) as a light yellow solid. $^1$H NMR (400 MHz, DMSO-d$_6$) δ 1.22 (t, J=7.0 Hz, 3H), 4.19 (q, J=7.0 Hz, 2H), 5.01 (s, 2H), 6.87 (d, J=8.6 Hz, 1H), 7.20 (d, J=8.3 Hz, 1H), 7.32 (s, 2H), 7.56 (t, J=8.6 Hz, 1H), 9.53 (br s, 1H).

Example 115b

Ethyl 2-(3-amino-2-cyanophenoxy)acetate

Prepared in a similar manner as Example 111b from ethyl 2-(3-amino-2-nitrophenoxy)acetate (Example 115c) to provide ethyl 2-(3-amino-2-cyanophenoxy)acetate (539 mg, 56%) as an off-white solid. $^1$H NMR (400 MHz, DMSO-d$_6$) δ 1.21 (t, J=7.6 Hz, 3H), 4.17 (q, J=7.6 Hz, 2H), 4.85 (s, 2H), 6.06 (br s, 2H), 6.10 (d, J=8.0 Hz, 1H), 6.38 (dd, J=8.6, 0.8 Hz, 1H), 7.17 (t, J=8.4 Hz, 1H).

Example 115c

Ethyl 2-(3-amino-2-nitrophenoxy)acetate

To a solution of 2-hydroxy-6-nitrobenzonitrile (Example 115d) (616 mg, 4.33 mmol) and K$_2$CO$_3$ (718 mg, 5.20 mmol) in acetone (8 mL), was added ethyl bromoacetate (0.576 mL, 5.20 mmol). The reaction was refluxed under N$_2$ for 4.5 hours. Upon completion, the reaction was filtered, and the filtrate was concentrated and dried to yield ethyl 2-(3-amino-2-nitrophenoxy). $^1$H NMR (400 MHz, DMSO-d$_6$) δ 1.23 (t, J=7.0 Hz, 3H), 4.20 (q, J=7.1 Hz, 2H), 5.19 (s, 2H), 7.69 (dd, J=8.6, 0.8 Hz, 1H), 7.89 (t, J=8.4 Hz, 1H), 7.97 (dd, J=8.3, 0.8 Hz, 1H).

Example 115d

2-Hydroxy-6-nitrobenzonitrile

To a solution of 2,6-dinitrobenzonitrile (10.0 g, 52.3 mmol) in MeOH (215 mL), was added a solution of Na (1.32 g, 57.5 mmol) in MeOH (23.3 mL). The reaction was refluxed under N$_2$ for 2.5 hours, cooled to rt and the precipitate was collected by filtration. The resulting residue was combined with pyridine hydrochloride (15.1 g, 130 mmol), and the solids were melted at 200° C. for 18 hours. Upon completion, the reaction was cooled to rt, washed with brine (1×300 mL) and extracted with EtOAc (2×500 mL). The organic layers were combined, dried over MgSO$_4$, filtered and concentrated to provide 2-hydroxy-6-nitrobenzonitrile (6.70 g, 87%). $^1$H NMR (400 MHz, MeOD) δ 7.35 (dd, J=8.3, 0.8 Hz, 1H), 7.67 (t, J=8.2 Hz, 1H), 7.77 (dd, J=8.2, 1.1 Hz, 1H).

Example 116

4-Amino-5-(isopropoxy)-1H-benzo[c][1,2,6]thiadiazine-2,2-dioxide

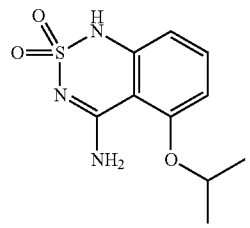

538

Prepared in a similar manner as Example 111 from 2-sulfamoylamino-6-isopropxybenzonitrile (Example 116a) to provide 4-amino-5-(isopropoxy)-1H-benzo[c][,6]thiadiazine-2,2-dioxide (50 mg, 171%). $^1$H NMR (400 MHz, DMSO-d$_6$) δ 1.38 (d, J=5.8 Hz, 6H), 4.84 (sept, J=5.9 Hz, 1H), 6.59 (d, J=8.7 Hz, 1H), 6.77 (d, J=8.7 Hz, 1H), 7.45 (d, J=8.7 Hz, 1H), 7.81 (br s, 1H), 8.32 (br s, 1H), 10.94 (br s, 1H). MS 256 (MH$^+$).

Example 116a

2-Sulfamoylamino-6-isopropoxybenzonitrile

Prepared in a similar manner as Example 111a from 2-amino-6-isopropoxybenzonitrile (Example 6b) to provide 2-sulfamoylamino-6-isopropoxybenzonitrile (21 mg, 8%). $^1$H NMR (400 MHz, MeOD) δ 1.37 (d, J=5.6 Hz, 6H), 4.67 (sept, J=6.0 Hz, 1H), 6.29 (d, J=8.2 Hz, 1H), 6.36 (dd, J=8.1, 0.8 Hz, 1H), 7.07 (t, J=8.2 Hz, 1H).

Example 116b

2-Amino-6-isopropoxybenzonitrile

Prepared in a similar manner as Example 113b from 2-nitro-6-isopropoxybenzonitrile (Example 116c) to provide 2-amino-6-isopropoxybenzonitrile (201 mg, 76%) as a yellow oil. $^1$H NMR (400 MHz, MeOD) δ 1.34 (d, J=6.0 Hz, 6H), 4.64 (sept, J=6.1 Hz, 1H), 6.25 (d, J=8.1 Hz, 1H), 6.34 (dd, J=8.2, 0.8 Hz, 1H), 7.18 (t, J=8.3 Hz, 1H).

Example 116c

2-Nitro-6-isopropoxybenzonitrile

Prepared in a similar manner as Example 115c from 2-hydroxy-6-nitrobenzonitrile (Example 115d) and isopropyl bromide to provide 2-nitro-6-isopropoxybenzonitrile (324 mg, 64%). $^1$H NMR (400 MHz, MeOD) 61.43 (d, J=6.2 Hz, 6H), 4.89 (sept, J=6.2 Hz, 1H), 7.61 (dd, J=8.0, 1.0 Hz, 1H), 7.80 (t, J=8.2 Hz, 1H), 7.85 (dd, J=8.2, 1.2 Hz, 1H).

Example 117

4-Amino-5-(benzyloxy)-1H-benzo[c][,6]thiadiazine-2,2-dioxide

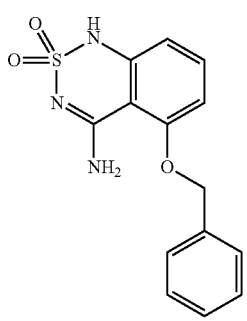

539

Prepared as in Example 111 from 2-sulfamoylamino-6-(benzyloxy)benzonitrile (Example 117a) to provide 4-amino-5-(benzyloxy)-1H-benzo[c][1,2,6]thiadiazine-2,2-dioxide (42 mg, 61%). $^1$H NMR (400 MHz, MeOD) δ 5.32 (s, 2H), 6.65 (dd, J=8.3, 1.2 Hz, 1H), 6.85 (dd, J=8.6, 1.0 Hz, 1H), 7.36-7.52 (m, 6H). MS 304 (MH$^+$).

Example 117a

2-Sulfamoylamino-6-(benzyloxy)benzonitrile

Prepared as in Example 111a from 2-amino-6-(benzyloxy)benzonitrile (Example 117b) to provide 2-sulfamoylamino-6-(benzyloxy)benzonitrile (74 mg, 30%). $^1$H NMR (400 MHz, MeOD) δ 5.22 (s, 2H), 6.94 (d, J=8.5 Hz, 1H), 7.26 (d, J=8.2 Hz, 1H), 7.32 (m, 1H), 7.38 (t, J=7.2 Hz, 2H), 7.47 (d, J=7.4 Hz, 2H), 7.51 (t, J=8.2 Hz, 1H).

Example 117b

2-Amino-6-(benzyloxy)benzonitrile

Prepared as in Example 113b from 2-nitro-6-(benzyloxy)benzonitrile (Example 117c) to provide 2-amino-6-(benzyloxy)benzonitrile (215 mg, 63%). $^1$H NMR (400 MHz, MeOD) δ 5.15 (s, 2H), 6.32 (d, J=8.2 Hz, 1H), 6.39 (d, J=8.2 Hz, 1H), 7.20 (t, J=8.4 Hz, 1H), 7.38 (t, J=7.6 Hz, 2H), 7.46 (d, J=7.4 Hz, 2H). MS 225 (MH$^+$).

Example 117c

2-Nitro-6-(benzyloxy)benzonitrile

To a solution of 2-hydroxy-6-nitrobenzonitrile (Example 115) (1.0 g, 6.09 mmol) and Cs$_2$CO$_3$ (2.16 g, 6.64 mmol) in acetone (14 mL) was added benzyl bromide (1.16 g, 6.76 mmol). The reaction was refluxed under N$_2$ for 1.5 hours, then filtered and the filtrate concentrated. The residue was purified by flash chromatography 3:2 Hexane:EtOAc to provide 2-nitro-6-(benzyloxy)benzonitrile (500 mg, 32%). $^1$H NMR (400 MHz, MeOD) δ 5.40 (s, 2H), 7.34-7.45 (m, 3H), 7.53 (m, 2H), 7.69 (dd, J=8.6, 0.8 Hz, 1H), 7.82 (t, J=8.4 Hz, 1H), 7.91 (t, J=8.2, 0.8 Hz, 1H).

Example 118

4-Amino-5-(ethoxy)-1H-benzo[c][1,2,6]thiadiazine-2,2-dioxide

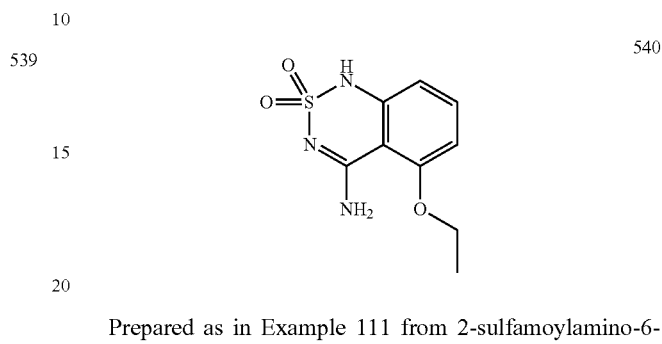

540

Prepared as in Example 111 from 2-sulfamoylamino-6-ethoxybenzonitrile (Example 118a) to provide 4-amino-5-ethoxy-1H-benzo[c][,6]thiadiazine-2,2-dioxide (120 mg, 50%). $^1$H NMR (400 MHz, DMSO-d$_6$) δ 1.37 (t, J=6.9 Hz, 3H), 4.18 (q, J=6.9 Hz, 2H), 6.96 (d, J=8.8 Hz, 1H), 7.16 (d, J=8.8 Hz, 1H), 7.27 (br s, 2H), 7.57 (t, J=8.4 Hz, 1H), 9.44 (br s, 1H). MS 242 (MH$^+$).

Example 118a

2-Sulfamoylamino-6-ethoxybenzonitrile

Prepared in a similar manner as Example 111a from 2-amino-6-ethoxybenzonitrile (Example 8b) to provide 2-sulfamoylamino-6-ethoxybenzonitrile (161 mg, 67%). MS 242 (MH$^+$).

Example 118b

2-Amino-6-ethoxybenzonitrile

Prepared in a similar manner as Example 111b from 2-nitro-6-ethoxybenzonitrile (Example 8c) to provide 2-amino-6-ethoxybenzonitrile (162 mg, 100%). MS 163 (MH$^+$).

Example 118c

2-Nitro-6-ethoxybenzonitrile

Prepared in a similar manner as Example 115c from 2-hydroxy-6-nitrobenzonitrile (Example 115d) and ethyl bromide to provide 2-nitro-6-ethoxybenzonitrile (192 mg, 50%).

Example 119

4-Amino-5-(butoxy)-1H-benzo[c][1,2,6]thiadiazine-2,2-dioxide

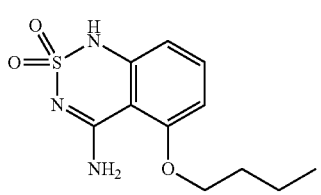

541

Prepared in a similar manner as Example 111 from 2-sulfamoylamino-6-butoxybenzonitrile (Example 119a) to provide 4-amino-5-butoxy-1H-benzo[c][1,2,6]thiadiazine-2,2-dioxide (67 mg, 50%). $^1$H NMR (400 MHz, DMSO-d$_6$) δ 0.95 (t, J=7.4 Hz, 3H), 1.44 (sext, J=7.4 Hz, 2H), 1.81 (quint, J=7.9 Hz, 2H), 4.17 (t, J=6.7 Hz, 2H), 6.61 (d, J=8.2 Hz, 1H), 6.76 (d, J=8.2 Hz, 1H), 7.46 (t, J=8.2 Hz, 1H), 7.82 (br s, 1H), 8.35 (br s, 1H), 10.96 (br s, 1H). MS 270 (MH$^+$).

Example 119a

2-Sulfamoylamino-6-butoxybenzonitrile

Prepared in a similar manner as Example 111a from 2-amino-6-butoxybenzonitrile (Example 9b) to provide 2-sulfamoylamino-6-butoxybenzonitrile. MS 270 (MH$^+$).

Example 119b

2-Amino-6-butoxybenzonitrile

Prepared in a similar manner as Example 111b from 2-nitro-6-butoxybenzonitrile (Example 9c) to provide 2-amino-6-butoxybenzonitrile (190 mg, 71%). MS 191 (MH$^+$).

Example 119c 2-nitro-6-butoxybenzonitrile

Prepared in a similar manner as Example 115c from 2-hydroxy-6-nitrobenzonitrile (Example 115d) and butyl bromide to provide 2-nitro-6-butoxybenzonitrile.

Example 120

4-Amino-1-methyl-M-pyrazolo[c][,6]thiadiazine-2,2-dioxide

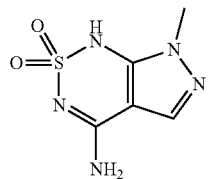

542

Prepared in a similar manner as Example 111 from 5-sulfamoylamino-1-methyl-1H-pyrazole-4-carbonitrile (Example 120a) to provide 4-Amino-1-methyl-1H-pyrazolo[c][1,2,6]thiadiazine-2,2-dioxide (100 mg, 50%). $^1$H NMR (400 MHz, DMSO-d$_6$) δ 3.76 (s, 3H), 7.43 (s, 2H), 7.98 (s, 1H), 9.84 (s, 1H).

Example 120a 5-sulfamoylamino-1-methyl-1H-pyrazole-4-carbonitrile

Prepared in a similar manner as Example 111a from 5-amino-1-methyl-1H-pyrazole-4-carbonitrile to provide 5-sulfamoylamino-1-methyl-1H-pyrazole-4-carbonitrile.

Example 121

4-Amino-2H-pyrazolo[c][1,2,6]thiadiazine-2,2-dioxide

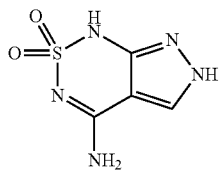

543

Prepared in a similar manner as Example 111 from 3-sulfamoylamino-1H-pyrazole-4-carbonitrile (Example 11a) to provide 4-amino-2H-pyrazolo[c][1,2,6]thiadiazine-2,2-dioxide (90 mg, 48%). $^1$H NMR (400 MHz, DMSO-d$_6$) δ 6.97 (s, 2H), 8.47 (s, 1H), 9.71 (s, 1H), 13.36 (s, 1H).

Example 121a

3-Sulfamoylamino-1H-pyrazole-4-carbonitrile

Prepared in a similar manner as Example 111a from 3-amino-1H-pyrazole-4-carbonitrile to provide 3-sulfamoylamino-1H-pyrazole-4-carbonitrile.

Example 122

4-Amino-7-methoxy-M-benzo[c][,6]thiadiazine-2,2-dioxide

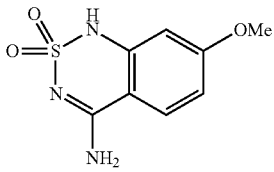

544

Prepared in a similar manner as Example 111 from 2-sulfamoylamino-4-methoxybenzonitrile (Example 122a) to provide 4-amino-7-methoxy-1H-benzo[c][1,2,6]thiadiazine-2,2-dioxide (49 mg, 65%). $^1$H NMR (400 MHz, DMSO-d$_6$) δ 3.81 (s, 3H), 6.58 (d, J=2.3 Hz, 1H), 6.75 (dd, J=9.1, 2.7 Hz, 1H), 7.82 (d, J=8.8 Hz, 1H), 10.85 (br s, 1H), 10.99 (br s, 1H). MS 228 (ME).

Example 122a

2-Sulfamoylamino-4-methoxybenzonitrile

Prepared in a similar manner as Example 114a from 2-amino-4-methoxybenzonitrile (Example 122b) to provide 2-sulfamoylamino-4-methoxybenzonitrile as white crystals (111 mg, 44%). $^1$H NMR (400 MHz, MeOD) δ 3.85 (s, 3H), 6.73 (dd, J=9.0, 2.8 Hz, 1H), 7.54 (d, J=9.0 Hz, 1H), 7.84 (d, J=2.4 Hz, 1H). MS 228 (MH$^+$).

Example 122b

2-Amino-4-methoxybenzonitrile

Prepared in a similar manner as Example 111b from 2-nitro-4-methoxybenzonitrile to provide 2-amino-4-methoxybenzonitrile (910 mg, 78%). $^1$H NMR (400 MHz, CDCl$_3$) δ 3.79 (s, 3H), 4.73 (br s, 2H), 6.20 (m, 1H), 6.31 (m, 1H), 7.30 (d, J=8.7 Hz, 1H).

Example 123

Ethyl 4-amino-5-methyl-2-oxo-1,2-dihydrothieno[c][1,3,6]thiadiazine-2,2-dioxide-6-carboxylate

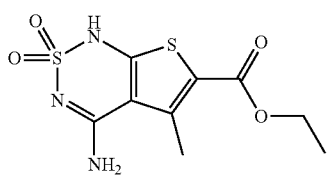

545

Prepared in a similar manner as Example 111 from ethyl 5-sulfamoylamino-4-cyano-3-methylthiophene-2-carboxylate (Example 123a) to provide ethyl 4-amino-5-methyl-2-oxo-1,2-dihydrothieno[c][1,3,6]thiadiazine-2,2-dioxide-6-carboxylate (1.22 g, 72%). $^1$H NMR (400 MHz, DMSO-$d_6$) δ 1.26 (t, J=6.9 Hz, 3H), 2.73 (s, 3H), 4.17 (q, J=7.0 Hz, 2H). MS 290 (MH$^+$).

Example 123a

Ethyl 5-sulfamoylamino-4-cyano-3-methylthiophene-2-carboxylate

Prepared in a similar manner as Example 114a from ethyl 5-amino-4-cyano-3-methylthiophene-2-carboxylate (Example 123b) to provide ethyl 5-sulfamoylamino-4-cyano-3-methylthiophene-2-carboxylate (1.73 g, 80%). $^1$H NMR (400 MHz, DMSO-$d_6$) δ 1.28 (t, J=7.0 Hz, 3H), 2.36 (s, 3H), 4.24 (q, J=7.1 Hz, 2H).

Example 123b

Ethyl 5-amino-4-cyano-3-methylthiophene-2-carboxylate

To a solution of ethyl 3-oxobutanoate (3.0 mL, 23.5 mmol), malononitrile (1.55 g, 23.5 mmol) and sulfur (753 mg, 23.5 mmol) in EtOH (39 mL), was added Et$_3$N (3.28 mL, 23.5 mmol). The reaction was refluxed under N$_2$ for 3 hours, then directly purified by flash chromatography (99:1 CH$_2$Cl$_2$:EtOAc) to provide ethyl 5-amino-4-cyano-3-methylthiophene-2-carboxylate (2.18 g, 44%). $^1$H NMR (400 MHz, DMSO-$d_6$) δ 1.21 (t, J=7.0 Hz, 3H), 2.36 (s, 3H), 4.15 (q, J=7.2 Hz, 2H).

Example 124

4-Amino-7-methyl-1H-benzo[c][1,2,6]thiadiazine-2,2-dioxide

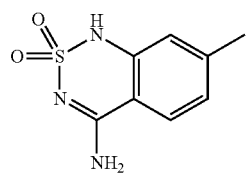

546

Prepared in a similar manner as Example 111 from 2-sulfamoylamino-4-methylbenzonitrile (Example 124a) to provide 4-amino-7-methyl-1H-benzo[c][1,2,6]thiadiazine-2,2-dioxide (50 mg, 50%). $^1$H NMR (400 MHz, MeOD) δ 2.40 (s, 3H), 6.92 (s, 1H), 7.03 (m, 1H), 7.70 (d, J=8.2 Hz, 1H). MS 212 (MH$^+$).

Example 124a

2-Sulfamoylamino-4-methylbenzonitrile

Prepared in a similar manner as Example 114a from 2-amino-4-methylbenzonitrile (Example 14b) to provide 2-sulfamoylamino-4-methylbenzonitrile (205 mg, 82%). $^1$H NMR (400 MHz, CDCl$_3$) δ 2.35 (s, 3H), 6.88 (m, 1H), 7.38 (d, J=7.7 Hz, 1H), 7.72 (br s, 1H), 7.97 (s, 1H), 9.37 (s, 1H), MS 212 (MH$^+$).

Example 124b

2-Amino-4-methylbenzonitrile

A solution of 2-bromo-4-methylbenzonitrile (2.0 g, 10.7 mmol) and CuCN (1.92 g, 21.4 mmol) in NMP (10 mL) was reacted in a microwave for 20 min at 200° C. Upon completion the reaction was cooled to 0° C., and 15% aqueous NH$_4$OH (215 mL) was slowly added. The mixture was stirred at rt for 30 min, then extracted with CH$_2$Cl$_2$. The organic layer was washed with H$_2$O, brine, dried over MgSO$_4$, filtered and concentrated. The residue was purified by flash chromatography (3:1 Hexane:EtOAc) to provide 2-amino-4-methylbenzonitrile (1.24 g, 88%). $^1$H NMR (400 MHz, CDCl$_3$) δ 1.45 (s, 3H), 5.70 (m, 1H), 5.84 (m, 1H), 6.41 (d, J=8.0 Hz, 1H).

Example 125

4-Amino-8-methyl-1H-benzo[c][1,2,6]thiadiazine-2,2-dioxide

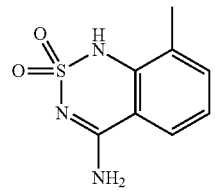

547

Prepared in a similar manner as Example 111 from 2-sulfamoylamino-3-methylbenzonitrile (Example 125a) to provide 4-amino-8-methyl-1H-benzo[c][1,2,6]thiadiazine-2,2-dioxide (9 mg, 8%). $^1$H NMR (400 MHz, MeOD) δ 2.37 (s, 3H), 7.09 (t, J=7.7 Hz, 1H), 7.45 (d, J=7.3 Hz, 1H), 8.04 (d, J=7.7 Hz, 1H). MS 212 (MH$^+$).

Example 125a

2-Sulfamoylamino-3-methylbenzonitrile

Prepared in a similar manner as Example 114a from 2-amino-3-methylbenzonitrile (Example 15b) to provide 2-sulfamoylamino-3-methylbenzonitrile (115 mg, 46%). $^1$H NMR (400 MHz, MeOD) δ 2.34 (s, 3H), 7.31 (t, J=7.5 Hz, 1H), 7.57 (m, 2H). MS 212 (MH⁺).

Example 126

4-Amino-7-cyano-1H-benzo[c][1,2,6]thiadiazine-2,2-dioxide

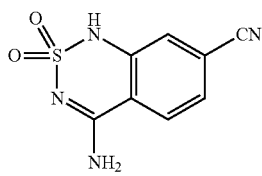

548

Prepared in a similar manner as Example 114a from 2-aminoterephthalonitrile (Example 126a) to provide 4-amino-7-cyano-1H-benzo[c][1,2,6]thiadiazine-2,2-dioxide (40 mg, 16%). ¹H NMR (400 MHz, DMSO-d₆) δ 7.37 (d, J=1.5 Hz, 1H), 7.57 (dd, J=8.2, 1.6 Hz, 1H), 8.12 (d, J=8.5 Hz, 1H), 8.51 (br s, 2H), 11.51 (s, 1H). MS 223 (MH⁺).

Example 126a

2-Aminoterephthalonitrile

Prepared in a similar manner as Example 124b from 2,5-dibromoaniline to provide 2-aminoterephthalonitrile (1.14 g, 100%). ¹H NMR (400 MHz, MeOD) δ 6.91 (dd, J=8.2, 1.6 Hz, 1H), 7.12 (d, J=1.6 Hz, 1H), 7.51 (d, J=8.0 Hz, 1H).

Example 127

4-Amino-8-methoxy-M-benzo[c][1,2,6]thiadiazine-2,2-dioxide

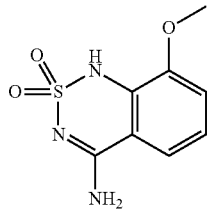

549

Prepared in a similar manner as Example 111 from 2-sulfamoylamino-3-methoxybenzonitrile (Example 127a) to provide 4-amino-8-methoxy-1H-benzo[c][,6]thiadiazine-2,2-dioxide (11 mg, 15%). ¹H NMR (400 MHz, MeOD) δ 3.97 (s, 3H), 7.14 (t, J=7.9 Hz, 1H), 7.22 (dd, J=7.8, 1.2 Hz, 1H), 7.72 (d, J=8.2, 1.2 Hz, 1H). MS 228 (MH⁺).

Example 127a

2-Sulfamoylamino-3-methoxybenzonitrile

Prepared in a similar manner as Example 114a from 2-amino-3-methoxybenzonitrile (Example 127b) to provide 2-sulfamoylamino-3-methoxybenzonitrile (113 mg, 45%). ¹H NMR (400 MHz, DMSO-d₆) δ 3.85 (s, 3H), 7.27 (m, 1H), 7.30 (dd, J=7.7, 1.7 Hz, 1H), 7.35 (dd, J=7.9, 1.7 Hz, 1H), 8.87 (s, 1H), 9.09 (br s, 1H). MS 228 (MH⁺).

Example 127b

2-Amino-3-methoxybenzonitrile

Prepared in a similar manner as Example 111b from 3-methoxy-2-nitrobenzonitrile to provide 2-amino-3-methoxybenzonitrile (346 mg, 60%). ¹H NMR (400 MHz, MeOD) δ 3.87 (s, 3H), 6.65 (t, J=7.7 Hz, 1H), 6.95 (dd, J=7.7, 1.2 Hz, 1H), 7.00 (dd, J=8.2, 1.2 Hz, 1H). MS 149 (MH⁺).

Example 128

4-Amino-7-hydroxy-1H-benzo[c][,6]thiadiazine-2,2-dioxide

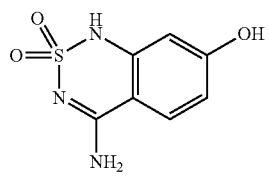

550

Prepared in a similar manner as Example 111 from 2-sulfamoylamino-4-hydroxybenzonitrile (Example 128a) to provide 4-amino-7-hydroxy-1H-benzo[c][1,2,6]thiadiazine-2,2-dioxide (7 mg, 14%). ¹H NMR (400 MHz, MeOD) δ 6.50 (d, J=2.0 Hz, 1H), 6.65 (dd, J=9.0, 2.4 Hz, 1H), 7.82 (d, J=8.8 Hz, 1H). MS 214 (MH⁺).

Example 128a

2-Sulfamoylamino-4-hydroxybenzonitrile

Prepared in a similar manner as Example 114a from 2-amino-4-hydroxybenzonitrile (Example 18b) to provide 2-sulfamoylamino-4-hydroxybenzonitrile (51 mg, 22%). ¹H NMR (400 MHz, MeOD) δ 6.56 (dd, J=8.6, 2.4 Hz, 1H), 7.43 (d, J=8.6 Hz, 1H), 7.68 (d, J=2.2 Hz, 1H). MS 214 (MH⁺).

Example 128b

2-Amino-4-hydroxybenzonitrile

Prepared in a similar manner as Example 111b from 4-hydroxy-2-nitrobenzonitrile (Example 128c) to provide 2-Amino-4-hydroxybenzonitrile (286 mg, 100%). ¹H NMR (400 MHz, MeOD) δ 6.15 (dd, J=8.5, 2.3 Hz, 1H), 6.20 (d, J=1.9 Hz, 1H), 7.18 (d, J=8.6 Hz, 1H).

Example 128c

4-Hydroxy-2-nitrobenzonitrile

A mixture of 4-methoxy-2-nitrobenzonitrile (820 mg, 4.6 mmol) and pyridine hydrochloride (755 mg, 4.6 mmol) was heated at 200° C. under N₂ for 18 hours. Upon completion, the reaction was cooled to room temperature, washed with brine and extracted with EtOAc (2×100 mL). The organic layers were combined, dried over MgSO₄, filtered and concentrated. The residue was purified by flash chromatography (1:1 Hexane:EtOAc) to provide 4-hydroxy-2-nitrobenzonitrile (200

Example 129

4-Amino-5-(2-methylprop-1-enyl)-1H-benzo[c][1,2,3]thiadiazine-2,2-dioxide

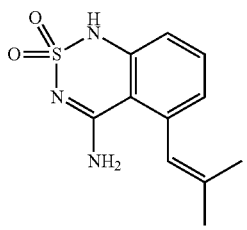

To a stirred solution of 2-sulfamoylamino-6-(2-methylprop-1-enyl)benzonitrile (Example 129a) (1.69 g, 6.73 mmol) in EtOH (29.0 mL), under a nitrogen atmosphere, an aqueous solution of NaOH (2.0M, 6.73 mL, 13.45 mmol) was added at room temperature. The obtained mixture was heated at reflux for 4 h, cooled to room temperature and neutralized with 10% AcOH (pH~6). The neutralized mixture was kept in an ice bath for 30 min. The obtained precipitate was filtered, washed with cold water and dried, to give 1.49 g (88%) of the title compound as a white solid. The product was purified by crystallization from ethanol. m.p.: >260° C. $^1$H-NMR (400 MHz, DMSO-$d_6$) δ 10.91 (broad s, 1H), 8.30 (broad s, 1H), 7.46 (t, J=8.00 Hz, 1H), 6.96 (broad s, 1H), 6.92 (d, J=8.4 Hz, 1H), 6.83 (d, J=7.2 Hz, 1H), 6.46 (broad s, 1H), 1.89-1.87 (m, 3H), 1.65-1.63 (m, 3H). $^{13}$C-NMR (100 MHz, DMSO-$d_6$) δ 162.1, 143.1, 138.8, 137.6, 132.9, 124.4, 123.3, 115.7, 110.7, 25.8 and 19.2. MS 252 (MH$^+$).

Example 129a

2-Sulfamoylamino-6-(2-methylprop-1-enyl)benzonitrile

A solution of 2-amino-6-(2-methylprop-1-enyl)benzonitrile (Example 129b) (1.24 g; 7.23 mmol) in N,N-dimethylacetamide (DMA) (20.0 mL), under a nitrogen atmosphere, was treated with sulfamoyl chloride (1.67 g; 14.45 mmol) at room temperature. The obtained mixture was stirred at room temperature for 2 h and the reaction was quenched with water (40 mL). The mixture was extracted with EtOAc (4×80 mL), the combined extract was washed with water (2×20 mL) and brine, and dried with MgSO$_4$. The filtrate was evaporated and the residue was purified by chromatography on silica gel using gradient (Hexanes/EtOAc 1:0 to 1:1), to give 1.69 g (93%) of the title compound as a white solid. $^1$H-NMR (400 MHz, DMSO-$d_6$) δ 9.42 (broad s, 1H), 7.61 (t, J=8.0 Hz, 1H), 7.44 (d, J=8.0 Hz, 1H), 7.24 (broad s, 2H), 7.19 (d, J=8.0 Hz, 1H), 6.35 (broad s, 1H), 1.92-1.95 (m, 3H), 1.76-1.79 (m, 3H).

Example 129b

2-Amino-6-(2-methylprop-1-enyl)benzonitrile

Concentrated HCl (65.5 mL) was added slowly to a solution of 2-nitro-6-(2-methylprop-1-enyl)benzonitrile (Example 129c) (2.00 g; 9.89 mmol) in EtOH (120.2 mL) at room temperature. Then, the obtained mixture was treated with iron powder (5.52 g; 98.91 mmol), added in small portions at the same temperature. The mixture was stirred at room temperature for 15 min, and then heated at reflux for 30 min. The mixture was cooled to room temperature, EtOH was evaporated and the pH was adjusted to pH~10 with aqueous NaOH (2.0M). The basified mixture was extracted with EtOAc (4×100 mL) and the combined extract was dried with anhydrous MgSO$_4$. The filtrate was evaporated and the residue was purified by chromatography on silica gel using gradient hexanes to hexanes/EtOAc (8:2), to afford 1.32 g (77%) of the title compound as yellow oil. $^1$H-NMR (400 MHz, DMSO-$d_6$) δ 7.19-7.25 (m, 1H), 6.62 (d, J=8.4 Hz, 1H), 6.46 (d, J=7.2 Hz, 1H), 6.23 (broad s, 1H), 5.91 (broad s, 2H), 1.86-1.88 (m, 3H), 1.72-1.74 (m, 3H).

Example 129c

2-Nitro-6-(2-methylprop-1-enyl)benzonitrile

A suspension of 2-cyano-3-nitrophenyl trifluoromethanesulfonate (Example 129d) (4.80 g; 16.21 mmol), 2-methyl-1-propenylboronic acid (2.43 g; 24.32 mmol), tetrakis(triphenylphosphine)palladium(0) (1.87 g; 1.62 mmol), sodium carbonate (1.89 g; 17.83 mmol) and water (33.0 mL) in dimethoxyethane (DME) (132.0 mL) was heated at reflux for 4 h, under a nitrogen atmosphere. The reaction mixture was cooled to room temperature and diluted with water (100 mL) and EtOAc (250 mL). The organic phase was separated and the aqueous phase was extracted with EtOAc (3×100 mL). The combined extract was washed with brine and dried with anhydrous MgSO$_4$. The filtrate was evaporated and the residue was purified by chromatography on silica gel using gradient hexanes to hexanes/EtOAc (7:3), to give 2.01 g (61%) of the title compound as a yellow solid. $^1$H-NMR (400 MHz, DMSO-$d_6$) δ 8.19-8.23 (m, 1H), 7.83-7.93 (m, 2H), 6.45 (broad s, 1H), 1.95-1.98 (m, 3H), 1.75-1.79 (m, 3H).

Example 129d

2-Cyano-3-nitrophenyl trifluoromethanesulfonate

To a solution of 2-hydroxy-6-nitrobenzonitrile (Example 129e) (2.90 g, 17.67 mmol) in CH$_2$Cl$_2$ (90.0 mL), at 0° C. and under a nitrogen atmosphere, triethylamine (3.58 g, 4.93 mL, 35.34 mmol) was added, followed by drop wise addition of trifluoromethanesulfonic anhydride (7.48 g, 4.46 mL, 26.51 mmol). The reaction mixture was stirred at 0° C. for 30 min and the reaction was quenched with saturated aqueous Na$_2$CO$_3$ solution (100 mL). The organic layer was separated and the aqueous phase was extracted with CH$_2$Cl$_2$ (3×100 mL). The combined extract was dried with anhydrous MgSO$_4$, filtered and evaporated. The residue was purified by chromatography on silica gel using gradient hexanes to hexanes/EtOAc (6:4), to afford 5.23 g (100%) of the title compound as a brown solid. $^1$H-NMR (400 MHz, DMSO-$d_6$) δ 8.49-8.53 (m, 1H), 8.23-8.27 (m, 1H), 8.13-8.19 (m, 1H).

Example 129e

2-Hydroxy-6-nitrobenzonitrile

2-Methoxy-6-nitrobenzonitrile (Example 1290 (10.73 g, 60.2 mmol) and pyridine hydrochloride (16.0 g, 138 mmol) were mixed together as solids under nitrogen, and then heated in a preheated oil bath at 200° C. for 40 min. After cooling to room temperature, water (200 mL) and CH$_2$Cl$_2$ (200 mL) were added and stirred vigorously for 1 hour. Then, the precipitated product was collected by filtration and recrystallized from water, to give 8.2 g, (83%) of 2-hydroxy-6-nitrobenzonitrile as a brown solid. $^1$H-NMR (400 MHz, DMSO-d$_6$) δ 12.13 (broad s, 1H), 7.68-7.79 (m, 2H), 7.39-7.44 (m, 1H).

Example 129f

2-Methoxy-6-nitrobenzonitrile

A solution of sodium methoxide, obtained by adding sodium (1.68 g, 73.1 mmol) to anhydrous MeOH (73 mL), was added to 2,6-dinitrobenzonitrile (13.20 g, 68.4 mmol) in dry MeOH (284 mL) under nitrogen at room temperature over 10 min. The reaction was refluxed for 1 hour, and then MeOH was removed under vacuum. Dichloromethane (400 mL) was added, and the insoluble solids were filtered out. The organic layer was washed with brine (100 mL), dried with MgSO$_4$, and removed under vacuum to give 11.45 g (94%) of 2-methoxy-6-nitrobenzonitrile, which was used without further purification. $^1$H-NMR (400 MHz, DMSO-d$_6$) δ 7.87-7.94 (m, 2H), 7.68-7.75 (m, 1H), 4.01 (s, 3H).

Example 130

4-Amino-5-((E)-prop-1-enyl)-1H-benzo[c][1,2,3] thiadiazine-2,2-dioxide

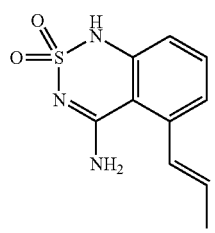

To a stirred solution of (E)-2-sulfamoylamino-6-(prop-1-enyl)benzonitrile (Example 130a) (0.82 g, 3.45 mmol) in EtOH (15.0 mL), under a nitrogen atmosphere, an aqueous solution of NaOH (2.0 M, 3.45 mL, 6.90 mmol) was added at room temperature. The obtained mixture was heated at reflux for 4 h. The mixture was cooled to room temperature and neutralized (pH~6) with 10% AcOH. The neutralized mixture was kept in an ice bath for 30 min. The obtained precipitate was filtered, washed with water and dried to afford 0.70 g (86%) of the title compound. The product was purified by crystallization from ethanol. m.p.: >260° C. $^1$H-NMR (400 MHz, DMSO-d$_6$) δ 10.90 (broad s, 1H), 8.32 (broad s, 1H), 7.45 (t, J=7.6 Hz, 1H), 7.11 (d, J=7.6 Hz, 1H), 6.95 (broad s, 1H), 6.91 (d, J=7.2 Hz, 1H), 6.75 (dd, J=15.6 Hz, 1.2 Hz, 1H), 6.23 (dq, J=15.6 Hz, J=6.8 Hz, 1H), 1.88 (dd, J=6.8 Hz, J=1.6 Hz, 3H). $^{13}$C-NMR (100 MHz, DMSO-d$_6$) δ 162.2, 142.9, 138.3, 133.2, 131.2, 128.8, 121.7, 115.8, 110.4, and 18.7. MS 238 (MH$^+$).

Example 130a (E)-2-Sulfamoylamino-6-(prop-1-enyl)benzonitrile

A solution of (E)-2-amino-6-(prop-1-enyl)benzonitrile (Example 130b) (0.60 g, 3.82 mmol) in N,N-dimethylacetamide (DMA) (15.5 mL), under a nitrogen atmosphere, was treated with sulfamoyl chloride (0.88 g, 7.63 mmol) at room temperature. The obtained mixture was stirred at room temperature for 2 h and the reaction was quenched with water (20 mL). The mixture was extracted with EtOAc (4×80 mL), the combined extract was washed with water (2×20 mL) and brine, and dried with MgSO$_4$. The filtrate was evaporated and the residue was purified by chromatography on silica gel using gradient hexanes to hexanes/EtOAc (1:1) to give 0.83 g (92%) of the title compound as a white solid. $^1$H-NMR (400 MHz, DMSO-d$_6$) δ 9.39 (broad s, 1H), 7.48-7.60 (m, 2H), 7.38-7.43 (m, 1H), 7.21 (broad s, 2H), 6.51-6.65 (m, 2H), 1.88-1.94 (m, 3H).

Example 130b (E)-2-Amino-6-(prop-1-enyl)benzonitrile

Concentrated HCl (34.5 mL) was added slowly to a solution of (E)-2-nitro-6-(prop-1-enyl)benzonitrile (Example 2c) (0.98 g, 5.21 mmol) in EtOH (63.5 mL) at room temperature. Then, the obtained mixture was treated with iron powder (2.91 g, 52.08 mmol), added in small portions at the same temperature. The mixture was stirred at room temperature for 15 min. and then heated at reflux for 30 min. The mixture was cooled to room temperature, EtOH was evaporated and the pH was adjusted to pH~10 with aqueous solution of NaOH (2.0M). The basified mixture was extracted with EtOAc (4×100 mL) and the combined extract was dried with anhydrous MgSO$_4$. The filtrate was evaporated and the residue was purified by chromatography on silica gel using gradient hexanes to hexanes/EtOAc (8:2), to afford 0.67 g (81%) of the title compound as a white solid. $^1$H-NMR (400 MHz, DMSO-d$_6$) δ 7.16-7.23 (m, 1H), 6.78 (d, J=7.2 Hz, 1H), 6.59-6.64 (m, 1H), 6.35-6.53 (m, 2H), 5.92 (broad s, 2H), 1.83-1.89 (m, 3H).

Example 130c (E)-2-Nitro-6-(prop-1-enyl)benzonitrile

A suspension of 2-iodo-6-nitrobenzonitrile (Example 130d) (1.52 g, 5.53 mmol), tetrakis(tiphenylphosphine)palladium(0) (0.64 g, 0.55 mmol), trans-1-propen-1-ylboronic acid (0.95 g, 11.06 mmol), sodium carbonate (0.65 g, 6.08 mmol) and water (10.0 mL) in dimethoxyethane (DME) (40.0 mL) was heated at reflux for 15 h, under a nitrogen atmosphere. The reaction mixture was cooled to room temperature and diluted with water (20 mL) and EtOAc (100 mL). The organic phase was separated and the aqueous phase was extracted with EtOAc (3×50 mL). The combined extract was washed with brine and dried with anhydrous MgSO$_4$. The filtrate was evaporated and the residue was purified by chromatography on silica gel using gradient hexanes to hexanes/EtOAc (7:3), to give 0.98 g (94%) of the title compound as a white solid. $^1$H-NMR (400 MHz, DMSO-d$_6$) δ 8.16-8.24 (m, 2H), 7.83-7.89 (m, 1H), 6.71-6.84 (m, 2H), 1.90-2.02 (m, 3H).

Example 130d

2-Iodo-6-nitrobenzonitrile

2-Amino-6-nitrobenzonitrile (Example 130e) (4.32 g, 26.5 mmol) was added in small portions to a suspension of sodium nitrite (2.19 g, 31.7 mmol) in concentrated H$_2$SO$_4$ (43 mL) and acetic acid (43 mL) at 45° C. The reaction was heated at 45° C. for 1 h and then added in small portions to a solution of potassium iodide (7.47 g, 45.0 mmol) in $H_2SO_4$ (1 M, 43 mL). After stirring at room temperature for 1.5 h, iced water was added to the reaction and the precipitated product was collected by filtration. The product was purified by chromatography on silica gel eluting with $CH_2Cl_2$, to give 2-iodo-6-nitrobenzonitrile (3.86 g, 53%) as a yellow solid. $^1$H-NMR (400 MHz, DMSO-$d_6$) δ 8.46-8.52 (m, 1H), 8.34-8.38 (m, 1H), 7.66-7.71 (m, 1H).

Example 130e

2-Amino-6-nitrobenzonitrile

Concentrated HCl (39 mL) was added to a solution of 2,6-dinitrobenzonitrile (11.3 g, 58.5 mmol) in MeOH (235 mL) and 1,4-dioxane (145 mL) at 70° C. External heating was removed, and iron powder (11.44 g, 205 mmol) was added slowly in portions at a rate which maintained a temperature of 70° C. After the addition of iron was complete, the reaction was heated at reflux for a further 30 min, then cooled to room temperature and poured into EtOAc (400 mL) and water (400 mL). The solids were filtered out and extracted twice with boiling EtOAc (300 mL). The combined organic extract was dried with $MgSO_4$, filtered and evaporated to give 2-amino-6-nitrobenzonitrile (6.5 g, 68%) as a red solid, which was used without further purification. $^1$H-NMR (400 MHz, DMSO-$d_6$) δ 7.48-7.54 (m, 1H), 7.41-7.45 (m, 1H), 7.18-7.22 (m, 1H), 6.74 (broad s, 2H).

Example 131

4-Amino-5-((Z)-prop-1-enyl)-1H-benzo[c][1,2,3]thiadiazine-2,2-dioxide

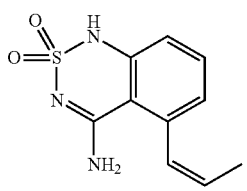

553

Prepared as in Example 129 from (Z)-2-sulfamoylamino-6-(prop-1-enyl)benzonitrile (Example 131a) to provide 4-Amino-5-((Z)-prop-1-enyl)-1H-benzo[c][1,2,3]thiadiazine-2,2-dioxide (28.2 mg, 91%) as a white solid. $^1$H NMR (400 MHz, DMSO-$d_6$) δ 10.92 (broad s, 1H), 8.30 (broad s, 1H), 7.44-7.51 (m, 1H), 6.90-7.00 (m, 2H), 6.83-6.89 (m, 1H), 6.65-6.73 (m, 1H), 5.88-5.99 (m, 1H), 1.60-1.66 (m, 3H).

Example 131a (Z)-2-Sulfamoylamino-6-(prop-1-enyl)benzonitrile

Prepared as in Example 129a from (Z)-2-amino-6-(prop-1-enyl)benzonitrile (Example 3b) in amount of 32.7 mg (92%) as a white solid. $^1$H NMR (400 MHz, DMSO-$d_6$) δ 9.45 (broad s, 1H), 7.59-7.65 (m, 1H), 7.47 (d, J=7.6 Hz, 1H), 7.18-7.28 (m, 3H), 6.50-6.57 (m, 1H), 5.99-6.09 (m, 1H), 1.74-1.79 (m, 3H).

Example 131b (Z)-2-Amino-6-(prop-1-enyl)benzonitrile

Concentrated HCl (1.54 mL) was added to a suspension of (Z)-2-nitro-6-(prop-1-enyl)benzonitrile (Example 3c) (0.35 g, 1.86 mmol) in MeOH (30 mL) and 1,4-dioxane (15 mL) at room temperature, followed by portion wise addition of iron powder (0.73 g, 13.0 mmol). The obtained mixture was heated at refluxed for 2.5 h, cooled to 0° C. and the pH was adjusted to pH~10 with aqueous 50% solution of NaOH. The mixture was extracted with EtOAc (3×50 mL), the combined extract was dried with $MgSO_4$, filtered and concentrated. The residue was purified by chromatography on silica gel eluting with gradient 0% to 100% DCM in hexanes, to give 0.24 g (80%) of (Z)-2-amino-6-(prop-1-enyl)benzonitrile as a yellow oil. $^1$H NMR (400 MHz, DMSO-$d_6$) δ 7.24-7.30 (m, 1H), 6.68 (d, J=8.4 Hz, 1H), 6.55 (d, J=7.2 Hz, 1H), 6.42-6.48 (m, 1H), 5.98 (broad s, 2H), 5.89-5.97 (m, 1H), 1.74-1.78 (m, 3H). MS 159 (MH$^+$).

Example 131c (Z)-2-Nitro-6-(prop-1-enyl)benzonitrile

Prepared as in Example 129c from 2-cyano-3-nitrophenyl trifluoromethanesulfonate Example (129d) and cis-1-propen-1-ylboronic acid. The crude product was purified by chromatography on silica gel eluting with solvent gradient 0% to 100% DCM in hexanes, to give 0.80 g (97%) of (Z)-2-nitro-6-(prop-1-enyl)benzonitrile (97%) as a yellow solid. $^1$H NMR (400 MHz, DMSO-$d_6$) δ 8.25-8.30 (m, 1H), 7.90-7.98 (m, 2H), 6.25-6.70 (m, 1H), 6.17-6.28 (m, 1H), 1.78-1.82 (m, 3H).

Example 132

4,5-Diamino-1H-benzo[c][1,2,3]thiadiazine-2,2-dioxide

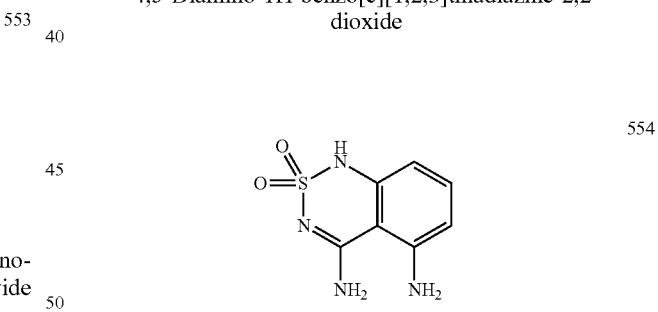

554

Prepared as in Example 129 from 2-sulfamoylamino-6-aminobenzonitrile (Example 132a) in amount of 95.3 mg (84%) as a brown solid. $^1$H NMR (400 MHz, DMSO-$d_6$) δ 10.55 (broad s, 1H), 7.80 (broad s, 2H), 7.09-7.16 (t, J=8.0 Hz, 1H), 6.42 (d, J=8.4 Hz, 1H), 6.22 (d, J=8.4 Hz, 1H), 5.79 (broad s, 2H).

Example 132a

2-Sulfamoylamino-6-aminobenzonitrile

Prepared as in Example 129a from 2,6-diaminobenzonitrile (Example 132b) in amount of 129.4 mg (60%) as a brown solid. $^1$H NMR (400 MHz, DMSO-$d_6$) δ 9.00 (broad s, 1H), 7.18 (t, J=8.0 Hz, 1H), 7.08 (broad s, 2H), 6.62-6.67 (m, 1H), 6.49-6.54 (m, 1H), 5.95 (broad s, 2H).

Example 132b

2,6-Diamonobenzonitrile

Concentrated HCl (44.3 mL) was added to a solution of 2,6-dinitrobenzonitrile (12.9 g, 67.1 mmol) in MeOH (269 mL) and 1,4-dioxane (166 mL) at 70° C. External heating was removed, and iron powder (13.1 g, 235 mmol) was added slowly in portions at a rate which maintained a temperature of 70° C. After the addition of iron was complete, the reaction was heated at reflux for a further 30 min, then cooled to room temperature and poured into EtOAc (400 mL) and water (400 mL). The solids were filtered out and extracted twice with boiling EtOAc (300 mL). The organic layers were combined, dried with $MgSO_4$, filtered and concentrated. The crude product was purified by reverse phase chromatography (0-100% $CH_3CN$ in $H_2O$) to give the title compound (1.0 g, 11%), which was used without further purification. MS 134 ($MH^+$).

Example 133

4-Amino-5-vinyl-1H-benzo[c][1,2,3]thiadiazine-2,2-dioxide

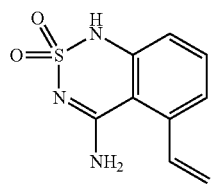

555

Prepared as in Example 129 from 2-sulfamoylamino-6-vinylbenzonitrile (Example 133a) in amount of 30.0 mg (48%) as a white solid. $^1$H NMR (400 MHz, DMSO-$d_6$) δ 10.95 (broad s, 1H), 8.33 (broad s, 1H), 7.48 (t, J=8.0 Hz, 1H), 7.18 (d, J=7.6 Hz, 1H), 7.09 (dd, J=17.6, 10.8 Hz, 1H), 6.90-6.99 (m, 2H), 5.78 (dd, J=17.6, 1.6 Hz, 1H), 5.47 (dd, J=11.2, 1.2 Hz, 1H).

Example 133a

2-Sulfamoylamino-6-vinylbenzonitrile

Prepared as in Example 129a from 2-amino-6-vinylbenzonitrile (Example 133b) in amount of 63.0 mg (81%), as a white solid. $^1$H NMR (400 MHz, DMSO-$d_6$) δ 9.46 (broad s, 1H), 7.59-7.67 (m, 2H), 7.46-7.52 (m, 1H), 7.23 (broad s, 2H), 6.93 (dd, J=17.2, 10.8 Hz, 1H), 6.08 (d, J=17.2 Hz, 1H), 5.59 (d, J=11.2 Hz, 1H).

Example 133b

2-Amino-6-vinylbenzonitrile

Prepared as in Example 129b from 2-nitro-6-vinylbenzonitrile (Example 133c) in amount of 123.9 mg (71%) as a white solid. $^1$H NMR (400 MHz, DMSO-$d_6$) δ 7.25 (t, J=8.0 Hz, 1H), 6.87 (d, J=7.2 Hz, 1H), 6.80 (dd, J=17.2, 11.6 Hz, 1H), 6.69 (d, J=8.4 Hz, 1H), 6.00 (broad s, 2H), 5.92 (d, J=17.2 Hz, 1H), 5.44 (d, J=10.8 Hz, 1H).

Example 133c

2-Nitro-6-vinylbenzonitrile

Prepared as in Example 129c from 2-cyano-3-nitrophenyl trifluoromethanesulfonate Example (129d) in amount of 0.61 g (86%) as a yellow solid. $^1$H NMR (400 MHz, DMSO-$d_6$) δ 8.26-8.34 (m, 2H), 7.90-7.98 (m, 1H), 7.09 (dd, J=17.6, 11.2 Hz, 1H), 6.26 (d, J=17.6 Hz, 1H), 5.80 (d, J=11.6 Hz, 1H).

Example 134

4-Amino-6-fluoro-5-(2-methylprop-1-enyl)-1H-benzo[c][1,2,3]thiadiazine-2,2-dioxide

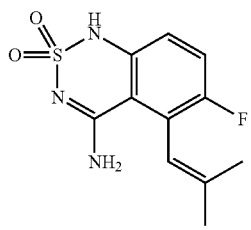

556

Prepared as in Example 129 from 3-fluoro-2-(2-methylprop-1-enyl)-6-sulfamoylaminobenzonitrile (Example 134a) in amount of 125.0 mg (86%) as a white solid. m.p.: >250° C. $^1$H NMR (400 MHz, DMSO-$d_6$) δ 1.51 (s, 3H), 1.90 (s, 3H), 6.27 (s, 1H), 7.00 (m, 1H), 7.10 (broad s, 1H), 7.45 (m, 1H), 8.35 (broad s, 1H), 10.95 (broad s, 1H). MS 270 ($MH^+$).

Example 134a

3-Fluoro-2-(2-methylprop-1-enyl)-6-sulfamoylaminobenzonitrile

Prepared as in Example 129a from 6-amino-3-fluoro-2-(2-methylprop-1-enyl)benzonitrile (Example 134b) in amount of 156.0 mg (88%), as a white solid. MS 270 ($MH^+$).

Example 134b

6-Amino-3-fluoro-2-(2-methylprop-1-enyl)benzonitrile

Prepared as in Example 129b from 3-fluoro-2-(2-methylprop-1-enyl)-6-nitrobenzonitrile (Example 134c) in amount of 0.38 g, (84%) as a white solid. MS 191 ($MH^+$).

Example 134c

3-Fluoro-2-(2-methylprop-1-enyl)-6-nitrobenzonitrile

2-Bromo-3-fluoro-6-nitrobenzonitrile (Example 134d) (0.62 g, 2.53 mmol), 2-methylprop-1-enylboronic acid (0.50 g, 5.05 mmol), palladium(II) acetate (0.023 g, 0.102 mmol), $K_3PO_4$ (1.61 g, 7.58 mmol), and dicyclohexyl(2',6'-dimethoxybiphenyl-2-yl)phosphine (0.083 g, 0.202 mmol) were suspended in anhydrous THF (16 mL) under nitrogen and heated at 70° C. for 4.5 h. Solvent was removed under vacuum, and the product was purified by chromatography on silica gel eluting with gradient 0% to 100% ethyl acetate in hexanes, to give 3-fluoro-2-(2-methylprop-1-enyl)-6-nitrobenzonitrile 0.44 g (78%) as a yellow solid. MS 221 (MH+).

Example 134d

2-Bromo-3-fluoro-6-nitrobenzonitrile

Triethylamine (2.53 mL, 18.2 mmol) was added to a suspension of 2-bromo-3-fluoro-6-nitrobenzamide (Example 6e) (1.60 g, 6.08 mmol) in POCl$_3$ (32 mL), and the mixture was heated at 75° C. for 1.5 h. The mixture was carefully poured into a mixture of ice and water (400 mL) and extracted twice with CH$_2$Cl$_2$. The combined extract was dried MgSO$_4$, filtered and concentrated under vacuum. The residue was purified by chromatography on silica gel eluting with solvent gradient 0% to 100% EtOAc in hexanes, to give 2-bromo-3-fluoro-6-nitrobenzonitrile 0.95 g, (64%) as a yellow solid.

Example 134e

2-Bromo-3-fluoro-6-nitrobenzamide

2-Bromo-3-fluoro-6-nitrobenzoic acid (Example 134f) (24.83 g, 94.0) mmol, (mixture of two regioisomers) was dissolved in anhydrous THF (200 mL) under a nitrogen atmosphere at room temperature. Anhydrous DMF (0.75 mL) was added and the obtained mixture was cooled to 0° C. Oxalyl chloride (12.3 mL, 141 mmol) was slowly added and the reaction mixture was stirred at 0° C. for 10 min, and at room temperature for a further 2 h. The reaction was evaporated to dryness, suspended in anhydrous THF (100 mL) and added slowly to concentrated ammonium hydroxide (350 mL) at 0° C. After stirring for 45 minutes at 0° C. the mixture was extracted with CH$_2$Cl$_2$ (5×100 mL), and the organic extractions were then discarded. At this point the desired regioisomer existed as an insoluble precipitate in the aqueous layer, which was collected by filtration to give 10.3 g (42%) of 2-bromo-3-fluoro-6-nitrobenzamide which was used without further purification. $^1$H NMR (400 MHz, DMSO-d$_6$) δ 8.27 (dd, J=8.8, 4.4 Hz, 1H), 8.10 (broad s, 1H), 7.95 (broad s, 1H), 7.66 (dd, J=9.6, 7.6 Hz, 1H).

Example 134f

2-Bromo-3-fluoro-6-nitrobenzoic acid

In a 1 L, three necked flask fitted with a dropping funnel and a thermometer were charged 2-bromo-3-fluorobenzoic acid (Example 134 g) (28.23 g, 0.13 mol) and concentrated H$_2$SO$_4$ (200 mL). After cooling to 0° C., HNO$_3$ (70%, 16.0 mL) was added dropwise over 30 min, keeping the temperature between 0 to 10° C. After 1 h, the reaction mixture was poured into the crushed ice keeping the temperature below 20° C. The mixture was extracted with EtOAc (2×200 mL), the combined extract was washed with brine and dried with MgSO$_4$. The filtrate was evaporated to give 27.27 g (77%) of a mixture of 2-bromo-3-fluoro-6-nitrobenzoic acid and 2-bromo-3-fluoro-5-nitrobenzoic acid (1:0.4) as a brown solid. $^1$H NMR (400 MHz, DMSO-d$_6$) δ 8.33 (dd, J=9.6, 4.8 Hz, 1H), 7.21 (dd, J=10.0, 8.0 Hz, 1H).

Example 134g

2-Bromo-3-fluorobenzoic acid

In a 1 L, three necked flask fitted with a dropping funnel and thermometer, were charged 2-amino-3-fluorobenzoic acid (20.0 g, 0.13 mol) and acetonitrile (160 mL). After cooling to 0° C., HBr (47%, 160 mL) was added drop wise over 10 min. To the resulting solution a solution of NaNO$_2$ (10.0 g, 0.14 mol) in water (20.0 mL) was added drop wise over 1 h. After addition, the reaction mixture was stirred at 0° C. for 5 min, and copper(I) bromide (22.0 g, 0.15 mol) was added portionwise over 30 min. Stirring was continued at 70° C. in a an oil bath for 1 h. After cooling to 0° C., 700 mL of water was added and the precipitate was filtered, washed with cold water and dried under vacuum to give 28.23 g (100%) of the title compound as a white solid. The crude product was used in the next step without purification.

Example 135

4-Amino-5-(cyclopenten-1-yl)-1H-benzo[c][1,2,3]thiadiazine-2,2-dioxide

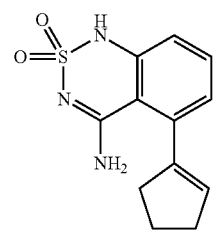

557

Prepared as in Example 129 from 2-sulfamoylamino-6-(cyclopenten-1-yl)benzonitrile (Example 135a) in amount of 36.0 mg (33%) as a white solid. $^1$H NMR (400 MHz, DMSO-d$_6$) δ 1.97 (m, 2H), 2.48 (m, 2H), 2.58 (m, 2H), 5.94 (m, 1H), 6.83 (broad s, 1H), 6.92 (m, 2H), 7.46 (m, 1H), 8.25 (broad s, 1H), 11.02 (broad s, 1H). MS 264 (MH+).

Example 135a

2-Sulfamoylamino-6-(cyclopenten-1-yl)benzonitrile

Prepared as in Example 129a from 2-amino-6-(cyclopenten-1-yl)benzonitrile (Example 135b) in amount of 156.0 mg (88%), as a white solid.

Example 135b

2-Amino-6-(cyclopenten-1-yl)benzonitrile

Prepared as in Example 129b from 2-(cyclopenten-1-yl)-6-nitrobenzonitrile (Example 135c) in amount of 0.44 g, (84%) as a white solid. MS 185 (MH+).

Example 135c 2-(Cyclopenten-1-yl)-6-nitrobenzonitrile

Prepared as in Example 129c from 2-cyano-3-nitrophenyl trifluoromethanesulfonate (Example 129d) in amount of 0.62 g (84%) as a white solid.

Example 136

4-Amino-5-n-propyl-1H-benzo[c][1,2,3]thiadiazine-2,2-dioxide

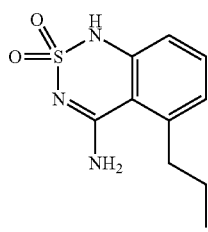

558

Prepared as in Example 129 from 2-sulfamoylamino-6-n-propylbenzonitrile (Example 136a) in amount of 144.3 mg (66%) as a white solid. $^1$H NMR (400 MHz, DMSO-$d_6$) δ 10.73 (broad s, 1H), 8.14 (broad s, 1H), 7.44 (broad s, 1H), 7.38 (t, J=8.0 Hz, 1H), 6.97 (d, J=6.8 Hz, 1H), 6.86 (d, J=8.0 Hz, 1H), 2.97 (t, J=7.6 Hz, 2H), 1.51 (hex, J=7.6 Hz, 2H), 0.81 (t, J=7.6 Hz, 3H).

Example 136a

2-Sulfamoylamino-6-n-propylbenzonitrile

Prepared as in Example 129a from 2-amino-6-n-propylbenzonitrile (Example 136b) in amount of 238.4 mg (91%), as a white solid. $^1$H NMR (400 MHz, DMSO-$d_6$) δ 9.37 (broad s, 1H), 7.55 (t, J=8.4 Hz, 1H), 7.39-7.44 (m, 1H), 7.17-7.23 (m, 3H), 2.71 (t, J=8.0 Hz, 2H), 1.60 (hex, J=7.6 Hz, 2H), 0.90 (t, J=7.6 Hz, 3H).

Example 136b

2-Amino-6-n-propylbenzonitrile (Z)-2-Amino-6-(prop-1-enyl)benzonitrile (Example 131b) (0.45 g, 2.82 mmol) and 10% Pd/C (0.17 g) were stirred in EtOH (15 mL) under a hydrogen atmosphere for 4 h. The catalyst was filtered out, and the organic layer was concentrated under vacuum to give 0.43 g (96%) of 2-amino-6-n-propylbenzonitrile as yellow oil, which was used without further purification. MS 161 (MH$^+$).

Example 137

4-Amino-5-methoxy-1H-benzo[c][1,2,3]thiadiazine-2,2-dioxide

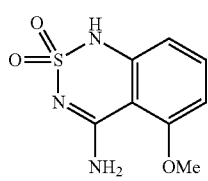

559

Prepared as in Example 129 from 2-sulfamoylamino-6-methoxybenzonitrile (Example 137a) in amount of 138.9 mg (93%) as a white solid. $^1$H NMR (400 MHz, DMSO-$d_6$) δ 10.09 (broad s, 1H), 8.28 (broad s, 1H), 8.03 (broad s, 1H), 7.44 (t, J=8.0 Hz, 1H), 6.70 (d, J=8.4 Hz, 1H), 6.58 (d, J=8.0 Hz, 1H), 3.89 (s, 3H).

Example 137a

2-Sulfamoylamino-6-methoxybenzonitrile

Prepared as in Example 129a from 2-amino-6-methoxybenzonitrile (Example 137b) in amount of 175.9 mg (84%), as a white solid. $^1$H NMR (400 MHz, DMSO-$d_6$) δ 9.44 (broad s, 1H), 7.56 (t, J=8.4 Hz, 1H), 7.25 (broad s, 2H), 7.14 (d, J=8.0 Hz, 1H), 6.93 (d, J=8.8 Hz, 1H), 3.87 (s, 3H).

Example 137b

2-Amino-6-methoxybenzonitrile

A solution of 2-methoxy-6-nitrobenzonitrile (1.01 g, 5.69 mmol), cyclohexene (2.84 g, 3.51 mL, 34.58 mmol) and 10% Pd/C (0.58 g) in EtOH (25 mL) was refluxed for 1.5 h. The mixture was cooled to room temperature, filtered and evaporated, to afford the title compound 0.83 g (98%). The crude product was used in the next step without further purification. $^1$H NMR (400 MHz, DMSO-$d_6$) δ 7.17 (t, J=8.0 Hz, 1H), 6.31-6.35 (m, 1H), 6.17-6.21 (m, 1H), 5.97 (broad s, 2H), 3.76 (s, 3H).

Example 138

4-Amino-5-(prop-1-en-2-yl)-1H-benzo[c][1,2,3]thiadiazine-2,2-dioxide

560

Prepared as in Example 129 from 2-sulfamoylamino-6-(prop-1-en-2-yl)benzonitrile (Example 138a) in amount of 63.8 mg (82%) as a white solid. $^1$H NMR (400 MHz, DMSO-$d_6$) δ 11.05 (broad s, 1H), 8.32 (broad s, 1H), 7.44-7.52 (m, 1H), 6.94-7.00 (m, 1H), 6.84-6.89 (m, 1H), 6.82 (broad s, 1H), 5.16-5.19 (m, 1H), 5.31-5.35 (m, 1H), 2.00 (s, 3H).

Example 138a

2-Sulfamoylamino-6-(prop-1-en-2-yl)benzonitrile

Prepared as in Example 129a from 2-amino-6-(prop-1-en-2-yl)benzonitrile (Example 138b) in amount of 80.5 mg (100%), as a yellow solid. $^1$H NMR (400 MHz, DMSO-$d_6$) δ 9.40 (broad s, 1H), 7.58-7.64 (m, 1H), 7.48-7.52 (m, 1H), 7.25 (broad s, 2H), 7.18-7.24 (m, 1H), 5.34-5.40 (m, 1H), 5.10-5.14 (m, 1H), 2.10 (s, 3H).

Example 138b

2-Amino-6-(prop-1-en-2-yl)benzonitrile

Prepared as in Example 129b from 2-nitro-6-(prop-1-en-2-yl)benzonitrile (Example 138c) in amount of 303.4 mg (83%), as a yellow solid. $^1$H NMR (400 MHz, DMSO-d$_6$) δ 7.18-7.25 (m, 1H), 6.67-6.72 (m, 1H), 6.47-6.51 (m, 1H), 5.97 (broad s, 2H), 5.24-5.27 (m, 1H), 5.07-5.10 (m, 1H), 2.03-2.06 (m, 3H)

Example 138c

2-Nitro-6-(prop-1-en-2-yl)benzonitrile

A suspension of 2-cyano-3-nitrophenyl trifluoromethanesulfonate (Example 129d) (0.93 g, 3.15 mmol), potassium trifluoro(prop-1-en-2-yl)borate (0.70 g, 4.73 mmol), dichloro 1,1'-bis(diphenylphosphino)ferrocene palladium(II) (0.26 g, 0.32 mmol), cesium carbonate (3.08 g, 9.45 mmol) and water (5.6 mL) in THF (56 mL) was heated at reflux for 25 min, under a nitrogen atmosphere. The reaction mixture was cooled to room temperature and diluted with water (100 mL) and EtOAc (100 mL). The organic phase was separated and the aqueous phase was extracted with EtOAc (3×100 mL). The combined extract was washed with diluted HCl (1.5M), brine and dried with anhydrous MgSO$_4$. The filtrate was evaporated and the residue was purified by chromatography on silica gel using gradient hexanes to hexanes/EtOAc (7:3), to give 0.30 g (49%) of the title compound as a yellow solid. $^1$H NMR (400 MHz, DMSO-d$_6$) δ 8.24-8.29 (m, 1H), 7.86-7.95 (m, 2H), 5.47-5.52 (m, 1H), 5.20-5.23 (m, 1H), 2.12-2.15 (m, 3H).

Example 139

4-Amino-5-ethyl-1H-benzo[c][1,2,3]thiadiazine-2,2-dioxide

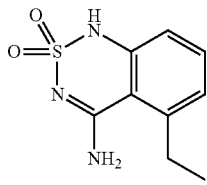

Prepared as in Example 129 from 2-sulfamoylamino-6-vinylbenzonitrile (Example 139a) in amount of 84.2 mg (80%) as a white solid. $^1$H NMR (400 MHz, DMSO-d$_6$) δ 10.74 (broad s, 1H), 8.16 (broad s, 1H), 7.24-7.52 (m, 2H), 6.99 (d, J=7.2 Hz, 1H), 6.84-6.88 (m, 1H), 3.00 (q, J=7.6 Hz, 2H), 1.12 (t, J=7.6 Hz, 3H).

Example 139a

2-Sulfamoylamino-6-vinylbenzonitrile

Prepared as in Example 129a from 2-amino-6-ethylbenzonitrile (Example 139b) in amount of 280.3 mg (98%), as a white solid. $^1$H NMR (400 MHz, DMSO-d$_6$) δ 9.36 (broad s, 1H), 7.52-7.60 (t, J=8.4 Hz, 1H), 7.38-7.43 (m, 1H), 7.19 7.24 (m, 1H), 7.19 (broad s, 2H), 2.75 (q, J=8.0, 2H), 1.18 (t, J=7.6 Hz, 3H).

Example 139b

2-Amino-6-ethylbenzonitrile

Prepared as in Example 129b from 2-ethyl-6-nitrobenzonitrile (Example 139c) in amount of 0.46 g (74%), as a orange solid. $^1$H NMR (400 MHz, DMSO-d$_6$) δ 7.18 (t, J=8.0 Hz, 1H), 6.59 (d, J=8.0 Hz, 1H), 6.47 (d, J=7.2 Hz, 1H), 5.89 (broad s, 2H), 2.60 (q, J=7.6 Hz, 2H), 1.15 (t, J=7.6 Hz, 3H).

Example 139c

2-Ethyl-6-nitrobenzonitrile

A suspension of 2 ethyl-6-nitroaniline (Example 139d) (1.96 g, 11.80 mmol) in a solution of HCl (3.0M, 24.5 mL) was stirred at room temperature for 20 min. After cooling to 0-5° C., a solution of NaNO$_2$ (1.63 g, 23.6 mmol) in water (12.25 mL) was added over a period of 10 min. The obtained mixture was stirred at 0-5° C. for 30 min, and the obtained homogeneous solution was transferred to a solution of CuCN (2.63 g, 29.5 mmol) and KCN (5.06 g, 77.8 mmol) in water (60 mL) and EtOH (31.0 mL). The resulting mixture was stirred vigorously at room temperature for 30 min, and then heated at 70° C. for another 30 min to complete the reaction. The cold mixture was filtered and extracted with EtOAc (3×100 mL). The combined extract was washed with NaOH (0.5M) and brine, and dried with anhydrous MgSO$_4$. The filtrate was evaporated and the residue was purified by chromatography on silica gel eluting with 30% EtOAc in hexanes, to afford 0.66 g (33%) of the title compound as an orange solid. $^1$H NMR (400 MHz, DMSO-d$_6$) δ 8.18-8.24 (m, 1H), 7.85-7.97 (m, 2H), 2.93 (q, J=7.2 Hz, 2H), 1.24 (t, J=7.2 Hz, 3H).

Example 139d

2 Ethyl-6-nitroaniline

A solution of N-(2-ethyl-6-nitrophenyl)actamide (Example 139e) (0.62 g, 2.98 mmol) in EtOH (21 mL) and concentrated HCl (13 mL) was refluxed for 24 h. EtOH was evaporated, the residue was diluted with water (10 mL) and the pH was adjusted to pH~8 with NaOH (2.0M aqueous solution). The neutralized solution was extracted with EtOAc (3×50 mL), the combined extract was washed with water and brine, and dried with anhydrous MgSO$_4$. The filtrate was evaporated and the residue was purified on HPLC to give 0.32 g (64%) of 2-ethyl-6-nitroaniline as an orange solid. $^1$H NMR (400 MHz, DMSO-d$_6$) δ 7.82-7.87 (m, 1H), 7.27-7.32 (m, 1H), 7.16 (broad s, 2H), 6.55-6.62 (m, 1H), 2.55 (q, J=7.2 Hz, 2H), 1.13 (t, J=7.2 Hz, 3H).

Example 139e

N-(2-ethyl-6-nitrophenyl)acetamide

A solution of nitric acid (4.2 mL) in glacial acetic acid (5.2 mL)) was added drop wise to solution of N-(2-ethylphenyl) acetamide (Example 139f)(1.00 g, 6.13 mmol) in AcOH (22 mL) and acetic anhydride (18 mL) at 0° C. The reaction was stirred at 0° C. for 1 h, diluted with water (50 mL) and neutralized with Na$_2$CO$_3$ (pH~8). The neutralized mixture was extracted with EtOAc (3×50 mL), the combined extract was washed with water and brine, and dried with anhydrous MgSO$_4$. The filtrate was evaporated and the residue was purified on HPLC to give 0.62 g (48%) of the title compound as a white solid. $^1$H NMR (400 MHz, DMSO-d$_6$) δ 9.81 (broad s, 1H), 7.68-7.73 (m, 1H), 7.57-7.62 (m, 1H), 7.39 (t, J=8.0 Hz, 1H), 2.64 (q, J=8.0 Hz, 2H), 2.00 (s, 3H), 1.10 (t, J=8.0 Hz, 3H).

Example 139f

N-(2-ethylphenyl)acetamide

2-Ethylaniline (9.70 g, 80.0 mmol) was added to a mixture of glacial AcOH (30 mL) and acetic anhydride (20 mL), and the resulting mixture was refluxed at 120° C. for 3 h. The reaction mixture was then cooled to room temperature and poured into a boiling mixture of water and EtOH (20 mL each). The mixture was stirred at rt for 1 h and then cooled (0-5° C.) overnight. EtOH was evaporated and the remainder of the mixture was diluted with water (100 mL). The obtained mixture was neutralized with $Na_2CO_3$ and extracted with EtOAc. The combined extract was washed with brine, dried with anhydrous $MgSO_4$, filtered and evaporated. The residue was purified by chromatography on silica gel eluting with 5% MeOH in $CH_2Cl_2$, to afford 5.50 g (42%) of the title compound as a pink solid. $^1$H NMR (400 MHz, DMSO-$d_6$) δ 9.25 (broad s, 1H), 7.05-7.40 (m, 4H), 2.55 (q, J=7.6 Hz, 2H), 2.02 (s, 3H), 1.09 (t, J=7.6 Hz, 3H).

Example 140

4-Amino-5-hydroxy-1H-benzo[c][1,2,3]thiadiazine-2,2-dioxide

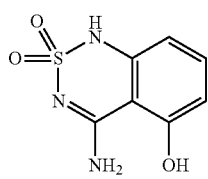

562

Prepared as in Example 129 from 2-sulfamoylamino-6-hydroxybenzonitrile (Example 140a) in amount of 50.6 mg (20%) as a brown solid. $^1$H NMR (400 MHz, DMSO-$d_6$) δ 11.00 (broad s, 1H), 9.24 (broad s, 1H), 7.37 (t, J=8.0 Hz, 1H), 7.18 (broad s, 2H), 6.97 (d, J=8.4 Hz, 1H), 6.71 (d, J=8.4 Hz, 1H).

Example 140a

2-Sulfamoylamino-6-hydroxybenzonitrile

Prepared as in Example 129a from 2-amino-6-hydroxybenzonitrile (Example 140b) in amount of 0.25 g (99%), as a brown solid. $^1$H NMR (400 MHz, DMSO-$d_6$) δ 11.01 (broad s, 1H), 9.25 (broad s, 1H), 7.37 (t, J=8.0 Hz, 1H), 7.18 (broad s, 2H), 6.95-6.99 (m, 1H), 6.69-6.74 (m, 1H).

Example 140b

2-Amino-6-hydroxybenzonitrile

A solution of 2-methoxy-6-nitrobenzonitrile (Example 1290 (1.11 g, 6.76 mmol) in EtOH (120 mL) was hydrogenated over a catalytic amount of 10% Pd/C (0.15 g) at room temperature under hydrogen (1 atm). After 2 h, the mixture was filtered and the catalyst was washed with EtOAc (150 mL). The combined extract was evaporated, to give 1.11 g (100%) of the title compound as a brown solid. The crude product was used in the next step without further purification.

$^1$H NMR (400 MHz, DMSO-$d_6$) δ 10.39 (broad s, 1H), 7.00 (t, J=8.0 Hz, 1H), 6.12-6.17 (m, 1H), 6.01-6.05 (m, 1H), 5.77 (broad s, 2H).

Example 141

4-Amino-5-phenyl-1H-benzo[c][1,2,3]thiadiazine-2,2-dioxide

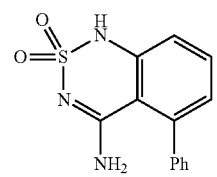

563

Prepared as in Example 129 from 2-sulfamoylamino-6-phenylbenzonitrile (Example 141a) in amount of 114.7 mg (90%) as a white solid. $^1$H NMR (400 MHz, DMSO-$d_6$) δ 11.12 (broad s, 1H), 8.04 (broad s, 1H), 7.52-7.58 (m, 1H), 7.39-7.50 (m, 3H), 7.32-7.38 (m, 2H), 7.02-7.07 (m, 1H), 6.97-7.01 (m, 1H), 5.61 (broad s, 1H).

Example 141a

2-Sulfamoylamino-6-phenybenzonitrile

Prepared as in Example 129a from 3-aminobiphenyl-2-carbonitrile (Example 141b) in amount of 142.3 mg (94%), as a white solid. $^1$H NMR (400 MHz, DMSO-$d_6$) δ 9.49 (broad s, 1H), 7.68-7.74 (m, 1H), 7.58-7.62 (m, 1H), 7.44-7.53 (m, 5H), 7.30-7.34 (m, 1H), 7.29 (broad s, 2H).

Example 141b

3-Aminobiphenyl-2-carbonitrile

Prepared as in Example 129b from 3-nitrobiphenyl-2-carbonitrile (Example 141c) in amount of 117.0 mg (80%), as a white solid. MS 195 (MH$^+$).

Example 141c

3-Nitrobiphenyl-2-carbonitrile

Prepared as in Example 129c from 2-cyano-3-nitrophenyl trifluoromethanesulfonate (Example 129d) and phenylboronic acid.

Example 142

4-Amino-5-isopropyl-1H-benzo[c][1,2,3]thiadiazine-2,2-dioxide

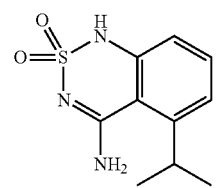

564

Prepared as in Example 129 from 2-sulfamoylamino-6-isopropylbenzonitrile (Example 142a) in amount of 53.7 mg (49%) as a white solid. $^1$H NMR (400 MHz, DMSO-$d_6$) δ 10.74 (broad s, 1H), 8.19 (broad s, 1H), 7.42 (t, J=8.0 Hz, 1H), 7.15 (broad s, 1H), 7.07-7.13 (m, 1H), 6.83-6.88 (m, 1H), 3.71 (hep, J=6.4 Hz, 1H), 1.18 (d, J=6.8 Hz, 6H).

Example 142a

2-Sulfamoylamino-6-isopropylbenzonitrile

Prepared as in Example 129a from 2-amino-6-isopropylbenzonitrile (Example 142b) in amount of 112.0 mg (97%), as a white solid. $^1$H NMR (400 MHz, DMSO-$d_6$) δ 9.35 (broad s, 1H), 7.60 (t, J=8.4 Hz, 1H), 7.41 (d, J=8.0 Hz, 1H), 7.27 (d, J=7.6 Hz, 1H), 7.20 (broad s, 2H), 3.20 (hep, J=6.8 Hz, 1H), 1.23 (d, J=6.8 Hz, 6H).

Example 142b

2-Amino-6-isopropylbenzonitrile

Prepared as in Example 136b from 2-Amino-6-(prop-1-en-2-yl)benzonitrile (Example 138b) in amount of 112.0 mg (97%), as a white solid. NMR (400 MHz, DMSO-$d_6$) δ 7.21 (t, J=8.0 Hz, 1H), 6.60 (d, J=8.4 Hz, 1H), 6.52 (d, J=7.2 Hz, 1H), 5.87 (broad s, 2H), 3.03 (hep, J=6.8 Hz, 1H), 1.18 (d, J=6.8 Hz, 6H).

Example 143

4-Amino-5-isobutyl-1H-benzo[c][1,2,3]thiadiazine-2,2-dioxide

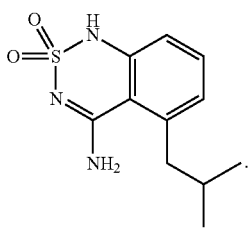

565

Prepared as in Example 129 from 2-sulfamoylamino-6-isobutylbenzonitrile (Example 143a) in amount of 32.5 mg (63%) as a white solid. $^1$H NMR (400 MHz, DMSO-$d_6$) δ 10.70 (broad s, 1H), 8.08 (broad s, 1H), 7.55 (broad s, 1H), 7.36 (t, J=8.0 Hz, 1H), 6.89-6.94 (m, 1H), 6.84-6.88 (m, 1H), 2.87 (d, J=6.8 Hz, 2H), 1.69-1.81 (m, 1H), 0.72 (d, J=6.8 Hz, 6H).

Example 143a

2-Sulfamoylamino-6-isobutylbenzonitrile

Prepared as in Example 129a from 2-amino-6-isobutylbenzonitrile (Example 143b) in amount of 52.0 mg (91%), as a white solid. $^1$H NMR (400 MHz, DMSO-$d_6$) δ 9.36 (broad s, 1H), 7.55 (t, J=8.0 Hz, 1H), 7.41 (d, J=8.0 Hz, 1H), 7.21 (broad s, 2H), 7.16 (d, J=6.8 Hz, 1H), 2.62 (d, J=7.6 Hz, 2H), 1.82-1.96 (m, 1H), 0.88 (d, J=6.4 Hz, 6H).

Example 143b

2-Amino-6-isobutylbenzonitrile

Prepared as in Example 136b from 2-Amino-6-(2-methylprop-1-enyl)benzonitrile (Example 129b) in amount of 76.4 mg (98%), as a yellow oil. $^1$H NMR (400 MHz, DMSO-$d_6$) δ 7.17 (t, J=8.0 Hz, 1H), 6.60 (d, J=8.4 Hz, 1H), 6.42 (d, J=7.6 Hz, 1H), 5.88 (broad s, 2H), 2.47 (d, J=7.6 Hz, 2H), 1.78-1.92 (m, 1H), 0.86 (d, J=6.4 Hz, 6H).

Example 144

4-Amino-5-trifluoromethyl-1H-benzo[c][1,2,3]thiadiazine-2,2-dioxide

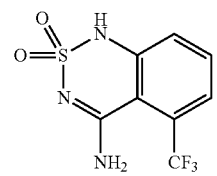

566

Prepared as in Example 129 from 2-sulfamoylamino-6-trifluoromethylbenzonitrile (Example 144a) in amount of 114.8 mg (96%) as a white solid. $^1$H NMR (400 MHz, DMSO-$d_6$) δ 11.41 (broad s, 1H), 7.64-7.72 (m, 1H), 7.50 (d, J=7.2 Hz, 1H), 7.38-7.68 (broad s, 1H), 7.31 (d, J=8.4 Hz, 1H), 3.10-3.60 (broad s, 1H).

Example 144a

2-Sulfamoylamino-6-trifluoromethylbenzonitrile

Prepared as in Example 129a from 2-amino-6-trifluoromethylbenzonitrile (Example 144b) in amount of 138.5 mg (82%), as a white solid. $^1$H NMR (400 MHz, DMSO-$d_6$) δ 9.91 (broad s, 1H), 7.84-7.92 (m, 2H), 7.69-7.76 (m, 1H), 7.42 (broad s, 2H).

Example 144b

2-Amino-6-trifluorobenzonitrile 2-(4-Methoxybenzylamino)-6-(trifluoromethyl)benzonitrile (Example 144c) (3.49 g, 11.4 mmol) was treated with trifluoroacetic acid (TFA) (35 mL) at 0° C., and then stirred at room temperature for 20 min. The TFA was removed under vacuum, and the residue was dissolved in $CH_2Cl_2$ (150 mL) and washed with 1M NaOH. The organic layer was dried with $MgSO_4$, filtered and removed under vacuum. The crude product was purified by chromatography on silica gel eluting with $CH_2Cl_2$ to give 2.12 g (99%) 2-amino-6-(trifluoromethyl)benzonitrile as a white solid. $^1$H NMR (400 MHz, DMSO-$d_6$) δ 7.45 (m, 1H), 7.07 (m, 1H), 6.96 (m, 1H), 6.60 (br s, 2H).

Example 144c 2-(4-Methoxybenzylamino)-6-(trifluoromethyl)benzonitrile

2-Fluoro-6-(trifluoromethyl)benzonitrile (2.44 g, 12.9 mmol) and 4-methoxybenzylamine (7.09 g, 51.7 mmol) were suspended in 1,4-dioxane (10 mL) and heated in a microwave at 180° C. for 30 min. The 1,4-dioxane was removed under vacuum, and the crude material was purified by chromatography on silica gel eluting with $CH_2Cl_2$ to give 3.71 g of 2-(4-methoxybenzylamino)-6-(trifluoromethyl)benzonitrile (94%) as an off white solid. $^1$H NMR (400 MHz, DMSO-$d_6$) δ 3.71 (s, 3H), 4.42 (d, J=5.6 Hz, 2H), 6.89 (m, 2H), 6.97 (m, 2H), 7.29 (m, 3H), 7.48 (m, 1H).

Example 145

4-Amino-8-hydroxy-1H-benzo[c][1,2,3]thiadiazine-2,2-dioxide

567

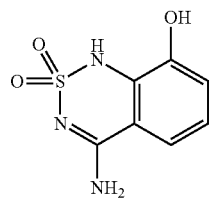

Prepared as in Example 129 from 2-sulfamoylamino-3-hydroxybenzonitrile (Example 145a) in amount of 53.9 mg (66%) as a white solid. $^1$H NMR (400 MHz, DMSO-$d_6$) δ 10.14 (broad s, 2H), 8.04 (broad s, 2H), 7.31-7.39 (m, 1H), 6.97-7.03 (m, 1H), 6.88 (t, J=7.6 Hz, 1H).

Example 145a

2-Sulfamoylamino-3-hydroxybenzonitrile

Prepared as in Example 129a from 2-amino-3-hydroxybenzonitrile (Example 145b) in amount of 83.5 mg (39%), as a white solid. $^1$H NMR (400 MHz, DMSO-$d_6$) δ 10.23 (broad s, 1H), 8.66 (broad s, 1H), 7.14-7.27 (m, 3H), 6.71 (broad s, 2H).

Example 145b

2-Amino-3-hydroxybenzonitrile

To a solution of 2-amino-3-methoxybenzonitrile (Example 127b) (0.98 g, 6.59 mmol) in $CH_2Cl_2$ (25.0 mL), a solution of $BBr_3$ in $CH_2Cl_2$ (1.0M, 19.8 mL, 19.77 mmol) was added drop wise at −78° C. under a nitrogen atmosphere. The obtained mixture was stirred at −78° C. for 30 min, and then at room temperature overnight. The reaction was quenched with water, basified with saturated aqueous $NaHCO_3$ (pH~8) and extracted with $CH_2Cl_2$. The combined extract was dried with $MgSO_4$, filtered and evaporated. The title compound was obtained in amount of 0.80 g (91%) as orange solid and was used in the next step without further purification. $^1$H NMR (400 MHz, DMSO-$d_6$) δ 9.86 (broad s, 1H), 6.82-6.87 (m, 2H), 6.46 (t, J=8.0 Hz, 1H), 5.34 (broad s, 2H).

Example 146

4-Amino-5,6-(5',7'-dihydro-4'H-[2',3'-c]pyrano)thieno[2,3-d]-pyrimidine-2(1H)-one

568

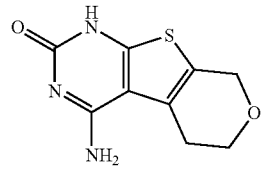

A solution of N-(3-cyano-5,7-dihydro-4H-thieno[2,3-c]pyran-2-ylcarbamoyl)benzamide (Example 146a) (500 mg, 1.53 mmol) and NaOH (2 N, 2.1 mL) in EtOH (40 mL) was stirred at 100° C. under nitrogen overnight. After cooling to room temperature, the clear reaction solution was filtered, and the filtrate was carefully neutralized with 10% AcOH with vigorous stirring at 0° C. The resultant precipitate was collected by filtration, washed with water and then 20% EtOH in water to give the final product (280 mg, 82%) as an off-white solid, which was dried under vacuum overnight. M.p.: >260° C. $^1$H NMR (400 MHz, DMSO-$d_6$) δ 2.83 (t, J=5.6 Hz, 2H), 3.86 (t, J=5.6 Hz, 2H), 4.58 (s, 2H), 7.23 (brs, 2H), 11.56 (brs, 1H). MS 224 (MH$^+$).

Example 146a

N-(3-cyano-5,7-dihydro-4H-thieno[2,3-c]pyran-2-ylcarbamoyl)benzamide

To a solution of 2-amino-5,7-dihydro-4H-thieno[2,3-c]pyran-3-carbonitrile (Example 146b) (400 mg, 2.22 mmol) in 1,4-dioxane (30 mL) was added benzoyl isocyanate (327 mg, 2.22 mmol). The reaction mixture was then stirred at room temperature under nitrogen overnight. The precipitate was collected by filtration, washed with 1,4-dioxane, and dried in the air to give the title compound (577 mg, 80%) as a light yellow solid. NMR (400 MHz, DMSO-$d_6$) δ 2.62 (t, J=5.2 Hz, 2H), 3.87 (t, J=5.2 Hz, 2H), 4.62 (s, 2H), 7.56-7.53 (m, 2H), 7.67-7.65 (m, 1H), 8.04-8.01 (m, 2H), 11.60 (brs, 1H), 12.13 (brs, 1H).

Example 146b 2-amino-5,7-dihydro-4H-thieno[2,3-c]pyran-3-carbonitrile

To a mixture of dihydro-2H-pyran-4(3H)-one (820 mg, 8.19 mmol), malononitrile (541 mg, 8.19 mmol) and sulfur (263 mg, 8.19 mmol) in Ethanol (50 mL) was added triethylamine (1.14 mL, 8.19 mmol). The reaction mixture was then refluxed under nitrogen overnight. After cooling to room temperature, the precipitate was collected by filtration, washed with ethanol, and dried in the air to give the title compound (1.15 g, 78%) as a light brown solid. $^1$H NMR (400

MHz, DMSO-d$_6$) δ 2.43-2.40 (m, 2H), 3.80 (t, J=5.6 Hz, 2H), 4.40 (t, J=2.0 Hz, 2H), 7.09 (s, 2H). MS 181 (MH$^+$).

Example 147

(E)-4-amino-5-(3-methoxyprop-1-enyl)quinazolin-2(1H)-one

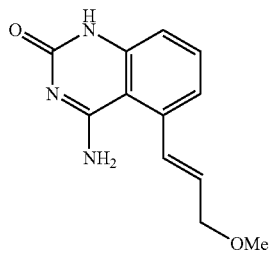

569

Prepared as in Example 146 from (E)-2-amino-6-(3-methoxyprop-1-enyl)benzonitrile (Example 97a) as a white solid. $^1$H NMR (400 MHz, DMSO-d$_6$) δ 3.28 (s, 3H), 4.02 (dd, J=6.0, 1.2 Hz, 2H), 6.13 (dt, J=16.0, 3.8 Hz, 1H), 7.06 (d, J=8.0 Hz, 1H), 7.23 (d, J=8.0 Hz, 1H), 7.52 (t, J=8.0 Hz, 1H), 7.80 (d, J=16.0 Hz, 1H), 11.07 (s, 1H), 11.13 (s, 1H). $^{13}$C NMR (DMSO-d$_6$) δ 58.0, 72.9, 111.4, 115.5, 121.9, 129.9, 131.2, 134.7, 140.2, 142.7, 150.6, 164.1.

Example 148

4-Amino-5,6-(2',3'-dihydro-1'H-cyclopenta[b])-thieno[2,3-d]pyrimidin-2(1H)-one-2,2-dioxide

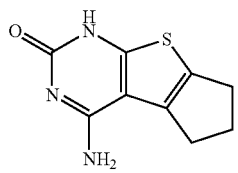

570

Prepared as in Example 4 from N-(3-cyano-5,6-dihydro-4H-cyclopenta[b]thiophen-2-ylcarbamoyl)benzamide (Example 148a). $^1$H NMR (400 MHz, DMSO-d$_6$) δ 2.33 (m, 2H), 2.76 (t, 2H), 2.87 (t, 2H), 7.51 (br-s, 2H), 11.56 (br-s, 1H). MS 208 (MH$^+$).

Example 148a

N-(3-cyano-5,6-dihydro-4H-cyclopenta[b]thiophen-2-ylcarbamoyl)benzamide

Prepared as in Example 4a from 2-amino-5,6-dihydro-4H-cyclopenta[b]thiophene-3-carbonitrile (Example 148b). $^1$H NMR (400 MHz, DMSO-d$_6$) δ 2.34 (m, 2H), 2.72 (t, 2H), 2.82 (t, 2H), 7.52 (t, 2H), 7.65 (t, 1H), 8.01 (d, 2H), 11.56 (s, 1H), 12.06 (s, 1H)

Example 148b 2-amino-5,6-dihydro-4H-cyclopenta[b]thiophene-3-carbonitrile

Prepared as in Example 5b from cyclopentanone. $^1$H NMR (400 MHz, DMSO-d$_6$) δ 2.23 (m, 2H), 2.53 (m, 2H), 2.63 (m, 2H), 7.00 (s, 2H) $^1$H NMR (400 MHz, DMSO-d$_6$) δ 2.23 (m, 2H), 2.53 (t, 2H), 2.62 (t, 2H), 7.00 (s, 2H).

Example 149

4-amino-5,6-(1',2',3',4'-tetrahydrobenzo[b])-thieno[2,3-d]pyrimidin-2(1H)-one-2,2-dioxide

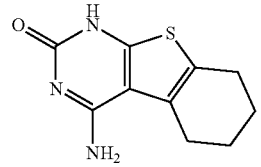

571

Prepared as in Example 4 from N-(3-cyano-4,5,6,7-tetrahydrobenzo[b]thiophen-2-ylcarbamoyl)benzamide (Example 149a). $^1$H NMR (400 MHz, DMSO-d$_6$) δ 1.73 (m, 4H), 2.57 (t, 2H), 2.72 (t, 2H). MS 222 (MH$^+$).

Example 149a

N-(3-cyano-4,5,6,7-tetrahydrobenzo[b]thiophen-2-ylcarbamoyl)benzamide

Prepared as in Example 4a from 2-amino-4,5,6,7-tetrahydrobenzo[b]thiophene-3-carbonitrile (Example 5b). $^1$H NMR (400 MHz, DMSO-d$_6$) δ 1.75 (m, 4H), 2.51 (t, 2H), 2.60 (t, 2H), 7.54 (t, 2H), 7.66 (t, 1H), 8.02 (d, 2H), 11.57 (s, 1H), 12.06 (s, 1H).

Example 150

4-Amino-5-(2-methylprop-1-enyl)quinazolin-2(1H)-one

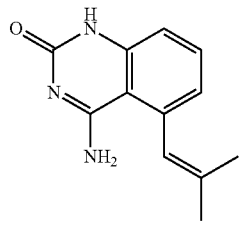

572

A suspension of N-(2-cyano-3-(2-methylprop-1-enyl)phenyl carbamoyl)benzamide (Example 150a) (0.133 g, 0.416 mmol) in EtOH (3 mL) was treated with a solution of NaOH (2 M, 0.416 mL, 0.832 mmol) at room temperature. The obtained mixture was heated at 90° C. for 30 min, cooled to room temperature and neutralized with 10% AcOH. The precipitated product was collected by filtration to give 69.0 mg (77%) of 4-amino-5-(2-methylprop-1-enyl)quinazolin-2(1H)-one as a white solid. $^1$H NMR (400 MHz, DMSO-d$_6$) δ 1.60 (d, J=1.2 Hz, 3H), 1.93 (d, J=1.2 Hz, 3H), 6.58 (s, 1H), 6.67 (broad s, 1H), 6.73 (m, 1H), 7.05 (m, 1H), 7.48 (m, 1H), 7.93 (broad s, 1H), 10.72 (broad s, 1H). MS 216 (MH$^+$).

Example 150a

N-(2-cyano-3-(2-methylprop-1-enyl)phenylcarbamoyl)benzamide

Benzoyl isocyanate (88.1 mg, 0.60 mmol) was added to a solution of 2-amino-6-(2-methylprop-1-enyl)benzonitrile (Example 129b) (75.2 mg, 0.44 mmol) in anhydrous 1,4-dioxane under nitrogen, and was stirred at room temperature for 12 h. The mixture was concentrated under vacuum, and purified by chromatography on silica gel eluting with solvent gradient 0% to 15% MeOH in $CH_2Cl_2$, to give 125.0 mg (86%) of N-(2-cyano-3-(2-methylprop-1-enyl)phenylcarbamoyl)benzamide as a white solid. $^1$H NMR (400 MHz, DMSO-$d_6$) δ 1.80 (d, J=1.2 Hz, 3H), 1.95 (d, J=1.2 Hz, 3H), 6.40 (s, 1H), 7.19 (m, 1H), 7.55 (m, 2H), 7.67 (m, 2H), 8.03 (m, 2H), 8.13 (m, 1H), 11.33 (s, 1H), 11.48 (s, 1H).

Example 151

4-Amino-5-vinylquinazolin-2(1H)-one

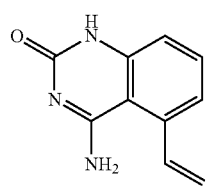

573

Prepared as in Example 150 from N-(2-cyano-3-vinylphenylcarbamoyl)benzamide (Example 151a) in amount of 20.0 mg (33%), as a white solid. $^1$H NMR (400 MHz, DMSO-$d_6$) δ 5.53 (m, 1H), 5.64 (m, 1H), 6.50 (broad s, 1H), 6.98 (m, 1H), 7.08 (m, 1H), 7.37 (m, 1H), 7.50 (m, 1H), 8.0 (broad s, 1H), 10.75 (broad s, 1H). MS 188 (MH$^+$).

Example 151a

N-(2-cyano-3-vinylphenylcarbamoyl)benzamide

Prepared as in Example 150a from 2-amino-6-vinylbenzonitrile (Example 133b) in amount of 99.3 mg (83%), as a white solid.

Example 152

4-Amino-5-(prop-1-en-2-yl)quinazolin-2(1H)-one

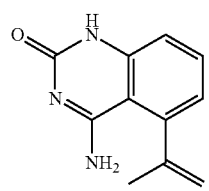

574

Prepared as in Example 150 from N-(2-Cyano-3-(prop-1-en-2-yl)phenylcarbamoyl)benzamide (Example 152a) in amount of 30.0 mg (47%), as a white solid. $^1$H NMR (400 MHz, DMSO-$d_6$) δ 2.07 (s, 3H), 5.14 (m, 1H), 5.43 (m, 1H), 6.67 (broad s, 1H), 6.80 (m, 1H), 7.11 (m, 1H), 7.50 (m, 1H), 7.99 (broad s, 1H), 10.81 (broad s, 1H). MS 202 (MH$^+$).

Example 152a

N-(2-Cyano-3-(prop-1-en-2-yl)phenylcarbamoyl)benzamide

Prepared as in Example 150a from 2-amino-6-(prop-1-en-2-yl)benzonitrile (Example 138b) in amount of 96.0 mg (72%), as a white solid. $^1$H NMR (400 MHz, DMSO-$d_6$) δ 2.15 (s, 3H), 5.23 (m, 1H), 5.43 (m, 1H), 7.25 (m, 1H), 7.55 (m, 2H), 7.68 (m, 2H), 8.04 (m, 2H), 8.19 (m, 1H), 11.35 (s, 1H), 11.54 (s, 1H).

Example 153

4-Amino-5-cyclopentenylquinazolin-2(1H)-one

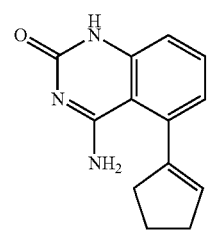

575

Prepared as in Example 150 from N—(Cyano-3-cyclopentenylphenylcarbamoyl)benzamide (Example 153a) in amount of 60.0 mg (75%), as a white solid. $^1$H NMR (400 MHz, DMSO-$d_6$) δ 2.01 (m, 2H), 2.55 (m, 2H), 2.61 (m, 2H), 5.91 (s, 1H), 6.49 (broad s, 1H), 6.81 (m, 1H), 7.08 (m, 1H), 7.48 (m, 1H), 7.88 (broad s, 1H), 10.76 (s, 1H). MS 228 (MH$^+$).

Example 153a

N-(Cyano-3-cyclopentenylphenylcarbamoyl)benzamide

Prepared as in Example 150a from 2-amino-6-(cyclopenten-1-yl)benzonitrile (Example 135b) in amount of 117.0 mg (93%), as a white solid. $^1$H NMR (400 MHz, DMSO-$d_6$) δ 1.99 (m, 2H), 2.57 (m, 2H), 2.78 (m, 2H), 6.45 (m, 1H), 7.26 (m, 1H), 7.57 (m, 2H), 7.68 (m, 2H), 8.06 (m, 2H), 8.15 (m, 1H), 11.34 (br s, 1H), 11.51 (s, 1H).

Example 154

(E)-4-Amino-5-(prop-1-enyl)quinazolin-2(1H)-one

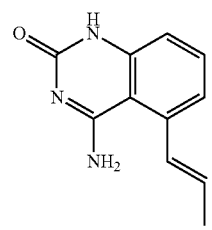

576

Prepared as in Example 150 from (E)-N-(2-Cyano-3-(prop-1-enyl)phenylcarbamoyl)benzamide (Example 154a) in amount of 13.0 mg (8%), as a white solid. $^1$H NMR (400 MHz, DMSO-$d_6$) δ 1.91 (m, 3H), 6.09 (m, 1H), 6.40 (broad s, 1H), 6.91 (m, 2H), 7.03 (m, 1H), 7.45 (m, 1H), 7.9 (broad s, 1H), 10.70 (s, 1H). MS 202 (MH$^+$).

Example 154a (E)-N-(2-Cyano-3-(prop-1-enyl)phenylcarbamoyl)benzamide

Prepared as in Example 150a from (E)-2-amino-6-(prop-1-enyl)benzonitrile (Example 130b) in amount of 0.22 g (88%), as a white solid. $^1$H NMR (400 MHz, DMSO-$d_6$) δ 11.50 (broad s, 1H), 11.34 (broad s, 1H), 8.13 (d, J=8.4 Hz, 1H), 8.02-8.08 (m, 2H), 7.64-7.70 (m, 2H), 7.52-7.59 (m, 2H), 7.20 (d, J=8.0 Hz, 1H), 5.50-5.18 (m, 2H), 3.55-3.59 (m, 3H).

Example 155

4-amino-5-cyclopropylquinazolin-2(1H)-one

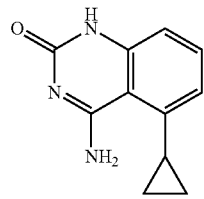
577

A solution of 2-amino-6-cyclopropylbenzonitrile (Example 92a) (1.0 eq., 1.0 mmol, 158 mg) and benzoyl isocyanate (90% pure, 1.0 eq., 1.0 mmol, 1.171 g/mL, 140 µL) in dioxane (15 mL) was stirred at room temperature. After 2 hours, the volatiles were removed on a rotary evaporator. The resulting crude N-benzoyl urea was suspended in EtOH (10 mL, 200 proof) and NaOH (2.5 eq., 2.5 mmol, 1N, 2.50 mL) was added. The reaction was heated to 75° C. with stirring for 7 hours. The solvent were evaporated and the residue diluted with water (10 mL). The reaction mixture was acidified with 10% citric acid/water solution and carefully titrated to pH 7-8 with saturated NaHCO$_3$ solution. The precipitated product was collected by vacuum filtration, washing with water. The residue was suspended in EtOH (3 mL, 200 proof) and HCl was added (12.1N, 3 mL). The mixture was heated to 90° C. for 1 hour. The reaction mixture was cooled to room temperature and diluted with water (20 mL), filtered (0.45 µm PTFE frit), and the filtrate concentrated on a rotary evaporator. The residue was further purified by preparative TLC (1000 µm, 10/90 MeOH/DCM) and trituration with methanol at room temperature. The reaction gives 25 mg (12.4%) of the title compound as an off-white solid. $^1$H NMR (400 MHz, DMSO-$d_6$) δ 0.802 (m, 2H), 1.086 (m, 2H), 2.345 (m, 1H), 6.922 (d, J=8 Hz, 1H), 7.000 (d, J=8 Hz, 1H), 7.253 (br. s, 1H), 7.397 (t, J=8 Hz, 1H), 8.022 (br. s, 1H), 10.644 (s, 1H). MS 202 (MH$^+$).

Example 156

N$^5$-methyl-1H-benzo[c][1,2,6]thiadiazine-4,5-diamine-2,2-dioxide

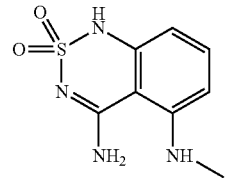
578

Prepared as in Example 90 from 2-amino-6-(methylamino)benzonitrile sulfamide (Example 156a) to give N$^5$-methyl-1H-benzo[c][,6]thiadiazine-4,5-diamine-2,2-dioxide (27.7 mg, 45%). $^1$H NMR (400 MHz, DMSO-$d_6$) δ 2.67 (d, J=2 Hz, 3H), 5.91 (bs, NH), 6.21-6.17 (m, 2H), 7.17 (t, J=8 Hz, 1H), 7.51 (bs, 2H), 10.6 (bs, NH). MS 227 (MH$^+$).

Example 156a 2-amino-6-(methylamino)benzonitrile sulfamide

Prepared as in Example 90a from 2-amino-6-(methylamino)benzonitrile (Example 156b) to give 2-amino-6-(methylamino)benzonitrile sulfamide (65 mg, 30%). $^1$H NMR (400 MHz, CDCl$_3$) δ 2.88 (d, J=5.2 Hz, 3H), 4.23 (bs, NH), 4.66 (bs, NH), 4.87 (bs, 2H), 6.44 (d, J=8 Hz, 1H), 6.90 (d, J=8 Hz, 1H), 7.39 (t, J=8 Hz, 1H). MS 227 (MH$^+$).

Example 156b 2-amino-6-(methylamino)benzonitrile

Prepared as in Example 90b from 2-methylamino-6-nitrobenzonitrile (example 156b) to give 2-amino-6-(methylamino)benzonitrile (0.30 g, 85%) as a brown oil which was used in the next step without any further purification. $^1$H NMR (400 MHz, CDCl$_3$) δ 2.87 (d, J=5.2 Hz, 3H), 4.25 (bs, 2H), 4.47 (bs, NH), 5.96 (d, J=8.8 Hz, 1H), 6.02 (d, J=8.4 Hz, 1H), 7.13 (t, J=8 Hz, 1H). Ms 148 (MH$^+$).

Example 156c 2-methylamino-6-nitrobenzonitrile

Prepared as in Example 90c from 2,6-dinitrobenzonitrile and methylamine to give 2-methylamino-6-nitrobenzonitrile (0.42 g, 79%). $^1$H NMR (400 MHz, DMSO-$d_6$) δ 2.85 (d, J=5.2 Hz, 3H), 6.75 (d, J=4.8 Hz, NH), 7.16 (d, J=8.4 Hz, 1H), 7.45 (d, J=7.6 Hz, 1H), 7.64 (t, J=8.4 Hz, 1H).

Example 157

4-amino-5-(methylamino)quinazolin-2(1H)-one

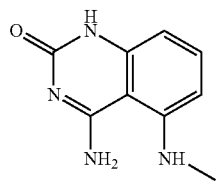

579

A solution of N-(2-cyano-3-(methylamino)phenylcarbamoyl)benzamide (Example 157a) (0.05 g, 0.17 mmol) and NaOH (2N, 0.17 mL) in EtOH (6 mL) was stirred at 90° C. under nitrogen for half an hour. The reaction mixture was cooled down to room temperature, and concentrated under vacuum. H$_2$O (1 mL) was added and the reaction mixture was neutralized to pH~4 with 10% AcOH. The resultant precipitation was filtered and dried under vacuum. The crude product was purified by preparative thin layer chromatography using a DCM/MeOH (9:1) solution as eluant, to give 4-amino-5-(methylamino)quinazolin-2(1H)-one (18.2 mg, 56%). $^1$H NMR (400 MHz, DMSO-d$_6$) δ 2.76 (s, 3H), 6.10 (d, J=7.6 Hz, 1H), 6.12 (d, J=8 Hz, 1H), 7.13 (t, J=8 Hz, 1H), 7.25 (bs, NH), 9.66 (bs, NH,) 10.13 (bs, 2H). MS 191 (MH$^+$).

Example 157a

N-(2-cyano-3-(methylamino)phenylcarbamoyl)benzamide

To a solution of 2-amino-6-(methylamino)benzonitrile (example 156b) (0.14 g, 0.97 mmol) in 1,4-dioxane (3 mL) was added benzoyl isocyanate (0.17 g, 1.17 mmol). The reaction mixture was stirred at room temperature under nitrogen overnight. The obtained precipitate was filtered and dried under vacuum to give N-(2-cyano-3-(methylamino)phenylcarbamoyl)benzamide (57 mg, 20%). $^1$H NMR (400 MHz, DMSO-d$_6$) δ 2.75 (d, J=4.4 Hz, 3H), 6.26 (d, J=4.8 Hz, NH), 6.43 (d, J=9.6 Hz, 1H), 7.40-7.43 (m, 2H), 7.51-7.55 (m, 2H), 7.63-7.65 (m, 1H), 8.01 (d, J=8.4 Hz, 2H), 11.23 (s, NH), 11.30 (s, NH). MS 295 (MH$^+$).

Example 158

N$^5$-propyl-1H-benzo[c][,6]thiadiazine-4,5-diamine-2,2-dioxide

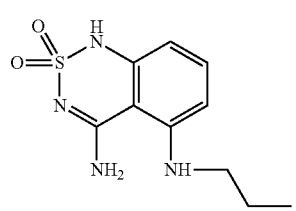

580

Prepared as in Example 90 from 2-amino-6-(propylamino) benzonitrile sulfamide (Example 158a) to give N$^5$-propyl-1H-benzo[c][1,2,6]thiadiazine-4,5-diamine-2,2-dioxide (183 mg, 74%). $^1$H NMR (400 MHz, DMSO-d$_6$) δ 0.91 (t, J=7.2 Hz, 3H), 1.57-1.63 (m, 2H), 2.48 (q, J=7.2, 2H), 5.85-5.88 (m, NH), 6.27 (d, J=8 Hz, 1H), 6.37 (d, J=8.4 Hz, 1H), 7.24 (t, J=8 Hz, 1H), 7.87 (bs, 2H), 10.65 (bs, NH). MS 255 (MH$^+$).

Example 158a 2-amino-6-(propylamino)benzonitrile sulfamide

Prepared as in Example 90a from 2-amino-6-(propylamino)benzonitrile (Example 158l) to give 2-amino-6-(propylamino)benzonitrile sulfamide (254 mg, 43%). $^1$H NMR (400 MHz, CDCl$_3$) δ 0.87 (t, J=7.2 Hz, 3H), 1.48-1.57 (m, 2H), 3.10 (q, J=6, J=5.6, 2H), 5.86-5.89 (m, NH), 6.49 (d, J=8.4 Hz, 1H), 6.69 (d, J=7.6 Hz, 1H), 7.13 (s, 2H), 7.29 (t, J=8 Hz, 1H), 9.06 (s, NH). MS 255 (MH$^+$).

Example 158b 2-amino-6-(propylamino)benzonitrile

Prepared as in Example 90b from 2-propylamino-6-nitrobenzonitrile (example 158c) to give 2-amino-6-(propylamino)benzonitrile (0.41 g, 91%) as a brown oil which was used in the next step without any further purification. MS 175 (MN).

Example 158c 2-propylamino-6-nitrobenzonitrile

Prepared as in Example 90c from 2,6-dinitrobenzonitrile and propylamine 2-propylamino-6-nitrobenzonitrile (0.53 g, 86%). $^1$H NMR (400 MHz, DMSO-d$_6$) δ 0.88 (t, J=7.2 Hz, 3H), 1.51-1.57 (m, 2H), 3.22 (q, J=5.6, J=6.4, 2H), 6.60-6.63 (m, NH), 7.22 (d, J=8.8 Hz, 1H), 7.40 (d, J=7.6 Hz, 1H), 7.58 (t, J=8.4 Hz, 1H).

Example 159

5-(pyrrolidin-1-yl)-1H-benzo[c][1,2,6]thiadiazin-4-amine-2,2-dioxide

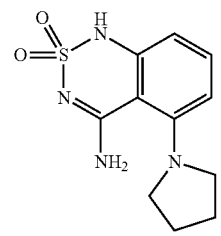

581

Prepared as in Example 90 from 2-amino-6-(pyrrolidin-1-yl)benzonitrile sulfamide (example 159a) to give 5-(pyrrolidin-1-yl)-1H-benzo[c][1,2,6]thiadiazin-4-amine-2,2-dioxide (14.2 mg, 11%). $^1$H NMR (400 MHz, DMSO-d$_6$) δ 1.88-1.86 (m, 4H), 3.16-3.10 (m, br, 4H), 6.45 (d, J=7.6 Hz, 1H), 6.64 (d, J=8.4 Hz, 1H), 7.30 (t, J=8.0 Hz, 1H), 7.83 (s, 1H, NH2), 8.14 (s, 1H, NH2), 10.79 (s, 1NH). MS 267 (MH+).

Example 159a 2-amino-6-(pyrrolidin-1-yl)benzonitrile sulfamide

Prepared as in Example 90a from 2-amino-6-(pyrrolidin-1-yl)benzonitrile (Example 159b) to give 2-amino-6-(pyrrolidin-1-yl)benzonitrile sulfamide (0.34 g, 100%). $^1$H NMR (400 MHz, DMSO-$d_6$) δ 1.94-1.91 (m, 4H), 3.48-3.45 (m, 4H), 6.55 (d, J=7.6 Hz, 1H), 6.81 (d, J=8.0 Hz, 1H), 7.15 (s, 2H, NH$_2$), 7.32 (t, J=8.0 Hz, 1H), 8.9 (s, 1NH). MS 267 (MH+).

Example 159b 2-amino-6-(pyrrolidin-1-yl)benzonitrile

Prepared as in Example 90b from 2-nitro-6-(pyrrolidin-1-yl)benzonitrile (example 159c) to give 2-amino-6-(pyrrolidin-1-yl)benzonitrile (0.48 g, 85%) as a brown oil which was used in the next step without any further purification. $^1$H NMR (400 MHz, DMSO-$d_6$) δ 1.91-1.88 (m, 4H), 3.43-3.40 (m, 4H), 5.61 (s, 2H, NH$_2$), 5.86 (d, J=8.8 Hz, 1H), 6.06 (d, J=8.0 Hz, 1H), 6.99 (t, J=8.0 Hz, 1H). MS 188 (MH+).

Example 159c 2-nitro-6-(pyrrolidin-1-yl)benzonitrile

Prepared as in Example 90c from 2,6-dinitrobenzonitrile and pyrrolidin to give 2-nitro-6-(pyrrolidin-1-yl)benzonitrile which was used in the next step without any further purification. $^1$H NMR (400 MHz, DMSO-$d_6$) δ 1.97-1.94 (m, 4H), 3.60-3.57 (m, 4H), 7.22 (d, J=8.0 Hz, 1H), 7.41 (d, J=6.8 Hz, 1H), 7.58 (t, J=8.0 Hz, 1H). MS 218 (MH+).

Example 160

4-Amino-5-isobutoxy-1H-benzo[c][1,2,6]thiadiazine-2,2-dioxide

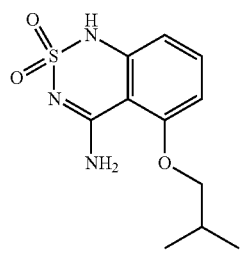

582

Prepared in the same manner as example 111 from 2-sulfamoylamino-6-isobutoxybenzonitrile (example 160a) to provide 4-amino-5-isobutoxy-1H-benzo[c][1,2,6]thiadiazine-2,2-dioxide (65 mg, 50%). $^1$H NMR (400 MHz, DMSO-$d_6$) δ 1.01 (d, J=6.7 Hz, 6H), 2.06 (sept, J=6.6 Hz, 1H), 3.90 (d, J=6.2 Hz, 2H), 6.96 (d, J=8.3 Hz, 1H), 7.15 (d, J=8.0 Hz, 1H), 7.27 (br s, 2H), 7.56 (t, J=8.7 Hz, 1H), 9.46 (s, 1H). MS 270 (MH+).

Example 160a

2-Sulfamoylamino-6-isobutoxybenzonitrile

Prepared in a similar manner as example 111a from 2-amino-6-isobutoxybenzonitrile (example 160b) to provide 2-sulfamoylamino-6-isobutoxybenzonitrile (130 mg, 50%). MS 191 (MH+—NH$_2$SO$_2$).

Example 160b

2-Amino-6-isobutoxybenzonitrile

Prepared in a similar manner as example 111b from 2-isobutoxy-6-nitrobenzonitrile (example 160c) to provide 2-amino-6-isobutoxybenzonitrile. MS 191 (MH+).

Example 160c

2-Isobutoxy-6-nitrobenzonitrile

Prepared in a similar manner as example 160c from 2,6-dinitrobenzonitrile and isobutanol to provide 2-isobutoxy-6-nitrobenzonitrile. $^1$H NMR (400 MHz, DMSO-$d_6$) δ 1.05 (d, J=6.4 Hz, 6H), 2.11 (sept, J=6.6 Hz, 1H), 4.07 (d, J=6.5 Hz, 2H), 7.75 (dd, J=8.0, 1.9 Hz, 1H), 7.91 (t, J=8.2 Hz, 1H), 7.94 (dd, J=8.2, 1.9 Hz, 1H).

Example 161

4-Amino-5-sec-butoxy-1H-benzo[c][1,2,6]thiadiazine-2,2-dioxide

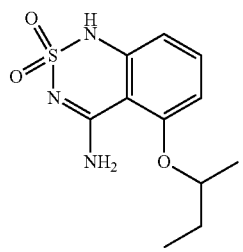

583

Prepared in a similar manner as example 111 from 2-sulfamoylamino-6-sec-butoxybenzonitrile (example 161a) to provide 4-amino-5-sec-butoxy-1H-benzo[c][1,2,6]thiadiazine-2,2-dioxide (57 mg, 44%). $^1$H NMR (400 MHz, DMSO-$d_6$) δ 0.95 (t, J=7.9 Hz, 3H), 1.28 (d, J=5.9 Hz, 3H), 1.67 (m, J=7.4 Hz, 2H), 4.57 (sext, J=5.9 Hz, 1H), 6.98 (d, J=8.7 Hz, 1H), 7.13 (d, J=8.3 Hz, 1H), 7.27 (br s, 2H), 7.55 (t, J=8.3 Hz, 1H), 9.41 (s, 1H). MS 270 (MH+).

Example 161a

2-Sulfamoylamino-6-sec-butoxybenzonitrile

Prepared in a similar manner as example 1a from 2-amino-6-sec-butoxybenzonitrile (example 20b) to provide 2-sulfamoylamino-6-sec-butoxybenzonitrile. MS 191 (MH+—NH$_2$SO$_2$).

Example 161b

2-Amino-6-sec-butoxybenzonitrile

Prepared in a similar manner as example 111b from 2-sec-butoxy-6-nitrobenzonitrile (example 161c) to provide 2-amino-6-sec-butoxybenzonitrile. MS 191 (MH+).

Example 161c

2-sec-Butoxy-6-nitrobenzonitrile

Prepared in a similar manner as example 161c from 2,6-dinitrobenzonitrile and sec-butanol to provide 2-sec-butoxy-6-nitrobenzonitrile. $^1$H NMR (400 MHz, DMSO-$d_6$) δ 0.98 (t, J=7.5 Hz, 3H), 1.33 (d, J=5.9 Hz, 3H), 1.73 (m, 2H), 4.76 (sext, J=5.9 Hz, 1H), 7.78 (dd, J=6.8, 2.8 Hz, 1H), 7.90 (m, 2H).

Example 162

4-Amino-cyclobutoxy-1H-benzo[c][,6]thiadiazine-2,2-dioxide

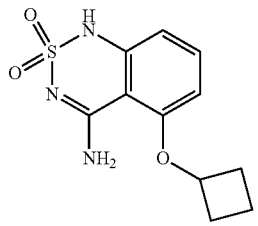

584

Prepared in a similar manner as example 111 from 2-sulfamoylamino-6-cyclobutoxybenzonitrile (example 162a) to provide 4-amino-cyclobutoxy-1H-benzo[c][1,2,6]thiadiazine-2,2-dioxide (19.4 mg, 10%) as a white solid. $^1$H NMR (400 MHz, DMSO-$d_6$) δ 1.65 (m, 1H), 1.79 (m, 1H), 2.19 (m, 2H), 2.43 (m, 2H), 4.82 (m, 1H), 6.52 (d, J=7.9 Hz, 1H), 6.58 (d, J=8.2 Hz, 1H), 7.40 (t, J=8.1 Hz, 1H), 7.78 (br s, 1H), 8.31 (br s, 1H), 10.92 (br s). MS 268 (MH+).

Example 162a

2-Sulfamoylamino-6-cyclobutoxybenzonitrile

Prepared in a similar manner as example 111a from 2-amino-6-cyclobutoxybenzonitrile (example 162b) to provide 2-sulfamoylamino-6-cyclobutoxybenzonitrile (231 mg, 100%) as a white solid. $^1$H NMR (400 MHz, DMSO-$d_6$) δ 1.67 (m, 1H), 1.82 (m, 1H), 2.08 (m, 2H), 2.47 (m, 2H), 4.83 (pent, J=7.2 Hz, 1H), 6.79 (d, J=8.2 Hz, 1H), 7.15 (d, J=8.2 Hz, 1H), 7.28 (br s, 1H), 7.54 (t, J=8.2 Hz, 1H), 9.46 (br s, 1H). MS 268 (MH+).

Example 162b

2-Amino-6-cyclobutoxybenzonitrile

Prepared in a similar manner as example 111b from 2-cyclobutoxy-6-nitrobenzonitrile (example 162c) to provide 2-amino-6-cyclobutoxybenzonitrile (174 mg, 70%) as white needles. $^1$H NMR (400 MHz, DMSO-$d_6$) δ 1.65 (m, 1H), 1.81 (m, 1H), 2.06 (m, 2H), 2.44 (m, 2H), 4.72 (pent, J=7.3 Hz, 1H), 6.00 (br s, 2H), 6.07 (d, J=7.8 Hz, 1H), 6.34 (dd, J=8.2, 0.8 Hz, 1H), 7.17 (t, J=8.1 Hz, 1H). MS 189 (MH+).

Example 162c

2-Cyclobutoxy-6-nitrobenzonitrile

Prepared in a similar manner as example 111c from 2,6-dinitrobenzonitrile and cyclobutanol to provide 2-amino-6-cyclobutoxybenzonitrile (298 mg, 34%) as a white solid. $^1$H NMR (400 MHz, DMSO-$d_6$) δ 1.69 (m, 1H), 1.85 (m, 1H), 2.14 (m, 2H), 2.52 (m, 2H), 4.98 (pent, J=7.3 Hz, 1H), 7.55 (dd, J=8.2, 1.1 Hz, 1H), 7.87 (t, J=8.2 Hz, 1H), 7.92 (dd, J=8.4, 1.3 Hz, 1H).

Example 163

4-Amino-5-cyclobutoxyquinazolin-2(1H)-one

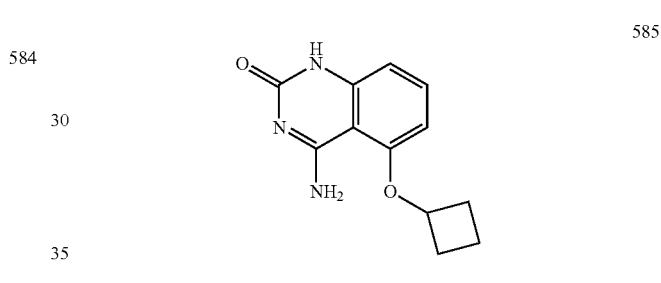

585

Prepared in a similar manner as example 111 from N-(2-cyano-3-cyclobutoxyphenylcarbamoyl)benzamide (example 163a) to provide 4-amino-5-cyclobutoxyquinazolin-2(1H)-one (19.4 mg, 76%) as an off-white solid. $^1$H NMR (400 MHz, DMSO-$d_6$) δ 1.68 (m, 1H), 1.84 (m, 1H), 2.20 (m, 2H), 2.49 (m, 2H), 4.87 (pent, J=7.2 Hz, 1H), 7.52 (d, J=8.2 Hz, 1H), 6.71 (d, J=8.2 Hz, 1H), 7.92 (t, J=8.2 Hz, 1H), 7.48 (br s, 1H), 7.88 (br s, 1H), 10.65 (br s, 1H). MS 232 (MH+).

Example 163a

N-(2-Cyano-3-cyclobutoxyphenylcarbamoyl)benzamide

To a solution of 2-amino-6-cyclobutoxybenzonitrile (example 162b) (30 mg, 0.16 mmol) in 1,4-dioxane (2 mL) was added benzoyl isocyanate (23 mg, 0.16 mmol). The reaction was stirred at rt under $N_2$ for 19 hours. Upon completion, the reaction was diluted with EtOAc, washed with saturated NaHCO$_3$ (2×), water, brine, dried over MgSO$_4$, filtered and concentrated to provide N-(2-cyano-3-cyclobutoxyphenylcarbamoyl)benzamide (38 mg, 71%). $^1$H NMR (400 MHz, DMSO-$d_6$) δ 1.64 (m, 1H), 1.81 (m, 2H), 2.05 (m, 1H), 2.42 (m, 2H), 4.71 (pent, J=7.1 Hz, 1H), 6.05 (d, J=8.2 Hz, 1H), 6.33 (d, J=8.3 Hz, 1H), 7.15 (t, J=8.5 Hz, 1H), 7.45 (m, 1H), 7.56 (m, 2H), 7.87 (m, 1H), 8.05 (m, 1H), 11.35 (s, 1H).

Example 164

4-Amino-5-(3-methylbut-2-en-2-yl)quinazolin-2 (1H)-one

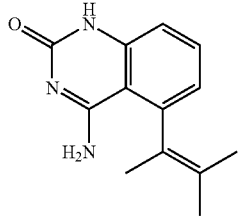

586

Prepared in a similar manner to example 146 from 1N-(2-cyano-3-(3-methylbut-2-en-2-yl)phenylcarbamoyl)benzamide (example 164a) as a white solid. $^1$H NMR (400 MHz, CDCl$_3$) δ 1.44 (s, 3H), 1.83 (s, 3H), 1.89 (s, 3H), 6.65 (dd, J=7.2, 1.0 Hz, 1H), 6.69 (bs, 2H), 7.04 (dd, J=7.2, 1.0 Hz, 1H), 7.48 (t, J=7.2 Hz, 1H), 10.74 (s, 1H). MS 230 (MH$^+$).

Example 164a

N-(2-cyano-3-(3-methylbut-2-en-2-yl)phenyl carbamoyl)benzamide

Prepared in a similar manner to example 146a from 2-amino-6-(3-methylbut-2-en-2-yl)benzonitrile (Example 98a) as a white solid. $^1$H NMR (400 MHz, DMSO-d$_6$) δ 1.47 (s, 3H), 1.81 (s, 3H), 1.92 (s, 3H), 7.01-7.04 (m, 1H), 7.51-7.56 (m, 1H), 7.62-7.69 (m, 3H), 8.01-8.04 (m, 2H), 8.12-8.15 (m, 1H), 11.32 (s, 1H), 11.49 (s, 1H). MS 334 (MH$^+$).

Example 165

Improved synthesis of 4-Amino-5,6-dimethylthieno[2,3-d]pyrimidine-2(1H)-one hydrochloride

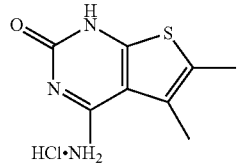

587

This example describes an improved method for preparing the HCl salt of compound I. Specifically, the improved method involves a particular washing protocol and formation of the HCl salt as the final step. When compared to the general method for preparing HCl salt, this method provides significantly more pure material with improved solubility and ease of handling.

To a solution of 4-amino-5,6-dimethylthieno[2,3-d]pyrimidine-2(1H)-one (Example 165a) (1082 g, 5.54 moles) in water (8.1 L) was added an ethanolic solution of HCl (1.25 N in 200 proof ethanol). The resulting slurry was heated to reflux for 15 minutes to afford a clear solution. (In some cases additional 1:1H$_2$O:1.25 N HCl in ethanol must be added to obtain a clear solution). The solution was filtered while hot and the filtrate cooled to 0° C. while stirring. The resulting precipitate was collected by filtration, and washed with acetone (3×5.4 L) and heptane (3×5.4 L). The solids were placed in drying trays and dried under vacuum overnight to give 4-amino-5,6-dimethylthieno[2,3-d]pyrimidine-2(1H)-one hydrochloride as an off white powder (1176 g, 92% yield). >99% pure as determined by HPLC. M.p.: >260° C. $^1$H NMR (400 MHz, DMSO-d$_6$) δ 2.30 (s, 6H), 8.56 (bs, 1H), 9.54 (bs, 1H), 12.92 (bs, 2H). $^{13}$C NMR (400 MHz, DMSO-d$_6$) δ 12.2, 13.3, 106.5, 125.5, 125.7, 146.1, 154.9, 155.3. MS 196.2 (MH$^+$). Purity as determined by HPLC, 99.64%.

Example 165a 4-amino-5,6-dimethylthieno[2,3-d]pyrimidine-2 (1H)-one

Ethanol was added to a 50 L three neck flask (30.8 L) and stirring was initiated. N-(3-cyano-4,5-dimethylthiophen-2-ylcarbamoyl)benzamide (Example 165b) (933 g, 3.12 mol) was added followed by the addition of NaOH (2 N, 4.5 L) The reaction mixture was heated to reflux (~0.77° C.) and stirred under nitrogen for 2.5 hours. The solution was then cooled to 65° C. and treated with charcoal (233 g). After stirring for 30 minutes the hot solution was filtered and the filtrate was slowly cooled to room temperature. The filtrate was carefully neutralized with 4 N HCl with vigorous stirring, then further cooled to −5° C. to 5° C. The resulting precipitate was collected by filtration, washed with water (3×14 L), DMF (1×18.7 L), acetone (3×14 L) and water (3×14 L). The solids were placed in drying trays and dried under vacuum overnight to give 4-amino-5,6-dimethylthieno[2,3-d]pyrimidine-2(1H)-thione (573 g, 87%) as an off-white solid. M.p.: >260° C. $^1$H NMR (400 MHz, DMSO-d$_6$) δ 7.95 (bs, 1H), 2.25 (s, 3H), 2.16 (s, 3H). MS 196 (MH$^+$). Purity as determined by HPLC, 99.64%

Example 165b

N-(3-Cyano-4,5-dimethylthiophen-2-ylcarbamoyl) benzamide

To a solution of 2-amino-4,5-dimethylthiophene-3-carbonitrile (1680 g, 11.04 mol) in 1,4-dioxane (42 L) was added benzoylisocyanate (1624 g, 11.04 mol). The reaction mixture was then stirred at room temperature under nitrogen overnight. The resulting precipitate was collected by filtration, washed with 1,4-dioxane (3×1.7 l) and heptane (3×1.7 L), and dried under vacuum overnight to give N-(3-Cyano-4,5-dimethylthiophen-2-ylcarbamoyl)benzamide as a white solid (2800 g, 84.7% yield). $^1$H NMR (400 MHz, DMSO-d$_6$) δ 2.10 (s, 3H), 2.24 (s, 3H), 7.52-7.56 (m, 2H), 7.64-7.69 (m, 1H), 8.01-8.03 (m, 2H), 11.57 (brs, 1H), 12.05 (brs, 1H). MS 300 (MH$^+$).

Example 166

4-(2-(4-Amino-1H-benzo[c][1,2,6]thiadiazine-2,2-dioxide-5-yloxy)ethyl)piperidinium chloride

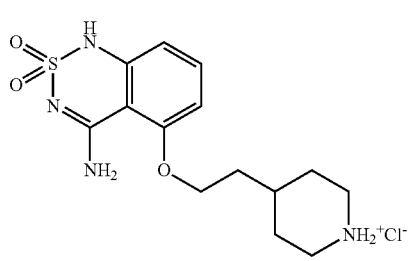

588 tert-Butyl-4-(2-(4-Amino-M-benzo[c][1,2,6]thiadiazine-2,2-dioxide-5-yloxy)ethyl)piperidine-1-carboxylate (Example 166a) (20 mg, 0.047 mmol) was dissolved in a solution of HCl in EtOH (1 mL, 1.25 M). The reaction was stirred at reflux under $N_2$. Upon completion, the precipitate was collected by vacuum filtration to provide the desired product (17 mg, 100%) as a white solid. $^1$H NMR (400 MHz, DMSO-$d_6$) δ 1.38 (m, 2H), 1.73 (m, 1H), 1.81 (m, 2H), 1.87 (m, 2H), 2.84 (m, 2H), 3.24 (m, 2H), 4.21 (t, J=6.4 Hz, 2H), 6.64 (d, J=8.1 Hz, 1H), 6.78 (d, J=8.3 Hz, 1H), 7.47 (t, J=8.3 Hz, 1H), 7.81 (br s, 1H), 8.35 (br s, 1H), 8.59 (m, 1H), 8.85 (m, 1H), 10.99 (br s, 1H). MS 325 (MH$^+$).

Example 166a tert-Butyl 4-(2-(4-amino-1H-benzo[c][1,2,6]thiadiazine-2,2-dioxide-5-yloxy)ethyl)piperidine-1-carboxylate Prepared as in Example 111 from tert-butyl 4-(2-(2-cyano-3-(sulfamoylamino)phenoxy)ethyl)piperidine-1-carboxylate (Example 166b) in 15% yield as a white solid. $^1$H NMR (400 MHz, DMSO-$d_6$) δ 1.07 (qd, J=12.8, 4.6 Hz, 2H), 1.40 (s, 9H), 1.60 (m, 1H), 1.70 (m, 2H), 1.79 (q, J=6.7 Hz, 2H), 2.70 (m, 2H), 3.93 (m, 2H), 4.21 (t, J=6.7 Hz, 2H), 6.62 (d, J=8.1 Hz, 1H), 6.78 (d, J=8.3 Hz, 1H), 7.46 (t, J=8.3 Hz, 1H), 7.82 (br s, 1H), 8.34 (br s, 1H), 10.96 (br s, 1H).

Example 166b tert-Butyl-4-(2-(2-cyano-3-(sulfamoylamino)phenoxy)ethyl)piperidine-1-carboxylate Prepared as in Example 111a from tert-butyl 4-(2-(3-amino-2-cyanophenoxy)ethyl)piperidine-1-carboxylate (Example 166c) in 72% yield as a clear syrup. $^1$H NMR (400 MHz, DMSO-$d_6$) δ 1.08 (m, 2H), 1.40 (s, 9H), 1.71 (m, 5H), 2.70 (m, 2H), 3.93 (m, 2H), 4.17 (t, J=6.3 Hz, 2H), 6.98 (d, J=8.6 Hz, 1H), 7.16 (d, J=8.3 Hz, 1H), 7.28 (br s, 2H), 7.57 (t, J=8.3 Hz, 1H), 9.45 (br s, 1H).

Example 166c tert-Butyl 4-(2-(3-amino-2-cyanophenoxy)ethyl)piperidine-1-carboxylate Prepared as in Example 111b from tert-butyl 4-(2-(2-cyano-3-nitrophenoxy)ethyl)piperidine-1-carboxylate (Example 166d) in 36% as a white foam. $^1$H NMR (400 MHz, CDCl$_3$) δ 1.06 (m, 2H), 1.40 (s, 9H), 1.68 (m, 5H), 2.70 (m, 2H), 3.93 (m, 2H), 4.05 (t, J=6.0 Hz, 2H), 5.98 (br s, 2H), 6.23 (d, J=8.4 Hz, 1H), 6.34 (d, J=8.4 Hz, 1H), 7.18 (t, J=8.2 Hz, 1H).

Example 166d tert-Butyl-4-(2-(2-cyano-3-nitrophenoxy)ethyl)piperidine-1-carboxylate To a suspension of tert-butyl-4-(2-hydroxyethyl)piperidine-1-carboxylate (769 µL, 3.50 mmol) and NaH (118 mg, 3.50 mmol, 60% dispersion in mineral oil) in dry DMF (5 mL) at 0° C., was added a solution of 2,6-dinitrobenzonitrile (614 mg, 3.18 mmol) in dry DMF (4 mL). The reaction was stirred under $N_2$, warming to rt. Upon completion, the reaction was quenched with $H_2O$ (50 mL), and the precipitate was collected by vacuum filtration to provide tert-butyl-4-(2-(2-cyano-3-nitrophenoxy)ethyl)piperidine-1-carboxylate (955 mg, 80%) as a tan solid $^1$H NMR (400 MHz, CDCl$_3$) δ 1.09 (m, 2H), 1.40 (s, 9H), 1.73 (m, 5H), 2.70 (m, 2H), 3.94 (m, 2H), 4.32 (t, J=6.8 Hz, 2H), 7.75 (m, 1H), 7.92 (m, 2H).

Example 167

4-(2-(4-Amino-2-oxo-1,2-dihydroquinazolin-5-yloxy)ethyl)piperidinium chloride

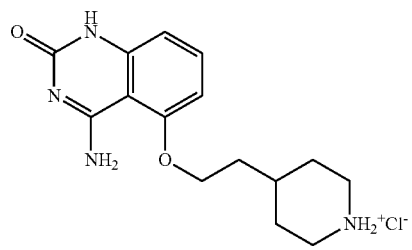

589

Prepared as in Example 166 from tert-butyl 4-(2-(4-amino-2-oxo-1,2-dihydroquinazolin-5-yloxy)ethyl)piperidine-1-carboxylate (Example 167a) in 92% yield as a white solid. $^1$H NMR (400 MHz, DMSO-$d_6$) δ 1.36 (m, 2H), 1.70 (m, 1H), 1.83 (q, J=6.5 Hz, 2H), 1.88 (m, 2H), 2.84 (m, 2H), 3.26 (m, 2H), 4.36 (t, J=6.4 Hz, 2H), 6.86 (d, J=8.3 Hz, 1H), 6.99 (d, J=8.3 Hz, 1H), 7.76 (t, J=8.3 Hz, 1H), 8.50 (br s, 1H), 8.74 (br s, 1H), 8.98 (br s, 1H), 9.46 (br s, 1H), 11.99 (br s, 1H). MS 289 (MH$^+$).

Example 167a tert-Butyl 4-(2-(4-amino-2-oxo-1,2-dihydroquinazolin-5-yloxy)ethyl)piperidine-1-carboxylate Prepared as in Example 111 from tert-butyl 4-(2-(3-(3-benzoylureido)-2-cyanophenoxy)ethyl)piperidine-1-carboxylate (Example 167b) in 31% yield. $^1$H NMR (400 MHz, DMSO-$d_6$) δ 1.08 (qd, J=12.8, 4.6 Hz, 2H), 1.40 (s, 9H), 1.60 (m, 1H), 1.70 (m, 2H), 1.79 (q, J=6.4 Hz, 2H), 2.69 (m, 2H), 3.93 (m, 2H), 4.23 (t, J=6.9 Hz, 2H), 6.73 (m, 2H), 7.47 (t, J=8.2 Hz, 1H), 7.57 (br s, 1H), 7.93 (br s, 1H), 10.73 (br s, 1H).

Example 167b tert-Butyl 4-(2-(3-(3-benzoylureido)-2-cyanophenoxy)ethyl)piperidine-1-carboxylate Prepared as in Example 146a from tert-butyl 4-(2-(3-amino-2-cyanophenoxy)ethyl)piperidine-1-carboxylate (Example 167c) in 100% yield as a white solid. $^1$H NMR (400 MHz, DMSO-$d_6$) δ 1.09 (m, 2H), 1.40 (s, 9H), 1.60 (m, 1H), 1.71 (m, 5H), 2.71 (m, 2H), 3.94 (m, 2H), 4.21 (t, J=6.5 Hz, 2H), 7.01 (d, J=8.5 Hz, 1H), 7.56 (t, J=7.4 Hz, 2H), 7.47 (t, J=8.2 Hz, 1H), 7.64 (t, J=8.5 Hz, 1H), 7.68 (tt, J=7.3, 1.5 Hz, 1H), 7.87 (d, J=8.3 Hz, 1H), 8.05 (m, 2H), 11.35 (br s, 1H), 11.49 (br s, 1H).

Example 168

4-Amino-5-(cyclohexyloxy)-1H-benzo[c][1,2,6]thiadiazine-2,2-dioxide

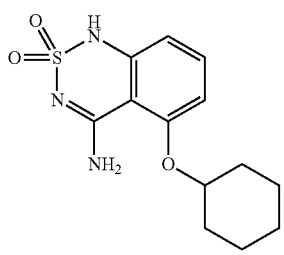

590

Prepared as in Example 111 from 2-sulfamoylamino-6-hexyloxybenzonitrile (Example 168a) in 63% yield as a white crystalline solid. M.p.: 215-216° C. $^1$H NMR (400 MHz, DMSO-d$_6$) δ 1.30-1.71 (m, 8H), 1.99 (m, 2H), 4.63 (m, 1H), 6.60 (dd, J=8.2, 0.8 Hz, 1H), 6.82 (d, J=8.2 Hz, 1H), 7.45 (t, J=8.3 Hz, 1H), 7.83 (br d, J=2.0 Hz, 1H), 8.40 (br d, J=2.4 Hz, 1H), 10.95 (br s, 1H). MS 296 (MH$^+$).

Example 168a

2-Sulfamoylamino-6-cyclohexyloxybenzonitrile

Prepared as in Example 111a from 2-amino-6-cyclohexyloxybenzonitrile (Example 168b) in 91% yield as a white solid. $^1$H NMR (400 MHz, DMSO-d$_6$) δ 1.37 (m, 3H), 1.51 (m, 3H), 1.70 (m, 2H), 1.85 (m, 2H), 4.55 (m, 1H), 6.98 (d, J=8.1 Hz, 1H), 7.10 (d, J=8.5 Hz, 1H), 7.24 (br s, 2H), 7.51 (t, J=8.5 Hz, 1H), 9.39 (s, 1H).

Example 168b

2-Amino-6-cyclohexyloxybenzonitrile

Prepared as in Example 111b from 2-Nitro-6-cyclohexyloxybenzonitrile to provide 2-amino-6-cyclohexyloxybenzonitrile (420 mg, 27%) as a green syrup. $^1$H NMR (400 MHz, CDCl$_3$) δ 1.37 (m, 3H), 1.50 (m, 3H), 1.71 (m, 2H), 1.85 (m, 2H), 4.43 (m, 1H), 5.94 (br s, 2H), 6.26 (d, J=8.6 Hz, 1H), 6.31 (d, J=8.1 Hz, 1H), 7.16 (t, J=8.1 Hz, 1H). MS 215 (MH$^+$).

Example 168c

2-Nitro-6-cyclohexyloxybenzonitrile

Prepared as in Example 166d from 2-nitro-6-cyclohexyloxybenzonitrile and cyclohexanol in 100% yield as a light tan solid. $^1$H NMR (400 MHz, CDCl$_3$) δ 1.45 (m, 4H), 1.60 (m, 2H), 1.74 (m, 2H), 1.90 (m, 2H), 4.76 (m, 1H), 7.79 (m, 1H), 7.89 (m, 2H).

Example 169

4-Amino-5-(cyclopentoxy)-1H-benzo[c][1,2,6]thiadiazine-2,2-dioxide

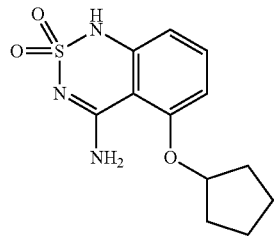

591

Prepared as in Example 111 from 2-sulfamoylamino-6-pentoxybenzonitrile (Example 169a) in 38% yield as off-white needles M.p.: >260° C. $^1$H NMR (400 MHz, DMSO-d$_6$) δ 1.67 (m, 4H), 1.85 (m, 2H), 1.98 (m, 2H), 5.05 (m, 1H), 6.61 (d, J=7.8 Hz, 1H), 6.76 (d, J=7.8 Hz, 1H), 7.46 (t, J=7.8 Hz, 1H), 7.72 (br s, 1H), 8.35 (br s, 1H), 10.96 (br s, 1H). MS 282 (MH$^+$).

Example 169a

2-Sulfamoylamino-6-cyclopentoxybenzonitrile

Prepared as in Example 111a from 2-amino-6-cyclopentoxybenzonitrile (Example 169b) in 100% yield as a light brown syrup. $^1$H NMR (400 MHz, DMSO-d$_6$) δ 1.61 (m, 2H), 1.74 (m, 4H), 1.93 (m, 2H), 4.98 (m, 1H), 6.96 (d, J=9.0 Hz, 1H), 7.14 (d, J=8.2 Hz, 1H), 7.28 (br s, 2H), 7.55 (t, J=8.2 Hz, 1H), 9.43 (s, 1H).

Example 169b

2-Amino-6-cyclopentoxybenzonitrile

Prepared as in Example 111b from 2-Nitro-6-cyclopentoxybenzonitrile (Example 169c) in 84% yield as a green syrup. $^1$H NMR (400 MHz, CDCl$_3$) δ 1.58 (m, 2H), 1.71 (m, 4H), 1.89 (m, 2H), 4.84 (m, 1H), 5.94 (br s, 2H), 6.20 (d, J=8.0 Hz, 1H), 6.31 (d, J=8.3 Hz, 1H), 7.17 (t, J=8.3 Hz, 1H).

Example 169c

2-Nitro-6-cyclopentoxybenzonitrile

Prepared as in Example 166d from 2,6-dinitrobenzonitrile and cyclopentanol in 78% yield as a light tan solid. $^1$H NMR (400 MHz, CDCl$_3$) δ 1.64 (m, 2H), 1.77 (m, 4H), 1.97 (m, 2H), 5.14 (m, 1H), 7.73 (m, 1H), 7.88 (m, 2H).

Example 170

4-(2-(4-Amino-1H-benzo[c][1,2,6]thiadiazine-2,2-dioxide-5-yloxy)methyl)piperidinium chloride

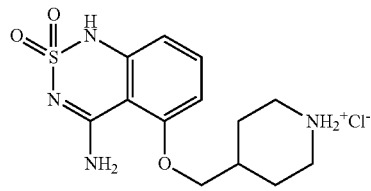

592

Prepared as in Example 166 from tert-butyl 4-(2-(4-amino-1H-benzo[c][1,2,6]thiadiazine-2,2-dioxide-5-yloxy)methyl)piperidine-1-carboxylate (Example 170a) in 89% yield as a white solid. ¹H NMR (400 MHz, DMSO-d₆) δ 1.49 (m, 2H), 1.90 (d, J=13.1 Hz, 2H), 223 (m, 1H), 2.89 (q, J=11.6 Hz, 2H), 3.30 (d, J=12.3 Hz, 2H), 4.09 (br s, J=6.6 Hz, 2H), 6.65 (d, J=8.2 Hz, 1H), 6.82 (d, J=8.2 Hz, 1H), 7.48 (t, J=8.2 Hz, 1H), 7.74 (br s, 1H), 8.33 (br s, 1H), 8.69 (m, 1H), 8.92 (m, 1H), 11.01 (s, 1H). MS 272 (MH⁺).

Example 170a tert-Butyl 4-(2-(4-amino-1H-benzo[c][1,2,6]thiadiazine-2,2-dioxide-5-yloxy)methyl)piperidine-1-carboxylate Prepared as in Example 111 from tert-butyl 44(2-cyano-3-(sulfamoylamino)phenoxy)methyl)piperidine-1-carboxylate (Example 170b) in 91% as a white solid. MS 355 (MH⁺—C(CH₃)₃).

Example 170b tert-Butyl 4-((2-cyano-3-(sulfamoylamino)phenoxy)methyl)piperidine-1-carboxylate Prepared as in Example 111a from tert-butyl 4-((3-amino-2-cyanophenoxy)methyl)piperidine-1-carboxylate (Example 170c) in 56% yield as a white solid. ¹H NMR (400 MHz, DMSO-d₆) δ ¹H NMR (400 MHz, DMSO-d₆) δ 1.20 (m, 2H), 1.41 (s, 9H), 1.76 (d, J=13.2 Hz, 2H), 1.97 (m, 2H), 4.00 (m, 4H), 6.96 (d, J=8.6 Hz, 1H), 7.16 (d, J=8.3 Hz, 1H), 7.28 (s, 2H), 7.57 (t, J=8.3 Hz, 1H), 9.47 (s, 1H).

Example 170c tert-Butyl 4-((3-amino-2-cyanophenoxy)methyl)piperidine-1-carboxylate Prepared as in Example 111b from tert-butyl 4-((2-cyano-3-nitrophenoxy)methyl)piperidine-1-carboxylate (Example 170d) in 74% yield as a white solid. ¹H NMR (400 MHz, DMSO-d₆) δ 1.18 (qd, J=12.6, 3.8 Hz, 2H), 1.41 (s, 9H), 1.74 (d, J=12.6 Hz, 2H), 1.93 (m, 2H), 2.75 (m, 2H), 3.88 (d, J=6.6 Hz, 2H), 3.99 (br d, J=12.1 Hz, 2H), 6.00 (br s, 2H), 6.21 (d, J=8.2 Hz, 1H), 6.34 (d, J=8.3 Hz, 1H), 7.18 (t, J=8.2 Hz, 1H).

Example 170d tert-Butyl 4-((2-cyano-3-nitrophenoxy)methyl)piperidine-1-carboxylate Prepared as in Example 111c from 2,6-dinitrobenzonitrile and tert-butyl 4-(hydroxymethyl)piperidine-1-carboxylate in 73% as a tan solid. ¹H NMR (400 MHz, MeOD) δ 1.24 (qd, J=12.8, 4.4 Hz, 2H), 1.41 (s, 9H), 1.78 (br d, J=12.1 Hz, 2H), 2.02 (m, 2H), 2.77 (m, 2H), 4.00 (br d, J=13.1 Hz, 2H), 4.15 (d, J=6.3 Hz, 2H), 7.74 (dd, J=7.5, 1.5 Hz, 1H), 7.91 (m, 2H).

Example 171

4-Amino-5-(cyclobutylmethoxy)-1H-benzo[c][1,2,6]thiadiazine-2,2-dioxide

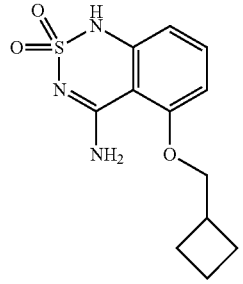

593

Prepared as in Example 111 from 2-sulfamoylamino-6-cyclobutylmethoxybenzonitrile (Example 171a) in 21% yield as a yellow solid. ¹H NMR (400 MHz, DMSO-d₆) δ 1.88 (m, 4H), 2.08 (m, 2H), 2.86 (sept, J=7.9 Hz, 1H), 4.16 (d, J=6.9 Hz, 2H), 6.62 (dd, J=8.2, 1.2 Hz, 1H), 6.77 (dd, J=8.6, 0.7 Hz, 1H), 7.47 (t, J=8.2 Hz, 1H), 7.76 (br s, 1H), 8.39 (br s, 1H), 10.98 (br s, 1H). MS 282 (MH⁺).

Example 171a

2-Sulfamoylamino-6-cyclobutylmethoxybenzonitrile

Prepared as in Example 111a from 2-amino-6-cyclobutylmethoxybenzonitrile (Example 171b) in 94% as a light yellow solid. ¹H NMR (400 MHz, DMSO-d₆) δ 1.94 (m, 4H), 2.12 (m, 2H), 2.86 (sept, J=7.5 Hz, 1H), 4.13 (d, J=6.3 Hz, 2H), 7.00 (d, J=8.4 Hz, 1H), 7.19 (d, J=8.2 Hz, 1H), 7.31, (br s, 2H), 7.60 (t, J=8.4 Hz, 1H), 9.48 (br s, 1H).

Example 171b

2-Amino-6-cyclobutylmethoxybenzonitrile

Prepared as in Example 111b from 2-nitro-6-cyclobutylmethoxybenzonitrile (Example 171c) in 41% yield as a yellow oil. MS 203 (MH⁺).

Example 171c

2-Nitro-6-cyclobutylmethoxybenzonitrile

Prepared as in Example 166d from 2,6-dinitrobenzonitrile and cyclobutylmethanol in 68% as a tan solid. ¹H NMR (400 MHz, DMSO-d₆) δ 1.93 (m, 4H), 2.10 (m, 2H), 2.79 (m, 1H), 4.25 (d, J=6.3 Hz, 2H), 7.74 (dd, J=8.5, 2.2 Hz, 1H), 7.91 (m, 2H).

Example 172

4-Amino-5-(tetrahydro-2H-pyran-4-yloxy)-1H-benzo[c][1,2,6]thiadiazine-2,2-dioxide

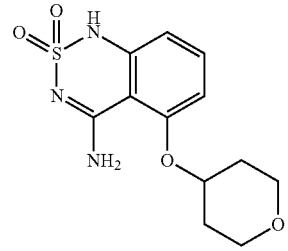

594

Prepared as in Example 111 from 2-sulfamoylamino-6-(tetrahydro-2H-pyran-4-yloxy)benzonitrile (Example 172a) in 69% yield as a white solid. ¹H NMR (400 MHz, DMSO-d₆) δ 1.77 (m, 2H), 2.05 (m, 2H), 3.51 (td, J=11.6, 2.1 Hz, 2H), 3.85 (dt, J=11.4, 3.9 Hz, 2H), 4.83 (sept, J=4.1 Hz, 1H), 6.62 (d, J=8.0 Hz, 1H), 6.88 (d, J=8.4 Hz, 1H), 7.46 (t, J=8.2 Hz, 1H), 7.78 (br s, 1H), 8.39 (br s, 1H), 10.96 (br s, 1H). MS 298 (MH⁺).

Example 172a

2-Sulfamoylamino-6-(tetrahydro-2H-pyran-4-yloxy)benzonitrile

Prepared as in Example 111a from 2-amino-6-(tetrahydro-2H-pyran-4-yloxy)benzonitrile (Example 172b) in 58% as a light orange solid. ¹H NMR (400 MHz, DMSO-d₆) δ 1.64 (m, 2H), 1.99 (m, 2H), 3.53 (ddd, J=11.6, 8.3, 3.1 Hz, 2H), 3.85 (m, 2H), 4.80 (sept, J=4.0 Hz, 1H), 7.07 (d, J=8.3 Hz, 1H), 7.16 (d, J=8.1 Hz, 1H), 7.28 (br s, 2H), 7.56 (t, J=8.5 Hz, 1H), 9.47 (br s, 1H).

Example 172b

2-Amino-6-(tetrahydro-2H-pyran-4-yloxy)benzonitrile

Prepared as in Example 111b from 2-nitro-6-(tetrahydro-2H-pyran-4-yloxy)benzonitrile (Example 172c) in 49% as an orange syrup. MS 219 (MH⁺).

Example 172c

2-Nitro-6-(tetrahydro-2H-pyran-4-yloxy)benzonitrile

Prepared as in Example 166d from 2,6-dinitrobenzonitrile and tetrahydro-2H-pyran-4-ol in 100% yield as a tan solid. ¹H NMR (400 MHz, DMSO-d₆) δ 1.69 (m, 2H), 2.03 (m, 2H), 3.56 (m, 2H), 3.87 (m, 2H), 4.98 (sept, J=3.8 Hz, 1H), 7.90 (m, 3H).

Example 173

4-Amino-5-(cyclopentyloxy)quinazolin-2(1H)-one

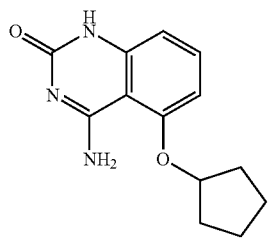

595

Prepared as in Example 111 from N-(2-cyano-3-(cyclopentyloxy)phenylcarbamoyl)benzamide (Example 173a) in 45% yield as a white solid. ¹H NMR (400 MHz, DMSO-d₆) δ 1.68 (m, 4H), 1.84 (m, 2H), 1.99 (m, 2H), 5.06 (m, 1H), 6.70 (d, J=8.3 Hz, 2H), 7.43 (s, 1H), 7.45 (t, J=8.2 Hz, 1H), 7.85 (br s, 1H), 10.65 (br s, 1H).

Example 173a

N-(2-Cyano-3-(cyclopentyloxy)phenylcarbamoyl)benzamide

Prepared as in Example 146a from 2-amino-6-cyclopentoxybenzonitrile (Example 173b) in 70% yield as a yellow solid. ¹H NMR (400 MHz, DMSO-d₆) δ 1.63 (m, 2H), 1.77 (m, 4H), 1.98 (m, 2H), 5.03 (m, 1H), 6.98 (d, J=8.6 Hz, 1H), 7.55 (t, J=7.6 Hz, 2H), 7.62 (t, J=8.6 Hz, 1H), 7.67 (tt, J=7.4, 1.2 Hz, 1H), 7.87 (d, J=8.0 Hz, 1H), 8.06 (m, 2H), 11.37 (br s, 1H), 11.54 (br s, 1H).

Example 174

4-Amino-5-(tetrahydrofuran-3-yloxy)-1H-benzo[c][1,2,6]thiadiazine-2,2-dioxide

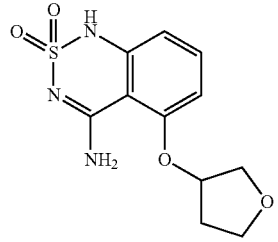

596

Prepared as in Example 111 from 2-sulfamoylamino-6-(tetrahydrofuran-3-yloxy)benzonitrile (Example 174a) in 33% yield as a white solid. ¹H NMR (400 MHz, DMSO-d₆) δ 2.07 (m, 1H), 2.26 (m, 1H), 3.74 (td, J=8.4, 4.7 Hz, 1H), 3.84 (m, 2H), 3.95 (d, J=10.4 Hz, 1H), 5.23 (m, 1H), 6.61 (d, J=8.1 Hz, 1H), 6.73 (d, J=8.4 Hz, 1H), 7.45 (t, J=8.1 Hz, 1H), 7.64 (br s, 1H), 8.33 (br s, 1H), 10.97 (br s, 1H). MS 284 (MH⁺).

Example 174a

2-Sulfamoylamino-6-(tetrahydrofuran-3-yloxy)benzonitrile

Prepared as in Example 111a from 2-amino-6-(tetrahydrofuran-3-yloxy)benzonitrile (Example 174b) in 40% yield as an off-white solid. ¹H NMR (400 MHz, DMSO-d₆) δ 1.99 (m, 1H), 2.28 (m, 1H), 3.77 (td, J=8.3, 4.7 Hz, 1H), 3.83 (m, 1H), 3.87 (d, J=7.3 Hz, 1H), 3.92 (dd, J=10.2, 4.4 Hz, 1H), 5.19 (m, 1H), 6.96 (d, J=8.3 Hz, 1H), 7.18 (d, J=8.3 Hz, 1H), 7.29 (s, 2H), 7.58 (t, J=8.3 Hz, 1H), 9.49 (br s, 1H).

Example 174b

2-Amino-6-(tetrahydrofuran-3-yloxy)benzonitrile

Prepared as in Example 111b from 2-nitro-6-(tetrahydrofuran-3-yloxy)benzonitrile (Example 174c) in 97% yield as a light brown syrup. MS 205 (MH⁺).

Example 174c

2-Nitro-6-(tetrahydrofuran-3-yloxy)benzonitrile

Prepared as in Example 166d from 2,6-dinitrobenzonitrile and tetrahydrofuran-3-ol in 50% yield as a light yellow solid. ¹H NMR (400 MHz, DMSO-d₆) δ 2.04 (m, 1H), 2.32 (m, 1H), 3.81 (td, J=8.3, 4.6 Hz, 1H), 3.89 (m, 2H), 3.98 (dd, J=10.8, 4.5 Hz, 1H), 5.36 (m, 1H), 7.75 (dd, J=8.1, 1.5 Hz, 1H), 7.91 (t, J=8.2 Hz, 1H), 7.95 (dd, J=8.2, 1.6 Hz, 1H).

Example 175

4-Amino-5-(1-isopropylpiperidin-4-yloxy)-1H-benzo[c][1,2,6]thiadiazine-2,2-dioxide

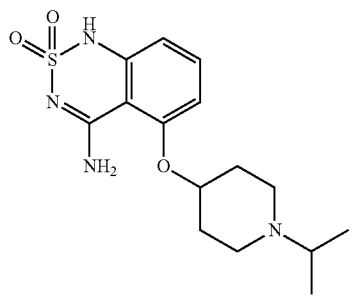

597

Prepared as in Example 111 from 2-sulfamoylamino-6-(1-isopropylpiperidin-4-yloxy)benzonitrile (Example 175b) in 12% yield as a white solid. $^1$H NMR (400 MHz, DMSO-d$_6$) δ 1.24 (d, J=6.7 Hz, 6H), 2.11 (m, 2H), 2.28 (m, 2H), 3.13 (m, 4H), 4.87 (m, 1H), 6.67 (d, J=8.0 Hz, 1H), 6.87 (d, J=8.6 Hz, 1H), 7.49 (t, J=8.3 Hz, 1H), 7.67 (br s, 1H), 8.43 (br s, 1H), 10.79 (br s, 1H). MS 339 (MH$^+$).

Example 175a

2-Sulfamoylamino-6-(1-isopropylpiperidin-4-yloxy)benzonitrile

Prepared as in Example 111a from 2-amino-6-(1-isopropylpiperidin-4-yloxy)benzonitrile (Example 175b). The product was carried onto the next step without further purification.

Example 175b

2-Amino-6-(1-isopropylpiperidin-4-yloxy)benzonitrile

Prepared as in Example 111b from 2-nitro-6-(1-isopropylpiperidin-4-yloxy)benzonitrile (Example 175c) in 80% yield as a brown syrup. MS 260 (MH$^+$).

Example 175c

2-Nitro-(1-isopropylpiperidin-4-yloxy)-6-benzonitrile

Prepared as in Example 166d from 2,6-dinitrobenzonitrile and 1-isopropylpiperidin-4-ol in 90% yield as a tan solid. $^1$H NMR (400 MHz, DMSO-d$_6$) δ 0.99 (d, J=6.8 Hz, 6H), 1.72 (m, 2H), 1.95 (m, 2H), 2.41 (m, 2H), 2.71 (m, 3H), 4.80 (m, 1H), 7.81 (dd, J=8.2, 1.3 Hz, 1H), 7.89 (m, 2H).

Example 176

(R)-4-Amino-5-((1-butyrylpyrrolidin-2-yl)methoxy)-1H-benzo[c][1,2,6]thiadiazine-2,2-dioxide

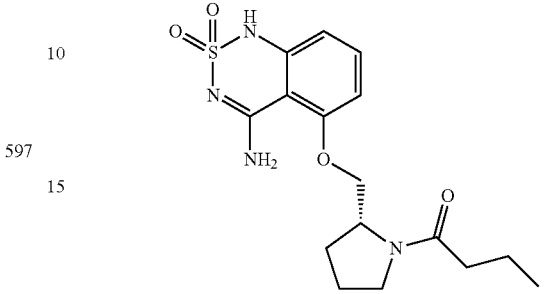

598

To a solution of (R)-2-amino-6-((1-butyrylpyrrolidin-2-yl)methoxy)benzonitrile (84 mg, 0.29 mmol) (Example 176a) in acetonitrile (9 mL), was added sulfamoyl chloride (70 mg, 0.60 mmol). The reaction was stirred at rt for 20 h, and upon completion was concentrated in vacuo. The resulting residue was dissolved in EtOH (1 mL), and 2N aqueous NaOH (4 mL) was added. The mixture was refluxed for 2 h, and upon completion was cooled to rt, neutralized with 1N HCl and stirred at 0° C. The resulting precipitate was collected by vacuum filtration to provide the desired product (38 mg, 35%) as a white solid. $^1$H NMR (400 MHz, DMSO-d$_6$) δ 0.89 (t, J=7.3 Hz, 3H), 1.54 (sext, J=7.3 Hz, 2H), 1.94 (m, 4H), 2.26 (t, J=7.3 Hz, 2H), 3.49 (m, 2H), 4.10 (m, 1H), 4.25 (m, 1H), 4.43 (m, 1H), 6.62 (d, J=8.2 Hz, 1H), 6.90 (d, J=8.2 Hz, 1H), 7.45 (t, J=8.2 Hz, 1H), 8.08 (br s, 1H), 8.34 (br s, 1H), 10.93 (br s, 1H). MS 367 (MH$^+$).

Example 176a (R)-2-Amino-6-((1-butyrylpyrrolidin-2-yl)methoxy)benzonitrile

Prepared as in Example 111b from (R)-2-((1-butyrylpyrrolidin-2-yl)methoxy)-6-nitrobenzonitrile (Example 176b) in 77% yield. MS 274 (MH$^+$).

Example 176b (R)-2-((1-Butyrylpyrrolidin-2-yl)methoxy)-6-nitrobenzonitrile

To a suspension of (R)-2-((2-cyano-3-nitrophenoxy)methyl)pyrrolidinium chloride (140 mg, 0.49 mmol) (Example 176c) in THF (3 mL) were added Et$_3$N (143 μL, 1.03 mmol) and butyryl chloride (56 μL, 0.54 mmol). The reaction was stirred for 72 h at rt under N$_2$. Upon completion, the reaction was filtered, and the filtrate was concentrated to provide (R)-2-((1-butyrylpyrrolidin-2-yl)methoxy)-6-nitrobenzonitrile (127 mg, 82%) as a yellow syrup. MS 318 (MH$^+$).

Example 176c (R)-2-((2-Cyano-3-nitrophenoxy)methyl)pyrrolidinium chloride

Prepared as in Example 166 from (R)-tert-butyl 2-((2-cyano-3-nitrophenoxy)methyl)pyrrolidine-1-carboxylate (Example 176d) in 71% yield as an off-white solid. $^1$H NMR (400 MHz, DMSO-d$_6$) δ 1.92 (m, 2H), 2.14 (m, 2H), 3.28 (m, 2H), 4.07 (m, 2H), 4.50 (dd, J=710.6, 6.4 Hz, 1H), 4.57 (dd, J=10.9, 3.5 Hz, 1H), 7.77 (d, J=8.0 Hz, 1H), 7.98 (m, 2H), 9.36 (br s, 1H), 9.74 (br s, 1H).

Example 176d (R)-tert-Butyl 2((2-cyano-3-nitrophenoxy)methyl)pyrrolidine-1-carboxylate Prepared as in Example 166d from 2,6-dinitrobenzonitrile and (R)-tert-butyl 2-(hydroxymethyl)pyrrolidine-1-carboxylate in 87% yield as a tan solid. $^1$H NMR (400 MHz, DMSO-$d_6$) δ 1.39 (s, 9H), 1.82 (m, 1H), 2.02 (m, 3H), 3.32 (m, 2H), 4.08 (m, 1H), 4.32 (m, 2H), 7.79 (d, J=8.0 Hz, 1H), 7.91 (m, 2H).

Example 177

(R)-2-((4-Amino-1H-benzo[c][1,2,6]thiadiazine-2,2-dioxide-5-yloxy)methyl)-N-propylpyrrolidine-1-carboxamide

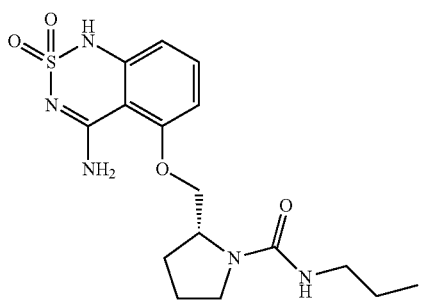

599

Prepared as in Example 176 from (R)-2-((3-amino-2-cyanophenoxy)methyl)-N-propylpyrrolidine-1-carboxamide (Example 177a) in 57% yield as a white solid. $^1$H NMR (400 MHz, DMSO-$d_6$) δ 0.83 (t, J=7.6 Hz, 3H), 1.42 (sext, J=7.3 Hz, 2H), 1.90 (m, 4H), 3.00 (m, 2H), 3.20 (m, 1H), 3.43 (m, 2H), 4.01 (m, 1H), 4.16 (m, 1H), 4.33 (m, 1H), 6.27 (m, 1H), 6.61 (d, J=8.4 Hz, 1H), 6.89 (d, J=8.3 Hz, 1H), 7.45 (t, J=8.2 Hz, 1H), 8.19 (br s, 1H), 8.27 (br s, 1H), 10.91 (s, 1H). MS 382 (MH$^+$).

Example 177a (R)-2-((3-Amino-2-cyanophenoxy)methyl)-N-propylpyrrolidine-1-carboxamide Prepared as in Example 111b from (R)-2-((2-cyano-3-nitrophenoxy)methyl)-N-propylpyrrolidine-1-carboxamide (Example 177b) in 14% yield. MS 303 (MH$^+$).

Example 177b (R)-2-((2-Cyano-3-nitrophenoxy)methyl)-N-propylpyrrolidine-1-carboxamide Prepared as in Example 176b from (R)-2-((2-cyano-3-nitrophenoxy)methyl)pyrrolidinium chloride (Example 176c) and propyl isocyanate in 100% yield as a light yellow solid. MS 333 (MH$^+$).

Example 178

(R)-2-((4-Amino-1H-benzo[c][1,2,6]thiadiazine-2,2-dioxide-5-yloxy)methyl)-N-ethylpyrrolidine-1-carboxamide

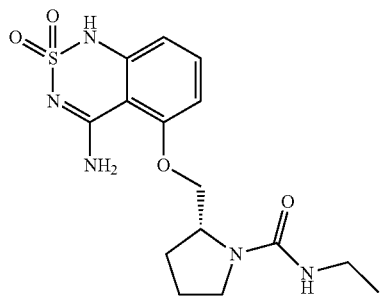

600

Prepared as in Example 176 from (R)-2-((3-amino-2-cyanophenoxy)methyl)-N-ethylpyrrolidine-1-carboxamide (Example 178a) in 60% yield as a white solid. $^1$H NMR (400 MHz, DMSO-$d_6$) δ 1.02 (t, J=6.8 Hz, 3H), 1.90 (m, 4H), 3.08 (quint, J=6.8 Hz, 2H), 3.20 (m, 2H), 4.01 (m, 1H), 4.16 (m, 1H), 4.33 (m, 1H), 6.27 (m, 1H), 6.62 (d, J=8.4 Hz, 1H), 6.89 (d, J=8.4 Hz, 1H), 7.46 (t, J=8.4 Hz, 1H), 8.20 (br s, 1H), 8.27 (br s, 1H), 10.91 (s, 1H). MS 368 (MH$^+$).

Example 178a (R)-2-((3-Amino-2-cyanophenoxy)methyl)-N-ethylpyrrolidine-1-carboxamide Prepared as in Example 111b from (R)-2-((2-cyano-3-nitrophenoxy)methyl)-N-ethylpyrrolidine-1-carboxamide (Example 178b) in 62% yield. MS 289 (MH$^+$).

Example 178b (R)-2-((2-Cyano-3-nitrophenoxy)methyl)-N-ethylpyrrolidine-1-carboxamide Prepared as in Example 176b from (R)-2-((2-cyano-3-nitrophenoxy)methyl)pyrrolidinium chloride (Example 176c) and ethyl isocyanate in 95% yield as a light yellow solid. MS 319 (MH$^+$).

Example 179

(R)-4-Amino-5-((1-isobutyrylpyrrolidine-2-yl)methoxy)-1H-benzo[c][,6]thiadiazine-2,2-dioxide

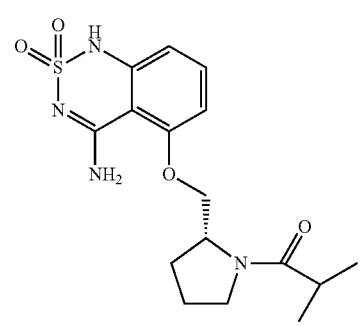

601

Prepared as in Example 176 from (R)-2-amino-6-((1-isobutyrylpyrrolidine-2-yl)methoxy)benzonitrile (Example 179b) in 100% yield as a white solid. ¹H NMR (400 MHz, DMSO-d₆) δ 1.02 (d, J=6.3 Hz, 6H), 1.94 (m, 4H), 2.70 (m, 1H), 3.55 (m, 2H), 4.12 (m, 1H), 4.24 (m, 1H), 4.43 (m, 1H), 6.62 (d, J=7.9 Hz, 1H), 6.91 (d, J=8.1 Hz, 1H), 7.47 (t, J=8.1 Hz, 1H), 8.04 (br s, 1H), 8.34 (br s, 1H), 10.93 (br s, 1H). MS 367 (MH⁺).

Example 179a (R)-2-Amino-6-((1-isobutyrylpyrrolidine-2-yl)methoxy)benzonitrile

Prepared as in Example 111b from (R)-2-(O-isobutyrylpyrrolidine-2-yl)methoxy)-6-nitrobenzonitrile (Example 179b) in 80% yield as a clear syrup. MS 288 (MH⁺).

Example 179b (R)-2-((1-Isobutyrylpyrrolidine-2-yl)methoxy)-6-nitrobenzonitrile

Prepared as in Example 176b from (R)-2-((2-cyano-3-nitrophenoxy)methyl)pyrrolidinium chloride and isobutyryl chloride in 100% yield as a yellow solid. ¹H NMR (400 MHz, DMSO-d₆) δ 0.96 (dd, J=6.6, 3.5 Hz, 6H), 1.93 (m, 4H), 2.14 (m, 1H), 2.66 (sept, J=6.6 Hz, 1H), 3.55 (m, 1H), 4.28 (m, 3H), 7.79 (dd, J=7.6, 1.8 Hz, 1H), 7.89 (m, 2H).

Example 180

(R)-4-Amino-5-((1-pivaloylpyrrolidin-2-yl)methoxy)-1H-benzo[c][1,2,6]thiadiazine-2,2-dioxide

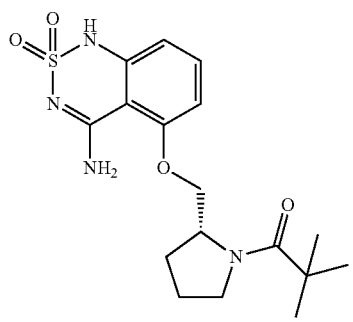

602

Prepared as in Example 176 from (R)-2-amino-6-((1-pivaloylpyrrolidin-2-yl)methoxy)benzonitrile (Example 180a) in 64% yield as a white solid. ¹H NMR (400 MHz, DMSO-d₆) δ 1.18 (s, 9H), 1.92 (m, 4H), 3.55 (m, 1H), 3.73 (m, 1H), 4.13 (m, 1H), 4.27 (m, 1H), 4.48 (m, 1H), 6.62 (d, J=8.2 Hz, 1H), 6.92 (d, J=8.2 Hz, 1H), 7.47 (t, J=8.2 Hz, 1H), 7.95 (br s, 1H), 8.37 (br s, 1H), 10.95 (br s, 1H). MS 381 (MH⁺).

Example 180a (R)-2-Amino-6-((1-pivaloylpyrrolidin-2-yl)methoxy)benzonitrile

Prepared as in Example 111b from (R)-2-((1-pivaloylpyrrolidin-2-yl)methoxy)-6-nitrobenzonitrile (Example 180bW) in 91% yield as a clear syrup. MS 302 (MH⁺).

Example 180b (R)-2-((1-Pivaloylpyrrolidin-2-yl)methoxy)-6-nitrobenzonitrile

Prepared as in Example 176b from (R)-2-((2-cyano-3-nitrophenoxy)methyl)pyrrolidinium chloride and pivaloyl chloride in 99%. ¹H NMR (400 MHz, DMSO-d₆) δ 1.16 (s, 9H), 1.91 (m, 3H), 2.13 (m, 1H), 3.70 (m, 2H), 4.35 (m, 3H), 7.81 (dd, J=7.5, 2.1 Hz, 1H), 7.92 (m, 2H).

Example 181

(R)-2-((4-Amino-1H-benzo[c][,6]thiadiazine-2,2-dioxide-5-yloxy)methyl)-N-isopropylpyrrolidine-1-carboxamide

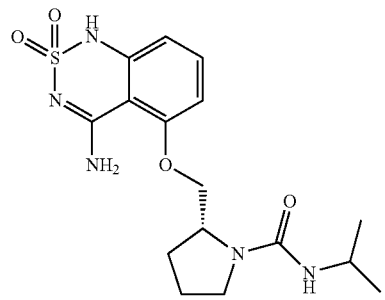

603

Prepared as in Example 176 from (R)-2-((3-amino-2-cyanophenoxy)methyl)-N-isopropylpyrrolidine-1-carboxamide (Example 181a) in 23% yield as an off-white solid. ¹H NMR (400 MHz, DMSO-d₆) δ 1.05 (d, J=6.4 Hz, 6H), 1.87 (m, 4H), 3.17 (m, 1H), 3.79 (m, 1H), 3.98 (m, 1H), 4.15 (m, 1H), 4.31 (m, 1H), 5.88 (d, J=7.4 Hz, 1H), 6.59 (d, J=8.2 Hz, 1H), 6.86 (d, J=8.5 Hz, 1H), 7.43 (t, J=8.2 Hz, 1H), 8.18 (br s, 1H), 8.23 (br s, 1H), 10.88 (s, 1H). MS 382 (MH⁺).

Example 181a (R)-2-((3-Amino-2-cyanophenoxy)methyl)-N-isopropylpyrrolidine-1-carboxamide Prepared as in Example 111b from (R)-2-((2-cyano-3-nitrophenoxy)methyl)-N-isopropylpyrrolidine-1-carboxamide (Example 181b) in 86% yield as a clear syrup. ¹H NMR (400 MHz, DMSO-d₆) δ 1.07 (d, J=5.9 Hz, 6H), 1.89 (m, 3H), 2.10 (m, 1H), 3.16 (m, 1H), 3.45 (m, 1H), 3.78 (m, 1H), 3.91 (m, 1H), 4.06 (m, 1H), 4.12 (m, 1H), 5.85 (d, J=7.7 Hz, 6.00 (br s, 2H), 6.31 (d, J=8.4 Hz, 1H), 6.34 (d, J=8.4 Hz, 1H), 7.18 (t, J=8.4 Hz, 1H).

Example 181b (R)-2-((2-Cyano-3-nitrophenoxy)methyl)-N-isopropylpyrrolidine-1-carboxamide Prepared as in Example 176b from (R)-2-((2-cyano-3-nitrophenoxy)methyl)pyrrolidinium chloride (Example 176c) and isopropyl isocyanate in 100% yield as a yellow solid. ¹H NMR (400 MHz, DMSO-d₆) δ 1.07 (d, J=6.5 Hz, 6H), 1.91 (m, 3H), 2.13 (m, 1H), 3.17 (m, 1H), 3.79 (m, 1H), 4.19 (m, 2H), 4.32 (d, J=8.8 Hz, 1H), 5.91 (d, J=8.1 Hz, 1H), 7.89 (m, 3H).

Example 182

(R)-2-((4-Amino-1H-benzo[c][1,2,6]thiadiazine-2,2-dioxide-5-yloxy)methyl)-N-tert-butylpyrrolidine-1-carboxamide

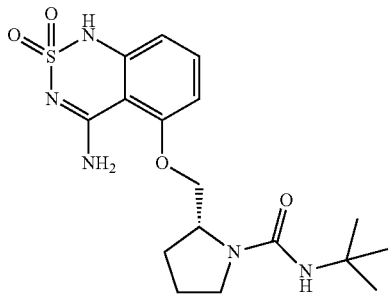

Prepared as in Example 176 from (R)-2-((3-amino-2-cyanophenoxy)methyl)-N-tert-butylpyrrolidine-1-carboxamide (Example 182a) in 56% yield as an off-white solid. $^1$H NMR (400 MHz, DMSO-d$_6$) δ 1.27 (s, 9H), 1.89 (m, 4H), 3.21 (m, 1H), 4.02 (m, 1H), 4.19 (m, 1H), 4.34 (m, 1H), 5.35 (s, 1H), 6.62 (m, 1H), 6.86 (m, 1H), 7.46 (m, 1H), 8.23 (br s, 1H), 8.25 (br s, 1H), 10.91 (s, 1H). MS 396 (MH$^+$).

Example 182a (R)-2-((3-Amino-2-cyanophenoxy)methyl)-N-tert-butylpyrrolidin-1-carboxamide Prepared as in Example 111b from (R)-2-((2-cyano-3-nitrophenoxy)methyl)-N-tert-butylpyrrolidine-1-carboxamide (Example 182b) in 96% yield as a white solid. MS 317 (MH$^+$).

Example 182b (R)-2-((2-Cyano-3-nitrophenoxy)methyl)-N-tert-butylpyrrolidine-1-carboxamide Prepared as in Example 176b from (R)-2-((2-cyano-3-nitrophenoxy)methyl)pyrrolidinium chloride (Example 176c) and ten-butyl isocyanate in 100% yield as an off-white solid. $^1$H NMR (400 MHz, DMSO-d$_6$) δ 1.s7 (s, 9H), 1.86 (m, 1H), 1.95 (m, 2H), 2.12 (m, 1H), 3.18 (m, 1H), 3.37 (m, 1H), 4.20 (m, 1H), 4.23 (dd, J—16.0, 6.3 Hz, 1H), 4.31 (dd, J=9.7, 2.7 Hz, 1H), 5.36 (s, 1H), 7.84 (dd, J=7.4, 0.9 Hz, 1H), 7.91 (m, 2H).

Example 183

4-Amino-5-(pentan-3-yloxy)-1H-benzo[c][1,2,6]thiadiazine-2,2-dioxide

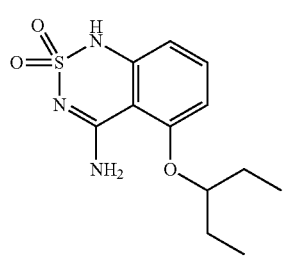

Prepared as in Example 111 from 2-sulfamoylamino-6-(pentan-3-yloxy)benzonitrile (Example 183a) in 48.7% yield. $^1$H NMR (400 MHz, DMSO-d$_6$) δ 0.91 (t, J=7.6 Hz, 6H), 1.73 (m, 4H), 4.54 (m, 1H), 6.59 (dd, J=8.4, 1.2 Hz, 1H), 6.79 (d, J=8.0 Hz, 1H), 7.45 (t, J=8.4 Hz, 1H), 7.84 (br d, J=2.8 Hz, 1H), 8.38 (br d, J=1.6 Hz, 1H), 10.96 (s, 1H). MS 284 (MH$^+$).

Example 183a

2-Sulfamoylamino-6-(pentan-3-yloxy)benzonitrile

Prepared as in Example 111a from 2-amino-6-(pentan-3-yloxy)benzonitrile (Example 183b) in 68.1% yield. MS 284 (MH$^+$).

Example 183b

2-Amino-6-(pentan-3-yloxy)benzonitrile

Prepared as in Example 111b from 2-nitro-6-(pentan-3-yloxy)benzonitrile (Example 183c) in 100% yield. MS 205 (MH$^+$).

Example 183c

2-Nitro-6-(pentan-3-yloxy)benzonitrile

Prepared as in Example 111c from pentan-3-ol and 2,6-dinitrobenzonitrile in 86.5% yield. $^1$H NMR (400 MHz, DMSO-d$_6$) δ 0.94 (t, J=7.6 Hz, 6H), 1.70 (m, 4H), 4.62 (m, 1H), 7.78 (dd, J=7.2, 2.4 Hz, 1H), 7.88 (m, 2H).

Example 184

(S)-4-Amino-5-(sec-butoxy)-1H-benzo[c][1,2,6]thiadiazine-2,2-dioxide

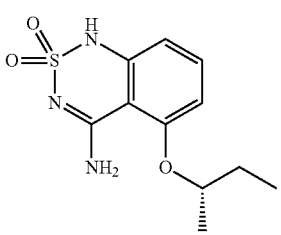

Prepared as in Example 111 from (S)-2-sulfamoylamino-6-sec-butoxybenzonitrile (Example 184a) in 43.2% yield. $^1$H NMR (400 MHz, DMSO-d$_6$) 0.94 (t, J=7.6 Hz, 3H), 1.29 (d, J=6.4 Hz, 1H), 1.69 (m, 2H), 4.72 (m, 1H), 6.59 (dd, J=8.4, 1.2 Hz, 1H), 6.79 (d, J=8.0 Hz, 1H), 7.45 (t, J=8.4 Hz, 1H), 7.84 (br d, J=2.8 Hz, 1H), 8.38 (br d, J=1.6 Hz, 1H), 10.96 (s, 1H). MS 270 (MH$^+$).

Example 184a (S)-2-Sulfamoylamino-6-sec-butoxybenzonitrile

Prepared as in Example 111a from (S)-2-amino-6-sec-butoxybenzonitrile (Example 184b) in 69.1% yield. MS 270 (MH$^+$).

Example 184b (S)-2-Amino-6-sec-butoxybenzonitrile

Prepared as in Example 111b from (S)-2-sec-butoxy-6-nitrobenzonitrile (Example 184c) in 100% yield. MS 191 (MH+).

Example 184c (S)-2-sec-Butoxy-6-nitrobenzonitrile

Prepared as in Example 111c from (S)-butan-2-ol and 2,6-dinitrobenzonitrile in 85.2% yield. $^1$H NMR (400 MHz, DMSO-$d_6$) δ 0.94 (t, J=7.6 Hz, 3H), 1.29 (d, J=6.4 Hz, 1H), 1.69 (m, 2H), 4.72 (m, 1H), 7.74 (dd, J=6.8, 2.4 Hz, 1H), 7.86 (m, 1H).

Example 185

(S)-4-Amino-5-(methoxypropoxy)-1H-benzo[c][1,2,6]thiadiazine-2,2-dioxide

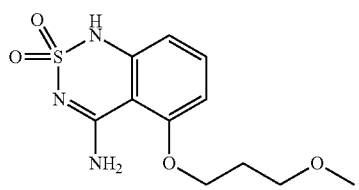

607

Prepared as in Example 111 from 2-sulfamoylamino-6-(3-methoxypropoxy)benzonitrile (Example 185a) in 69.3% yield. $^1$H NMR (400 MHz, DMSO-$d_6$) δ 2.03 (m, 2H), 3.23 (s, 3H), 3.50 (t, J=5.4 Hz, 2H), 4.18 (t, J=5.6 Hz, 2H), 6.58 (dd, J=8.0, 0.8 Hz, 1H), 6.70 (dd, J=8.4, 0.8 Hz, 1H), 7.43 (t, J=8.0 Hz, 1H), 78.22 (br s, 1H), 8.31 (br s, 1H), 10.90 (s, 1H). MS 286 (MH+).

Example 185a

2-Sulfamoylamino-6-(3-methoxypropoxy)benzonitrile

Prepared as in Example 111a from 2-amino-6-(3-methoxypropoxy)benzonitrile (Example 185b) in 69.7% yield. MS 286 (MH+).

Example 185b

2-Amino-6-(3-methoxypropoxy)benzonitrile

Prepared as in Example 111b from 2-(3-methoxypropoxy)-6-nitrobenzonitrile (Example 185c) in 100% yield. MS 207 (MH+).

Example 185c 2-(3-Methoxypropoxy)-6-nitrobenzonitrile

Prepared as in Example 111c from 3-methoxypropan-1-ol and 2,6-dinitrobenzonitrile in 63.6% yield. $^1$H NMR (400 MHz, CDCl$_3$) δ 2.16 (m, 2H), 3.36 (s, 3H), 3.63 (t, J=5.6 Hz, 2H), 4.29 (t, J=6.4 Hz, 2H), 7.35 (dd, J=8.8, 0.8 Hz, 1H), 7.69 (t, J=8.8 Hz, 1H), (dd, J=8.4, 0.8 Hz, 1H).

Example 186

(S)-4-Amino-5-(cyclopropylmethoxy)-1H-benzo[c][1,2,6]thiadiazine-2,2-dioxide

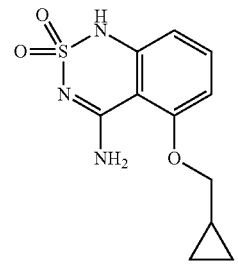

608

Prepared as in Example 111 from 2-sulfamoylamino-6-(cyclopropylmethoxy)benzonitrile (Example 186a) in 49.4% yield. M.P.: 246-247° C. $^1$H NMR (400 MHz, DMSO-$d_6$) δ 0.39 (m, 2H), 1.60 (m, 2H), 1.36 (m, 1H), 4.02 (d, J=7.2 Hz, 2H), 6.60 (dd, J=8.4, 0.8 Hz, 1H), 6.73 (d, J=8.4 Hz, 1H), 7.45 (t, J=8.8 Hz, 1H), 7.99 (br d, J=1.6 Hz, 1H), 8.41 (br d, J=1.6 Hz, 1H), 10.96 (br s, 1H). MS 268 (MH+).

Example 186a

2-Sulfamoylamino-6-(cyclopropylmethoxy)benzonitrile

Prepared as in Example 111a from 2-amino-6-(cyclopropylmethoxy)benzonitrile (Example 186b) in 87.5% yield. $^1$H NMR (400 MHz, DMSO-$d_6$) δ 0.18 (m, 2H), 0.41 (m, 2H), 1.07 (m, 1H), 3.80 (d, J=7.2 Hz, 2H), 6.76 (d, J=8.0 Hz, 1H), 6.96 (d, J=7.6 Hz, 1H), 7.09 (br s, 2H), 7.37 (t, 8.0 Hz, 1H). MS 268 (MH+).

Example 186b

2-Amino-6-(cyclopropylmethoxy)benzonitrile

Prepared as in Example 111b from 2-(cyclopropylmethoxy)-6-benzonitrile (Example 186c) in 100% yield. $^1$H NMR (400 MHz, DMSO-$d_6$) δ 0.35 (m, 2H), 0.58 (m, 2H), 1.23 (m, 1H), 3.86 (d, J=7.6 Hz, 2H), 5.98 (br s, 2H), 6.20 (d, J=8.0 Hz, 1H), 6.32 (dd, J=8.8, 0.8 Hz, 1H), 7.17 (t, 8.8 Hz, 1H) MS 189 (MH+).

Example 186c 2-(Cyclopropylmethoxy)-6-benzonitrile

Prepared as in Example 111c from 2,6-dinitrobenzonitrile and cyclopropylmethanol in 90%. $^1$H NMR (400 MHz,

Example 187

4-Amino-5-(methoxytetrahydro-2H-pyran-4-yl)-1H-benzo[c][1,2,6]thiadiazine-2,2-dioxide

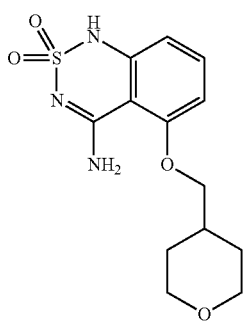

Prepared as in Example 111 from 2-sulfamoylamino-6-(tetrahydro-2H-pyran-4-yl)benzonitrile (Example 187a) in 92% yield as a cream colored solid. $^1$H NMR (400 MHz, DMSO-$d_6$) δ 1.31 (m, 4H), 1.63 (br m, 4H), 3.31 (br m, 2H), 3.86 (br m, 2H), 4.01 (d, J=6.8 Hz, 2H), 6.57 (d, J=8.4 Hz, 1H), 6.71 (d, J=8.0 Hz, 1H), 7.41 (t, J=8.0 Hz, 1H), 7.68 (br, 1H), 8.24 (s, 1H), 10.90 (br, 1H). MS 312 (MH$^+$).

Example 187a

2-Sulfamoylamino-6-(tetrahydro-2H-pyran-4-yl)benzonitrile

Prepared as in Example 111a from 2-amino-6-((tetrahydro-2H-pyran-4-yl)methoxy)benzonitrile (Example 187b) in 51% yield as an orange solid. $^1$H NMR (400 MHz, DMSO-$d_6$) δ 1.35 (m, 2H), 1.66 (br, 2H), 2.01 (br, 1H), 3.32 (br, 2H), 3.87 (br m, 2H), 3.96 (d, J=6.4 Hz, 2H), 6.92 (d, J=8.4 Hz, 1H), 7.12 (d, J=8.4 Hz, 1H), 7.19 (br s, 2H), 7.52 (t, J=8.4 Hz, 1H), 9.44 (br s, 1H).

Example 187b

2-Amino-6-((tetrahydro-2H-pyran-4-yl)methoxy)benzonitrile

Prepared as in Example 111b from 2-nitro-6-((tetrahydro-2H-pyran-4-yl)methoxy)benzonitrile (Example 187c) in 80% yield as a yellow solid. $^1$H NMR (400 MHz, DMSO-$d_6$) δ 1.32 (m, 2H), 1.64 (m, 2H), 1.97 (br, 1H), 3.31 (m, 2H), 3.86 (m, 4H), 5.97 (s, 2H), 6.19 (d, J=8.4 Hz, 1H), 6.31 (d, 1H), 7.15 (t, J=8.4 Hz, 1H).

Example 187c

2-Nitro-6-((tetrahydro-2H-pyran-4-yl)methoxy)benzonitrile

To a solution of tetrahydropyran-4-methanol (782 mg, 6.73 mmol) in THF (25 mL), was added slowly 1.38M nBuLi (4.13 mL, 5.70 mmol) in hexane at −78° C. under nitrogen. At one hour a solution of 2,6-dinitrobenzonitrile (1.00 g, 5.18 mmol) in THF (25 mL) was added. The reaction was stirred under N$_2$ overnight at rt, then was quenched with water (100 mL). The precipitate was collected by filtration to provide 2-nitro-6-((tetrahydro-2H-pyran-4-yl)methoxy)benzonitrile (1.13 g, 83%) as a light brown solid. $^1$H NMR (400 MHz, DMSO-$d_6$) δ 1.68 (m, 2H), 2.06 (br, 1H), 3.33 (m, 2H), 3.88 (m, 2H), 4.11 (d, J=6.0 Hz, 2H), 7.72 (d, J=6.0 Hz, 1H), 7.89-7.85 (m, 2H).

Example 188

4-Amino-5-(methoxytetrahydrofuran-3-yl)-1H-benzo[c][1,2,6]thiadiazine-2,2-dioxide

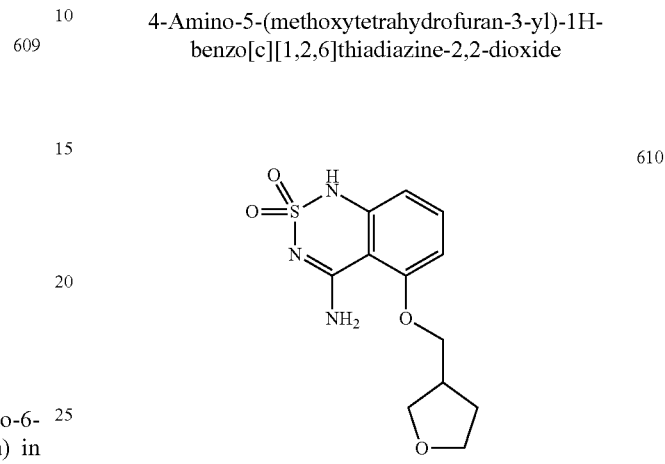

Prepared as in Example 111 from 2-sulfamoylamino-6-(methoxytetrahydrofuran-3-yl)benzonitrile (Example 188a) in 26% yield as a white solid. $^1$H NMR (400 MHz, DMSO-$d_6$) δ 1.64 (m, 1H), 1.99 (m, 1H), 2.73 (m, 1H), 3.56 (m, 2H), 3.67 (m, 1H), 3.75 (m, 1H), 4.04 (m, 2H), 6.51 (d, J=8.4 Hz, 1H), 6.62 (d, J=8.4 Hz, 1H), 7.34 (t, J=8.0 Hz, 1H), 7.70 (br s, 1H), 8.09 (br s, 1H), 10.92 (br s, 1H), MS 298 (MH$^+$).

Example 188a

2-Sulfamoylamino-6-(methoxytetrahydrofuran-3-yl)benzonitrile

Prepared as in Example 111a from 2-amino-6-((tetrahydrofuran-3-yl)methoxy)benzonitrile (Example 188b) in 14% yield as a white solid. $^1$H NMR (400 MHz, DMSO-$d_6$) δ 1.62 (m, 1H), 1.96 (m, 1H), 2.43 (m, 1H), 2.61 (m, 1H), 3.48 (m, 1H), 3.60 (m, 1H), 3.71 (m, 2H), 3.99 (m, 2H), 6.90 (d, J=8.8 Hz, 1H), 7.09 (d, J=8.0 Hz, 1H), 7.19 (s, 1H), 7.49 (t, J=8.4 Hz, 1H), 9.42 (s, 1H).

Example 188b

2-Amino-6-((tetrahydrofuran-3-yl)methoxy)benzonitrile

Prepared as in Example 111b from 2-nitro-6-((tetrahydrofuran-3-yl)methoxy)benzonitrile (Example 188c) in 99% yield as a golden brown oil. MS 219 (MH$^+$).

Example 188c

2-Nitro-6-((tetrahydrofuran-3-yl)methoxy)benzonitrile

Prepared as in Example 166d from 2,6-dinitrobenzonitrile and 3-hydroxymethyltetrahydrofuran in 48% yield as an orange-red solid. $^1$H NMR (400 MHz, DMSO-$d_6$) δ 1.68 (m, 1H), 2.00 (m, 1H), 2.70 (m, 1H), 3.54 (m, 1H), 3.66 (m, 1H), 3.76 (m, 2H), 4.03 (m, 1H), 4.19 (m, 1H), 7.73 (d, J=7.6 Hz, 1H), 7.90-7.95 (m, 2H).

Example 189

4-Amino-5-((tetrahydrofuran-2-yl)methoxy)quinazolin-2(1H)-one

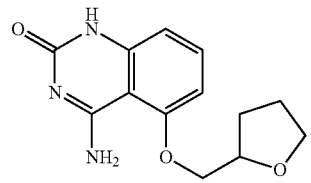

611

Prepared as in Example 111 from N-(2-cyano-3-((tetrahydrofuran-2-yl)methoxy)phenylcarbamoyl)benzamide (Example 189a) in 39% yield. $^1$H NMR (400 MHz, d-DMSO) δ 1.65 (br m, 1H), 1.85 (br m, 2H), 1.99 (br m, 1H), 3.71 (m, 2H), 3.78 (m, 1H), 3.98 (m, 1H), 6.70-6.67 (m, 2H), 7.42 (t, J=8.0 Hz, 1H), 7.62 (s, 1H), 7.88 (s, 1H), 10.62 (s, 1H).

Example 189a

N-(2-Cyano-3-((tetrahydrofuran-2-yl)methoxy)phenyl carbamoyl)benzamide

Prepared as in Example 146a from 2-amino-6-((tetrahydrofuran-2-yl)methoxy)benzonitrile (Example 189b) in 45% yield as a white solid. $^1$H NMR (400 MHz, d-DMSO) δ 1.98-1.74 (m, 4H), 3.54 (m, 1H), 3.69 (m, 1H), 4.20-4.07 (m, 3H), 6.97 (d, J=8.8 Hz, 1H), 7.67-7.51 (m, 4H).

Example 189b

2-Amino-6-((tetrahydrofuran-2-yl)methoxy)benzonitrile

Prepared as in Example 111b from 2-nitro-6-((tetrahydrofuran-2-yl)methoxy)benzonitrile (Example 189c) in 92% yield as a light blue clear oil. $^1$H NMR (400 MHz, MeOD) δ 1.97-1.68 (m, 4H), 3.75-3.64 (m, 1H), 3.80-3.75 (m, 1H), 3.98-3.90 (m, 2H), 4.15-4.12 (m, 1H), 5.96 (s, 1H), 6.18 (d, J=8.0 Hz, 1H), 6.31 (d, J=8.0 Hz, 1H), 7.14 (t, J=8.4 Hz, 1H).

Example 189c

2-Nitro-6-((tetrahydrofuran-2-yl)methoxy)benzonitrile

Prepared as in Example 166d from 2,6-dinitrobenzonitrile and tetrafurfuryl alcohol in 68% yield. $^1$H NMR (400 MHz, MeOD) δ 2.10-1.70 (m, 7H), 3.68-3.66 (m, 1H), 3.80-3.78 (m, 1H), 4.29-4.20 (m, 3H), 7.72 (d, J=6.0 Hz, 1H), 7.90-7.84 (m, 2H).

Example 190

4-Amino-5-(2-methoxybenzyloxy)-1H-benzo[c][,6] thiadiazine-2,2-dioxide

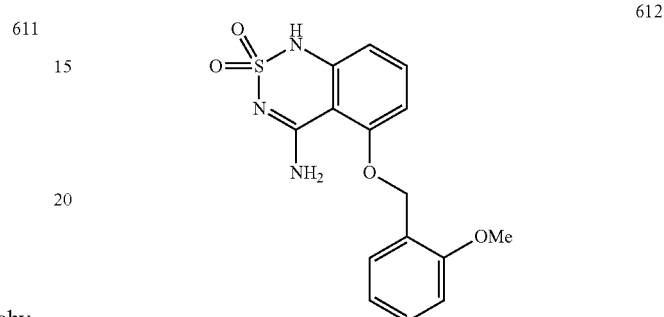

612

Prepared as in Example 111 from 2-sulfamoylamino-6-(4-methoxybenzyloxy)benzonitrile (Example 190a) in 85% yield. $^1$H NMR (400 MHz, DMSO-d$_6$) δ 3.81 (s, 3H), 5.25 (s, 2H), 6.59 (d, J=8.4 Hz, 1H), 6.86 (d, J=8.0 Hz, 1H), 6.96 (t, J=7.2 Hz, 1H), 7.09 (d, J=8.0 Hz, 1H), 7.37 (t, J=8.0 Hz, 1H), 7.46-7.42 (m, 2H), 7.91 (s, 1H), 8.31 (s, 1H), 10.96 (s, 1H). MS 334 (MH$^+$).

Example 190a

2-Sulfamoylamino-6-(2-methoxybenzyloxy)benzonitrile

Prepared as in Example 111a from 2-amino-6-((tetrahydrofuran-2-yl)methoxy)benzonitrile (Example 190b) in 23% yield. $^1$H NMR (400 MHz, d-DMSO) δ 3.80 (s, 3H), 6.88 (d, J=8.4 Hz, 1H), 6.88 (d, J=8.1 Hz 1H), 6.96 (t, J=7.6 Hz, 1H), 7.06 (d, J=8.0 Hz, 2H), 7.16 (d, J=8.4 Hz, 1H), 7.39-7.33 (m, 5H), 7.45 (d, J=7.2 Hz, 1H), 11.20 (s, 1H).

Example 190b

2-Amino-6-(2-methoxybenzyloxy)benzonitrile

Prepared as in Example 111b from 2-nitro-6-(2-methoxybenzyloxy)benzonitrile (example 190c) in 56% yield. $^1$H NMR (400 MHz, MeOD) δ 3.79 (s, 3H), 5.04 (s, 2H), 6.30-6.26 (m, 2H), 7.06-6.94 (m, 3H), 7.33-7.28 (m, 3H), 7.54 (s, 1H).

Example 190c

2-Nitro-6-(2-methoxybenzyloxy)benzonitrile

Prepared as in Example 111c from 2,6-dinitrobenzonitrile and 2-methoxybenzyl alcohol in 58% yield. $^1$H NMR (400 MHz, DMSO) δ 3.82 (s, 3H), 5.34 (s, 2H), 6.99 (t, J=7.6 Hz, 1H), 7.08 (d, J=8.4 Hz, 1H), 7.37 (t, J=8.4 Hz, 1H), 7.46 (d, J=6.0 Hz, 1H), 7.81 (d, J=7.6 Hz, 1H), 7.93-7.87 (m, 2H).

Example 191

4-Amino-5-(methoxytetrahydrofuran-2-yl)-1H-benzo[c][1,2,6]thiadiazine-2,2-dioxide

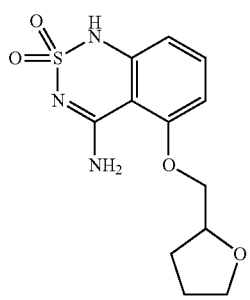

613

Prepared as in Example 111 from 2-sulfamoylamino-6-(methoxytetrahydrofuran-2-yl)benzonitrile (Example 191a) in 100% yield as a white solid. ¹H NMR (400 MHz, DMSO-d₆) δ 1.65 (m, 1H), 1.86 (m, 1H), 1.98 (m, 1H), 3.69 (m, 1H), 3.78 (m, 1H), 3.98 (m, 1H) 4.25 (m, 1H), 6.61 (d, J=7.2 Hz, 1H), 6.74 (d, J=8.0 Hz, 1H).

Example 191a

2-Sulfamoylamino-6-(methoxytetrahydrofuran-2-yl)benzonitrile

Prepared as in Example 111a from 2-amino-6-((tetrahydrofuran-2-yl)methoxy)benzonitrile (Example 189b) in 79% yield as a light yellow solid. ¹H NMR (400 MHz, DMSO-d₆) δ 2.02-1.68 (m, 2H), 3.66 (m, 1H), 3.81-3.76 (m, 1H), 4.20-4.03 (m, 3H), 6.93 (d, J=8.4 Hz, 1H), 7.12 (d, J=8.4 Hz, 1H), 7.23 (s, 1H), 7.53 (t, J=8.4 Hz, 1H), 9.34 (br s, 1H).

Example 192

4-Amino-5-(furan-3-ylmethoxy)-1H-benzo[c][1,2,6]thiadiazine-2,2-dioxide

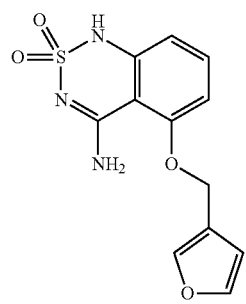

614

Prepared as in Example 111 from 2-sulfamoylamino-6-(furan-3-ylmethoxy)benzonitrile (Example 192a) in 45% yield as an off white solid. ¹H NMR (400 MHz, DMSO-d₆) δ 5.11 (s, 2H), 6.54 (d, J=0.4 Hz, 1H), 6.56 (s, 1H), 6.80 (d, J=8.8 Hz, 1H), 7.39 (t, J=8.4 Hz, 1H), 7.64 (s, 1H), 7.74 (s, 1H), 7.81 (s, 1H), 8.23 (s, 1H), 10.90 (s, 1H). MS 294 (MH⁺).

Example 192a

2-Sulfamoylamino-6-(furan-3-ylmethoxy)benzonitrile

Prepared as in Example 111a from 2-amino-6-(furan-3-ylmethoxy)benzonitrile (Example 192b) in 57% yield as an off white solid. ¹H NMR (400 MHz, d-DMSO) δ 5.04 (s, 2H), 6.62 (s, 1H), 6.88 (d, J=8.8 Hz, 1H), 7.15 (d, J=8.1, 0.8 Hz, 1H), 7.35 (d, J=8.8 Hz, 1H), 7.39-7.32 (m, 2H), 7.67 (s, 1H), 7.79 (s, 1H), 7.86 (s, 1H), 7.93 (s, 1H), 10.91 (s, 1H).

Example 192b

2-Amino-6-(furan-3-ylmethoxy)benzonitrile

Prepared as in Example 111b from 2-nitro-6-(furan-3-ylmethoxy)benzonitrile (Example 192c) in 21% yield as a light yellow oil. ¹H NMR (400 MHz, d-DMSO) δ 4.92 (s, 2H), 6.31-6.26 (m, 2H), 6.59 (s, 1H), 6.99 (t, J=8.4 Hz, 1H), 7.27 (s, 1H), 7.45 (s, 1H), 7.66 (s, 1H), 7.76 (s, 1H).

Example 192c

2-Nitro-6-(furan-3-ylmethoxy)benzonitrile

Prepared as in Example 111c from 2,6-dinitrobenzonitrile and 3-furanmethanol in 100% yield. ¹H NMR (400 MHz, d-DMSO) δ 5.27 (s, 2H), 6.59 (s, 1H), 7.69 (s, 1H), 7.91-7.84 (m, 4H).

Example 193

4-Amino-5-(3-methoxybenzyloxy)-1H-benzo[c][1,2,6]thiadiazine-2,2-dioxide

615

Prepared as in Example 111 from 2-sulfamoylamino-6-(3-methoxybenzyloxy)benzonitrile (Example 193a) in 54% yield. ¹H NMR (400 MHz, d-DMSO) δ 3.74 (s, 3H), 5.27 (s, 2H), 6.59 (d, J=8.0 Hz, 1H), 6.79 (d, J=8.0 Hz, 1H), 6.90 (d, J=8.0 Hz, 1H), 7.04 (d, J=7.2 Hz, 1H), 7.08 (s, 1H), 7.31 (t, J=8.4 Hz, 1H), 7.42 (t, J=8.0 Hz, 1H), 7.89 (br s, 1H), 8.32 (br s, 1H), 10.96 (br s, 1H). MS 334 (MH⁺).

Example 193a

2-Sulfamoylamino-6-(3-methoxybenzyloxy)benzonitrile

Prepared as in Example 111a from 2-amino-6-(3-methoxybenzyloxy)benzonitrile (Example 193b) in 17% yield as a white solid. MS 334 (MH$^+$).

Example 193b

2-Amino-6-(3-methoxybenzyloxy)benzonitrile

To a mixture of 2-nitro-6-(3-methoxybenzyloxy)benzonitrile (Example 193c) (480 mg, 1.69 mmol) in 5:1 acetone:water (9 mL) was added zinc (552 mg, 8.44 mmol) and ammonium chloride (911 mg, 16.9 mmol). The reaction was stirred at room temperature for 30 minutes, then filtered and concentrated. The residue was purified by flash chromatography (55:45 EtOAc:Hexane) to provide 2-amino-6-(benzyloxy)benzonitrile (337 mg, 78%). $^1$H NMR (400 MHz, d-DMSO) δ 3.73 (s, 3H), 5.04 (s, 1H), 6.27 (d, J=8.0 Hz, 1H), 6.31 (d, J=8.4 Hz, 1H), 7.06-6.97 (m, 3H), 7.27 (t, J=8.0 Hz, 1H), 7.36 (s, 1H), 7.55 (s, 1H).

Example 193c 2-(3-Methoxybenzyloxy)-6-nitrobenzonitrile

Prepared as in Example 111c from 2,6-dinitrobenzonitrile and 3-methoxybenzylalcohol in 83% yield. $^1$H NMR (400 MHz, d-DMSO) δ 3.75 (s, 3H), 5.38 (s, 2H), 6.91 (d, J=8.0 Hz, 1H), 7.04 (d, J=7.6 Hz, 1H), 7.07 (s, 1H), 7.33 (t, J=8.0 Hz, 1H), 7.78 (d, J=8.8 Hz, 4H), 7.93-7.87 (m, 2H).

Example 194

4-(2-(4-Amino-1H-benzo[c][1,2,6]thiadiazine-2,2-dioxide-5-yloxy)methyl)pyrrolidinium chloride

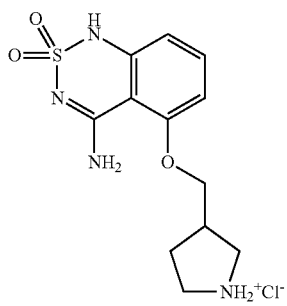

616

Prepared as in Example 166 from tert-Butyl 3-(2-(4-amino-1H-benzo[c][1,2,6]thiadiazine-2,2-dioxide-5-yloxy)methyl)pyrrolidine-1-carboxylate (Example 194a) in 27% yield as a white solid. $^1$H NMR (400 MHz, DMSO-d$_6$) δ 1.72 (m, 1H), 2.07 (m, 1H), 2.52 (m, 1H), 2.64 (m, 1H), 2.94-2.74 (m, 3H), 3.79 (m, 2H), 6.26 (d, J=8.0 Hz, 1H), 6.37 (d, J=8.8 Hz, 1H), 7.09 (t, J=8.0 Hz, 1H), 7.31 (br s, 1H), 7.96 (br s, 1H), 9.03 (br s, 1H).

Example 194a tert-Butyl 3-(2-(4-amino-1H-benzo[c][1,2,6]thiadiazine-2,2-dioxide-5-yloxy)methyl)pyrrolidine-1-carboxylate Prepared as in Example 111 from tert-butyl-3-((2-cyano-3-(sulfamoylmethyl)phenoxy)methyl)pyrrolidine-1-carboxylate (Example 194b) in 94% yield as a white solid. $^1$H NMR (400 MHz, DMSO-d$_6$) δ 1.37 (s, 9H), 1.66 (br m, 1H), 1.97 (br m, 1H), 2.78 (br m, 1H), 3.48-3.20 (br m, 4H), 4.12 (br, m 2H), 6.60 (d, J=8.0 Hz, 1H), 6.74 (d, J=8.4 Hz, 1H), 7.44 (t, J=8.4 Hz, 1H), 7.70 (s, 1H), 8.33 (s, 1H), 10.95 (s, 1H).

Example 194b tert-Butyl 3-((2-cyano-3-(sulfamoylamino)phenoxy)methyl)pyrrolidine-1-carboxylate Prepared as in Example 111a from tert-butyl 34(3-amino-2-cyanophenoxy)methyl)pyrrolidine-1-carboxylate (Example 194c) in 47% yield as a white solid. $^1$H NMR (400 MHz, DMSO-d$_6$) δ 1.37 (s, 9H), 1.70 (br, 1H), 1.97 (br, 1H), 2.63 (br, 1H), 3.47-2.98 (br m, 4H), 4.08 (br m, 2H), 6.94 (d, J=8.8 Hz, 1H), 7.14 (d, J=8.4 Hz, 1H), 7.24 (s, 1H), 7.48 (s, 1H), 7.54 (t, J=8.0, 1H), 9.48 (br s, 1H).

Example 194c tert-Butyl 3-((3-amino-2-cyanophenoxy)methyl)pyrrolidine-1-carboxylate Prepared as in Example 111b from tert-butyl-((2-cyano-3-nitrophenoxy)methyl)pyrrolidine-1-carboxylate (Example 194d) in 100% yield as a clear oil. $^1$H NMR (400 MHz, DMSO-d$_6$) δ 1.37 (s, 9H), 1.69 (br, 1H), 1.96 (br, 1H), 2.59 (br, 1H), 3.07 (br, 1H), 3.23 (br, 1H), 3.35 (br, 1H), 3.40 (br, 1H), 3.96 (m, 2H), 5.98 (s, 2H), 6.20 (d, J=8.0 Hz, 1H), 6.32 (d, J=8.0 Hz, 1H), 7.15 (t, J=8.4 Hz, 1H).

Example 194d tert-Butyl-((2-cyano-3-nitrophenoxy)methyl)pyrrolidine-1-carboxylate Prepared as in Example 166d from 2,6-dinitrobenzonitrile and tert-butyl 3-(hydroxymethyl)pyrrolidine-1-carboxylate in 69% yield as a yellow solid. MS 347 (MH$^+$).

Example 195

(R)-4-Amino-5-((1-acetylpyrrolidin-2-yl)methoxy)-1H-benzo[c][1,2,6]thiadiazine-2,2-dioxide

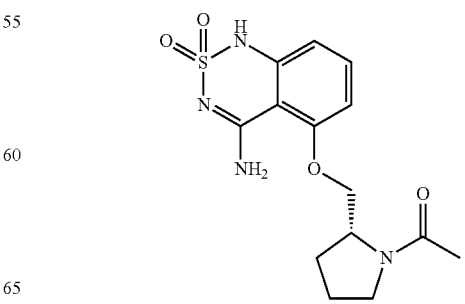

617

Prepared as in Example 176 from (R)-2-amino-6-((1-acetylpyrrolidin-2-yl)methoxy)benzonitrile (Example 195a) in 31% yield as a white solid. $^1$H NMR (400 MHz, DMSO-$d_6$) δ 1.90 (m, 4H), 2.00 (s, 3H), 3.49 (m, 2H), 4.09 (dd, J=9.7, 6.1 Hz, 1H), 4.24 (dd, J=9.8, 5.7 Hz, 1H), 4.41 (m, 1H), 6.62 (d, J=8.2 Hz, 1H), 6.87 (d, J=8.5 Hz, 1H), 7.46 (t, J=8.3 Hz, 1H), 8.12 (br s, 1H), 8.33 (br s, 1H), 10.93 (br s, 1H). MS 339 (MH$^+$).

Example 195a (R)-2-Amino-6-((1-acetylpyrrolidin-2-yl)methoxy)benzonitrile

Prepared as in Example 111b from (R)-2-((1-acetylpyrrolidin-2-yl)methoxy)-6-nitrobenzonitrile (Example 195b) in 77% yield as a clear syrup. MS 260 (MH$^+$).

Example 195b (R)-2-((1-Acetylpyrrolidin-2-yl)methoxy)-6-nitrobenzonitrile

Prepared as in Example 176b from (R)-2-((2-cyano-3-nitrophenoxy)methyl)pyrrolidinium chloride and acetyl chloride in 100% yield as a yellow syrup. MS 290 (MH$^+$).

Example 196

4-Amino-5-(methoxy-3-pyrrolidine-1-propionyl)-1H-benzo[c][1,6]thiadiazine-2,2-dioxide

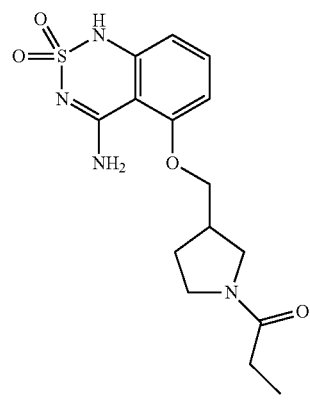

618

Prepared as in Example 111 from 2-sulfamoylamino-6-((1-propionylpyrrolidine-3-yl)methoxybenzonitrile (Example 196a) in 29% yield as an off-white solid. $^1$H NMR (400 MHz, DMSO-$d_6$) δ 0.95 (t, J=7.6 Hz, 3H), 1.66 (m, 1H), 1.77 (m, 1H), 1.97 (m, 1H), 2.05 (m, 1H), 2.21 (q, J=8.0 Hz, 2H), 2.74 (m, 1H), 2.86 (m, 1H), 3.63-3.23 (m, 4H), 4.13 (m, 2H), 6.60 (d, J=8.0 Hz, 1H), 6.75 (d, J=8.4 Hz, 1H), 7.44 (t, J=8.0 Hz, 1H), 7.72 (s, 1H), 8.37-8.32 (m, 1H), 10.94 (s, 1H).

Example 196a

2-Sulfamoylamino-6-((1-propionylpyrrolidine-3-yl)methoxybenzonitrile

Prepared as in Example 111a from 2-amino-6-((1-propionylpyrrolidine-3-yl)methoxy)benzonitrile (Example 196b) in 27% yield as a white solid. MS 353 (MH$^+$).

Example 196b

2-Amino-6-((1-propionylpyrrolidine-3-yl)methoxy)benzonitrile

Prepared as in Example 111b from 2-nitro-6-((1-propionylpyrrolidine-3-yl)methoxy)benzonitrile (Example 196c) in 100% yield as a clear oil. MS 274 (MH$^+$).

Example 196c

2-Nitro-6-((1-propionylpyrrolidine-3-yl)methoxy)benzonitrile

Prepared as in Example 176b from 2-nitro-6-(pyrrolidin-3-ylmethoxy)benzonitrile hydrochloride (Example 196d) and propionyl chloride in 51% as a yellow solid. MS 304 (MH$^+$).

Example 196d

2-Nitro-6-(pyrrolidin-3-ylmethoxy)benzonitrile hydrochloride

Prepared as in Example 166 from tert-butyl-((2-cyano-3-nitrophenoxy)methyl)pyrrolidine-1-carboxylate (Example 194d) in 100% yield as a yellow solid. MS 248 (MH$^+$).

Example 197

4-Amino-5-(methoxy-3-pyrrolidine-1-butyryl)-1H-benzo[c][1,2,6]thiadiazine-2,2-dioxide

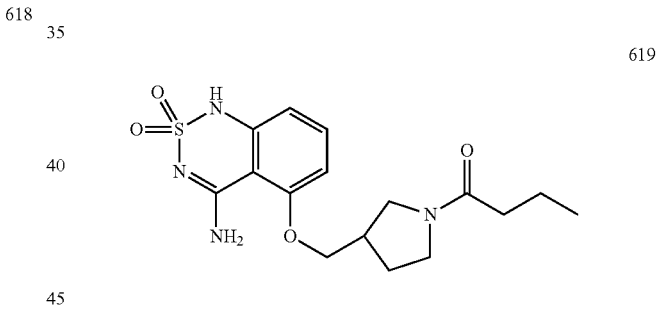

619

Prepared as in Example 111 from 2-sulfamoylamino-6-((1-butyrylpyrrolidin-3-yl)methoxybenzonitrile (Example 197a) in 73% yield as a white solid. $^1$H NMR (400 MHz, DMSO-$d_6$) δ 0.86 (t, J=7.6 Hz, 3H), 1.48 (q, J=7.6 Hz, 2H), 1.65 (m, 1H), 1.76 (m, 1H), 1.97 (m, 1H), 2.05 (m, 1H), 2.17 (t, J=7.2 Hz, 2H), 2.74 (m, 1H), 2.85 (m, 1H), 3.10 (m, 1H), 3.64-3.23 (m, 4H), 4.12 (m, 1H), 6.60 (d, J=8.0 Hz, 1H), 6.75 (d, J=8.8 Hz, 1H), 7.44 (t, J=8.4 Hz, 1H), 7.71 (s, 1H), 8.35-8.32 (m; 1H), 10.94 (s, 1H).

Example 197a

2-Sulfamoylamino-6-((1-butyryl pyrrolidin-3-yl)methoxybenzonitrile

Prepared as in Example 111a from 2-amino-6-((1-butyrylpyrrolidin-3-yl)methoxy)benzonitrile (Example 197b) in 19% yield as a white solid. $^1$H NMR (400 MHz, DMSO-$d_6$) δ 0.85 (t, J=7.6 Hz, 3H), 1.48 (q, J=7.6 Hz, 2H), 2.13-1.64 (m, 2H), 2.17 (m, 2H), 2.75-2.53 (m, 2H), 3.65-3.18 (m, 4H), 4.09 (m, 2H), 6.94 (m, 1H), 7.13 (m, 1H), 7.25 (s, 1H), 7.54 (m, 1H), 9.45 (m, 1H).

Example 197b

2-Amino-6-((1-butyrylpyrrolidin-3-yl)methoxy)benzonitrile

Prepared as in Example 111b from 2-nitro-6-((1-butyrylpyrrolidin-3-yl)methoxy)benzonitrile (Example 197c) in 100% yield as a brown oil. MS 288 (MH+).

Example 197c

2-Nitro-6-((1-butyrylpyrrolidin-3-yl)methoxy)benzonitrile

Prepared as in Example 176b from 2-nitro-6-(pyrrolidin-3-ylmethoxy)benzonitrile hydrochloride (Example 196d) and butyryl chloride in 100% yield as an orange solid. MS 318 (MH+).

Example 198

(E)-4-Amino-5-(1-(propylcarbamoyl)cyclopropylmethoxy)-1H-benzo[c][1,2,6]thiadiazine-2,2-dioxide

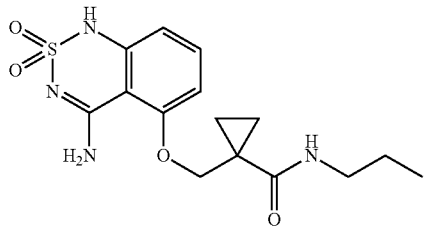

620

Prepared as in Example 111 from 14(2-cyano-3-(sulfamoylamino)phenoxy)methyl)-N-propylcyclopropanecarboxamide (Example 198a) in 94% yield as a white solid. $^1$H-NMR (400 MHz, DMSO-$d_6$) δ 10.95 (broad s, 1H), 8.35 (broad s, 1H), 7.95 (broad s, 1H), 7.76 (t, J=5.2 Hz, 1H), 7.45 (t, J=8.0 Hz, 1H), 6.69 (d, J=8.8 Hz, 1H), 6.61 (d, J=7.6 Hz, 1H), 4.22 (s, 2H), 3.01 (q, J=6.4 Hz, 2H), 1.40 (hex, J=6.8 Hz, 2H), 1.12-1.18 (m, 2H), 0.88-0.95 (m, 2H), 0.80 (t, J=7.6 Hz, 3H). MS 353 (MH+).

Example 198a 1-((2-Cyano-3-(sulfamoylamino)phenoxy)methyl)-N-propylcyclopropanecarboxamide Prepared as in Example 111a from 1-((3-amino-2-cyanophenoxy)methyl)-N-propylcyclopropanecarboxamide (Example 198b) and sulfamoyl chloride in 78% yield as a white solid. $^1$H-NMR (400 MHz, DMSO-$d_6$) δ 9.45 (broad s, 1H), 7.51-7.61 (m, 2H), 7.26 (broad s, 2H), 7.16 (d, J=8.0 Hz, 1H), 6.91 (d, J=8.4 Hz, 1H), 4.24 (s, 2H), 3.04 (q, J=6.4 Hz, 2H), 1.43 (hex, J=7.6 Hz, 2H), 1.08-1.14 (m, 2H), 0.83-0.88 (m, 2H), 0.82 (t, J=7.2 Hz, 3H).

Example 198b 1-((3-Amino-2-cyanophenoxy)methyl)-N-propylcyclopropanecarboxamide A solution of 1-(hydroxymethyl)-N-propylcyclopropanecarboxamide (Example 198c) (0.67 g, 4.25 mmol) in anhydrous THF (10 mL) was treated with NaH (0.17 g, 4.25 mmol, 60% suspension in mineral oil) at 0° C., under a nitrogen atmosphere. The obtained mixture was stirred at 0° C. for 10 min and at rt over 30 min. Then, a solution of 2-amino-6-fluorobenzonitrile (0.53 g, 3.86 mmol) in THF (5.0 mL) was added and the obtained mixture was heated at reflux overnight. The cold mixture was quenched with saturated aqueous solution of NH$_4$Cl (20 mL) and extracted with EtOAc (3×50 mL). The combined extract was washed with brine, dried over anhydrous MgSO$_4$, filtered and evaporated. The residue was purified by chromatography on silica gel using gradient hexanes→hexanes/EtOAc (4:6), to give 0.75 g (71%) of the title compound as a yellow solid. $^1$H-NMR (400 MHz, DMSO-$d_6$) δ 7.51 (t, J=6.0 Hz, 1H), 7.17 (t, J=8.0 Hz, 1H), 6.34 (d, J=8.4 Hz, 1H), 6.19 (d, J=8.4 Hz, 1H), 5.97 (broad s, 2H), 4.13 (s, 2H), 3.04 (q, J=6.4 Hz, 2H), 1.43 (hex, J=6.8 Hz, 2H), 1.05-1.11 (m, 2H), 0.78-0.86 (m, 5H).

Example 198c 1-(Hydroxymethyl)-N-propylcyclopropanecarboxamide

To a solution of ethyl 1-(propylcarbamoyl)cyclopropanecarboxylate (Example 198d) (1.65 g, 8.27 mmol) in EtOH (70 mL) was added NaBH$_4$ (0.97 g, 25.64 mmol) at rt. The obtained mixture was stirred at rt over 2 days, quenched with 1.5M HCl and concentrated under reduced pressure. The concentrated mixture was extracted with EtOAc (4×70 mL), the combined extract was washed with saturated NaHCO$_3$ and brine, and was dried over MgSO$_4$. The filtrate was evaporated and the residue was purified by chromatography on silica gel using the solvent gradient hexanes→hexanes/EtOAc (1:9), to furnish 1.14 g (88%) of the product as a white solid. $^1$H-NMR (400 MHz, DMSO-$d_6$) δ 7.49 (broad s, 1H), 5.09 (broad s, 1H), 3.49 (s, 2H), 3.05 (q, J=6.4 Hz, 2H), 1.41 (hex, J=7.6 Hz, 2H), 0.86-0.91 (m, 2H), 0.83 (t, J=7.2 Hz, 3H), 0.55-0.60 (m, 2H).

Example 198d

Ethyl 1-(propylcarbamoyl)cyclopropanecarboxylate

To a solution of 1-(ethoxycarbonyl)cyclopropanecarboxylic acid (Wheeler, T. N.; Ray, J. A. *Synthetic Communications* 1988, 18(2), 141) (1.52 g, 9.62 mmol) and n-propylamine (0.63 g, 10.58 mmol) in anhydrous DMF (65 mL) at rt, were added NaHCO$_3$ (4.04 g, 48.11 mmol), N-(3-dimethylaminopropyl)-N'-ethylcarbodiimide hydrochloride (2.21 g, 11.54 mmol) and 1-hydroxybenzotriazole hydrate (1.77 g, 11.54 mmol) under a nitrogen atmosphere. After being stirred at rt overnight, the mixture was partitioned between water (100 mL) and EtOAc (300 mL). The organic phase was separated, washed with water and brine, and was dried over anhydrous MgSO$_4$. The filtrate was evaporated to give 1.65 g (86%) of the crude product which was used in the next step without purification. $^1$H-NMR (400 MHz, DMSO-$d_6$) δ 8.33 (broad s, 1H), 4.08 (q, J=6.8 Hz, 2H), 3.07 (q, J=6.4 Hz, 2H), 1.43 (hex, J=6.4 Hz, 2H), 1.31 (s, 4H), 1.17 (t, J=6.4 Hz, 3H), 0.85 (t, J=7.2 Hz, 3H).

Example 199

(E)-4-Amino-5-(4-methoxybut-2-enyloxy)-1H-benzo[c][1,2,6]thiadiazine-2,2-dioxide

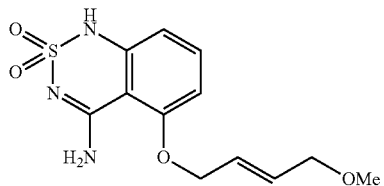

621

Prepared as in Example 111 from 2-sulfamoylamino-6-(4-methoxybut-2-enyloxy)benzonitrile (Example 199a) in 91% yield as a white solid. $^1$H-NMR (400 MHz, DMSO-d$_6$) δ 10.94 (broad s, 1H), 8.34 (broad s, 1H), 7.90 (broad s, 1H), 7.45 (t, J=8.4 Hz, 1H), 6.75 (d, J=7.6 Hz, 1H), 6.61 (d, J=8.0 Hz, 1H), 5.88-6.02 (m, 2H), 4.75-4.81 (m, 2H), 3.88-3.93 (m, 2H), 3.22 (s, 3H). MS 298 (MH$^+$).

Example 199a

2-Sulfamoylamino-6-(4-methoxybut-2-enyloxy)benzonitrile

Prepared as in Example 111a from (E)-2-amino-6-(4-methoxybut-2-enyloxy)benzonitrile (Example 199b) in 93% yield as a white solid. $^1$H-NMR (400 MHz, DMSO-d$_6$) δ 9.46 (broad s, 1H), 7.56 (t, J=8.4 Hz, 1H), 7.26 (broad s, 2H), 7.15 (d, J=8.0 Hz, 1H), 6.96 (d, J=8.8 Hz, 1H), 5.84-6.00 (m, 2H), 4.68-4.76 (m, 2H), 3.89-3.95 (m, 2H), 3.23 (s, 3H).

Example 199b (E)-2-Amino-6-(4-methoxybut-2-enyloxy)benzonitrile

To a solution of (E)-2-(4-methoxybut-2-enyloxy)-6-nitrobenzonitrile (Example 199c) (0.25 g, 1.00 mmol) in a mixture of AcOH, EtOH and water (33 mL, 1:1:1) was added iron powder (0.56 g, 10.00 mmol) at rt. The obtained mixture was stirred at rt for 20 min, then was heated to 50° C. for a further 15 min, and allowed to cool. The suspension was concentrated under reduced pressure; the residue was treated with water (50 mL) and extracted with EtOAc (4×50 mL). The combined extract was washed with saturated aqueous NaHCO$_3$ and brine, and was dried over anhydrous MgSO$_4$. The filtrate was evaporated and the residue was purified by silica gel flash chromatography using gradient hexanes→hexanes/EtOAc (1:1), to give 0.19 g (86%) of the title compound as a white solid. $^1$H-NMR (400 MHz, DMSO-d$_6$) 7.17 (t, J=8.4 Hz, 1H), 6.34 (d, J=8.8 Hz, 1H), 6.22 (d, J=8.4 Hz, 1H), 6.00 (broad s, 2H), 5.82-5.96 (m, 2H), 4.56-4.62 (m, 2H), 3.88-3.93 (m, 2H), 3.23 (s, 3H).

Example 199c (E)-2-(4-Methoxybut-2-enyloxy)-6-nitrobenzonitrile

To a solution of (E)-2-(4-hydroxybut-2-enyloxy)-6-nitrobenzonitrile (Example 199d) (0.50 g, 2.13 mmol) and 2,6-di-tert-butyl-4-methylpyridine (2.18 g, 10.65 mmol) in CH$_2$Cl$_2$ (15.0 mL) at rt, was added trimethyloxonium tetrafluoroborate (1.58 g, 10.65 mmol) under a nitrogen atmosphere. After 1 h at rt, the reaction was quenched with water (50 mL) and extracted with EtOAc (4×50 mL). The combined extract was washed with water, 1.5M HCl, saturated aqueous NaHCO$_3$ and brine, and was dried over anhydrous MgSO$_4$. The filtrate was evaporated and the residue was purified by chromatography on silica gel using the solvent gradient hexanes→hexanes/EtOAc (3:7), to give 0.25 g (72%) of the title compound as a yellow solid. $^1$H-NMR (400 MHz, DMSO-d$_6$) δ 7.84-7.92 (m, 2H), 7.68-7.73 (m, 1H), 5.82-6.03 (m, 2H), 4.82-4.88 (m, 2H), 3.87-3.93 (m, 2H), 3.21 (s, 3H).

Example 199d (E)-2-(4-Hydroxybut-2-enyloxy)-6-nitrobenzonitrile

Prepared as in Example 166d from (E)-but-2-ene-1,4-diol (Miller, A. E. G.; Biss, J. W.; Schwartzman, L. H. *J. Org. Chem.* 1959, 24, 627 in 30% yield as a yellow solid. $^1$H-NMR (400 MHz, DMSO-d$_6$) δ 7.83-7.94 (m, 2H), 7.67-7.74 (m, 1H), 5.97-6.07 (m, 1H), 5.78-5.89 (m, 1H), 4.80-89 (m, 3H), 3.94-4.02 (m, 2H).

Example 200

4-Amino-5-(2-(hydroxymethyl)allyloxy)-1H-benzo[c][1,2,6]thiadiazine-2,2-dioxide

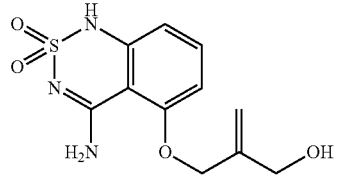

622

Prepared as in Example 111 from 2-((2-cyano-3-(sulfamoylamino)phenoxy)methyl)allyl acetate (Example 200a) in 44% yield as a white solid. $^1$H-NMR (400 MHz, DMSO-d$_6$) δ 10.95 (broad s, 1H), 8.34 (broad s, 1H), 8.01 (broad s, 1H), 7.45 (t, J=8.0 Hz, 1H), 6.76 (d, J=8.4 Hz, 1H), 6.61 (d, J=8.0 Hz, 1H), 5.26 (s, 1H), 5.20 (s, 1H), 5.14 (t, J=5.2 Hz, 1H), 4.78 (s, 2H), 4.03 (d, J=5.2 Hz, 2H). MS 284 (MH$^+$).

Example 200a 2-((2-Cyano-3-(sulfamoylamino)phenoxy)methyl)allyl acetate

Prepared as in Example 111a from 24(3-amino-2-cyanophenoxy)methyl)allyl acetate (Example 200b) in 87% yield as a white solid. $^1$H-NMR (400 MHz, DMSO-d$_6$) δ 9.50 (broad s, 1H), 7.57 (t, J=8.4 Hz, 1H), 7.28 (broad s, 2H), 7.17 (d, J=8.0 Hz, 1H), 6.97 (d, J=8.4 Hz, 1H), 5.39 (broad s, 1H), 5.33 (broad s, 1H), 4.74 (s, 2H), 4.63 (s, 2H), 2.05 (s, 3H).

Example 200b 2-((3-Amino-2-cyanophenoxy)methyl)allyl acetate

Prepared as in Example 199b from 24(2-cyano-3-nitrophenoxy)methyl)allyl acetate (Example 200c) in 76% yield as a yellow oil. $^1$H-NMR (400 MHz, DMSO-d$_6$) δ 7.18 (t, J=8.4

Hz, 1H), 6.35 (d, J=8.8 Hz, 1H), 6.23 (d, J=8.0 Hz, 1H), 6.03 (broad s, 2H), 5.34-5.38 (m, 1H), 5.28-5.31 (m, 1H), 4.61 (s, 4H), 2.05 (s, 3H).

Example 200c 2-((2-Cyano-3-nitrophenoxy)methyl)allyl acetate

To a solution of 2-(2-(hydroxymethyl)allyloxy)-6-nitrobenzonitrile (Example 200d) (0.40 g, 1.73 mmol), 4-dimethylaminopyridine (0.21 g, 1.73 mmol) and pyridine (0.68 g, 8.64 mmol) in $CH_2Cl_2$ (10.0 mL) at 0° C., was added $Ac_2O$ (0.53 g, 5.19 mmol) under a nitrogen atmosphere. After being stirred at 0° C. for 10 min, the mixture was stirred at rt overnight. The reaction mixture was diluted with EtOAc (100 mL), washed with 1.5M HCl, saturated aqueous $NaHCO_3$ and brine, and was dried over $MgSO_4$. The filtrate was evaporated and the residue was purified by chromatography on silica gel using the solvent gradient hexanes→hexanes/EtOAc (3:7), to furnish 0.40 g (84%) of the title compound as a yellow solid. $^1$H-NMR (400 MHz, DMSO-$d_6$) δ 7.95 (dd, J=8.4 Hz, J=1.2 Hz, 1H), 7.91 (t, J=8.4 Hz, 1H), 7.74 (dd, J=8.4 Hz, J=1.2 Hz, 1H), 5.43-5.46 (m, 1H), 5.36-5.40 (m, 1H), 4.90 (s, 2H), 4.66 (s, 2H), 2.05 (s, 3H).

Example 200d 2-(2-(Hydroxymethyl)allyloxy)-6-nitrobenzonitrile

Prepared as in Example 166d from 2,6-dinitrobenzonitrile and 2-methylenepropane-1,3-diol in 55% yield as a white solid. $^1$H-NMR (400 MHz, DMSO-$d_6$) δ 7.93 (dd, J=8.4 Hz, J=0.8 Hz, 1H), 7.89 (t, J=8.0 Hz, 1H), 7.73 (dd, J=7.6 Hz, J=0.8 Hz, 1H), 5.23-5.29 (m, 2H), 5.03 (t, J=5.6 Hz, 1H), 4.85 (s, 2H), 4.06 (d, J=5.2 Hz, 2H). |ΠατΑππ1009_Λ1|ZZMΠΤΑΓ|

Example 201

4-Amino-5-(4,5-dihydrofuran-2-yl)-1H-benzo[c][,6]thiadiazine-2,2-dioxide

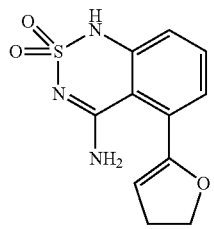

623

Prepared as in Example 111 from 2-sulfamoylamino-6-(4,5-dihydrofuran-2-yl)benzonitrile (Example 201a) in 31% yield as a white solid. $^1$H NMR (400 MHz, DMSO-$d_6$) δ 2.75-2.81 (m, 2H), 4.43 (t, J=9.2 Hz, 2H), 5.35-5.36 (m, 1H), 7.07 (dd, J=1.2, 8.0 Hz, 1H), 7.12 (dd, J=1.2, 7.2 Hz, 1H), 7.50-7.54 (m, 1H), 8.2-8.4 (broad s, 1H), 11.09 (s, 1H). MS 266 (MH$^+$).

Example 201a

2-Sulfamoylamino-6-(4,5-dihydrofuran-2-yl)benzonitrile

Prepared as in Example 111a from 2-amino-6-(4,5-dihydrofuran-2-yl)benzonitrile (Example 201b) in 19% yield as a white solid. $^1$H NMR (400 MHz, DMSO-$d_6$) δ 2.82-2.88 (m, 2H), 4.45 (t, J=9.6 Hz, 2H), 5.89 (t, J=3.2 Hz, 1H), 7.29 (s, 2H), 7.47 (d, J=7.2 Hz, 1H), 7.56 (d, J=7.6 Hz, 1H), 7.67 (t, J=8.0 Hz, 1H), 9.42 (s, 1H). MS 266 (MH$^+$).

Example 201b 2-amino-6-(4,5-dihydrofuran-2-yl)benzonitrile

2-Amino-6-bromobenzonitrile (0.75 g, 3.81 mmol), (4,5-dihydrofuran-2-yl)trimethylstannane (Menez, P.; Fargeas, V.; Poisson, J.; Ardisson, J.; Lallemand, J.-Y.; Pancrazi, A. *Tetrahedron Letters* 1994, 35(42), 7767) (1.02 g, 4.38 mmol), and palladium tetrakis(triphenylphosphine) (0.33 g, 0.28 mmol) were refluxed in toluene (10.0 mL) under nitrogen for 1.5 h. Saturated ammonium chloride (12 mL) and ammonium hydroxide (4 mL) were added, and the mixture was extracted with EtOAc. The organic layer was concentrated under vacuum and the residue was purified by chromatography on silica using 35% EtOAc/hexanes to give 0.48 g (68%) of the title compound as yellow oil. $^1$H NMR (400 MHz, Acetone-$d_6$) δ 2.78-2.83 (m, 2H), 4.40 (t, J=9.2 Hz, 2H), 5.76 (t, J=3.2 Hz, 1H), 6.04 (s, 2H), 6.77-6.80 (m, 2H), 7.28 (t, J=8.0 Hz, 1H). MS 187 (MH$^+$).

Example 202

4-Amino-5-(tetrahydrofuran-2-yl)-1H-benzo[c][1,2,6]thiadiazine-2,2-dioxide

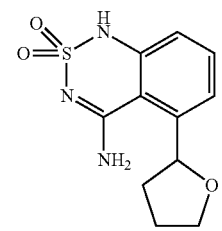

624

Prepared as in Example 111 from 2-sulfamoylamino-6-(tetrahydrofuran-2-yl)benzonitrile (Example 202a) in 52% yield as a white solid. $^1$H NMR (400 MHz, DMSO-$d_6$) δ 1.94-2.05 (m, 3H), 2.21-2.28 (m, 1H), 3.81-3.87 (m, 1H), 3.92-3.97 (m, 1H), 5.23-5.27 (m, 1H), 7.02 (d, J=8.0 Hz, 1H), 7.30 (d, J=7.6 Hz, 1H), 7.51 (t, J=7.6 Hz, 1H), 7.9-8.5 (broad, 2H), 10.94 (s, 1H). MS 268 (MH$^+$).

Example 202a

2-Sulfamoylamino-6-(tetrahydrofuran-2-yl)benzonitrile

2-Amino-6-(4,5-dihydrofuran-2-yl)benzonitrile (Example 202b) (0.24 g, 1.28 mmol), 10% Pd/C (0.24 g), and ammonium formate (2.40 g, 38.1 mmol) were refluxed in MeOH (25 mL) under nitrogen for 1.5 h. The insoluble solids were filtered out and discarded, and the solvent was removed under vacuum. The resultant residue was dissolved in EtOAc, washed with saturated $Na_2CO_3$ and brine, dried over $MgSO_4$ and concentrated under vacuum. The residue was dissolved in anhydrous DMA (2.0 mL) and was treated with sulfamoyl chloride (0.11 g, 0.97 mmol). The reaction mixture was stirred under nitrogen for 30 minutes, quenched with water (5.0 mL) and extracted with EtOAc (3×50 mL). The combined extract was dried over MgSO₄, filtered and concentrated under vacuum. The crude product was purified by silica gel prep-TLC using 65% EtOAc/hexanes to give 45.0 mg (13%) of the title compound as a white solid. ¹H NMR (400 MHz, Acetone-d₆) δ 1.71-1.78 (m, 1H), 2.02-2.07 (m, 2H), 2.45-2.52 (m, 1H), 3.90-3.95 (m, 1H), 4.10-4.15 (m, 1H), 5.08 (t, J=6.8 Hz, 1H), 6.6-6.8 (broad, 2H), 7.36-7.39 (m, 1H), 7.62-7.63 (m, 2H), 8.22 (broad s, 1H). MS 268 (MH⁺).

Example 203

4-Amino-5-(3-(pyridin-2-yl)propoxy)-1H-benzo[c][1,2,6]thiadiazine-2,2-dioxide

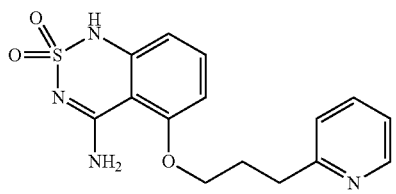

625

Prepared as in Example 111 from 2-sulfamoylamino-6-(3-(pyridin-2-yl)propoxy)benzonitrile (Example 203a) in 58% yield as a white solid. ¹H NMR (400 MHz, DMSO-d₆) δ 2.37 (quint, J=6.8 Hz, 2H), 2.89 (t, J=7.2 Hz, 2H), 4.19 (t, J=6.0 Hz, 2H), 6.60 (d, J=8.4 Hz, 1H), 6.73 (d, J=8.8 Hz, 1H), 7.19-7.22 (m, 1H), 7.29 (d, J=8.0 Hz, 1H), 7.44 (t, J=8.4 Hz, 1H), 7.68-7.72 (m, 1H), 7.92 (s, 1H), 8.36 (s, 1H), 8.49 (d, J=4.0 Hz, 1H), 10.94 (broad s, 1H). MS 333 (MH⁺).

Example 203a

2-Sulfamoylamino-6-(3-(pyridin-2-yl)propoxy)benzonitrile

Prepared as in Example 111a from 2-amino-6-(3-(pyridin-2-yl)propoxy)benzonitrile (Example 203b) in 97% yield as a white solid. ¹H NMR (400 MHz, DMSO-d₆) δ 2.15 (quint, J=6.4 Hz, 2H), 2.92 (t, J=7.6 Hz, 2H), 4.15 (t, J=6.0 Hz, 2H), 6.93 (d, J=8.4 Hz, 1H), 7.14 (d, J=8.4 Hz, 1H), 7.20-7.29 (m, 4H), 7.55 (t, J=8.4 Hz, 1H), 7.68-7.72 (m, 1H), 8.48 (d, J=4.8 Hz, 1H), 9.49 (broad s, 1H). MS 333 (MH⁺).

Example 203b

2-Amino-6-(3-(pyridin-2-yl)propoxy)benzonitrile

Prepared as in Example 199b from 2-nitro-6-(3-(pyridin-2-yl)propoxy)benzonitrile (Example 203c) in 85% yield as a white solid. ¹H NMR (400 MHz, DMSO-d₆) δ 2.12 (quint, J=6.8 Hz, 2H), 2.90 (t, J=7.2 Hz, 2H), 4.02 (t, J=6.4 Hz, 2H), 5.99 (s, 2H), 6.18 (d, J=8.0 Hz, 1H), 6.33 (d, J=8.8 Hz, 1H), 7.14-7.22 (m, 2H), 7.26 (d, J=8.0 Hz, 1H), 7.67-7.71 (m, 1H), 8.49 (d, J=3.6 Hz, 1H). MS 254 (MH⁺).

Example 203c

2-Nitro-6-(3-(pyridin-2-yl)propoxy)benzonitrile

Prepared as in Example 187c from 3-(pyridin-2-yl)propan-1-ol 2,6-dinitrobenzonitrile in 86% yield as a white solid. ¹H NMR (400 MHz, DMSO-d₆) δ 2.21 (quint, J=6.4 Hz, 2H), 2.95 (t, J=7.2 Hz, 2H), 4.31 (t, J=6.4 Hz, 2H), 7.19-7.22 (m, 1H), 7.28 (d, J=7.6 Hz, 1H), 7.67-7.74 (m, 2H), 7.86-7.92 (m, 2H), 8.48 (d, J=4.8 Hz, 1H). MS 284 (MH⁺).

Example 204

4-Amino-5-(2-(pyridin-2-yl)ethoxy)-1H-benzo[c][1,2,6]thiadiazine-2,2-dioxide

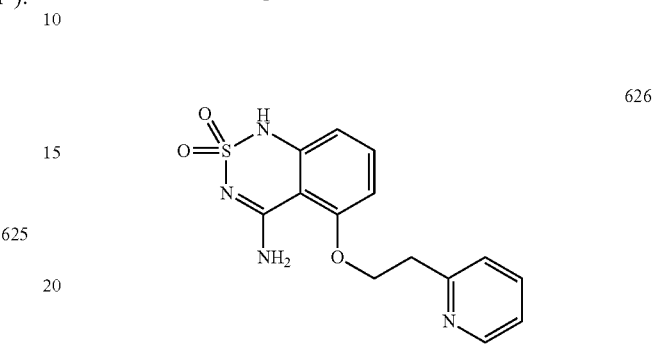

626

Prepared as in Example 111 from 2-sulfamoylamino-6-(2-(pyridin-2-yl)ethoxy)benzonitrile (Example 204a) in 22% yield as a white solid. ¹H NMR (400 MHz, DMSO-d₆) δ 3.29 (t, J=5.6 Hz, 2H), 4.46 (t, J=5.6 Hz, 2H), 6.59 (d, J=8.0 Hz, 1H), 6.75 (d, J=8.8 Hz, 1H), 7.28-7.31 (m, 1H), 7.40-7.46 (m, 2H), 7.75-7.80 (m, 1H), 8.33-8.52 (m, 3H), 10.91 (s, 1H). MS 319 (MH⁺).

Example 204a

2-Sulfamoylamino-6-(2-(pyridin-2-yl)ethoxy)benzonitrile

Prepared as in Example 111a from 2-amino-6-(2-(pyridin-2-yl)ethoxy)benzonitrile (Example 204b) in 67% yield as a white solid. ¹H NMR (400 MHz, DMSO-d₆) δ 3.22 (t, J=6.4 Hz, 2H), 4.48 (t, J=6.4 Hz, 2H), 7.00 (d, J=8.8 Hz, 1H), 7.14 (d, J=8.4 Hz, 1H), 7.23-7.26 (m, 3H), 7.39 (d, J=7.6 Hz, 1H), 7.55 (t, J=8.4 Hz, 1H), 7.73 (t, J=7.2 Hz, 1H), 8.51 (d, J=4.4 Hz, 1H), 9.42 (s, 1H). MS 319 (MH⁺).

Example 204b

2-Amino-6-(2-(pyridin-2-yl)ethoxy)benzonitrile

Prepared as in Example 2b from 2-nitro-6-(2-(pyridin-2-yl)propoxy)benzonitrile (Example 221c) in 60% yield as a white solid. ¹H NMR (400 MHz, DMSO-d₆) δ 3.18 (t, J=6.8 Hz, 2H), 4.36 (t, J=6.8 Hz, 2H), 5.97 (s, 2H), 6.25 (d, J=8.4 Hz, 1H), 6.32 (d, J=8.4 Hz, 1H), 7.17 (t, J=8.0 Hz, 1H), 7.22-7.26 (m, 1H), 7.37 (d, J=8.0 Hz, 1H), 7.70-7.75 (m, 1H), 8.51 (d, J=4.4 Hz, 1H). MS 240 (MH⁺).

Example 204c

2-Nitro-6-(2-(pyridin-2-yl)ethoxy)benzonitrile

Prepared as in Example 187c from 2-(pyridin-2-yl)ethanol and 2,6-dinitrobenzonitrile in 82% yield as a yellow solid. ¹H NMR (400 MHz, DMSO-d₆) δ 3.27 (t, J=6.4 Hz, 2H), 4.64 (t, J=6.4 Hz, 2H), 7.23-7.27 (m, 1H), 7.41 (d, J=8.0 Hz, 1H), 7.71-7.79 (m, 2H), 7.86-7.91 (m, 2H), 8.50-8.52 (m, 1H). MS 270 (MH⁺).

Example 205

4-Amino-5-((5-methylisoxazol-3-yl)methoxy)-1H-benzo[c][,6]thiadiazine-2,2-dioxide

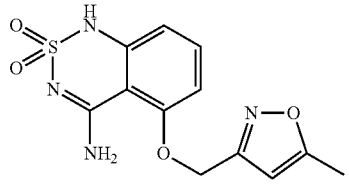

627

Prepared as in Example 111 from 2-sulfamoylamino-6-((5-methylisoxazol-3-yl)methoxy)benzonitrile (Example 205a) in 83% yield as a white solid. $^1$H NMR (400 MHz, DMSO-d$_6$) δ 2.42 (s, 3H), 5.40 (s, 2H), 6.36 (s, 1H), 6.65 (d, J=8.4 Hz, 1H), 6.81 (d, J=8.4 Hz, 1H), 7.48 (t, J=8.4 Hz, 1H), 8.06 (s, 1H), 8.40 (s, 1H), 11.02 (s, 1H). MS 309 (MH⁺).

Example 205a

2-Sulfamoylamino-6-((5-methylisoxazol-3-yl)methoxy)benzonitrile

Prepared as in Example 111a from 2-amino-6-((5-methylisoxazol-3-yl)methoxy)benzonitrile (Example 222b) in 85% yield as a white solid. $^1$H NMR (400 MHz, DMSO-d$_6$) δ 2.42 (s, 3H), 5.32 (s, 2H), 6.34 (s, 1H), 7.07 (d, J=8.0 Hz, 1H), 7.19 (d, J=8.0 Hz, 1H), 7.30 (s, 2H), 7.59 (t, J=8.8 Hz, 1H), 9.53 (s, 1H). MS 309 (MH⁺).

Example 205b

2-Amino-6-((5-methylisoxazol-3-yl)methoxy)benzonitrile

Prepared as in Example 199b from 24(5-methylisoxazol-3-yl)methoxy)-6-nitrobenzonitrile (Example 205c) in 52% yield as a yellow solid. $^1$H NMR (400 MHz, DMSO-d$_6$) δ 2.42 (s, 3H), 5.19 (s, 2H), 6.07 (s, 2H), 6.31-6.33 (m, 2H), 6.37 (d, J=8.4 Hz, 1H), 7.20 (t, J=8.4 Hz, 1H). MS 230 (MH⁺).

Example 205c

2-((5-Methylisoxazol-3-yl)methoxy)-6-nitrobenzonitrile

Prepared as in Example 187c from (5-methylisoxazol-3-yl)methanol and 2,6-dinitrobenzonitrile in 86% yield as a yellow solid. $^1$H NMR (400 MHz, DMSO-d$_6$) δ 2.43 (d, J=0.8 Hz, 3H), 5.50 (s, 2H), 6.38 (d, J=0.4 Hz, 1H), 7.83 (dd, J=1.2, 8.4 Hz, 1H), 7.91-7.98 (m, 2H). MS 260 (MH⁺).

Example 206

4-Amino-5-(2-cyclopropylethoxy)-1H-benzo[c][1,2,6]thiadiazine-2,2-dioxide

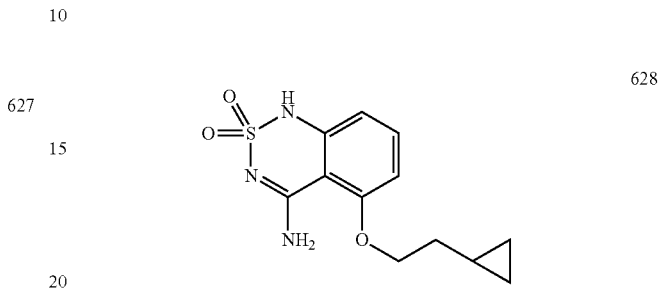

628

Prepared as in Example 111 from 2-sulfamoylamino-6-(2-cyclopropylethoxy)benzonitrile (Example 206a) in 94% yield as a white solid. $^1$H NMR (400 MHz, DMSO-d$_6$) δ 0.11-0.15 (m, 2H), 0.43-0.48 (m, 2H), 0.77-0.81 (m, 1H), 1.73 (q, J=6.8 Hz, 2H), 4.21 (t, J=6.8 Hz, 2H), 6.61 (d, J=8.0 Hz, 1H), 6.77 (d, J=8.4 Hz, 1H), 7.46 (t, J=8.4 Hz, 1H), 7.87 (s, 1H), 8.39 (s, 1H), 10.96 (s, 1H). MS 282 (MH⁺).

Example 206a

2-Sulfamoylamino-6-(2-cyclopropylethoxy)benzonitrile

Prepared as in Example 111a from 2-amino-6-(2-cyclopropylethoxy)benzonitrile (Example 206b) in 80% yield as a white solid. $^1$H NMR (400 MHz, DMSO-d$_6$) δ 0.13-0.17 (m, 2H), 0.41-0.46 (m, 2H), 0.82-0.87 (m, 1H), 1.64 (q, J=6.4 Hz, 2H), 4.16 (t, J=6.4 Hz, 2H), 6.96 (d, J=8.0 Hz, 1H), 7.14 (d, J=8.8 Hz, 1H), 7.27 (s, 2H), 7.56 (t, J=8.8 Hz, 1H), 9.44 (s, 1H). MS 282 (MH⁺).

Example 206b

2-Amino-6-(2-cyclopropylethoxy)benzonitrile

Prepared as in Example 199b from 2-(2-cyclopropylethoxy)-6-nitrobenzonitrile (Example 206c) in 90% yield as a yellow oil. $^1$H NMR (400 MHz, DMSO-d$_6$) δ 0.13-0.16 (m, 2H), 0.40-0.45 (m, 2H), 0.81-0.85 (m, 1H), 1.61 (q, J=6.8 Hz, 2H), 4.04 (t, J=6.4 Hz, 2H), 5.97 (s, 2H), 6.21 (d, J=8.0 Hz, 1H), 6.32 (d, J=8.8 Hz, 1H), 7.17 (t, J=8.4 Hz, 1H). MS 203 (MH⁺).

Example 206c

2-(2-Cyclopropylethoxy)-6-nitrobenzonitrile

Prepared as in Example 187c from 2-cyclopropylethanol and 2,6-dinitrobenzonitrile in 85% yield as a yellow oil. $^1$H NMR (400 MHz, DMSO-d$_6$) δ 0.15-0.20 (m, 2H), 0.43-0.47

Example 207

4-Amino-5-(hydroxymethyl)-1H-benzo[c][1,2,6]thiadiazine-2,2-dioxide

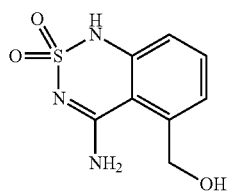

Prepared as in Example 111 from 2-cyano-3-(sulfamoylamino)benzyl acetate (Example 207a) in 53% yield as a white solid. $^1$H NMR (400 MHz, DMSO-$d_6$) δ 4.60 (s, 2H), 6.62-6.63 (m, 1H), 7.04 (d, J=8.0 Hz, 1H), 7.09 (d, J=7.2 Hz, 1H), 7.51 (t, J=7.6 Hz, 1H), 8.33 (broad s, 1H), 8.86 (broad s, 1H), 10.92 (s, 1H). MS 228 (MH$^+$).

Example 207a

2-Cyano-3-(sulfamoylamino)benzyl acetate

Prepared as in Example 111a from 3-amino-2-cyanobenzyl acetate (Example 207b) in 90% yield as a white solid. $^1$H NMR (400 MHz, Acetone-$d_6$) δ 2.09 (s, 3H), 5.24 (s, 2H), 6.76 (broad s, 2H), 7.38 (dd, J=0.8, 7.2 Hz, 1H), 7.66-7.75 (m, 2H), 8.40 (broad s, 1H). MS 270 (MH$^+$).

Example 207b

3-Amino-2-cyanobenzyl acetate

Prepared as in Example 199b from 2-cyano-3-nitrobenzyl acetate (Example 207c) in 84% yield as yellow oil. $^1$H NMR (400 MHz, Methanol-$d_4$) δ 2.10 (s, 3H), 5.11 (s, 2H), 6.70 (d, J=7.2 Hz, 1H), 6.78 (d, J=8.8 Hz, 1H), 7.28 (t, J=8.4 Hz, 1H). MS 191 (MH$^+$).

Example 207c

2-Cyano-3-nitrobenzyl acetate

Acetic anhydride (0.84 mL, 8.87 mmol) was added to a solution of 2-(hydroxymethyl)-6-nitrobenzonitrile (Example 207d) (0.31 g, 1.77 mmol), pyridine (0.86 mL, 10.6 mmol), and DMAP (0.22 g, 1.77 mmol) in CH$_2$Cl$_2$ (10 mL), and stirred for 24 h at rt. The mixture was washed mice with AcOH (1 M, 20 mL), dried with MgSO$_4$, concentrated, and purified by chromatography on silica using CH$_2$Cl$_2$, to give the title compound in amount of 0.36 g (92%) as a yellow solid. $^1$H NMR (400 MHz, DMSO-$d_6$) δ 2.12 (s, 3H), 5.35 (s, 2H), 7.99 (t, J=8.0 Hz, 1H), 8.06 (dd, J=0.8, 8.0 Hz, 1H), 8.37 (dd, J=0.8, 8.0 Hz, 1H).

Example 207d 2-(Hydroxymethyl)-6-nitrobenzonitrile

Sodium borohydride (92.0 mg, 2.43 mmol) was added to a solution of 2-formyl-6-nitrobenzonitrile (Example 207e) (0.86 g, 4.88 mmol) in MeOH (38 mL) and THF (38 mL) at −8° C., and was stirred at that temperature for no more than 30 min. The reaction was quenched with HCl (6 M, 4.88 mL), followed by addition of water (50 mL), and brine (50 mL). The mixture was extracted with EtOAc, the combined extract was dried over MgSO$_4$, filtered and concentrated. The crude product was purified by chromatography on silica using the solvent gradient CH$_2$Cl$_2$→CH$_2$Cl$_2$/MeOH (8:2) to give the title compound in amount of 0.32 g, (37%), which was used immediately in the next step. $^1$H NMR (400 MHz, DMSO-$d_6$) δ 4.77 (d, J=5.6 Hz, 2H), 5.87 (t, J=5.6 Hz, 1H), 7.97 (t, J=8.0 Hz, 1H), 8.07 (dd, J=0.4, 8.0 Hz, 1H), 8.28 (dd, J=0.8, 8.0 Hz, 1H).

Example 207e

2-Formyl-6-nitrobenzonitrile 1,1-Dimethoxy-N,N-dimethylmethanamine (13.56 mL, 102 mmol) was added to a solution of 2-methyl-6-nitrobenzonitrile (15.0 g, 92.5 mmol) in anhydrous DMF (60 mL) under nitrogen and was heated at 130° C. for 15 h. Ice water (300 mL) was added, and the resultant dark precipitate was collected by filtration and dried under vacuum. Phosphate buffer (pH 7, 350 mL) and then NaIO$_4$ (40 g, 187 mmol) were added to a solution of the dark precipitate in THF (350 mL) and stirred at rt for 3 h. The mixture was extracted with EtOAc, the combined extract was washed with brine and dried with MgSO$_4$. The filtrate was concentrated and the residue was purified by chromatography on silica using the solvent gradient hexanes→EtOAc, to give 3.07 g (19%) of the title compound as a yellow solid. $^1$H NMR (400 MHz, DMSO-$d_6$) δ 8.15 (t, J=8.4 Hz, 1H), 8.41 (dd, J=1.2, 7.6 Hz, 1H), 8.62 (dd, J=1.2, 8.4 Hz, 1H), 10.25 (s, 1H).

Example 208

(E)-4-Amino-5-(4-oxo-4-(propylamino)but-2-enyloxy)-1H-benzo[c][1,2,6]thiadiazine-2,2-dioxide

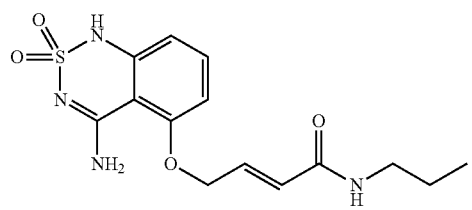

Prepared as in Example 111 from (E)-4-(2-cyano-3-(sulfamoylamino)phenoxy)-N-propylbut-2-enamide (Example 208a) in 19% yield as a white solid. $^1$H NMR (400 MHz, Acetone-$d_6$) δ 0.87 (t, J=7.2 Hz, 3H), 1.47 (hex, J=7.6 Hz, 2H), 3.11-3.17 (m, 4H), 5.35 (q, J=7.2 Hz, 1H), 6.70 (d, J=6.0 Hz, 1H), 6.77 (d, J=8.0 Hz, 1H), 6.87 (d, J=8.0 Hz, 1H), 7.2-7.5 (broad s, 2H), 7.51 (t, J=8.0 Hz, 1H), 8.19 (broad s, 1H), 9.5-10.5 (broad s, 1H). MS 339 (MH$^+$).

Example 208a (E)-4-(2-Cyano-3-(sulfamoylamino)phenoxy)-N-propylbut-2-enamide Prepared as in Example 111a from (E)-4-(3-amino-2-cyanophenoxy)-N-propylbut-2-enamide (Example 208b) in 87% yield as a white solid. $^1$H NMR (400 MHz, DMSO-d$_6$) δ 0.84 (t, J=7.2 Hz, 3H), 1.43 (hex, J=6.8 Hz, 2H), 3.06 (q, J=6.8 Hz, 2H), 4.90 (d, J=2.8 Hz, 2H), 6.15 (d, J=15.6 Hz, 1H), 6.70-6.77 (m, 1H), 6.91 (d, J=8.8 Hz, 1H), 7.17 (d, J=8.4 Hz, 1H), 7.27 (broad s, 2H), 7.57 (t, J=8.8 Hz, 1H), 8.13-8.16 (m, 1H), 9.52 (broad s, 1H). MS 339 (MH$^+$).

Example 208b (E)-4-(3-Amino-2-cyanophenoxy)-N-propylbut-2-enamide

Prepared as in Example 199b from (E)-4-(2-cyano-3-nitrophenoxy)-N-propylbut-2-enamide (Example 208c) in 73% yield as yellow solid. $^1$H NMR (400 MHz, DMSO-d$_6$) δ 0.84 (t, J=7.2 Hz, 3H), 1.42 (hex, J=7.2 Hz, 2H), 3.06 (q, J=6.8 Hz, 2H), 4.77-4.79 (m, 2H), 6.04 (s, 2H), 6.11-6.20 (m, 2H), 6.35 (d, J=8.4 Hz, 1H), 6.67-6.74 (m, 1H), 7.18 (t, J=8.0 Hz, 1H), 8.11-8.14 (m, 1H). MS 260 (MH$^+$).

Example 208c (E)-4-(2-Cyano-3-nitrophenoxy)-N-propylbut-2-enamide (E)-4-Bromo-N-propylbut-2-enamide (Elliott, M.; Farnham, A. W.; Janes, N. F.; Johnson, D. M.; Pulman, D. A. *Pesticide Science* 1987 18(4) 229) (0.14 g, 0.70 mmol), 2-hydroxy-6-nitrobenzonitrile (0.14 g, 0.88 mmol), potassium carbonate (0.39 g, 2.81 mmol), and 18-crown-6 (0.11 g, 0.42 mmol) were refluxed in acetone (6 mL) for 2 h, and then poured into ice water (45 mL). The resultant precipitate was collected by filtration to give 0.16 g (79%) of the title compound as an off white solid. $^1$H NMR (400 MHz, DMSO-d$_6$) δ 0.84 (t, J=7.2 Hz, 3H), 1.42 (hex, J=7.2 Hz, 2H), 3.06 (q, J=6.8 Hz, 2H), 5.07 (d, J=2.8 Hz, 2H), 6.16 (d, J=16.0 Hz, 1H), 6.71-6.78 (m, 1H), 7.69 (d, J=8.0 Hz, 1H), 7.88-7.96 (m, 2H), 8.11-8.14 (m, 1H).

Example 209

(S)-4-Amino-5-((1-acetylpyrrolidin-2-yl)methoxy)-1H-benzo[c][1,2,6]thiadiazine-2,2-dioxide

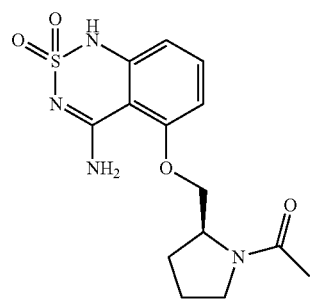

631

Prepared as in Example 176 from (S)-2-amino-6-((1-acetylpyrrolidin-2-yl)methoxy)benzonitrile (Example 209a) in 10% yield as a white solid. $^1$H NMR (400 MHz, DMSO-d$_6$) δ 1.93 (m, 4H), 2.00 (s, 3H), 3.50 (m, 2H), 4.09 (dd, J=10.0, 6.2 Hz, 1H), 4.24 (dd, J=10.0, 5.6 Hz, 1H), 4.41 (m, 1H), 6.62 (d, J=8.2 Hz, 1H), 6.87 (d, J=8.5 Hz, 1H), 7.46 (t, J=8.5 Hz, 1H), 8.12 (br s, 1H), 8.33 (br s, 1H), 10.93 (br s, 1H). MS 339 (MH$^+$).

Example 209a (S)-2-Amino-6((1-acetylpyrrolidin-2-yl)methoxy)benzonitrile

To a suspension of (S)-2-((2-cyano-3-nitrophenoxy)methyl)pyrrolidinium chloride (130 mg, 0.46 mmol) (Example 209b) in THF (5 mL) were added Et$_3$N (135 µL, 0.97 mmol) and acetyl chloride (36 µL, 0.50 mmol). The reaction was stirred at rt for 18 h, filtered and diluted with EtOH (20 mL). The resulting solution was hydrogenated (20 Bar) using 10% Pd/C as the catalyst. Upon completion, the reaction mixture was concentrated to provide the title compound (61 mg, 51%) as a clear syrup. MS 260 (MH$^+$).

Example 209b (S)-2-((2-Cyano-3-nitrophenoxy)methyl)pyrrolidinium chloride

Prepared as in Example 166 from (S)-tert-butyl-2-((2-cyano-3-nitrophenoxy)methyl)pyrrolidine-1-carboxylate (Example 209c) in 81% yield as an off-white solid. MS 248 (MH$^+$-HCl).

Example 209c (S)-tert-Butyl 2-((2-cyano-3-nitrophenoxy)methyl)pyrrolidine-1-carboxylate Prepared as in Example 166d from 2,6-dinitrobenzonitrile and (S)-tert-butyl 2-(hydroxymethyl)pyrrolidine-1-carboxylate in 89% yield as a tan solid. $^1$H NMR (400 MHz, DMSO-d$_6$) δ 1.40 (s, 9H), 1.81 (m, 1H), 2.03 (m, 3H), 3.32 (m, 2H), 4.08 (m, 1H), 4.33 (m, 2H), 7.79 (d, J=7.8 Hz, 1H), 7.93 (m, 2H).

Example 210

(S)-4-Amino-5-((1-propionylpyrrolidine-2-yl)methoxy)-1H-benzo[c][1,2,6]thiadiazine-2,2-dioxide

632

Prepared as in Example 176 from (S)-2-amino-6-((1-propionylpyrrolidine-2-yl)methoxy)benzonitrile (Example 210a) in 17% yield as an off-white solid. $^1$H NMR (400 MHz, DMSO-d$_6$) δ 1.01 (t, J=7.8 Hz, 3H), 1.95 (m, 4H), 2.31 (m, 2H), 3.48 (m, 2H), 4.11 (dd, J=10.0, 6.4 Hz, 1H), 4.27 (dd, J=9.8, 5.0 Hz, 1H), 4.43 (m, 1H), 6.64 (d, J=7.9 Hz, 1H), 6.92 (d, J=8.4 Hz, 1H), 7.48 (t, J=8.2 Hz, 1H), 8.09 (br s, 1H), 8.34 (br s, 1H), 10.95 (br s, 1H). MS 353 (MH$^+$).

Example 210a (S)-2-Amino-6-((1-propionylpyrrolidine-2-yl)methoxy)benzonitrile

Prepared as in Example 209a from (S)-2-((2-cyano-3-nitrophenoxy)methyl)pyrrolidinium chloride (Example 210b) and propionyl chloride in 90% yield as a clear syrup. MS 274 (MH$^+$).

Example 211

(S)-4-Amino-5-((1-butyrylpyrrolidin-2-yl)methoxy)-1H-benzo[c][1,2,6]thiadiazine-2,2-dioxide

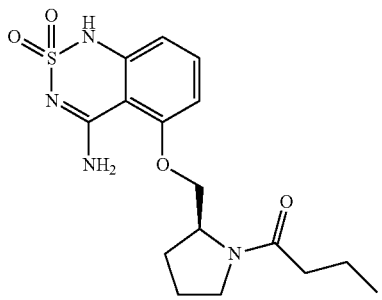

633

Prepared as in Example 176 from (3)-2-amino-6-((1-butyrylpyrrolidin-2-yl)methoxy)benzonitrile (Example 211a) in 78% yield as an off-white solid. $^1$H NMR (400 MHz, DMSO-$d_6$) δ 0.88 (t, J=7.5 Hz, 3H), 1.54 (q, J=7.5 Hz), 1.94 (m, 4H), 2.26 (t, J=7.5 Hz, 2H), 3.48 (m, 2H), 4.10 (m, 1H), 4.25 (m, 1H), 4.43 (m, 1H), 6.62 (d, J=8.1 Hz, 1H), 6.89 (d, J=8.6 Hz, 1H), 7.47 (t, J=8.3 Hz, 1H), 8.08 (hr s, 1H), 8.32 (br s, 1H), 10.93 (br s, 1H). MS 367 (MH$^+$).

Example 211a (S)-2-Amino-6-((1-butyrylpyrrolidin-2-yl)methoxy)benzonitrile

Prepared as in Example 209a from (S)-2-((2-cyano-3-nitrophenoxy)methyl)pyrrolidinium chloride (Example 209b) and butyryl chloride to in 90% yield as a white solid. MS 288 (MH$^+$).

Example 212

(S)-2-((4-Amino-1H-benzo[c][1,2,6]thiadiazine-2,2-dioxide-5-yloxy)methyl)-N-methylpyrrolidine-1-carboxamide

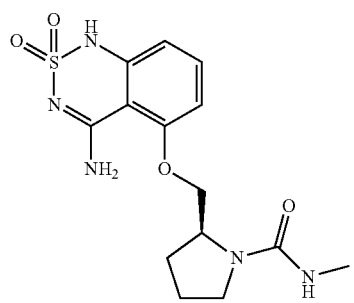

634

Prepared as in Example 176 from (S)-2-((3-amino-2-cyanophenoxy)methyl)-N-methylpyrrolidine-1-carboxamide (Example 212a) in 30% yield as an off-white solid. $^1$H NMR (400 MHz, DMSO-$d_6$) δ 1.89 (m, 4H), 2.60 (d, J=3.9 Hz, 3H), 3.20 (m, 2H), 4.01 (m, 1H), 4.16 (m, 1H), 432 (m, 1H), 6.23 (m, 1H), 6.62 (d, J=8.2 Hz, 1H), 6.89 (d, J=8.5 Hz, 1H), 7.46 (t, J=8.2 Hz, 1H), 8.19 (br s, 1H), 8.27 (br s, 1H), 10.92 (s, 1H). MS 354 (MH$^+$).

Example 212a (S)-2-((3-Amino-2-cyanophenoxy)methyl)-N-methylpyrrolidine-1-carboxamide Prepared as in Example 209a from (S)-2-((2-cyano-3-nitrophenoxy)methyl)pyrrolidinium chloride (Example 209b) and methyl isocyanate in 53% yield as a white solid. MS 275 (MH$^+$).

Example 213

(S)-2-((4-Amino-1H-benzo[c][1,2,6]thiadiazine-2,2-dioxide-5-yloxy)methyl)-N-ethylpyrrolidine-1-carboxamide

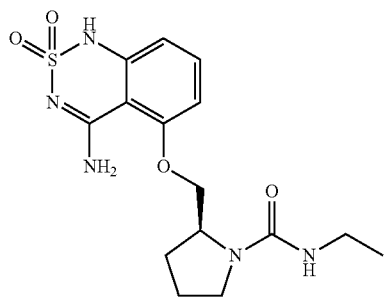

635

Prepared as in Example 276 from (5)-2-((3-amino-2-cyanophenoxy)methyl)-N-ethylpyrrolidine-1-carboxamide (Example 213a) in 68% yield as an off-white solid. $^1$H NMR (400 MHz, DMSO-$d_6$) δ 1.03 (t, J=6.9 Hz, 6H), 1.90 (m, 4H), 3.08 (quint, J=6.6 Hz, 2H), 3.20 (m, 1H), 3.31 (m, 1H), 4.00 (dd, J=9.7, 6.7 Hz, 1H), 4.17 (dd, J=9.7, 6.0 Hz, 1H), 4.33 (m, 1H), 6.27 (d, J=5.7 Hz, 1H), 6.62 (d, J=8.2 Hz, 1H), 6.89 (d, J=8.3 Hz, 1H), 7.46 (t, J=8.2 Hz, 1H), 8.20 (br s, 1H), 8.26 (br s, 1H), 10.91 (s, 1H). MS 368 (MH$^+$).

Example 213a (S)-2-((3-Amino-2-cyanophenoxy)methyl)-N-ethylpyrrolidine-1-carboxamide Prepared as in Example 209a from (S)-2-((2-cyano-3-nitrophenoxy)methyl)pyrrolidinium chloride (Example 209bW) and ethyl isocyanate in 100% yield as a white solid. MS 289 (MH$^+$).

Example 214

(S)-2-((4-Amino-1H-benzo[c][1,2,6]thiadiazine-2,2-dioxide-5-yloxy)methyl)-N-propylpyrrolidine-1-carboxamide

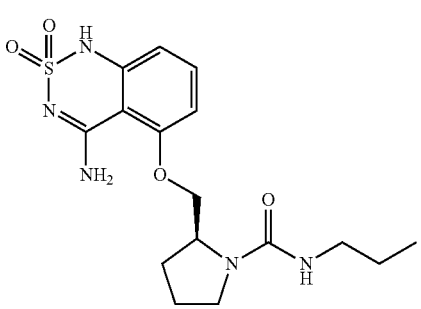

636

Prepared as in Example 276 from (S)-2-((3-amino-2-cyanophenoxy)methyl)-N-propylpyrrolidine-1-carboxamide (Example 214a) in 37% yield as an off-white solid. $^1$H NMR (400 MHz, DMSO-$d_6$) δ 0.84 (t, J=7.6 Hz, 6H), 1.43 (sext, J=7.4 Hz, 2H), 1.92 (m, 4H), 3.01 (m, 2H), 3.21 (m, 1H), 3.33 (m, 1H), 4.02 (dd, J=9.7, 6.4 Hz, 1H), 4.18 (dd, J=9.7, 5.9 Hz, 1H), 4.34 (m, 1H), 6.27 (d, J=5.6 Hz, 1H), 6.62 (d, J=8.4 Hz, 1H), 6.89 (d, J=8.6 Hz, 1H), 7.46 (t, J=8.3 Hz, 1H), 8.20 (br s, 1H), 8.27 (br s, 1H), 10.91 (s, 1H). MS 382 (MH$^+$).

Example 214a (S)-2-((3-Amino-2-cyanophenoxy)methyl)-N-propylpyrrolidine-1-carboxamide Prepared as in Example 209a from (5)-2-((2-cyano-3-nitrophenoxy)methyl)pyrrolidinium chloride (Example 209b) and propyl isocyanate in 100% yield as a white solid. MS 303 (MH$^+$).

Example 215

3-(4-Amino-2,2-dioxide-1H-benzo[c][1,2,6]thiadiazin-5-yloxy)-2',2'-dimethyl-N-propylpropanamide

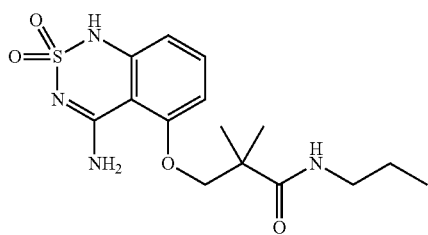

637

To a stirred solution of 3-(3-sulfamoylamino-2-cyanophenoxy)-2,2-dimethyl-N-propylpropanamide (18.52 g, 52.55 mmol) (Example 215a) in EtOH (150 mL) was added NaOH solution (2.0 N, 52.3 mL) at room temperature. The reaction mixture was then refluxed for 2 hrs until the reaction was complete by TLC. The solution was cooled to 0° C. and neutralized carefully with 10% acetic acid and the precipitate was collected by filtration and washed with water. The product was further purified by recrystallization from EtOH/H$_2$O (1:4), dried under vacuum to give the title compound as a white solid (13.5 g, 73%). M.p.: 225-226° C. $^1$H NMR (400 MHz, DMSO-$d_6$) δ 0.75 (t, J=7.4 Hz, 3H), 1.22 (s, 6H), 1.38 (m, 2H), 3.01 (q, J=6.5 Hz, 2H), 4.07 (s, 2H), 6.59 (d, J=8.0 Hz, 1H), 6.71 (d, J=8.0 Hz, 1H), 7.44 (t, J=8.0 Hz, 1H)), 7.82 (t, J=5.6 Hz, 1H), 7.92 (s, 1H), 8.33 (s, 1H), 10.93 (s, 1H). MS 355 (MH$^+$).

Example 215a 3-(3-sulfamoylamino-2-cyanophenoxy)-2,2-dimethyl-N-propyl-propanamide To a solution of 3-(3-amino-2-cyanophenoxy)-2,2-dimethyl-N-propylpropanamide (16.5 g, 59.92 mmol) (Example 215b) in DMA (50 mL) was added sulfamoyl chloride (13.85 g, 119.84 mmol) at 0° C. under nitrogen. The reaction mixture was then stirred at room temperature under nitrogen for 3 hrs then diluted, with EtOAc, washed successively with NaHCO$_3$, brine, dried over Na$_2$SO$_4$, filtered and evaporated to give the title compound as a off white solid (18.52 g, 87%). $^1$H NMR (400 MHz, DMSO-$d_6$) δ 0.79 (t, J=7.6 Hz, 3H), 1.20 (s, 6H), 1.38 (m, 2H), 3.01 (q, J=6.5 Hz, 2H), 4.05 (s, 2H), 6.92 (d, J=8.4 Hz, 1H), 7.13 (d, J=8.4 Hz, 1H), 7.24 (s, 2H), 7.53 (t, J=8.4 Hz, 1H), 7.55 (t, J=5.6 Hz, 1H), 9.42 (s, 1H). MS 355 (MH$^+$).

Example 215b 3-(3-amino-2-cyanophenoxy)-2,2-dimethyl-N-propylpropanamide

Method A:
To a solution of 3-(2-cyano-3-nitrophenoxy)-2,2-dimethyl-N-propylpropanamide (305 mg, 1.0 mmol) (Example 215c) in EtOAc (20.0 mL) was added 10% Pd/C (50 mg). The suspension was stirred under an atmosphere of H$_2$ at room temperature overnight. The Pd/C was filtered off, and washed with EtOAc. The filtrate was concentrated under reduced pressure and the residue was purified by chromatography on silica gel eluting with 50% EtOAc in hexanes to give the title compound (267 mg, 97%) as a white solid. MS 276 (MH$^+$).

Method B:
To a solution of 3-hydroxy-2,2-dimethyl-N-propylpropanamide (20.2 g, 0.127 mol) (Example 215d) in thy THF (500 mL) was carefully added NaH (60% in mineral oil, 7.64 g, 0.191 mol) in small portions at 0° C. under nitrogen. The reaction mixture was then warmed to room temperature and stirred under nitrogen for 1 hr. To this solution was slowly added at room temperature 2-amino-6-fluorobenzonitrile (17.3 g, 0.127 mol) in THF (100 mL) and the reaction mixture refluxed overnight under nitrogen then cooled down to room temperature, quenched with brine, and extracted with EtOAc (3×). The combined organic layers were washed with brine, dried over Na$_2$SO$_4$, evaporated and the residue was crystallized from EtOAc/Hexane to give the compound as a white solid (16.5 g, 48%). MS 276 (MH$^+$).

Example 215c 3-(2-cyano-3-nitrophenoxy)-2,2-dimethyl-N-propylpropanamide

To a solution of 3-hydroxy-2,2-dimethyl-N-propylpropanamide (1.59 g, 10.0 mmol) (Example 215d) in dry THF (30 mL) was carefully added NaH (60% in mineral oil, 400 mg, 10.0 mmol) in small portions at 0° C. under nitrogen. The reaction mixture was stirred at 0° C. under nitrogen for 2 hrs. To this solution was added 2,6-dinitrobenzonitrile (1.93, 10.0 mmol), and the reaction solution was stirred at 0° C.—RT under nitrogen overnight. The reaction mixture was quenched with brine, and extracted with EtOAc (3×). The combined organic layers were washed with brine, dried over Na$_2$SO$_4$. After evaporation of the solvent, the residue was purified by chromatography on silica gel eluting with 60% EtOAc in hexanes to give the title compound as a pale yellow solid (2.21 g, 72%). MS 306 (MH$^+$).

Example 215d 3-hydroxy-2,2-dimethyl-N-propylpropanamide

Method A:
A solution of methyl 3-hydroxy-2,2-dimethylpropanoate (2.64 g, 20 mmol) and n-propylamine (1.81 g, 30 mmol) was heated at 190° C. under microwave for 10 hrs. The excessive amine was removed under vacuum to give the title compound as colorless oil (3.18 g, 100%). MS 160 (MH+).

Method B:

To a solution of 3-hydroxy-2,2-dimethylpropanoic acid (20.0 g, 0.169 mol), propylamine (15.3 mL, 0.186 mol), and HOBt (25.1 g, 0.186 mol) in dry dichloromethane (500 mL) was added EDCI (35.6 g, 0.186 mmol) at room temperature under nitrogen. The reaction mixture was then stirred at room temperature under nitrogen overnight. The reaction quenched with brine, and extracted EtOAc (8×). The combined organic layers were washed with saturated $NaHCO_3$ solution, dilute HCl, brine, and dried over $Na_2SO_4$. Evaporation of the solvent under reduced pressure gave the title compound as colorless oil (19.2 g, 71%). MS 160 (MH+).

Example 216

N-(1-(4-amino-2,2-dioxide-1H-benzo[c][,6]thiadiazin-5-yloxy)-2'-methylpropan-2'-yl)benzamide

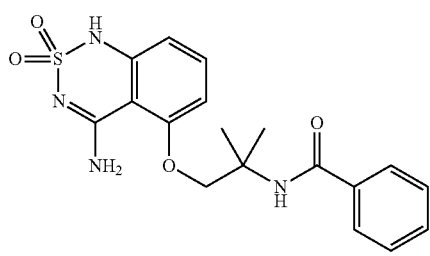

638

Prepared as in Example 215 from N-(1-(3-sulfamoylamino-2-cyanophenoxy)-2-methylpropan-2-yl)benzamide (Example 216a) in 93% yield as a white solid. M.p.: 235-236° C. $^1$H NMR (400 MHz, DMSO-$d_6$) δ 1.47 (s, 6H), 4.38 (s, 2H), 6.61 (d, J=8.4 Hz, 1H), 6.77 (d, J=8.0 Hz, 1H), 7.39-7.51 (m, 4H), 7.75 (d, J=7.6 Hz, 2H), 7.90 (s, 1H), 8.17 (s, 1H), 8.47 (s, 1H), 10.97 (s, 1H). MS 389 (MH+).

Example 216a

N-(1-(3-sulfamoylamino-2-cyanophenoxy)-2-methylpropan-2-yl)benzamide

Prepared as in Example 215a from N-(1-(3-amino-2-cyanophenoxy)-2-methylpropan-2-yl)benzamide (Example 216b) in 98% yield as a white solid. MS 389 (MH+).

Example 216b

N-(1-(3-amino-2-cyanophenoxy)-2-methylpropan-2-yl)benzamide

Prepared as in Example 215b (Method A) from N-(1-(2-cyano-3-nitrophenoxy)-2-methylpropan-2-yl)benzamide (Example 216c) in 96% yield as a white solid. MS 310 (MH+).

Example 216c

N-(1-(2-cyano-3-nitrophenoxy)-2-methylpropan-2-yl)benzamide

Prepared as in Example 215c from N-(1-hydroxy-2-methylpropan-2-yl)benzamide (Boyd, R. N.; Hansen, R. H. *J. Am. Chem. Soc.* 1953, 75, 5896) and 2,6-dinitrobenzonitrile in 91% yield as a pale yellow solid. MS 340 (MH+).

Example 217

5-(neopentyloxy)-1H-benzo[c][,6]thiadiazin-4-amine-2,2-dioxide

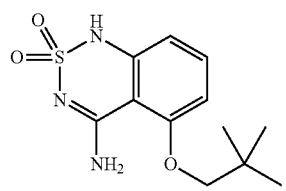

639

Prepared as in Example 215 from 2-sulfamoylamino-6-(neopentyloxy)benzonitrile (Example 217a) in 73% yield as a white solid. $^1$H NMR (400 MHz, DMSO-$d_6$) δ 1.01 (s, 9H), 3.86 (s, 2H), 6.61 (d, J=8.0 Hz, 1H), 6.77 (d, J=8.0 Hz, 1H), 7.45 (t, J=8.0 Hz, 1H), 7.66 (s, 1H), 8.49 (s, 1H), 10.99 (s, 1H). MS 284 (MH+).

Example 217a 2-sulfamoylamino-6-(neopentyloxy)benzonitrile

Prepared as in Example 215a from 2-amino-6-(neopentyloxy)benzonitrile (Example 217b) in 92% yield. MS 284 (MH+).

Example 217b 2-amino-6-(neopentyloxy)benzonitrile

Prepared as in Example 215b (Method A) from 2-(neopentyloxy)-6-nitrobenzonitrile (Example 217c) in 96% yield. MS 205 (MH+).

Example 217c 2-(neopentyloxy)-6-nitrobenzonitrile

Prepared as in Example 215c from 2,2-dimethylpropan-1-ol and 2,6-dinitrobenzonitrile in 80% yield. MS 235 (MH+).

Example 218

3-(4-amino-2,2-dioxide-1H-benzo[c][1,2,6]thiadiazin-5-yloxy)-N-(2''-(benzyloxy)ethyl)-2',2'-dimethylpropanamide

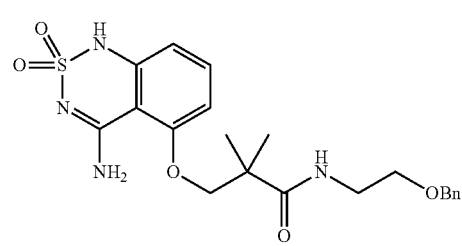

640

Prepared as in Example 215 from 3-(3-sulfamoylamino-2-cyanophenoxy)-N-(2-(benzyloxy)ethyl)-2,2-dimethylpropanamide (Example 218a) in 92% yield as a white solid. $^1$H NMR (400 MHz, DMSO-$d_6$) δ 1.22 (s, 6H), 3.26 (q, J=5.8 Hz, 2H), 3.41 (t, J=5.8 Hz, 2H), 4.07 (s, 2H), 4.36 (s, 2H), 6.60 (d, J=7.6 Hz, 1H), 6.71 (d, J=7.6 Hz, 1H), 7.19-7.28 (m, 4H), 7.43 (t, J=8.0 Hz, 2H), 7.91 (s, 1H), 7.97 (t, J=5.8 Hz, 1H), 8.34 (s, 1H), 10.93 (s, 1H). MS 447 (MH$^+$).

Example 218a 3-(3-sulfamoylamino-2-cyanophenoxy)-N-(2-(benzyloxy)ethyl)-2,2-dimethylpropanamide Prepared as in Example 215a from 3-(3-amino-2-cyanophenoxy)-N-(2-(benzyloxy)ethyl)-2,2-dimethylpropanamide (Example 218b) in 100% yield. MS 447 (MH$^+$).

Example 218b 3-(3-amino-2-cyanophenoxy)-N-(2-(benzyloxy)ethyl)-2,2-dimethylpropanamide Prepared as in Example 215b (Method B) from N-(2-(benzyloxy)ethyl)-3-hydroxy-2,2-dimethylpropanamide (Example 218c) and 2-amino-6-fluorobenzonitrile in 82% yield. MS 368 (MH$^+$).

Example 218c

N-(2-(benzyloxy)ethyl)-3-hydroxy-2,2-dimethylpropanamide

To a solution of 3-hydroxy-2,2-dimethylpropanoic acid (2.36 g, 20 mmol), 2-(benzyloxy)ethanamine (3.02 g, 20 mmol), and HOBt (2.71 g, 20 mmol) in dry dichloromethane (100 mL) was added EDCI (3.82 g, 20 mmol) at room temperature under nitrogen. The reaction mixture was then stirred at room temperature under nitrogen overnight. The reaction was quenched with brine, and extracted with EtOAc (3×). The combined organic layers were washed with saturated NaHCO$_3$ solution, dilute HCl, brine, and dried over Na$_2$SO$_4$. After evaporation of the solvent, the residue was purified by chromatography on silica gel eluting with 40% EtOAc in hexanes to give the title compound as colorless oil (4.89 g) in 97% yield. MS 252 (MH$^+$).

Example 219

3-(4-amino-2,2-dioxide-1H-benzo[c][1,2,6]thiadiazin-5-yloxy)-N-(2''-hydroxyethyl)-2',2'-dimethylpropanamide

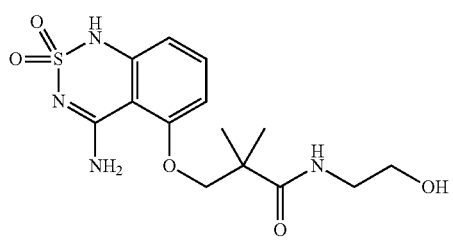

641

To a solution of 3-(4-amino-1H-benzo[c][1,2,6]thiadiazin-5-yloxy)-2,2-dioxide-N-(2'-(benzyloxy)ethyl)-2',2'-dimethylpropanamide (Example 218, 112 mg, 0.25 mmol) in EtOAc/EtOH/THF (1:1:1, 20.0 mL) was added 10% Pd/C (50 mg). And the suspension was stirred under an atmosphere of H$_2$ at room temperature for 2 hrs. The Pd/C was filtered off, and washed with MeOH. The filtration was concentrated under reduced pressure, and the residue was purified by recrystallization from EtOH to give the title compound as a white solid (81 mg) in 90% yield. $^1$H NMR (400 MHz, DMSO-$d_6$) δ 1.22 (s, 6H), 3.11 (q, J=6.0 Hz, 2H), 3.35 (q, J=6.0 Hz, 2H), 4.05 (s, 2H), 4.61 (t, J=6.0 Hz, 1H), 6.59 (d, J=8.0 Hz, 1H), 6.70 (d, J=8.0 Hz, 1H), 7.43 (t, J=8.0 Hz, 1H), 7.78 (t, J=6.0 Hz, 1H), 7.93 (s, 1H), 8.29 (s, 1H), 10.93 (s, 1H). MS 357 (MH$^+$).

Example 220

3-(4-amino-2,2-dioxide-1H-benzo[c][1,2,6]thiadiazin-5-yloxy)-N-(4''-methoxybenzyl)-2',2'-dimethylpropanamide

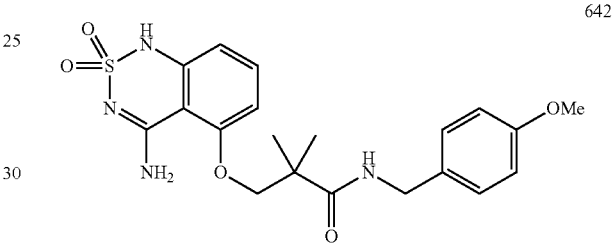

642

Prepared as in Example 215 from 3-(3-sulfamoylamino-2-cyanophenoxy)-N-(4-methoxybenzyl)-2,2-dimethylpropanamide (Example 220a) in 92% yield as a white solid. $^1$H NMR (400 MHz, DMSO-$d_6$) δ 1.25 (s, 6H), 3.66 (s, 3H), 4.12 (s, 2H), 4.21 (d, J=5.6 Hz, 2H), 6.61 (d, J=8.4 Hz, 1H), 6.71 (d, J=8.4 Hz, 1H), 6.73 (d, J=8.0 Hz, 2H), 7.06 (d, J=8.0 Hz, 2H), 7.44 (t, J=8.4 Hz, 1H), 7.87 (s, 1H), 8.31 (s, 1H), 8.35 (t, J=5.6 Hz, 1H), 10.95 (s, 1H). MS 433 (MH$^+$).

Example 220a 3-(3-sulfamoylamino-2-cyanophenoxy)-N-(4-methoxybenzyl)-2,2-dimethylpropanamide Prepared as in Example 215a from 3-(3-amino-2-cyanophenoxy)-N-(4-methoxybenzyl)-2,2-dimethylpropanamide (Example 220b) in 100% yield. MS 433 (MH$^+$).

Example 220b 3-(3-amino-2-cyanophenoxy)-N-(4-methoxybenzyl)-2,2-dimethylpropanamide To a solution of 3-(2-cyano-3-nitrophenoxy)-N-(4-methoxybenzyl)-2,2-dimethyl-propanamide (1.15 g, 3.0 mmol) (Example 220c) in diglyme (30 mL) was added dropwise a solution of SnCl$_2$·2H$_2$O (2.03 g, 9.0 mmol) in concentrated HCl (15 mL) at 0° C. The reaction mixture was then stirred at 0° C. for another 1 hr. The reaction solution was neutralized with 2 N NaOH at 0° C., and extracted with EtOAc (2×). The combined organic layers were washed with brine, dried over Na$_2$SO$_4$. After evaporation of the solvent, the residue was purified by chromatography on silica gel eluting with 50% EtOAc in hexanes to give the title compound as a white solid (0.91 g) in 86% yield. MS 354 (MH$^+$).

Example 220c 3-(2-cyano-3-nitrophenoxy)-N-(4-methoxybenzyl)-2,2-dimethylpropanamide Prepared as in Example 215c from 3-hydroxy-N-(4-methoxybenzyl)-2,2-dimethylpropanamide (Example 220d) and 2,6-dinitrobenzonitrile in 95% yield as a pale yellow solid. MS 384 (MH+).

Example 220d 3-hydroxy-N-(4-methoxybenzyl)-2,2-dimethylpropanamide

Prepared as in Example 4c from 3-hydroxy-2,2-dimethylpropanoic acid and 4-methoxybenzylamine in 97% yield as a white solid. MS 238 (MH+).

Example 221

3-(4-amino-2,2-dioxide-1H-benzo[c][1,2,6]thiadiazin-5-yloxy)-N,2',2'-trimethylpropanamide

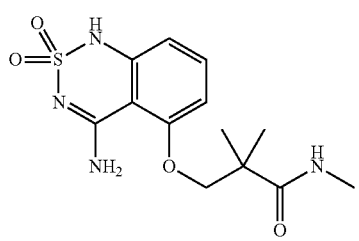

643

Prepared as in Example 215 from 3-(3-sulfamoylamino-2-cyanophenoxy)-N,2,2-trimethylpropanamide (Example 221a) in 62% yield as a white solid. ¹H NMR (400 MHz, DMSO-d₆) δ 1.21 (s, 6H), 2.58 (d, J=1.2 Hz, 3H), 4.05 (s, 2H), 6.60 (d, J=8.0 Hz, 1H), 6.72 (d, J=8.0 Hz, 1H), 7.44 (t, J=8.0 Hz, 1H), 7.80 (q, J=1.2 Hz, 1H), 7.96 (s, 1H), 8.33 (s, 1H), 10.93 (s, 1H). MS 327 (MH+).

Example 221a 3-(3-sulfamoylamino-2-cyanophenoxy)-N,2,2-trimethylpropanamide

Prepared as in Example 215a from 3-(3-amino-2-cyanophenoxy)-N,2,2-trimethylpropanamide (Example 221b) in 69% yield. MS 327 (MH+).

Example 221b 3-(3-amino-2-cyanophenoxy)-N,2,2-trimethylpropanamide

Prepared as in Example 215b (Method A) from 3-(2-cyano-3-nitrophenoxy)-N,2,2-trimethylpropanamide (Example 221c) in 95% yield as a white solid. MS 248 (MH+).

Example 221c 3-(2-cyano-3-nitrophenoxy)-N,2,2-trimethylpropanamide

Prepared as in Example 215c from 3-hydroxy-N,2,2-trimethylpropanamide (Example 221d) and 2,6-dinitrobenzonitrile in 77% yield as a pale yellow solid. MS 378 (MH+).

Example 221d 3-hydroxy-N,2,2-trimethylpropanamide

Prepared as in Example 215d from methyl 3-hydroxy-2,2-dimethylpropanoate and methylamine in 51% yield. MS 132 (MH+).

Example 222

3-(4-amino-2-oxo-1,2-dihydroquinazolin-5-yloxy)-2,2-dimethyl-N-propylpropanamide

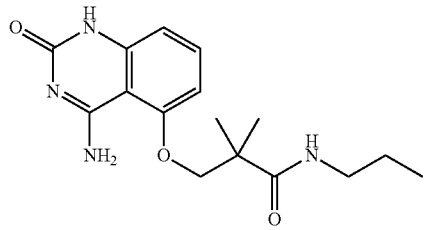

644

A solution of N-(2-cyano-3-(2,2-dimethyl-3-oxo-3-(propylamino)propoxy)-phenylcarbamoyl)benzamide (example 222a) (141 mg, 0.3 mmol) and NaOH (2 N, 0.3 mL) in EtOH (5 mL) was stirred at 100° C. under nitrogen for 2 hrs. After cooling to room temperature, the clear reaction solution was filtered, and the filtrate was carefully neutralized with 10% AcOH with vigorous stirring at 0° C. The resultant precipitate was collected by filtration, washed with water and then 20% EtOH in water to give the final product (81 mg) in 76% yield as an off-white solid. ¹H NMR (400 MHz, DMSO-d₆) δ 0.73 (t, J=7.4 Hz, 3H), 1.21 (s, 6H), 1.33-1.41 (m, 2H), 3.01 (q, J=7.4 Hz, 2H), 4.08 (s, 2H), 6.64 (d, J=8.0 Hz, 1H), 6.69 (d, J=8.0 Hz, 1H), 7.42 (t, J=8.0 Hz, 1H), 7.47 (s, 1H), 7.79 (t, J=7.4 Hz, 1H), 7.84 (s, 1H), 10.60 (s, 1H). MS 319 (MH+).

Example 222a

N-(2-cyano-3-(2,2-dimethyl-3-oxo-3-(propylamino)propoxy)phenyl-carbamoyl)benzamide Prepared as in Example 146a from 3-(3-amino-2-cyanophenoxy)-2,2-dimethyl-N-propyl-propanamide (Example 215b, Method A) and benzoyl isocyanate in 85% yield as a white solid. MS 423 (MH+).

Example 223

4-amino-5-(neopentyloxy)quinazolin-2(1H)-one

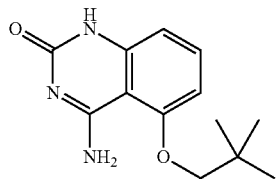

645

Prepared as in Example 222 from N-(2-cyano-3-(neopentyloxy)phenylcarbamoyl)benzamide (Example 223a) in 90% yield as a white solid. ¹H NMR (400 MHz, DMSO-d₆) δ 1.03 (s, 9H), 3.90 (s, 2H), 5.96 (s, 2H), 6.15 (d, J=7.6 Hz, 1H), 6.30 (d, J=7.6 Hz, 1H), 7.14 (t, J=7.6 Hz, 1H), 11.22 (s, 1H). MS 248 (MH+).

Example 223a N-(2-cyano-3-(neopentyloxy)phenyl-carbamoyl)benzamide

Prepared as in Example 146a from 2-amino-6-(neopentyloxy)-benzonitrile (Example 217b) and benzoyl isocyanate in 96% yield as a white solid. MS 352 (MH$^+$).

Example 224

5-(3-methoxy-3-methylbutoxy)-1H-benzo[c][1,2,6]thiadiazin-4-amine-2,2-dioxide

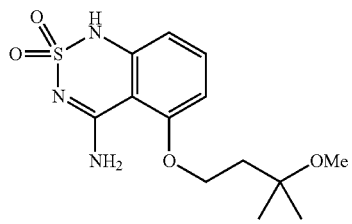

646

Prepared as in Example 215 from 2-sulfamoylamino-6-(3-methoxy-3-methylbutoxy)benzonitrile (Example 224a) in 52% yield as a white solid. $^1$H NMR (400 MHz, DMSO-d$_6$) δ 1.16 (s, 6H), 1.98 (t, J=6.2 Hz, 2H), 3.09 (s, 3H), 4.18 (t, J=6.2 Hz, 2H), 8.57 (d, J=8.0 Hz, 1H), 6.73 (d, J=8.0 Hz, 1H), 7.43 (t, J=8.0 Hz, 1H), 8.25 (s, 1H), 8.30 (s, 1H), 10.89 (s, 1H). MS 314 (MH$^+$).

Example 224a 2-sulfamoylamino-6-(3-methoxy-3-methylbutoxy)benzonitrile

Prepared as in Example 215a from 2-amino-6-(3-methoxy-3-methylbutoxy)benzonitrile (Example 224b) in 95% yield. MS 314 (MH$^+$).

Example 224b 2-amino-6-(3-methoxy-3-methylbutoxy)benzonitrile

Prepared as in Example 215b (Method A) from 2-(3-methoxy-3-methylbutoxy)-6-nitrobenzonitrile (Example 224c) in 62% yield. MS 235 (MH$^+$).

Example 224c 2-(3-methoxy-3-methylbutoxy)-6-nitrobenzonitrile

Prepared as in Example 215c from 3-methoxy-3-methylbutan-1-ol and 2,6-dinitrobenzonitrile in 52% yield. MS 265 (MH$^+$).

Example 225

3-(4-amino-2,2-dioxide-1H-benzo[c][,6]thiadiazin-5-yloxy)-N-(2''-methoxyethyl)-2',2'-dimethylpropanamide

647

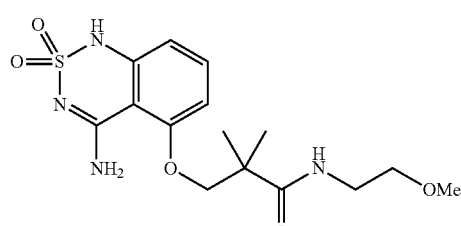

Prepared as in Example 215 from 3-(3-sulfamoylamino-2-cyanophenoxy)-N-(2-methoxyethyl)-2,2-dimethylpropanamide (Example 225a) in 12% yield as a white solid. $^1$H NMR (400 MHz, DMSO-d$_6$) δ 1.21 (s, 6H), 3.13 (s, 3H), 3.17-3.22 (m, 2H), 3.28 (t, J=6.0 Hz, 2H), 4.07 (s, 2H), 6.59 (d, J=8.0 Hz, 1H), 6.71 (d, J=8.0 Hz, 1H), 7.43 (t, J=8.0 Hz, 1H), 7.87 (s, 1H), 7.91 (t, J=5.6 Hz, 1H), 8.33 (s, 1H), 10.92 (s, 1H). MS 371 (MH$^+$).

Example 225a 3-(3-sulfamoylamino-2-cyanophenoxy)-N-(2-methoxyethyl)-2,2-dimethylpropanamide Prepared as in Example 215a from 3-(3-amino-2-cyanophenoxy)-N-(2-methoxyethyl)-2,2-dimethylpropanamide (Example 225b) in 41% yield. MS 371 (MH$^+$).

Example 225b 3-(3-amino-2-cyanophenoxy)-N-(2-methoxyethyl)-2,2-dimethylpropanamide Prepared as in Example 215b (Method A) from 3-(2-cyano-3-nitrophenoxy)-N-(2-methoxyethyl)-2,2-dimethylpropanamide (Example 225c) in 91% yield. MS 292 (MH$^+$).

Example 225c 3-(2-cyano-3-nitrophenoxy)-N-(2-methoxyethyl)-2,2-dimethylpropanamide Prepared as in Example 215c from 3-hydroxy-N-(2-methoxyethyl)-2,2-dimethylpropanamide (Example 225d) and 2,6-dinitrobenzonitrile in 55% yield. MS 322 (MH$^+$).

Example 225d 3-hydroxy-N-(2-methoxyethyl)-2,2-dimethylpropanamide

Prepared as in Example 215d (Method A) from methyl 3-hydroxy-2,2-dimethylpropanoate and 2-methoxyethanamine in 100% yield. MS 176 (MH$^+$).

Example 226

N-(3-(4-amino-)-2,2-dioxide-1H-benzo[c][,6]thiadiazin-5-yloxy-2',2'-dimethylpropyl)propionamide

648

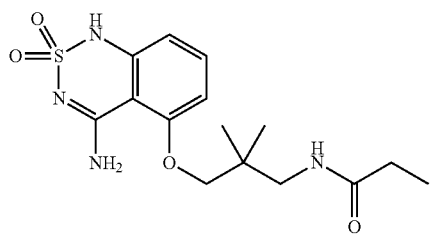

Prepared as in Example 215a from N-(3-(3-amino-2-cyanophenoxy)-2,2-dimethylpropyl)propionamide (Example 226a) and sulfamoyl chloride in 17% yield as a white solid. $^1$H NMR (400 MHz, DMSO-d$_6$) δ 0.93-0.96 (m, 9H), 2.06-2.11 (m, 2H), 3.07 (d, J=6.0 Hz, 2H), 3.74 (s, 2H), 6.58 (t, J=8.4 Hz, 1H), 6.69 (d, J=8.8 Hz, 1H), 7.41 (t, J=8.4 Hz, 1H), 7.93-7.98 (m, 2H), 8.35 (brs, 1H), 10.91 (brs, 1H). MS 355 (MH+).

Example 226a

N-(3-(3-amino-2-cyanophenoxy)-2,2-dimethylpropyl)propionamide

Prepared as in Example 215b (Method A) from N-(3-(2-cyano-3-nitrophenoxy)-2,2-dimethylpropyl)propionamide (Example 226b) in 100% yield. MS 276 (MH+).

Example 226b

N-(3-(2-cyano-3-nitrophenoxy)-2,2-dimethylpropyl)propionamide

Prepared as in Example 215c from N-(3-hydroxy-2,2-dimethylpropyl)propionamide (Example 226c) and 2,6-dinitrobenzonitrile in 68% yield. MS 306 (MH+).

Example 226c

N-(3-hydroxy-2,2-dimethylpropyl)propionamide

Prepared according to the literature (Boyd, R. N.; Hansen, R. H. *J. Am. Chem. Soc.* 1953, 75, 5896) from 2-amino-2-methylpropan-1-ol and benzoyl chloride in 84% yield as a white solid. MS 160 (MH+).

Example 227

1-(3-(4-amino-2,2-dioxide-1H-benzo[c][1,2,6]thiadiazin-5-yloxy)-2',2'-dimethylpropyl)-3'-ethylurea

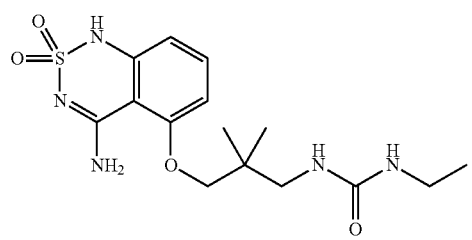

649

Prepared as in Example 215 from 1-(3-(3-sulfamoylamino-2-cyanophenoxy)-2,2-dimethylpropyl)-3-ethylurea (Example 227a) in 55% yield as a white solid. ¹H NMR (400 MHz, DMSO-d₆) δ 0.88-0.96 (m, 9H), 2.90-2.97 (m, 2H), 3.01 (d, J=6.4 Hz, 2H), 3.72 (s, 2H), 5.75 (t, J=5.6 Hz, 1H), 6.07 (t, J=6.4 Hz, 1H), 6.56 (d, J=8.4 Hz, 1H), 6.67 (d, J=8.8 Hz, 1H), 7.39 (t, J=8.4 Hz, 1H), 8.05 (brs, 1H), 8.25 (brs, 1H), 10.89 (s, 1H). MS 370 (MH+).

Example 227a 1-(3-(3-sulfamoylamino-2-cyanophenoxy)-2,2-dimethylpropyl)-3-ethylurea Prepared as in Example 215a from 1-(3-(3-amino-2-cyanophenoxy)-2,2-dimethylpropyl)-3-ethylurea (Example 227b) in 100% yield. MS 370 (MH+).

Example 227b 1-(3-(3-amino-2-cyanophenoxy)-2,2-dimethylpropyl)-3-ethylurea

Prepared as in Example 215b (Method A) from 1-(3-(2-cyano-3-nitrophenoxy)-2,2-dimethylpropyl)-3-ethylurea (Example 227c) in 90% yield. MS 291 (MH+).

Example 227c 1-(3-(2-cyano-3-nitrophenoxy)-2,2-dimethylpropyl)-3-ethylurea

Prepared as in Example 215c from 1-ethyl-3-(3-hydroxy-2,2-dimethylpropyl)urea (Example 227d) and 2,6-dinitrobenzonitrile in 47% yield. MS 321 (MH+).

Example 227d 1-ethyl-3-(3-hydroxy-2,2-dimethylpropyl)urea

To a solution of 3-amino-2,2-dimethylpropan-1-ol (1.03 g, 10 mmol) in dry 1,4-dioxane (20 mL) was added dropwise ethyl isocyanate (0.71 g, 10 mmol) at room temperature under nitrogen. The reaction mixture was then stirred at room temperature under nitrogen overnight. The solvent was removed under reduced pressure to give the title compound as colorless oil (1.74 g, 100%). MS 175 (MH+).

Example 228

3-(4-amino-2,2-dioxide-1H-benzo[c][1,2,6]thiadiazin-5-yloxy)-N-butyl-2',2'-dimethylpropanamide

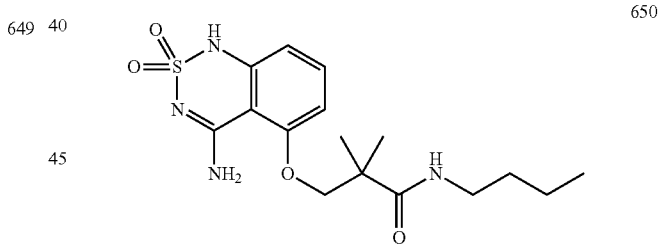

650

Prepared as in Example 215 and 1a from 3-(3-amino-2-cyanophenoxy)-N-butyl-2,2-dimethylpropanamide (Example 228a) and sulfamoyl chloride in 14% yield as a white solid. ¹H NMR (400 MHz, DMSO-d₆) δ 0.78 (t, J=7.2 Hz, 3H), 1.14-1.22 (m, 8H), 1.33-1.37 (m, 2H), 3.02-3.07 (m, 2H), 4.07 (s, 2H), 6.60 (d, J=8.0 Hz, 1H), 6.71 (d, J=8.8 Hz, 1H), 7.44 (t, J=8.4 Hz, 1H), 7.80 (t, J=5.6 Hz, 1H), 7.91 (s, 1H), 8.33 (s, 1H), 10.92 (s, 1H). MS 369 (MH+).

Example 228a 3-(3-amino-2-cyanophenoxy)-N-butyl-2,2-dimethylpropanamide

Prepared as in Example 215b (Method A) from N-butyl-3-(2-cyano-3-nitrophenoxy)-2,2-dimethylpropanamide (Example 228b) in 89% yield. MS 290 (MH+).

Example 228b

N-butyl-3-(2-cyano-3-nitrophenoxy)-2,2-dimethylpropanamide

Prepared as in Example 215c from N-butyl-3-hydroxy-2,2-dimethylpropanamide (Example 228c) and 2,6-dinitrobenzonitrile in 66% yield. MS 320 (MH$^+$).

Example 228c

N-butyl-3-hydroxy-2,2-dimethylpropanamide

Prepared as in Example 215d (Method A) from methyl 3-hydroxy-2,2-dimethylpropanoate and n-butyl amine in 100% yield. MS 174 (MH$^+$).

Example 229

N-(1-(4-amino-2,2-dioxide-1H-benzo[c][1,2,6]thiadiazin-5-yloxy)-2'-methylpropan-2'-yl)butyramide

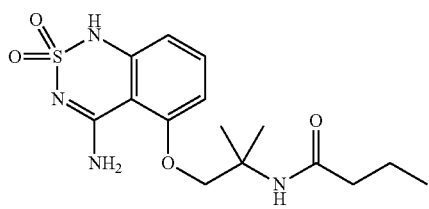

651

Prepared as in Example 215 from N-(1-(3-sulfamoylamino-2-cyanophenoxy)-2-methylpropan-2-yl)butyramide (Example 229a) and sodium hydroxide in 54% yield as a white solid. $^1$H NMR (400 MHz, DMSO-d$_6$) δ 0.78 (t, J=7.2 Hz, 3H), 1.32 (s, 6H), 1.43-1.44 (m, 2H), 2.00 (t, J=7.2 Hz, 2H), 4.24 (s, 2H), 6.60 (d, J=8.0 Hz, 1H), 6.73 (d, J=8.4 Hz, 1H), 7.44 (t, J=8.4 Hz, 1H), 7.77 (s, 1H), 7.82 (s, 1H), 8.42 (s, 1H), 10.97 (s, 1H). MS 355 (MH$^+$).

Example 229a

N-(1-(3-sulfamoylamino-2-cyanophenoxy)-2-methylpropan-2-yl)-butyramide

Prepared as in Example 215a from N-(1-(3-amino-2-cyanophenoxy)-2-methylpropan-2-yl)butyramide (Example 229b) and sulfamoyl chloride in 100% yield. MS 355 (MH$^+$).

Example 229b

N-(1-(3-amino-2-cyanophenoxy)-2-methylpropan-2-yl)butyramide

Prepared as in Example 215b (Method A) from N-(1-(2-cyano-3-nitrophenoxy)-2-methylpropan-2-yl)butyramide (Example 229c) in 100% yield. MS 276 (MH$^+$).

Example 229c

N-(1-(2-cyano-3-nitrophenoxy)-2-methylpropan-2-yl)butyramide

Prepared as in Example 215c from N-(1-hydroxy-2-methylpropan-2-yl)butyramide (Example 229d) and 2,6-dinitrobenzonitrile in 72% yield. MS 306 (MH$^+$).

Example 229d

N-(1-hydroxy-2-methylpropan-2-yl)butyramide

Prepared according to the literature (Boyd, R. N.; Hansen, R. H. *J. Am. Chem. Soc.* 1953, 75, 5896) from 2-amino-2-methylpropan-1-ol and butyryl chloride in 32% yield. MS 160 (MH$^+$).

Example 230

1-(1-(4-amino-2,2-dioxide-1H-benzo[c][1,2,6]thiadiazin-5-yloxy)-2'-methylpropan-2'-yl)-3'-ethylurea

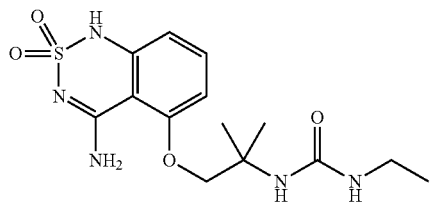

652

Prepared as in Example 215 from 1-(1-(3-sulfamoylamino-2-cyanophenoxy)-2-methylpropan-2-yl)-3-ethylurea (Example 230a) in 37% yield as a white solid. $^1$H NMR (400 MHz, DMSO-d$_6$) δ 0.92 (t, J=7.2 Hz, 3H), 1.27 (s, 6H), 2.90-2.93 (m, 2H), 4.21 (s, 2H), 5.63 (t, J=5.2 Hz, 1H), 5.95 (s, 1H), 6.59 (d, J=8.0 Hz, 1H), 6.72 (d, J=8.4 Hz, 1H), 7.42 (t, J=8.4 Hz, 1H), 7.94 (s, 1H), 8.34 (s, 1H), 10.94 (s, 1H). MS 356 (MH$^+$).

Example 230a 1-(1-(3-sulfamoylamino-2-cyanophenoxy)-2-methylpropan-2-yl)-3-ethylurea Prepared as in Example 215a from 1-(1-(3-amino-2-cyanophenoxy)-2-methylpropan-2-yl)-3-ethylurea (Example 230b) and sulfamoyl chloride in 100% yield. MS 356 (MB).

Example 230b 1-(1-(3-amino-2-cyanophenoxy)-2-methylpropan-2-yl)-3-ethylurea

Prepared as in Example 215b (Method A) from 1-(1-(2-cyano-3-nitrophenoxy)-2-methylpropan-2-yl)-3-ethylurea (Example 230c) in 86% yield. MS 277 (MH$^+$).

Example 230c 1-(1-(2-cyano-3-nitrophenoxy)-2-methylpropan-2-yl)-3-ethylurea

Prepared as in Example 215c from 1-ethyl-3-(1-hydroxy-2-methylpropan-2-yl)urea (Example 230d) and 2,6-dinitrobenzonitrile in 65% yield. MS 307 (MH$^+$).

Example 230d 1-ethyl-3-(1-hydroxy-2-methylpropan-2-yl)urea

Prepared as in Example 227d from 2-amino-2-methylpropan-1-ol and ethyl isocyanate in 94% yield. MS 161 (MH$^+$).

Example 231

4-(4-amino-2,2-dioxide-1H-benzo[c][1,2,6]thiadiazin-5-yloxy)-2'-methylbutan-2'-ol

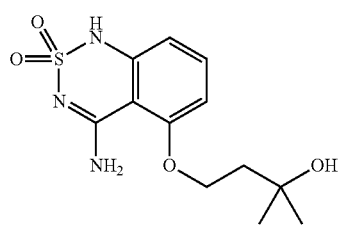
653

Prepared as in Example 215 from 4-(2-cyano-3-(sulfamoylamino)phenoxy)-2-methylbutan-2-yl acetate (Example 231a) in 20% yield as a white solid. $^1$H NMR (400 MHz, DMSO-$d_6$) δ 1.15 (s, 6H), 1.89 (t, J=6.4 Hz, 2H), 4.22 (t, J=6.4 Hz, 2H), 4.62 (s, 1H), 6.57 (d, J=8.0 Hz, 1H), 6.73 (d, J=8.4 Hz, 1H), 7.43 (t, J=8.4 Hz, 1H), 8.22 (s, 1H), 8.30 (s, 1H), 10.87 (s, 1H). MS 300 (MH$^+$).

Example 231a 4-(2-cyano-3-(sulfamoylamino)phenoxy)-2-methylbutan-2-yl acetate Prepared as in Example 215a from 4-(3-amino-2-cyanophenoxy)-2-methylbutan-2-yl acetate (Example 231b) and sulfamoyl chloride in 100% yield. MS 342 (MH$^+$).

Example 231b 4-(3-amino-2-cyanophenoxy)-2-methylbutan-2-yl acetate

Prepared as in Example 215b (Method A) from 4-(2-cyano-3-nitrophenoxy)-2-methylbutan-2-yl acetate (Example 231c). MS 263 (MH$^+$).

Example 231c 4-(2-cyano-3-nitrophenoxy)-2-methylbutan-2-yl acetate

To a solution of 2-(3-hydroxy-3-methylbutoxy)-6-nitrobenzonitrile (Example 231d) (250 mg, 1 mmol), triethylamine (3 equiv.), and DMAP (0.1 equiv.) in dry dichloromethane (20 mL) was added dropwise acetyl chloride (1.5 equiv.) at 0° C. under nitrogen. The reaction mixture was then stirred at 0° C.—room temperature overnight. The reaction was diluted with EtOAc, washed with brine, and dried over Na$_2$SO$_4$. After evaporation of the solvent, the residue was purified by chromatography on silica gel eluting with 20% EtOAc in hexanes to give the title compound (137 mg, 47%). MS 293 (MH$^+$).

Example 231d 2-(3-hydroxy-3-methylbutoxy)-6-nitrobenzonitrile

Prepared as in Example 215c from 3-methylbutane-1,3-diol and 2,6-dinitrobenzonitrile in 81% yield. MS 251 (MH$^+$).

Example 232

2-((4-amino-2,2-dioxide-1H-benzo[c][1,2,6]thiadiazin-5-yloxy)methyl)-2'-ethylbutan-1'-ol

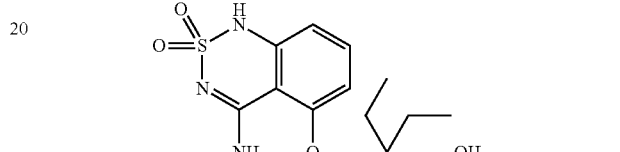
654

Prepared as in Example 215 from 2-ethyl-2-((2-methyl-3-(sulfamoylamino)phenoxy)methyl)butyl acetate (Example 232a) in 20% yield as a white solid. $^1$H NMR (400 MHz, DMSO-$d_6$) δ 0.73-0.80 (m, 6H), 1.21-1.37 (m, 4H), 3.31-3.33 (m, 2H), 3.89 (s, 2H), 4.92 (brs, 1H), 6.56 (d, J=8.0 Hz, 1H), 6.73 (d, J=8.4 Hz, 1H), 7.40 (t, J=8.4 Hz, 1H), 8.16 (brs, 2H), 10.91 (brs, 1H). MS 328 (MH$^+$).

Example 232a 2-((2-cyano-3-(sulfamoylamino)phenoxy)methyl)-2-ethylbutyl acetate Prepared as in Example 215a from 2-((3-amino-2-cyanophenoxy)methyl)-2-ethylbutyl acetate (Example 232b) and sulfamoyl chloride in 90% yield. $^1$H NMR (400 MHz, DMSO-$d_6$) δ 0.80 (t, J=7.6 Hz, 6H), 1.37-1.43 (m, 4H), 1.98 (s, 3H), 3.87 (s, 2H), 3.96 (s, 2H), 6.98 (d, J=8.8 Hz, 1H), 7.13 (d, J=8.4 Hz, 1H), 7.25 (s, 2H), 7.54 (t, J=8.4 Hz, 1H), 9.46 (s, 1H).

Example 232b 2-((3-amino-2-cyanophenoxy)methyl)-2-ethylbutyl acetate

Prepared as in Example 215b (Method A) from 2-((2-cyano-3-nitrophenoxy)methyl)-2-ethylbutyl acetate (Example 232c) in 91% yield. $^1$H NMR (400 MHz, DMSO-$d_6$) δ 0.79 (t, J=7.6 Hz, 6H), 1.34-1.41 (m, 4H), 1.97 (s, 3H), 3.76 (s, 2H), 3.94 (s, 2H), 5.97 (s, 2H), 6.21 (d, J=8.0 Hz, 1H), 6.31 (d, J=8.4 Hz, 1H), 7.15 (t, J=8.0 Hz, 1H). MS 291 (MH$^+$).

Example 232c 2-((2-cyano-3-nitrophenoxy)methyl)-2-ethylbutyl acetate

Prepared as in Example 231c from 2-(2-ethyl-2-(hydroxymethyl)butoxy)-6-nitrobenzonitrile (Example 232d) and acetyl chloride in 82% yield. MS 321 (MH$^+$).

Example 232d

2-(2-ethyl-2-(hydroxymethyl)butoxy)-6-nitrobenzonitrile

Prepared as in Example 215c from 2,2-diethylpropane-1,3-diol and 2,6-dinitrobenzonitrile in 86% yield. $^1$H NMR (400 MHz, DMSO-$d_6$) δ 0.80 (t, J=7.6 Hz, 6H), 1.34 (q, J=7.6 Hz, 4H), 3.33 (d, J=5.6 Hz, 2H), 3.96 (s, 2H), 4.57 (t, J=5.2 Hz, 1H), 7.74-7.76 (m, 1H), 7.84-7.90 (m, 2H).

Example 233

3-(4-amino-2,2-dioxide-1H-benzo[c][1,2,6]thiadiazin-5-yloxy)-2',2'-dimethylpropan-1'-ol

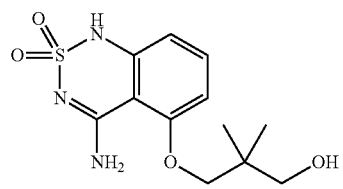

655

Prepared as in Example 215 from 3-(2-cyano-3-(sulfamoyl-amino)phenoxy)-2,2-dimethylpropyl acetate (Example 233a) in 30% yield as a white solid. $^1$H NMR (400 MHz, DMSO-$d_6$) δ 0.94 (s, 6H), 3.29-3.31 (m, 2H), 3.88 (s, 2H), 5.01 (t, J=4.4 Hz, 1H), 6.58 (d, J=8.4 Hz, 1H), 6.71 (d, J=8.4 Hz, 1H), 7.42 (t, J=8.0 Hz, 1H), 8.14 (s, 1H), 8.32 (s, 1H), 10.92 (s, 1H). MS 300 (MH$^+$).

Example 233a

3-(2-cyano-3-(sulfamoylamino)phenoxy)-2,2-dimethylpropyl acetate

Prepared as in Example 215a from 3-(3-amino-2-cyanophenoxy)-2,2-dimethylpropyl acetate (Example 233b) and sulfamoyl chloride in 60% yield. $^1$H NMR (400 MHz, DMSO-$d_6$) δ 0.99 (s, 6H), 1.98 (s, 3H), 3.85 (s, 2H), 3.91 (s, 2H), 6.91 (d, J=8.4 Hz, 1H), 7.12 (d, J=8.0 Hz, 1H), 7.23 (s, 2H), 7.52 (t, J=8.0 Hz, 1H), 9.45 (s, 1H).

Example 233b

3-(3-amino-2-cyanophenoxy)-2,2-dimethylpropyl acetate

Prepared as in Example 215b (Method A) from 3-(2-cyano-3-nitrophenoxy)-2,2-dimethylpropyl acetate (Example 233c) in 77% yield. $^1$H NMR (400 MHz, DMSO-$d_6$) δ 0.98 (s, 6H), 2.00 (s, 3H), 3.75 (s, 2H), 3.90 (s, 2H), 5.99 (s, 2H), 6.17 (d, J=8.4 Hz, 1H), 6.31 (d, J=8.4 Hz, 1H), 7.15 (t, J=8.0 Hz, 1H).

Example 233c

3-(2-cyano-3-nitrophenoxy)-2,2-dimethylpropyl acetate

Prepared as in Example 231c from 2-(3-hydroxy-2,2-dimethylpropoxy)-6-nitrobenzonitrile (Example 233d) and acetyl chloride in 66% yield. $^1$H NMR (400 MHz, DMSO-$d_6$) δ 1.04 (s, 6H), 2.00 (s, 3H), 3.95 (s, 2H), 4.02 (s, 2H), 7.70-7.72 (m, 1H), 7.85-7.92 (m, 2H).

Example 233d

2-(3-hydroxy-2,2-dimethylpropoxy)-6-nitrobenzonitrile

Prepared as in Example 215c from 2,2-dimethylpropane-1,3-diol and 2,6-dinitrobenzonitrile in 73% yield. $^1$H NMR (400 MHz, DMSO-$d_6$) δ 0.94 (s, 6H), 3.29-3.31 (m, 2H), 3.95 (s, 2H), 4.69 (t, J=5.6 Hz, 1H), 7.69-7.71 (m, 1H), 7.84-7.90 (m, 2H).

Example 234

N-(4-(4-amino-2,2-dioxide-1H-benzo[c][1,2,6]thiadiazin-5-yloxy)butyl)-acetamide

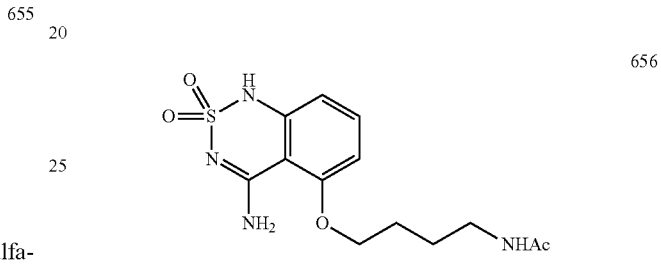

656

Prepared as in Example 215 from N-(4-(2-cyano-3-(sulfamoylamino)phenoxy)butyl)acetamide (Example 234a) in 30% yield. $^1$H NMR (400 MHz, DMSO-$d_6$) δ 1.48-1.51 (m, 2H), 1.77-1.81 (m, 5H), 3.03-3.08 (m, 2H), 4.14 (t, J=6.0 Hz, 2H), 6.59 (d, J=8.0 Hz, 1H), 6.73 (d, J=8.4 Hz, 1H), 7.43 (t, J=8.4 Hz, 1H), 7.78 (s, 1H). 7.84 (brs, 1H), 8.32 (s, 1H), 10.93 (s, 1H). MS 327 (MH$^+$).

Example 234a

N-(4-(2-cyano-3-(sulfamoylamino)phenoxy)butyl)acetamide

Prepared as in Example 215a from N-(4-(3-amino-2-cyanophenoxy)butyl)acetamide (Example 234b) and sulfamoyl chloride in 100% yield. $^1$H NMR (400 MHz, DMSO-$d_6$) δ 1.51-1.54 (m, 2H), 1.70-1.73 (m, 2H), 1.77 (s, 3H), 3.04-3.09 (m, 2H), 4.09 (t, J=6.4 Hz, 2H), 6.93 (d, J=8.4 Hz, 1H), 7.13 (d, J=8.0 Hz, 1H), 7.25 (s, 2H), 7.54 (t, J=8.0 Hz, 1H), 7.85 (brs, 1H), 9.42 (s, 1H).

Example 234b

N-(4-(3-amino-2-cyanophenoxy)butyl)acetamide

Prepared as in Example 215b (Method A) from N-(4-(2-cyano-3-nitrophenoxy)butyl)acetamide (Example 234c) in 85% yield. $^1$H NMR (400 MHz, DMSO-$d_6$) δ 1.49-1.54 (m, 2H), 1.66-1.70 (m, 2H), 1.77 (s, 3H), 3.03-3.08 (m, 2H), 3.97 (t, J=6.8 Hz, 2H), 5.95 (s, 2H), 6.18 (d, J=8.0 Hz, 1H), 6.31 (d, J=7.6 Hz, 1H), 7.15 (t, J=8.4 Hz, 1H), 7.83 (brs, 1H).

Example 234c

N-(4-(2-cyano-3-nitrophenoxy)butyl)acetamide

To a solution of 2-(4-aminobutoxy)-6-nitrobenzonitrile (Example 234d) (235 mg, 1.0 mmol), triethylamine (3 equiv.), and DMAP (0.1 equiv.) in dry dichloromethane (20 mL) was added dropwise acetyl chloride (1.5 equiv.) at 0° C. under nitrogen. The reaction mixture was then stirred at 0° C.—RT overnight. The reaction was diluted with EtOAc, washed with brine, and dried over $Na_2SO_4$. After evaporation of the solvent, the residue was purified by chromatography on silica gel eluting with 50% EtOAc in hexanes to give the title compound (158 mg, 57%). MS 278 ($MH^+$).

Example 234d 2-(4-aminobutoxy)-6-nitrobenzonitrile

A solution of tert-butyl 4-(2-cyano-3-nitrophenoxy)butylcarbamate (Example 234e) (671 mg, 2 mmol) in DCM/TFA (1:1, 20 mL) was stirred at room temperature for 2 hrs. The solvent was removed under vacuum to give the title compound (698 mg, 100%). MS 236 ($MH^+$).

Example 234e tert-butyl 4-(2-cyano-3-nitrophenoxy)butylcarbamate

Prepared as in Example 215c from tert-butyl 4-hydroxybutylcarbamate and 2,6-dinitrobenzonitrile in 7% yield as a pale yellow solid. $^1$H NMR (400 MHz, DMSO-$d_6$) δ 1.35 (s, 9H), 1.52-1.55 (m, 2H), 1.72-1.76 (m, 2H), 2.94-2.99 (m, 2H), 4.24 (t, J=6.8 Hz, 2H), 6.86 (brs, 1H), 7.69-7.72 (m, 1H), 7.85-7.90 (m, 2H).

Example 235

4-(4-amino-2,2-dioxide-1H-benzo[c][1,2,6]thiadiazin-5-yloxy)butyl sulfamate

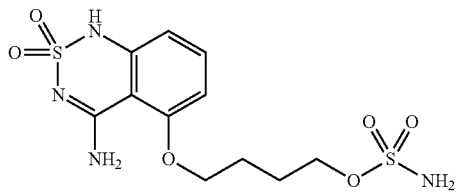

657

Prepared as in Example 215 from 4-(2-cyano-3-(sulfamoylamino)phenoxy)butyl sulfamate (Example 235a) in 31% yield. $^1$H NMR (400 MHz, DMSO-$d_6$) δ 1.74-1.79 (m, 2H), 1.85-1.91 (m, 2H), 4.07 (t, J=6.4 Hz, 2H), 4.18 (t, J=6.8 Hz, 2H), 6.58-6.60 (m, 1H), 6.74 (d, J=8.4 Hz, 1H), 7.42-7.46 (m, 3H), 7.79 (s, 1H), 8.32 (s, 1H), 10.93 (s, 1H). MS 365 ($MH^+$).

Example 235a 4-(2-cyano-3-(sulfamoylamino)phenoxy)butyl sulfamate

Prepared as in Example 215a from 2-amino-6-(4-(tert-butyldimethylsilyloxy)butoxy)benzonitrile (Example 235b) and sulfamoyl chloride in 63% yield. MS 382 ($M^+$+$H_2O$).

Example 235b 2-amino-6-(4-(tert-butyldimethylsilyloxy)butoxy)benzonitrile

Prepared as in Example 215b (Method A) from 2-(4-(tert-butyldimethylsilyloxy)butoxy)-6-nitrobenzonitrile (Example 235c) in 76% yield. MS 321 ($MH^+$).

Example 235c 2-(4-(tert-butyldimethylsilyloxy)butoxy)-6-nitrobenzonitrile

Prepared as in Example 215c from 4-(tert-butyldimethylsilyloxy)butan-1-ol and 2,6-dinitrobenzonitrile in 25% yield as a pale yellow solid. $^1$H NMR (400 MHz, DMSO-$d_6$) δ 0.01 (s, 6H), 0.81-0.83 (m, 9H), 1.61-1.66 (m, 2H), 1.76-1.81 (m, 2H), 3.63 (t, J=6.8 Hz, 2H), 4.26 (t, J=6.4 Hz, 2H), 7.68-7.70 (m, 1H), 7.84-7.89 (m, 2H).

Example 236

4-(4-amino-2,2-dioxide-1H-benzo[c][1,2,6]thiadiazin-5-yloxy)-butan-1'-ol

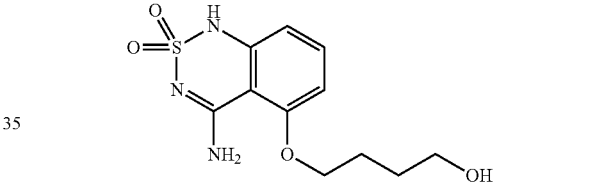

658

Prepared as in Example 215 from 4-(2-cyano-3-(sulfamoylamino)phenoxy)butyl sulfamate (Example 235a) in 2% yield. $^1$H NMR (400 MHz, $CD_3OD$) δ 1.69-1.73 (m, 2H), 1.95-1.99 (m, 2H), 3.63 (t, J=6.4 Hz, 2H), 4.24 (t, J=6.4 Hz, 2H), 6.61-6.63 (m, 1H), 6.75-6.77 (m, 1H), 7.45 (m, J=8.0 Hz, 1H). MS 286 ($MH^+$).

Example 237

3-(4-amino-2,2-dioxide-1H-benzo[c][1,2,6]thiadiazin-5-yloxy)-2'-methylpropan-1'-ol

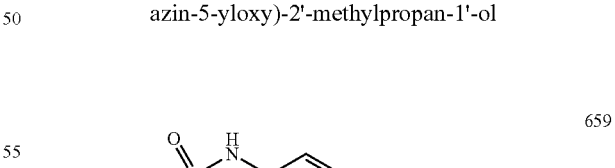

659

Prepared as in Example 215 from 3-(2-cyano-3-(sulfamoylamino)phenoxy)-2-methylpropyl acetate (Example 237a) in 41% yield as a white solid. $^1$H NMR (400 MHz, DMSO-$d_6$) δ 0.94 (d, J=6.4 Hz, 3H), 2.09-2.13 (m, 1H), 3.36-3.42 (m, 1H), 3.46-3.50 (m, 1H), 4.05 (d, J=6.4 Hz, 2H), 4.84 (t, J=5.6 Hz, 1H), 6.57 (d, J=7.6 Hz, 1H), 6.70 (d, J=8.4 Hz, 1H), 7.42 (t, J=8.4 Hz, 1H), 8.05 (brs, 1H), 8.24 (brs, 1H), 10.91 (s, 1H). MS 286 (MH⁺).

Example 237a 33-(2-cyano-3-(sulfamoylamino)phenoxy)-2-methyl-propyl acetate

Prepared as in Example 215a from 3-(3-amino-2-cyanophenoxy)-2-methylpropyl acetate (Example 237b) and sulfamoyl chloride in 78% yield. $^1$H NMR (400 MHz, DMSO-d$_6$) δ 1.02 (d, J=6.8 Hz, 3H), 2.01 (s, 3H), 2.23-2.27 (m, 1H), 3.99-4.07 (m, 4H), 6.94 (d, J=8.8 Hz, 1H), 7.14 (d, J=8.0 Hz, 1H), 7.26 (s, 2H), 7.55 (t, J=8.0 Hz, 1H), 9.47 (s, 1H).

Example 237b 3-(3-amino-2-cyanophenoxy)-2-methylpropyl acetate

Prepared as in Example 215b (Method A) from 3-(2-cyano-3-nitrophenoxy)-2-methylpropyl acetate (Example 237c) in 73% yield. $^1$H NMR (400 MHz, DMSO-d$_6$) δ 0.99 (d, J=7.2 Hz, 3H), 2.00 (s, 3H), 2.19-2.24 (m, 1H), 3.91 (d, J=5.2 Hz, 2H), 3.97-4.06 (m, 2H), 5.98 (s, 2H), 6.19 (d, J=8.0 Hz, 1H), 6.32 (d, J=8.4 Hz, 1H), 7.16 (t, J=8.0 Hz, 1H).

Example 237c 3-(2-cyano-3-nitrophenoxy)-2-methylpropyl acetate

Prepared as in Example 231c from 2-(3-hydroxy-2-methylpropoxy)-6-nitrobenzonitrile (Example 237d) and acetyl chloride in 41% yield. $^1$H NMR (400 MHz, DMSO-d$_6$) δ 1.04 (d, J=6.8 Hz, 3H), 2.00 (s, 3H), 2.28-2.33 (m, 1H), 4.05-4.08 (m, 2H), 4.18 (d, J=6.0 Hz, 2H), 7.71-7.73 (m, 1H), 7.86-7.92 (m, 2H).

Example 237d 2-(3-hydroxy-2-methylpropoxy)-6-nitrobenzonitrile

Prepared as in Example 215c from 2-methylpropane-1,3-diol and 2,6-dinitrobenzonitrile in 37% yield. MS 237 (MH⁺).

Example 238

3-(4-amino-2,2-dioxide-1H-benzo[c][1,2,6]thiadiazin-5-yloxy)propan-1'-ol

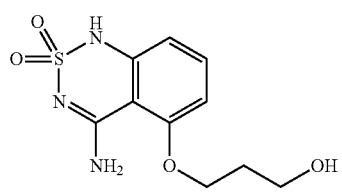

660

Prepared as in Example 215 from 3-(2-cyano-3-(sulfamoylamino)phenoxy)propyl sulfamate (Example 238a) in 6% yield. $^1$H NMR (400 MHz, DMSO-d$_6$) δ 1.92-1.97 (m, 2H), 3.55-3.59 (m, 2H), 4.20 (t, J=6.4 Hz, 2H), 4.79 (t, J=4.8 Hz, 1H), 6.57-6.59 (m, 1H), 6.71-6.73 (m, 1H), 7.43 (t, J=8.4 Hz, 1H), 8.12 (brs, 1H), 8.28 (brs, 1H), 10.90 (s, 1H). MS 272 (MH⁺).

Example 238a 3-(2-cyano-3-(sulfamoylamino)phenoxy)propyl sulfamate

Prepared as in Example 215a from 2-amino-6-(3-hydroxypropoxy)benzonitrile (Example 238b) and sulfamoyl chloride in 30% yield. $^1$H NMR (400 MHz, DMSO-d$_6$) δ 2.11-2.14 (m, 2H), 4.16-4.21 (m, 4H), 6.96 (d, J=8.0 Hz, 1H), 7.15 (d, J=7.6 Hz, 1H), 7.26 (s, 2H), 7.49 (s, 2H), 7.56 (t, J=8.4 Hz, 1H), 9.46 (s, 1H).

Example 238b 2-amino-6-(3-hydroxypropoxy)benzonitrile

Prepared as in Example 215b (Method A) from 2-(3-hydroxypropoxy)-6-nitrobenzonitrile (Example 238c) in 100% yield. $^1$H NMR (400 MHz, DMSO-d$_6$) δ 1.79-1.85 (m, 2H), 3.52-3.56 (m, 2H), 4.04 (t, J=6.4 Hz, 2H), 4.54 (t, J=5.2 Hz, 1H), 5.93 (s, 2H), 6.19 (d, J=8.0 Hz, 1H), 6.30 (d, J=8.4 Hz, 1H), 7.15 (t, J=8.0 Hz, 1H).

Example 238c 2-(3-hydroxypropoxy)-6-nitrobenzonitrile

Prepared as in Example 215c from propane-1,3-diol and 2,6-dinitrobenzonitrile in 61% yield as a pale yellow solid. $^1$H NMR (400 MHz, DMSO-d$_6$) δ 1.89-1.93 (m, 2H), 3.56-3.61 (m, 2H), 4.30 (t, J=6.4 Hz, 2H), 4.61 (t, J=5.2 Hz, 1H), 7.71-7.74 (m, 1H), 7.85-7.91 (m, 2H).

Example 239

5-(butylthio)-1H-benzo[c][,6]thiadiazin-4-amine-2,2-dioxide

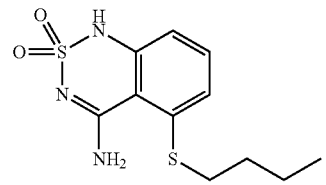

661

Prepared as in Example 215 from 2-sulfamoylamino-6-(butylthio)benzonitrile (Example 239a) in 12% yield as a white solid. $^1$H NMR (400 MHz, DMSO-d$_6$) δ 0.85 (t, J=7.6 Hz, 3H), 1.34-1.41 (m, 2H), 1.49-1.56 (m, 2H), 2.97 (t, J=7.2 Hz, 2H), 6.87 (d, J=8.4 Hz, 1H), 7.12 (d, J=7.6 Hz, 1H), 7.41 (t, J=7.6 Hz, 1H), 8.12 (brs, 2H), 11.02 (brs, 1H). MS 286 (MH⁺).

Example 239a 2-sulfamoylamino-6-(butylthio)benzonitrile

Prepared as in Example 215a from 2-amino-6-(butylthio) benzonitrile (Example 239b) in 76% yield. $^1$H NMR (400 MHz, DMSO-d$_6$) δ 0.88 (t, J=7.2 Hz, 3H), 1.36-1.45 (m, 2H), 1.54-1.61 (m, 2H), 3.07 (t, J=7.6 Hz, 2H), 7.25-7.27 (m, 3H), 7.33-7.36 (m, 1H), 7.57 (t, J=8.4 Hz, 1H), 9.50 (s, 1H).

Example 239b

2-amino-6-(butylthio)benzonitrile

Prepared as in Example 215b (Method A) from 2-nitro-6-(butylthio)benzonitrile (Example 239c) in 87% yield. $^1$H NMR (400 MHz, CDCl$_3$) δ 0.93 (t, J=7.2 Hz, 3H), 1.42-1.52 (m, 2H), 1.63-1.70 (m, 2H), 2.97 (t, J=6.8 Hz, 2H), 4.43 (brs, 2H), 6.52-6.54 (m, 1H), 6.67-6.69 (m, 1H), 7.21 (t, J=8.0 Hz, 1H).

Example 239c

2-nitro-6-(butylthio)benzonitrile

Prepared as in Example 215c from butane-1-thiol and 2,6-dinitrobenzonitrile in 90% yield. $^1$H NMR (400 MHz, CDCl$_3$) δ 0.97 (t, J=7.2 Hz, 3H), 1.42-1.55 (m, 2H), 1.70-1.77 (m, 2H), 3.09 (t, J=7.2 Hz, 2H), 7.63-7.69 (m, 2H), 7.99-8.01 (m, 1H).

Example 240

6-(4-amino-2,2-dioxide-1H-benzo[c][,6]thiadiazin-5-yloxy)hexyl sulfamate

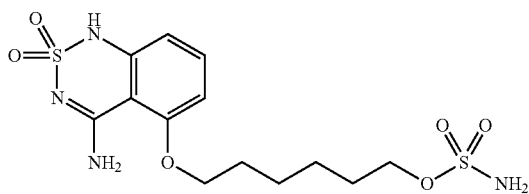 [SMILES: NC1=NS(=O)(=O)Nc2cccc(OCCCCCCOS(N)(=O)=O)c21]

Prepared as in Example 215 from 6-(2-cyano-3-(sulfamoylamino)phenoxy)hexyl sulfamate (Example 240a) in 46% yield. $^1$H NMR (400 MHz, DMSO-d$_6$) δ 1.03-1.05 (m, 4H), 1.28 (m, 2H), 1.45 (m, 2H), 3.64 (t, J=6.4 Hz, 2H), 3.78 (t, J=6.4 Hz, 2H), 6.22 (d, J=7.6 Hz, 1H), 6.37 (d, J=7.6 Hz, 1H), 7.02 (s, 2H), 7.07 (t, J=7.6 Hz, 1H), 7.44 (s, 1H), 7.96 (s, 1H), 10.56 (s, 1H). MS 393 (MH$^+$).

Example 240a

6-(2-cyano-3-(sulfamoylamino)phenoxy)hexyl sulfamate

Prepared as in Example 215a from 2-amino-6-(6-hydroxyhexyloxy)benzonitrile (Example 240b) and sulfamoyl chloride in 20% yield. MS 393 (MH$^+$).

Example 240b

2-amino-6-(6-hydroxyhexyloxy)benzonitrile

Prepared as in Example 215b (Method A) from 2-(6-hydroxyhexyloxy)-6-nitrobenzonitrile (Example 240c) in 99% yield. MS 235 (MH$^+$).

Example 240c

2-(6-hydroxyhexyloxy)-6-nitrobenzonitrile

Prepared as in Example 215c from hexane-1,6-diol and 2,6-dinitrobenzonitrile in 88% yield as a pale yellow solid. MS 265 (MH$^+$).

Example 241

5-(4-amino-2,2-dioxide-1H-benzo[c][1,2,6]thiadiazin-5-yloxy)pentyl sulfamate

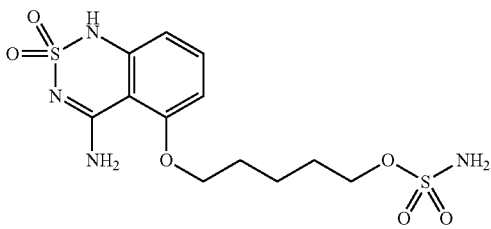

663

Prepared as in Example 215 from 5-(2-cyano-3-(sulfamoylamino)-phenoxy)pentyl sulfamate (Example 241a) in 44% yield. $^1$H NMR (400 MHz, DMSO-d$_6$) δ 1.09 (m, 2H), 1.33 (m, 2H), 1.47 (m, 2H), 3.66 (t, J=6.6 Hz, 2H), 3.79 (t, J=6.6 Hz, 2H), 6.22 (d, J=8.0 Hz, 1H), 6.37 (d, J=8.0 Hz, 1H), 7.03 (s, 2H), 7.07 (t, J=8.0 Hz, 1H), 7.43 (s, 1H), 7.95 (s, 1H), 10.57 (s, 1H). MS 379 (MH$^+$).

Example 241a

5-(2-cyano-3-(sulfamoylamino)phenoxy)pentyl sulfamate

Prepared as in Example 215a from 2-amino-6-(5-(tert-butyldimethylsilyloxy)pentyloxy)benzonitrile (Example 241b) and sulfamoyl chloride in 26% yield. MS 379 (MH$^+$).

Example 241b

2-amino-6-(5-(tert-butyldimethylsilyloxy)pentyloxy)benzonitrile

Prepared as in Example 215b (Method A) from 2-(5-(tert-butyldimethyl-silyloxy)pentyloxy)-6-nitrobenzonitrile (Example 241c) in 93% yield. MS 335 (MH$^+$).

Example 241c

2-(5-(tert-butyldimethylsilyloxy)pentyloxy)-6-nitrobenzonitrile

Prepared as in Example 215c from 5-(tert-butyldimethylsilyloxy)pentan-1-ol and 2,6-dinitrobenzonitrile as a pale yellow solid in 46% yield. MS 365 (MH$^+$).

Example 242

5-(4-amino-2,2-dioxide-1H-benzo[c][1,2,6]thiadiazin-5-yloxy)pentan-1'-ol

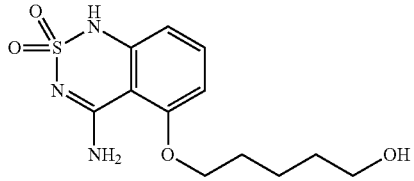

664

Prepared as in Example 215 from 2-sulfamoylamino-6-(5-hydroxy-pentyloxy)benzonitrile (Example 242a) in 32% yield. $^1$H NMR (400 MHz, DMSO-d$_6$) δ 1.39-1.49 (m, 4H), 1.77-1.84 (m, 2H), 3.31-3.44 (m, 2H), 4.14 (t, J=6.4 Hz, 2H), 4.35 (m, 1H), 6.59 (d, J=8.0 Hz, 1H), 6.74 (d, J=8.0 Hz, 1H), 7.44 (t, J=8.0 Hz, 1H), 7.81 (s, 1H), 8.34 (s, 1H), 10.93 (s, 1H). MS 300 (MH⁺).

Example 242a 2-sulfamoylamino-6-(5-hydroxypentyloxy)benzonitrile

Prepared as in Example 215a from 2-amino-6-(5-(tert-butyldimethylsilyloxy)pentyloxy)benzonitrile (Example 241b) and sulfamoyl chloride in 4% yield. MS 300 (MH⁺).

Example 243

1-(4-amino-2,2-dioxide-1H-benzo[c][1,2,6]thiadiazin-5-yloxy)-2',2',4'-trimethylpentan-3'-ol

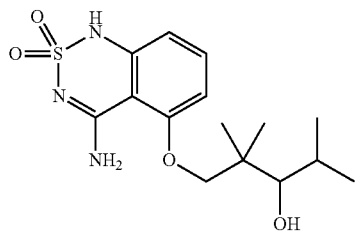

665

Prepared as in Example 215 from 1-(2-cyano-3-(sulfamoylamino)-phenoxy)-2,2,4-trimethylpentan-3-yl acetate (Example 243a) in 35% yield as a white solid. ¹H NMR (400 MHz, DMSO-d₆) δ 0.76-0.78 (d, 3H), 0.93 (s, 6H), 1.05 (s, 3H), 1.86-1.89 (m, 1H), 3.18-3.19 (d, 1H), 3.73-3.75 (d, 1H), 3.99-4.02 (d, 1H), 4.98-4.99 (d, 1H), 6.57-6.59 (d, J=8 Hz, 1H), 6.70-6.72 (d, J=8 Hz, 1H), 7.43 (t, J=8 Hz, 1H), 8.29 (s, 1H), 8.43 (s, 1H), 10.88 (s, 1H). MS 342 (MH⁺).

Example 243a 1-(2-cyano-3-(sulfamoylamino)phenoxy)-2,2,4-trimethylpentan-3-yl acetate Prepared as in Example 215a from 1-(3-amino-2-cyanophenoxy)-2,2,4-trimethylpentan-3-yl acetate (Example 243b) and sulfamoyl chloride in 90% yield. MS 384 (MH⁺).

Example 243b 1-(3-amino-2-cyanophenoxy)-2,2,4-trimethylpentan-3-yl acetate

Prepared as in Example 215b (Method A) from 1-(2-cyano-3-nitrophenoxy)-2,2,4-trimethylpentan-3-yl acetate (Example 243c) in 83% yield. MS 305 (MH⁺).

Example 243c 1-(2-cyano-3-nitrophenoxy)-2,2,4-trimethylpentan-3-yl acetate

Prepared as in Example 231c from 2-(3-hydroxy-2,2,4-trimethylpentyloxy)-6-nitrobenzonitrile (Example 243d) and acetyl chloride in 50% yield. MS 335 (MH⁺).

Example 243d 2-(3-hydroxy-2,2,4-trimethylpentyloxy)-6-nitrobenzonitrile

Prepared as in Example 215c from 2,2,4-trimethylpentane-1,3-diol and 2,6-dinitrobenzonitrile in 90% yield. MS 293 (MH⁺).

Example 244

5-(4-(methylthio)butoxy)-1H-benzo[c][1,2,6]thiadiazin-4-amine-2,2-dioxide

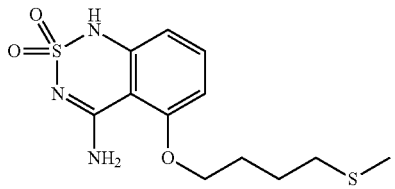

666

Prepared as in Example 215 from 2-sulfamoylamino-6-(4-(methylthio)butoxy)benzonitrile (Example 244a) in 79% yield. ¹H NMR (400 MHz, DMSO-d₆) δ 1.63-1.67 (m, 2H), 1.86-1.90 (m, 2H), 2.02 (s, 3H), 2.48-2.53 (m, 2H), 4.16 (t, 2H), 6.57-6.60 (d, J=8.4 Hz, 1H), 6.72-6.74 (d, J=8.4 Hz, 1H), 7.43 (t, J=8 Hz, 1H), 7.80 (s, 1H), 8.35 (s, 1H), 10.92 (s, 1H). MS 316 (MH⁺).

Example 244a 2-sulfamoylamino-6-(4-(methylthio)butoxy)benzonitrile

Prepared as in Example 215a from 2-amino-6-(4-(methylthio)-butoxy)benzonitrile (Example 244b) and sulfamoyl chloride in 66% yield. MS 316 (MH⁺).

Example 244b 2-amino-6-(4-(methylthio)butoxy)benzonitrile

Prepared as in Example 215b (Method A) from 2-(4-(methylthio)butoxy)-6-nitrobenzonitrile (Example 244c) in 95% yield. MS 237 (MH⁺).

Example 244c 2-(4-(methylthio)butoxy)-6-nitrobenzonitrile

Prepared as in Example 215c from 4-(methylthio)butan-1-ol and 2,6-dinitrobenzonitrile in 89% yield. MS 267 (MH⁺).

Example 245

5-(4-(methylsulfinyl)butoxy)-1H-benzo[c][1,2,6]thiadiazin-4-amine-2,2-dioxide

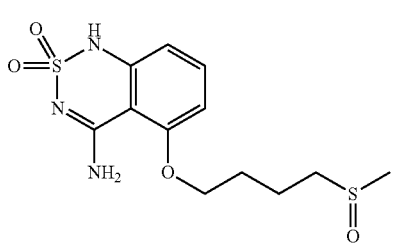

667

To a solution of 5-(4-(methylthio)butoxy)-1H-benzo[c][1,2,6]thiadiazin-4-amine-2,2-dioxide (Example 244) (79 mg, 0.25 mmol) in DCM/CH$_3$CO$_2$H (20:1, 20 mL) was added MCPBA (1.0 equiv.) at room temperature. The reaction mixture was then stirred at room temperature overnight. The solvent was evaporated under reduced pressure, and the residue was purified by chromatography on silica gel eluting with 15% MeOH in dichloromethane to give the title compound (74 mg, 90%) as a white solid. $^1$H NMR (400 MHz, DMSO-d$_6$) δ 1.74-1.77 (m, 2H), 1.88-1.95 (m, 2H), 2.50 (s, 3H), 2.68-2.73 (m, 1H), 2.77-2.83 (m, 1H), 4.19 (t, 2H), 6.58-6.60 (d, J=8.4 Hz, 1H), 6.73-6.75 (d, J=8.0 Hz, 1H), 7.44 (t, J=8.0 Hz, 1H), 7.79 (s, 1H), 8.33 (s, 1H), 10.92 (s, 1H). MS 332 (MH$^+$).

Example 246

5-(4-(methylsulfonyl)butoxy)-1H-benzo[c][1,2,6]thiadiazin-4-amine-2,2-dioxide

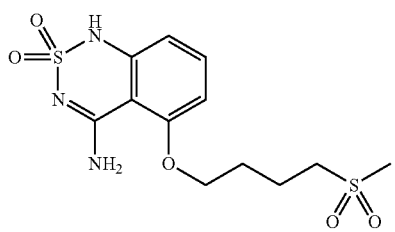

668

Prepared as in Example 245 from 5-(4-(methylthio)butoxy)-1H-benzo[c][,6]thiadiazin-4-amine-2,2-dioxide (Example 244) by the reaction with 3 equivalent of MCPBA as a white solid in 88% yield. $^1$H NMR (400 MHz, DMSO-d$_6$) δ 1.80-1.82 (m, 2H), 1.91-1.95 (m, 2H), 2.93 (s, 3H), 3.18 (t, 2H), 4.18 (t, 2H), 6.58-6.60 (d, J=8.4 Hz, 1H), 6.73-6.75 (d, J=8.0 Hz, 1H), 7.44 (t, J=8.0 Hz, 1H), 7.79 (s, 1H), 8.34 (s, 1H), 10.92 (s, 1H). MS 348 (MH$^+$).

Example 247

5-(3-(methylthio)propoxy)-1H-benzo[c][,6]thiadiazin-4-amine-2,2-dioxide

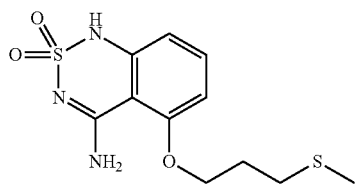

669

Prepared as in Example 215 from 2-sulfamoylamino-6-(3-(methylthio)propoxy)benzonitrile (Example 247a) in 69% yield. $^1$H NMR (400 MHz, DMSO-d$_6$) δ 2.05 (s, 3H), 2.08 (m, 2H), 2.59 (t, J=7.2 Hz, 2H), 4.21 (t, J=6.4 Hz, 2H), 6.59-6.61 (d, J=8.0 Hz, 1H), 673-6.75 (d, J=8.8 Hz, 1H), 7.44 (t, J=8.0 Hz, 1H), 7.79 (s, 1H), 8.33 (s, 1H), 10.93 (s, 1H). MS 302 (MH$^+$).

Example 247a 2-sulfamoylamino-6-(3-(methylthio)propoxy)benzonitrile

Prepared as in Example 215a from 2-amino-6-(3-(methylthio)propoxy)benzonitrile (Example 247b) and sulfamoyl chloride in 69% yield. MS 302 (MH$^+$).

Example 247b 2-amino-6-(3-(methylthio)propoxy)benzonitrile

Prepared as in Example 215b (Method A) from 2-(3-(methylthio)propoxy)-6-nitrobenzonitrile (Example 247c) in 98% yield. MS 223 (MH$^+$).

Example 247c 2-(3-(methylthio)propoxy)-6-nitrobenzonitrile

Prepared as in Example 215c from 4-(methylthio)butan-1-ol and 2,6-dinitrobenzonitrile in 89% yield. MS 253 (MH$^+$).

Example 248

5-(3-(methylsulfinyl)propoxy)-1H-benzo[c][1,2,6]thiadiazin-4-amine-2,2-dioxide

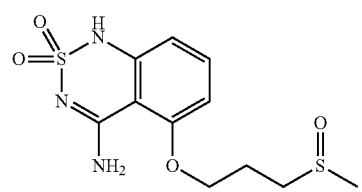

670

Prepared as in Example 245 from 5-(3-(methylthio)propoxy)-1H-benzo[c][1,2,6]thiadiazin-4-amine-2,2-dioxide (Example 247) by the reaction with 1.0 equivalent of MCPBA as a white solid in 90% yield. $^1$H NMR (400 MHz, DMSO-d$_6$) δ 2.18-2.22 (m, 2H), 2.54 (s, 3H), 2.75-2.78 (m, 1H), 2.89-2.93 (m, 1H), 4.26 (t, J=6.4 Hz, 2H), 6.60-6.61 (d, J=8.4 Hz, 1H), 6.73-6.75 (d, J=8.0 Hz, 1H), 7.44 (t, J=8.0 Hz, 1H), 7.83 (s, 1H), 8.30 (s, 1H), 10.92 (s, 1H). MS 318 (MH$^+$).

Example 249

5-(3-(methylsulfonyl)propoxy)-1H-benzo[c][1,2,6]thiadiazin-4-amine-2,2-dioxide

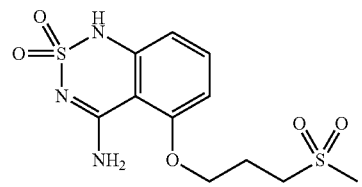

671

Prepared as in Example 245 from 5-(3-(methylthio)propoxy)-1H-benzo[c][1,2,6]thiadiazin-4-amine-2,2-dioxide (Example 247) by the reaction with 3.0 equivalent of MCPBA in 87% yield as a white solid. $^1$H NMR (400 MHz, DMSO-d$_6$) δ 2.24-2.27 (m, 2H), 3.00 (s, 3H), 3.26 (t, J=7.6 Hz, 2H), 4.24 (t, J=6.4 Hz, 2H), 6.60-6.62 (d, J=8.0 Hz, 1H), 6.72-6.74 (d, J=8.0 Hz, 1H), 7.45 (t, J=8.0 Hz, 1H), 7.79 (s, 1H), 8.31 (s, 1H), 10.93 (s, 1H). MS 334 (MH$^+$).

Example 250

5-(2-(2-ethoxyethoxy)ethoxy)-1H-benzo[c][1,2,6]thiadiazin-4-amine-2,2-dioxide

672

Prepared as in Example 215 from 2-sulfamoylamino-6-(2-(2-ethoxyethoxy)ethoxy)benzonitrile (Example 250a) in 52% yield. $^1$H NMR (400 MHz, DMSO-$d_6$) δ 1.05 (t, J=7.2 Hz, 3H), 3.37-3.43 (m, 2H), 3.47 (t, 2H), 3.58 (t, 2H), 3.81 (t, 2H), 4.26 (t, 2H), 6.60-6.62 (d, J=8.0 Hz, 1H), 673-6.75 (d, J=8.0 Hz, 1H), 7.45 (t, J=8.4 Hz, 1H), 7.99 (s, 1H), 8.32 (s, 1H), 10.97 (s, 1H). MS 330 (MH$^+$).

Example 250a 2-sulfamoylamino-6-(2-(2-ethoxyethoxy)ethoxy)benzonitrile

Prepared as in Example 215a from 2-amino-6-(2-(2-ethoxyethoxy)ethoxy)benzonitrile (Example 250b) and sulfamoyl chloride in 69% yield. MS 330 (MH$^+$).

Example 250b 2-amino-6-(2-(2-ethoxyethoxy)ethoxy)benzonitrile

Prepared as in Example 215b (Method A) from 2-(2-(2-ethoxyethoxy)ethoxy)-6-nitrobenzonitrile (Example 250c) in 98% yield. MS 251 (MH$^+$).

Example 250c 2-(2-(2-ethoxyethoxy)ethoxy)-6-nitrobenzonitrile

Prepared as in Example 215c from 2-(2-ethoxyethoxy)ethanol and 2,6-dinitrobenzonitrile in 66% yield. MS 281 (MH$^+$).

Example 251

5-(3-methylcyclopentyloxy)-1H-benzo[c][1,2,6]thiadiazin-4-amine-2,2-dioxide

673

Prepared as in Example 215 from 2-sulfamoylamino-6-(3-methylcyclopentyloxy)benzonitrile (Example 251a) in 45% yield. $^1$H NMR (400 MHz, DMSO-$d_6$) δ 0.97-1.04 (m, 3H), 1.28-1.37 (m, 2H), 1.75-2.03 (m, 4H), 2.31-2.38 (m, 1H), 4.95-5.02 (m, 1H), 6.56-6.58 (d, J=7.6 Hz, 1H), 6.67-6.69 (d, J=8.4 Hz, 1H), 7.42 (t, J=8.4 Hz, 1H), 7.69-7.72 (m, 1H), 8.30-8.36 (m, 1H), 10.92 (s, 1H). MS 296 (MH$^+$).

Example 251a 2-sulfamoylamino-6-(3-methylcyclopentyloxy)benzonitrile

Prepared as in Example 215a from 2-amino-6-(3-methylcyclopentyloxy)benzonitrile (Example 251b) and sulfamoyl chloride in 52% yield. MS 296 (MH$^+$).

Example 251b 2-amino-6-(3-methylcyclopentyloxy)benzonitrile

Prepared as in Example 215b (Method A) from 2-(3-methylcyclopentyloxy)-6-nitrobenzonitrile (Example 251c) in 98% yield. MS 217 (MH$^+$).

Example 251c 2-(3-methylcyclopentyloxy)-6-nitrobenzonitrile

Prepared as in Example 215c from 3-methylcyclopentanol and 2,6-dinitrobenzonitrile in 70% yield. MS 247 (MH$^+$).

Example 252

1-(3-(4-amino-2,2-dioxide-1H-benzo[c][1,2,6]thiadiazin-5-yloxy)-2',2'-dimethylpropyl)-3'(4"-methoxybenzyl)urea

674

Prepared as in Example 215 from 1-(3-(3-sulfamoylamino-2-cyanophenoxy)-2,2-dimethylpropyl)-3-(4-methoxybenzyl)urea (Example 252a) in 77% yield as a white solid. $^1$H NMR (400 MHz, DMSO-$d_6$) δ 0.92 (s, 6H), 3.06 (d, J=6.4 Hz, 2H), 3.32 (s, 2H), 3.67 (s, 3H), 4.06 (d, J=6.0 Hz, 2H), 6.29 (t, J=6.0 Hz, 2H), 6.61 (d, J=8.0 Hz, 1H), 6.71 (d, J=8.0 Hz, 1H), 6.74 (d, J=8.8 Hz, 2H), 7.06 (d, J=8.8 Hz, 2H), 7.44 (t, J=8.0 Hz, 1H), 8.12 (s, 1H), 8.34 (s, 1H), 10.90 (s, 1H). MS 462 (MH$^+$).

Example 252a 1-(3-(3-sulfamoylamino-2-cyanophenoxy)-2,2-dimethylpropyl)-3-(4-methoxybenzyl)urea Prepared as in Example 215a from 1-(3-(3-amino-2-cyanophenoxy)-2,2-dimethylpropyl)-3-(4-methoxybenzyl)urea (Example 252b) and sulfamoyl chloride in 100% yield. MS 462 (MH$^+$).

Example 252b 1-(3-(3-amino-2-cyanophenoxy)-2,2-dimethylpropyl)-3-(4-methoxybenzyl)urea Prepared as in Example 215b (Method B) from 1-(3-hydroxy-2,2-dimethylpropyl)-3-(4-methoxybenzyl)urea (Example 252c) and 2-amino-6-fluorobenzonitrile in 60% yield. MS 383 (MH+).

Example 252c 1-(3-hydroxy-2,2-dimethylpropyl)-3-(4-methoxybenzyl)urea

Prepared as in Example 227d from 3-amino-2,2-dimethylpropan-1-ol and 4-methoxybenzyl isocyanate in 100% yield. MS 267 (MH+).

Example 253

5-(prop-1-ynyl)-1H-benzo[c][1,2,6]thiadiazin-4-amine-2,2-dioxide

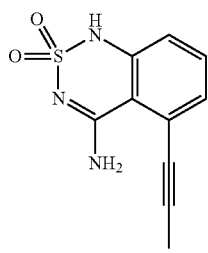

675

Prepared as in Example 215 from 2-sulfamoylamino-6-(3-(trimethylsilyl)prop-1-ynyl)benzonitrile (Example 253a) in 10% yield. $^1$H NMR (400 MHz, DMSO-d$_6$) δ 1.28 (s, 2H), 2.16 (s, 3H), 6.99-7.01 (d, J=8.4 Hz, 1H), 7.21-7.23 (d, J=7.8 Hz, 1H), 7.45 (t, J=7.8 Hz, 1H). MS 236 (MH+).

Example 253a 2-sulfamoylamino-6-(3-(trimethylsilyl)prop-1-ynyl)benzonitrile

A solution of 2-amino-6-(3-(trimethylsilyl)prop-1-ynyl)benzonitrile (Example 253b) (557 mg, 2.0 mmol) and NH$_2$SO$_2$NH$_2$ (0.96 g, 10 mmol) in dry 1,4-dioxane (50 mL) was refluxed under nitrogen for 2 days. The solvent was evaporated under reduced pressure, and the residue was purified by chromatography on silica gel eluting with 70% EtOAc in hexanes to give the title compound (31 mg, 5%) as a white solid. MS 308 (MH+).

Example 253b 2-amino-6-(3-(trimethylsilyl)prop-1-ynyl)benzonitrile

To a stirred solution of trimethyl(prop-2-ynyl)silane (1.12 g, 10 mmol), 2-amino-6-bromobenzonitrile (Klaubert, D. H.; Sellstedt, J. H.; Guinosso, C. J.; Capetola, R. J.; Bell, S. C. *J. Med. Chem.* 1981, 24, 742) (1.0 g, 5 mmol), CuI (0.01 equiv.) in triethylamine (50 mL) was added Pd(PPh$_3$)$_4$ (0.1 equiv.) at room temperature under nitrogen. The reaction mixture was then refluxed under nitrogen overnight. The solvent was evaporated, and the residue was titrated with EtOAc/water. The organic layer was separated, were washed with brine, and dried over Na$_2$SO$_4$. After evaporation of the solvent, the residue was purified by chromatography on silica gel eluting with 15% EtOAc in hexanes to give the title compound (1.43 g, 63%) as a as a liquid. MS 229 (MH+).

Example 254

5-((2-methyleyclopropyl)methoxy)-1H-benzo[c][1,2,6]thiadiazin-4-amine-2,2-dioxide

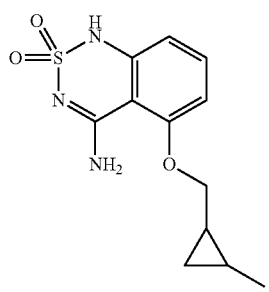

676

Prepared as in Example 111 from 2-amino-6-((2-methylcyclopropyl)methoxy)benzonitrile sulfamide (example 254a) in 68% yield (mixture of diastereoisomers). $^1$H NMR (400 MHz, DMSO-d$_6$) δ 0.17-0.40 (m, 1H), 0.54-0.58 (m, 1H), 0.76-0.85 (m, 1H), 0.99-1.12 (m, 4H), 3.96-4.33 (m, 2H), 6.58-6.61 (m, 1H), 6.67-6.77 (m, 1H), 7.41-7.47 (m, 1H), 7.97 (s, NH), 8.38 (s, NH), 10.97 (s, NH). MS 282 (MH+).

Example 254a 2-amino-6-((2-methylcyclopropyl)methoxy)benzonitrile sulfamide

Prepared as in example 90a from 2-amino-6-((2-methylcyclopropyl)methoxy)benzonitrile (Example 254b) in 100% yield. $^1$H NMR (400 MHz, DMSO-d$_6$) δ 0.34-0.36 (m, 1H), 0.51-0.53 (m, 1H), 0.77-0.79 (m, 1H), 0.95-0.97 (m, 1H), 1.04-1.09 (m, 3H), 3.92-4.03 (m, 2H), 6.86-6.88 (bm, 1H), 7.11-7.18 (bm, 3H), 7.48-7.52 (bm, 1H), 9.53 (bs, NH). MS 282 (MH+).

Example 254b 2-amino-6-((2-methylcyclopropyl)methoxy)benzonitrile

A solution of 2-((2-methylcyclopropyl)methoxy)-6-nitrobenzonitrile (example 254c) (0.29 g, 1.25 mmol) in EtOAc/EtOH 1:1 (30 mL) was hydrogenated in an H-cube apparatus using 10% Pd/C as catalyst. The solution was evaporated to give 2-amino-6-((2-methylcyclopropyl)methoxy)benzonitrile (0.20 g, 79%) as a yellow oil. MS 203 (MH+).

Example 254c 2-((2-methylcyclopropyl)methoxy)-6-nitrobenzonitrile

Prepared as in Example 166d from (2-methylcyclopropyl)methanol and 2,6-dinitrobenzonitrile in 81% yield. MS 233 (MH+).

Example 255

N5-isobutyl-1H-benzo[c][1,2,6]thiadiazine-4,5-diamine-2,2-dioxide

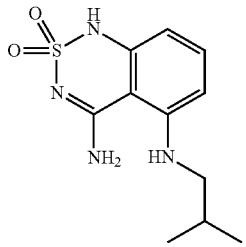

Prepared as in Example 111 from 2-amino-6-(isobutylamino)benzonitrile sulfamide (Example 255a) in 23% yield. 1H NMR (400 MHz, DMSO-$d_6$) δ 0.95 (d, J=6.8 Hz, 6H), 1.88-1.95 (m, 1H), 2.84 (t, J=6.8 Hz, 2H), 5.87 (t, J=6.4 Hz, NH), 6.31 (dd, J=0.8 Hz, J=8.0 Hz, 1H), 6.40 (d, J=8.0 Hz, 1H), 7.26 (t, J=8.4 Hz, 1H), 7.88 (s, NH$_2$), 10.70 (s, NH). MS 269 (MH$^+$).

Example 255a 2-amino-6-(isobutylamino)benzonitrile sulfamide

Prepared as in Example 90a from 2-amino-6-(isobutylamino)benzonitrile (Example 255b) and used in the next step without any further purification. MS 269 (MH$^+$).

Example 255b 2-amino-6-(isobutylamino)benzonitrile

Prepared as in Example 90b from 2-(isobutylamino)-6-nitrobenzonitrile (Example 255 in 66% yield. MS 190 (MH$^+$).

Example 255c 2-(isobutylamino)-6-nitrobenzonitrile

Prepared as in Example 90c from 2,6-dinitrobenzonitrile and methylamine in 92% yield. MS 220 (MH$^+$).

Example 256

5-((1-methylcyclopropyl)methoxy)-1H-benzo[c][,6]thiadiazin-4-amine-2,2-dioxide

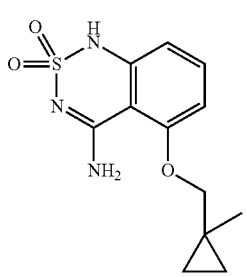

Prepared as in Example 111 from 2-amino-6-((1-methylcyclopropyl)methoxy)benzonitrile sulfamide (Example 256a), in 39% yield. $^1$H NMR (400 MHz, DMSO-$d_6$) δ 0.44-0.46 (m, 2H), 0.59-0.62 (m, 2H), 1.2 (s, 3H), 3.96 (s, 2H), 6.59 (d, J=8.4 Hz, 1H), 6.66 (d, J=8.0 Hz, 1H), 7.43 (t, J=8.0 Hz, 1H), 7.83 (bs, NH), 8.40 (bs, NH), 9.45 (bs, NH). MS 282 (MH$^+$).

Example 256a 2-amino-6-((1-methylcyclopropyl)methoxy)benzonitrile sulfamide

Prepared as in example 90a from 2-amino-6-((1-methylcyclopropyl)methoxy)benzonitrile (Example 256b) in 100% yield. $^1$H NMR (400 MHz, DMSO-$d_6$) δ 0.40-0.43 (m, 2H), 0.53-0.56 (m, 2H), 1.20 (s, 3H), 3.89 (s, 2H), 6.85 (d, J=8.0 Hz, 1H), 7.11-7.23 (bs, NH$_2$), 7.12 (d, J=8.0 Hz, 1H), 7.51 (t, J=8.4 Hz, 1H), 9.45 (bs, NH). MS 282 (MH$^+$).

Example 256b 2-amino-6-((1-methylcyclopropyl)methoxy)benzonitrile

Prepared as in Example 254b from 2-((1-methylcyclopropyl)methoxy)-6-nitrobenzonitrile (Example 256c) in 88% yield as a yellow oil. MS 203 (MH$^+$).

Example 256c 2-((1-methylcyclopropyl)methoxy)-6-nitrobenzonitrile

Prepared as in Example 166d from (1-methylcyclopropyl)methanol and 2,6-dinitrobenzonitrile in 65% yield. $^1$H NMR (400 MHz, DMSO-$d_6$) δ 0.44-0.46 (m, 2H), 0.57-0.59 (m, 2H), 1.22 (s, 3H), 4.06 (s, 2H), 7.67 (dd, J=1.6 Hz, J=8.0 Hz, 1H), 7.85-7.92 (m, 2H).

Example 257

1-(2-(4-amino-1H-benzo[c][1,2,6]thiadiazin-5-yloxy)ethyl)pyrrolidin-2-one-2,2-dioxide

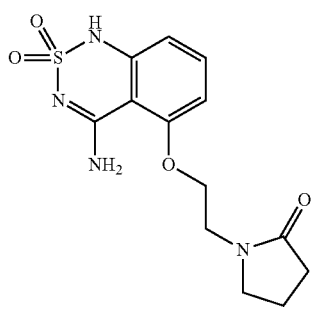

Prepared as in Example 111 from 2-amino-6-(2-(2-oxopyrrolidin-1-yl)ethoxy)benzonitrile sulfamide (Example 257a) in 45% yield. $^1$H NMR (400 MHz, DMSO-$d_6$) δ 1.94 (q, J=7.2 Hz, 2H), 2.26 (t, J=7.6 Hz, 2H), 3.43 (t, J=7.2 Hz, 2H), 3.68 (t, J=4.4 Hz, 2H), 4.23 (t, J=4.4 Hz, 2H), 6.59 (d, J=7.6 Hz, 1H), 6.70 (d, J=8.8 Hz, 1H), 7.43 (t, J=8.4 Hz, 1H), 7.82 (bs, NH), 8.21 (bs, NH), 10.98 (bs, NH). MS 325 (MH$^+$).

Example 257a 2-amino-6-(2-(2-oxopyrrolidin-1-yl)ethoxy)benzonitrile sulfamide Prepared as in example 90a from 2-amino-6-(2-(2-oxopyrrolidin-1-yl)ethoxy)benzonitrile (Example 257b) in 100% yield. $^1$H NMR (400 MHz, DMSO-$d_6$) δ 1.94 (q, J=8.4 Hz, 2H), 2.22 (t, J=8.4 Hz, 2H), 3.50-3.58 (m, 4H), 4.21 (t, J=4.8 Hz, 2H), 6.94 (bs, 1H), 7.17 (d, J=7.6 Hz, 1H), 7.24 (bs, NH$_2$), 7.54 (t, J=7.2 Hz, 1H), 9.49 (bs, NH). MS 325 (MH$^+$).

Example 257b 2-amino-6-(2-(2-oxopyrrolidin-1-yl)ethoxy)benzonitrile

Prepared as in example 254b from 2-nitro-6-(2-(2-oxopyrrolidin-1-yl)ethoxy)benzonitrile (Example 257c) using trifluoroethanol/hexafluoroisopropanol (1:1) as solvent in 100% yield MS 246 (MH$^+$).

Example 257c 2-nitro-6-(2-(2-oxopyrrolidin-1-yl)ethoxy)benzonitrile

Prepared as in Example 166d from 1-(2-hydroxyethyl)pyrrolidin-2-one and 2,6-dinitrobenzonitrile in 74% yield. MS 276 (MH$^+$).

Example 258

N5-(3-methoxypropyl)-1H-benzo[c][1,2,6]thiadiazine-4,5-diamine-2,2-dioxide

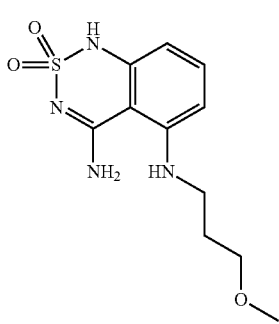

680

Prepared as in Example 90 from 2-amino-6-(3-methoxypropylamino)benzonitrile sulfamide (Example 258a) in 69% yield. $^1$H NMR (400 MHz, DMSO-$d_6$) δ 1.79-1.85 (m, 2H), 3.06 (q, J=6.8 Hz, J=6.8 Hz, 2H), 3.22 (s, 3H), 3.42 (t, J=6.0 Hz, 2H), 5.94 (t, J=5.0 Hz, NH), 6.26 (d, J=8.4 Hz, 1H), 6.34 (d, J=8.0 Hz, 1H), 7.23 (t, J=8.0 Hz, 1H), 7.88 (s, NH$_2$), 10.64 (s, NH). MS 285 (MH$^+$).

Example 258a 2-amino-6-(3-methoxypropylamino)benzonitrile sulfamide

Prepared as in Example 90a from 2-amino-6-(3-methoxypropylamino)benzonitrile in 65% yield. $^1$H NMR (400 MHz, DMSO-$d_6$) δ 1.74-1.79 (m, 2H), 3.19 (q, J=6.8 Hz, J=7.2 Hz, 2H), 3.22 (s, 3H), 3.39 (t, J=6.2 Hz, 2H), 5.96 (t, J=5.6 Hz, NH), 6.47 (d, J=8.8 Hz, 1H), 6.70 (d, J=8.0 Hz, 1H), 7.09 (s, NH$_2$), 7.31 (t, J=8.0 Hz, 1H), 9.09 (s, NH). MS 285 (MH$^+$).

Example 258b 2-amino-6-(3-methoxypropylamino)benzonitrile

To a solution of 2-(3-methoxypropylamino)-6-nitrobenzonitrile (Example 258c) (0.58 g, 2.48 mmol) in EtOH (20 mL) was added cyclohexene (1.26 mL, 12.4 mmol). Then 10% Pd/C (1.32 g) was added, and the reaction mixture was refluxed at 100° C. for 20 minutes, cooled to room temperature, filtered through Celite which was washed with EtOH (3×20 mL), and evaporated to give 2-amino-6-(3-methoxypropylamino)benzonitrile (0.43 g, 84%) as a colorless oil. $^1$H NMR (400 MHz, DMSO-$d_6$) δ 1.71-1.77 (m, 2H), 3.10 (q, J=6.8 Hz, J=6.8 Hz, 2H), 3.22 (s, 3H), 3.37 (t, J=3.2 Hz, 2H), 5.55 (t, J=5.2 Hz, NH), 5.63 (s, NH$_2$), 5.79 (d, J=7.6 Hz, 1H), 5.93 (d, J=8.0 Hz, 1H), 6.98 (t, J=8.0 Hz, 1H). MS 206 (MH$^+$).

Example 258c 2-(3-methoxypropylamino)-6-nitrobenzonitrile

Prepared as in Example 90c from 2,6-dinitrobenzonitrile and 3-methoxypropylamine in 83% yield. $^1$H NMR (400 MHz, DMSO-$d_6$) δ 1.76-1.81 (m, 2H), 3.23 (s, 3H), 3.28-3.33 (m, 2H), 3.40 (t, J=5.6 Hz, 2H), 6.66 (t, J=4.8 Hz, NH), 7.30 (d, J=8.8 Hz, 1H), 7.42 (d, J=8.0 Hz, 1H), 7.60 (t, J=8.0 Hz, 1H).

Example 259

N5-ethyl-1H-benzo[c][1,2,6]thiadiazine-4,5-diamine-2,2-dioxide

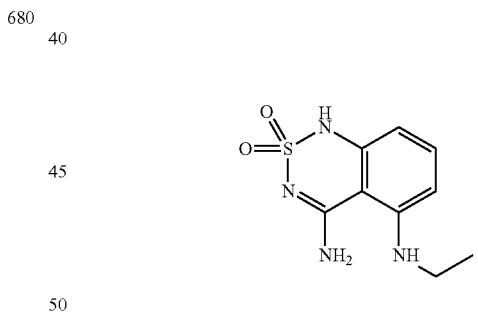

681

Prepared as in Example 111 from 2-amino-6-(ethylamino)benzonitrile sulfamide (Example 259a) in 57% yield. $^1$H NMR (400 MHz, DMSO-$d_6$) δ 1.18 (t, J=6.8 Hz, 3H), 2.99-3.06 (m, 2H), 5.87 (t, J=5.2 Hz, NH), 6.30 (d, J=7.6 Hz, 1H), 6.38 (d, J=7.6 Hz, 1H), 7.26 (t, J=8.0 Hz, 1H), 7.90 (s, NH$_2$), 10.68 (s, NH). MS 241 (MH$^+$).

Example 259a 2-amino-6-(ethylamino)benzonitrile sulfamide

Prepared as in Example 90a from 2-amino-6-(ethylamino)benzonitrile (Example 259b) in 47% yield. $^1$H NMR (400 MHz, DMSO-$d_6$) δ 1.14 (t, J=7.2 Hz, 3H), 3.15-3.22 (m, 2H), 5.84 (bs, NH), 6.48 (d, J=8.8 Hz, 1H), 6.72 (d, J=8.0 Hz, 1H), 7.02 (bs, NH$_2$), 7.31 (t, J=8.0 Hz, 1H), 9.14 (bs, NH). MS 241 (MH$^+$).

Example 259b 2-amino-6-(ethylamino)benzonitrile

Prepared as in Example 254b from 2-(ethylamino)-6-nitrobenzonitrile (Example 259c) using Trifluoroethanol/Hexafluoroisopropanol (2:1) as solvent, in 81% yield. $^1$H NMR (400 MHz, DMSO-$d_6$) δ 1.14 (t, J=7.2 Hz, 3H), 3.15-3.22 (m, 2H), 5.41 (bt, J=5.2 Hz, NH), 5.64 (s, NH$_2$), 5.82 (d, J=8.0 Hz, 1H), 5.96 (d, J=8.0 Hz, 1H), 7.00 (t, J=8.4 Hz, 1H). MS 162 (MH$^+$).

Example 259c 2-(ethylamino)-6-nitrobenzonitrile

Prepared as in Example 90c from 2,6-dinitrobenzonitrile and a 2M ethylamine solution in THF in 88% yield. $^1$H NMR (400 MHz, DMSO-$d_6$) δ 1.13 (t, J=7.6 Hz, 3H), 3.26-3.33 (m, 2H), 6.59 (bt, J=5.2 Hz, NH), 7.22 (d, J=9.2 Hz, 1H), 7.42 (d, J=8.0 Hz, 1H), 7.60 (t, J=8.4 Hz, 1H). MS 162 (M-Et).

Example 260

N5-(2-(benzyloxy)ethyl)-1H-benzo[c][1,2,6]thiadiazine-4,5-diamine-2,2-dioxide

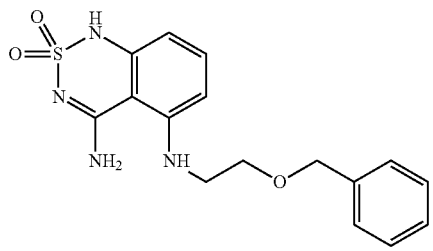

682

Prepared as in example 90 from 2-amino-6-(2-(benzyloxy)ethylamino)benzonitrile sulfamide (Example 260a) in 68% yield. NMR (400 MHz, DMSO-$d_6$) δ 3.25 (q, J=5.2 Hz, J=6.4 Hz, 2H), 3.64 (t, J=5.6 Hz, 2H), 4.49 (s, 2H), 5.91 (t, J=5.2 Hz, NH), 6.28 (d, J=8.4 Hz, 1H), 6.40 (d, J=8.4 Hz, 1H), 7.23 (t, J=8.0 Hz, 1H), 7.25-7.35 (m, 5H), 7.90 (s, NH$_2$), 10.68 (s, NH). MS 347 (MH$^+$).

Example 260a 2-amino-6-(2-(benzyloxy)ethylamino)benzonitrile sulfamide

Prepared as in Example 90a from 2-amino-6-(2-(benzyloxy)ethylamino)benzonitrile (Example 260b) in 45%. $^1$H NMR (400 MHz, CDCl$_3$) δ 3.36 (q, J=5.2 Hz, J=5.6 Hz, 2H), 3.57 (t, J=5.6 Hz, 2H), 4.49 (s, 2H), 5.76 (t, J=5.6 Hz, NH), 6.55 (d, J=8.4 Hz, 1H), 6.72 (d, J=8.0 Hz, 1H), 7.12 (s, NH$_2$), 7.25-7.32 (m, 6H), 9.12 (s, NH). MS 347 (MH$^+$).

Example 260b 2-amino-6-(2-(benzyloxy)ethylamino)benzonitrile

Prepared as in Example 90b from 2-(2-(benzyloxy)ethylamino)-6-nitrobenzonitrile (Example 260c) in 100% yield as a brown oil. $^1$H NMR (400 MHz, CDCl$_3$) δ 3.27 (q, J=5.2 Hz, J=6.0 Hz, 2H), 3.56 (t, J=5.6 Hz, 2H), 4.49 (s, 2H), 5.34 (t, J=5.6 Hz, NH), 5.67 (s, NH$_2$), 5.84 (d, J=8.0 Hz, 1H), 5.95 (d, J=8.4 Hz, 1H), 6.98 (t, J=8.2 Hz, 1H), 7.30-7.34 (m, 5H). Ms 268 (MH$^+$).

Example 260c 2-(2-(benzyloxy)ethylamino)-6-nitrobenzonitrile

Prepared as in Example 90c from 2-(benzyloxy)ethanamine and 2,6-dinitrobenzonitrile in 77% yield. $^1$H NMR (400 MHz, DMSO-$d_6$) δ 3.49 (q, J=5.2 Hz, J=5.6 Hz, 2H), 3.59 (t, J=5.6 Hz, 2H), 4.49 (s, 2H), 6.47 (t, J=5.8 Hz, NH), 7.23-7.31 (m, 6H), 7.43 (d, J=8.0 Hz, 1H), 7.58 (t, J=8.4 Hz, 1H).

Example 261

2-(4-amino-1H-benzo[c][,6]thiadiazin-5-ylamino)ethanol-2,2-dioxide

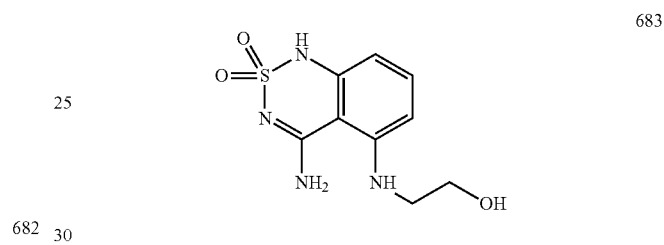

683

A solution of N$^5$-(2-(benzyloxy)-ethylamino)-1H-benzo[c][1,2,6]thiadiazine-4,5-diamine-2,2-dioxide (Example 260) (0.10 g, 0.29 mmol) in EtOH (20 mL) was charged with 30 mg of 10% Pd/C and H$_2$ balloon and stirred at room temperature for 24 hours. The reaction mixture was filtered through Celite which was washed with EtOH, the combined organic phases were evaporated, and the residue was purified by flash chromatography using a DCM/MeOH (9:1) solution as eluant, to give 2-(4-amino-1H-benzo[c][1,2,6]thiadiazin-5-ylamino)ethanol-2,2-dioxide (64.8 mg, 87%). $^1$H NMR (400 MHz, DMSO-$d_6$) δ 3.11 (q, J=5.6 Hz, J=5.6 Hz, 2H), 3.58-3.59 (m, 2H), 4.84 (bs, 1H), 5.84 (t, J=5.2 Hz, NH), 6.26 (d, J=8.0 Hz, 1H), 6.37 (d, J=8.4 Hz, 1H), 7.22 (t, J=8.0 Hz, 1H), 7.86 (s, NH$_2$), 10.65 (bs, NH). MS 257 (MH$^+$).

Example 262

3-((4-Amino-1H-benzo[c][1,2,6]thiadiazin-5-yloxy)methyl)-N-propylpiperidine-1-carboxamide-2,2-dioxide

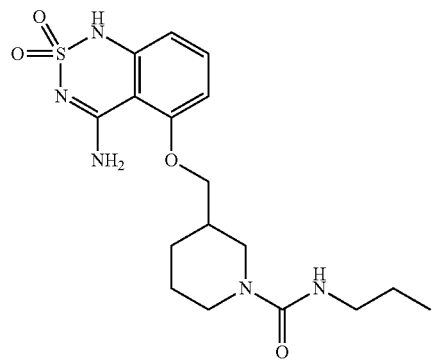

684

Prepared as in Example 111 from 3-((3-amino-2-cyanophenoxy)methyl)-N-propylpiperidine-1-carboxamide sulfamide (Example 262a) in 88% yield. $^1$H NMR (400 MHz, DMSO-$d_6$) δ 0.81 (t, J=6.8 Hz, 3H), 1.23-1.43 (m, 4H), 1.60-1.63 (bm, 1H), 1.81-1.84 (bm, 1H), 1.99-2.05 (bm, 1H), 2.67-2.75 (m, 1H), 2.80-2.85 (m, 1H), 2.93-2.98 (m, 2H), 3.71 (bd, J=12.8, 1H), 3.90 (bd, J=10.8, 1H), 3.98-4.08 (m, 2H), 6.44 (d, J=6.0 Hz, NH), 6.62 (d, J=8.0 Hz, 1H), 6.76 (d, J=8.4 Hz, 1H), 7.46 (t, J=8.4 Hz, 1H), 7.80 (s, NH), 8.37 (s, NH), 10.95 (s, NH). MS 396 (MH$^+$).

Example 262a 3-((3-amino-2-cyanophenoxy)methyl)-N-propylpiperidine-1 carboxamide sulfamide Prepared as in Example 90a from 3-((3-amino-2-cyanophenoxy)methyl)-N-propylpiperidine-1-carboxamide (Example 262b) in 100% yield. $^1$H NMR (400 MHz, DMSO-$d_6$) δ 0.81 (t, J=7.2 Hz, 3H), 1.31-1.44 (m, 4H), 1.61-1.64 (bm, 1H), 1.85-1.87 (bm, 2H), 2.60-2.75 (m, 2H), 2.94-2.98 (m, 2H), 3.78 (bd, J=12.8 Hz, 1H), 3.93-3.97 (m, 1H), 4.01-4.10 (m, 2H), 6.38 (d, J=6.0 Hz, NH), 6.96 (d, J=8.8 Hz, 1H), 7.16 (d, J=8.4 Hz, 1H), 7.27 (s, NH), 7.41 (s, NH), 7.57 (t, J=8.4 Hz, 1H), 9.48 (s, NH). MS 396 (MH$^+$).

Example 262b 3-((3-amino-2-cyanophenoxy)methyl)-N-propylpiperidine-1-carboxamide Prepared as in Example 254b from 3-((2-cyano-3-nitrophenoxy)methyl)-N-propylpiperidine-1-carboxamide (Example 262c) in 94% yield. MS 317 (MH$^+$).

Example 262c 3-((2-cyano-3-nitrophenoxy)methyl)-N-propylpiperidine-1-carboxamide To a solution of 2-nitro-6-(piperidin-3-ylmethoxy)benzonitrile hydrochloride (Example 262d) (0.10 g, 0.34 mmol) in THF (6 mL) were added triethylamine (0.10 mL, 0.76 mmol) and propylisocyanate (0.05 mL, 0.52 mmol) and the reaction mixture was stirred at r.t. under nitrogen for 3 hour then filtered and evaporated, to give 3-((2-cyano-3-nitrophenoxy)methyl)-N-propylpiperidine-1-carboxamide (0.13 g, 100%). $^1$H NMR (400 MHz, DMSO-$d_6$) δ 0.81 (t, J=7.2 Hz, 3H), 1.34-1.41 (m, 4H), 1.62-1.64 (bm, 1H), 1.87-1.95 (bm, 2H), 2.64-2.77 (m, 2H), 2.93-2.98 (m, 2H), 3.77 (bd, J=12.8 Hz, 1H), 3.98 (bd, J=12.8 Hz, 1H), 4.09-4.13 (m, 1H), 4.17-4.20 (m, 1H), 6.38 (d, J=5.6 Hz, NH), 7.74 (bdd, J=1.6 Hz, J=8.0 Hz, 1H), 7.88-7.94 (m, 2H). MS 347 (MH$^+$).

Example 262d 2-nitro-6-(piperidin-3-ylmethoxy)benzonitrile hydrochloride

Prepared as in example 166 from tert-butyl 3-((2-cyano-3-nitrophenoxy)methyl)piperidine-1-carboxylate (Example 262e) in 98% yield. MS 262 (MH$^+$).

Example 262e tert-butyl 3-((2-cyano-3-nitrophenoxy)methyl)piperidine-1-carboxylate Prepared as in Example 215c from tert-butyl 3-(hydroxymethyl)piperidine-1-carboxylate and 2,6-dinitrobenzonitrile in 58% yield. MS 263 [M+H-Boc]$^+$.

Example 263

Tert-butyl 3-((4-amino-1H-benzo[c][1,2,6]thiadiazin-5-yloxy)methyl)piperidine-1-carboxylate-2,2-dioxide

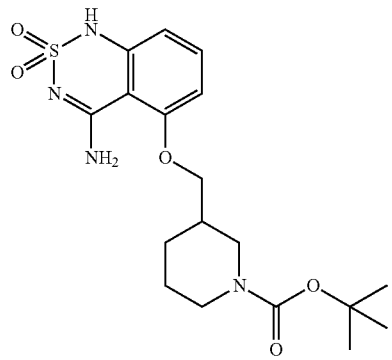

Prepared as in Example 111 from tert-butyl 3-((3-amino-2-cyanophenoxy)methyl)piperidine-1-carboxylate sulfamide (Example 263a), keeping the pH above 3 upon acidification, to give tert-butyl 3-((4-amino-1H-benzo[c][1,2,6]thiadiazin-5-yloxy)methyl)piperidine-1-carboxylate-2,2-dioxide (33 mg, 23%). $^1$H NMR (400 MHz, DMSO-$d_6$) δ 1.27-1.40 (bs, 11H), 1.62-1.66 (bm, 1H), 1.78-1.83 (bm, 1H), 2.05-2.12 (bm, 1H), 2.87-2.94 (m, 2H), 3.64-3.71 (bm, 1H), 3.83-3.86 (bm, 1H), 4.04 (bd, J=7.2 Hz, 2H), 6.62 (d, J=8.0 Hz, 1H), 6.77 (d, J=8.4 Hz, 1H), 7.46 (t, J=8.4 Hz, 1H), 7.76 (bs, NH), 8.37 (bs, NH), 10.95 (s, NH). MS 311 [M+H-Boc]$^+$.

Example 263a tert-butyl 3-((3-amino-2-cyanophenoxy)methyl)piperidine-1-carboxylate sulfamide Prepared as in Example 90a from tert-butyl 3-((3-amino-2-cyanophenoxy)methyl)piperidine-1-carboxylate (Example 263b). Upon extraction, NaOH 1M (1.56 mL, 1.56 mmol) was added to the ice-cooled reaction medium triggering formation of a sticky orangy material. Water was poured away and the residue diluted in EtOAc, and extracted, to give tert-butyl 3-((3-amino-2-cyanophenoxy)methyl)piperidine-1-carboxylate sulfamide (0.15 g, 84%). $^1$H NMR (400 MHz, DMSO-$d_6$) δ 1.35-1.40 (bs, 11H), 1.63-1.66 (bm, 1H), 1.79-1.83 (bm, 1H), 1.88-1.93 (bm, 1H), 2.78-2.85 (m, 2H), 3.74-3.78 (bm, 1H), 3.92-4.04 (m, 3H), 6.96 (d, J=8.4 Hz, 1H), 7.15 (d, J=8.4 Hz, 1H), 7.27 (s, NH$_2$), 7.56 (t, J=8.8 Hz, 1H), 9.47 (s, NH). MS 311 [M+H-Boc]$^+$.

Example 263b tert-butyl 3-((3-amino-2-cyanophenoxy)methyl)piperidine-1-carboxylate Prepared as in example 254b from tert-butyl 3-((2-cyano-3-nitrophenoxy)methyl)piperidine-1-carboxylate (Example 262e) in 100% yield as an oil. MS 232 [M+H-Boc]$^+$.

Example 264

4-Amino-5-(trans-2-methylcyclopentyloxy)-1H-benzo[c][1,2,6]thiadiazine-2,2-dioxide

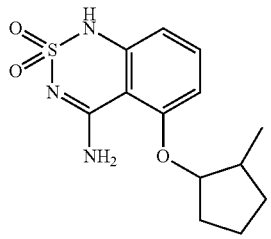

To a solution of 2-amino-6-(trans-2-methylcyclopentyloxy)benzonitrile (Example 264a) (150 mg, 0.694 mmol) in dimethylacetamide (3 mL) under $N_2$ was added sulfamoyl chloride (3 equiv.). The reaction mixture was stirred at room temperature under $N_2$ for 2 hours, diluted with ethyl acetate (50 mL) and quenched with water (20 mL). The layers were separated. The organic extract was evaporated. Ethanol (3 mL) and aqueous NaOH (2N, 2.5 equiv.) were consecutively added to the residue. The resulting mixture was heated at 90° C. for 16 hours. The workup was performed as in Example 111 to provide the desired product (160 mg, 78%) as a white powder. $^1$H NMR (400 MHz, DMSO-$d_6$) δ 1.02 (d, J=6.4 Hz, 3H), 1.26 (m, 1H), 1.71 (br s, 3H), 1.89 (m, 1H), 2.12 (m, 1H), 2.24 (m, 1H), 4.55 (br s, 1H), 6.60 (d, J=8.0 Hz, 1H), 6.71 (d, J=8.0 Hz, 1H), 7.45 (t, J=8.0 Hz, 1H), 7.73 (br s, 1H), 8.35 (br s, 1H), 10.96 (br s, 1H). MS 296 (MH$^+$).

Example 264a

2-Amino-6-(trans-2-methylcyclopentyloxy)benzonitrile

Prepared as in Example 111b from 2-(trans-2-methylcyclopentyloxy)-6-nitrobenzonitrile (Example 264b) to give the title compound in quantitative yield as a colorless oil. $^1$H NMR (400 MHz, CDCl$_3$) δ 1.04 (d, J=7.2 Hz, 3H), 1.23 (m, 1H), 1.72 (m, 1H), 1.81 (m, 2H), 1.99 (m, 2H), 2.26 (m, 1H), 4.28 (m, 1H), 4.36 (br s, 2H), 6.18 (d, J=8.4 Hz, 1H), 6.18 (d, J=8.4 Hz, 1H), 7.18 (t, J=8.4 Hz, 1H). MS 296 (MH$^+$).

Example 264b

2-(trans-2-Methylcyclopentyloxy)-6-nitrobenzonitrile

Prepared as in Example 111c from 2,6 dinitrobenzonitrile and trans-2-methylcyclopentanol in 65% as a yellow solid. MS 247 (MH$^+$).

Example 265

4-Amino-5-(((2R,3S,4R)-3,4-dihydroxy-5-methoxytetrahydrofuran-2-yl)methoxy)-1H-benzo[c][,6]thiadiazine-2,2-dioxide

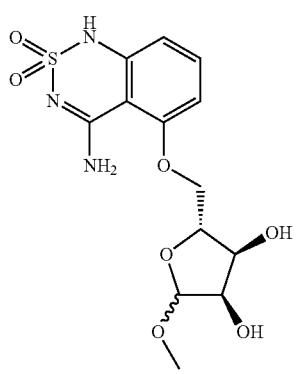

To a solution of 4-Amino-5-(((2R,3S,4R)-3,4,5-trihydroxytetrahydrofuran-2-yl)methoxy)-1H-benzo[c][1,2,6]thiadiazine-2,2-dioxide (Example 265a) (7 mg, 0.020 mmol) in dry methanol (1 mL) was added trifluoroacetic acid 0.2 mL) and the mixture was refluxed overnight. The resulting solution was evaporated to dryness to provide the title compound as a white powder (7.28 mg, 100%, mixture of diastereomers ~4/1). $^1$H NMR (400 MHz, DMSO-$d_6$): δ [3.17 (s, ¾H)], 3.22 (s, 3H), 3.81 (d, J=4.0 Hz, 1H), [3.93 (m, ½H)], 4.12 (m, 3H), 4.39 (m, 1H), 4.71 (s, 1H), [4.85 (d, J=4.0 Hz, % H)], 5.44 (br s, 2H), 6.65 (d, J=8.0 Hz, 1H), 6.81 (d, J=8.0 Hz, 1H), 7.48 (t, J=8.0 Hz, 1H), 7.95 (s, 1H), 8.41 (s, 1H), 11.00 (s, 1H), [11.01 (s, % H)].

Example 265a

4-Amino-5-(((2R,3S,4R)-3,4,5-trihydroxytetrahydrofuran-2-yl)methoxy)-1H-benzo[c][1,2,6]thiadiazine-2,2-dioxide To a suspension of 4-Amino-5-(((3aR,4R,6R,6aR)-6-methoxy-2,2-dimethyltetrahydrofuro[3,4-d][1,3]dioxol-4-yl)methoxy)-1H-benzo[c][1,2,6]thiadiazine-2,2-dioxide (Example 265b) (15 mg, 0.038 mmol) in water (1 mL) was added trifluoroacetic acid (0.2 mL) and the mixture was heated overnight at 80° C. The reaction mixture was evaporated to dryness to furnish the title compound as a white solid in quantitative yield (mixture of diastereomers~10/1). $^1$H NMR (400 MHz, DMSO-$d_6$): δ 3.71 (m, 4H), 4.12 (m, 3H), 4.35 (m, 1H), 5.02 (s, 1H), 6.63 (d, J=8.0 Hz, 1H), 6.79 (d, J=8.0 Hz, 1H), 7.47 (t, J=8.0 Hz, 1H), 8.03 (br s, 1H), 8.31 (br s, 1H), 10.96 (br s, 1H), [11.00 (br s, 0.1H)].

Example 265b

4-Amino-5-(((3aR,4R,6R,6aR)-6-methoxy-2,2-dimethyltetrahydrofuro[3,4-d][1,3]dioxol-4-yl)methoxy)-1H-benzo[c][1,2,6]thiadiazine-2,2-dioxide Prepared as in Example 111 from 2-sulfamoylamino-6-(((3aR,4R,6R,6aR)-6-methoxy-2,2-dimethyltetrahydrofuro[3,4-d][1,3]dioxol-4-yl)methoxy)benzonitrile (Example 265c) in 78% yield as a beige solid. $^1$H NMR (400 MHz, DMSO-$d_6$) δ 1.28 (s, 3H), 1.41 (s, 3H), 3.18 (s, 3H), 4.00 (t, J=9.2 Hz, 1H), 4.32 (dd, J=5.2, 10.0 Hz, 1H), 4.59 (dd, J=5.2, 8.8 Hz, 1H), 4.63 (d, J=6.0 Hz, 1H), 4.82 (d, J=6.0 Hz, 1H), 5.02 (s, 1H), 6.64 (d, J=8.4 Hz, 1H), 6.70 (d, J=8.4 Hz, 1H), 7.48 (t, J=8.4 Hz, 1H), 7.98 (br s, 1H), 8.43 (br s, 1H), 11.02 (br s, 1H).

Example 265c

2-Sulfamoylamino-6-(((3aR,4R,6R,6aR)-6-methoxy-2,2-dimethyltetrahydrofuro[3,4-d][1,3]dioxol-4-yl)methoxy)benzonitrile Prepared as in Example 111a from 2-amino-6-(((3aR,4R,6R,6aR)-6-methoxy-2,2-dimethyltetrahydrofuro[3,4-d][1,3]dioxol-4-yl)methoxy)benzonitrile (Example 265d) in 77% yield as a white solid. $^1$H NMR (400 MHz, CDCl$_3$) δ 1.34 (s, 3H), 1.50 (s, 3H), 3.33 (s, 3H), 4.08 (m, 2H), 4.51 (da, J=6.4, 7.6 Hz, 1H), 4.65 (d, J=6.0 Hz, 1H), 4.79 (d, J=6.0 Hz, 1H), 5.01 (s, 1H), 5.25 (br s, 2H), 6.70 (d, J=8.4 Hz, 1H), 7.28 (br s, 1H), 7.30 (d, J=8.0 Hz, 1H), 7.51 (t, J=8.4 Hz, 1H).

Example 265d

2-Amino-6-(((3aR,4R,6R,6aR)-6-methoxy-2,2-dimethyltetrahydrofuro[3,4-d][1,3]dioxol-4-yl)methoxy)benzonitrile Prepared as in Example 111b from 2-(((3aR,4R,6R,6aR)-6-methoxy-2,2-dimethyltetrahydrofuro[3,4-d][1,3]dioxol-4-yl)methoxy)-4-nitrobenzonitrile (Example 252e) in 40% yield as colorless sticky material. $^1$H NMR (400 MHz, CDCl$_3$) δ 1.33 (s, 3H), 1.49 (s, 3H), 3.33 (s, 3H), 4.05 (m, 2H), 4.45 (br s, 2H), 4.56 (dd, J=6.0, 8.0 Hz, 1H), 4.65 (d, J=6.0 Hz, 1H), 4.82 (br d, J=6.0 Hz, 1H), 5.00 (s, 1H), 6.21 (dd, J=0.8, 8.4 Hz, 1H), 6.33 (dd, J=0.8, 8.4 Hz, 1H), 7.20 (t, J=8.4 Hz, 1H).

Example 265e 2-(((3aR,4R,6R,6aR)-6-Methoxy-2,2-dimethyltetrahydrofuro[3,4-d][1,3]dioxol-4-yl)methoxy)-6-nitrobenzonitrile Prepared as in Example 111c from 2,6 dinitrobenzonitrile and ((3aR,4R,6R,6aR)-6-methoxy-2,2-dimethyltetrahydrofuro[3,4-d][1,3]dioxol-4-yl)methanol in 70% yield as white solid. $^1$H NMR (400 MHz, CDCl$_3$) δ 1.33 (s, 3H), 1.49 (s, 3H), 3.32 (s, 3H), 4.23 (d, J=2.0 Hz, 1H), 4.24 (s, 1H), 4.60 (br t, J=6.0 Hz, 1H), 4.67 (d, J=6.0 Hz, 1H), 4.86 (br d, J=6.0 Hz, 1H), 5.01 (s, 1H), 7.35 (d, J=8.4 Hz, 1H), 7.72 (t, J=8.4 Hz, 1H), 7.87 (dd, J=0.8, 8.4 Hz, 1H).

Example 266

4-Amino-5-(((3aR,5aS,8aS,8bS)-2,2,7,7-tetramethyltetrahydro-3aH-bis[1,3]dioxolo[4,5-b:4',5'-d]pyran-5-yl)methoxy)-1H-benzo[c][,6]thiadiazine-2,2-dioxide

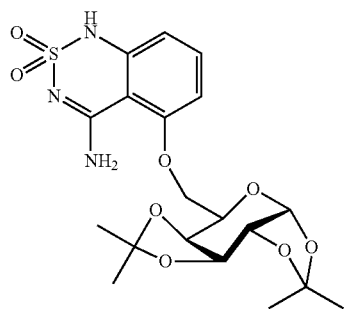

688

Prepared as in Example 264 from 2-amino-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile (Example 266a) in 72% yield as a white solid. $^1$H NMR (400 MHz, DMSO-d$_6$) δ 1.29 (s, 3H), 1.31 (s, 3H), 1.38 (s, 3H), 1.43 (s, 3H), 4.07 (m, 2H), 4.19 (br d, J=8.4 Hz, 1H), 4.36 (dd, J=1.2, 8.0 Hz, 1H), 4.41 (dd, J=2.4, 5.2 Hz, 1H), 4.44 (dd, J=2.4, 10.0 Hz, 1H), 4.67 (dd, J=2.4, 8.0 Hz, 1H), 5.51 (d, J=4.8 Hz, 1H), 6.63 (d, J=8.0 Hz, 1H), 6.77 (d, J=8.4 Hz, 1H), 7.45 (t, J=8.4 Hz, 1H), 7.86 (br s, 1H), 8.41 (br s, 1H), 10.98 (br s, 1H). MS 456 (MH$^+$).

Example 266a

2-Amino-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile Prepared as in Example 111b from 2-nitro-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile (Example 266b) in quantitative yield. $^1$H NMR (400 MHz, DMSO-d$_6$) δ 1.28 (s, 3H), 1.31 (s, 3H), 1.37 (s, 3H), 1.39 (s, 3H), 4.05 (m, 2H), 4.16 (dd, J=4.0, 8.8 Hz, 1H), 4.37 (m, 2H), 4.67 (dd, J=2.4, 8.0 Hz, 1H), 5.47 (d, J=4.8 Hz, 1H), 6.01 (br s, 2H), 6.23 (d, J=8.0 Hz, 1H), 6.35 (d, J=8.4 Hz, 1H), 7.17 (t, J=8.4 Hz, 1H).

Example 266b

2-Nitro-6-(((3aR,5aS,8aS,8bS)-2,2,7,7-tetramethyltetrahydro-3aH-bis[1,3]dioxolo[4,5-b:4',5'-d]pyran-5-yl)methoxy)benzonitrile Prepared as in Example 111c from 2,6 dinitrobenzonitrile and ((3aR,5aS,8as,8bS)-2,2,7,7-tetramethyltetrahydro-3aH-bis[1,3]dioxolo[4,5-b:4',5'-d]pyran-5-yl)methanol in 59% yield as white sticky material. MS 408 (MH$^+$), 424 (MH$_2$O$^+$).

Example 267

4-Amino-5-(1-(2-methoxyethyl)-1H-1,2,3-triazol-4-yl)-1H-benzo[c][1,2,6]thiadiazine-2,2-dioxide

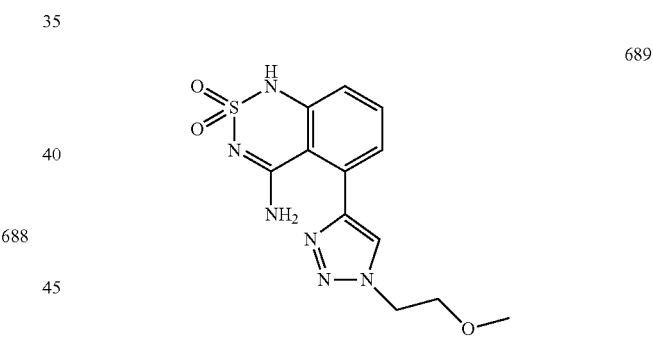

689

Prepared as in Example 111 from 2-sulfamoylamino-6-(1-(2-methoxyethyl)-1H-1,2,3-triazol-4-yl)benzonitrile (Example 267a) in 78% yield. $^1$H NMR (400 MHz, DMSO-d$_6$) δ 3.27 (s, 3H), 3.78 (t, J=5.2 Hz, 2H), 4.59 (t, J=5.2 Hz, 2H), 6.90 (br s, 1H), 7.09 (dd, J=0.8, 8.0 Hz, 1H), 7.20 (dd, J=0.8, 7.6 Hz, 1H), 7.58 (t, J=7.6 Hz, 1H), 8.15 (br s, 1H), 8.32 (s, 1H), 11.09 (br s, 1H). MS 323 (MH$^+$).

Example 267a

2-Sulfamoylamino-6-(1-(2-methoxyethyl)-1H-1,2,3-triazol-4-yl)benzonitrile

Prepared as in Example 111a from 2-amino-6-(1-(2-methoxyethyl)-1H-1,2,3-triazol-4-yl)benzonitrile (Example 267b) in 90% yield. $^1$H NMR (400 MHz, DMSO-d$_6$) δ 3.28 (s, 3H), 3.79 (t, J=5.2 Hz, 2H), 4.66 (t, J=5.2 Hz, 2H), 7.32 (br s, 2H), 7.60 (dd, J=1.2, 8.0 Hz, 1H), 7.76 (t, J=8.0 Hz, 1H), 7.82 (dd, J=1.2, 8.0 Hz, 1H), 8.64 (s, 1H), 9.52 (br s, 1H).

Example 267b

2-Amino-6-(1-(2-methoxyethyl)-1H-1,2,3-triazol-4-yl)benzonitrile

To a solution of 1-bromo-2-methoxyethane (5.00 g, 35.97 mmol) in DMF (25 mL), was added sodium azide (3 equiv.) and the mixture was heated at 50° C. for 48 hours. The reaction mixture was diluted with water (75 mL) and extracted with diethyl ether. The organic extract was dried over MgSO$_4$ and concentrated to furnish 1-azido-2-methoxyethane as a yellow liquid. This azide (200 mg, 1.94 mmol) was added to a solution of 2-Amino-6-ethynylbenzonitrile (250 mg, 1.76 mmol) (Example 267c) in H$_2$O/tert-BuOH=1:2 (15 mL) and the solution was treated consecutively with sodium ascorbate (0.264 mmol) and CuSO$_4$ (0.035 mmol). The reaction mixture was stirred at room temperature for 48 hours, diluted with water and extracted with ethyl acetate. The organic extract was dried over MgSO$_4$ and purified over silica gel (ethyl acetate/hexane 6:4) to furnish the title compound as a white solid in 88% yield. $^1$H NMR (400 MHz, DMSO-d$_6$) δ 3.26 (s, 3H), 3.78 (t, J=5.2 Hz, 2H), 4.23 (t, J=5.2 Hz, 2H), 6.13 (br s, 2H), 6.80 (dd, J=1.2, 8.4 Hz, 1H), 7.09 (dd, J=1.2, 7.6 Hz, 1H), 7.36 (t, J=8.4 Hz, 1H), 8.52 (s, 1H). MS 244 (MH$^+$).

Example 267c

2-Amino-6-ethynylbenzonitrile

To a solution of 2-amino-6-bromobenzonitrile (1.25 g, 6.34 mmol) and ethynyltrimethylsilane (2.42 g, 12.7 mmol) in dry Et$_3$N (15 mL) was added under N$_2$ Cu(I) (60 mg), Pd(PPh$_3$)$_4$ (360 mg) and the mixture was stirred at 80° C. for 20 hours. The reaction mixture was cooled down to room temperature, diluted with ethyl acetate and washed with brine. The organic layer was evaporated and the residue was dissolved in methanol (20 mL), treated with 1M aqueous NaOH solution (1.05 equiv.) and stirred at room temperature for 1 hour. Methanol was evaporated off and the aqueous residue was extracted with CH$_2$Cl$_2$, dried over MgSO$_4$, and purified over silica gel (ethyl acetate/hexanes 75/25) to furnish the desired product in 93% yield as light yellow solid. $^1$H NMR (400 MHz, DMSO-d$_6$) δ 4.54 (s, 1H), 6.24 (br s, 2H), 6.76 (dd, J=0.8, 7.6 Hz, 1H), 6.82 (dd, J=0.8, 8.4 Hz, 1H), 7.28 (dd, J=7.6, 8.4 Hz, 1H). MS 143 (MH$^+$).

Example 268

4-Amino-5-(furan-3-yl)-1H-benzo[c][1,2,6]thiadiazine-2,2-dioxide

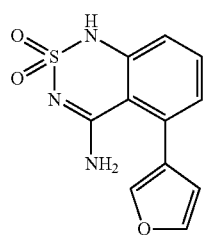

690

Prepared as in Example 111 from 2-sulfamoylamino-6-(furan-3-yl)benzonitrile (Example 268a) in 47% yield as a beige solid. $^1$H NMR (400 MHz, DMSO-d$_6$) δ 6.34 (br s, 1H), 6.51 (dd, J=0.8, 2.0 Hz, 1H), 7.03 (m, 2H), 7.52 (dd, J=7.6, 8.0 Hz, 1H), 7.79 (t, J=1.6 Hz, 1H), 7.93 (dd, J=0.8, 1.6 Hz, 1H), 8.23 (br s, 1H), 11.09 (s, 1H). MS 264 (MH$^+$)

Example 268a

2-Sulfamoylamino-6-(furan-3-yl)benzonitrile

Prepared as in Example 111a from 2-amino-6-(furan-3-yl)benzonitrile (Example 268b) in 63% yield as a white solid. $^1$H NMR (400 MHz, DMSO-d$_6$) δ 6.97 (dd, J=0.8, 2.0 Hz, 1H), 7.29 (br s, 2H), 7.46 (dd, J=0.8, 7.6 Hz, 1H), 7.54 (dd, J=0.8, 8.0 Hz, 1H), 7.69 (t, J=8.0 Hz, 1H), 7.85 (t, J=1.6 Hz, 1H), 8.21 (dd, J=0.8, 1.6 Hz, 1H), 9.48 (br s, 1H).

Example 268b

2-Amino-6-(furan-3-yl)benzonitrile

Prepared as in Example 129c from furan-3-ylboronic acid and 2-amino-6-bromobenzonitrile in 74% yield as a yellow solid. $^1$H NMR (400 MHz, CDCl$_3$) δ 4.51 (br s, 2H), 6.66 (dd, J=1.2, 8.4 Hz, 1H), 6.78 (dd, J=1.2, 2.0 Hz, 1H), 6.82 (dd, J=1.2, 8.0 Hz, 1H), 7.31 (t, J=8.0 Hz, 1H), 7.50 (t, J=1.6 Hz, 1H), 7.95 (dd, J=1.2, 1.6 Hz, 1H).

Example 269

4-Amino-5-(thiophen-3-yl)-1H-benzo[c][1,2,6]thiadiazine-2,2-dioxide

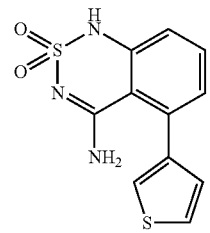

691

Prepared as in Example 111 from 2-sulfamoylamino-6-(thiophen-3-yl)benzonitrile (Example 269a) in 52% yield as a beige solid. $^1$H NMR (400 MHz, DMSO-d$_6$) δ 5.82 (br s, 1H), 7.05 (m, 3H), 7.54 (t, J=8.0 Hz, 1H), 7.67 (m, 1H), 8.15 (br s, 1H), 11.13 (s, 1H). MS 280 (MH$^+$).

Example 269a

2-Sulfamoylamino-6-(thiophen-3-yl)benzonitrile

Prepared as in Example 111a from 2-amino-6-(thiophen-3-yl)benzonitrile (Example 269b) in 60% yield as a white solid. $^1$H NMR (400 MHz, DMSO-d$_6$) δ 7.31 (br s, 2H), 7.42 (dd, J=1.2, 2.8 Hz, 1H), 7.43 (d, J=1.6 Hz, 1H), 7.57 (dd, J=0.8, 8.0 Hz, 1H), 7.70 (t, J=8.0 Hz, 1H), 7.73 (dd, J=2.8, 4.8 Hz, 1H), 7.88 (dd, J=1.2, 2.8 Hz, 1H), 9.48 (br s, 1H).

Example 269b

2-Amino-6-(thiophen-3-yl)benzonitrile

Prepared as in Example 129c from thiophen-3-ylboronic acid and 2-amino-6-bromobenzonitrile in 94% yield as a beige solid. $^1$H NMR (400 MHz, DMSO-$d_6$) δ 6.08 (br s, 2H), 6.70 (dd, J=1.2, 7.6 Hz, 1H), 6.77 (dd, J=1.2, 8.4 Hz, 1H), 7.31 (dd, J=7.6, 8.4 Hz, 1H), 7.38 (dd, J=1.2, 4.8 Hz, 1H), 7.66 (dd, J=2.8, 4.8 Hz, 1H), 7.78 (dd, J=1.2, 2.8 Hz, 1H).

Example 270

5-(2,2-dimethylcyclopropyl)-1H-benzo[c][1,2,6]thiadiazin-4-amine-2,2-dioxide

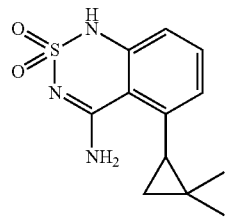

692

A solution of 2-amino-6-(2,2-dimethylcyclopropyl)benzonitrile (381 μmol, 71 mg) (Example 270a) and sulfamoyl chloride (572 μmol, 66 mg) in DMA (1 mL) was stirred at room temperature. After 1 hour, the reaction mixture was diluted with NaOH (1N, 572 μmol, 572 μL) and water (~30 mL). The precipitate was filtered off, washed with water (3×5 mL) then dissolved in EtOH (10 mL) and NaOH (1N, 953 μL) was added. The reaction was heated to 80° C. with stirring. After completion the solvent were evaporated and the residue was partitioned between water (20 mL) and ether (5 mL). The aqueous layer was extracted with ether (2×5 mL), then acidified to pH~3 with 1N HCl. The precipitate was collected, washed with water, dried in vacuo to give the desired product (59 mg, 58%) as an off-white solid. $^1$H NMR (400 MHz, DMSO-$d_6$) δ 0.610 (m, 1H), 0.63 (s, 3H), 0.89 (m, 1H), 1.20 (s, 3H), 2.48 (m, 1H), 6.88 (d, J=8 Hz, 1H), 6.92 (d, J=8 Hz, 1H), 7.21 (br. s, 1H), 7.39 (t, J=8 Hz, 1H), 8.42 (br. s, 1H), 10.74 (s, 1H). MS 266 (MH$^+$).

Example 270a 2-amino-6-cyclopropylbenzonitrile

To a degassed solution of 2-amino-6-bromobenzonitrile (851 μmol, 168 mg), 2,2-dimethylcyclopropylboronic acid (1.106 μmol, 126 mg) (Example 270b), and $Cs_2CO_3$ (2.979 mmol, 970 mg) in DME (3.4 mL) and water (850 μL) was added tetrakis(triphenylphosphino)palladium(0) (43 μmol, 50 mg) under nitrogen and the reaction mixture microwaved for 2 hours at 160° C. The reaction mixture was cooled to room temperature and extracted with EtOAc (3×5 mL). The combined organic layers was washed once with brine (5 mL), dried over sodium sulfate, filtered and evaporated. The crude product was purified on silica gel (EtOAc/hexanes 10%-40%) to give the desired product (71 mg, 45%) as a waxy, yellow solid. $^1$H NMR (400 MHz, CDCl$_3$) δ 0.82 (m, 1H), 0.82 (s, 3H), 0.85 (m, 1H), 1.33 (s, 3H), 1.92 (m, 1H), 4.36 (br. s, 2H), 6.47 (d, J=8 Hz, 1H), 6.56 (d, J=8 Hz, 1H), 7.20 (t, J=8 Hz, 1H).

Example 270b 2,2-dimethylcyclopropylboronic acid

To a solution of 1-bromo-2,2-dimethylcyclopropane (7.48 mmol, 1.115 g) (Example 270c) in anhydrous THF (20 mL) was added tBuLi (8.23 mmol, 1.7 M in pentane, 4.85 mL) dropwise at −78° C. under nitrogen. After 1 hour at −78° C., trimethylborate (8.23 mmol, 920 μL) was added and the reaction mixture was stirred for 2 hours at −78° C., warmed to room temperature, stirred for 1 hour, and quenched with sat. NH$_4$Cl solution (20 mL). The reaction mixture was diluted to a total volume of 100 mL with DCM and treated with HCl (6N in water, 22.45 mmol, 3.74 mL). The layers were separated, the aqueous layer extracted with dicholrometane (2×50 mL), the combined organic layers were washed with brine (25 mL), dried over sodium sulfate, filtered and evaporated. The residue was diluted with acetone (50 mL) and a few drops of water, then carefully concentrated in vacuo to give 214 mg (25.1%) of product as an off-white solid. $^1$H NMR (400 MHz, acetone-$d_6$) δ 0.00 (m, 1H), 0.13 (m, 1H), 0.755 (d of d, J=4 Hz, 8 Hz, 1H), 0.865 (d of d, J=4 Hz, 8 Hz, 1H), 1.39 (s, 3H), 1.46 (s, 3H), 6.81 (s, 2H).

Example 270c 1-bromo-2,2-dimethylcyclopropane

To a suspension of Zinc (dust, 319.4 mmol, 20.88 g) in EtOH (20 mL) was added HCl (12 N, 5 mL) at 0° C. A solution of 1,1-dibromo-2,2-dimethylcyclopropane (18.2 g) (example 270d) in EtOH (20 mL) was added to the mixture over 5 minutes with stirring. The reaction mixture was allowed to warm slowly to room temperature overnight. The zinc salts were filtered off through a pad of Celite, the Celite washed with EtOH (50 mL), and the resulting solution partitioned between water (200 mL), and pentane (200 mL). The aqueous layer was further extracted with pentane (2×100 mL), and the combined organic extracts successively washed with water (4×75 mL), brine (25 mL), dried over sodium sulfate, filtered, and evaporated to gives the product (1.115 g, 9.4%) as a volatile, colorless liquid. $^1$H NMR (400 MHz, acetone-$d_6$) δ 0.602 (d of d, J=4 Hz, 6 Hz, 1H), 1.025 (d of d, J=6 Hz, 8 Hz, 1H), 1.116 (s, 3H), 1.233 (s, 3H), 2.963 (d of d, J=4 Hz, 8 Hz, 1H).

Example 270d 1,1-dibromo-2,2-dimethylcyclopropane

To a solution of pentane (200 mL) cooled to −5° C. was added isobutylene (457.7 mmol, 25.68 g) followed by potassium tert-butoxide (549.2 mmol, 61.63 g). Then bromoform (457.7 mmol, 40.0 mL) was added dropwise with vigorous stirring over about 1 hour at −5° C. The reaction mixture was allowed to warm slowly to room temperature and then partitioned between pentane (100 mL) and water (200 mL). The aqueous layer was extracted with pentane (2×50 mL) and the combined organic layers washed with water (4×75 mL), brine (50 mL), dried over sodium sulfate, filtered and evaporated. The orange residue was pushed through a silica plug eluting with pentane. The solvent was evaporated to give the desired product (65.70 g, 57.3%) as a colorless oil. $^1$H NMR (400 MHz, acetone-$d_6$) δ 1.392 (s, 6H), 1.505 (s, 2H).

Example 271

(±)-trans-5-(2-(methoxymethyl)cyclopropyl)-1H-benzo[c][1,2,6]thiadiazin-4-amine-2,2-dioxide

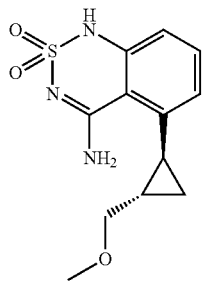

693

Prepared as in Example 270 from (±)-trans-2-amino-6-(2-(methoxymethyl)cyclopropyl)benzonitrile (example 271a) and sulfamoyl chloride in 34% as an off-white solid. $^1$H NMR (400 MHz, DMSO-d$_6$) δ 0.976 (m, 1H), 1.172 (m, 1H), 1.340 (m, 1H), 2.282 (m, 1H), 3.175 (d of d, J=8 Hz, 10 Hz, 1H), 3.252 (s, 3H), 3:576 (d of d, J=5 Hz, 10 Hz, 1H), 6.802 (d, J=8 Hz, 1H), 6.855 (d, J=8 Hz, 1H), 7.376 (t, J=8 Hz, 1H), 8.396 (br. s, 1H), 8.473 (br. s, 1H), 10.823 (s, 1H). MS 282 (MH$^+$).

Example 271a (±)-trans-2-amino-6-(2-(methoxymethyl)cyclopropyl)benzonitrile

Prepared as in Example 270a from (t)-trans-2-(methoxymethyl)cyclopropylboronic acid (example 271b) and 2-amino-6-bromobenzonitrile in 64% yield as a yellowish brown waxy solid. $^1$H NMR (400 MHz, DMSO-d$_6$) δ 0.932 (m, 2H), 1.341 (m, 1H), 1.879 (m, 1H), 2.324 (s, 3H), 3.351 (d, J=6 Hz, 2H), 5.896 (br. s, 2H), 6.148 (d, J=8 Hz, 1H), 6.550 (d, J=8 Hz, 1H), 7.130 (t, J=8 Hz, 1H).

Example 271b (±)-trans-2-(methoxymethyl)cyclopropylboronic acid

To a solution of (±)-trans-2-(methoxymethyl)cyclopropyl)-4,4,5,5-tetramethyl-1,3,2-dioxaborolane (10.0 mmol, 2.121 g) (example 271c) dissolved in THF (64 mL) was added NaIO$_4$ (30.0 mmol, 6.417 g) and water (16 mL). The reaction mixture was stirred at room temperature for 3 minutes then treated with aqueous HCl (2N, 3.33 mL). The reaction mixture was stirred for one hour at room temperature, partitioned with EtOAc (100 mL), the aqueous layer extracted with EtOAC (2×50 mL), the combined organic layers washed with brine (25 mL), dried over sodium sulfate, filtered, and evaporated. The mixture was taken up in acetone, treated with a few drops of water, and carefully evaporated to a viscous oil, which slowly solidified at room temperature to give the desired product in quantitative yield. $^1$H NMR (400 MHz, DMSO-d$_6$) δ -0.467 (m, 1H), 0.324 (m, 1H), 0.532 (m, 1H), 1.055 (m, 1H), 3.099 (d of d, J=7 Hz, 10 Hz, 1H), 3.186 (d of d, J=7 Hz, 10 Hz, 1H), 3.206 (s, 3H), 7.344 (s, 2H).

Example 271c (±)-trans-2-(methoxymethyl)cyclopropyl)-4,4,5,5-tetramethyl-1,3,2-dioxaborolane To a solution of (E)-2-(3-methoxyprop-1-enyl)-4,4,5,5-tetramethyl-1,3,2-dioxaborolane (32.2 mmol, 6.3710 g) in anhydrous toluene (50 mL) under nitrogen was added diethyl zinc (0.59 M in hexanes, 32.2 mmol, 54.6 mL), followed by CH$_2$I$_2$ (45.08 mmol, 3.63 mL). The flask was heated to 50° C. under nitrogen. After 4 hours, another portion of diethyl zinc (54.6 mL) and CH$_2$I$_2$ (3.63 mL) was added and heated overnight under nitrogen. The reaction mixture was cooled to room temperature and quenched with saturated aqueous NH$_4$Cl (50 mL). The reaction mixture was partitioned with ether (200 mL), the layers separated, the organic layer washed with brine (25 mL), dried over sodium sulfate, filtered and evaporated. The residue was purified on silica gel (EtOAc/hexanes 1% to 15%) to give the desired product (5.552 g, 81.3%) as a light-yellow oil. $^1$H NMR (400 MHz, acetone) 80.012 (m, 1H), 0.804 (m, 1H), 0.944 (m, 1H), 1.172 (m, 1H), 3.484 (dd, J=6 Hz, 10 Hz, 1H), 3.553 (dd, J=6 Hz, 10 Hz, 1H), 3.570 (s, 3H).

Example 272

(E)-4-(4-amino-2,2-dioxo-1H-benzo[c][,6]thiadiazin-5-yl)but-3-en-1-ol

694

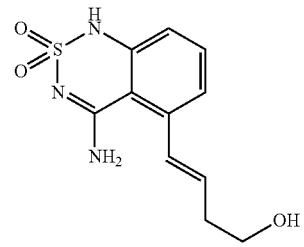

To a solution of (E)-5-(4-(tetrahydro-2H-pyran-2-yloxy)but-1-enyl)-1H-benzo[c][1,2,6]thiadiazin-4-amine-2,2-dioxide (322 μmol, 43 mg) (Example 273) in THF (860 μL) was added AcOH (1.7 mL) and water (430 μL) and the solution heated overnight at 45° C. The solution was cooled to room temperature and the solvent evaporated. The residue was triturated with boiling water then cooled to room temperature. The resulting solid was collected and washed with water to give the desired product (69 mg, 80%) as a light yellow solid. $^1$H NMR (400 MHz, DMSO-d$_6$) δ 2.365 (q, J=6 Hz, 2H), 3.568 (q, J=6 Hz, 2H), 4.681 (t, J=6 Hz, 1H), 6.186 (d of t, J=7 Hz, 16 Hz, 1H), 6.786 (d, J=16 Hz, 1H), 6.922 (d, J=8 Hz, 1H), 7.022 (br. s, 1H), 7.088 (d, J=8 Hz, 1H), 7.468 (t, J=8 Hz, 1H), 8.388 (br. s, 1H), 10.935 (s, 1H). MS 268 (MH$^+$).

Example 273

(E)-5-(4-(tetrahydro-2H-pyran-2-yloxy)but-1-enyl)-1H-benzo[c][1,2,6]thiadiazin-4-amine-2,2-dioxide

695

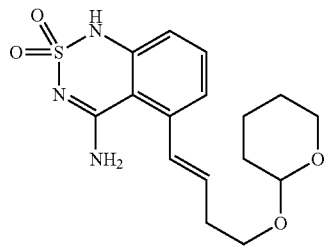

Prepared as in Example 270 from (E)-2-amino-6-(4-(tetrahydro-2H-pyran-2-yloxy)but-1-enyl)benzonitrile (example 273a) and sulfamoyl chloride in 61% yield as an off-white solid. $^1$H NMR (400 MHz, DMSO-d$_6$) δ 1.459 (m, 4H), 1.610 (m, 2H), 1.700 (m, 2H), 2.479 (q, J=6 Hz, 2H), 3.428 (m, 1H), 3.528 (m, 1H), 3.765 (m, 2H), 4.579 (m, 1H), 6.200 (d of t, J=7 Hz, 16 Hz, 1H), 6.823 (d, J=16 Hz, 1H), 6.867 (br. s, 1H), 6.931 (d, J=8 Hz, 1H), 7.087 (d, J=8 Hz, 1H), 7.472 (t, J=8 Hz, 1H), 8.401 (br. s, 1H), 10.945 (s, 1H). MS 352 (MH$^+$).

Example 273a (E)-2-amino-6-(4-(tetrahydro-2H-pyran-2-yloxy)but-1-enyl)benzonitrile Prepared as in Example 270a from (E)-4,4,5,5-tetramethyl-2-(4-(tetrahydro-2H-pyran-2-yloxy)but-1-enyl)-1,3,2-dioxaborolane (Example 273b) and 2-amino-6-bromobenzonitrile in 47% yield as a yellow gum. $^1$H NMR (400 MHz, CDCl$_3$) δ 1.570 (m, 4H), 1.727 (m, 2H), 1.837 (m, 2H), 2.565 (q, J=6 Hz, 2H), 3.541 (m, 2H), 3.879 (m, 2H), 4.387 (br. s, 2H), 4.635 (m, 1H), 6.423 (d of t, J=7 Hz, 16 Hz, 1H), 6.586 (d, J=8 Hz, 1H), 6.710 (d, J=16 Hz, 1H), 6.905 (d, J=8 Hz, 1H), 7.237 (t, J=8 Hz, 1H).

Example 273b (E)-4,4,5,5-tetramethyl-2-(4-(tetrahydro-2H-pyran-2-yloxy)but-1-enyl)-1,3,2-dioxaborolane Neat 2-(but-3-ynyloxy)tetrahydro-2H-pyran (12.8 mmol, 2.0 mL) was treated with pinacolborane (19.1 mmol, 2.78 mL) at 60° C. under nitrogen. After 2 hours, another portion of pinacolborane (12.8 mmol, 1.86 mL) was added and continued heating at 60° C. After 8 hours, the reaction mixture was diluted with hexanes (30 mL) and treated dropwise with water (1 mL), stirring until gas evolution ceased. The layers were separated, the water layer extracted with hexanes (2×5 mL), the combined organic layers washed with brine (5 mL), dried over magnesium sulfate, filtered, and evaporated. The crude product was purified on silica gel (EtOAc/hexanes 10% to 30%) to give the product (1.73 g, 48% yield) as an oil. $^1$H NMR (400 MHz, CDCl$_3$) δ 1.262 (s, 3H), 1.531 (m, 2H), 1.699 (m, 1H), 1.812 (m, 1H), 2.469 (d of q, J=2 Hz, 7 Hz, 2H), 3.495 (m, 1H), 3.832 (m, 2H), 4.593 (d of d, J=3 Hz, 4 Hz, 1H), 5.523 (d of t, J=2 Hz, 18 Hz, 1H), 6.634 (d of t, J=7 Hz, 18 Hz, 1H).

Example 274

8-(4-amino-2,2-dioxo-1H-benzo[c][1,6]thiadiazin-5-yloxy)octan-1-ol

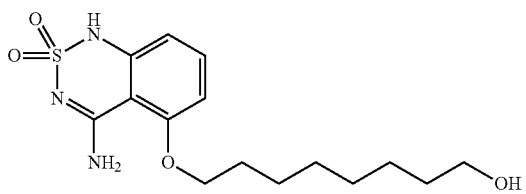

696

To a solution of 8-(3-amino-2-cyanophenoxy)octyl acetate (746 µmol, 227 mg) in DMA (3 mL) was added sulfamoyl chloride (1.492 mmol, 172 mg) and pyridine (4.476 mmol, 362 µL). The reaction mixture was stirred at room temperature until completion, then quenched with sat. NaHCO$_3$ (15 mL) and solid NaCl added. The precipate was collected and washed with water. The wet precipitate was suspended in EtOH (15 mL) and treated with NaOH (8.952 mmol, 1N, 8.95 mL). The reaction mixture was refluxed until completion then cooled to room temperature. Most of the EtOH and water were removed in vacuo, then the reaction mixture was dissolved in water (15 mL), extracted with ether (3×5 mL), filtered through a 0.45 PTFE frit, then acidified with 10% citric acid/water solution to pH 4-5. The precipitate was filtered off, washed with water and dried to give the desired product 146 mg (57.3%) as an off-white solid. $^1$H NMR (400 MHz, DMSO-d$_6$) δ 1.265 (m, 6H), 1.380 (m, 4H), 1.785 (pentet, J=7 Hz, 2H), 3.348 (q, J=6 Hz, 2H), 4.303 (t, J=5 Hz, 2H), 6.580 (d, J=8 Hz, 1H), 6.724 (d, J=8 Hz, 1H), 7.428 (t, J=8 Hz, 1H), 7.796 (br. s, 1H), 8.329 (br. s, 1H), 10.922 (s, 1H). MS 342 (MH$^+$).

Example 274a 8-(3-amino-2-cyanophenoxy)octyl acetate

A solution of 8-(2-cyano-3-nitrophenoxy)octyl acetate (802 µmol, 268 mg) (Example 274c) in EtOH (15 mL) was hydrogenated in an H-cube apparatus's using 10% Pd/C as catalyst. The solution was evaporated to give 8-(3-amino-2-cyanophenoxy)octyl acetate (244 mg, 244 mg). MS 305 (MH$^+$)

Example 274b 8-(2-cyano-3-nitrophenoxy)octyl acetate 2-(8-hydroxyoctyloxy)-6-nitrobenzonitrile (804 µmol, 235 mg) (Example 274c) was dissolved in dry DCM (10 mL), cooled to 0° C., and treated successively with pyridine (3.216 mmol, 260 µL) and acetyl chloride (1.608 mmol, 114 µL). The reaction mixture was stirred and allowed to warm slowly to room temperature. When the reaction was complete, the volatiles were removed in vacuo and the crude product purified on silica gel (10% to 50% EtOAc in hexanes) to give the desired product (268 mg, 100%). MS 335 (MH$^+$).

Example 274c 2-(8-hydroxyoctyloxy)-6-nitrobenzonitrile

To a solution of 1,8-octanediol (3.87 mmol, 566 mg) in THF (dry, 10 mL) was added 2,6-dinitrobenzonitrile (1.29 mmol, 250 mg) and DBU (1.30 mmol, 194 µL). The reaction mixture was stirred for 24 hours at room temperature an evaporated. The oily residue was triturated with 10% citric acid/water and solid NaCl added. The precipitate was collected, washed with water, dried in vacuo and purified on silica gel (40% to 100% EtOAc in hexanes) to give the desired product (235 mg, 62.3%) as a pinkish solid. MS 293 (MH$^+$).

Example 275

7-(4-amino-2,2-dioxo-1H-benzo[c][1,2,6]thiadiazin-5-yloxy)heptan-1-ol

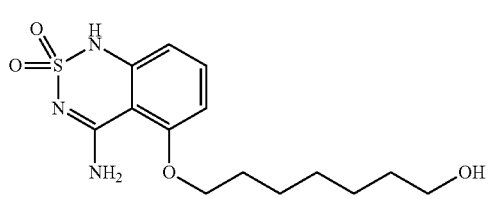

697

Prepared as in Example 274 from 7-(3-amino-2-cyanophenoxy)heptyl acetate (Example 275a) and sulfamoyl chloride in 79.4% yield. ¹H NMR (400 MHz, DMSO-d₆) δ 1.320 (m, 4H), 1.405 (m, 4H), 1.811 (pentet, J=7 Hz, 2H), 3.378 (q, J=6 Hz, 2H), 4.154 (t, J=6 Hz, 2H), 4.331 (t, J=5 Hz, 1H), 6.605 (d, J=8 Hz, 1H), 6.752 (d, J=8 Hz, 1H), 7.454 (t, J=8 Hz, 1H), 7.823 (br. s, 1H), 8.358 (br. s, 1H), 10.946 (s, 1H). MS 328 (MH⁺).

Example 275a 7-(3-amino-2-cyanophenoxy)heptyl acetate

Prepared as in Example 274a from 7-(2-cyano-3-nitrophenoxy)heptyl acetate
(Example 275b) in 89% yield. MS 291 (MH⁺)

Example 275b 7-(2-cyano-3-nitrophenoxy)heptyl acetate

Prepared as in Example 274b from 2-(7-hydroxyheptyloxy)-6-nitrobenzonitrile (Example 275c) in 100% yield. MS 321 (MH⁺).

Example 275c 2-(7-hydroxyheptyloxy)-6-nitrobenzonitrile

Prepared as in Example 274c (except DBU was replaced with KOtBu) from 1,7-heptanediol in 65% yield. MS 279 (MH⁺).

Example 276

9-(4-amino-2,2-dioxo-1H-benzo[c][1,2,6]thiadiazin-5-yloxy)nonan-1-ol

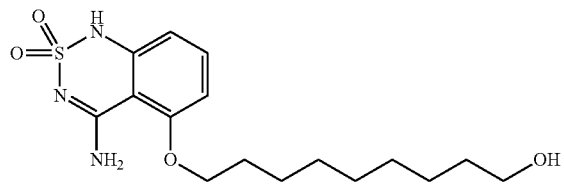

698

Prepared as in Example 274 from 9-(3-amino-2-cyanophenoxy)nonyl acetate (Example 276a) and sulfamoyl chloride in 62.3% yield. ¹H NMR (400 MHz, DMSO-d₆) δ 1.250 (m, 8H), 1.381 (m, 4H), 1.791 (pentet, J=7 Hz, 2H), 3349 (q, J=6 Hz, 2H), 4.135 (t, J=6 Hz, 2H), 4.301 (t, J=5 Hz, 1H), 6.585 (d, J=8 Hz, 1H), 6.728 (d, J=8 Hz, 1H), 7.434 (t, J=8 Hz, 1H), 7.798 (br. s, 1H), 8.329 (br. s, 1H). 10.924 (s, 1H). MS 356 (MH⁺).

Example 276a 9-(3-amino-2-cyanophenoxy)nonyl acetate

Prepared as in Example 274a from 9-(2-cyano-3-nitrophenoxy)nonyl acetate
(Example 276b) in 99.3% yield. MS 319 (MH⁺)

Example 276b 9-(2-cyano-3-nitrophenoxy)nonyl acetate

Prepared as in Example 274b from 2-(9-hydroxynonyloxy)-6-nitrobenzonitrile (Example 276c) in 100% yield. MS 349 (MH⁺).

Example 276c 2-(9-hydroxynonyloxy)-6-nitrobenzonitrile

Prepared as in Example 274c (except DBU was replaced with 1,1,3,3-tetramethylguanidine) from 1,9-nonanediol and 2,6-dinitrobenzonitrile in 30.7% yield. MS 307 (MH⁺).

Example 277

N-(6-(4-amino-2,2-dioxo-1H-benzo[c][,6]thiadiazin-5-yloxy)hexyl)-2-hydroxy-2-methylpropanamide

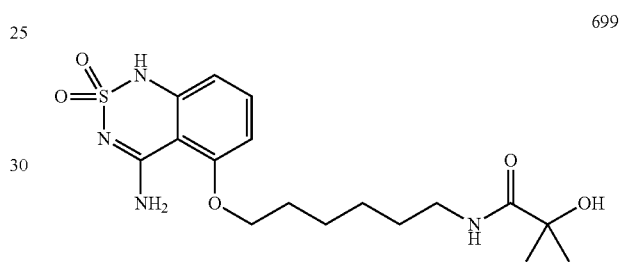

699

Prepared as in Example 274 from 1-(6-(3-amino-2-cyanophenoxy)hexylamino)-2-methyl-1-oxopropan-2-yl acetate (Example 277a) in 65.5% yield. ¹H NMR (400 MHz, DMSO-d₆) δ 1.201 (s, 6H), 1.289 (m, 2H), 1.399 (m, 4H), 1.790 (pentet, J=7 Hz, 2H), 3.036 (q, J=6 Hz, 2H), 4.130 (t, J=6 Hz, 2H), 5.272 (s, 1H), 6.587 (d, J=8 Hz, 1H), 6.728 (d, J=8 Hz, 1H), 7.436 (t, J=8 Hz, 1H), 7.594 (br. t, 1H), 7.804 (br. s, 1H), 8.326 (br. s, 1H), 10.924 (s, 1H). MS 399 (MH⁺).

Example 277a 1-(6-(3-amino-2-cyanophenoxy)hexylamino)-2-methyl-1-oxopropan-2-yl acetate Prepared as in Example 274a from 1-(6-(2-cyano-3-nitrophenoxy)hexylamino)-2-methyl-1-oxopropan-2-yl acetate (Example 274b) in 94.4% yield. MS 362 (MH⁺)

Example 277b 1-(6-(2-cyano-3-nitrophenoxy)hexylamino)-2-methyl-1-oxopropan-2-yl acetate To a solution of tert-butyl 6-(2-cyano-3-nitrophenoxy) hexylcarbamate (333 μmol, 121 mg) (Example 277c) in dioxane (2 mL) was added con. HCl (1 mL). After 15 minutes, the solution was concentrated in vacuo and dried on high vacuum. The crude HCl salt was suspended in DCM (dry, 10 mL) and treated with pyridine (2.664 mmol, 215 μL) and 1-chloro-2-methyl-1-oxopropan-2-yl acetate (1.332 mmol, 193 μL). The reaction mixture was refluxed under a nitrogen atmosphere until clear (6 h), then cooled to room temperature and the volatiles removed in vacuo. The residue was purified on silica gel (40% to 100% EtOAc in hexanes) to give the product (117 mg, 90%) as a light yellow heavy oil. MS 392 (MH⁺).

Example 277c tert-butyl 6-(2-cyano-3-nitrophenoxy)hexylcarbamate

Prepared as in Example 215c from tert-butyl 6-hydroxyhexylcarbamate in 53.8% yield as light yellow solid. MS 364 (MH⁺).

Example 278

1-(6-(4-amino-2,2-dioxo-1H-benzo[c][1,2,6]thiadiazin-5-yloxy)hexyl)urea

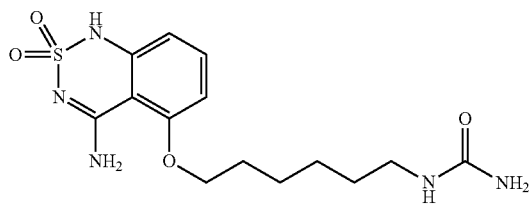

A solution of 1-(6-(4-amino-2,2-dioxo-1H-benzo[c][1,2,6]thiadiazin-5-yloxy)hexyl)-3-(4-methoxybenzyl)urea (122 μmol, 58 mg) (Example 279) in DCM (2.5 mL) was treated with TFA (2.5 mL). The reaction mixture was stirred at room temperature for 4 hours, then the volatiles were removed under a stream of nitrogen. The oily residue was triturated with ether, the precipitate collected, washed with ether, then dissolved in MeOH and evaporated to gives the desired product (44 mg, 100% yield). ¹H NMR (400 MHz, DMSO-d₆) δ 1.364 (m, 6H), 1.812 (pentet, J=7 Hz, 2H), 2.943 (br t, 2H), 4.154 (d, J=7 Hz, 2H), 4.131 (t, J=7 Hz, 2H), 5.349 (br. s, 2H), 5.894 (br. s, 1H), 6.607 (d, J=8 Hz, 1H), 6.752 (d, J=8 Hz, 1H), 7.456 (t, J=8 Hz, 1H), 7.824 (br. s, 1H), 8.351 (br. s, 1H), 10.945 (s, 1H). MS 356 (MH⁺).

Example 279

1-(6-(4-amino-2,2-dioxo-1H-benzo[c][,6]thiadiazin-5-yloxy)hexyl)-3-(4-methoxybenzyl)urea

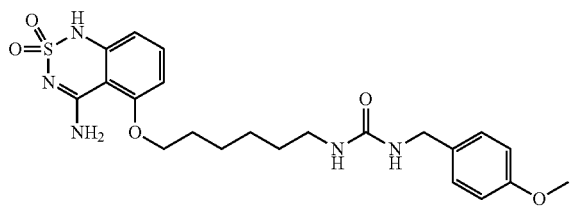

To a suspension of 6-(4-amino-2,2-dioxo-1H-benzo[c][1,2,6]thiadiazin-5-yloxy)hexan-1-aminium chloride (166 mmol, 52 mg) (Example 280) in dry DCM (6 mL) was successively added Et₃N (332 μmol, 46 μL) and 1-(isocyanatomethyl)-4-methoxybenzene (183 μmol, 26 μL). The reaction was stirred for 48 hours at room temperature then concentrated in vacuo. The residue was washed with water, dried, then purified on silica gel (20% to 100% EtOAc in hexanes) to give the desired product (64 mg, 81.0% yield). ¹H NMR (400 MHz, DMSO-d₆) δ 1.296 (m, 2H), 1.371 (m, 4H), 1.791 (pentet, J=8 Hz, 2H), 2.980 (q, J=6 Hz, 2H), 3.695 (s, 3H), 4.086 (d, J=6 Hz, 2H), 4.131 (t, J=6 Hz, 2H), 5.836 (br. t, J=5 Hz, 1H), 6.141 (br. t, J=6 Hz, 1H), 6.585 (d, J=8 Hz, 1H), 6.727 (d, J=8 Hz, 1H), 6.840 (d, J=9 Hz, 2H), 7.137 (d, J=9 Hz, 2H), 7.433 (t, J=8 Hz, 1H), 7.803 (br. s, 1H), 8.321 (br. s, 1H), 10.926 (s, 1H). MS 476 (MH⁺).

Example 280

6-(4-amino-2,2-dioxo-1H-benzo[c][1,2,6]thiadiazin-5-yloxy)hexan-1-aminium chloride

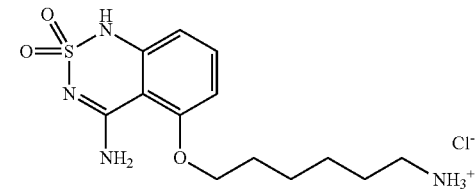

To a solution of tert-butyl 6-(4-amino-2,2-dioxo-1H-benzo[c][1,2,6]thiadiazin-5-yloxy)hexylcarbamate (118 mg, 286 umol) (Example 281) in dioxane (2 mL) was added con. HCl (1 mL) and the solution stirred at room temperature for 15 minutes. The solvents were removed in vacuo and the residue triturated with hot ethanol. After cooling to room temperature, the precipitated was collected, washed with hot ethanol, and dried in vacuo to give the desired product 56 mg (62.9%) as an off-white powder. ¹H NMR (400 MHz, DMSO-d₆) δ 1.367 (m, 4H), 1.529 (pentet, J=7 Hz, 2H), 1.795 (pentet, J=7 Hz, 2H), 2.741 (br m, 2H), 4.144 (t, J=7 Hz, 2H), 6.596 (d, J=8 Hz, 1H), 6.733 (d, J=8 Hz, 1H), 7.440 (t, J=8 Hz, 1H), 7.725 (br. s, 3H), 7.795 (br. s, 1H), 8.350 (br. s, 1H), 10.954 (s, 1H). MS 313 (MH⁺).

Example 281 tert-butyl 6-(4-amino-2,2-dioxo-1H-benzo[c][1,2,6]thiadiazin-5-yloxy)hexylcarbamate

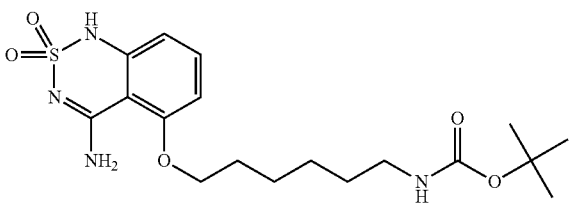

Prepared as in Example 274 from tert-butyl 6-(3-amino-2-cyanophenoxy)hexylcarbamate (Example 281a) and sulfamoyl chloride in 59.5% yield. ¹H NMR (400 MHz, DMSO-d₆) δ 1.274 (m, 2H), 1.339 (s, 9H), 1.361 (m, 4H), 1.779 (pentet, J=7 Hz, 2H), 2.878 (q, J=6 Hz, 2H), 4.122 (t, J=6 Hz, 2H), 6.580 (d, J=8 Hz, 1H), 6.722 (d, J=8 Hz, 1H), 6.75 (br t, J=6 Hz, 1H), 7.428 (t, J=8 Hz, 1H), 7.798 (br. s, 1H), 8.323 (br. s, 1H), 10.921 (s, 1H). MS 413 (MH⁺).

Example 281a tert-butyl 6-(3-amino-2-cyanophenoxy)hexylcarbamate

Prepared as in Example 274a from tert-butyl 6-(2-cyano-3-nitrophenoxy)hexylcarbamate (example 277c) in quantitative yield. MS 334 (MH$^+$).

Example 282

5-(2-(1H-pyrrol-1-yl)ethoxy)-1H-benzo[c][1,2,6]thiadiazin-4-amine-2,2-dioxide

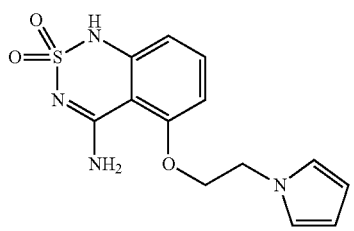

Prepared as in Example 274 from 2-(2-(1H-pyrrol-1-yl)ethoxy)-6-aminobenzonitrile (Example 282a) and sulfamoyl chloride in 66.6% yield. $^1$H NMR (400 MHz, DMSO-d$_6$) δ 4.392 (m, 4H), 5.992 (t, J=2 Hz, 2H), 6.595 (d, J=8 Hz, 1H), 6.693 (d, J=8 Hz, 1H), 6.816 (t, J=2 Hz, 2H), 7.428 (t, J=8 Hz, 1H), 7.482 (br. s, 1H), 8.288 (br. s, 1H), 10.930 (s, 1H). MS 307 (MH$^+$).

Example 282a 2-(2-(1H-pyrrol-1-yl)ethoxy)-6-aminobenzonitrile

Prepared as in Example 274a from 2-(2-(1H-pyrrol-1-yl)ethoxy)-6-nitrobenzonitrile (Example 282b) in 85.2% yield. MS 228 (MH$^+$).

Example 282b 2-(2-(1H-pyrrol-1-yl)ethoxy)-6-nitrobenzonitrile

Prepared as in Example 166d from 2-(1H-pyrrol-1-yl)ethanol and 2,6-dinitrobenzonitrile, in 42.5% yield. MS 258 (MH$^+$).

Example 283

5-(2-(1H-pyrazol-1-yl)ethoxy)-1H-benzo[c][1,2,6]thiadiazin-4-amine-2,2-dioxide

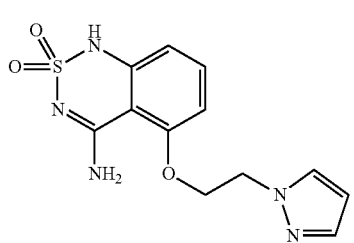

Prepared as in Example 274 from 2-(2-(1H-pyrazol-1-yl)ethoxy)-6-aminobenzonitrile (Example 283a) and sulfamoyl chloride in 54.5% yield. $^1$H NMR (400 MHz, DMSO-d$_6$) δ 4.406 (t, J=5 Hz, 2H), 4.630 (t, J=5 Hz, 2H), 6.266 (t, J=2 Hz, 1H), 6.593 (d, J=8 Hz, 1H), 6.689 (d, J=8 Hz, 1H), 7.445 (br s, 1H), 7.425 (t, J=8 Hz, 1H), 7.805 (d, J=2 Hz, 1H), 8.224 (br. s, 1H), 8.301 (br. s, 1H), 10.904 (s, 1H). MS 308 (MH$^+$).

Example 283a 2-(2-(1H-pyrazol-1-yl)ethoxy)-6-aminobenzonitrile

Prepared as in Example 274a from 2-(2-(1H-pyrazol-1-yl)ethoxy)-6-nitrobenzonitrile (Example 283b) in 46.2% yield. MS 229 (MH$^+$).

Example 283b 2-(2-(1H-pyrazol-1-yl)ethoxy)-6-nitrobenzonitrile

Prepared as in Example 215c from 2-(1H-pyrazol-1-yl)ethanol and 2,6-dinitrobenzonitrile in 89.2% yield. MS 259 (MH$^+$).

Example 284

5-(2-(3,5-dimethyl-1H-pyrazol-1-yl)ethoxy)-1H-benzo[c][1,2,6]thiadiazin-4-amine-2,2-dioxide

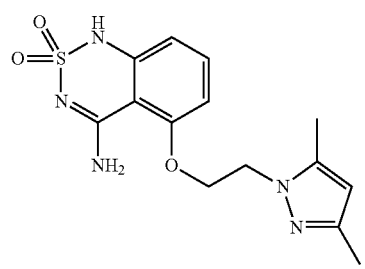

Prepared as in Example 274 from 2-(2-(3,5-dimethyl-1H-pyrazol-1-yl)ethoxy)-6-aminobenzonitrile (Example 284a) and sulfamoyl chloride in 18.2% yield. $^1$H NMR (400 MHz, DMSO-d$_6$) δ 2.066 (s, 3H), 2.215 (s, 3H), 4.313 (t, J=4 Hz, 2H), 4.397 (t, J=4 Hz, 2H), 5.801 (s, 1H), 6.584 (d, J=8 Hz, 1H), 6.645 (d, J=8 Hz, 1H), 7.418 (t, J=8 Hz, 1H), 8.395 (br. s, 1H), 8.677 (br. s, 1H), 10.885 (s, 1H). MS 336 (MH$^+$).

Example 284a 2-(2-(3,5-dimethyl-1H-pyrazol-1-yl)ethoxy)-6-aminobenzonitrile

Prepared as in Example 274a from 2-(2-(3,5-dimethyl-1H-pyrazol-1-yl)ethoxy)-6-nitrobenzonitrile (example 284b) in 69.3% yield. MS 257 (MH$^+$).

Example 284b 2-(2-(3,5-dimethyl-1H-pyrazol-1-yl)ethoxy)-6-nitrobenzonitrile

Prepared as in Example 215c from 2-(3,5-dimethyl-1H-pyrazol-1-yl)ethanol and 2,6-dinitrobenzonitrile in 90.7% yield. MS 287 (MH$^+$).

Experiment 4

Biological Assay

An HEK293 cell line derivative (Chandrashekar et al., Cell 100, 703-711, 2000) which stably expresses Gα15 and hT1R2/hT1R3 (Li et al., Proc Natl Acad Sci USA 99, 4692-4696, 2002) (see also, International Publication No. WO 03/001876) was used in biological assays in association with identifying compounds with sweet taste enhancing properties.

Compounds were initially selected based on their activity on the hT1R2/hT1R3-HEK293-Gα15 cell line Li et al., supra. Activity was determined using an automated fluorometric imaging assay on a FLIPR instrument (Fluorometric Intensity Plate Reader, Molecular Devices, Sunnyvale, Calif.) (designated FLIPR assay). Cells from one clone (designated clone S-9) were seeded into 384-well plates (at approximately 50,000 cells per well) in a medium containing DMEM Low Glucose (Invitrogen, Carlsbad, Calif.), 10% dialyzed fetal bovine serum (Invitrogen, Carlsbad, Calif.), 100 Units/ml Penicillin G, and 100 µg/ml Streptomycin (Invitrogen, Carlsbad, Calif.) (Li et al., 2002) (see also, International Publication No. WO 03/001876).

S-9 cells were grown for 24 hours at 37° C. S-9 cells were then loaded with the calcium dye Fluo-3AM (Molecular Probes, Eugene, Oreg.), 4 µM in a phosphate buffered saline (D-PBS) (Invitrogen, Carlsbad, Calif.), for 1 hour at room temperature. After replacement with 25 µl D-PBS, stimulation was performed in the FLIPR instrument and at room temperature by the addition of 25 µl D-PBS supplemented with compounds at concentrations corresponding to three times the desired final level (Stimulation 1).

Cells were incubated with the compounds for 7.5 minutes and then another stimulation was performed in the FLIPR instrument by the addition of 25 µl of D-PBS supplemented with a sub-optimal concentration of sweeteners (producing about 5% to 20% receptor activity) (Stimulation 2).

Alternatively after replacement with 25 µl D-PBS per well, stimulation was performed in the FLIPR instrument at room temperature by addition of 25 µl D-PBS supplemented with different stimuli.

Typical sweeteners used include, but are not limited to D-Glucose, D-Fructose, Sucralose, Aspartame and Sucrose. Receptor activity was then quantified by determining the maximal fluorescence increases (using a 480 nm excitation and 535 nm emission) after normalization to basal fluorescence intensity measured before stimulation. Compounds producing an increase in sweetener-mediated receptor activity were chosen for further characterization and quantification of potential enhancement properties.

In this follow assay, a fixed concentration of compounds was added in duplicates to 10 consecutive columns (20 wells total) during stimulation 1. Typical compound concentrations tested were 300 µM, 100 µM, 50 µM, 30 µM, 10 µM, 3 µM and 1 µM, 0.3 µM, 0.1 µM, or 0.03 µM. After the 7.5 minute incubation period, increasing concentrations of sweetener (to generate a dose-response curve) was presented in the same wells, in duplicates, during stimulation 2. The relative efficacy of compounds at enhancing the receptor was determined by the calculating the magnitude of a shift in the $EC_{50}$ for the sweetener. Enhancement was defined as a ratio ($EC_{50}R$) corresponding to the $EC_{50}$ of sweeteners, determined in the absence of the test compound, divided by the $EC_{50}$ of the sweetener, determined in the presence of the test compound. In some embodiments, compounds have an $EC_{50}R$ between about 1 (e.g., >1) and about 1000. In other embodiments, compounds have an $EC_{50}R$ between about 1.25 and about 500. In still other embodiments, compounds have an $EC_{50}R$ between about 1.50 and about 100. In yet other embodiments, compounds have an $EC_{50}R$ between about 1 (e.g., >1) and about 50.

In still other embodiment, compounds at about 50 µM have an $EC_{50}R$ between about 1 (e.g., >1) and about 1000, between about 1.25 and about 500, between about 1.50 and about 100, or between about 1 (e.g., >1) and about 50. Assay results for compounds are illustrated in Table A below.

In one illustrative example, the pre-incubated sucralose $EC_{50}R$ at 50 µM for one group of specific compounds of the present invention generally ranges from 0.73 to 5.20, while the co-stimulation sucralose $EC_{50}R$ at 50 µM for the same group of compounds generally ranges from 0.72 to 4.46. In another illustrative example, the co-stimulated sucrose $EC_{50}R$ at 50 µM for one group of specific compounds of the present invention generally ranges from 1.30 to 4.35, the co-stimulation sucralose $EC_{50}R$ at 50 µM for the same group of compounds generally ranges from 1.73 to 24.09, and the co-stimulation fructose $EC_{50}R$ at 50 µM for the same group of compounds generally ranges from 0.81 to 4.46. In another illustrative example, the co-stimulated sucrose $EC_{50}R$ at 50 µM for one group of specific compounds of the present invention generally ranges from 1.05 to 2.44, the co-stimulation sucralose $EC_{50}R$ at 50 µM for the same group of compounds generally ranges from 1.57 to 11.63, and the co-stimulation fructose $EC_{50}R$ at 50 µM for the same group of compounds generally ranges from 0.99 to 1.78. In another illustrative example, the co-stimulated sucrose $EC_{50}R$ at 50 µM for one group of specific compounds of the present invention generally ranges from 1.27 to 116.56, the co-stimulation sucralose $EC_{50}R$ at 50 µM for the same group of compounds generally ranges from 1.48 to 157.63, and the co-stimulation fructose $EC_{50}R$ at 50 µM for the same group of compounds generally ranges from 0.68 to 9.56. In another illustrative example, the co-stimulated sucrose $EC_{50}R$ at 50 µM for one group of specific compounds of the present invention generally ranges from 0.88 to 36.66, the co-stimulation sucralose $EC_{50}R$ at 50 µM for the same group of compounds generally ranges from 1.07 to 101.15, and the co-stimulation fructose $EC_{50}R$ at 50 µM for the same group of compounds generally ranges from 0.71 to 7.09. In another illustrative example, the co-stimulated sucrose $EC_{50}R$ at 50 µM for one group of specific compounds of the present invention generally ranges from 1.39 to 17.17, the co-stimulation sucralose $EC_{50}R$ at 50 µM for the same group of compounds generally ranges from 3.80 to 49.89, and the co-stimulation fructose $EC_{50}R$ at 50 µM for the same group of compounds generally ranges from 0.92 to 6.07. In another illustrative example, the co-stimulated sucrose $EC_{50}R$ at 50 µM for one group of specific compounds of the present invention generally ranges from 1.30 to 56.27, the co-stimulation sucralose $EC_{50}R$ at 50 µM for the same group of compounds generally ranges from 1.26 to 204.98, and the co-stimulation fructose $EC_{50}R$ at 50 µM for the same group of compounds generally ranges from 1.14 to 8.37.

Experiment 5

Sweet Flavor and Sweet Flavor Enhancement Measurement Using Human Panelists Conducting a Scaling Test Test samples containing experimental compounds were compared to a dose-response curve for perceived sweetness intensity of sweeteners (such as, for example, sucralose, sucrose, fructose and other sweeteners) concentrations to determine equivalent sweetness intensity.

A group of eight or more panelists tasted solutions including sweeteners at various concentrations, as well as the experimental compound both with and without added sweetener. Panelists then rated sweetness intensity of all samples on a structured horizontal line scale, anchored from 0 to 15, where 0 equals no sweetness and 15 equals equivalent sweetness to a 15% sucrose sample. Scores for sweetness intensity were averaged across panelists. Then using the average scores and/or equation of the line for the sweetener dose-response curve, equivalent sweetness concentrations were determined for the samples containing experimental compounds.

Subjects had been previously familiarized with the key attribute taste and were trained to use the 0 to 15 point line scale. Subjects refrained from eating or drinking (except water) for at least 1 hour prior to the test. Subjects ate a cracker and rinsed with water several times to clean the mouth.

Sweetener solutions are provided at a wide range of concentrations such as 100 ppm, 200 ppm, 300 ppm, 400 ppm, and 500 ppm for sucralose, or between 0% and 12% for sucrose or fructose, in order to create a dose-response curve. Samples containing experimental compound were prepared both alone and in a 100 ppm sucralose solution or a 6% sucrose or fructose solution. All samples were made up in low sodium buffer pH 7.1. In order to aid dispersion, solutions can be made up in 0.1% ethanol.

The solutions were dispensed in 20 ml volumes into 1 oz. sample cups and served to the subjects at room temperature. All samples were presented in randomized counterbalanced order to reduce response bias. Further, two sessions of testing may be used to check panel precision.

Subjects tasted each sample individually and rate sweetness intensity on the line scale prior to tasting the next sample. All samples were expectorated. Subjects may retaste the samples but can only use the volume of sample given. Subjects must rinse with water between samples. Eating an unsalted cracker between samples may be required depending on the samples tasted.

The scores for each sample were averaged across subjects and standard error was calculated. The dose-response curve was plotted graphically, and this may be used to ensure the panel is rating accurately; i.e., increasing the concentration of sucralose should correspond to increased average scores for sweetness. A 2-way ANOVA (factors being samples and panelists) and multiple comparison tests (such as Tukey's Honestly Significant Difference test) can be used to determine differences among samples and/or panelists. A 3-way ANOVA, with sessions as the third factor, can be used to determine if there is any difference in the ratings between sessions.

The compounds tested in this Experiment, namely, compounds C1 to C21, are representative compounds of the present invention including compounds of structural Formula (I) and its subgeneric formulas.

The results of human taste tests with a compound C1 are found below. Table 1 indicates that 100 μM compound C1 in 100 ppm sucralose has sweetness equivalent to 200 ppm sucralose. Table 2 indicates that 100 μM compound C1 alone has no sweetness, and therefore can be defined as a true sweet enhancer.

TABLE 1

| Sample | Average | Standard Error | Tukey's HSD Significance (5%) |
|---|---|---|---|
| 100 ppm Sucralose | 6.3 | 0.3 | A |
| 100 ppm Sucralose + 100 μM C1 | 10.2 | 0.5 | B |
| 200 ppm Sucralose | 10.4 | 0.5 | B |
| 300 ppm Sucralose | 11.5 | 0.4 | Bc |
| 400 ppm Sucralose | 12.3 | 0.4 | C |

Average sweetness scores for various sucralose samples, including 100 ppm sucralose with 100 μM compound C1, n = 32 (16 Panelists × 2 replicates).
Tukey's value = 1.409 (α = 0.05).

TABLE 2

| Sample | Average | Standard Error | Tukey's HSD Significance (5%) |
|---|---|---|---|
| Low Sodium Buffer (contains no sweeteners) | 0.1 | 0.1 | A |
| 100 μM 7 | 0.1 | 0.1 | A |

Average sweetness scores for 100 μM compound C1 and low sodium buffer, n = 15 (15 Panelists × 1 rep).
Tukey's value = 0.186 (α = 0.05).

The results of human taste tests with compound C2 are found below. Table 3 indicates that 100 μM compound in 100 ppm sucralose has sweetness equivalent to about 600 ppm sucralose. Table 4 shows a dose response curve of compound C2 with 100 ppm sucralose which shows that the sweetness of sucralose is significantly enhanced by addition of increasing amounts of compound C2. Table 5 indicates that 100 μM compound C2 alone has little or no sweetness, and therefore can be defined as a true sweet enhancer.

TABLE 3

| Treatment | Average | SD | St Er | Tukey (5%) | Tukey (10%) |
|---|---|---|---|---|---|
| 100 ppm Sucralose | 7.4 | 1.7 | 0.5 | a | a |
| 200 ppm Sucralose | 10.4 | 1.9 | 0.6 | b | b |
| 300 ppm Sucralose | 10.5 | 2.8 | 0.8 | b | b |
| 400 ppm Sucralose | 11.2 | 2.4 | 0.7 | bc | bc |
| 600 ppm Sucralose | 13.0 | 1.4 | 0.4 | c | c |
| 100 μM C2 + 100 ppm Sucralose | 13.3 | 1.6 | 0.5 | c | c |

Average sweetness scores, n = 12 (12 Panelists × 1 rep).
Tukey's value = 2.449 (α = 0.05), 2.209 (α = 0.10).

TABLE 4

| Treatment | Average | SD | St Er | Tukey (5%) | Tukey (10%) |
|---|---|---|---|---|---|
| 100 ppm sucralose | 6.3 | 1.5 | 0.3 | a | a |
| 100 ppm sucralose + 3.12 μM C2 | 7.4 | 1.7 | 0.3 | ab | ab |
| 100 ppm sucralose + 6.25 μM C2 | 8.4 | 1.8 | 0.4 | bc | bc |
| 100 ppm sucralose + 12.5 μM C2 | 9.1 | 1.9 | 0.4 | cd | cd |
| 200 ppm sucralose | 9.5 | 2.0 | 0.4 | cd | cd |
| 300 ppm sucralose | 10.3 | 2.7 | 0.5 | d | d |
| 100 ppm sucralose + 25 μM C2 | 10.3 | 1.6 | 0.3 | d | d |
| 400 ppm sucralose | 12.1 | 1.9 | 0.4 | e | e |
| 100 ppm sucralose + 50 μM C2 | 12.3 | 1.5 | 0.3 | e | e |

Average sweetness scores, n = 26 (14 Panelists × 1 rep; 12 panelists × 1 rep).
Tukey's value = 1.584 (α = 0.05), 1.452 (α = 0.10).

TABLE 5

| Treatment | Average | SD | St Er | Tukey (5%) | Tukey (10%) |
|---|---|---|---|---|---|
| 0% Sucrose | 0.0 | 0.0 | 0.0 | a | a |
| 100 μM C2 in LSB | 0.2 | 0.3 | 0.1 | a | a |
| 2% Sucrose | 2.4 | 1.0 | 0.3 | b | b |

Average sweetness scores, n = 12 (12 Panelists × 1 rep).
Tukey's value = 0.809 (α = 0.05), 0.723 (α = 0.10).

The results of human taste tests with compound C3 are found below. Table 6 indicates that 100 μM compound in 100 ppm sucralose has sweetness equivalent to about between 200 and 300 ppm sucralose. Table 7 indicates that 100 μM compound C3 alone has no sweetness, and therefore can be defined as a true sweet enhancer.

TABLE 6

| Treatment | Average | SD | St Er | Tukey (5%) | Tukey (10%) |
|---|---|---|---|---|---|
| 100 ppm Sucralose | 6.5 | 1.3 | 0.4 | a | a |
| 200 ppm Sucralose | 9.1 | 2.0 | 0.6 | b | b |
| 100 ppm Sucralose + 100 μM C3 | 9.8 | 1.8 | 0.5 | b | bc |
| 300 ppm Sucralose | 10.8 | 2.8 | 0.8 | b | bc |
| 400 ppm Sucralose | 11.2 | 2.3 | 0.6 | b | c |

Average sweetness scores, n = 13 (13 Panelists × 1 rep).
Tukey's value = 2.333 (α = 0.05), 2.087 (α = 0.10).

TABLE 7

| Treatment | Average | SD | St Er | Tukey (5%) | Tukey (10%) |
|---|---|---|---|---|---|
| 100 μM C3 in LSB | 0.0 | 0.0 | 0.0 | a | a |
| 0% Sucrose | 0.0 | 0.1 | 0.0 | a | a |
| 2% Sucrose | 1.8 | 1.0 | 0.3 | b | b |

Average sweetness scores, n = 13 (13 Panelists × 1 rep).
Tukey's value = 0.906 (α = 0.05), 0.811 (α = 0.10).

The results of human taste tests with a compound C4 are found below. Table 8 indicates that 100 μM compound C4 in 6% sucrose has sweetness equivalent to 8% sucrose. Table 9 indicates that 100 μM compound C4 alone has no sweetness, and therefore can be defined as a true sweet enhancer.

TABLE 8

| Treatment | Average | SD | St Er | Tukey (5%) | Tukey (10%) |
|---|---|---|---|---|---|
| 6% Sucrose | 6.6 | 1.0 | 0.2 | a | a |
| 8% Sucrose | 8.1 | 2.1 | 0.4 | b | b |
| 6% Sucrose + 100 μM C4 | 8.1 | 1.1 | 0.2 | b | b |
| 9% Sucrose | 8.6 | 1.9 | 0.4 | bc | b |
| 10% Sucrose | 9.6 | 0.6 | 0.1 | c | c |

Average sweetness scores for various sucrose samples, including 6% sucrose with 100 μM compound C4, n = 28 (14 Panelists × 2 replicates).
Tukey's value = 1.091 (α = 0.05), 0.976 (α = 0.10).

TABLE 9

| Treatment | Average | SD | St Er | Tukey (5%) | Tukey (10%) |
|---|---|---|---|---|---|
| 100 μM C4 in LSB | 0.3 | 0.6 | 0.2 | a | a |
| 0% Sucrose | 0.3 | 1.1 | 0.3 | a | a |
| 2% Sucrose | 2.2 | 0.6 | 0.2 | b | b |
| 4% Sucrose | 4.0 | 0.9 | 0.2 | c | c |
| 6% Sucrose | 5.5 | 0.9 | 0.2 | d | d |

Average sweetness scores, n = 14 (14 Panelists × 1 rep).
Tukey's value = 0.876 (α = 0.05), 0.784 (α = 0.10).

The results of human taste tests with a compound C5 are found below. Table 10 indicates that 100 μM compound C5 in 6% sucrose has sweetness equivalent to 9% sucrose. Table 11 indicates that 100 μM compound C5 alone has no sweetness, and therefore can be defined as a true sweet enhancer.

TABLE 10

| Treatment | Average | SD | St Er | Tukey (5%) | Tukey (10%) |
|---|---|---|---|---|---|
| 6% Sucrose | 7.3 | 1.3 | 0.3 | a | a |
| 8% Sucrose | 7.9 | 1.3 | 0.3 | ab | ab |
| 9% Sucrose | 8.6 | 1.1 | 0.2 | bc | bc |
| 6% Sucrose + 100 μM C5 | 8.8 | 0.9 | 0.2 | cd | c |
| 10% Sucrose | 9.6 | 0.7 | 0.1 | d | d |

Average Sweetness, n = 24 (12 Panelists × 2 rep).
Tukey's value = 0.832 (α = 0.05), 0.744 (α = 0.10).

TABLE 11

| Treatment | Average | SD | St Er | Tukey (5%) | Tukey (10%) |
|---|---|---|---|---|---|
| LSB + 100 μM C5 | 0.2 | 0.5 | 0.1 | a | a |
| 0% Sucrose | 0.4 | 1.5 | 0.4 | a | a |
| 2% Sucrose | 2.1 | 0.8 | 0.2 | b | b |
| 4% Sucrose | 3.9 | 0.7 | 0.2 | c | c |
| 6% Sucrose | 5.7 | 0.7 | 0.2 | d | d |

Average Sweetness, n = 14 (14 Panelists × 1 rep).
Tukey's value = 0.981 (α = 0.05), 0.877 (α = 0.10).

The results of human taste tests with a compound C6 are found below. Table 12 indicates that 100 μM compound C6 in 6% sucrose has sweetness equivalent to about 10% sucrose. Table 13 indicates that 100 μM compound C6 alone has no sweetness, and therefore can be defined as a true sweet enhancer.

TABLE 12

| Treatment | Average | SD | St Er | Tukey (5%) | Tukey (10%) |
|---|---|---|---|---|---|
| 6% Sucrose | 6.8 | 1.2 | 0.2 | a | a |
| 8% Sucrose | 8.3 | 1.1 | 0.2 | b | b |
| 9% Sucrose | 8.6 | 1.3 | 0.3 | bc | bc |
| 6% Sucrose + 100 μM C6 | 9.3 | 1.0 | 0.2 | cd | cd |
| 10% Sucrose | 9.5 | 0.7 | 0.1 | d | d |

Average Sweetness, n = 28 (14 Panelists × 2 rep).
Tukey's value = 0.818 (α = 0.05), 0.732 (α = 0.10).

TABLE 13

| Treatment | Average | SD | St Er | Tukey (5%) | Tukey (10%) |
|---|---|---|---|---|---|
| 0% Sucrose | 0.0 | 0.1 | 0.0 | a | a |
| LSB + 100 μM C6 | 0.2 | 0.5 | 0.1 | a | a |
| 2% Sucrose | 1.9 | 0.9 | 0.2 | b | b |
| 4% Sucrose | 3.9 | 1.3 | 0.4 | c | c |
| 6% Sucrose | 5.5 | 2.0 | 0.5 | d | d |

Average Sweetness, n = 14 (14 Panelists × 1 rep).
Tukey's value = 1.238 (α = 0.05), 1.107 (α = 0.10).

The results of human taste tests with a compound C7 are found below. Table 14 indicates that 50 μM compound C7 in 6% sucrose has sweetness equivalent to about 9% sucrose.

TABLE 14

| Treatment | Average | SD | St Er | Tukey (5%) | Tukey (10%) |
|---|---|---|---|---|---|
| 6% Sucrose | 6.5 | 1.0 | 0.2 | a | a |
| 8% Sucrose | 8.5 | 1.3 | 0.2 | b | b |
| 9% Sucrose | 8.7 | 1.4 | 0.3 | b | b |
| 6% Sucrose + 50 μM C7 | 8.9 | 1.1 | 0.2 | bc | b |
| 10% Sucrose | 9.7 | 0.9 | 0.2 | c | c |

Average Sweetness, n = 26 (13 Panelists × 2 rep).
Tukey's value = 0.762 (α = 0.05), 0.682 (α = 0.10)

The results of human taste tests with a compound C8 are found below. Table 15 indicates that 100 μM compound C8 in 6% sucrose has sweetness equivalent to about 8% sucrose. Table 16 indicates that 100 μM compound C8 alone has no sweetness, and therefore can be defined as a true sweet enhancer.

TABLE 15

| Treatment | Average | SD | St Er | Tukey (5%) | Tukey (10%) |
|---|---|---|---|---|---|
| 6% Sucrose | 7.0 | 1.3 | 0.3 | a | a |
| 6% Sucrose + 50 μM C8 | 8.2 | 1.3 | 0.3 | b | b |
| 8% Sucrose | 8.4 | 1.5 | 0.3 | bc | bc |
| 9% Sucrose | 9.0 | 1.0 | 0.2 | bc | c |
| 10% Sucrose | 9.1 | 1.0 | 0.2 | c | c |

Average Sweetness, n = 28 (14 Panelists × 2 rep).
Tukey's value = 0.859 (α = 0.05), 0.768 (α = 0.10).

TABLE 16

| Treatment | Average | SD | St Er | Tukey (5%) | Tukey (10%) |
|---|---|---|---|---|---|
| 0% Sucrose | 0.0 | 0.0 | 0.0 | a | a |
| 100 μM C8 in LSB | 0.2 | 0.3 | 0.1 | a | a |
| 2% Sucrose | 2.0 | 0.9 | 0.2 | b | b |
| 4% Sucrose | 4.1 | 1.4 | 0.4 | c | c |
| 6% Sucrose | 5.7 | 1.4 | 0.4 | d | d |

Average Sweetness, n = 14 (14 Panelists × 1 rep).
Tukey's value = 1.029 (α = 0.05), 0.921 (α = 0.10).

The results of human taste tests with a compound C9 are found below. Table 17 indicates that from about 40 to about 55 μM compound C9 in 100 ppm sucralose has sweetness equivalent to about 400 ppm sucralose. Table 18 indicates that from about 40 to about 55 μM compound C9 alone has no sweetness, and therefore can be defined as a true sweet enhancer.

TABLE 17

| Treatment | Average | SD | St Er | Tukey (5%) | Tukey (10%) |
|---|---|---|---|---|---|
| 100 ppm sucralose | 6.5 | 2.0 | 0.4 | a | a |
| 200 ppm sucralose | 9.0 | 1.8 | 0.3 | b | b |
| 300 ppm sucralose | 10.9 | 1.6 | 0.3 | c | c |
| 100 ppm sucralose + 40-55 μM C9 | 12.2 | 1.3 | 0.3 | cd | d |
| 400 ppm sucralose | 12.3 | 1.8 | 0.3 | d | d |

Average Sweetness, n = 28 (14 Panelists × 2 rep).
Tukey's value = 1.304 (α = 0.05), 1.178 (α = 0.10).

TABLE 18

| Treatment | Average | SD | St Er | Tukey (5%) | Tukey (10%) |
|---|---|---|---|---|---|
| LSB + 40-55 μM C9 | 0.1 | 0.4 | 0.1 | a | a |
| 0% Sucrose | 0.2 | 0.6 | 0.1 | a | a |
| 2% Sucrose | 2.4 | 0.8 | 0.2 | b | b |
| 4% Sucrose | 4.2 | 1.1 | 0.2 | c | c |
| 6% Sucrose | 5.9 | 1.1 | 0.2 | d | d |

Average Sweetness, n = 22 (11 Panelists × 2 rep).
Tukey's value = 0.693 (α = 0.05), 0.619 (α = 0.10).

The results of human taste tests with a compound C10 are found below. Table 19 indicates that 25 μM compound C10 in 6% sucrose has sweetness equivalent to about 8% sucrose.

TABLE 19

| Treatment | Average | SD | St Er | Tukey (5%) | Tukey (10%) |
|---|---|---|---|---|---|
| 6% Sucrose | 7.3 | 1.4 | 0.3 | a | a |
| 6% Sucrose + 25 μM C10 | 8.4 | 1.1 | 0.2 | b | b |
| 8% Sucrose | 8.6 | 1.2 | 0.2 | bc | bc |
| 9% Sucrose | 9.1 | 0.9 | 0.2 | cd | cd |
| 10% Sucrose | 9.7 | 0.5 | 0.1 | d | d |

Average Sweetness, n = 28 (14 Panelists × 2 rep).
Tukey's value = 0.747 (α = 0.05), 0.668 (α = 0.10).

Table 20 indicates that 25 μM of compounds C10 alone has no sweetness, and therefore can be defined as true sweet enhancers.

TABLE 20

| Treatment | Average | SD | St Er | Tukey (5%) | Tukey (10%) |
|---|---|---|---|---|---|
| 0% Sucrose | 7.3 | 1.4 | 0.3 | a | a |
| LSB + 25 μM C10 | 8.4 | 1.1 | 0.2 | a | a |
| 2% Sucrose | 8.6 | 1.2 | 0.2 | b | b |
| 4% Sucrose | 9.1 | 0.9 | 0.2 | c | c |
| 6% Sucrose | 9.7 | 0.5 | 0.1 | d | d |

Average Sweetness, n = 14 (14 Panelists × 1 rep).
Tukey's value = 0.957 (α = 0.05), 0.856 (α = 0.10).

The results of human taste tests with a compound C11 are found below. Table 21 indicates that 50 μM compound C11 in 6% sucrose has sweetness equivalent to about 8% sucrose.

TABLE 21

| Treatment | Average | SD | St Er | Tukey (5%) | Tukey (10%) |
|---|---|---|---|---|---|
| 6% Sucrose | 6.5 | 0.9 | 0.2 | a | a |
| 8% Sucrose | 8.3 | 0.9 | 0.2 | b | b |
| 6% Sucrose + 50 μM C11 | 8.4 | 1.0 | 0.2 | b | b |
| 10% Sucrose | 9.4 | 0.9 | 0.2 | c | c |
| 9% Sucrose | 9.4 | 0.7 | 0.2 | c | c |

Average Sweetness, n = 15 (15 Panelists × 1 rep).
Tukey's value = 0.905 (α = 0.05), 0.810 (α = 0.10).

The results of human taste tests with a compound C12 are found below. Table 22 indicates that 50 μM compound C12 in 6% sucrose has sweetness equivalent to about 9%-10% sucrose.

TABLE 22

| Treatment | Average | SD | St Er | Tukey (5%) | Tukey (10%) |
|---|---|---|---|---|---|
| 6% Sucrose | 6.5 | 0.8 | 0.2 | a | a |
| 8% Sucrose | 8.2 | 1.0 | 0.2 | b | b |
| 6% Sucrose + 50 µM C12 | 9.0 | 0.8 | 0.2 | c | c |
| 9% Sucrose | 9.2 | 0.7 | 0.1 | c | c |
| 10% Sucrose | 9.4 | 0.9 | 0.2 | c | c |

Average Sweetness, n = 26 (13 Panelists × 2 rep).
Tukey's value = 0.492 (α = 0.05), 0.440 (α = 0.10).

The results of human taste tests with a compound C13 are found below. Table 23 indicates that 25 µM compound C13 in 6% sucrose has sweetness equivalent to about 8% sucrose.

TABLE 23

| Treatment | Average | SD | St Er | Tukey (5%) | Tukey (10%) |
|---|---|---|---|---|---|
| 6% Sucrose | 6.8 | 1.0 | 0.2 | a | a |
| 6% Sucrose + 25 µM C13 | 8.6 | 1.1 | 0.2 | b | b |
| 8% Sucrose | 8.7 | 1.0 | 0.2 | b | b |
| 9% Sucrose | 9.5 | 0.7 | 0.1 | c | c |
| 10% Sucrose | 9.5 | 0.8 | 0.2 | c | c |

Average Sweetness, n = 26 (13 Panelists × 2 rep).
Tukey's value = 0.636 (α = 0.05), 0.569 (α = 0.10).

The results of human taste tests with a compound C14 are found below. Table 24 indicates that 50 µM compound C14 in 6% sucrose has sweetness equivalent to about 8%-9% sucrose.

TABLE 24

| Treatment | Average | SD | St Er | Tukey (5%) | Tukey (10%) |
|---|---|---|---|---|---|
| 6% Sucrose | 6.5 | 1.0 | 0.2 | a | a |
| 8% Sucrose | 8.4 | 1.2 | 0.2 | b | b |
| 6% Sucrose + 50 µM C14 | 8.7 | 1.3 | 0.2 | bc | bc |
| 9% Sucrose | 9.2 | 1.2 | 0.2 | c | cd |
| 10% Sucrose | 9.4 | 0.7 | 0.1 | c | d |

Average Sweetness, n = 26 (12 Panelists × 1 rep; 14 Panelists × 1 rep).
Tukey's value = 0.782 (α = 0.05), 0.701 (α = 0.10).

The results of human taste tests with a compound C15 are found below. Table 25 indicates that 50 µM compound C15 in 6% sucrose has sweetness equivalent to about 9%-10% sucrose.

TABLE 25

| Treatment | Average | SD | St Er | Tukey (5%) | Tukey (10%) |
|---|---|---|---|---|---|
| 6% Sucrose | 6.7 | 0.9 | 0.2 | a | a |
| 8% Sucrose | 8.1 | 1.0 | 0.2 | b | b |
| 6% Sucrose + 50 µM C15 | 9.1 | 1.1 | 0.2 | c | c |
| 10% Sucrose | 9.2 | 0.9 | 0.2 | c | c |
| 9% Sucrose | 9.3 | 0.7 | 0.1 | c | c |

Average Sweetness, n = 25 (11 Panelists × 1 rep; 14 Panelists × 1 rep).
Tukey's value = 0.688 (α = 0.05), 0.617 (α = 0.10).

The results of human taste tests with compound C16 are found below. Table 26 indicates that 25 µM compound C16 in 6% sucrose has sweetness equivalent to about 10%12% sucrose. Table 27 shows a dose response curve of compound C16 with 6% sucrose which shows that the sweetness of sucrose is significantly enhanced by addition of increasing amounts of compound C16. Table 28 indicates that 14.11 µM compound C16 in 50 ppm sucralose has sweetness equivalent to about 200 ppm-300 ppm sucralose. Table 29 indicates that 25 µM compound C16 in 6% fructose has sweetness equivalent between 6% and 8% fructose. Table 29 indicates that 25 µM compound C16 alone has little or no sweetness, and therefore can be defined as a true sweet enhancer.

TABLE 26

| Treatment | Average | SD | St Er | Tukey (5%) | Tukey (10%) |
|---|---|---|---|---|---|
| 6% Sucrose | 6.2 | 1.5 | 0.3 | a | a |
| 8% Sucrose | 8.3 | 1.1 | 0.2 | b | b |
| 9% Sucrose | 9.3 | 1.4 | 0.3 | bc | c |
| 10% Sucrose | 9.8 | 1.2 | 0.2 | cd | cd |
| 6% Sucrose + 25 µM C16 | 10.6 | 1.7 | 0.3 | de | de |
| 12% Sucrose | 11.1 | 1.4 | 0.3 | e | e |

Average Sweetness, n = 24 (12 Panelists × 2 rep).
Tukey's value = 1.079 (α = 0.05), 0.974 (α = 0.10).

TABLE 27

| Treatment | Average | SD | St Er | Tukey (5%) | Tukey (10%) |
|---|---|---|---|---|---|
| 6% Sucrose | 6.7 | 1.0 | 0.2 | a | a |
| 6% Sucrose + 2.82 µM C16 | 7.5 | 1.6 | 0.3 | ab | ab |
| 6% Sucrose + 5.64 µM C16 | 8.0 | 1.1 | 0.2 | b | b |
| 8% Sucrose | 8.3 | 1.7 | 0.3 | b | b |
| 6% Sucrose + 11.29 µM C16 | 10.1 | 1.5 | 0.3 | c | c |
| 6% Sucrose + 19.75 µM C16 | 10.3 | 1.7 | 0.3 | cd | cd |
| 10% Sucrose | 10.3 | 1.8 | 0.4 | cd | cd |
| 6% Sucrose 28.22 µM C16 | 10.9 | 1.4 | 0.3 | cd | cd |
| 12% Sucrose | 11.2 | 1.0 | 0.2 | d | d |

Average Sweetness, n = 30 (15 Panelists × 2 rep).
Tukey's value = 1.138 (α = 0.05), 1.043 (α = 0.10).

TABLE 28

| Treatment | Average | SD | St Er | Tukey (5%) | Tukey (10%) |
|---|---|---|---|---|---|
| 50 ppm sucralose | 4.3 | 0.7 | 0.1 | a | a |
| 100 ppm sucralose | 6.2 | 1.6 | 0.3 | b | b |
| 150 ppm sucralose | 8.2 | 1.8 | 0.3 | cd | cd |
| 200 ppm sucralose | 8.9 | 1.6 | 0.3 | de | d |
| 50 ppm sucralose + 14.11 µM C16 | 9.9 | 2.3 | 0.4 | ef | e |
| 300 ppm sucralose | 10.3 | 1.7 | 0.3 | f | e |

Average Sweetness, n = 28 (14 Panelists × 2 rep).
Tukey's value = 0.969 (α = 0.05), 0.881 (α = 0.10).

TABLE 29

| Treatment | Average | SD | St Er | Tukey (5%) | Tukey (10%) |
|---|---|---|---|---|---|
| 6% Fructose | 6.9 | 1.0 | 0.2 | a | a |
| 6% Fructose + 25 µM C16 | 7.8 | 1.1 | 0.2 | b | b |
| 8% Fructose | 8.6 | 0.8 | 0.2 | c | c |
| 9% Fructose | 9.3 | 0.7 | 0.1 | cd | d |
| 10% Fructose | 9.5 | 0.7 | 0.1 | d | d |

Average Sweetness, n = 26 (13 Panelists × 2 rep).
Tukey's value = 0.714 (α = 0.05), 0.639 (α = 0.10).

TABLE 30

| Treatment | Average | SD | St Er | Tukey (5%) | Tukey (10%) |
|---|---|---|---|---|---|
| 0% Sucrose | 0.2 | 0.5 | 0.1 | a | a |
| LSB + 25 µM C16 | 0.6 | 0.8 | 0.2 | a | a |

TABLE 30-continued

| Treatment | Average | SD | St Er | Tukey (5%) | Tukey (10%) |
|---|---|---|---|---|---|
| 2% Sucrose | 2.3 | 0.8 | 0.2 | b | b |
| 4% Sucrose | 4.2 | 1.2 | 0.2 | c | c |
| 6% Sucrose | 5.8 | 0.6 | 0.1 | d | d |

Average Sweetness, n = 30 (15 Panelists × 2 rep).
Tukey's value = 0.535 ($\alpha$ = 0.05), 0.479 ($\alpha$ = 0.10).

The results of human taste tests with compound C17 are found below. Table 31 indicates that 8 µM compound C17 in 6% sucrose has sweetness equivalent to about 9%-10% sucrose. Table 32 indicates that 8 µM compound C17 alone has little or no sweetness, and therefore can be defined as a true sweet enhancer.

TABLE 31

| Treatment | Average | SD | St Er | Tukey (5%) | Tukey (10%) |
|---|---|---|---|---|---|
| 6% Sucrose | 6.8 | 1.2 | 0.2 | a | a |
| 8% Sucrose | 8.5 | 0.9 | 0.2 | b | b |
| 9% Sucrose | 8.6 | 0.8 | 0.2 | b | b |
| 6% Sucrose + 8 µM C17 | 9.0 | 1.1 | 0.2 | bc | bc |
| 10% Sucrose | 9.6 | 0.6 | 0.1 | c | c |

Average Sweetness, n = 28 (14 Panelists × 2 rep).
Tukey's value = 0.657 ($\alpha$ = 0.05), 0.588 ($\alpha$ = 0.10).

TABLE 32

| Treatment | Average | SD | St Er | Tukey (5%) | Tukey (10%) |
|---|---|---|---|---|---|
| 0% Sucrose | 0.1 | 0.4 | 0.1 | a | a |
| LSB + 8 µM C17 | 0.2 | 0.5 | 0.1 | a | a |
| 2% Sucrose | 2.3 | 0.7 | 0.1 | c | c |
| 4% Sucrose | 4.5 | 1.0 | 0.2 | d | d |
| 6% Sucrose | 5.8 | 0.6 | 0.1 | e | e |

Average Sweetness, n = 28 (14 Panelists × 2 rep).
Tukey's value = 0.467 ($\alpha$ = 0.05), 0.425 ($\alpha$ = 0.10).

Experiment 6

Sweet Flavor and Sweet Flavor Enhancement Measurement Using Human Panelists Conducting a Paired Comparison Test Test samples containing experimental compounds are presented in pairs to the panelist and they are asked to determine which of the sample is sweeter. A group of 10-16 or more panelists participated in each test. Subjects refrained from eating or drinking (except water) for at least 1 hour prior to the test. Subjects rinsed with water several times to clean the mouth.

All samples are prepared with ethanol to ensure dispersion of the compound in solution. This includes samples without compound; all solutions are balanced for 0.1% ethanol.

Samples are also prepared with low sodium buffer (pH 7.1) in place of water. Buffer contains 0.952 g of KCl, 5.444 g of $Na_2HPO_4$, and 0.952 g of $KH_2PO_4$ in 40 L of DIUF water. Sample volumes are usually 20 ml.

In one paired comparison test, the panelist is presented with two different samples and asked to identify the sample which is sweeter. The samples within a paired comparison test are presented in a randomized, counterbalanced order. Panelists have up to a 1 minute delay between taste tests to clear the mouth of any tastes.

Binomial probability tables are used to determine the probability of the correct number of responses occurring for each test at alpha=0.05.

The results of human taste tests with a compound C18 are found below. Table 33 indicates that panelists perceived 6% Fructose+100 µM C18 as being significantly sweeter than a solution of 6% Fructose (p<0.05)

TABLE 33

| Samples | Total |
|---|---|
| 6% Fructose | 6 |
| 6% Fructose + 100 µM 568 | 20 |
| Total | 26 |
| Confidence | 0.991 |
| 6% Fructose + 100 µM C18 (p-value) | 0.009 |

Sample selected as more sweet by panelists: n = 26 (13 panelists × 2 reps).

The results of human taste tests with a compound C19 are found below. Table 34 indicates that panelists perceived 6% Fructose+100 µM C19 as being significantly sweeter than a solution of 6% Fructose (p<0.05)

TABLE 34

| Samples | Total |
|---|---|
| 6% Fructose | 6 |
| 6% Fructose + 100 µM C19 | 18 |
| Total | 24 |
| Confidence | 0.977 |
| 6% Fructose + 100 µM C19 (p-value) | 0.023 |

Sample selected as more sweet by panelists: n = 24 (12 panelists × 2 reps).

The results of human taste tests with a compound C20 are found below. Table 34 indicates that panelists perceived 6% Fructose+100 µM C20 as being significantly sweeter than a solution of 6% Fructose (p<0.05). Table 36 indicates that 100 µM compound C20 alone has little or no sweetness on its own (Experiment 5).

TABLE 35

| Samples | Test 1 | Total |
|---|---|---|
| 6% Fructose | 0 | 0 |
| 6% Fructose + 100 µM C20 | 19 | 19 |
| Total | 19 | 19 |

Sample selected as more sweet by panelists: n = 19 (19 panelists × 1 rep).

TABLE 36

| Treatment | Average | SD | St Er | Tukey (5%) | Tukey (10%) |
|---|---|---|---|---|---|
| 0% Fructose | 0.2 | 0.5 | 0.1 | a | a |
| LSB + 100 µM C20 | 0.2 | 0.5 | 0.1 | a | a |
| 2% Fructose | 2.3 | 0.7 | 0.2 | b | b |
| 4% Fructose | 4.2 | 1.1 | 0.3 | c | c |
| 6% Fructose | 5.9 | 0.3 | 0.1 | d | d |

Average Sweetness, n = 13 (13 Panelists × 1 rep).
Tukey's Value = 0.753 ($\alpha$ = 0.05), 0.674 ($\alpha$ = 0.10).

The results of human taste tests with a compound C21 are found below. Table 37 indicates that panelists perceived 6% Fructose+25 µM C21 as being significantly sweeter than a solution of 6% Fructose (p<0.05). Table 38 indicates that panelists perceived 6% Fructose+25 µM C21 has the same sweetness intensity than a solution of 7% Fructose.

TABLE 37

| Samples | Test 1 |
|---|---|
| 6% Fructose | 5 |
| 6% fructose + 25 μM C21 | 20 |
| Total | 25 |
| Confidence | 0.999 |
| 6% fructose + 25 μM C21 (p-value) | 0.001 |

Sample selected as more sweet by panelists: n = 25 (25 panelists × 1 rep).

TABLE 38

| Samples | Test 1 |
|---|---|
| 7% Fructose | 13 |
| 6% fructose + 25 μM C21 | 12 |
| Total | 25 |
| Confidence | 0.166 |
| 6% fructose + 25 μM C21 (p-value) | 0.834 |

Sample selected as more sweet by panelists: n = 25 (25 panelists × 1 rep).

Experiment 7

Solubility Determination of the Compounds of the Present Invention and Their HCl Salts in Propylene Glycol The solubility of the present compounds and their HCl salts in propylene glycol was determined by shake flask method. Approximately 50 mg of the test compound was weighed out and added to a 4-mL glass vial, and then 1 mL of propylene glycol was added to the vial. The vial was sonicated for 10 minutes and then shaken for 24 hrs on an orbital shaker set at 300 rpm. An aliquot of 200 μL of the solution was transferred from the vial into a 1.5 mL centrifuge vial and centrifuged at 12,500 rpm for 10 min. An aliquot of 50 μL of the supernatant was diluted by 100 times with propylene glycol. Then 50 μL of this solution was further diluted 100 times with water and analyzed by liquid chromatography mass spectrometry (C18 column with gradient elution with a flow rate of 2.0 mL/min, water with 0.1% trifluoroacetic acid as mobile phase A and methanol with 0.1% trifluoraacetic acid as mobile phase B, mobile phase B % rising from 5% to 95% in 0.6 min and then being held at 95% for 1.4 min). The result of one exemplary solubility test is shown in Table A.

TABLE A

Solubility of Compound C2 and Its HCl Salt

| Compound | Solubility Average (mM) | Standard Deviation (mM) |
|---|---|---|
| C2 | 6.2 | 1.7 |
| C2.hydrochloride | 45.7 | 3.0 |

All publications and patent applications herein are incorporated by reference to the same extent as if each individual publication or patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A compound having structural Formula (IIIb):

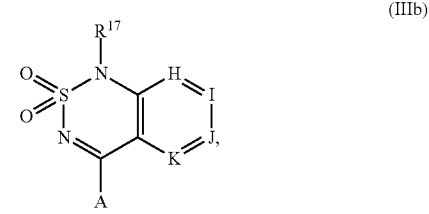

(IIIb)

or a salt or solvate thereof;

Wherein
  A is —NH$_2$;
  H is —C(R$^{35}$)— or —N—;
  I is —C(R$^{36}$) or —N—;
  J is —C(R$^{37}$)— or —N—;
  K is —C(R$^{38}$)—;
  R$^{17}$ is hydrogen;
  R$^{35}$ is hydrogen;
  R$^{36}$ is hydrogen;
  R$^{37}$ is hydrogen, fluoro, chloro, or bromo; and
  R$^{38}$ is alkenyl, substituted alkenyl, alkynyl, substituted alkynyl, cycloalkanyl, substituted cycloalkanyl, cycloalkenyl, substituted cycloalkenyl, heteroalkanyl, substituted heteroalkanyl, cycloheteroalkyl, substituted cycloheteroalkyl, —O-alkanyl, —O-(substituted alkanyl), —O-heteroalkanyl, —O-(substituted heteroalkanyl), —O-alkenyl, —O-(substituted alkenyl), —NH-alkanyl, —NH-(substituted alkanyl), —NH-alkenyl, —NH-(substituted alkenyl), —S-alkanyl, —S-(substituted alkanyl), —S-alkenyl, or —S-(substituted alkenyl).

2. The compound of claim 1, wherein
  H is —C(R$^{35}$)—;
  I is —C(R$^{36}$)—;
  J is —C(R$^{37}$)—; and
  K is —C(R$^{38}$)—.

3. A compound having structural Formula (IIIb1):

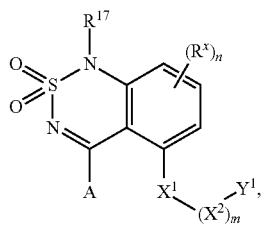

or a salt or solvate thereof;
wherein,
A is hydrogen, —CN, —OR$^9$, —NO$_2$, —S(O)$_c$R$^9$, —NOR$^9$, —NHOR$^9$, —NR$^9$COR$^{10}$, —NR$^9$R$^{10}$, —CONR$^9$R$^{10}$, —CO$_2$R$^9$ or —NR$^9$CO$_2$R$^{10}$;
R$^{17}$ is hydrogen, alkyl, substituted alkyl, arylalkyl, or substituted arylalkyl;
X$^1$ is —CH$_2$—, —O—, —NR$^9$—, —S—, —S(O)—, or —S(O)$_2$—;
X$^2$ is alkylene, substituted alkylene, heteroalkylene, or substituted heteroalkylene;
m is 0 or 1;
Y$^1$ is heteroaryl, substituted heteroaryl, cycloheteroalkyl, substituted cycloheteroalkyl, or

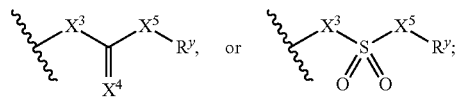

X$^3$ and X$^5$ are independently a covalent bond, —O— or —NR$^9$—;
X$^4$ is O, NR$^9$, N—OR$^9$, or S;
R$^x$ is halo, —NO$_2$, —CN, —OH, —NH$_2$, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;
n is 0, 1, 2, or 3;
R$^y$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl, —NR$^9$R$^{10}$; and
each R$^9$ and R$^{10}$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;
with the proviso that when X$^1$ is —O— or —S—, and m is zero; then X$^3$ is not —O—.

4. The compound of claim 3, wherein
X$^1$ is —CH$_2$—; and
Y$^1$ is

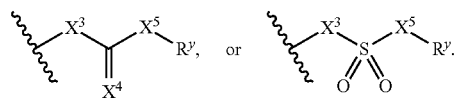

5. The compound of claim 3, wherein
X$^1$ is —O—, —NR$^9$—, or —S—;
m is 0 or 1, and
Y$^1$ is cycloheteroalkyl or substituted cycloheteroalkyl.

6. The compound of claim 3, wherein
X$^1$ is —O—, —NR$^9$—, or —S—;
m is 1, and
Y$^1$ is

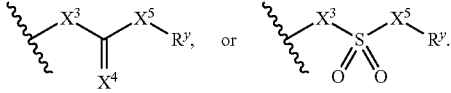

7. The compound of claim 3, wherein
X$^2$ is methylene, ethylene, propylene, iso-propylene, butylene, iso-butylene, sec-butylene, pentylene, hexylene, heptylene, dimethylethylene, methylcyclopropylene, cyclopropylmethylene, ethenylene, propenylene, or butenylene.

8. The compound of claim 3, wherein Y$^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, substituted oxetanyl, saccharide ring or its derivative, substituted saccharide ring or its derivative.

9. The compound of claim 3, wherein Y$^1$ is pyridinyl, substituted pyridinyl, pyrrolyl, substituted pyrrolyl, furanyl, substituted furanyl, pyrazolyl, substituted pyrazolyl, isoxazolyl, substituted isoxazolyl, oxazolyl, and substituted oxazolyl.

10. The compound of claim 3, wherein the substituted cycloheteroalkyl comprises one or more substituents selected from the group consisting of alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —OR$^9$, —NO$_2$, —S(O)$_c$R$^9$, —NOR$^9$, —NHOR$^9$, —NR$^9$COR$^{10}$, —NR$^9$R$^{10}$, —CONR$^9$R$^{10}$, —CO$_2$R$^9$, and —NR$^9$CO$_2$R$^{10}$.

11. The compound of claim 3, wherein Y$^1$ is

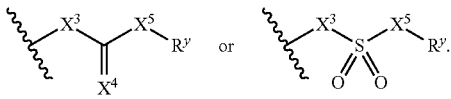

12. The compound of claim 3, wherein —X$^3$—C(X$^4$)—X$^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —O—C(NH)—O—, —NH—C(NH)—O—, —O—C(NH)—NH—, —C(N—OH)—, or —C(S)—.

13. The compound of claim 3, wherein
A is hydrogen, or —NR$^9$R$^{10}$;
R$^{17}$ is hydrogen; and
Y$^1$ is piperidinyl, substituted piperidinyl, tetrahydrofuranyl, substituted tetrahydrofuranyl, tetrahydropyranyl, substituted tetrahydropyranyl, dihydrofuranyl, substituted dihydrofuranyl, pyrrolidinyl, substituted pyrrolidinyl, oxetanyl, substituted oxetanyl, monosaccharide ring, substituted monosaccharide ring, pyridinyl, substituted pyridinyl, pyrrolyl, substituted pyrrolyl, furanyl, substituted furanyl, pyrazolyl, substituted pyrazolyl, isoxazolyl, substituted isoxazolyl, oxazolyl, or substituted oxazolyl.

14. The compound of claim 3, wherein

A is hydrogen, or —NR$^9$R$^{10}$;

R$^{17}$ is hydrogen;

Y$^1$ is —X$^3$—C(X$^4$)—X$^5$—; and

—X$^3$—C(X$^4$)—X$^5$— is —C(O)—, —C(O)—NH—, —NH—C(O)—, —NH—C(O)—NH—, —C(O)—O—, —O—C(O)—, —O—C(O)—O—, —NH—C(O)—O—, —O—C(O)—NH—, —C(NH)—, —C(NH)—NH—, —NH—C(NH)—, —NH—C(NH)—NH—, —C(NH)—O—, —O—C(NH)—, —O—C(NH)—O—, —NH—C(NH)—O—, —O—C(NH)—NH—, —S(O)$_2$—, —NH—S(O)$_2$—, —S(O)$_2$—NH—, —O—S(O)$_2$—, —S(O)$_2$—O—, —C(N—OH)—, or —C(S)—.

15. The compound of claim 1 or 3, having structural formula selected from the group consisting of

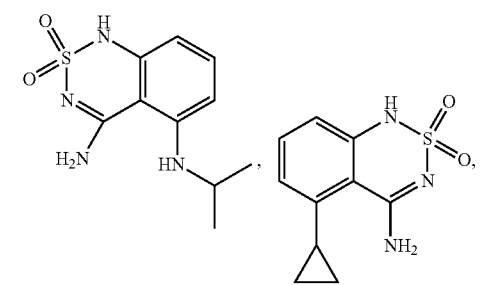

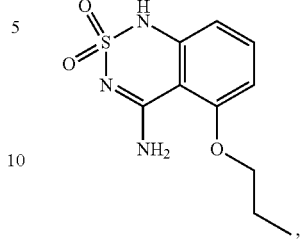

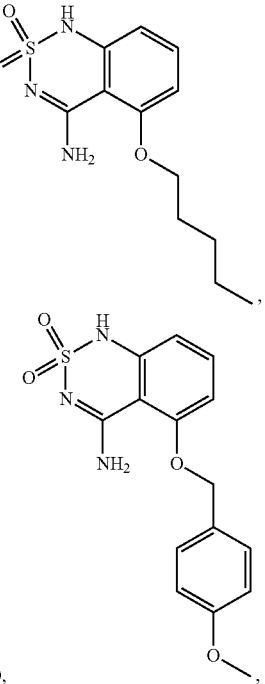

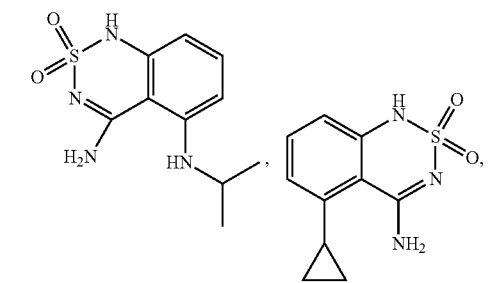

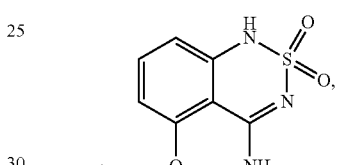

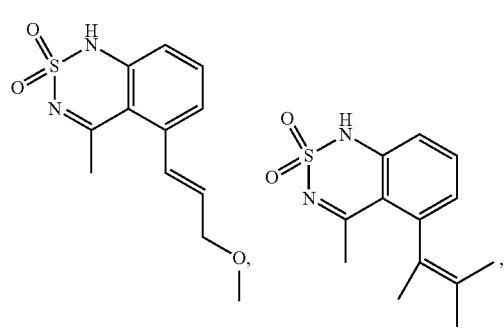

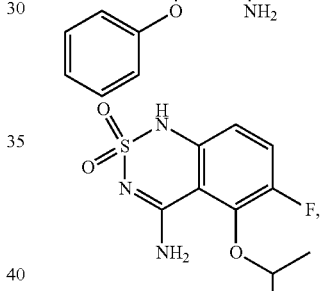

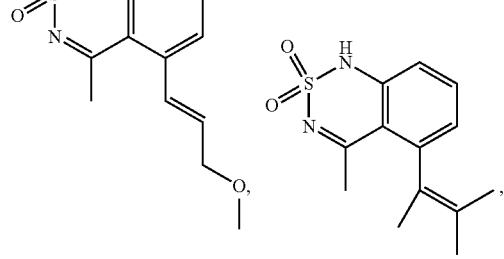

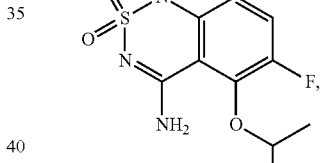

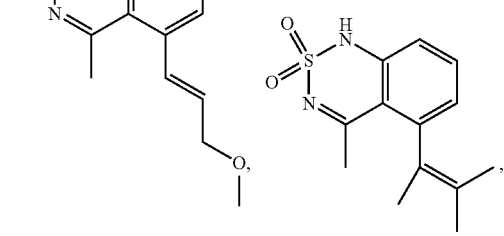

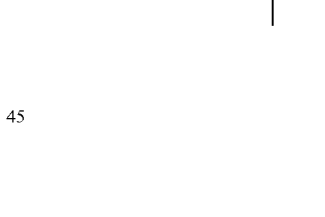

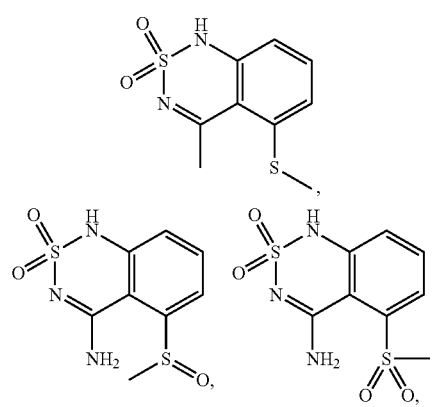

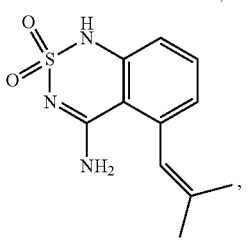

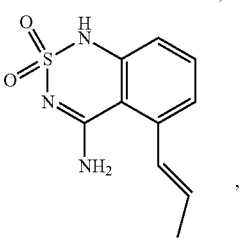

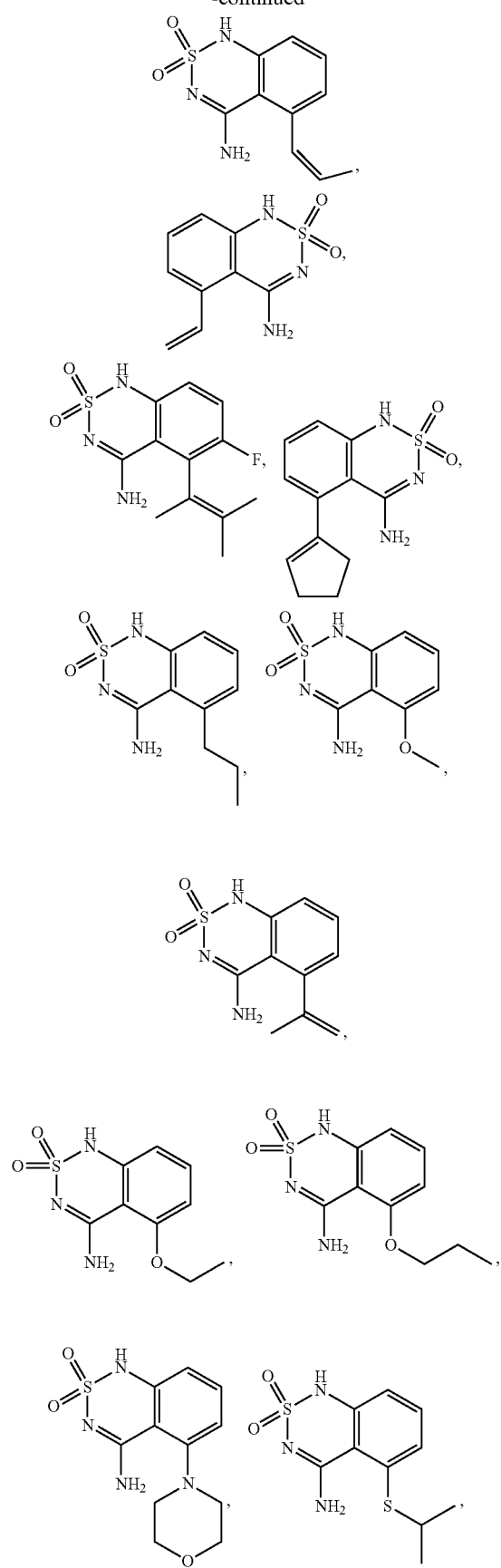
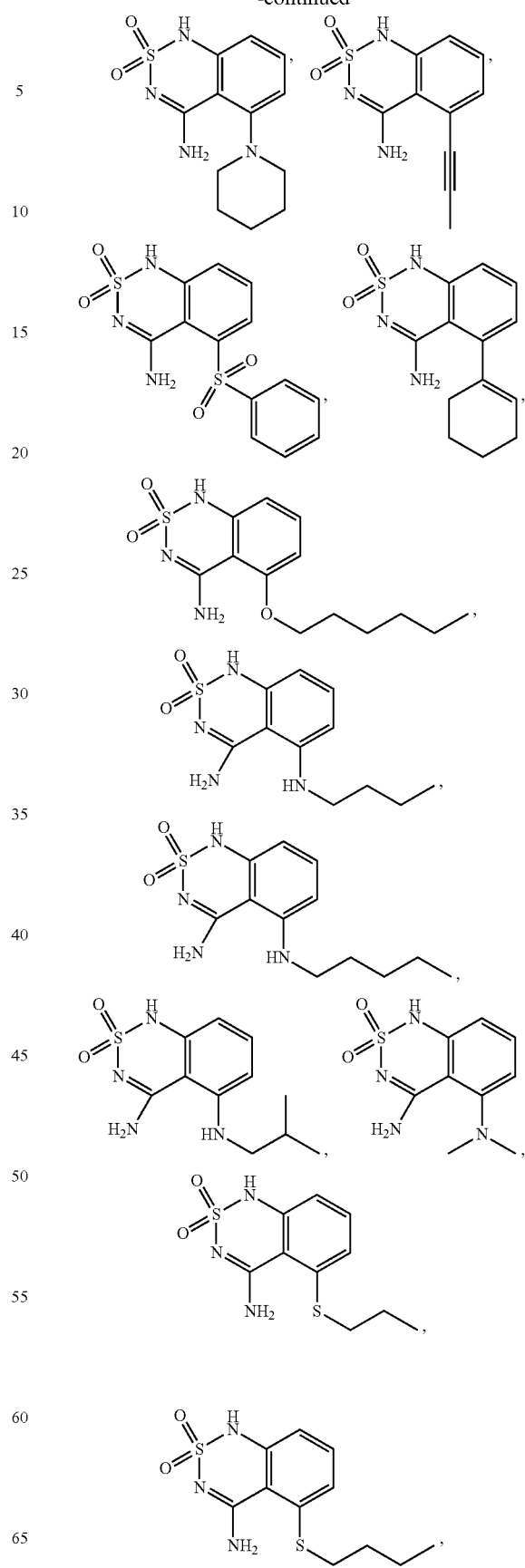

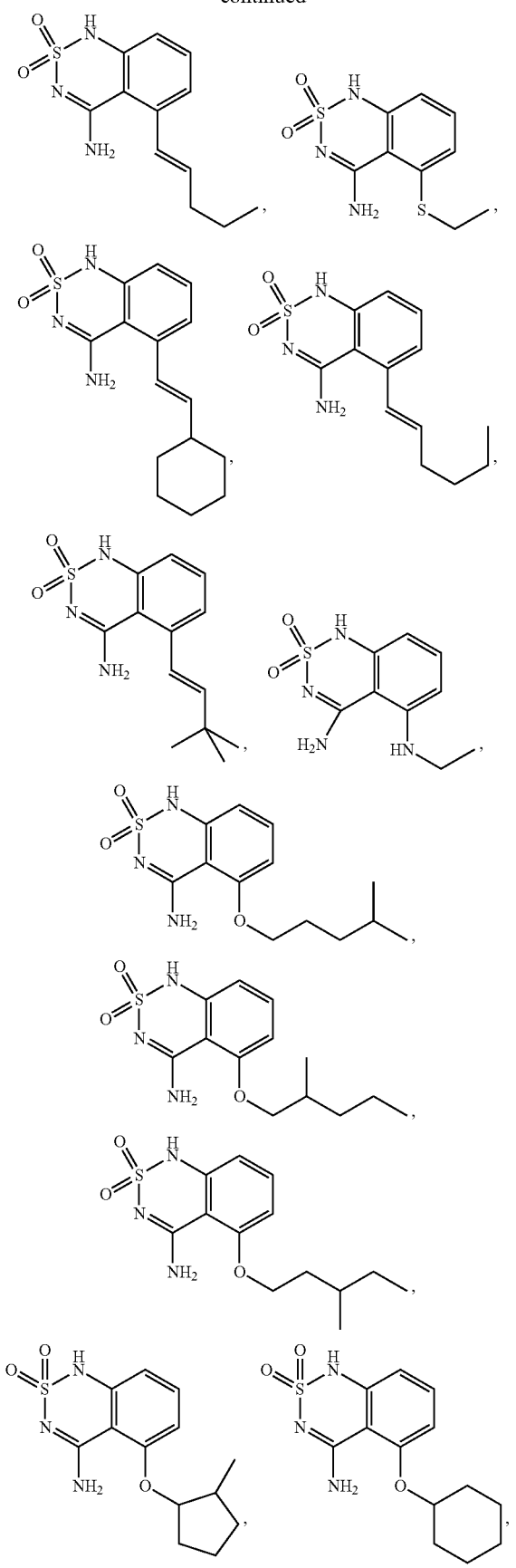
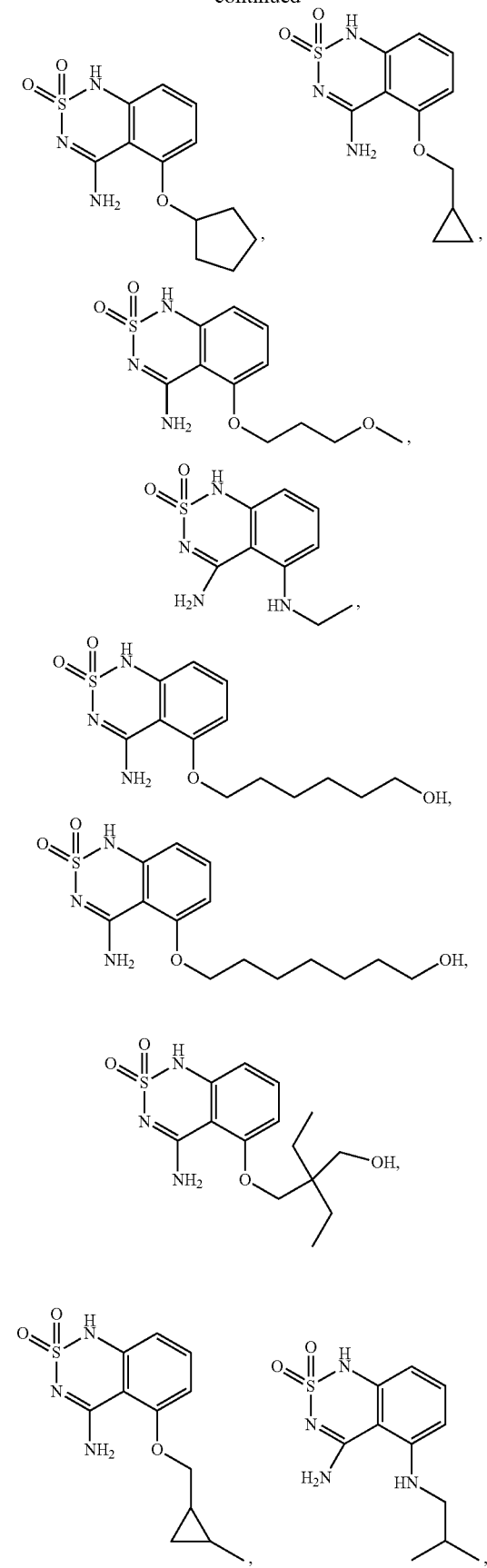

379
-continued
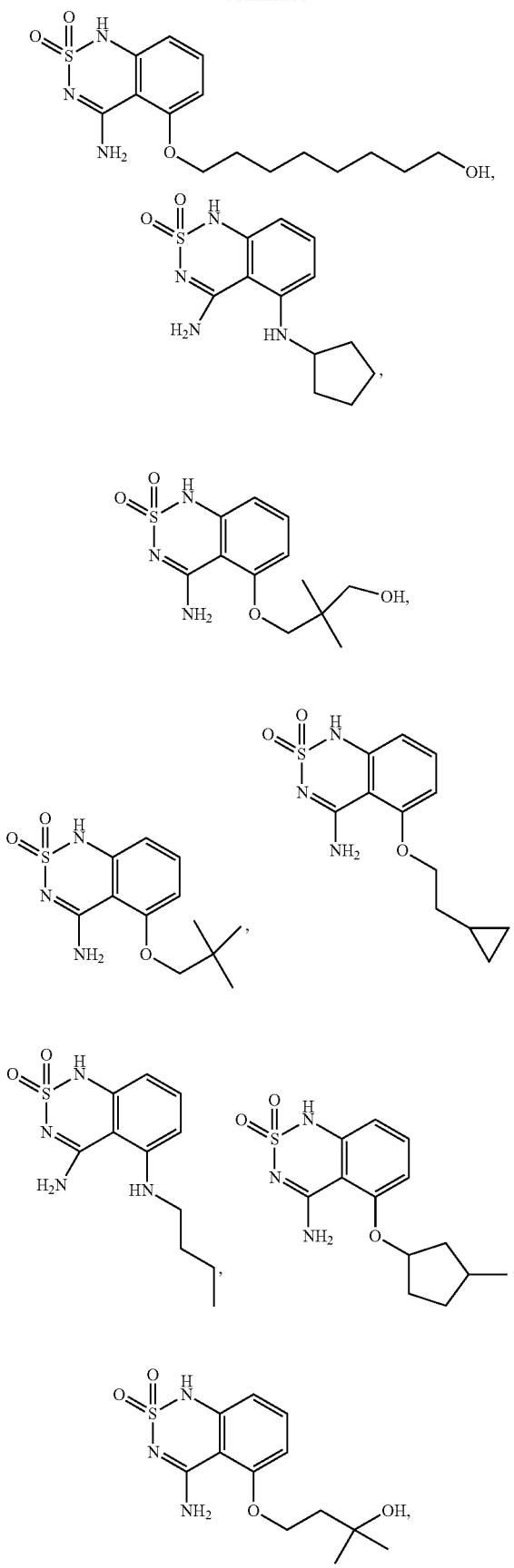
380
-continued
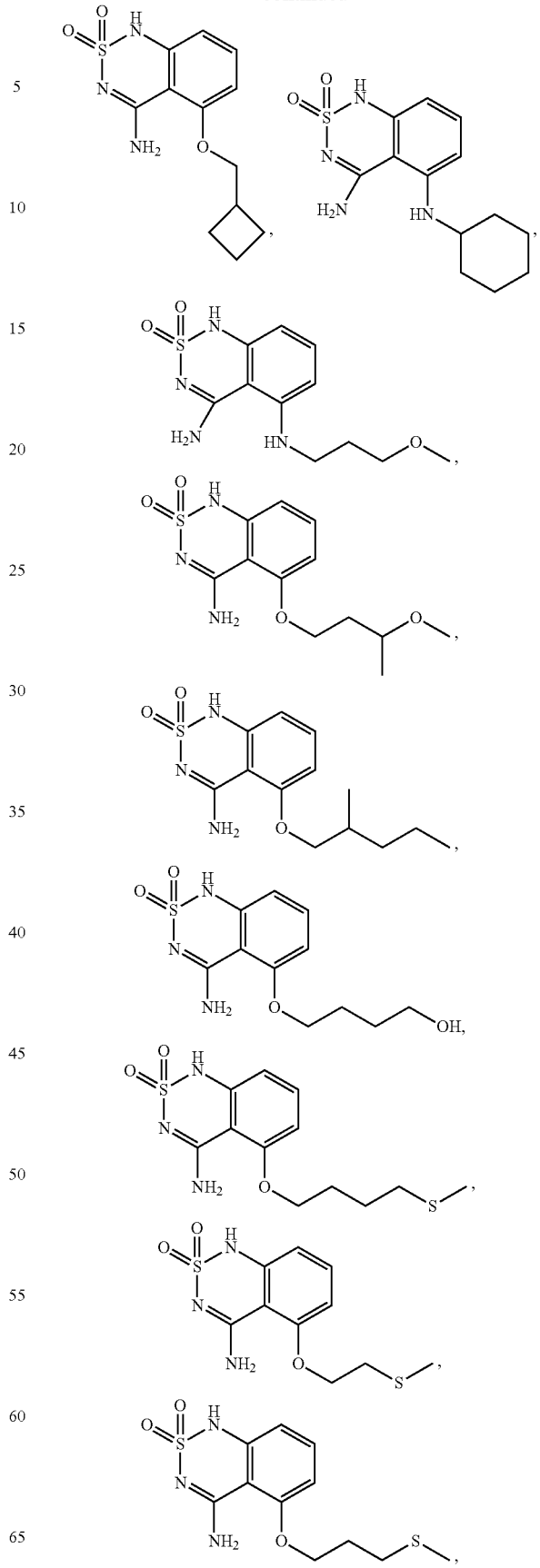

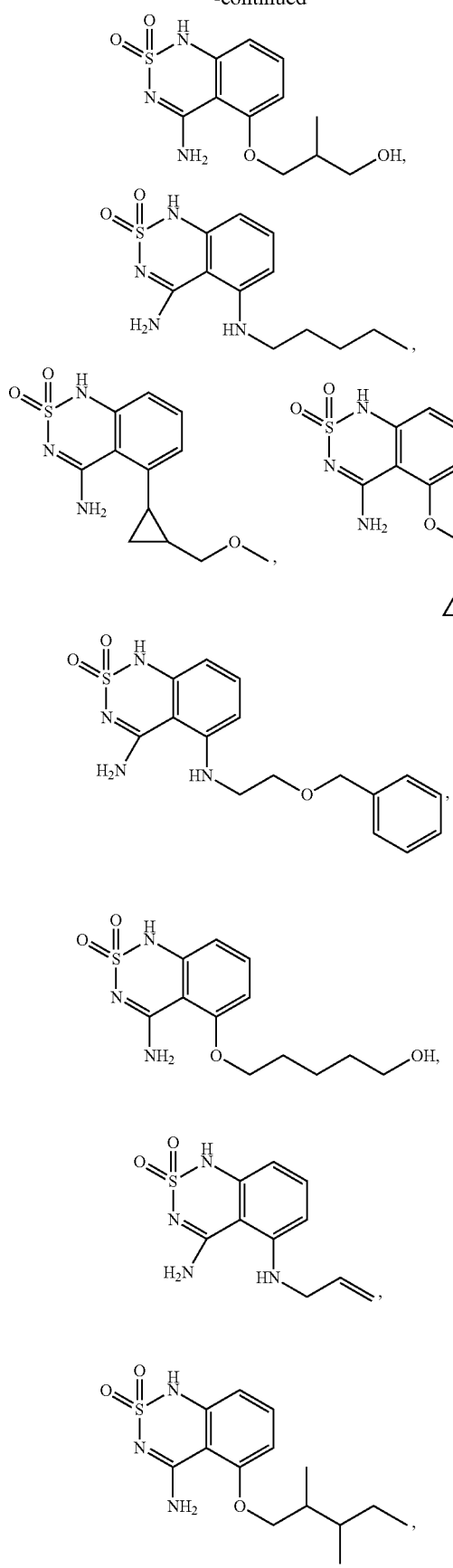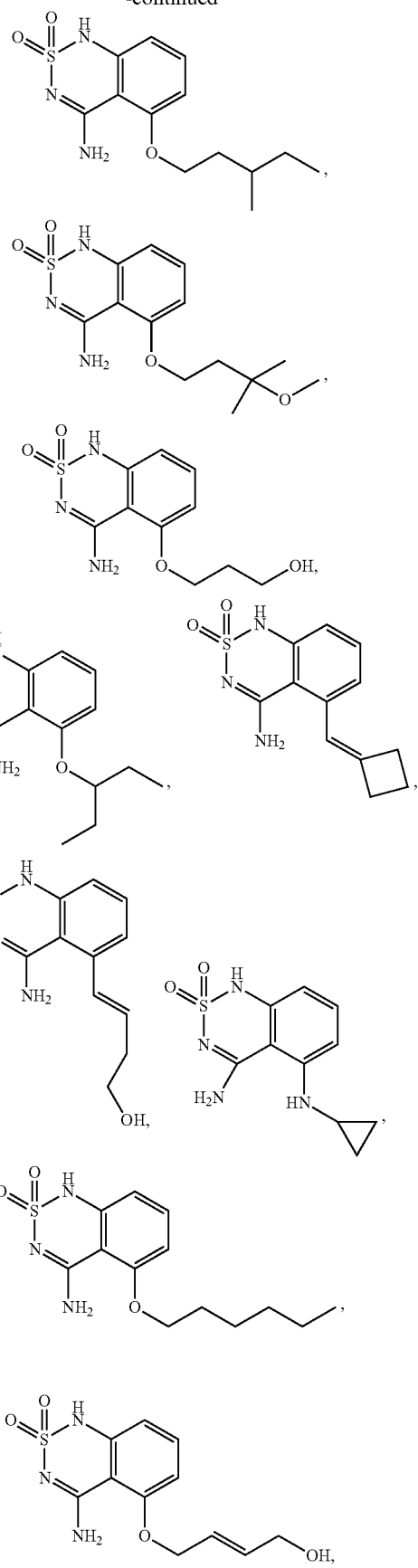

-continued
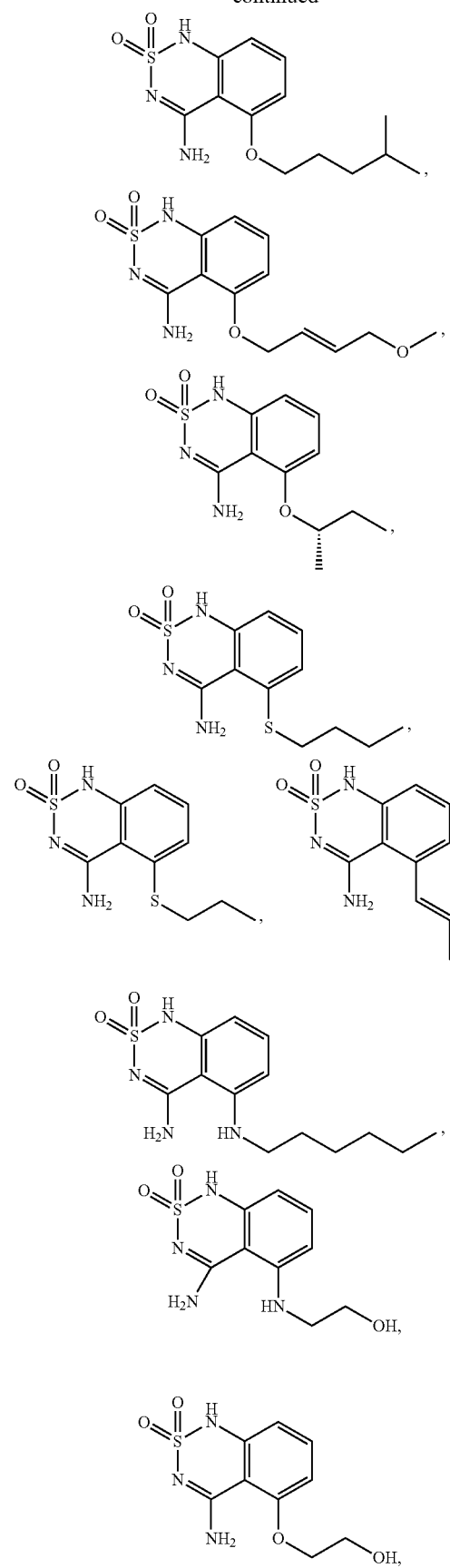
-continued
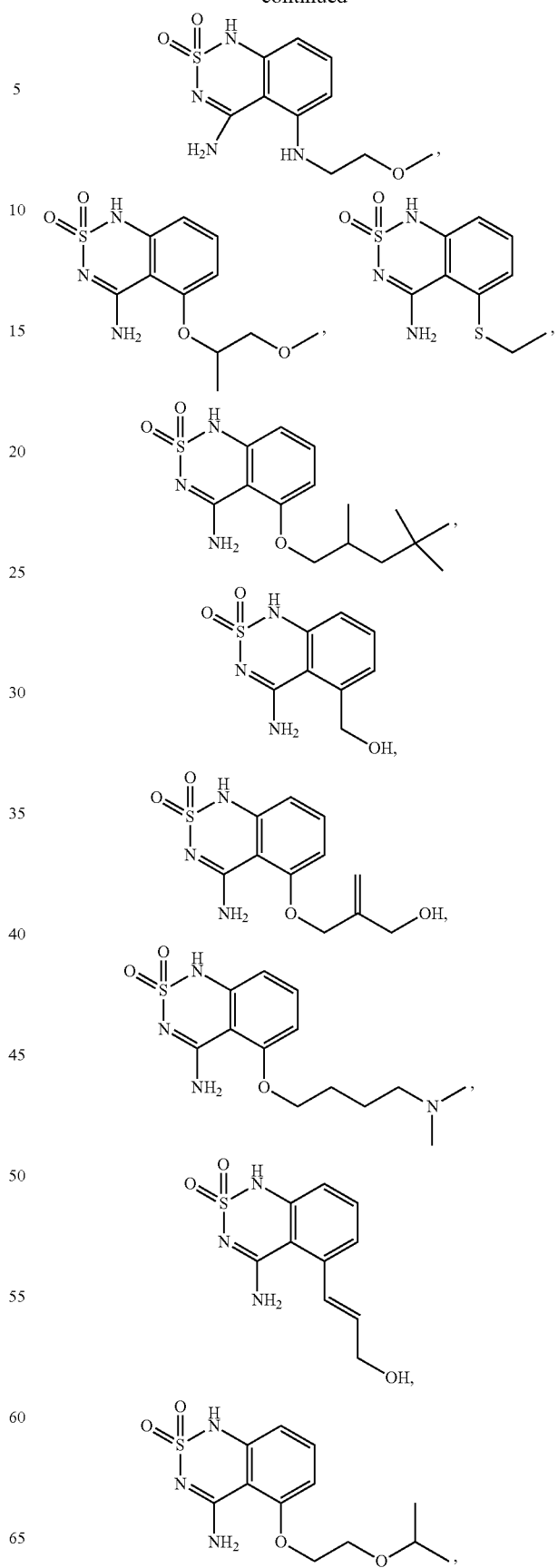

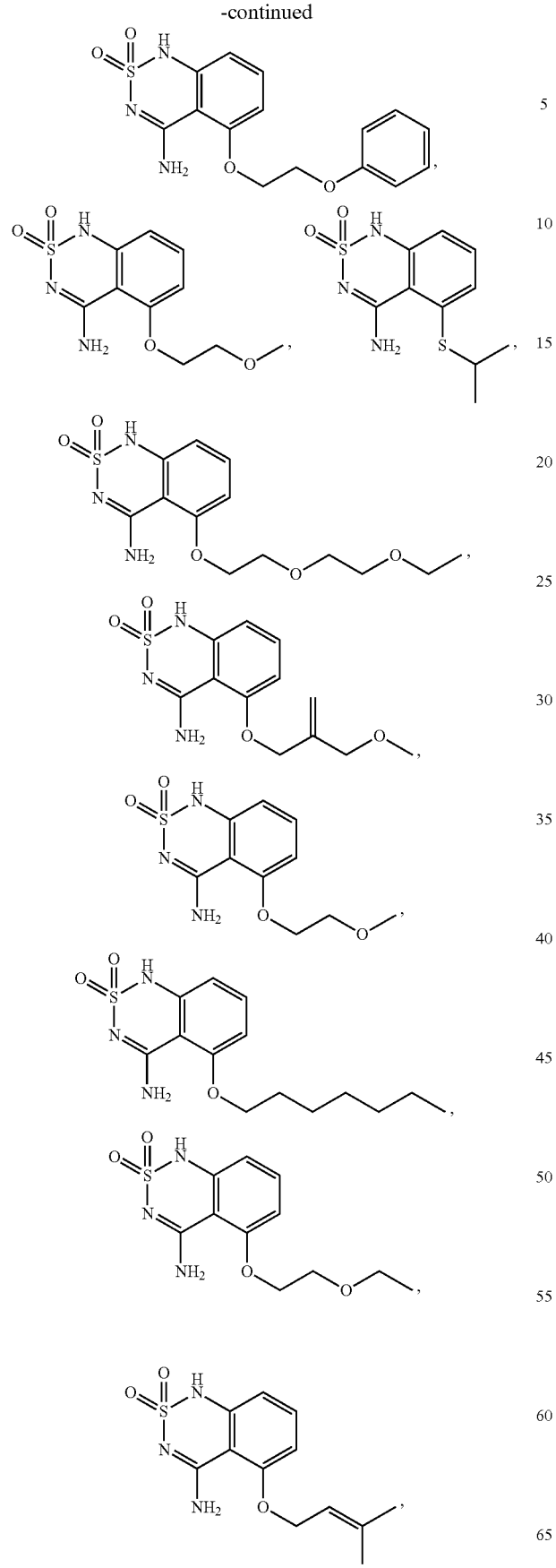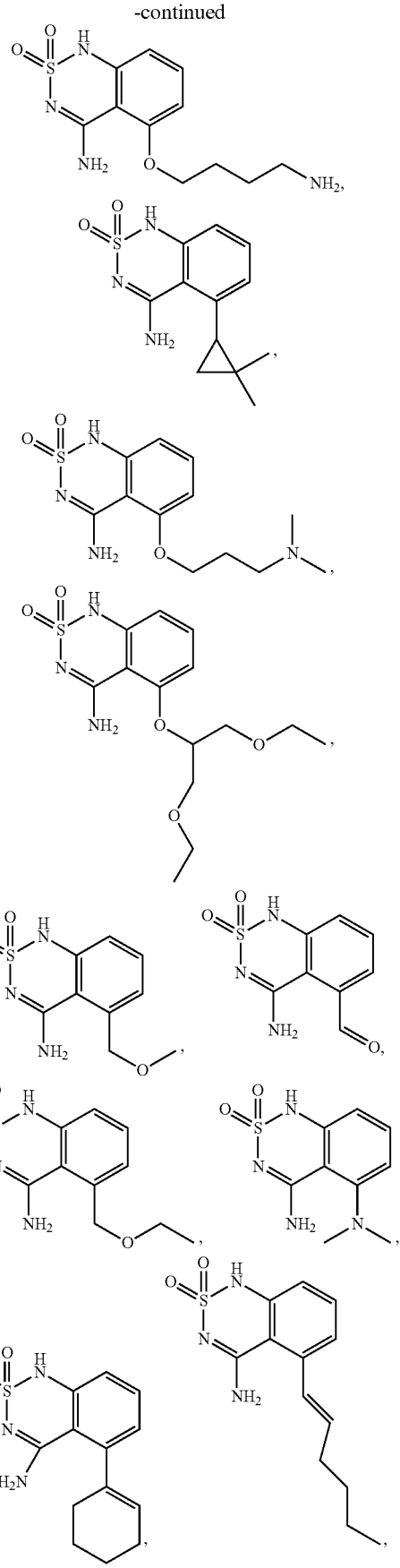

387
-continued
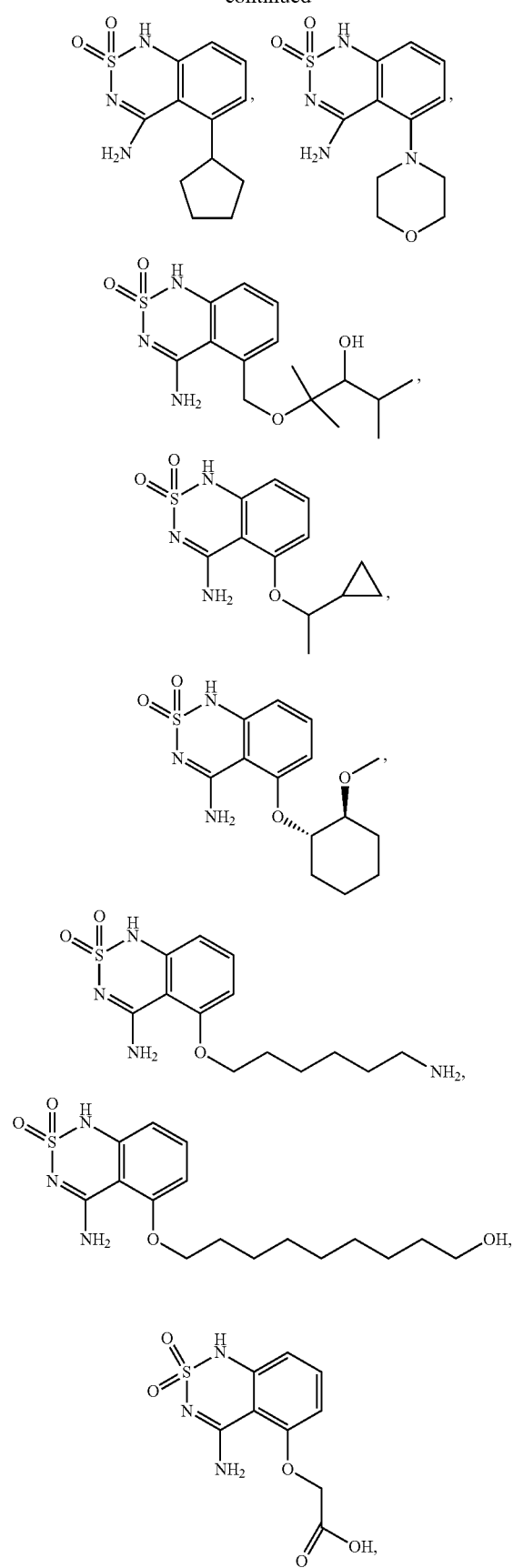
388
-continued
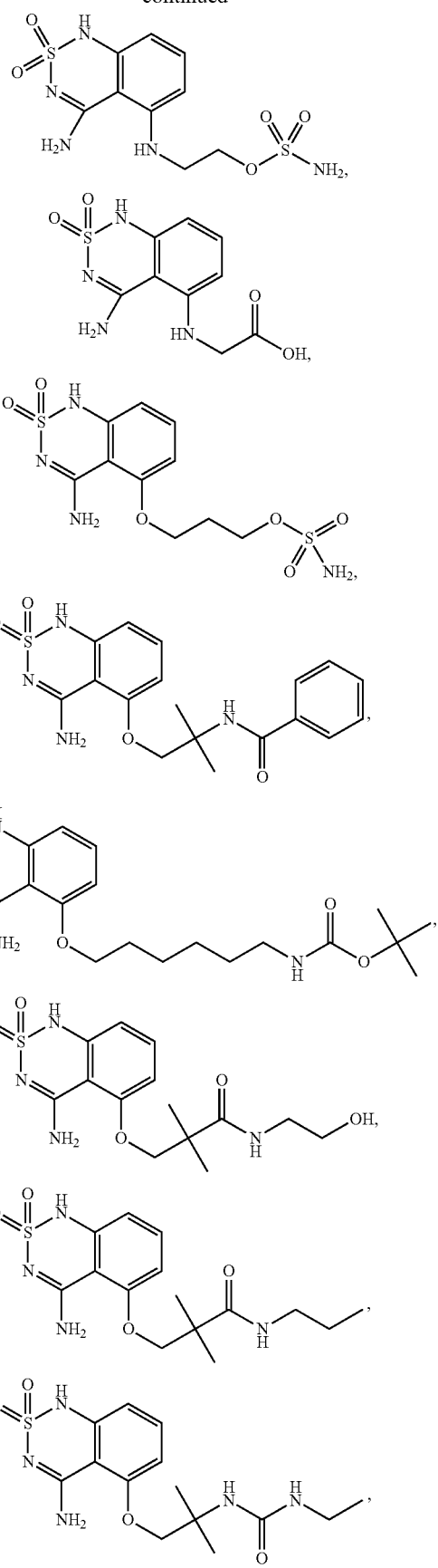

389
-continued
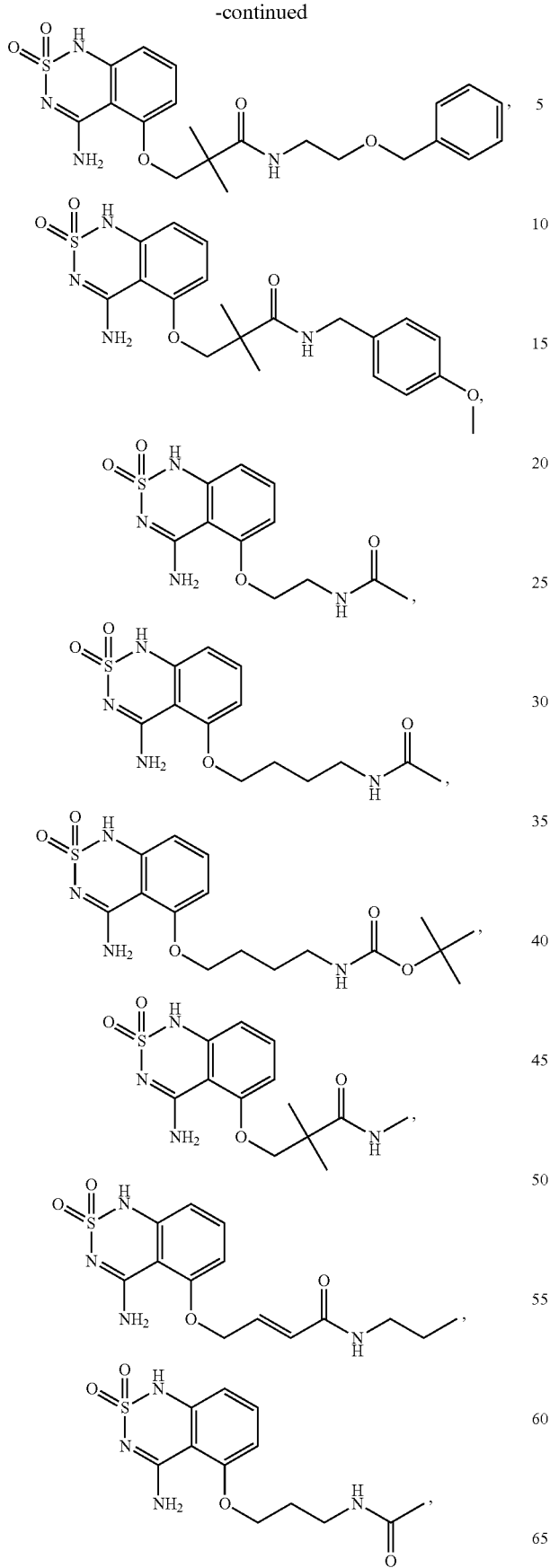
390
-continued
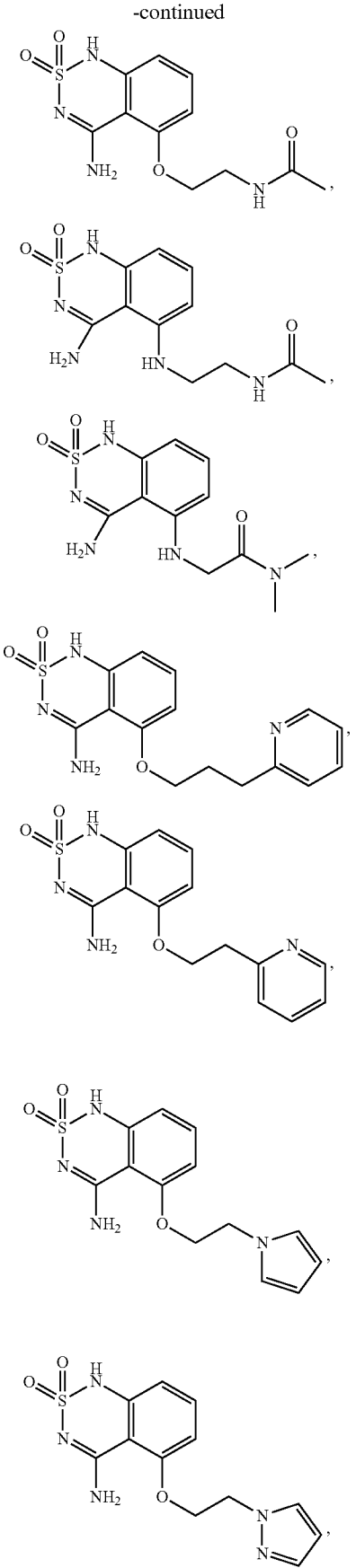

391
-continued
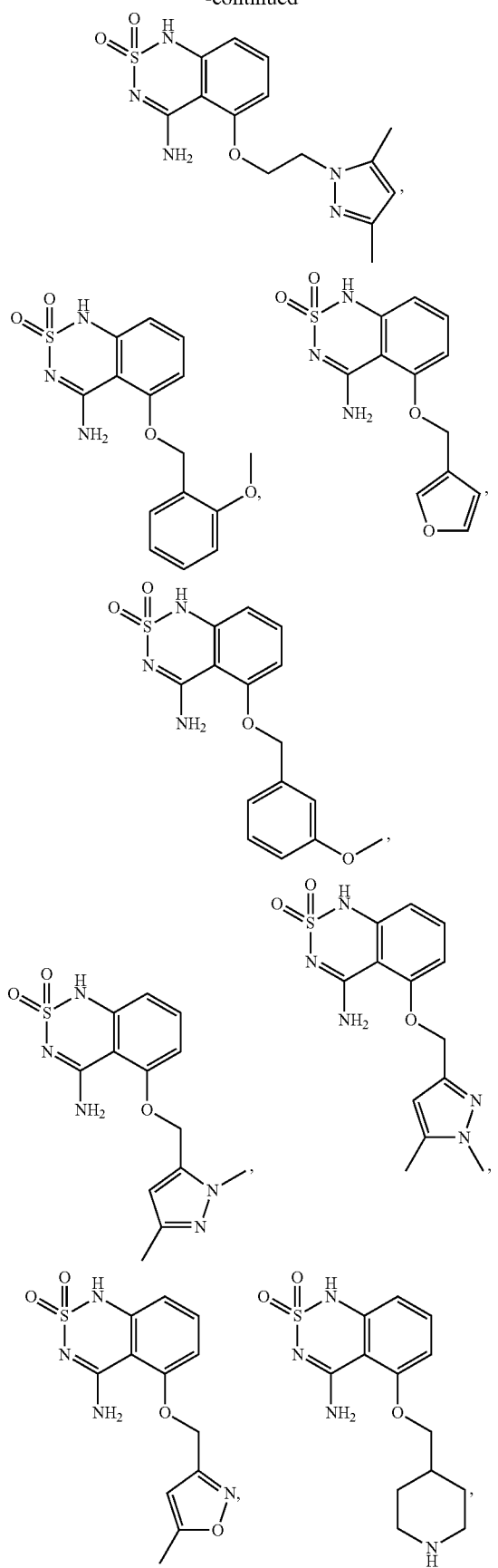
392
-continued
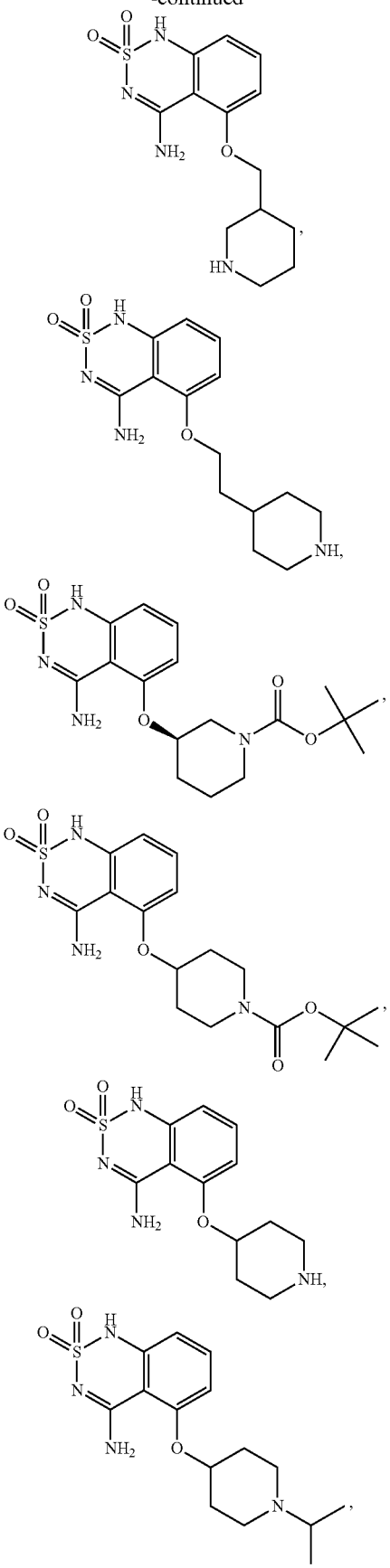

393
-continued
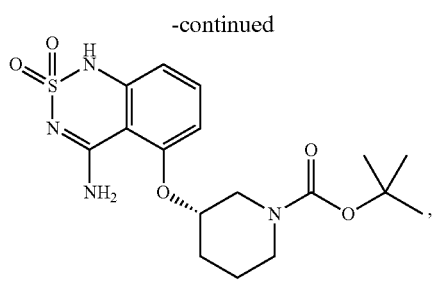
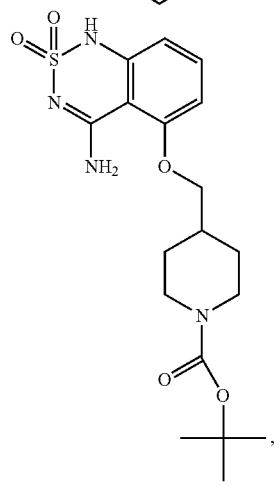
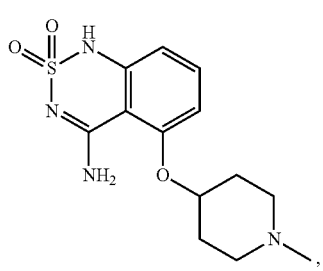
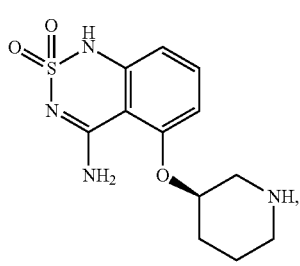
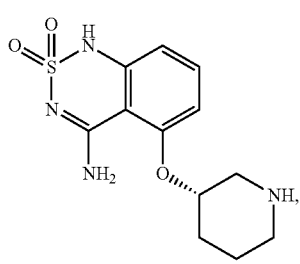
394
-continued
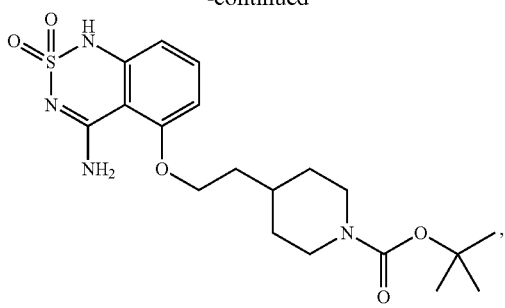
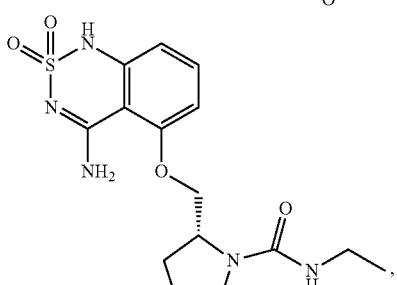
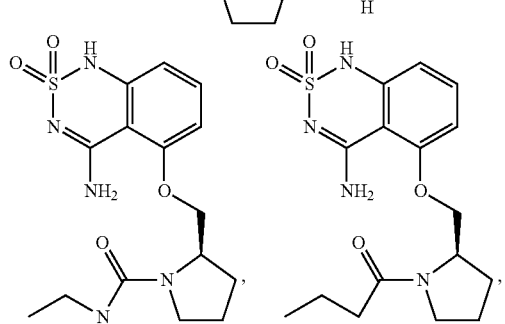
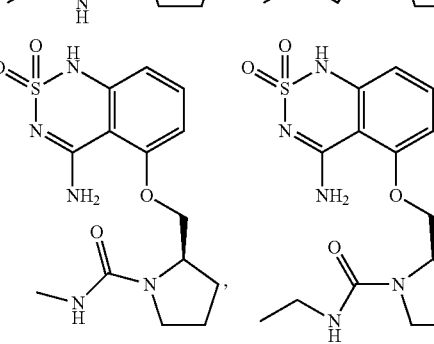
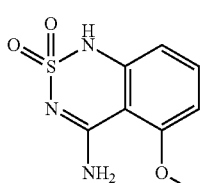
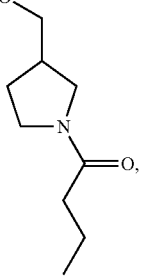

395
-continued
396
-continued
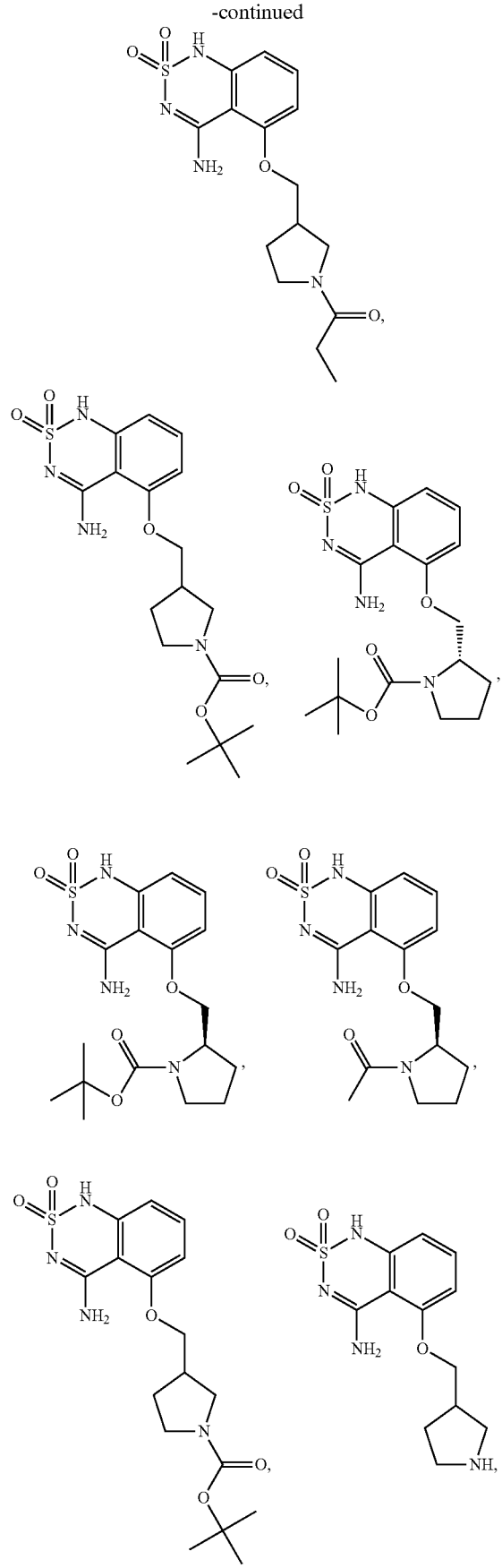
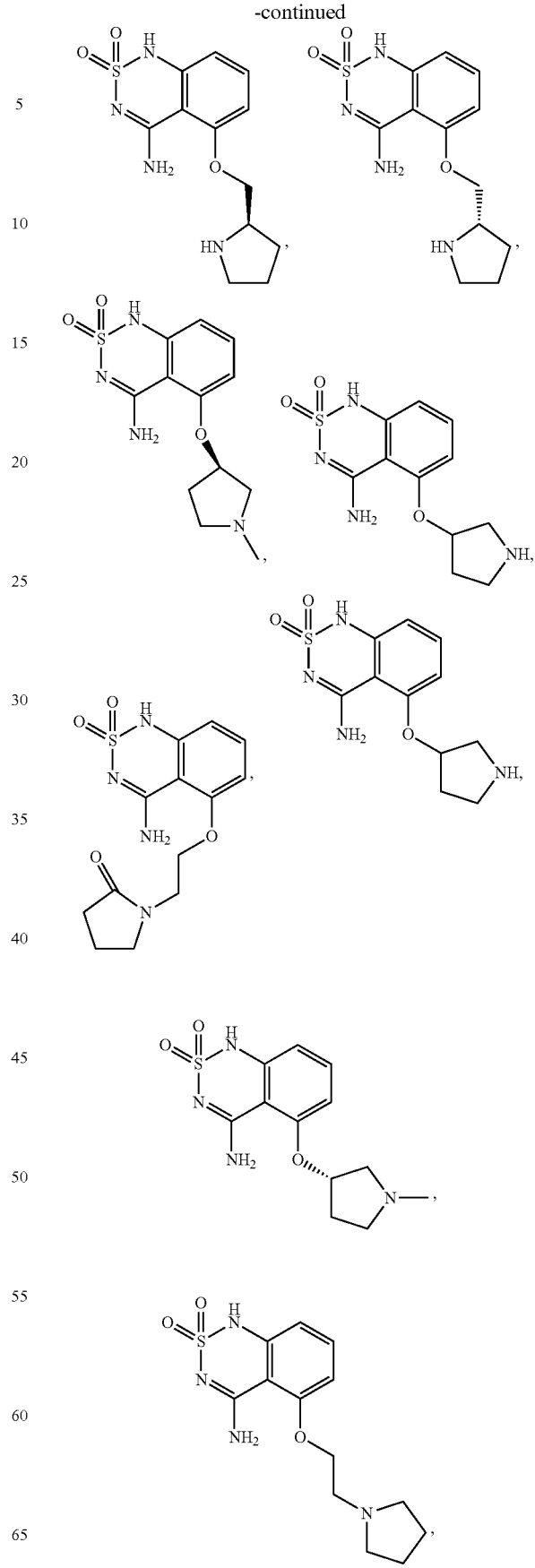

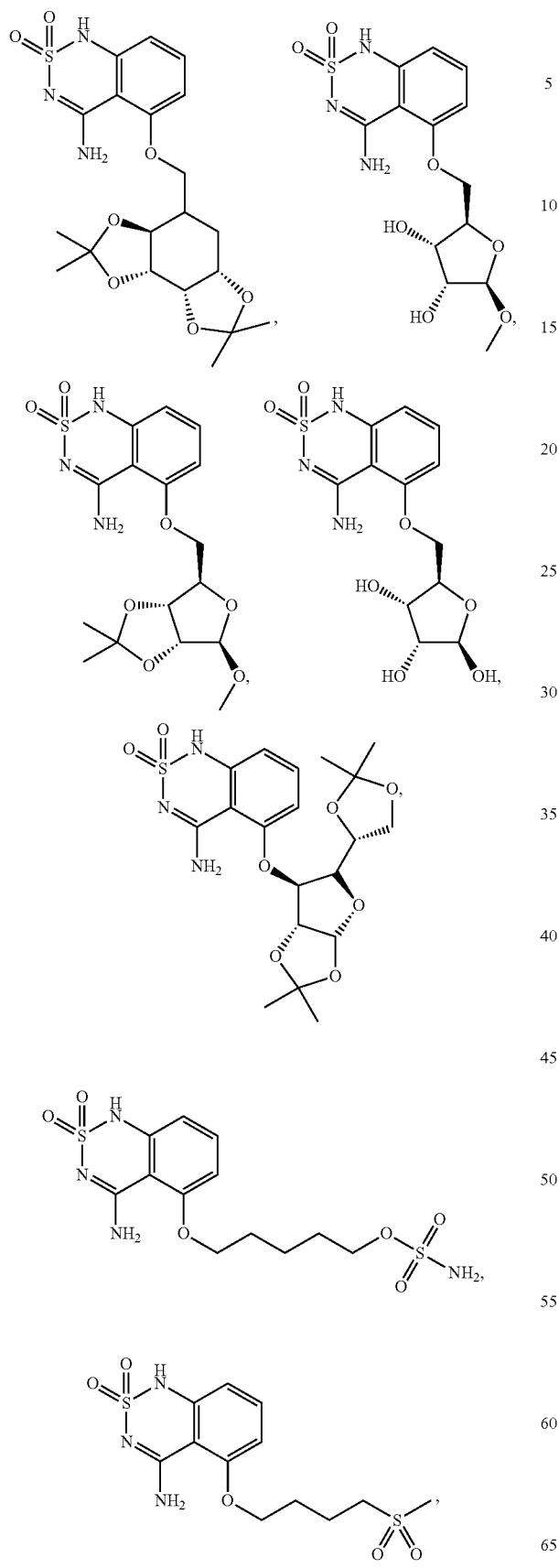
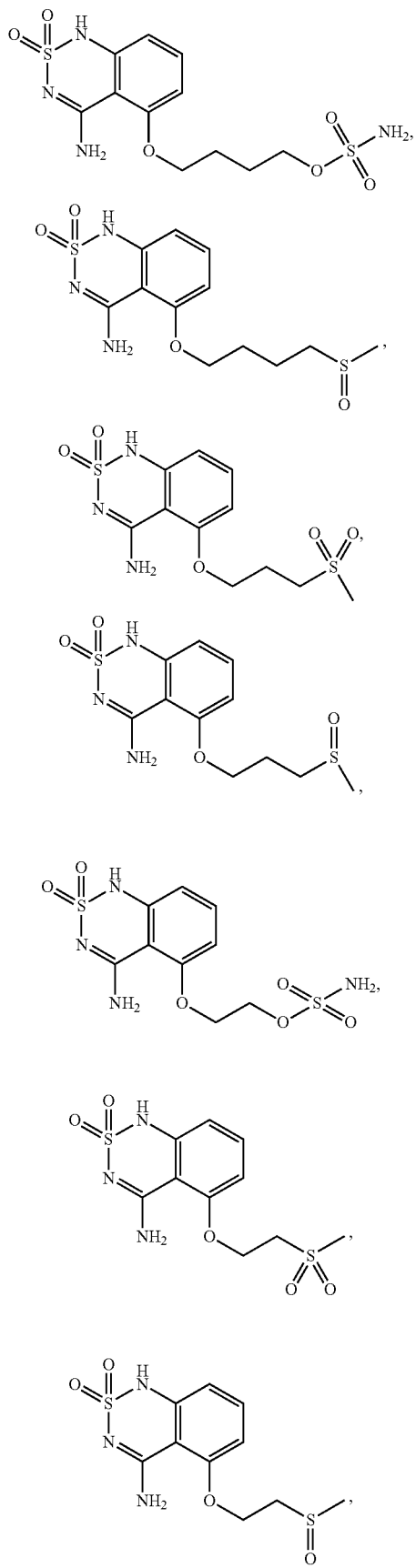

-continued
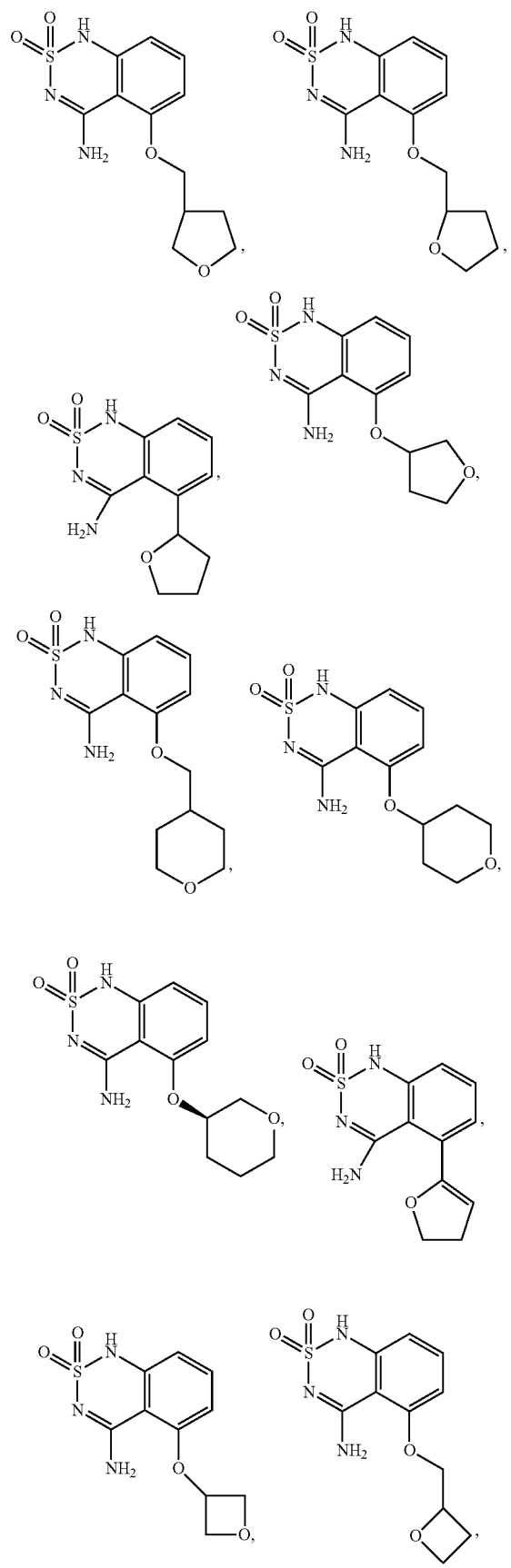
-continued
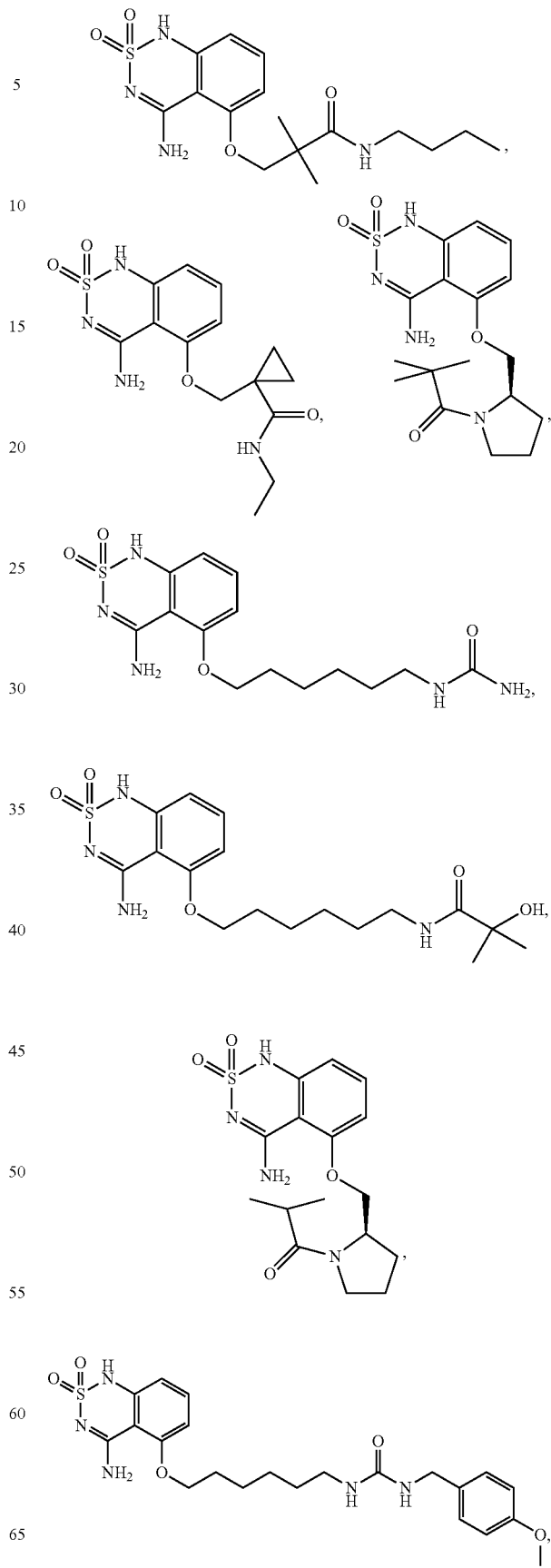

401
-continued
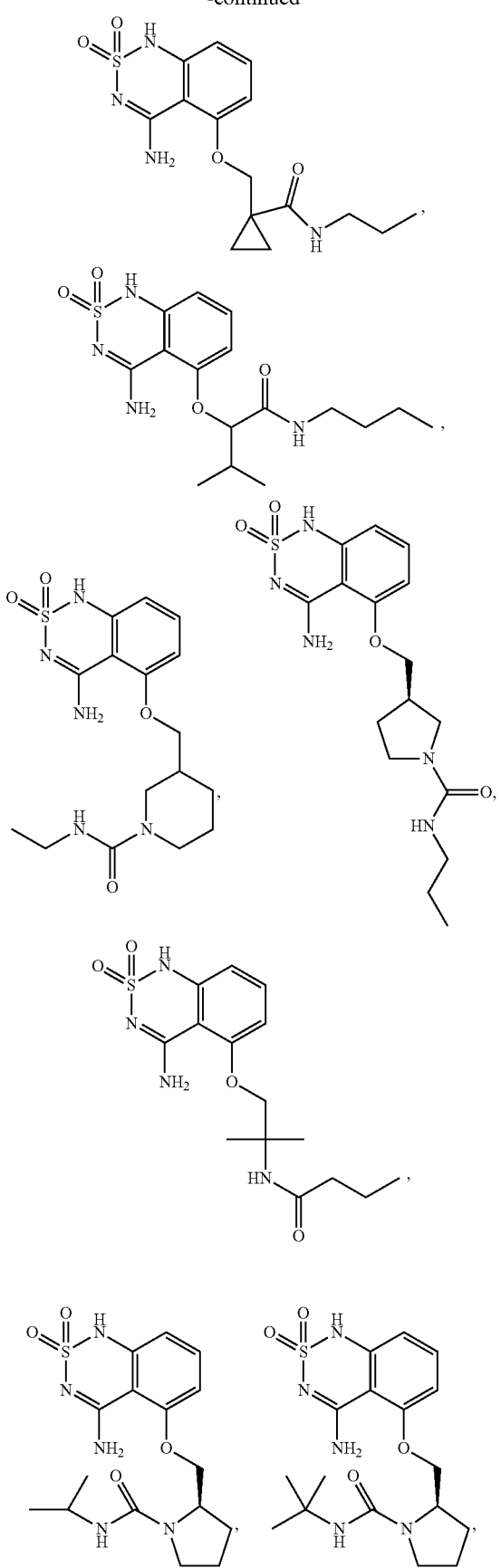
402
-continued
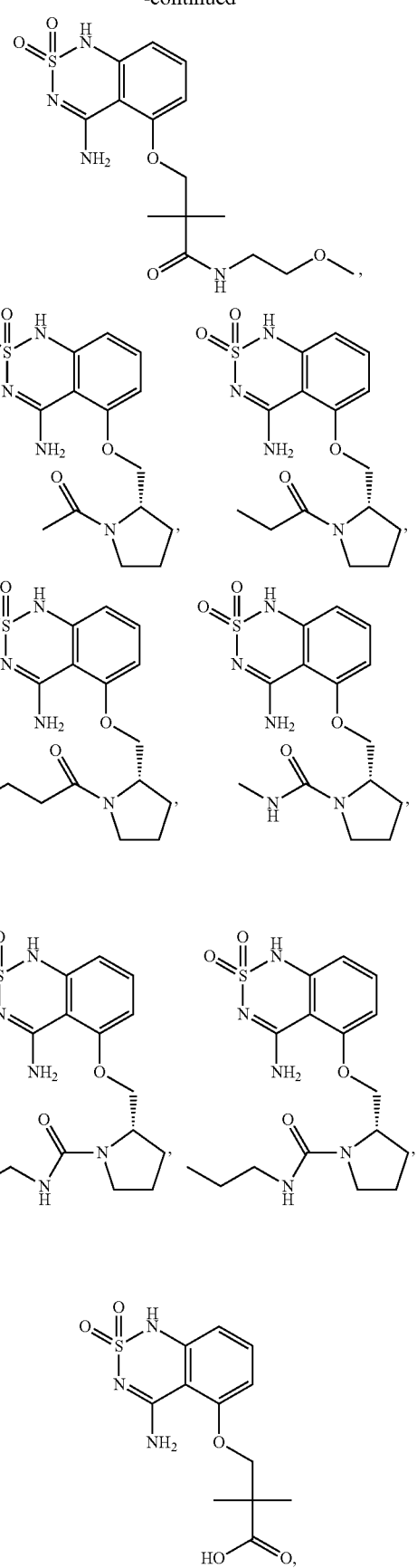

-continued

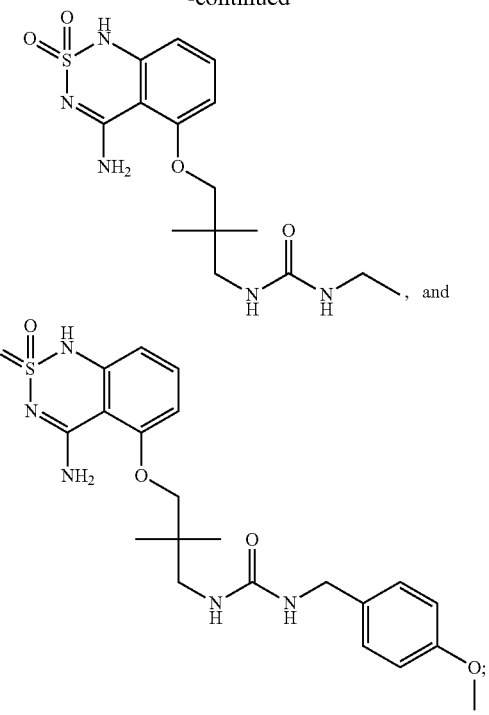

or a salt or solvate thereof.

16. A process of preparing a compound having structural Formula (e):

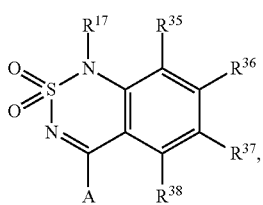

comprising reacting a compound having structural Formula (f)

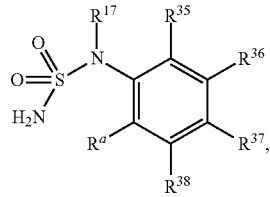

with a base,
wherein:
A is —NH$_2$ or —OR$^b$;
R$^{17}$ is hydrogen, alkyl, substituted alkyl, aryl, substituted aryl, arylalkyl, or substituted arylalkyl;
R$^{35}$, R$^{36}$, R$^{37}$, and R$^{38}$ are each independently hydrogen, alkyl, substituted alkyl, aryl, substituted aryl, arylalkyl, substituted arylalkyl, acyl, substituted acyl, halo, heteroalkyl, substituted heteroalkyl, heteroaryl, substituted heteroaryl, heteroarylalkyl or substituted heteroarylalkyl, —CN, —NO$_2$, —OR$^{41}$, —S(O)$_k$R$^{41}$, —NR$^{41}$R$^{42}$, —CONR$^{41}$R$^{42}$, —CO$_2$R$^{41}$, —SO$_2$NR$^{41}$R$^{42}$, and —NR$^{41}$SO$_2$R$^{42}$; or alternatively, R$^{35}$ and R$^{36}$, R$^{36}$ and R$^{37}$, or R$^{37}$ and R$^{38}$, together with the atoms to which they are bonded, form a cycloalkyl, substituted cycloalkyl, heterocycloalkyl, or substituted heterocycloalkyl ring;
R$^a$ is —CN, —C(O)R$^b$, —C(O)OR$^b$, —C(O)N(R$^b$)$_2$;
each R$^b$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl; and
R$^{41}$ and R$^{42}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; or alternatively R$^{41}$ and R$^{42}$, together with the atoms to which they are bonded, form a cycloheteroalkyl or substituted cycloheteroalkyl ring.

* * * * *

UNITED STATES PATENT AND TRADEMARK OFFICE
CERTIFICATE OF CORRECTION

| | | |
|---|---|---|
| PATENT NO. | : 8,633,186 B2 | Page 1 of 1 |
| APPLICATION NO. | : 12/663634 | |
| DATED | : January 21, 2014 | |
| INVENTOR(S) | : Tachdjian et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 742 days.

Signed and Sealed this
Second Day of September, 2014

Michelle K. Lee
*Deputy Director of the United States Patent and Trademark Office*